US010792357B2

(12) United States Patent
Parks et al.

(10) Patent No.: US 10,792,357 B2
(45) **Date of Patent: *Oct. 6, 2020**

(54) OPTIMIZED HIV ENVELOPE GENE AND EXPRESSION THEREOF

(71) Applicant: International AIDS Vaccine Initiative, New York, NY (US)

(72) Inventors: Christopher L. Parks, New York, NY (US); Maoli Yuan, New York, NY (US); Xinsheng Zhang, New York, NY (US); Aaron Wilson, New York, NY (US); Angela Grazia Lombardo, New York, NY (US); Eddy Sayeed, New York, NY (US); Josephine Helena Cox, New York, NY (US); Takashi Hironaka, Ibaraki (JP); Makoto Inoue, Ibaraki (JP); Hiroto Hara, Ibaraki (JP)

(73) Assignee: INTERNATIONAL AIDS VACCINE INITIATIVE, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/291,073

(22) Filed: Mar. 4, 2019

(65) Prior Publication Data

US 2019/0201522 A1 Jul. 4, 2019

Related U.S. Application Data

(63) Continuation of application No. 15/498,556, filed on Apr. 27, 2017, now Pat. No. 10,220,087, which is a continuation-in-part of application No. PCT/US2015/057452, filed on Oct. 27, 2015.

(60) Provisional application No. 62/069,022, filed on Oct. 27, 2014.

(51) Int. Cl.

| | |
|---|---|
| ***A61K 39/12*** | (2006.01) |
| ***A61K 39/21*** | (2006.01) |
| ***A61K 39/00*** | (2006.01) |
| ***C07K 14/005*** | (2006.01) |
| ***C12N 7/00*** | (2006.01) |
| ***C12N 15/86*** | (2006.01) |

(52) U.S. Cl.

CPC .............. *A61K 39/21* (2013.01); *A61K 39/12* (2013.01); *C07K 14/005* (2013.01); *C12N 7/00* (2013.01); *C12N 15/86* (2013.01); *A61K 2039/5256* (2013.01); *A61K 2039/53* (2013.01); *A61K 2039/543* (2013.01); *A61K 2039/545* (2013.01); *A61K 2039/55511* (2013.01); *A61K 2039/55555* (2013.01); *A61K 2039/57* (2013.01); *A61K 2039/575* (2013.01); *A61K 2039/70* (2013.01); *C12N 2740/16034* (2013.01); *C12N 2740/16134* (2013.01); *C12N 2740/16234* (2013.01); *C12N 2740/16271* (2013.01); *C12N 2740/16334* (2013.01); *C12N 2760/18443* (2013.01); *C12N 2760/18843* (2013.01); *C12N 2760/18871* (2013.01); *C12N 2760/20243* (2013.01)

(58) Field of Classification Search

CPC ...... A61K 39/21; A61K 39/12; C07K 14/005; C12N 2740/16122; C12N 2740/16134

See application file for complete search history.

(56) References Cited

U.S. PATENT DOCUMENTS

| | | | | |
|---|---|---|---|---|
| 2013/0266611 A1* | 10/2013 | Rabinovich ............ | A61K 39/21 | 424/208.1 |
| 2013/0266989 A1* | 10/2013 | Parks .................... | C07K 14/005 | 435/91.41 |
| 2014/0186397 A1* | 7/2014 | Hurwitz ................. | C07K 16/08 | 424/211.1 |
| 2014/0205652 A1* | 7/2014 | Voss ....................... | A61K 39/04 | 424/450 |

FOREIGN PATENT DOCUMENTS

| | | |
|---|---|---|
| EP | 1 682 666 | 7/2006 |
| EP | 2 644 701 | 10/2013 |
| WO | 2005/030964 | 4/2005 |

OTHER PUBLICATIONS

International Search Report and Written Opinion of the International Searching Authority dated Feb. 12, 2016, issued in International Application No. PCT/US15/57452.
International Search Report dated Apr. 13, 2016, issued in International Application No. PCT/US15/57446.
International Preliminary Report on Patentability and Written Opinion of the International Searching Authority dated May 11, 2017, issued in International Application No. PCT/US15/57446.
International Preliminary Report on Patentability and Written Opinion of the International Searching Authority dated May 11, 2017, issued in International Application No. PCT/US15/57452.

* cited by examiner

*Primary Examiner* — Barry A Chestnut
(74) *Attorney, Agent, or Firm* — Duane Morris LLP; Thomas J. Kowalski; Deborah L. Lu

(57) ABSTRACT

The present invention relates to a vector(s) containing and expressing an optimized HIV EnvF gene, methods for making the same and cell substrates qualified for vaccine production which may comprise vector(s) containing optimized HIV genes.

9 Claims, 97 Drawing Sheets

Specification includes a Sequence Listing.

DELETEMKCLLYLAFLFIGVNCKASAENLWVTVYYGVPVWKDAETTL
FCASDAKAYETEKHNVWATHACVPTDPNPQEIHLENVTEEFNMWKNN
MVEQMHTDIISLWDQSLKPCVKLTPLCVTLQCTNVTNNITDDMRGEL
KNCSFNMTTELRDKKQKVYSLFYRLDVVQINENQGNRSNNSNKEYRL
INCNTSAITQACPKVSFEPIPIHYCAPAGFAILKCKDKKFNGTGPCP
SVSTVQCTHGIKPVVSTQLLLNGSLAEEEVMIRSENITNNAKNILVQ
FNTPVQINCTRPNNNTRKSIRIGPGQAFYATGDIIGDIRQAHCTVSK
ATWNETLGKVVKQLRKHFGNNTIIRFANSSGGDLEVTTHSFNCGGEF
FYCNTSGLFNSTWISNTSVQGSNSTGSNDSITLPCRIKQIINMWQRI
GQAMYAPPIQGVIRCVSNITGLILTRDGGSTNSTTETFRPGGGDMRD
NWRSELYKYKVVKIEPLGVAPTRAKRRVVGREKRAVGIGAVFLGFLG
AAGSTMGAASMTLTVQARNLLSGIVQQQSNLLRAIEAQQHLLKLTVW
GIKQLQARVLAVERYLRDQQLLGIWGCSGKLICTTNVPWNSSWSNRN
LSEIWDNMTWLQWDKEISNYTQIIYGLLEESQNQQEKNEQDLLALDK
WASLWNWFDISNWLWYIKSSIASFFFIIGLIIGLFLVLRVGIYLCIK
LKHTKKRQIYTDIEMNRLGK*

- VSV G N-terminus (signal peptide)
- Amino acid linker (and a Nhe I restriction sites)
- VSV G Transmembrane region
- VSV G Cytoplasmic tail

FIG. 1

ATGaagtgcctttttgtacttagctttcttattcatcggggtgaattgcaaggc
tagcgcagagaatttgtgggtaacagtctactatggagtccctgtatggaagg
atgcagagacaacattgttctgtgctagtgacgcaaaggcttacgagacggag
aagcacaatgtgtgggcaactcacgcatgtgtcccaaccgatccaaatcctca
agagattcatctagagaatgtgactgaagaattcaatatgtggaagaataata
tggtagagcaaatgcatacagatatcattagtttatgggaccagtcacttaaa
ccctgcgttaaattgacgcctctatgtgtgacacttcaatgtactaatgttac
aaacaacataacagatgatatgagaggagaactgaagaactgtagtttcaaca
tgacgacagagttgcgtgacaagaaacagaaagtgtattcactattctatcgg
ttggatgtagtacagataaatgagaatcaaggaaacaggtccaacaactctaa
caaagagtacagacttattaattgcaataccagtgctatcacgcaagcctgcc
caaaggtttcatttgaaccaatacctattcattattgtgcacctgctggattc
gccatcctcaaatgtaaagacaagaagttcaatggaacaggaccctgcccatc
agtttcaaccgttcagtgcacccacggaatcaagcctgtagttagtactcaat
tattgttaaatgggagcttagctgaagaagaagttatgattagatcagagaat
attaccaataatgcgaagaacatcttggttcaattcaatactccagtccagat
caattgcacaaggcctaataataataccagaaagagtataagaattgggccag
gacaggcattctatgcaacaggagatataatcggagacattcgacaagcgcac
tgcactgtttctaaggccacttggaatgaaacattgggtaaagttgtaaagca
acttcggaagcatttcggaaataacacaattattagatttgcgaactcatctg
gaggggatctggaagtgacaacacactctttcaattgcggtggcgagttcttc
tattgtaatacaagtggattatttaactctacttggatttcaaatacctcagt
ccaaggatctaattcaacagggtctaacgattctataacattaccttgccgta
taaagcaaattattaatatgtggcaaagaatcgggcaagcgatgtatgctcca
cctattcaaggcgtgattcgttgcgtttcaaacataacagggttgatcctgac
cagggatggaggctctaccaattccaccaccgagaccttccgtcccggtggcg
gagatatgcgggataactggagatcagagctctataagtataaggttgtgaag
attgaacctcttggagttgcccctacaagagcaaagagaagggtggttggccg
agagaagagagcagttggcatcggtgctgtctttctcggatttcttggagcag
ctggatccactatgggagcagcatcaatgacactaacagtgcaggctagaaat
ttgcttagcggaatcgttcagcagcagagcaatttactaagagcaattgaagc
acagcaacatctcttaaagttgacggtgtggggcattaaacaactacaagcga
gagtgcttgccgtcgaaagatatttgcgagaccaacagctattgggtatttgg
ggttgttctgggaaattaatttgcacaacaaatgttccatggaactcctcctg
gagtaataggaatttaagtgagatatgggacaacatgacatggttgcagtggg
acaaggaaatctcaaattatacacagataatctatggattattagaagagtct
cagaatcagcaagagaagaatgaacaggatttgcttgcattggataagtgggc
ttctctatggaactggttcgatattagtaattggctctggtatattaagagct
ctattgcctctttttttctttatcatagggttaatcattggactattcttggtt
ctccgagttggtatttatctttgcattaaattaaagcacaccaagaaaagaca
gatttatacagacatagagatgaaccgacttggaaagTAAag

FIG. 2 ggagccaccatgaagtgtttgttgtatttggcattcttattcatcggagtgaattgtaag
GAGGAGAAAGCATTCTCACCTGAAGTGATCCCTATGTTCACAGCATTATCTGAGGGAGCT
ACTCCTCAAGATCTTAACACAATGCTTAACACAGTCGGAGGACATCAAGCAGCAATGCAA
ATGTTGAAAGATACAATTAACGAGGAAGCAGCAGAATGGGATAGAATCTATAAGAGATGG
ATAATATTAGGATTGAACAAGATTGTTAGAATGTATTCTCCTGTGTCAATCCTTGATATA
AGACAAGGACCTAAAGAGCCTTTCAGAGATTACGTCGATAGATTTGCAAGAAATTGTAGA
GCACCTAGAAAGAAGGGATGTTGGAAATGTGGGAAAGAAGGACATCAAATGAAAGATTGT
ACTGAGAGACAAGCTAACTTCTTGGGAAAGATATGGCCTTCAAGATGGAAACCTAAGATG
ATAGGAGGAATAGGAGGATTTATTAAAGTCAGACAATATGATCAAATATTGATTGAAATA
TGTGGACATAAAGCTATTGGAACAGTCCTAGTGGGTCCAACACCTGTCAACATCATTGGT
AGAAATCTTCTCACTCAAATCGGATGTACACTCAATTTCCCAATATCACCTATTGAGACC
GTGCCTGTCAAATTGAAACCTGGAATGGATGGACCTAAAGTCAAACAATGGCCATTAACT
GAGGAGAAGATTAAAGCACTGGTAGAAATTTGTACAGAGATGGAGAAAGAAGGAAAGATT
TCCAAGATTGGTCCTGAGAATCCTTATAATACTCCTGTCTTTGCTATTAAGAAGAAGGAT
AGTACCAAATGGAGGAAATTAGTCGATTTCAGAGAACTTAACAAGAGGACTCAAGACTTC
TGGGAAGTGCAATTGGGAATCCCACACCCTGCAGGATTGAAGAAGAAGAAGTCTGTCACT
GTCCTAGATGTGGGAGATGCATATTTCAGTGTCCCACTGGATGAAGGTTTCAGAAAGTAT
ACAGCATTCACAATCCCTTCCATTAATAATGAAACACCTGGAATAAGATATCAATATAAT
GTCTTACCTCAAGGGTGGAAAGGATCTCCAGCAATATTCCAATCATCAATGACAAAGATC
TTGGAGCCTTTCAGAGCTCAGAATCCAGAGATAGTTATTTACCAATACATGGATGATTTG
TATGTTGGGTCAGATCTCGAGATCGGACAGCACAGGATGGAGAATAGATGGCAAGTAATG
ATTGTCTGGCAAGTCGATAGAATGAGAATAAGAACATGGAAATCCTTGGTGAAACATCAC
CTTACAGAGGAGGCAGAACTGGAACTGGCAGAGAATAGGGAAATATTGAAAGATCCAGTG
CATGGTGTCTATTACGATCCTTCTAAAGATCTGATAGCAGAGATCCAGTACTGGCAAGCA
ACATGGATTCCTGAGTGGGAATTCGTCAACACACCTCCATTAGTGAAACTATGGTACCAA
TTAGAGAAGAATGTCACCGAGAACTTCAACATGTGGAAGAACGATATGGTAGATCAAATG
CACGAAGATATCATCTCCTTGTGGGATCAATCACTTAAACCTTGTGTTAAATTGACACCT
TGGGTACCTGCTCATAAAGGGATAGGAGGAAACGAACAAGTGGATAAATTGGTGTCCCAA
GGGATCAGGAAAGTCTTGTTCCTAGATGGAATTGATAAAGCTCAAGCAAAGGAAATTGTC
GCAAGCTGTGATAAGTGTCAATTAAAGGGAGAGGCAATGCACGGACAAGTCGATTGTTCA
CCTGGTATTTGGCAACTTGATTGTACACATTTGGAGGGTAAAGTTATTCTAGTAGCAGTA
CATGTCGCTTCTGGTTATATTGAGGCAGAAGTGATACCTGCTGAGACAGGACAGGAGACC
GCATACTTTCTACTTAAGTTAGCTATGAATAAGGAGCTCAAGAAGATAATAGGACAAGTT
AGAGATCAAGCAGAGCACCTTAAGACAGCTGTCCAAATGGCAGTGTTTATACACAACTTT
AAGAGAAAGGGTGGAATCGGAGGATATTCCGCAGGAGAGAGAATCTGGAAAGGTCCTGCT
AAATTGTTATGGAAAGGAGAAGGAGCAGTTGTAATACAAGATAATTCTGATATAAAGTA
GTCCCTAGAAGGAAAGCTAAGATTATTAGAGATTATGGAAACAAATGGCAGGAGCTGAT
TGTGTGTTTCTAGGAGCAGCAGGATCCACTATGGGAGCTGCATCAATGACACTTACCGTG
CAGGCTAGACAGCTTCTTTCAGGAATTGTACAGCAACAGAATAATTTGCTAAGAGCAATT
GAAGCTCAACAACACTTACTTCAACTTACAGTCTGGGGAATCAAGCAAGCATGTACACCT
TATGATATCAACCAAATGCTGAGAGGACCAGGAAGAGCATTTGTAACAATCCCTAATCCT
TTATTGGGTCTGGAT Epitope tag Kozak sequence VSV G leader peptide

FIG. 4

MEEKAFSPEVIPMFTALSEGATPQDLNTMLNTVGGHQAAMQMLKDTI
NEEAAEWDRIYKRWIILGLNKIVRMYSPVSILDIRQGPKEPFRDYVD
RFARNCRAPRKKGCWKCGKEGHQMKDCTERQANFLGKIWPSRWKPKM
IGGIGGFIKVRQYDQILIEICGHKAIGTVLVGPTPVNIIGRNLLTQI
GCTLNFPISPIETVPVKLKPGMDGPKVKQWPLTEEKIKALVEICTEM
EKEGKISKIGPENPYNTPVFAIKKKDSTKWRKLVDFRELNKRTQDFW
EVQLGIPHPAGLKKKKSVTVLDVGDAYFSVPLDEGFRKYTAFTIPSI
NNETPGIRYQYNVLPQGWKGSPAIFQSSMTKILEPFRAQNPEIVIYQ
YMDDLYVGSDLEIGQHRMENRWQVMIVWQVDRMRIRTWKSLVKHHLT
EEAELELAENREILKDPVHGVYYDPSKDLIAEIQYWQATWIPEWEFV
NTPPLVKLWYQLEKNVTENFNMWKNDMVDQMHEDIISLWDQSLKPCV
KLTPWVPAHKGIGGNEQVDKLVSQGIRKVLFLDGIDKAQAKEIVASC
DKCQLKGEAMHGQVDCSPGIWQLDCTHLEGKVILVAVHVASGYIEAE
VIPAETGQETAYFLLKLAMNKELKKIIGQVRDQAEHLKTAVQMAVFI
HNFKRKGGIGGYSAGERIWKGPAKLLWKGEGAVVIQDNSDIKVVPRR
KAKIIRDYGKQMAGADCVFLGAAGSTMGAASMTLTVQARQLLSGIVQ
QQNNLLRAIEAQQHLLQLTVWGIKQACTPYDINQMLRGPGRAFVTIP
NPLLGLD

FIG. 5 gccgccaccATGGAGGAGAAGGCCTTCAGCCCTGAGGTGATCCCCATGTTCACCGCCCTGTCCGAGGGCGCCACCCCCCA
GGACCTGAACACCATGCTGAACACCGTGGGCGGCCACCAGGCCGCCATGCAGATGCTGAAGGACACCATCAACGAGGAGG
CCGCCGAGTGGGACCGCATCTACAAGCGCTGGATCATCCTGGGCCTGAACAAGATCGTGCGCATGTACTCCCCCGTGTCC
ATCCTGGACATCCGCCAGGGCCCCAAGGAGCCCTTCCGCGACTACGTGGACCGCTTCGCCCGCAACTGCCGCGCCCCTCG
CAAGAAGGGCTGCTGGAAGTGCGGCAAGGAGGGCCACCAGATGAAGGACTGCACCGAGCGCCAGGCCAACTTCCTGGGCA
AGATCTGGCCCTCCCGCTGGAAGCCCAAGATGATTGGCGGATCGGCGGCTTCATCAAGGTGCGCCAGTACGACCAGATC
CTGATCGAGATCTGCGGCCACAAGGCCATCGGCACCGTGCTCGTGGGCCCCACCCCCGTGAACATCATCGGCCGCAACCT
GCTGACCCAGATCGGCTGCACCCTGAACTTCCCCATCTCCCCCATCGAGACCGTGCCCGTGAAGCTGAAGCCCGGCATGG
ACGGCCCCAAGGTGAAGCAGTGGCCCCTGACCGAGGAGAAGATCAAGGCCCTGGTGGAGATCTGCACCGAGATGGAGAAG
GAGGGCAAGATCTCCAAGATCGGCCCCGAGAACCCCTACAACACCCCCGTGTTCGCCATCAAGAAGAAGGACTCCACCAA
GTGGCGCAAACTGGTGGACTTCCGCGAGCTGAACAAGCGCACCCAGGACTTCTGGGAGGTGCAGCTGGGCATCCCCCACC
CTGCCGGCCTGAAGAAGAAGAAGTCCGTGACCGTGCTGGACGTGGGCGACGCCTACTTCTCCGTGCCCCTGGACGAGGGC
TTCCGCAAGTACACCGCCTTCACCATCCCCTCCATCAACAACGAGACCCCCGGCATCCGCTACCAGTACAACGTGCTGCC
CCAGGGCTGGAAGGGCTCCCCCGCCATCTTCCAGTCCTCCATGACCAAGATCCTGGAGCCCTTCCGCGCCCAGAACCCCG
AGATCGTGATCTACCAGTACATGGACGACCTGTACGTGGGCTCCGACCTGGAGATCGGCCAGCACCGCATGGAGAACCGC
TGGCAGGTGATGATCGTGTGGCAGGTGGACCGCATGCGCATCCGCACCTGGAAGTCCCTGGTGAAGCACCACCTGACCGA
GGAGGCCGAGCTGGAGCTGGCCGAGAACCGCGAGATCCTGAAGGACCCCGTGCACGGCGTGTACTACGACCCCTCCAAGG
ACCTGATCGCCGAGATCCAGTACTGGCAGGCCACCTGGATCCCCGAGTGGGAGTTCGTGAACACCCCACCCCTGGTGAAG
CTGTGGTACCAGCTGGAGAAGAACGTGACCGAGAACTTCAACATGTGGAAGAACGACATGGTGGACCAGATGCACGAGGA
CATCATCTCCCTGTGGGACCAGTCCCTGAAGCCCTGCGTGAAGCTGACCCCCTGGGTGCCCGCCCACAAGGGCATCGGCG
GCAACGAGCAGGTGGACAAGCTGGTGTCCCAGGGCATCCGCAAGGTGCTGTTCCTGGACGGCATCGACAAGGCCCAGGCC
AAGGAGATCGTGGCCTCCTGCGACAAGTGCCAGCTGAAGGGCGAGGCCATGCACGGCCAGGTGGACTGCTCCCCCGGCAT
CTGGCAGCTGGACTGCACCCACCTGGAGGGCAAGGTGATCCTGGTGGCCGTGCACGTGGCCTCCGGCTACATCGAGGCCG
AAGTGATTCCCGCCGAGACCGGCCAGGAGACCGCCTACTTCCTGCTGAAGCTGGCCATGAACAAGGAGCTGAAGAAGATC
ATCGGCCAGGTGCGCGACCAGGCCGAGCACCTGAAGACCGCCGTGCAGATGGCCGTGTTCATCCACAACTTCAAGCGCAA
GGGCGGAATCGGCGGCTACTCCGCCGGCGAGCGCATCTGGAAGGGCCCCGCCAAGCTGCTGTGGAAGGGCGAGGGCGCCG
TGGTGATCCAGGACAACTCCGACATCAAGGTGGTGCCCCGCCGCAAGGCCAAGATCATCCGCGACTACGGCAAGCAGATG
GCCGGTGCCGACTGCGTGTTCCTGGGCGCTGCCGGCTCCACCATGGGCGCCGCCTCCATGACCCTGACCGTGCAGGCCCG
CCAGCTGCTGTCCGGCATCGTGCAGCAGCAGAACAACCTGCTGCGCGCCATCGAGGCCCAGCAGCACCTGCTGCAGCTGA
CCGTGTGGGGCATCAAGCAGGCACCCACCAAGGCAAAGAGAAGAGTGGTGCAGAGAGAAAAGAGAtagtaa

FIG. 6A

```
     >Kozak
     |
gcc gcc acc ATG GAG GAG AAG GCC TTC AGC CCT GAG GTG ATC CCC ATG TTC ACC GCC CTG  < 60
            M   E   E   K   A   F   S   P   E   V   I   P   M   F   T   A   L
cgg cgg tgg TAC CTC CTC TTC CGG AAG TCG GGA CTC CAC TAG GGG TAC AAG TGG CGG GAC
            10             20             30             40             50

TCC GAG GGC GCC ACC CCC CAG GAC CTG AAC ACC ATG CTG AAC ACC GTG GGC GGC CAC CAG  < 120
S   E   G   A   T   P   Q   D   L   N   T   M   L   N   T   V   G   G   H   Q
AGG CTC CCG CGG TGG GGG GTC CTG GAC TTG TGG TAC GAC TTG TGG CAC CCG CCG GTG GTC
            70             80             90             100            110

GCC GCC ATG CAG ATG CTG AAG GAC ACC ATC AAC GAG GAG GCC GCC GAG TGG GAC CGC ATC  < 180
A   A   M   Q   M   L   K   D   T   I   N   E   E   A   A   E   W   D   R   I
CGG CGG TAC GTC TAC GAC TTC CTG TGG TAG TTG CTC CTC CGG CGG CTC ACC CTG GCG TAG
            130            140            150            160            170

TAC AAG CGC TGG ATC ATC CTG GGC CTG AAC AAG ATC GTG CGC ATG TAC TCC CCC GTG TCC  < 240
Y   K   R   W   I   I   L   G   L   N   K   I   V   R   M   Y   S   P   V   S
ATG TTC GCG ACC TAG TAG GAC CCG GAC TTG TTC TAG CAC GCG TAC ATG AGG GGG CAC AGG
            190            200            210            220            230

ATC CTG GAC ATC CGC CAG GGC CCC AAG GAG CCC TTC CGC GAC TAC GTG GAC CGC TTC GCC  < 300
I   L   D   I   R   Q   G   P   K   E   P   F   R   D   Y   V   D   R   F   A
TAG GAC CTG TAG GCG GTC CCG GGG TTC CTC GGG AAG GCG CTG ATG CAC CTG GCG AAG CGG
            250            260            270            280            290
```

FIG. 6B

```
CGC AAC TGC CGC GCC CCT CGC AAG AAG GGC TGC TGG AAG TGC GGC AAG GAG GGC CAC CAG  < 360
R   N   C   R   A   P   R   K   K   G   C   W   K   C   G   K   E   G   H   Q
GCG TTG ACG GCG CGG GGA GCG TTC TTC CCG ACG ACC TTC ACG CCG TTC CTC CCG GTG GTC
            310             320             330             340             350

ATG AAG GAC TGC ACC GAG CGC CAG GCC AAC TTC CTG GGC AAG ATC TGG CCC TCC CGC TGG  < 420
M   K   D   C   T   E   R   Q   A   N   F   L   G   K   I   W   P   S   R   W
TAC TTC CTG ACG TGG CTC GCG GTC CGG TTG AAG GAC CCG TTC TAG ACC GGG AGG GCG ACC
            370             380             390             400             410

AAG CCC AAG ATG ATT GGC GGG ATC GGC GGC TTC ATC AAG GTG CGC CAG TAC GAC CAG ATC  < 480
K   P   K   M   I   G   G   I   G   G   F   I   K   V   R   Q   Y   D   Q   I
TTC GGG TTC TAC TAA CCG CCC TAG CCG CCG AAG TAG TTC CAC GCG GTC ATG CTG GTC TAG
            430             440             450             460             470

CTG ATC GAG ATC TGC GGC CAC AAG GCC ATC GGC ACC GTG CTC GTG GGC CCC ACC CCC GTG  < 540
L   I   E   I   C   G   H   K   A   I   G   T   V   L   V   G   P   T   P   V
GAC TAG CTC TAG ACG CCG GTG TTC CGG TAG CCG TGG CAC GAG CAC CCG GGG TGG GGG CAC
            490             500             510             520             530

AAC ATC ATC GGC CGC AAC CTG CTG ACC CAG ATC GGC TGC ACC CTG AAC TTC CCC ATC TCC  < 600
N   I   I   G   R   N   L   L   T   Q   I   G   C   T   L   N   F   P   I   S
TTG TAG TAG CCG GCG TTG GAC GAC TGG GTC TAG CCG ACG TGG GAC TTG AAG GGG TAG AGG
            550             560             570             580             590

CCC ATC GAG ACC GTG CCC GTG AAG CTG AAG CCC GGC ATG GAC GGC CCC AAG GTG AAG CAG  < 660
P   I   E   T   V   P   V   K   L   K   P   G   M   D   G   P   K   V   K   Q
GGG TAG CTC TGG CAC GGG CAC TTC GAC TTC GGG CCG TAC CTG CCG GGG TTC CAC TTC GTC
            610             620             630             640             650
```

FIG. 6B CONT'D

```
TGG CCC CTG ACC GAG GAG AAG ATC AAG GCC CTG GTG GAG ATC TGC ACC GAG ATG GAG AAG  < 720
W   P   L   T   E   E   K   I   K   A   L   V   E   I   C   T   E   M   E   K
ACC GGG GAC TGG CTC CTC TTC TAG TTC CGG GAC CAC CTC TAG ACG TGG CTC TAC CTC TTC
            670             680             690                 700             710

GAG GGC AAG ATC TCC AAG ATC GGC CCC GAG AAC CCC TAC AAC ACC CCC GTG TTC GCC ATC  < 780
E   G   K   I   S   K   I   G   P   E   N   P   Y   N   T   P   V   F   A   I
CTC CCG TTC TAG AGG TTC TAG CCG GGG CTC TTG GGG ATG TTG TGG GGG CAC AAG CGG TAG
            730             740             750                 760             770

AAG AAG AAG GAC TCC ACC AAG TGG CGC AAA CTG GTG GAC TTC CGC GAG CTG AAC AAG CGC  < 840
K   K   K   D   S   T   K   W   R   K   L   V   D   F   R   E   L   N   K   R
TTC TTC TTC CTG AGG TGG TTC ACC GCG TTT GAC CAC CTG AAG GCG CTC GAC TTG TTC GCG
            790             800             810                 820             830
```

FIG. 6C

```
ACC CAG GAC TTC TGG GAG GTG CAG CTG GGC ATC CCC CAC CCT GCC GGC CTG AAG AAG AAG  < 900
T   Q   D   F   W   E   V   Q   L   G   I   P   H   P   A   G   L   K   K   K
TGG GTC CTG AAG ACC CTC CAC GTC GAC CCG TAG GGG GTG GGA CGG CCG GAC TTC TTC TTC
            850             860             870             880             890

AAG TCC GTG ACC GTG CTG GAC GTG GGC GAC GCC TAC TTC TCC GTG CCC CTG GAC GAG GGC  < 960
K   S   V   T   V   L   D   V   G   D   A   Y   F   S   V   P   L   D   E   G
TTC AGG CAC TGG CAC GAC CTG CAC CCG CTG CGG ATG AAG AGG CAC GGG GAC CTG CTC CCG
            910             920             930             940             950

TTC CGC AAG TAC ACC GCC TTC ACC ATC CCC TCC ATC AAC AAC GAG ACC CCC GGC ATC CGC  < 1020
F   R   K   Y   T   A   F   T   I   P   S   I   N   N   E   T   P   G   I   R
AAG GCG TTC ATG TGG CGG AAG TGG TAG GGG AGG TAG TTG TTG CTC TGG GGG CCG TAG GCG
            970             980             990             1000            1010

TAC CAG TAC AAC GTG CTG CCC CAG GGC TGG AAG GGC TCC CCC GCC ATC TTC CAG TCC TCC  < 1080
Y   Q   Y   N   V   L   P   Q   G   W   K   G   S   P   A   I   F   Q   S   S
ATG GTC ATG TTG CAC GAC GGG GTC CCG ACC TTC CCG AGG GGG CGG TAG AAG GTC AGG AGG
            1030            1040            1050            1060            1070
```

FIG. 6C CONT'D

```
ATG ACC AAG ATC CTG GAG CCC TTC CGC GCC CAG AAC CCC GAG ATC GTG ATC TAC CAG TAC  < 1140
M   T   K   I   L   E   P   F   R   A   Q   N   P   E   I   V   I   Y   Q   Y
TAC TGG TTC TAG GAC CTC GGG AAG GCG CGG GTC TTG GGG CTC TAG CAC TAG ATG GTC ATG
            1090        1100        1110        1120        1130

ATG GAC GAC CTG TAC GTG GGC TCC GAC CTG GAG ATC GGC CAG CAC CGC ATG GAG AAC CGC  < 1200
M   D   D   L   Y   V   G   S   D   L   E   I   G   Q   H   R   M   E   N   R
TAC CTG CTG GAC ATG CAC CCG AGG CTG GAC CTC TAG CCG GTC GTG GCG TAC CTC TTG GCG
            1150        1160        1170        1180        1190

TGG CAG GTG ATG ATC GTG TGG CAG GTG GAC CGC ATG CGC ATC CGC ACC TGG AAG TCC CTG  < 1260
W   Q   V   M   I   V   W   Q   V   D   R   M   R   I   R   T   W   K   S   L
ACC GTC CAC TAC TAG CAC ACC GTC CAC CTG GCG TAC GCG TAG GCG TGG ACC TTC AGG GAC
            1210        1220        1230        1240        1250

GTG AAG CAC CAC CTG ACC GAG GAG GCC GAG CTG GAG CTG GCC GAG AAC CGC GAG ATC CTG  < 1320
V   K   H   H   L   T   E   E   A   E   L   E   L   A   E   N   R   E   I   L
CAC TTC GTG GTG GAC TGG CTC CTC CGG CTC GAC CTC GAC CGG CTC TTG GCG CTC TAG GAC
            1270        1280        1290        1300        1310
```

FIG. 6C CONT'D

```
AAG GAC CCC GTG CAC GGC GTG TAC TAC GAC CCC TCC AAG GAC CTG ATC GCC GAG ATC CAG  < 1380
K   D   P   V   H   G   V   Y   Y   D   P   S   K   D   L   I   A   E   I   Q
TTC CTG GGG CAC GTG CCG CAC ATG ATG CTG GGG AGG TTC CTG GAC TAG CGG CTC TAG GTC
            1330            1340            1350            1360            1370

TAC TGG CAG GCC ACC TGG ATC CCC GAG TGG GAG TTC GTG AAC ACC CCA CCC CTG GTG AAG  < 1440
Y   W   Q   A   T   W   I   P   E   W   E   F   V   N   T   P   P   L   V   K
ATG ACC GTC CGG TGG ACC TAG GGG CTC ACC CTC AAG CAC TTG TGG GGT GGG GAC CAC TTC
            1390            1400            1410            1420            1430

CTG TGG TAC CAG CTG GAG AAG AAC GTG ACC GAG AAC TTC AAC ATG TGG AAG AAC GAC ATG  < 1500
L   W   Y   Q   L   E   K   N   V   T   E   N   F   N   M   W   K   N   D   M
GAC ACC ATG GTC GAC CTC TTC TTG CAC TGG CTC TTG AAG TTG TAC ACC TTC TTG CTG TAC
            1450            1460            1470            1480            1490

GTG GAC CAG ATG CAC GAG GAC ATC ATC TCC CTG TGG GAC CAG TCC CTG AAG CCC TGC GTG  < 1560
V   D   Q   M   H   E   D   I   I   S   L   W   D   Q   S   L   K   P   C   V
CAC CTG GTC TAC GTG CTC CTG TAG TAG AGG GAC ACC CTG GTC AGG GAC TTC GGG ACG CAC
            1510            1520            1530            1540            1550
```

FIG. 6D

```
AAG CTG ACC CCC TGG GTG CCC GCC CAC AAG GGC ATC GGC GGC AAC GAG CAG GTG GAC AAG  < 1620
K   L   T   P   W   V   P   A   H   K   G   I   G   G   N   E   Q   V   D   K
TTC GAC TGG GGG ACC CAC GGG CGG GTG TTC CCG TAG CCG CCG TTG CTC GTC CAC CTG TTC
            1570          1580          1590          1600          1610

CTG GTG TCC CAG GGC ATC CGC AAG GTG CTG TTC CTG GAC GGC ATC GAC AAG GCC CAG GCC  < 1680
L   V   S   Q   G   I   R   K   V   L   F   L   D   G   I   D   K   A   Q   A
GAC CAC AGG GTC CCG TAG GCG TTC CAC GAC AAG GAC CTG CCG TAG CTG TTC CGG GTC CGG
            1630          1640          1650          1660          1670

AAG GAG ATC GTG GCC TCC TGC GAC AAG TGC CAG CTG AAG GGC GAG GCC ATG CAC GGC CAG  < 1740
K   E   I   V   A   S   C   D   K   C   Q   L   K   G   E   A   M   H   G   Q
TTC CTC TAG CAC CGG AGG ACG CTG TTC ACG GTC GAC TTC CCG CTC CGG TAC GTG CCG GTC
            1690          1700          1710          1720          1730

GTG GAC TGC TCC CCC GGC ATC TGG CAG CTG GAC TGC ACC CAC CTG GAG GGC AAG GTG ATC  < 1800
V   D   C   S   P   G   I   W   Q   L   D   C   T   H   L   E   G   K   V   I
CAC CTG ACG AGG GGG CCG TAG ACC GTC GAC CTG ACG TGG GTG GAC CTC CCG TTC CAC TAG
            1750          1760          1770          1780          1790
```

FIG. 6D CONT'D

```
CTG GTG GCC GTG CAC GTG GCC TCC GGC TAC ATC GAG GCC GAA GTG ATT CCC GCC GAG ACC  < 1860
L   V   A   V   H   V   A   S   G   Y   I   E   A   E   V   I   P   A   E   T
GAC CAC CGG CAC GTG CAC CGG AGG CCG ATG TAG CTC CGG CTT CAC TAA GGG CGG CTC TGG
            1810            1820            1830            1840            1850

GGC CAG GAG ACC GCC TAC TTC CTG CTG AAG CTG GCC ATG AAC AAG GAG CTG AAG AAG ATC  < 1920
G   Q   E   T   A   Y   F   L   L   K   L   A   M   N   K   E   L   K   K   I
CCG GTC CTC TGG CGG ATG AAG GAC GAC TTC GAC CGG TAC TTG TTC CTC GAC TTC TTC TAG
            1870            1880            1890            1900            1910

ATC GGC CAG GTG CGC GAC CAG GCC GAG CAC CTG AAG ACC GCC GTG CAG ATG GCC GTG TTC  < 1980
I   G   Q   V   R   D   Q   A   E   H   L   K   T   A   V   Q   M   A   V   F
TAG CCG GTC CAC GCG CTG GTC CGG CTC GTG GAC TTC TGG CGG CAC GTC TAC CGG CAC AAG
            1930            1940            1950            1960            1970
```

FIG. 6D CONT'D

```
ATC CAC AAC TTC AAG CGC AAG GGC GGA ATC GGC GGC TAC TCC GCC GGC GAG CGC ATC TGG  < 2040
I   H   N   F   K   R   K   G   G   I   G   G   Y   S   A   G   E   R   I   W
TAG GTG TTG AAG TTC GCG TTC CCG CCT TAG CCG CCG ATG AGG CGG CCG CTC GCG TAG ACC
            1990            2000            2010             2020            2030

AAG GGC CCC GCC AAG CTG CTG TGG AAG GGC GAG GGC GCC GTG GTG ATC CAG GAC AAC TCC  < 2100
K   G   P   A   K   L   L   W   K   G   E   G   A   V   V   I   Q   D   N   S
TTC CCG GGG CGG TTC GAC GAC ACC TTC CCG CTC CCG CGG CAC CAC TAG GTC CTG TTG AGG
            2050            2060            2070             2080            2090

GAC ATC AAG GTG GTG CCC CGC CGC AAG GCC AAG ATC ATC CGC GAC TAC GGC AAG CAG ATG  < 2160
D   I   K   V   V   P   R   R   K   A   K   I   I   R   D   Y   G   K   Q   M
CTG TAG TTC CAC CAC GGG GCG GCG TTC CGG TTC TAG TAG GCG CTG ATG CCG TTC GTC TAC
            2110            2120            2130             2140            2150
```

FIG. 6E

```
GCC GGT GCC GAC TGC GTG TTC CTG GGC GCT GCC GGC TCC ACC ATG GGC GCC GCC TCC ATG  < 2220
A   G   A   D   C   V   F   L   G   A   A   G   S   T   M   G   A   A   S   M
CGG CCA CGG CTG ACG CAC AAG GAC CCG CGA CGG CCG AGG TGG TAC CCG CGG CGG AGG TAC
            2170          2180          2190          2200          2210

ACC CTG ACC GTG CAG GCC CGC CAG CTG CTG TCC GGC ATC GTG CAG CAG CAG AAC AAC CTG  < 2280
T   L   T   V   Q   A   R   Q   L   L   S   G   I   V   Q   Q   Q   N   N   L
TGG GAC TGG CAC GTC CGG GCG GTC GAC GAC AGG CCG TAG CAC GTC GTC GTC TTG TTG GAC
            2230          2240          2250          2260          2270

CTG CGC GCC ATC GAG GCC CAG CAG CAC CTG CTG CAG CTG ACC GTG TGG GGC ATC AAG CAG  < 2340
L   R   A   I   E   A   Q   Q   H   L   L   Q   L   T   V   W   G   I   K   Q
GAC GCG CGG TAG CTC CGG GTC GTC GTG GAC GAC GTC GAC TGG CAC ACC CCG TAG TTC GTC
            2290          2300          2310          2320          2330

                            >C5 tag
                            |
GCA CCC ACC AAG GCA AAG AGA AGA GTG GTG CAG AGA GAA AAG AGA tag taa  < 2391
A   P   T   K   A   K   R   R   V   V   Q   R   E   K   R   *   *
CGT GGG TGG TTC CGT TTC TCT TCT CAC CAC GTC TCT CTT TTC TCT atc att
            2350          2360          2370          2380          2390

Features :
Kozak    : [1 : 9]
C5 tag   : [2341 : 2385]
```

FIG. 6E CONT'D

MEEKAFSPEVIPMFTALSEGATPQDLNTMLNTVGGHQAAMQMLKDTINEEAAEWDRIYKRWIILGLNKIVRMYSP
VSILDIRQGPKEPFRDYVDRFARNCRAPRKKGCWKCGKEGHQMKDCTERQANFLGKIWPSRWKPKMIGGIGGFIK
VRQYDQILIEICGHKAIGTVLVGPTPVNIIGRNLLTQIGCTLNFPISPIETVPVKLKPGMDGPKVKQWPLTEEKI
KALVEICTEMEKEGKISKIGPENPYNTPVFAIKKKDSTKWRKLVDFRELNKRTQDFWEVQLGIPHPAGLKKKKSV
TVLDVGDAYFSVPLDEGFRKYTAFTIPSINNETPGIRYQYNVLPQGWKGSPAIFQSSMTKILEPFRAQNPEIVIY
QYMDDLYVGSDLEIGQHRMENRWQVMIVWQVDRMRIRTWKSLVKHHLTEEAELELAENREILKDPVHGVYYDPSK
DLIAEIQYWQATWIPEWEFVNTPPLVKLWYQLEKNVTENFNMWKNDMVDQMHEDIISLWDQSLKPCVKLTPWVPA
HKGIGGNEQVDKLVSQGIRKVLFLDGIDKAQAKEIVASCDKCQLKGEAMHGQVDCSPGIWQLDCTHLEGKVILVA
VHVASGYIEAEVIPAETGQETAYFLLKLAMNKELKKIIGQVRDQAEHLKTAVQMAVFIHNFKRKGGIGGYSAGER
IWKGPAKLLWKGEGAVVIQDNSDIKVVPRRKAKIIRDYGKQMAGADCVFLGAAGSTMGAASMTLTVQARQLLSGI
VQQQNNLLRAIEAQQHLLQLTVWGIKQAPTKAKRRVVQREKR*

FIG. 6F ggagccaccATGGAGGAGAAAGCATTCTCACCTGAAGTGATCCCTATGTTCACAGCATTATCTGAGGGAGCTACTCCTCA
AGATCTTAACACAATGCTTAACACAGTCGGAGGACATCAAGCAGCAATGCAAATGTTGAAAGATACAATTAACGAGGAAG
CAGCAGAATGGGATAGAATCTATAAGAGATGGATAATATTAGGATTGAACAAGATTGTTAGAATGTATTCTCCTGTGTCA
ATCCTTGATATAAGACAAGGACCTAAAGAGCCTTTCAGAGATTACGTCGATAGATTTGCAAGAAATTGTAGAGCACCTAG
AAAGAAGGGATGTTGGAAATGTGGGAAAGAAGGACATCAAATGAAAGATTGTACTGAGAGACAAGCTAACTTCTTGGGAA
AGATATGGCCTTCAAGATGGAAACCTAAGATGATAGGAGGAATAGGAGGATTTATTAAAGTCAGACAATATGATCAAATA
TTGATTGAAATATGTGGACATAAAGCTATTGGAACAGTCCTAGTGGGTCCAACACCTGTCAACATCATTGGTAGAAATCT
TCTCACTCAAATCGGATGTACACTCAATTTCCCAATATCACCTATTGAGACCGTGCCTGTCAAATTGAAACCTGGAATGG
ATGGACCTAAAGTCAAACAATGGCCATTAACTGAGGAGAAGATTAAAGCACTGGTAGAAATTTGTACAGAGATGGAGAAA
GAAGGAAAGATTTCCAAGATTGGTCCTGAGAATCCTTATAATACTCCTGTCTTTGCTATTAAGAAGAAGGATAGTACCAA
ATGGAGGAAATTAGTCGATTTCAGAGAACTTAACAAGAGGACTCAAGACTTCTGGGAAGTGCAATTGGGAATCCCACACC
CTGCAGGATTGAAGAAGAAGAAGTCTGTCACTGTCCTAGATGTGGGAGATGCATATTTCAGTGTCCCACTGGATGAAGGT
TTCAGAAAGTATACAGCATTCACAATCCCTTCCATTAATAATGAAACACCTGGAATAAGATATCAATATAATGTCTTACC
TCAAGGGTGGAAAGGATCTCCAGCAATATTCCAATCATCAATGACAAAGATCTTGGAGCCTTTCAGAGCTCAGAATCCAG
AGATAGTTATTTACCAATACATGGATGATTTGTATGTTGGGTCAGATCTCGAGATCGGACAGCACAGGATGGAGAATAGA
TGGCAAGTAATGATTGTCTGGCAAGTCGATAGAATGAGAATAAGAACATGGAAATCCTTGGTGAAACATCACCTTACAGA
GGAGGCAGAACTGGAACTGGCAGAGAATAGGGAAATATTGAAAGATCCAGTGCATGGTGTCTATTACGATCCTTCTAAAG
ATCTGATAGCAGAGATCCAGTACTGGCAAGCAACATGGATTCCTGAGTGGGAATTCGTCAACACACCTCCATTAGTGAAA
CTATGGTACCAATTAGAGAAGAATGTCACCGAGAACTTCAACATGTGGAAGAACGATATGGTAGATCAAATGCACGAAGA
TATCATCTCCTTGTGGGATCAATCACTTAAACCTTGTGTTAAATTGACACCTTGGGTACCTGCTCATAAAGGGATAGGAG
GAAACGAACAAGTGGATAAATTGGTGTCCCAAGGGATCAGGAAAGTCTTGTTCCTAGATGGAATTGATAAAGCTCAAGCA
AAGGAAATTGTCGCAAGCTGTGATAAGTGTCAATTAAAGGGAGAGGCAATGCACGGACAAGTCGATTGTTCACCTGGTAT
TTGGCAACTTGATTGTACACATTTGGAGGGTAAAGTTATTCTAGTAGCAGTACATGTCGCTTCTGGTTATATTGAGGCAG
AAGTGATACCTGCTGAGACAGGACAGGAGACCGCATACTTTCTACTTAAGTTAGCTATGAATAAGGAGCTCAAGAAGATA
ATAGGACAAGTTAGAGATCAAGCAGAGCACCTTAAGACAGCTGTCCAAATGGCAGTGTTTATACACAACTTTAAGAGAAA
GGGTGGAATCGGAGGATATTCCGCAGGAGAGAGAATCTGGAAAGGTCCTGCTAAATTGTTATGGAAAGGAGAAGGAGCAG
TTGTAATACAAGATAATTCTGATATAAAAGTAGTCCCTAGAAGGAAAGCTAAGATTATTAGAGATTATGGAAACAAATG
GCAGGAGCTGATTGTGTGTTTCTAGGAGCAGCAGGATCCACTATGGGAGCTGCATCAATGACACTTACCGTGCAGGCTAG
ACAGCTTCTTTCAGGAATTGTACAGCAACAGAATAATTTGCTAAGAGCAATTGAAGCTCAACAACACTTACTTCAACTTA
CAGTCTGGGGAATCAAGCAAGCACCTACAAAAGCAAAGAGAAGAGTCGTCCAAAGAGAGAAAAGAtagtaa

FIG. 7A

```
      >Kozak
      |
ggagccaccATGGAGGAGAAAGCATTCTCACCTGAAGTGATCCCTATGTTCACAGCATTA  < 60
         M  E  E  K  A  F  S  P  E  V  I  P  M  F  T  A  L
cctcggtggTACCTCCTCTTTCGTAAGAGTGGACTTCACTAGGGATACAAGTGTCGTAAT
         10        20        30        40        50

TCTGAGGGAGCTACTCCTCAAGATCTTAACACAATGCTTAACACAGTCGGAGGACATCAA  < 120
S  E  G  A  T  P  Q  D  L  N  T  M  L  N  T  V  G  G  H  Q
AGACTCCCTCGATGAGGAGTTCTAGAATTGTGTTACGAATTGTGTCAGCCTCCTGTAGTT
         70        80        90        100       110

GCAGCAATGCAAATGTTGAAAGATACAATTAACGAGGAAGCAGCAGAATGGGATAGAATC  < 180
A  A  M  Q  M  L  K  D  T  I  N  E  E  A  A  E  W  D  R  I
CGTCGTTACGTTTACAACTTTCTATGTTAATTGCTCCTTCGTCGTCTTACCCTATCTTAG
         130       140       150       160       170

TATAAGAGATGGATAATATTAGGATTGAACAAGATTGTTAGAATGTATTCTCCTGTGTCA  < 240
Y  K  R  W  I  I  L  G  L  N  K  I  V  R  M  Y  S  P  V  S
ATATTCTCTACCTATTATAATCCTAACTTGTTCTAACAATCTTACATAAGAGGACACAGT
         190       200       210       220       230
```

FIG. 7B

```
ATCCTTGATATAAGACAAGGACCTAAAGAGCCTTTCAGAGATTACGTCGATAGATTTGCA  < 300
I  L  D  I  R  Q  G  P  K  E  P  F  R  D  Y  V  D  R  F  A
TAGGAACTATATTCTGTTCCTGGATTTCTCGGAAAGTCTCTAATGCAGCTATCTAAACGT
         250       260       270       280       290

AGAAATTGTAGAGCACCTAGAAAGAAGGGATGTTGGAAATGTGGGAAAGAAGGACATCAA  < 360
R  N  C  R  A  P  R  K  K  G  C  W  K  C  G  K  E  G  H  Q
TCTTTAACATCTCGTGGATCTTTCTTCCCTACAACCTTTACACCCTTTCTTCCTGTAGTT
         310       320       330       340       350

ATGAAAGATTGTACTGAGAGACAAGCTAACTTCTTGGGAAAGATATGGCCTTCAAGATGG  < 420
M  K  D  C  T  E  R  Q  A  N  F  L  G  K  I  W  P  S  R  W
TACTTTCTAACATGACTCTCTGTTCGATTGAAGAACCCTTTCTATACCGGAAGTTCTACC
         370       380       390       400       410

AAACCTAAGATGATAGGAGGAATAGGAGGATTTATTAAAGTCAGACAATATGATCAAATA  < 480
K  P  K  M  I  G  G  I  G  G  F  I  K  V  R  Q  Y  D  Q  I
TTTGGATTCTACTATCCTCCTTATCCTCCTAAATAATTTCAGTCTGTTATACTAGTTTAT
         430       440       450       460       470
```

FIG. 7B CONT'D

```
TTGATTGAAATATGTGGACATAAAGCTATTGGAACAGTCCTAGTGGGTCCAACACCTGTC  < 540
L  I  E  I  C  G  H  K  A  I  G  T  V  L  V  G  P  T  P  V
AACTAACTTTATACACCTGTATTTCGATAACCTTGTCAGGATCACCCAGGTTGTGGACAG
          490       500       510       520       530

AACATCATTGGTAGAAATCTTCTCACTCAAATCGGATGTACACTCAATTTCCCAATATCA  < 600
N  I  I  G  R  N  L  L  T  Q  I  G  C  T  L  N  F  P  I  S
TTGTAGTAACCATCTTTAGAAGAGTGAGTTTAGCCTACATGTGAGTTAAAGGGTTATAGT
          550       560       570       580       590
```

FIG. 7B CONT'D

```
CCTATTGAGACCGTGCCTGTCAAATTGAAACCTGGAATGGATGGACCTAAAGTCAAACAA  < 660
P  I  E  T  V  P  V  K  L  K  P  G  M  D  G  P  K  V  K  Q
GGATAACTCTGGCACGGACAGTTTAACTTTGGACCTTACCTACCTGGATTTCAGTTTGTT
         610       620       630       640       650

TGGCCATTAACTGAGGAGAAGATTAAAGCACTGGTAGAAATTTGTACAGAGATGGAGAAA  < 720
W  P  L  T  E  E  K  I  K  A  L  V  E  I  C  T  E  M  E  K
ACCGGTAATTGACTCCTCTTCTAATTTCGTGACCATCTTTAAACATGTCTCTACCTCTTT
         670       680       690       700       710

GAAGGAAAGATTTCCAAGATTGGTCCTGAGAATCCTTATAATACTCCTGTCTTTGCTATT  < 780
E  G  K  I  S  K  I  G  P  E  N  P  Y  N  T  P  V  F  A  I
CTTCCTTTCTAAAGGTTCTAACCAGGACTCTTAGGAATATTATGAGGACAGAAACGATAA
         730       740       750       760       770

AAGAAGAAGGATAGTACCAAATGGAGGAAATTAGTCGATTTCAGAGAACTTAACAAGAGG  < 840
K  K  K  D  S  T  K  W  R  K  L  V  D  F  R  E  L  N  K  R
TTCTTCTTCCTATCATGGTTTACCTCCTTTAATCAGCTAAAGTCTCTTGAATTGTTCTCC
         790       800       810       820       830
```

FIG. 7C

```
ACTCAAGACTTCTGGGAAGTGCAATTGGGAATCCCACACCCTGCAGGATTGAAGAAGAAG  < 900
T  Q  D  F  W  E  V  Q  L  G  I  P  H  P  A  G  L  K  K  K
TGAGTTCTGAAGACCCTTCACGTTAACCCTTAGGGTGTGGGACGTCCTAACTTCTTCTTC
         850       860       870       880       890

AAGTCTGTCACTGTCCTAGATGTGGGAGATGCATATTTCAGTGTCCCACTGGATGAAGGT  < 960
K  S  V  T  V  L  D  V  G  D  A  Y  F  S  V  P  L  D  E  G
TTCAGACAGTGACAGGATCTACACCCTCTACGTATAAAGTCACAGGGTGACCTACTTCCA
         910       920       930       940       950

TTCAGAAAGTATACAGCATTCACAATCCCTTCCATTAATAATGAAACACCTGGAATAAGA  < 1020
F  R  K  Y  T  A  F  T  I  P  S  I  N  N  E  T  P  G  I  R
AAGTCTTTCATATGTCGTAAGTGTTAGGGAAGGTAATTATTACTTTGTGGACCTTATTCT
         970       980       990       1000      1010

TATCAATATAATGTCTTACCTCAAGGGTGGAAAGGATCTCCAGCAATATTCCAATCATCA  < 1080
Y  Q  Y  N  V  L  P  Q  G  W  K  G  S  P  A  I  F  Q  S  S
ATAGTTATATTACAGAATGGAGTTCCCACCTTTCCTAGAGGTCGTTATAAGGTTAGTAGT
         1030      1040      1050      1060      1070
```

FIG. 7C CONT'D

```
ATGACAAAGATCTTGGAGCCTTTCAGAGCTCAGAATCCAGAGATAGTTATTTACCAATAC  < 1140
M  T  K  I  L  E  P  F  R  A  Q  N  P  E  I  V  I  Y  Q  Y
TACTGTTTCTAGAACCTCGGAAAGTCTCGAGTCTTAGGTCTCTATCAATAAATGGTTATG
            1090      1100      1110      1120      1130

ATGGATGATTTGTATGTTGGGTCAGATCTCGAGATCGGACAGCACAGGATGGAGAATAGA  < 1200
M  D  D  L  Y  V  G  S  D  L  E  I  G  Q  H  R  M  E  N  R
TACCTACTAAACATACAACCCAGTCTAGAGCTCTAGCCTGTCGTGTCCTACCTCTTATCT
            1150      1160      1170      1180      1190
```

FIG. 7C CONT'D

```
TGGCAAGTAATGATTGTCTGGCAAGTCGATAGAATGAGAATAAGAACATGGAAATCCTTG  < 1260
W  Q  V  M  I  V  W  Q  V  D  R  M  R  I  R  T  W  K  S  L
ACCGTTCATTACTAACAGACCGTTCAGCTATCTTACTCTTATTCTTGTACCTTTAGGAAC
         1210      1220      1230      1240      1250

GTGAAACATCACCTTACAGAGGAGGCAGAACTGGAACTGGCAGAGAATAGGGAAATATTG  < 1320
V  K  H  H  L  T  E  E  A  E  L  E  L  A  E  N  R  E  I  L
CACTTTGTAGTGGAATGTCTCCTCCGTCTTGACCTTGACCGTCTCTTATCCCTTTATAAC
         1270      1280      1290      1300      1310

AAAGATCCAGTGCATGGTGTCTATTACGATCCTTCTAAAGATCTGATAGCAGAGATCCAG  < 1380
K  D  P  V  H  G  V  Y  Y  D  P  S  K  D  L  I  A  E  I  Q
TTTCTAGGTCACGTACCACAGATAATGCTAGGAAGATTTCTAGACTATCGTCTCTAGGTC
         1330      1340      1350      1360      1370
```

FIG. 7D

```
TACTGGCAAGCAACATGGATTCCTGAGTGGGAATTCGTCAACACACCTCCATTAGTGAAA  < 1440
Y  W  Q  A  T  W  I  P  E  W  E  F  V  N  T  P  P  L  V  K
ATGACCGTTCGTTGTACCTAAGGACTCACCCTTAAGCAGTTGTGTGGAGGTAATCACTTT
          1390      1400      1410      1420      1430

CTATGGTACCAATTAGAGAAGAATGTCACCGAGAACTTCAACATGTGGAAGAACGATATG  < 1500
L  W  Y  Q  L  E  K  N  V  T  E  N  F  N  M  W  K  N  D  M
GATACCATGGTTAATCTCTTCTTACAGTGGCTCTTGAAGTTGTACACCTTCTTGCTATAC
          1450      1460      1470      1480      1490

GTAGATCAAATGCACGAAGATATCATCTCCTTGTGGGATCAATCACTTAAACCTTGTGTT  < 1560
V  D  Q  M  H  E  D  I  I  S  L  W  D  Q  S  L  K  P  C  V
CATCTAGTTTACGTGCTTCTATAGTAGAGGAACACCCTAGTTAGTGAATTTGGAACACAA
          1510      1520      1530      1540      1550
```

FIG.7D CONT'D

```
AAATTGACACCTTGGGTACCTGCTCATAAAGGGATAGGAGGAAACGAACAAGTGGATAAA  < 1620
K  L  T  P  W  V  P  A  H  K  G  I  G  G  N  E  Q  V  D  K
TTTAACTGTGGAACCCATGGACGAGTATTTCCCTATCCTCCTTTGCTTGTTCACCTATTT
          1570      1580      1590      1600      1610

TTGGTGTCCCAAGGGATCAGGAAAGTCTTGTTCCTAGATGGAATTGATAAAGCTCAAGCA  < 1680
L  V  S  Q  G  I  R  K  V  L  F  L  D  G  I  D  K  A  Q  A
AACCACAGGGTTCCCTAGTCCTTTCAGAACAAGGATCTACCTTAACTATTTCGAGTTCGT
          1630      1640      1650      1660      1670

AAGGAAATTGTCGCAAGCTGTGATAAGTGTCAATTAAAGGGAGAGGCAATGCACGGACAA  < 1740
K  E  I  V  A  S  C  D  K  C  Q  L  K  G  E  A  M  H  G  Q
TTCCTTTAACAGCGTTCGACACTATTCACAGTTAATTTCCCTCTCCGTTACGTGCCTGTT
          1690      1700      1710      1720      1730

GTCGATTGTTCACCTGGTATTTGGCAACTTGATTGTACACATTTGGAGGGTAAAGTTATT  < 1800
V  D  C  S  P  G  I  W  Q  L  D  C  T  H  L  E  G  K  V  I
CAGCTAACAAGTGGACCATAAACCGTTGAACTAACATGTGTAAACCTCCCATTTCAATAA
          1750      1760      1770      1780      1790
```

FIG.7D CONT'D

```
CTAGTAGCAGTACATGTCGCTTCTGGTTATATTGAGGCAGAAGTGATACCTGCTGAGACA  < 1860
L  V  A  V  H  V  A  S  G  Y  I  E  A  E  V  I  P  A  E  T
GATCATCGTCATGTACAGCGAAGACCAATATAACTCCGTCTTCACTATGGACGACTCTGT
         1810      1820      1830      1840      1850

GGACAGGAGACCGCATACTTTCTACTTAAGTTAGCTATGAATAAGGAGCTCAAGAAGATA  < 1920
G  Q  E  T  A  Y  F  L  L  K  L  A  M  N  K  E  L  K  K  I
CCTGTCCTCTGGCGTATGAAAGATGAATTCAATCGATACTTATTCCTCGAGTTCTTCTAT
         1870      1880      1890      1900      1910

ATAGGACAAGTTAGAGATCAAGCAGAGCACCTTAAGACAGCTGTCCAAATGGCAGTGTTT  < 1980
I  G  Q  V  R  D  Q  A  E  H  L  K  T  A  V  Q  M  A  V  F
TATCCTGTTCAATCTCTAGTTCGTCTCGTGGAATTCTGTCGACAGGTTTACCGTCACAAA
         1930      1940      1950      1960      1970
```

FIG.7E

```
ATACACAACTTTAAGAGAAAGGGTGGAATCGGAGGATATTCCGCAGGAGAGAGAATCTGG  < 2040
I  H  N  F  K  R  K  G  G  I  G  G  Y  S  A  G  E  R  I  W
TATGTGTTGAAATTCTCTTTCCCACCTTAGCCTCCTATAAGGCGTCCTCTCTCTTAGACC
         1990      2000      2010      2020      2030

AAAGGTCCTGCTAAATTGTTATGGAAAGGAGAAGGAGCAGTTGTAATACAAGATAATTCT  < 2100
K  G  P  A  K  L  L  W  K  G  E  G  A  V  V  I  Q  D  N  S
TTTCCAGGACGATTTAACAATACCTTTCCTCTTCCTCGTCAACATTATGTTCTATTAAGA
         2050      2060      2070      2080      2090

GATATAAAAGTAGTCCCTAGAAGGAAAGCTAAGATTATTAGAGATTATGGGAAACAAATG  < 2160
D  I  K  V  V  P  R  R  K  A  K  I  I  R  D  Y  G  K  Q  M
CTATATTTTCATCAGGGATCTTCCTTTCGATTCTAATAATCTCTAATACCCTTTGTTTAC
         2110      2120      2130      2140      2150
```

FIG. 7E CONT'D

```
GCAGGAGCTGATTGTGTGTTTCTAGGAGCAGCAGGATCCACTATGGGAGCTGCATCAATG  < 2220
A  G  A  D  C  V  F  L  G  A  A  G  S  T  M  G  A  A  S  M
CGTCCTCGACTAACACACAAAGATCCTCGTCGTCCTAGGTGATACCCTCGACGTAGTTAC
         2170      2180      2190      2200      2210

ACACTTACCGTGCAGGCTAGACAGCTTCTTTCAGGAATTGTACAGCAACAGAATAATTTG  < 2280
T  L  T  V  Q  A  R  Q  L  L  S  G  I  V  Q  Q  Q  N  N  L
TGTGAATGGCACGTCCGATCTGTCGAAGAAAGTCCTTAACATGTCGTTGTCTTATTAAAC
         2230      2240      2250      2260      2270

CTAAGAGCAATTGAAGCTCAACAACACTTACTTCAACTTACAGTCTGGGGAATCAAGCAA  < 2340
L  R  A  I  E  A  Q  Q  H  L  L  Q  L  T  V  W  G  I  K  Q
GATTCTCGTTAACTTCGAGTTGTTGTGAATGAAGTTGAATGTCAGACCCCTTAGTTCGTT
         2290      2300      2310      2320      2330
```

FIG. 7E CONT'D

```
                              >C5 tag
                              |
GCACCTACAAAAGCAAAGAGAAGAGTCGTCCAAAGAGAGAAAAGAtagtaa  < 2391
A   P   T   K   A   K   R   R   V   V   Q   R   E   K   R   *   *
CGTGGATGTTTTCGTTTCTCTTCTCAGCAGGTTTCTCTCTTTTCTatcatt
            2350       2360       2370       2380       2390
```

```
Features :
Kozak    : [1 : 9]
C5 tag   : [2341 : 2385]
```

FIG. 7F

EEKAFSPEVIPMFTALSEGATPQDLNTMLNTVGGHQAAMQ
MLKDTINEEAAEWDRIYKRWIILGLNKIVRMYSPVSILDI
RQGPKEPFRDYVDRFARNCRAPRKKGCWKCGKEGHQMKDC
TERQANFLGKIWPSRWKPKMIGGIGGFIKVRQYDQILIEI
CGHKAIGTVLVGPTPVNIIGRNLLTQIGCTLNFPISPIET
VPVKLKPGMDGPKVKQWPLTEEKIKALVEICTEMEKEGKI
SKIGPENPYNTPVFAIKKKDSTKWRKLVDFRELNKRTQDF
WEVQLGIPHPAGLKKKKSVTVLDVGDAYFSVPLDEGFRKY
TAFTIPSINNETPGIRYQYNVLPQGWKGSPAIFQSSMTKI
LEPFRAQNPEIVIYQYMDDLYVGSDLEIGQHRMENRWQVM
IVWQVDRMRIRTWKSLVKHHLTEEAELELAENREILKDPV
HGVYYDPSKDLIAEIQYWQATWIPEWEFVNTPPLVKLWYQ
LEKNVTENFNMWKNDMVDQMHEDIISLWDQSLKPCVKLTP
WVPAHKGIGGNEQVDKLVSQGIRKVLFLDGIDKAQAKEIV
ASCDKCQLKGEAMHGQVDCSPGIWQLDCTHLEGKVILVAV
HVASGYIEAEVIPAETGQETAYFLLKLAMNKELKKIIGQV
RDQAEHLKTAVQMAVFIHNFKRKGGIGGYSAGERIWKGPA
KLLWKGEGAVVIQDNSDIKVVPRRKAKIIRDYGKQMAGAD
CVFLGAAGSTMGAASMTLTVQARQLLSGIVQQQNNLLRAI
EAQQHLLQLTVWGIKQAPTKAKRRVVQREKR*

FIG. 7G

The nucleotide sequence of SeV(NP)

```
ACCAAACAAGAGAAAAAACATGTATGGGATATGTAATGAAGTTATACAGGATTTTAGGGT  60
CAAAGTATCCACCCTGAGGAGCAGGTTCCAGACCCTTTGCTTTGCTGCCAAAGTTCAC▓ 120
▓▓AGATCTTCACGATGGCCGGGTTGTTGAGCACCTTCGATACATTTAGCTCTAGGA  180
NotI          -> NP
GGAGCGAAAGTATTAATAAGTCGGGAGGAGGTGCTGTTATCCCCGGCCAGAGGAGCACAG  240
TCTCAGTGTTCGTACTAGGCCCAAGTGTGACTGATGATGCAGACAAGTTATTCATTGCAA  300
CTACCTTCCTAGCTCACTCATTGGACACAGATAAGCAGCACTCTCAGAGAGGGGGGTTCC  360
TCGTCTCTCTGCTTGCCATGGCTTACAGTAGTCCAGAATTGTACTTGACAACAAACGGAG  420
TAAACGCCGATGTCAAATATGTGATCTACAACATAGAGAAAGACCCTAAGAGGACGAAGA  480
CAGACGGATTCATTGTGAAGACGAGAGATATGGAATATGAGAGGACCACAGAATGGCTGT  540
TTGGACCTATGGTCAACAAGAGCCCACTCTTCCAGGGTCAACGGGATGCTGCAGACCCTG  600
ACACACTCCTTCAAATCTATGGGTATCCTGCATGCCTAGGAGCAATAATTGTCCAAGTCT  660
GGATTGTGCTGGTGAAGGCCATCACAAGCAGCGCCGGCTTAAGGAAAGGGTTCTTCAACA  720
GGTTAGAGGCGTTCAGACAAGACGGCACCGTGAAAGGTGCCTTAGTTTTCACTGGGGAGA  780
CAGTTGAGGGGATAGGCTCGGTTATGAGATCTCAGCAAAGCCTTGTATCTCTCATGGTTG  840
AGACCCTTGTGACTATGAATACTGCAAGATCTGATCTCACCACATTAGAGAAGAACATCC  900
AGATCGTTGGGAACTACATCCGAGATGCAGGGCTGGCTTCCTTCATGAACACTATTAAAT  960
ATGGGGTGGAAACAAAGATGGCAGCTCTAACGTTGTCAAACCTGAGGCCCGATATTAATA 1020
AGCTTAGAAGCCTCATAGACACCTACCTGTCAAAAGGCCCCAGAGCTCCCTTTATCTGTA 1080
TCCTCAAGGACCCTGTTCATGGTGAATTTGCTCCAGGCAATTATCCTGCACTATGGAGTT 1140
ACGCCATGGGAGTCGCCGTCGTACAGAACAAGGCAATGCAGCAGTACGTCACAGGGAGGA 1200
CATACCTTGATATGGAAATGTTCTTACTAGGACAAGCCGTGGCAAAGGATGCTGAATCGA 1260
AGATCAGCAGTGCCTTGGAAGATGAGTTAGGAGTGACGGATACAGCCAAGGGGAGGCTCA 1320
GACATCATCTGGCAAACTTGTCCGGTGGGGATGGTGCTTACCACAAACCAACAGGCGGTG 1380
GTGCAATTGAGGTAGCTCTAGACAATGCCGACATCGACCTAGAAACAAAAGCCCATGCGG 1440
ACCAGGACGCTAGGGGTTGGGGTGGAGATAGTGGTGAAAGATGGGCACGTCAGGTGAGTG 1500
GTGGCCACTTTGTCACACTACATGGGGCTGAACGGTTAGAGGAGGAAACCAATGATGAGG 1560
ATGTATCAGACATAGAGAGAAGAATAGCCATGAGACTCGCAGAGAGACGGCAAGAGGATT 1620
CTGCAACCCATGGAGATGAAGGCCGCAATAACGGTGTCGATCATGACGAAGATGACGATG 1680
CCGCAGCAGTAGCTGGGATAGGAGGAATCTAGGATCATACGAGGCTTCAAGGTACTTGAT 1740
CCGTAGTAAGAAAAACTTAGGGTGAAAGTTCATCCACCGATCGGCTCAGGCAAGGCCACA 1800
CCCAACCCCACCGACCACACCCAGCAGTCGAGACAGCCACGGCTTCGGCTACACTTACCG 1860
```

FIG. 8A

```
CATGGATCAAGATGCCTTCATTCTTAAAGAAGATTCTGAAGTTGAGAGGGAGGCGCCAGG 1920
 -> P
AGGACGAGAGTCGCTCTCGGATGTTATCGGATTCCTCGATGCTGTCCTGTCGAGTGAACC 1980

AACTGACATCGGAGGGGACAGAAGCTGGCTCCACAACACCATCAACACTCCCCAAGGACC 2040

AGGCTCTGCTCATAGAGCCAAAAGTGAGGGCGAAGGAGAAGTCTCAACACCGTCGACCCA 2100

AGATAATCGATCAGGTGAGGAGAGTAGAGTCTCTGGGAGAACAAGCAAGCCAGAGGCAGA 2160

AGCACATGCTGGAAACCTTGATAAACAAAATATACACCGGGCCTTTGGGGGAAGAACTGG 2220

TACAAACTCTGTATCTCAGGATCTGGGCGATGGAGGAGACTCCGGAATCCTTGAAAATCC 2280

TCCAAATGAGAGAGGATATCCGAGATCAGGTATTGAAGATGAAAACAGAGAGATGGCTGC 2340

GCACCCTGATAAGAGGGGAGAAGACCAAGCTGAAGGACTTCCAGAAGAGGTACGAGGAAG 2400

TACATCCCTACCTGATGAAGGAGAAGGTGGAGCAAGTAATAATGGAAGAAGCATGGAGCC 2460

TGGCAGCTCACATAGTGCAAGAGTAACTGGGGTCCTGGTGATTCCTAGCCCCGAACTTGA 2520

AGAGGCTGTGCTACGGAGGAACAAAAGAAGACCTACCAACAGTGGGTCCAAACCTCTTAC 2580

TCCAGCAACCGTGCCTGGCACCCGGTCCCCACCGCTGAATCGTTACAACAGCACAGGGTC 2640

ACCACCAGGAAAACCCCCATCTACACAGGATGAGCACATCAACTCTGGGGACACCCCCGC 2700

CGTCAGGGTCAAAGACCGGAAACCACCAATAGGGACCCGCTCTGTCTCAGATTGTCCAGC 2760

CAACGGCCGCCCAATCCACCCGGGTCTAGAGACCGACTCAACAAAAAGGGCATAGGAGA 2820

GAACACATCATCTATGAAAGAGATGGCTACATTGTTGACGAGTCTTGGTGTAATCCAGTC 2880

TGCTCAAGAATTCGAATCATCCCGAGACGCGAGTTATGTGTTTGCAAGACGTGCCCTAAA 2940

GTCTGCAAACTATGCAGAGATGACATTCAATGTATGCGGCCTGATCCTTTCTGCCGAGAA 3000

ATCTTCCGCTCGTAAGGTAGATGAGAACAAACAACTGCTCAAACAGATCCAAGAGAGCGT 3060

GGAATCATTCCGGGATATTTACAAGAGATTCTCTGAGTATCAGAAAGAACAGAACTCATT 3120

GCTGATGTCCAACCTATCTACACTTCATATCATCACAGATAGAGGTGGCAAGACTGACAA 3180

CACAGACTCCCTTACAAGGTCCCCCTCCGTTTTTGCAAAATCAAAAGAGAACAAGACTAA 3240

GGCTACCAGGTTTGACCCATCTATGGAGACCCTAGAAGATATGAAGTACAAACCGGACCT 3300

AATCCGAGAGGATGAATTTAGAGATGAGATCCGCAACCCGGTGTACCAAGAGAGGGACAC 3360

AGAACCCAGGGCCTCAAACGCATCACGTCTCCTCCCCTCCAAAGAGAAGCCCACAATGCA 3420

CTCTCTCAGGCTCGTCATAGAGAGCAGTCCCCTAAGCAGAGCTGAGAAAGTAGCATATGT 3480

GAAATCATTATCCAAGTGCAAGACAGACCAAGAGGTTAAGGCAGTCATGGAACTCGTAGA 3540

AGAGGACATAGAGTCACTGACCAACTAGATCCCGGGTGAGGCATCCTACCATCCTCAGTC 3600

ATAGAGAGATCCAATCTACCATCAGCATCAGCCAGTAAAGATTAAGAAAAACTTAGGGTG 3660

AAAGAAATTTCACCTAACACGGCGCAATGGCAGATATCTATAGATTCCCTAAGTTCTCAT 3720
                                   -> M
```

FIG. 8B

ATGAGGATAACGGTACTGTGGAGCCCCTGCCTCTGAGAACTGGTCCGGATAAGAAAGCCA 3780

TCCCCCACATCAGGATTGTCAAGGTAGGAGACCCTCCTAAACATGGAGTGAGATACCTAG 3840

ATTTATTGCTCTTGGGTTTCTTTGAGACACCGAAACAAACAACCAATCTAGGGAGCGTAT 3900

CTGACTTGACAGAGCCGACCAGCTACTCAATATGCGGCTCCGGGTCGTTACCCATAGGTG 3960

TGGCCAAATACTACGGGACTGATCAGGAACTCTTAAAGGCCTGCACCGATCTCAGAATTA 4020

CGGTGAGGAGGACTGTTCGAGCAGGAGAGATGATCGTATACATGGTGGATTCGATTGGTG 4080

CTCCACTCCTACCATGGTCAGGCAGGCTGAGACAGGGAATGATATTTAATGCAAACAAGG 4140

TCGCACTAGCTCCCCAATGCCTCCCTGTGGACAAGGACATAAGACTCAGAGTGGTGTTTG 4200

TCAATGGGACATCTCTAGGGGCAATCACCATAGCCAAGATCCCAAAGACCCTTGCAGACC 4260

TTGCATTGCCCAACTCTATATCTGTTAATTTACTGGTGACACTCAAGACCGGGATCTCCA 4320

CAGAACAAAAGGGGGTACTCCCAGTACTTGATGATCAAGGGGAGAAAAAGCTCAATTTTA 4380

TGGTGCACCTCGGGTTGATCAGGAGAAAGGTCGGGAAGATATACTCTGTTGAGTACTGCA 4440

AGAGCAAGATTGAGAGAATGCGGCTGATTTTCTCACTTGGGTTAATCGGCGGTATAAGCT 4500

TCCATGTTCAGGTTAATGGGACACTATCTAAGACATTCATGAGTCAGCTCGCATGGAAGA 4560

GGGCAGTCTGCTTCCCATTAATGGATGTGAATCCCCATATGAACATGGTGATTTGGGCGG 4620

CATCTGTAGAAATCACAGGCGTCGATGCGGTGTTCCAACCGGCCATCCCTCGTGATTTCC 4680

GCTACTACCCTAATGTTGTGGCTAAGAACATCGGAAGGATCAGAAAGCTGTAAATGTGCA 4740

CCCATCAGAGACCTGCGACAATGCCCCAAGCAGACACCACCTGGCAGTCGGAGCCACCGG 4800

GTCACTCCTTGTCTTAAATAAGAAAAACTTAGGGATAAAGTCCCTTGTGAGTGCTTGGTT 4860

GCAAAACTCTCCCCTTGGGAAACATGACAGCATATATCCAGAGATCACAGTGCATCTCAA 4920

-> F

CATCACTACTGGTTGTTCTCACCACATTGGTCTCGTGTCAGATTCCCAGGGATAGGCTCT 4980

CTAACATAGGGGTCATAGTCGATGAAGGGAAATCACTGAAGATAGCTGGATCCCACGAAT 5040

CGAGGTACATAGTACTGAGTCTAGTTCCGGGGGTAGACTTTGAGAATGGGTGCGGAACAG 5100

CCCAGGTTATCCAGTACAAGAGCCTACTGAACAGGCTGTTAATCCCATTGAGGGATGCCT 5160

TAGATCTTCAGGAGGCTCTGATAACTGTCACCAATGATACGACACAAAATGCCGGTGCTC 5220

CCCAGTCGAGATTCTTCGGTGCTGTGATTGGTACTATCGCACTTGGAGTGGCGACATCAG 5280

CACAAATCACCGCAGGGATTGCACTAGCCGAAGCGAGGGAGGCCAAAAGAGACATAGCGC 5340

TCATCAAAGAATCGATGACAAAAACACACAAGTCTATAGAACTGCTGCAAAACGCTGTGG 5400

GGGAACAAATTCTTGCTCTAAAGACACTCCAGGATTTCGTGAATGATGAGATCAAACCCG 5460

CAATAAGCGAATTAGGCTGTGAGACTGCTGCCTTAAGACTGGGTATAAAATTGACACAGC 5520

ATTACTCCGAGCTGTTAACTGCGTTCGGCTCGAATTTCGGAACCATCGGAGAGAAGAGCC 5580

FIG. 8C

TCACGCTGCAGGCGCTGTCTTCACTTTACTCTGCTAACATTACTGAGATTATGACCACAA 5640

TCAGGACAGGGCAGTCTAACATCTATGATGTCATTTATACAGAACAGATCAAAGGAACGG 5700

TGATAGATGTGGATCTAGAGAGATACATGGTCACCCTGTCTGTGAAGATCCCTATTCTTT 5760

CTGAAGTCCCAGGTGTGCTCATACACAAGGCATCATCTATTTCTTACAACATAGACGGGG 5820

AGGAATGGTATGTGACTGTCCCAGCCATATACTCAGTCGTGCTTCTTTCTTAGGGGGTG 5880

CAGACATAACCGATTGTGTTGAGTCCAGATTGACCTATATATGCCCCAGGGATCCCGCAC 5940

AACTGATACCTGACAGCCAGCAAAAGTGTATCCTGGGGGACACAACAAGGTGTCCTGTCA 6000

CAAAAGTTGTGGACAGCCTTATCCCCAAGTTTGCTTTTGTGAATGGGGGCGTTGTTGCTA 6060

ACTGCATAGCATCCACATGTACCTGCGGGACAGGCCGAAGACCAATCAGTCAGGATCGCT 6120

CTAAAGGTGTAGTATTCCTAACCCATGACAACTGTGGTCTTATAGGTGTCAATGGGGTAG 6180

AATTGTATGCTAACCGGAGAGGGCACGATGCCACTTGGGGGGTCCAGAACTTGACAGTCG 6240

GTCCTGCAATTGCTATCAGACCCGTTGATATTTCTCTCAACCTTGCTGATGCTACGAATT 6300

TCTTGCAAGACTCTAAGGCTGAGCTTGAGAAAGCACGGAAAATCCTCTCGGAGGTAGGTA 6360

GATGGTACAACTCAAGAGAGACTGTGATTACGATCATAGTAGTTATGGTCGTAATATTGG 6420

TGGTCATTATAGTGATCATCATCGTGCTTTATAGACTCAGAAGGTCAATGCTAATGGGTA 6480

ATCCAGATGACCGTATACCGAGGGACACATACACATTAGAGCCGAAGATCAGACATATGT 6540

ACACAAACGGTGGGTTTGATGCAATGGCTGAGAAAAGATGATCACGACCATTATCAGATG 6600

TCTTGTAAAGCAGGCATAGTATCCGTTGAGATCTGTATATAATAAGAAAAACTTAGGGTG 6660

AAAGTGAGGTCGCGCGGTACTTTAGCTTTCACCTCAAACAAGCACAGATCATGGATGGTG 6720

-> HN

ATAGGGGCAAACGTGACTCGTACTGGTCTACTTCTCCTAGTGGTAGCACCACAAAACCAG 6780

CATCAGGTTGGGAGAGGTCAAGTAAAGCCGACACATGGTTGCTGATTCTCTCATTCACCC 6840

AGTGGGCTTTGTCAATTGCCACAGTGATCATCTGTATCATAATTTCTGCTAGACAAGGGT 6900

ATAGTATGAAAGAGTACTCAATGACTGTAGAGGCATTGAACATGAGCAGCAGGGAGGTGA 6960

AAGAGTCACTTACCAGTCTAATAAGGCAAGAGGTTATAGCAAGGGCTGTCAACATTCAGA 7020

GCTCTGTGCAAACCGGAATCCCAGTCTTGTTGAACAAAAACAGCAGGGATGTCATCCAGA 7080

TGATTGATAAGTCGTGCAGCAGACAAGAGCTCACTCAGCACTGTGAGAGTACGATCGCAG 7140

TCCACCATGCCGATGGAATTGCCCCACTTGAGCCACATAGTTTCTGGAGATGCCCTGTCG 7200

GAGAACCGTATCTTAGCTCAGATCCTGAAATCTCATTGCTGCCTGGTCCGAGCTTGTTAT 7260

CTGGTTCTACAACGATCTCTGGATGTGTTAGGCTCCCTTCACTCTCAATTGGCGAGGCAA 7320

TCTATGCCTATTCATCAAATCTCATTACACAAGGTTGTGCTGACATAGGGAAATCATATC 7380

AGGTCCTGCAGCTAGGGTACATATCACTCAATTCAGATATGTTCCCTGATCTTAACCCCG 7440

FIG. 8D

TAGTGTCCCACACTTATGACATCAACGACAATCGGAAATCATGCTCTGTGGTGGCAACCG 7500

GGACTAGGGGTTATCAGCTTTGCTCCATGCCGACTGTAGACGAAAGAACCGACTACTCTA 7560

GTGATGGTATTGAGGATCTGGTCCTTGATGTCCTGGATCTCAAAGGGAGAACTAAGTCTC 7620

ACCGGTATCGCAACAGCGAGGTAGATCTTGATCACCCGTTCTCTGCACTATACCCCAGTG 7680

TAGGCAACGGCATTGCAACAGAAGGCTCATTGATATTTCTTGGGTATGGTGGACTAACCA 7740

CCCCTCTGCAGGGTGATACAAAATGTAGGACCCAAGGATGCCAACAGGTGTCGCAAGACA 7800

CATGCAATGAGGCTCTGAAAATTACATGGCTAGGAGGGAAACAGGTGGTCAGCGTGATCA 7860

TCCAGGTCAATGACTATCTCTCAGAGAGGCCAAAGATAAGAGTCACAACCATTCCAATCA 7920

CTCAAAACTATCTCGGGGCGGAAGGTAGATTATTAAAATTGGGTGATCGGGTGTACATCT 7980

ATACAAGATCATCAGGCTGGCACTCTCAACTGCAGATAGGAGTACTTGATGTCAGCCACC 8040

CTTTGACTATCAACTGGACACCTCATGAAGCCTTGTCTAGACCAGGAAATAAAGAGTGCA 8100

ATTGGTACAATAAGTGTCCGAAGGAATGCATATCAGGCGTATACACTGATGCTTATCCAT 8160

TGTCCCCTGATGCAGCTAACGTCGCTACCGTCACGCTATATGCCAATACATCGCGTGTCA 8220

ACCCAACAATCATGTATTCTAACACTACTAACATTATAAATATGTTAAGGATAAAGGATG 8280

TTCAATTAGAGGCTGCATATACCACGACATCGTGTATCACGCATTTTGGTAAAGGCTACT 8340

GCTTTCACATCATCGAGATCAATCAGAAGAGCCTGAATACCTTACAGCCGATGCTCTTTA 8400

AGACTAGCATCCCTAAATTATGCAAGGCCGAGTCTTAAATTTAACTGACTAGCAGGCTTG 8460

TCGGCCTTGCTGACACTAGAGTCATCTCCGAACATCCACAATATCTCTCAGTCTCTTACG 8520

TCTCTCACAGTATTAAGAAAAACCCAGGGTGAATGGGAAGCTTGCCATAGGTCATGGATG 8580

-> L

GGCAGGAGTCCTCCCAAAACCCTTCTGACATACTCTATCCAGAATGCCACCTGAACTCTC 8640

CCATAGTCAGGGGGAAGATAGCACAGTTGCACGTCTTGTTAGATGTGAACCAGCCCTACA 8700

GACTGAAGGACGACAGCATAATAAATATTACAAAGCACAAAATTAGGAACGGAGGATTGT 8760

CCCCCCGTCAAATTAAGATCAGGTCTCTGGGTAAGGCTCTTCAACGCACAATAAAGGATT 8820

TAGACCGATACACGTTTGAACCGTACCCAACCTACTCTCAGGAATTACTTAGGCTTGATA 8880

TACCAGAGATATGTGACAAAATCCGATCCGTCTTCGCGGTCTCGGATCGGCTGACCAGGG 8940

AGTTATCTAGTGGGTTCCAGGATCTTTGGTTGAATATCTTCAAGCAACTAGGCAATATAG 9000

AAGGAAGAGAGGGGTACGATCCGTTGCAGGATATCGGCACCATCCCGGAGATAACTGATA 9060

AGTACAGCAGGAATAGATGGTATAGGCCATTCCTAACTTGGTTCAGCATCAAATATGACA 9120

TGCGGTGGATGCAGAAGACCAGACCGGGGGGACCCCTCGATACCTCTAATTCACATAACC 9180

TCCTAGAATGCAAATCATACACTCTAGTAACATACGGAGATCTTGTCATGATACTGAACA 9240

AGTTGACATTGACAGGGTATATCCTAACCCCTGAGCTGGTCTTGATGTATTGTGATGTTG 9300

FIG. 8E

TAGAAGGAAGGTGGAATATGTCTGCTGCAGGGCATCTAGATAAGAAGTCCATTGGGATAA 9360
CAAGCAAAGGTGAGGAATTATGGGAACTAGTGGATTCCCTCTTCTCAAGTCTTGGAGAGG 9420
AAATATACAATGTCATCGCACTATTGGAGCCCCTATCACTTGCTCTCATACAACTAAATG 9480
ATCCTGTTATACCTCTACGTGGGGCATTTATGAGGCATGTGTTGACAGAGCTACAGACTG 9540
TTTTAACAAGTAGAGACGTGTACACAGATGCTGAAGCAGACACTATTGTGGAGTCGTTAC 9600
TCGCCATTTTCCATGGAACCTCTATTGATGAGAAAGCAGAGATCTTTTCCTTCTTTAGGA 9660
CATTTGGCCACCCCAGCTTAGAGGCTGTCACTGCCGCCGACAAGGTAAGGGCCCATATGT 9720
ATGCACAAAAGGCAATAAAGCTTAAGACCCTATACGAGTGTCATGCAGTTTTTTGCACTA 9780
TCATCATAAATGGGTATAGAGAGAGGCATGGCGGACAGTGGCCCCCCTGTGACTTCCCTG 9840
ATCACGTGTGTCTAGAACTAAGGAACGCTCAAGGGTCCAATACGGCAATCTCTTATGAAT 9900
GTGCTGTAGACAACTATACAAGTTTCATAGGCTTCAAGTTTCGGAAGTTTATAGAACCAC 9960
AACTAGATGAAGATCTCACAATATATATGAAAGACAAAGCACTATCCCCCAGGAAGGAGG 10020
CATGGGACTCTGTATACCCGGATAGTAATCTGTACTATAAAGCCCCAGAGTCTGAAGAGA 10080
CCCGGCGGCTTATTGAAGTGTTCATAAATGATGAGAATTTCAACCCAGAAGAAATTATCA 10140
ATTATGTGGAGTCAGGAGATTGGTTGAAAGACGAGGAGTTCAACATCTCGTACAGTCTCA 10200
AAGAGAAAGAGATCAAGCAAGAGGGTCGTCTATTCGCAAAAATGACTTATAAGATGCGAG 10260
CCGTACAGGTGCTGGCAGAGACACTACTGGCTAAAGGAATAGGAGAGCTATTCAGCGAAA 10320
ATGGGATGGTTAAAGGAGAGATAGACCTACTTAAAAGATTGACTACTCTTTCTGTCTCAG 10380
GCGTCCCCAGGACTGATTCAGTGTACAATAACTCTAAATCATCAGAGAAGAGAAACGAAG 10440
GCATGGAAAATAAGAACTCTGGGGGGTACTGGGACGAAAAGAAGAGGTCCAGACATGAAT 10500
TCAAGGCAACAGATTCATCAACAGACGGCTATGAAACGTTAAGTTGCTTCCTCACAACAG 10560
ACCTCAAGAAATACTGCTTAAACTGGAGATTTGAGAGTACTGCATTGTTTGGTCAGAGAT 10620
GCAACGAGATATTTGGCTTCAAGACCTTCTTTAACTGGATGCATCCAGTCCTTGAAAGGT 10680
GTACAATATATGTTGGAGATCCTTACTGTCCAGTCGCCGACCGGATGCATCGACAACTCC 10740
AGGATCATGCAGACTCTGGCATTTTCATACATAATCCTAGGGGGGCATAGAAGGTTACT 10800
GCCAGAAGCTGTGGACCTTAATCTCAATCAGTGCAATCCACCTAGCAGCTGTGAGAGTGG 10860
GTGTCAGGGTCTCTGCAATGGTTCAGGGTGACAATCAAGCTATAGCCGTGACATCAAGAG 10920
TACCTGTAGCTCAGACTTACAAGCAGAAGAAAAATCATGTCTATGAGGAGATCACCAAAT 10980
ATTTCGGTGCTCTAAGACACGTCATGTTTGATGTAGGGCACGAGCTAAAATTGAACGAGA 11040
CCATCATTAGTAGCAAGATGTTTGTCTATAGTAAAAGGATATACTATGATGGGAAGATTT 11100
TACCACAGTGCCTGAAAGCCTTGACCAAGTGTGTATTCTGGTCCGAGACACTGGTAGATG 11160

FIG. 8F

AAAACAGATCTGCTTGTTCGAACATCTCAACATCCATAGCAAAAGCTATCGAAAATGGGT 11220

ATTCTCCTATACTAGGCTACTGCATTGCGTTGTATAAGACCTGTCAGCAGGTGTGCATAT 11280

CACTAGGGATGACTATAAATCCAACTATCAGCCCGACCGTAAGAGATCAATACTTTAAGG 11340

GTAAGAATTGGCTGAGATGTGCAGTGTTGATTCCAGCAAATGTTGGAGGATTCAACTACA 11400

TGTCTACATCTAGATGCTTTGTTAGAAATATTGGAGACCCCGCAGTAGCAGCCCTAGCTG 11460

ATCTCAAAAGATTCATCAGAGCGGATCTGTTAGACAAGCAGGTATTATACAGGGTCATGA 11520

ATCAAGAACCCGGTGACTCTAGTTTTCTAGATTGGGCTTCAGACCCTTATTCGTGTAACC 11580

TCCCGCATTCTCAGAGTATAACTACGATTATAAAGAATATCACTGCTAGATCTGTGCTGC 11640

AGGAATCCCCGAATCCTCTACTGTCTGGTCTCTTCACCGAGACTAGTGGAGAAGAGGATC 11700

TCAACCTGGCCTCGTTCCTTATGGACCGGAAAGTCATCCTGCCGAGAGTGGCTCATGAGA 11760

TCCTGGGTAATTCCTTAACTGGAGTTAGGGAGGCGATTGCAGGGATGCTTGATACGACCA 11820

AGTCTCTAGTGAGAGCCAGCGTTAGGAAAGGAGGATTATCATATGGGATATTGAGGAGGC 11880

TTGTCAATTATGATCTATTGCAGTACGAGACACTGACTAGAACTCTCAGGAAACCGGTGA 11940

AAGACAACATCGAATATGAGTATATGTGTTCAGTTGAGCTAGCTGTCGGTCTAAGGCAGA 12000

AAATGTGGATCCACCTGACTTACGGGAGACCCATACATGGGCTAGAAACACCAGACCCTT 12060

TAGAGCTCTTGAGGGGAATATTTATCGAAGGTTCAGAGGTGTGCAAGCTTTGCAGGTCTG 12120

AAGGAGCAGACCCCATCTATACATGGTTCTATCTTCCTGACAATATAGACCTGGACACGC 12180

TTACAAACGGATGTCCGGCTATAAGAATCCCCTATTTTGGATCAGCCACTGATGAAAGGT 12240

CGGAAGCCCAACTCGGGTATGTAAGAAATCTAAGCAAACCCGCAAAGGCGGCCATCCGGA 12300

TAGCTATGGTGTATACGTGGGCCTACGGGACTGATGAGATATCGTGGATGGAAGCCGCTC 12360

TTATAGCCCAAACAAGAGCTAATCTGAGCTTAGAGAATCTAAAGCTGCTGACTCCTGTTT 12420

CAACCTCCACTAATCTATCTCATAGGTTGAAAGATACGGCAACCCAGATGAAGTTCTCTA 12480

GTGCAACACTAGTCCGTGCAAGTCGGTTCATAACAATATCAAATGATAACATGGCACTCA 12540

AAGAAGCAGGGGAGTCGAAGGATACTAATCTCGTGTATCAGCAGATTATGCTAACTGGGC 12600

TAAGCTTGTTCGAGTTCAATATGAGATATAAGAAAGGTTCCTTAGGGAAGCCACTGATAT 12660

TGCACTTACATCTTAATAACGGGTGCTGTATAATGGAGTCCCCACAGGAGGCGAATATCC 12720

CCCCAAGGTCCACATTAGATTTAGAGATTACACAAGAGAACAATAAATTGATCTATGATC 12780

CTGATCCACTCAAGGATGTGGACCTTGAGCTATTTAGCAAGGTCAGAGATGTTGTACACA 12840

CAGTTGACATGACTTATTGGTCAGATGATGAAGTTATCAGAGCAACCAGTATCTGTACTG 12900

CAATGACGATAGCTGATACAATGTCTCAATTAGATAGAGACAACTTAAAAGAGATGATCG 12960

CACTAGTAAATGACGATGATGTCAACAGCTTGATTACTGAGTTTATGGTGATTGATGTTC 13020

FIG. 8G

CTTTATTTTGCTCAACGTTCGGGGGTATTCTAGTCAATCAGTTTGCATACTCACTCTACG 13080

GCTTAAACATCAGAGGAAGGGAAGAAATATGGGGACATGTAGTCCGGATTCTTAAAGATA 13140

CCTCCCACGCAGTTTTAAAAGTCTTATCTAATGCTCTATCTCATCCCAAAATCTTCAAAC 13200

GATTCTGGAATGCAGGTGTCGTGGAACCTGTGTATGGGCCTAACCTCTCAAATCAGGATA 13260

AGATACTCTTGGCCCTCTCTGTCTGTGAATATTCTGTGGATCTATTCATGCACGATTGGC 13320

AAGGGGGTGTACCGCTTGAGATCTTTATCTGTGACAATGACCCAGATGTGGCCGACATGA 13380

GGAGGTCCTCTTTCTTGGCAAGACATCTTGCATACCTATGCAGCTTGGCAGAGATATCTA 13440

GGGATGGGCCAAGATTAGAATCAATGAACTCTCTAGAGAGGCTCGAGTCACTAAAGAGTT 13500

ACCTGGAACTCACATTTCTTGATGACCCGGTACTGAGGTACAGTCAGTTGACTGGCCTAG 13560

TCATCAAAGTATTCCCATCTACTTTGACCTATATCCGGAAGTCATCTATAAAAGTGTTAA 13620

GGACAAGAGGTATAGGAGTCCCTGAAGTCTTAGAAGATTGGGATCCCGAGGCAGATAATG 13680

CACTGTTAGATGGTATCGCGGCAGAAATACAACAGAATATTCCTTTGGGACATCAGACTA 13740

GAGCCCCTTTTTGGGGGTTGAGAGTATCCAAGTCACAGGTACTGCGTCTCCGGGGGTACA 13800

AGGAGATCACAAGAGGTGAGATAGGCAGATCAGGTGTTGGTCTGACGTTACCATTCGATG 13860

GAAGATATCTATCTCACCAGCTGAGGCTCTTTGGCATCAACAGTACTAGCTGCTTGAAAG 13920

CACTTGAACTTACCTACCTATTGAGCCCCTTAGTTGACAAGGATAAAGATAGGCTATATT 13980

TAGGGGAAGGAGCTGGGGCCATGCTTTCCTGTTATGACGCTACTCTTGGCCCATGCATCA 14040

ACTATTATAACTCAGGGGTATACTCTTGTGATGTCAATGGGCAGAGAGAGTTAAATATAT 14100

ATCCTGCTGAGGTGGCACTAGTGGGAAAGAAATTAAACAATGTTACTAGTCTGGGTCAAA 14160

GAGTTAAAGTGTTATTCAACGGGAATCCTGGCTCGACATGGATTGGGAATGATGAGTGTG 14220

AGGCTTTGATTTGGAATGAATTACAGAATAGCTCGATAGGCCTAGTCCACTGTGACATGG 14280

AGGGAGGAGATCATAAGGATGATCAAGTTGTACTGCATGAGCATTACAGTGTAATCCGGA 14340

TCGCGTATCTGGTGGGGGATCGAGACGTTGTGCTTATAAGCAAGATTGCTCCCAGGCTGG 14400

GCACGGATTGGACCAGGCAGCTCAGCCTATATCTGAGATACTGGGACGAGGTTAACCTAA 14460

TAGTGCTTAAAACATCTAACCCTGCTTCCACAGAGATGTATCTCCTATCGAGGCACCCCA 14520

AATCTGACATTATAGAGGACAGCAAGACAGTGTTAGCTAGTCTCCTCCCTTTGTCAAAAG 14580

AAGATAGCATCAAGATAGAAAAGTGGATCTTAATAGAGAAGGCAAAGGCTCACGAATGGG 14640

TTACTCGGGAATTGAGAGAAGGAAGCTCTTCATCAGGGATGCTTAGACCTTACCATCAAG 14700

CACTGCAGACGTTTGGCTTTGAACCAAACTTGTATAAATTGAGCAGAGATTTCTTGTCCA 14760

CCATGAACATAGCTGATACACACAACTGCATGATAGCTTTCAACAGGGTTTTGAAGGATA 14820

CAATCTTCGAATGGGCTAGAATAACTGAGTCAGATAAAAGGCTTAAACTAACTGGTAAGT 14880

FIG. 8H

ATGACCTGTATCCTGTGAGAGATTCAGGCAAGTTGAAGACAATTTCTAGAAGACTTGTGC 14940

TATCTTGGATATCTTTATCTATGTCCACAAGATTGGTAACTGGGTCATTCCCTGACCAGA 15000

AGTTTGAAGCAAGACTTCAATTGGGAATAGTTTCATTATCATCCCGTGAAATCAGGAACC 15060

TGAGGGTTATCACAAAAACTTTATTAGACAGGTTTGAGGATATTATACATAGTATAACGT 15120

ATAGATTCCTCACCAAAGAAATAAAGATTTTGATGAAGATTTTAGGGGCAGTCAAGATGT 15180

TCGGGGCCAGGCAAAATGAATACACGACCGTGATTGATGATGGATCACTAGGTGATATCG 15240

AGCCATATGACAGCTCGTAATAATTAGTCCCTATCGTGCAGAACGATCGAAGCTCCGCGG 15300

TACCTGGAAGTCTTGGACTTGTCCATATGACAATAGTAAGAAAAACTTACAAGAAGACAA 15360

GAAAATTTAAAAGGATACATATCTCTTAAACTCTTGTCTGGT 15402

NP: Blue characters, P: Green characters, M: Brown characters, F: Orange characters, HN: Pink characters, L: Violet characters The nucleotide sequence of SeV-sfEnvF(NP)

ACCAAACAAGAGAAAAAACATGTATGGGATATGTAATGAAGTTATACAGGATTTTAGGGT 60

CAAAGTATCCACCCTGAGGAGCAGGTTCCAGACCCTTTGCTTTGCTGCCAAAGTTCAC[redacted] 120

[redacted]CAAGGTTCACTTATGACAGCATATATCCAGAGATCACAGTGCATCTCAACATCA 180
NotI -> sfEnvF

CTACTGGTTGTTCTCACCACATTGGTCTCGTGTCAGGCTAGCGCAGAGAATTTGTGGGTA 240

ACAGTCTACTATGGAGTCCCTGTATGGAAGGATGCAGAGACAACATTGTTCTGTGCTAGT 300

GACGCAAAGGCTTACGAGACGGAGAAGCACAATGTGTGGGCAACTCACGCATGTGTCCCA 360

ACCGATCCAAATCCTCAAGAGATTCATCTAGAGAATGTGACTGAAGAATTCAATATGTGG 420

AAGAATAATATGGTAGAGCAAATGCATACAGATATCATTAGTTTATGGGACCAGTCACTT 480

AAACCCTGCGTTAAATTGACGCCTCTATGTGTGACACTTCAATGTACTAATGTTACAAAC 540

AACATAACAGATGATATGAGAGGAGAACTGAAGAACTGTAGTTTCAACATGACGACAGAG 600

TTGCGTGACAAGAAACAGAAAGTGTATTCACTATTCTATCGGTTGGATGTAGTACAGATA 660

AATGAGAATCAAGGAAACAGGTCCAACAACTCTAACAAAGAGTACAGACTTATTAATTGC 720

AATACCAGTGCTATCACGCAAGCCTGCCCAAAGGTTTCATTTGAACCAATACCTATTCAT 780

TATTGTGCACCTGCTGGATTCGCCATCCTCAAATGTAAAGACAAGAAGTTCAATGGAACA 840

GGACCCTGCCCATCAGTTTCAACCGTTCAGTGCACCCACGGAATCAAGCCTGTAGTTAGT 900

ACTCAATTATTGTTAAATGGGAGCTTAGCTGAAGAAGAAGTTATGATTAGATCAGAGAAT 960

ATTACCAATAATGCGAAGAACATCTTGGTTCAATTCAATACTCCAGTCCAGATCAATTGC 1020

ACAAGGCCTAATAATAATACCAGAAAGAGTATAAGAATTGGGCCAGGACAGGCATTCTAT 1080

GCAACAGGAGATATAATCGGAGACATTCGACAAGCGCACTGCACTGTTTCTAAGGCCACT 1140

TGGAATGAAACATTGGGTAAAGTTGTAAAGCAACTTCGGAAGCATTTCGGAAATAACACA 1200

FIG. 8I

```
ATTATTAGATTTGCGAACTCATCTGGAGGGGATCTGGAAGTGACAACACACTCTTTCAAT 1260
TGCGGTGGCGAGTTCTTCTATTGTAATACAAGTGGATTATTTAACTCTACTTGGATTTCA 1320
AATACCTCAGTCCAAGGATCTAATTCAACAGGGTCTAACGATTCTATAACATTACCTTGC 1380
CGTATAAAGCAAATTATTAATATGTGGCAAAGAATCGGGCAAGCGATGTATGCTCCACCT 1440
ATTCAAGGCGTGATTCGTTGCGTTTCAAACATAACAGGGTTGATCCTGACCAGGGATGGA 1500
GGCTCTACCAATTCCACCACCGAGACCTTCCGTCCCGGTGGCGGAGATATGCGGGATAAC 1560
TGGAGATCAGAGCTCTATAAGTATAAGGTTGTGAAGATTGAACCTCTTGGAGTTGCCCCT 1620
ACAAGAGCAAAGAGAAGGGTGGTTGGCCGAGAGAAGAGAGCAGTTGGCATCGGTGCTGTC 1680
TTTCTCGGATTTCTTGGAGCAGCTGGATCCACTATGGGAGCAGCATCAATGACACTAACA 1740
GTGCAGGCTAGAAATTTGCTTAGCGGAATCGTTCAGCAGCAGAGCAATTTACTAAGAGCA 1800
ATTGAAGCACAGCAACATCTCTTAAAGTTGACGGTGTGGGGCATTAAACAACTACAAGCG 1860
AGAGTGCTTGCCGTCGAAAGATATTTGCGAGACCAACAGCTATTGGGTATTTGGGGTTGT 1920
TCTGGGAAATTAATTTGCACAACAAATGTTCCATGGAACTCCTCCTGGAGTAATAGGAAT 1980
TTAAGTGAGATATGGGACAACATGACATGGTTGCAGTGGGACAAGGAAATCTCAAATTAT 2040
ACACAGATAATCTATGGATTATTAGAAGAGTCTCAGAATCAGCAAGAGAAGAATGAACAG 2100
GATTTGCTTGCATTGGATAAGTGGGCTTCTCTATGGAACTGGTTCGATATTAGTAATTGG 2160
CTCTGGTATATTAAGAACTCAAGAGAGACTGTGATTACGATCATAGTAGTTATGGTCGTA 2220
ATATTGGTGGTCATTATAGTGATCATCATCGTGCTTTATAGACTCAGAAGGTCAATGCTA 2280
ATGGGTAATCCAGATGACCGTATACCGAGGGACACATACACATTAGAGCCGAAGATCAGA 2340
CATATGTACACAAACGGTGGGTTTGATGCAATGGCTGAGAAAAGATGACCGTAGTAAGAA 2400
AAACTTAGGGTGAAAGTTCATC[redacted]AGATCTTCACGATGGCCGGGTTGTTGAGCA 2460
                      NotI          -> NP
CCTTCGATACATTTAGCTCTAGGAGGAGCGAAAGTATTAATAAGTCGGGAGGAGGTGCTG 2520
TTATCCCCGGCCAGAGGAGCACAGTCTCAGTGTTCGTACTAGGCCCAAGTGTGACTGATG 2580
ATGCAGACAAGTTATTCATTGCAACTACCTTCCTAGCTCACTCATTGGACACAGATAAGC 2640
AGCACTCTCAGAGAGGGGGGTTCCTCGTCTCTCTGCTTGCCATGGCTTACAGTAGTCCAG 2700
AATTGTACTTGACAACAAACGGAGTAAACGCCGATGTCAAATATGTGATCTACAACATAG 2760
AGAAAGACCCTAAGAGGACGAAGACAGACGGATTCATTGTGAAGACGAGAGATATGGAAT 2820
ATGAGAGGACCACAGAATGGCTGTTTGGACCTATGGTCAACAAGAGCCCACTCTTCCAGG 2880
GTCAACGGGATGCTGCAGACCCTGACACACTCCTTCAAATCTATGGGTATCCTGCATGCC 2940
TAGGAGCAATAATTGTCCAAGTCTGGATTGTGCTGGTGAAGGCCATCACAAGCAGCGCCG 3000
GCTTAAGGAAAGGGTTCTTCAACAGGTTAGAGGCGTTCAGACAAGACGGCACCGTGAAAG 3060
GTGCCTTAGTTTTCACTGGGGAGACAGTTGAGGGGATAGGCTCGGTTATGAGATCTCAGC 3120
```

FIG. 8J

AAAGCCTTGTATCTCTCATGGTTGAGACCCTTGTGACTATGAATACTGCAAGATCTGATC 3180

TCACCACATTAGAGAAGAACATCCAGATCGTTGGGAACTACATCCGAGATGCAGGGCTGG 3240

CTTCCTTCATGAACACTATTAAATATGGGGTGGAAACAAAGATGGCAGCTCTAACGTTGT 3300

CAAACCTGAGGCCCGATATTAATAAGCTTAGAAGCCTCATAGACACCTACCTGTCAAAAG 3360

GCCCCAGAGCTCCCTTTATCTGTATCCTCAAGGACCCTGTTCATGGTGAATTTGCTCCAG 3420

GCAATTATCCTGCACTATGGAGTTACGCCATGGGAGTCGCCGTCGTACAGAACAAGGCAA 3480

TGCAGCAGTACGTCACAGGGAGGACATACCTTGATATGGAAATGTTCTTACTAGGACAAG 3540

CCGTGGCAAAGGATGCTGAATCGAAGATCAGCAGTGCCTTGGAAGATGAGTTAGGAGTGA 3600

CGGATACAGCCAAGGGGAGGCTCAGACATCATCTGGCAAACTTGTCCGGTGGGGATGGTG 3660

CTTACCACAAACCAACAGGCGGTGGTGCAATTGAGGTAGCTCTAGACAATGCCGACATCG 3720

ACCTAGAAACAAAAGCCCATGCGGACCAGGACGCTAGGGGTTGGGGTGGAGATAGTGGTG 3780

AAAGATGGGCACGTCAGGTGAGTGGTGGCCACTTTGTCACACTACATGGGGCTGAACGGT 3840

TAGAGGAGGAAACCAATGATGAGGATGTATCAGACATAGAGAGAAGAATAGCCATGAGAC 3900

TCGCAGAGAGACGGCAAGAGGATTCTGCAACCCATGGAGATGAAGGCCGCAATAACGGTG 3960

TCGATCATGACGAAGATGACGATGCCGCAGCAGTAGCTGGGATAGGAGGAATCTAGGATC 4020

ATACGAGGCTTCAAGGTACTTGATCCGTAGTAAGAAAAACTTAGGGTGAAAGTTCATCCA 4080

CCGATCGGCTCAGGCAAGGCCACACCCAACCCCACCGACCACACCCAGCAGTCGAGACAG 4140

CCACGGCTTCGGCTACACTTACCGCATGGATCAAGATGCCTTCATTCTTAAAGAAGATTC 4200

-> P

TGAAGTTGAGAGGGAGGCGCCAGGAGGACGAGAGTCGCTCTCGGATGTTATCGGATTCCT 4260

CGATGCTGTCCTGTCGAGTGAACCAACTGACATCGGAGGGGACAGAAGCTGGCTCCACAA 4320

CACCATCAACACTCCCCAAGGACCAGGCTCTGCTCATAGAGCCAAAAGTGAGGGCGAAGG 4380

AGAAGTCTCAACACCGTCGACCCAAGATAATCGATCAGGTGAGGAGAGTAGAGTCTCTGG 4440

GAGAACAAGCAAGCCAGAGGCAGAAGCACATGCTGGAAACCTTGATAAACAAAATATACA 4500

CCGGGCCTTTGGGGGAAGAACTGGTACAAACTCTGTATCTCAGGATCTGGGCGATGGAGG 4560

AGACTCCGGAATCCTTGAAAATCCTCCAAATGAGAGAGGATATCCGAGATCAGGTATTGA 4620

AGATGAAAACAGAGAGATGGCTGCGCACCCTGATAAGAGGGGAGAAGACCAAGCTGAAGG 4680

ACTTCCAGAAGAGGTACGAGGAAGTACATCCCTACCTGATGAAGGAGAAGGTGGAGCAAG 4740

TAATAATGGAAGAAGCATGGAGCCTGGCAGCTCACATAGTGCAAGAGTAACTGGGGTCCT 4800

GGTGATTCCTAGCCCCGAACTTGAAGAGGCTGTGCTACGGAGGAACAAAAGAAGACCTAC 4860

CAACAGTGGGTCCAAACCTCTTACTCCAGCAACCGTGCCTGGCACCCGGTCCCCACCGCT 4920

GAATCGTTACAACAGCACAGGGTCACCACCAGGAAAACCCCCATCTACACAGGATGAGCA 4980

CATCAACTCTGGGGACACCCCCGCCGTCAGGGTCAAAGACCGGAAACCACCAATAGGGAC 5040

FIG. 8K

CCGCTCTGTCTCAGATTGTCCAGCCAACGGCCGCCCAATCCACCCGGGTCTAGAGACCGA 5100

CTCAACAAAAAAGGGCATAGGAGAGAACACATCATCTATGAAAGAGATGGCTACATTGTT 5160

GACGAGTCTTGGTGTAATCCAGTCTGCTCAAGAATTCGAATCATCCCGAGACGCGAGTTA 5220

TGTGTTTGCAAGACGTGCCCTAAAGTCTGCAAACTATGCAGAGATGACATTCAATGTATG 5280

CGGCCTGATCCTTTCTGCCGAGAAATCTTCCGCTCGTAAGGTAGATGAGAACAAACAACT 5340

GCTCAAACAGATCCAAGAGAGCGTGGAATCATTCCGGGATATTTACAAGAGATTCTCTGA 5400

GTATCAGAAAGAACAGAACTCATTGCTGATGTCCAACCTATCTACACTTCATATCATCAC 5460

AGATAGAGGTGGCAAGACTGACAACACAGACTCCCTTACAAGGTCCCCCTCCGTTTTTGC 5520

AAAATCAAAAGAGAACAAGACTAAGGCTACCAGGTTTGACCCATCTATGGAGACCCTAGA 5580

AGATATGAAGTACAAACCGGACCTAATCCGAGAGGATGAATTTAGAGATGAGATCCGCAA 5640

CCCGGTGTACCAAGAGAGGGACACAGAACCCAGGGCCTCAAACGCATCACGTCTCCTCCC 5700

CTCCAAAGAGAAGCCCACAATGCACTCTCTCAGGCTCGTCATAGAGAGCAGTCCCCTAAG 5760

CAGAGCTGAGAAAGTAGCATATGTGAAATCATTATCCAAGTGCAAGACAGACCAAGAGGT 5820

TAAGGCAGTCATGGAACTCGTAGAAGAGGACATAGAGTCACTGACCAACTAGATCCCGGG 5880

TGAGGCATCCTACCATCCTCAGTCATAGAGAGATCCAATCTACCATCAGCATCAGCCAGT 5940

AAAGATTAAGAAAAACTTAGGGTGAAAGAAATTTCACCTAACACGGCGCAATGGCAGATA 6000

-> M

TCTATAGATTCCCTAAGTTCTCATATGAGGATAACGGTACTGTGGAGCCCCTGCCTCTGA 6060

GAACTGGTCCGGATAAGAAAGCCATCCCCCACATCAGGATTGTCAAGGTAGGAGACCCTC 6120

CTAAACATGGAGTGAGATACCTAGATTTATTGCTCTTGGGTTTCTTTGAGACACCGAAAC 6180

AAACAACCAATCTAGGGAGCGTATCTGACTTGACAGAGCCGACCAGCTACTCAATATGCG 6240

GCTCCGGGTCGTTACCCATAGGTGTGGCCAAATACTACGGGACTGATCAGGAACTCTTAA 6300

AGGCCTGCACCGATCTCAGAATTACGGTGAGGAGGACTGTTCGAGCAGGAGAGATGATCG 6360

TATACATGGTGGATTCGATTGGTGCTCCACTCCTACCATGGTCAGGCAGGCTGAGACAGG 6420

GAATGATATTTAATGCAAACAAGGTCGCACTAGCTCCCCAATGCCTCCCTGTGGACAAGG 6480

ACATAAGACTCAGAGTGGTGTTTGTCAATGGGACATCTCTAGGGGCAATCACCATAGCCA 6540

AGATCCCAAAGACCCTTGCAGACCTTGCATTGCCCAACTCTATATCTGTTAATTTACTGG 6600

TGACACTCAAGACCGGGATCTCCACAGAACAAAAGGGGGTACTCCCAGTACTTGATGATC 6660

AAGGGGAGAAAAAGCTCAATTTTATGGTGCACCTCGGGTTGATCAGGAGAAAGGTCGGGA 6720

AGATATACTCTGTTGAGTACTGCAAGAGCAAGATTGAGAGAATGCGGCTGATTTTCTCAC 6780

TTGGGTTAATCGGCGGTATAAGCTTCCATGTTCAGGTTAATGGGACACTATCTAAGACAT 6840

TCATGAGTCAGCTCGCATGGAAGAGGGCAGTCTGCTTCCCATTAATGGATGTGAATCCCC 6900

ATATGAACATGGTGATTTGGGCGGCATCTGTAGAAATCACAGGCGTCGATGCGGTGTTCC 6960

FIG. 8L

AACCGGCCATCCCTCGTGATTTCCGCTACTACCCTAATGTTGTGGCTAAGAACATCGGAA 7020

GGATCAGAAAGCTGTAAATGTGCACCCATCAGAGACCTGCGACAATGCCCCAAGCAGACA 7080

CCACCTGGCAGTCGGAGCCACCGGGTCACTCCTTGTCTTAAATAAGAAAAACTTAGGGAT 7140

AAAGTCCCTTGTGAGTGCTTGGTTGCAAAACTCTCCCCTTGGGAAACATGACAGCATATA 7200
-> F

TCCAGAGATCACAGTGCATCTCAACATCACTACTGGTTGTTCTCACCACATTGGTCTCGT 7260

GTCAGATTCCCAGGGATAGGCTCTCTAACATAGGGGTCATAGTCGATGAAGGGAAATCAC 7320

TGAAGATAGCTGGATCCCACGAATCGAGGTACATAGTACTGAGTCTAGTTCCGGGGGTAG 7380

ACTTTGAGAATGGGTGCGGAACAGCCCAGGTTATCCAGTACAAGAGCCTACTGAACAGGC 7440

TGTTAATCCCATTGAGGGATGCCTTAGATCTTCAGGAGGCTCTGATAACTGTCACCAATG 7500

ATACGACACAAAATGCCGGTGCTCCCCAGTCGAGATTCTTCGGTGCTGTGATTGGTACTA 7560

TCGCACTTGGAGTGGCGACATCAGCACAAATCACCGCAGGGATTGCACTAGCCGAAGCGA 7620

GGGAGGCCAAAAGAGACATAGCGCTCATCAAAGAATCGATGACAAAAACACACAAGTCTA 7680

TAGAACTGCTGCAAAACGCTGTGGGGGAACAAATTCTTGCTCTAAAGACACTCCAGGATT 7740

TCGTGAATGATGAGATCAAACCCGCAATAAGCGAATTAGGCTGTGAGACTGCTGCCTTAA 7800

GACTGGGTATAAAATTGACACAGCATTACTCCGAGCTGTTAACTGCGTTCGGCTCGAATT 7860

TCGGAACCATCGGAGAGAAGAGCCTCACGCTGCAGGCGCTGTCTTCACTTTACTCTGCTA 7920

ACATTACTGAGATTATGACCACAATCAGGACAGGGCAGTCTAACATCTATGATGTCATTT 7980

ATACAGAACAGATCAAAGGAACGGTGATAGATGTGGATCTAGAGAGATACATGGTCACCC 8040

TGTCTGTGAAGATCCCTATTCTTTCTGAAGTCCCAGGTGTGCTCATACACAAGGCATCAT 8100

CTATTTCTTACAACATAGACGGGGAGGAATGGTATGTGACTGTCCCCAGCCATATACTCA 8160

GTCGTGCTTCTTTCTTAGGGGGTGCAGACATAACCGATTGTGTTGAGTCCAGATTGACCT 8220

ATATATGCCCCAGGGATCCCGCACAACTGATACCTGACAGCCAGCAAAAGTGTATCCTGG 8280

GGGACACAACAAGGTGTCCTGTCACAAAAGTTGTGGACAGCCTTATCCCCAAGTTTGCTT 8340

TTGTGAATGGGGGCGTTGTTGCTAACTGCATAGCATCCACATGTACCTGCGGGACAGGCC 8400

GAAGACCAATCAGTCAGGATCGCTCTAAAGGTGTAGTATTCCTAACCCATGACAACTGTG 8460

GTCTTATAGGTGTCAATGGGGTAGAATTGTATGCTAACCGGAGAGGGCACGATGCCACTT 8520

GGGGGGTCCAGAACTTGACAGTCGGTCCTGCAATTGCTATCAGACCCGTTGATATTTCTC 8580

TCAACCTTGCTGATGCTACGAATTTCTTGCAAGACTCTAAGGCTGAGCTTGAGAAAGCAC 8640

GGAAAATCCTCTCGGAGGTAGGTAGATGGTACAACTCAAGAGAGACTGTGATTACGATCA 8700

TAGTAGTTATGGTCGTAATATTGGTGGTCATTATAGTGATCATCATCGTGCTTTATAGAC 8760

TCAGAAGGTCAATGCTAATGGGTAATCCAGATGACCGTATACCGAGGGACACATACACAT 8820

TAGAGCCGAAGATCAGACATATGTACACAAACGGTGGGTTTGATGCAATGGCTGAGAAAA 8880

FIG. 8M

GATGATCACGACCATTATCAGATGTCTTGTAAAGCAGGCATAGTATCCGTTGAGATCTGT 8940

ATATAATAAGAAAAACTTAGGGTGAAAGTGAGGTCGCGCGGTACTTTAGCTTTCACCTCA 9000

AACAAGCACAGATCATGGATGGTGATAGGGGCAAACGTGACTCGTACTGGTCTACTTCTC 9060
-> HN

CTAGTGGTAGCACCACAAAACCAGCATCAGGTTGGGAGAGGTCAAGTAAAGCCGACACAT 9120

GGTTGCTGATTCTCTCATTCACCCAGTGGGCTTTGTCAATTGCCACAGTGATCATCTGTA 9180

TCATAATTTCTGCTAGACAAGGGTATAGTATGAAAGAGTACTCAATGACTGTAGAGGCAT 9240

TGAACATGAGCAGCAGGGAGGTGAAAGAGTCACTTACCAGTCTAATAAGGCAAGAGGTTA 9300

TAGCAAGGGCTGTCAACATTCAGAGCTCTGTGCAAACCGGAATCCCAGTCTTGTTGAACA 9360

AAAACAGCAGGGATGTCATCCAGATGATTGATAAGTCGTGCAGCAGACAAGAGCTCACTC 9420

AGCACTGTGAGAGTACGATCGCAGTCCACCATGCCGATGGAATTGCCCCACTTGAGCCAC 9480

ATAGTTTCTGGAGATGCCCTGTCGGAGAACCGTATCTTAGCTCAGATCCTGAAATCTCAT 9540

TGCTGCCTGGTCCGAGCTTGTTATCTGGTTCTACAACGATCTCTGGATGTGTTAGGCTCC 9600

CTTCACTCTCAATTGGCGAGGCAATCTATGCCTATTCATCAAATCTCATTACACAAGGTT 9660

GTGCTGACATAGGGAAATCATATCAGGTCCTGCAGCTAGGGTACATATCACTCAATTCAG 9720

ATATGTTCCCTGATCTTAACCCCGTAGTGTCCCACACTTATGACATCAACGACAATCGGA 9780

AATCATGCTCTGTGGTGGCAACCGGGACTAGGGGTTATCAGCTTTGCTCCATGCCGACTG 9840

TAGACGAAAGAACCGACTACTCTAGTGATGGTATTGAGGATCTGGTCCTTGATGTCCTGG 9900

ATCTCAAAGGGAGAACTAAGTCTCACCGGTATCGCAACAGCGAGGTAGATCTTGATCACC 9960

CGTTCTCTGCACTATACCCCAGTGTAGGCAACGGCATTGCAACAGAAGGCTCATTGATAT 10020

TTCTTGGGTATGGTGGACTAACCACCCCTCTGCAGGGTGATACAAAATGTAGGACCCAAG 10080

GATGCCAACAGGTGTCGCAAGACACATGCAATGAGGCTCTGAAAATTACATGGCTAGGAG 10140

GGAAACAGGTGGTCAGCGTGATCATCCAGGTCAATGACTATCTCTCAGAGAGGCCAAAGA 10200

TAAGAGTCACAACCATTCCAATCACTCAAAACTATCTCGGGGCGGAAGGTAGATTATTAA 10260

AATTGGGTGATCGGGTGTACATCTATACAAGATCATCAGGCTGGCACTCTCAACTGCAGA 10320

TAGGAGTACTTGATGTCAGCCACCCTTTGACTATCAACTGGACACCTCATGAAGCCTTGT 10380

CTAGACCAGGAAATAAAGAGTGCAATTGGTACAATAAGTGTCCGAAGGAATGCATATCAG 10440

GCGTATACACTGATGCTTATCCATTGTCCCCTGATGCAGCTAACGTCGCTACCGTCACGC 10500

TATATGCCAATACATCGCGTGTCAACCCAACAATCATGTATTCTAACACTACTAACATTA 10560

TAAATATGTTAAGGATAAAGGATGTTCAATTAGAGGCTGCATATACCACGACATCGTGTA 10620

TCACGCATTTTGGTAAAGGCTACTGCTTTCACATCATCGAGATCAATCAGAAGAGCCTGA 10680

ATACCTTACAGCCGATGCTCTTTAAGACTAGCATCCCTAAATTATGCAAGGCCGAGTCTT 10740

AAATTTAACTGACTAGCAGGCTTGTCGGCCTTGCTGACACTAGAGTCATCTCCGAACATC 10800

FIG. 8N

```
CACAATATCTCTCAGTCTCTTACGTCTCTCACAGTATTAAGAAAAACCCAGGGTGAATGG 10860
GAAGCTTGCCATAGGTCATGGATGGGCAGGAGTCCTCCCAAAACCCTTCTGACATACTCT 10920
                        -> L
ATCCAGAATGCCACCTGAACTCTCCCATAGTCAGGGGGAAGATAGCACAGTTGCACGTCT 10980
TGTTAGATGTGAACCAGCCCTACAGACTGAAGGACGACAGCATAATAAATATTACAAAGC 11040
ACAAAATTAGGAACGGAGGATTGTCCCCCCGTCAAATTAAGATCAGGTCTCTGGGTAAGG 11100
CTCTTCAACGCACAATAAAGGATTTAGACCGATACACGTTTGAACCGTACCCAACCTACT 11160
CTCAGGAATTACTTAGGCTTGATATACCAGAGATATGTGACAAAATCCGATCCGTCTTCG 11220
CGGTCTCGGATCGGCTGACCAGGGAGTTATCTAGTGGGTTCCAGGATCTTTGGTTGAATA 11280
TCTTCAAGCAACTAGGCAATATAGAAGGAAGAGAGGGGTACGATCCGTTGCAGGATATCG 11340
GCACCATCCCGGAGATAACTGATAAGTACAGCAGGAATAGATGGTATAGGCCATTCCTAA 11400
CTTGGTTCAGCATCAAATATGACATGCGGTGGATGCAGAAGACCAGACCGGGGGGACCCC 11460
TCGATACCTCTAATTCACATAACCTCCTAGAATGCAAATCATACACTCTAGTAACATACG 11520
GAGATCTTGTCATGATACTGAACAAGTTGACATTGACAGGGTATATCCTAACCCCTGAGC 11580
TGGTCTTGATGTATTGTGATGTTGTAGAAGGAAGGTGGAATATGTCTGCTGCAGGGCATC 11640
TAGATAAGAAGTCCATTGGGATAACAAGCAAAGGTGAGGAATTATGGGAACTAGTGGATT 11700
CCCTCTTCTCAAGTCTTGGAGAGGAAATATACAATGTCATCGCACTATTGGAGCCCCTAT 11760
CACTTGCTCTCATACAACTAAATGATCCTGTTATACCTCTACGTGGGGCATTTATGAGGC 11820
ATGTGTTGACAGAGCTACAGACTGTTTTAACAAGTAGAGACGTGTACACAGATGCTGAAG 11880
CAGACACTATTGTGGAGTCGTTACTCGCCATTTTCCATGGAACCTCTATTGATGAGAAAG 11940
CAGAGATCTTTTCCTTCTTTAGGACATTTGGCCACCCCAGCTTAGAGGCTGTCACTGCCG 12000
CCGACAAGGTAAGGGCCCATATGTATGCACAAAAGGCAATAAAGCTTAAGACCCTATACG 12060
AGTGTCATGCAGTTTTTTGCACTATCATCATAAATGGGTATAGAGAGAGGCATGGCGGAC 12120
AGTGGCCCCCCTGTGACTTCCCTGATCACGTGTGTCTAGAACTAAGGAACGCTCAAGGGT 12180
CCAATACGGCAATCTCTTATGAATGTGCTGTAGACAACTATACAAGTTTCATAGGCTTCA 12240
AGTTTCGGAAGTTTATAGAACCACAACTAGATGAAGATCTCACAATATATATGAAAGACA 12300
AAGCACTATCCCCCAGGAAGGAGGCATGGGACTCTGTATACCCGGATAGTAATCTGTACT 12360
ATAAAGCCCCAGAGTCTGAAGAGACCCGGCGGCTTATTGAAGTGTTCATAAATGATGAGA 12420
ATTTCAACCCAGAAGAAATTATCAATTATGTGGAGTCAGGAGATTGGTTGAAAGACGAGG 12480
AGTTCAACATCTCGTACAGTCTCAAAGAGAAAGAGATCAAGCAAGAGGGTCGTCTATTCG 12540
CAAAAATGACTTATAAGATGCGAGCCGTACAGGTGCTGGCAGAGACACTACTGGCTAAAG 12600
GAATAGGAGAGCTATTCAGCGAAAATGGGATGGTTAAAGGAGAGATAGACCTACTTAAAA 12660
GATTGACTACTCTTTCTGTCTCAGGCGTCCCCAGGACTGATTCAGTGTACAATAACTCTA 12720
```

FIG. 8O

AATCATCAGAGAAGAGAAACGAAGGCATGGAAAATAAGAACTCTGGGGGGTACTGGGACG 12780

AAAAGAAGAGGTCCAGACATGAATTCAAGGCAACAGATTCATCAACAGACGGCTATGAAA 12840

CGTTAAGTTGCTTCCTCACAACAGACCTCAAGAAATACTGCTTAAACTGGAGATTTGAGA 12900

GTACTGCATTGTTTGGTCAGAGATGCAACGAGATATTTGGCTTCAAGACCTTCTTTAACT 12960

GGATGCATCCAGTCCTTGAAAGGTGTACAATATATGTTGGAGATCCTTACTGTCCAGTCG 13020

CCGACCGGATGCATCGACAACTCCAGGATCATGCAGACTCTGGCATTTTCATACATAATC 13080

CTAGGGGGGGCATAGAAGGTTACTGCCAGAAGCTGTGGACCTTAATCTCAATCAGTGCAA 13140

TCCACCTAGCAGCTGTGAGAGTGGGTGTCAGGGTCTCTGCAATGGTTCAGGGTGACAATC 13200

AAGCTATAGCCGTGACATCAAGAGTACCTGTAGCTCAGACTTACAAGCAGAAGAAAAATC 13260

ATGTCTATGAGGAGATCACCAAATATTTCGGTGCTCTAAGACACGTCATGTTTGATGTAG 13320

GGCACGAGCTAAAATTGAACGAGACCATCATTAGTAGCAAGATGTTTGTCTATAGTAAAA 13380

GGATATACTATGATGGGAAGATTTTACCACAGTGCCTGAAAGCCTTGACCAAGTGTGTAT 13440

TCTGGTCCGAGACACTGGTAGATGAAAACAGATCTGCTTGTTCGAACATCTCAACATCCA 13500

TAGCAAAAGCTATCGAAAATGGGTATTCTCCTATACTAGGCTACTGCATTGCGTTGTATA 13560

AGACCTGTCAGCAGGTGTGCATATCACTAGGGATGACTATAAATCCAACTATCAGCCCGA 13620

CCGTAAGAGATCAATACTTTAAGGGTAAGAATTGGCTGAGATGTGCAGTGTTGATTCCAG 13680

CAAATGTTGGAGGATTCAACTACATGTCTACATCTAGATGCTTTGTTAGAAATATTGGAG 13740

ACCCCGCAGTAGCAGCCCTAGCTGATCTCAAAAGATTCATCAGAGCGGATCTGTTAGACA 13800

AGCAGGTATTATACAGGGTCATGAATCAAGAACCCGGTGACTCTAGTTTTCTAGATTGGG 13860

CTTCAGACCCTTATTCGTGTAACCTCCCGCATTCTCAGAGTATAACTACGATTATAAAGA 13920

ATATCACTGCTAGATCTGTGCTGCAGGAATCCCCGAATCCTCTACTGTCTGGTCTCTTCA 13980

CCGAGACTAGTGGAGAAGAGGATCTCAACCTGGCCTCGTTCCTTATGGACCGGAAAGTCA 14040

TCCTGCCGAGAGTGGCTCATGAGATCCTGGGTAATTCCTTAACTGGAGTTAGGGAGGCGA 14100

TTGCAGGGATGCTTGATACGACCAAGTCTCTAGTGAGAGCCAGCGTTAGGAAAGGAGGAT 14160

TATCATATGGGATATTGAGGAGGCTTGTCAATTATGATCTATTGCAGTACGAGACACTGA 14220

CTAGAACTCTCAGGAAACCGGTGAAAGACAACATCGAATATGAGTATATGTGTTCAGTTG 14280

AGCTAGCTGTCGGTCTAAGGCAGAAAATGTGGATCCACCTGACTTACGGGAGACCCATAC 14340

ATGGGCTAGAAACACCAGACCCTTTAGAGCTCTTGAGGGGAATATTTATCGAAGGTTCAG 14400

AGGTGTGCAAGCTTTGCAGGTCTGAAGGAGCAGACCCCATCTATACATGGTTCTATCTTC 14460

CTGACAATATAGACCTGGACACGCTTACAAACGGATGTCCGGCTATAAGAATCCCCTATT 14520

TTGGATCAGCCACTGATGAAAGGTCGGAAGCCCAACTCGGGTATGTAAGAAATCTAAGCA 14580

AACCCGCAAAGGCGGCCATCCGGATAGCTATGGTGTATACGTGGGCCTACGGGACTGATG 14640

FIG. 8P

AGATATCGTGGATGGAAGCCGCTCTTATAGCCCAAACAAGAGCTAATCTGAGCTTAGAGA 14700
ATCTAAAGCTGCTGACTCCTGTTTCAACCTCCACTAATCTATCTCATAGGTTGAAAGATA 14760
CGGCAACCCAGATGAAGTTCTCTAGTGCAACACTAGTCCGTGCAAGTCGGTTCATAACAA 14820
TATCAAATGATAACATGGCACTCAAAGAAGCAGGGGAGTCGAAGGATACTAATCTCGTGT 14880
ATCAGCAGATTATGCTAACTGGGCTAAGCTTGTTCGAGTTCAATATGAGATATAAGAAAG 14940
GTTCCTTAGGGAAGCCACTGATATTGCACTTACATCTTAATAACGGGTGCTGTATAATGG 15000
AGTCCCCACAGGAGGCGAATATCCCCCCAAGGTCCACATTAGATTTAGAGATTACACAAG 15060
AGAACAATAAATTGATCTATGATCCTGATCCACTCAAGGATGTGGACCTTGAGCTATTTA 15120
GCAAGGTCAGAGATGTTGTACACACAGTTGACATGACTTATTGGTCAGATGATGAAGTTA 15180
TCAGAGCAACCAGTATCTGTACTGCAATGACGATAGCTGATACAATGTCTCAATTAGATA 15240
GAGACAACTTAAAAGAGATGATCGCACTAGTAAATGACGATGATGTCAACAGCTTGATTA 15300
CTGAGTTTATGGTGATTGATGTTCCTTTATTTTGCTCAACGTTCGGGGGTATTCTAGTCA 15360
ATCAGTTTGCATACTCACTCTACGGCTTAAACATCAGAGGAAGGGAAGAAATATGGGGAC 15420
ATGTAGTCCGGATTCTTAAAGATACCTCCCACGCAGTTTTAAAAGTCTTATCTAATGCTC 15480
TATCTCATCCCAAAATCTTCAAACGATTCTGGAATGCAGGTGTCGTGGAACCTGTGTATG 15540
GGCCTAACCTCTCAAATCAGGATAAGATACTCTTGGCCCTCTCTGTCTGTGAATATTCTG 15600
TGGATCTATTCATGCACGATTGGCAAGGGGGTGTACCGCTTGAGATCTTTATCTGTGACA 15660
ATGACCCAGATGTGGCCGACATGAGGAGGTCCTCTTTCTTGGCAAGACATCTTGCATACC 15720
TATGCAGCTTGGCAGAGATATCTAGGGATGGGCCAAGATTAGAATCAATGAACTCTCTAG 15780
AGAGGCTCGAGTCACTAAAGAGTTACCTGGAACTCACATTTCTTGATGACCCGGTACTGA 15840
GGTACAGTCAGTTGACTGGCCTAGTCATCAAAGTATTCCCATCTACTTTGACCTATATCC 15900
GGAAGTCATCTATAAAAGTGTTAAGGACAAGAGGTATAGGAGTCCCTGAAGTCTTAGAAG 15960
ATTGGGATCCCGAGGCAGATAATGCACTGTTAGATGGTATCGCGGCAGAAATACAACAGA 16020
ATATTCCTTTGGGACATCAGACTAGAGCCCCTTTTTGGGGGTTGAGAGTATCCAAGTCAC 16080
AGGTACTGCGTCTCCGGGGGTACAAGGAGATCACAAGAGGTGAGATAGGCAGATCAGGTG 16140
TTGGTCTGACGTTACCATTCGATGGAAGATATCTATCTCACCAGCTGAGGCTCTTTGGCA 16200
TCAACAGTACTAGCTGCTTGAAAGCACTTGAACTTACCTACCTATTGAGCCCCTTAGTTG 16260
ACAAGGATAAAGATAGGCTATATTTAGGGGAAGGAGCTGGGGCCATGCTTTCCTGTTATG 16320
ACGCTACTCTTGGCCCATGCATCAACTATTATAACTCAGGGGTATACTCTTGTGATGTCA 16380
ATGGGCAGAGAGAGTTAAATATATATCCTGCTGAGGTGGCACTAGTGGGAAAGAAATTAA 16440
ACAATGTTACTAGTCTGGGTCAAAGAGTTAAAGTGTTATTCAACGGGAATCCTGGCTCGA 16500
CATGGATTGGGAATGATGAGTGTGAGGCTTTGATTTGGAATGAATTACAGAATAGCTCGA 16560

FIG. 8Q

TAGGCCTAGTCCACTGTGACATGGAGGGAGGAGATCATAAGGATGATCAAGTTGTACTGC 16620

ATGAGCATTACAGTGTAATCCGGATCGCGTATCTGGTGGGGGATCGAGACGTTGTGCTTA 16680

TAAGCAAGATTGCTCCCAGGCTGGGCACGGATTGGACCAGGCAGCTCAGCCTATATCTGA 16740

GATACTGGGACGAGGTTAACCTAATAGTGCTTAAAACATCTAACCCTGCTTCCACAGAGA 16800

TGTATCTCCTATCGAGGCACCCCAAATCTGACATTATAGAGGACAGCAAGACAGTGTTAG 16860

CTAGTCTCCTCCCTTTGTCAAAAGAAGATAGCATCAAGATAGAAAAGTGGATCTTAATAG 16920

AGAAGGCAAAGGCTCACGAATGGGTTACTCGGGAATTGAGAGAAGGAAGCTCTTCATCAG 16980

GGATGCTTAGACCTTACCATCAAGCACTGCAGACGTTTGGCTTTGAACCAAACTTGTATA 17040

AATTGAGCAGAGATTTCTTGTCCACCATGAACATAGCTGATACACACAACTGCATGATAG 17100

CTTTCAACAGGGTTTTGAAGGATACAATCTTCGAATGGGCTAGAATAACTGAGTCAGATA 17160

AAAGGCTTAAACTAACTGGTAAGTATGACCTGTATCCTGTGAGAGATTCAGGCAAGTTGA 17220

AGACAATTTCTAGAAGACTTGTGCTATCTTGGATATCTTTATCTATGTCCACAAGATTGG 17280

TAACTGGGTCATTCCCTGACCAGAAGTTTGAAGCAAGACTTCAATTGGGAATAGTTTCAT 17340

TATCATCCCGTGAAATCAGGAACCTGAGGGTTATCACAAAAACTTTATTAGACAGGTTTG 17400

AGGATATTATACATAGTATAACGTATAGATTCCTCACCAAAGAAATAAAGATTTTGATGA 17460

AGATTTTAGGGGCAGTCAAGATGTTCGGGGCCAGGCAAAATGAATACACGACCGTGATTG 17520

ATGATGGATCACTAGGTGATATCGAGCCATATGACAGCTCGTAATAATTAGTCCCTATCG 17580

TGCAGAACGATCGAAGCTCCGCGGTACCTGGAAGTCTTGGACTTGTCCATATGACAATAG 17640

TAAGAAAAACTTACAAGAAGACAAGAAAATTTAAAAGGATACATATCTCTTAAACTCTTG 1770

TCTGGT 17706 sfEnvF: Red characters
NP: Blue characters, P: Green characters, M: Brown characters, F: Orange characters, HN: Pink characters, L: Violet characters The nucleotide sequence of SeV-sgEnvG(NP)

ACCAAACAAGAGAAAAAACATGTATGGGATATGTAATGAAGTTATACAGGATTTTAGGGT 60

CAAAGTATCCACCCTGAGGAGCAGGTTCCAGACCCTTTGCTTTGCTGCCAAAGTTCAC[redacted] 120

[redacted]CAAGGTTCACTTATGAAGTGCCTTTTGTACTTAGCTTTCTTATTCATCGGGGTG 180
NotI -> sgEnvG

AATTGCAAGGCTAGCGCAGAGAATTTGTGGGTAACAGTCTACTATGGAGTCCCTGTATGG 240

AAGGATGCAGAGACAACATTGTTCTGTGCTAGTGACGCAAAGGCTTACGAGACGGAGAAG 300

CACAATGTGTGGGCAACTCACGCATGTGTCCCAACCGATCCAAATCCTCAAGAGATTCAT 360

CTAGAGAATGTGACTGAAGAATTCAATATGTGGAAGAATAATATGGTAGAGCAAATGCAT 420

FIG. 8R

ACAGATATCATTAGTTTATGGGACCAGTCACTTAAACCCTGCGTTAAATTGACGCCTCTA 480

TGTGTGACACTTCAATGTACTAATGTTACAAACAACATAACAGATGATATGAGAGGAGAA 540

CTGAAGAACTGTAGTTTCAACATGACGACAGAGTTGCGTGACAAGAAACAGAAAGTGTAT 600

TCACTATTCTATCGGTTGGATGTAGTACAGATAAATGAGAATCAAGGAAACAGGTCCAAC 660

AACTCTAACAAAGAGTACAGACTTATTAATTGCAATACCAGTGCTATCACGCAAGCCTGC 720

CCAAAGGTTTCATTTGAACCAATACCTATTCATTATTGTGCACCTGCTGGATTCGCCATC 780

CTCAAATGTAAAGACAAGAAGTTCAATGGAACAGGACCCTGCCCATCAGTTTCAACCGTT 840

CAGTGCACCCACGGAATCAAGCCTGTAGTTAGTACTCAATTATTGTTAAATGGGAGCTTA 900

GCTGAAGAAGAAGTTATGATTAGATCAGAGAATATTACCAATAATGCGAAGAACATCTTG 960

GTTCAATTCAATACTCCAGTCCAGATCAATTGCACAAGGCCTAATAATAATACCAGAAAG 1020

AGTATAAGAATTGGGCCAGGACAGGCATTCTATGCAACAGGAGATATAATCGGAGACATT 1080

CGACAAGCGCACTGCACTGTTTCTAAGGCCACTTGGAATGAAACATTGGGTAAAGTTGTA 1140

AAGCAACTTCGGAAGCATTTCGGAAATAACACAATTATTAGATTTGCGAACTCATCTGGA 1200

GGGGATCTGGAAGTGACAACACACTCTTTCAATTGCGGTGGCGAGTTCTTCTATTGTAAT 1260

ACAAGTGGATTATTTAACTCTACTTGGATTTCAAATACCTCAGTCCAAGGATCTAATTCA 1320

ACAGGGTCTAACGATTCTATAACATTACCTTGCCGTATAAAGCAAATTATTAATATGTGG 1380

CAAAGAATCGGGCAAGCGATGTATGCTCCACCTATTCAAGGCGTGATTCGTTGCGTTTCA 1440

AACATAACAGGGTTGATCCTGACCAGGGATGGAGGCTCTACCAATTCCACCACCGAGACC 1500

TTCCGTCCCGGTGGCGGAGATATGCGGGATAACTGGAGATCAGAGCTCTATAAGTATAAG 1560

GTTGTGAAGATTGAACCTCTTGGAGTTGCCCCTACAAGAGCAAAGAGAAGGGTGGTTGGC 1620

CGAGAGAAGAGAGCAGTTGGCATCGGTGCTGTCTTTCTCGGATTTCTTGGAGCAGCTGGA 1680

TCCACTATGGGAGCAGCATCAATGACACTAACAGTGCAGGCTAGAAATTTGCTTAGCGGA 1740

ATCGTTCAGCAGCAGAGCAATTTACTAAGAGCAATTGAAGCACAGCAACATCTCTTAAAG 1800

TTGACGGTGTGGGGCATTAAACAACTACAAGCGAGAGTGCTTGCCGTCGAAAGATATTTG 1860

CGAGACCAACAGCTATTGGGTATTTGGGGTTGTTCTGGGAAATTAATTTGCACAACAAAT 1920

GTTCCATGGAACTCCTCCTGGAGTAATAGGAATTTAAGTGAGATATGGGACAACATGACA 1980

TGGTTGCAGTGGGACAAGGAAATCTCAAATTATACACAGATAATCTATGGATTATTAGAA 2040

GAGTCTCAGAATCAGCAAGAGAAGAATGAACAGGATTTGCTTGCATTGGATAAGTGGGCT 2100

TCTCTATGGAACTGGTTCGATATTAGTAATTGGCTCTGGTATATTAAGAGCTCTATTGCC 2160

TCTTTTTTCTTTATCATAGGGTTAATCATTGGACTATTCTTGGTTCTCCGAGTTGGTATT 2220

FIG. 8S

TATCTTTGCATTAAATTAAAGCACACCAAGAAAAGACAGATTTATACAGACATAGAGATG 2280

AACCGACTTGGAAAGTAACCGTAGTAAGAAAAACTTAGGGTGAAAGTTCATC[redacted] 2340
NotI

AGATCTTCACGATGGCCGGGTTGTTGAGCACCTTCGATACATTTAGCTCTAGGAGGAGCG 2400
-> NP

AAAGTATTAATAAGTCGGGAGGAGGTGCTGTTATCCCCGGCCAGAGGAGCACAGTCTCAG 2460

TGTTCGTACTAGGCCCAAGTGTGACTGATGATGCAGACAAGTTATTCATTGCAACTACCT 2520

TCCTAGCTCACTCATTGGACACAGATAAGCAGCACTCTCAGAGAGGGGGGTTCCTCGTCT 2580

CTCTGCTTGCCATGGCTTACAGTAGTCCAGAATTGTACTTGACAACAAACGGAGTAAACG 2640

CCGATGTCAAATATGTGATCTACAACATAGAGAAAGACCCTAAGAGGACGAAGACAGACG 2700

GATTCATTGTGAAGACGAGAGATATGGAATATGAGAGGACCACAGAATGGCTGTTTGGAC 2760

CTATGGTCAACAAGAGCCCACTCTTCCAGGGTCAACGGGATGCTGCAGACCCTGACACAC 2820

TCCTTCAAATCTATGGGTATCCTGCATGCCTAGGAGCAATAATTGTCCAAGTCTGGATTG 2880

TGCTGGTGAAGGCCATCACAAGCAGCGCCGGCTTAAGGAAAGGGTTCTTCAACAGGTTAG 2940

AGGCGTTCAGACAAGACGGCACCGTGAAAGGTGCCTTAGTTTTCACTGGGGAGACAGTTG 3000

AGGGGATAGGCTCGGTTATGAGATCTCAGCAAAGCCTTGTATCTCTCATGGTTGAGACCC 3060

TTGTGACTATGAATACTGCAAGATCTGATCTCACCACATTAGAGAAGAACATCCAGATCG 3120

TTGGGAACTACATCCGAGATGCAGGGCTGGCTTCCTTCATGAACACTATTAAATATGGGG 3180

TGGAAACAAAGATGGCAGCTCTAACGTTGTCAAACCTGAGGCCCGATATTAATAAGCTTA 3240

GAAGCCTCATAGACACCTACCTGTCAAAAGGCCCCAGAGCTCCCTTTATCTGTATCCTCA 3300

AGGACCCTGTTCATGGTGAATTTGCTCCAGGCAATTATCCTGCACTATGGAGTTACGCCA 3360

TGGGAGTCGCCGTCGTACAGAACAAGGCAATGCAGCAGTACGTCACAGGGAGGACATACC 3420

TTGATATGGAAATGTTCTTACTAGGACAAGCCGTGGCAAAGGATGCTGAATCGAAGATCA 3480

GCAGTGCCTTGGAAGATGAGTTAGGAGTGACGGATACAGCCAAGGGGAGGCTCAGACATC 3540

ATCTGGCAAACTTGTCCGGTGGGGATGGTGCTTACCACAAACCAACAGGCGGTGGTGCAA 3600

TTGAGGTAGCTCTAGACAATGCCGACATCGACCTAGAAACAAAAGCCCATGCGGACCAGG 3660

ACGCTAGGGGTTGGGGTGGAGATAGTGGTGAAAGATGGGCACGTCAGGTGAGTGGTGGCC 3720

ACTTTGTCACACTACATGGGGCTGAACGGTTAGAGGAGGAAACCAATGATGAGGATGTAT 3780

CAGACATAGAGAGAAGAATAGCCATGAGACTCGCAGAGAGACGGCAAGAGGATTCTGCAA 3840

CCCATGGAGATGAAGGCCGCAATAACGGTGTCGATCATGACGAAGATGACGATGCCGCAG 3900

CAGTAGCTGGGATAGGAGGAATCTAGGATCATACGAGGCTTCAAGGTACTTGATCCGTAG 3960

TAAGAAAAACTTAGGGTGAAAGTTCATCCACCGATCGGCTCAGGCAAGGCCACACCCAAC 4020

CCCACCGACCACACCCAGCAGTCGAGACAGCCACGGCTTCGGCTACACTTACCGCATGGA 4080
-> P

FIG. 8T

TCAAGATGCCTTCATTCTTAAAGAAGATTCTGAAGTTGAGAGGGAGGCGCCAGGAGGACG 4140

AGAGTCGCTCTCGGATGTTATCGGATTCCTCGATGCTGTCCTGTCGAGTGAACCAACTGA 4200

CATCGGAGGGGACAGAAGCTGGCTCCACAACACCATCAACACTCCCCAAGGACCAGGCTC 4260

TGCTCATAGAGCCAAAAGTGAGGGCGAAGGAGAAGTCTCAACACCGTCGACCCAAGATAA 4320

TCGATCAGGTGAGGAGAGTAGAGTCTCTGGGAGAACAAGCAAGCCAGAGGCAGAAGCACA 4380

TGCTGGAAACCTTGATAAACAAAATATACACCGGGCCTTTGGGGGAAGAACTGGTACAAA 4440

CTCTGTATCTCAGGATCTGGGCGATGGAGGAGACTCCGGAATCCTTGAAAATCCTCCAAA 4500

TGAGAGAGGATATCCGAGATCAGGTATTGAAGATGAAAACAGAGAGATGGCTGCGCACCC 4560

TGATAAGAGGGGAGAAGACCAAGCTGAAGGACTTCCAGAAGAGGTACGAGGAAGTACATC 4620

CCTACCTGATGAAGGAGAAGGTGGAGCAAGTAATAATGGAAGAAGCATGGAGCCTGGCAG 4680

CTCACATAGTGCAAGAGTAACTGGGGTCCTGGTGATTCCTAGCCCCGAACTTGAAGAGGC 4740

TGTGCTACGGAGGAACAAAAGAAGACCTACCAACAGTGGGTCCAAACCTCTTACTCCAGC 4800

AACCGTGCCTGGCACCCGGTCCCCACCGCTGAATCGTTACAACAGCACAGGGTCACCACC 4860

AGGAAAACCCCCATCTACACAGGATGAGCACATCAACTCTGGGGACACCCCCGCCGTCAG 4920

GGTCAAAGACCGGAAACCACCAATAGGGACCCGCTCTGTCTCAGATTGTCCAGCCAACGG 4980

CCGCCCAATCCACCCGGGTCTAGAGACCGACTCAACAAAAAAGGGCATAGGAGAGAACAC 5040

ATCATCTATGAAAGAGATGGCTACATTGTTGACGAGTCTTGGTGTAATCCAGTCTGCTCA 5100

AGAATTCGAATCATCCCGAGACGCGAGTTATGTGTTTGCAAGACGTGCCCTAAAGTCTGC 5160

AAACTATGCAGAGATGACATTCAATGTATGCGGCCTGATCCTTTCTGCCGAGAAATCTTC 5220

CGCTCGTAAGGTAGATGAGAACAAACAACTGCTCAAACAGATCCAAGAGAGCGTGGAATC 5280

ATTCCGGGATATTTACAAGAGATTCTCTGAGTATCAGAAAGAACAGAACTCATTGCTGAT 5340

GTCCAACCTATCTACACTTCATATCATCACAGATAGAGGTGGCAAGACTGACAACACAGA 5400

CTCCCTTACAAGGTCCCCCTCCGTTTTTGCAAAATCAAAAGAGAACAAGACTAAGGCTAC 5460

CAGGTTTGACCCATCTATGGAGACCCTAGAAGATATGAAGTACAAACCGGACCTAATCCG 5520

AGAGGATGAATTTAGAGATGAGATCCGCAACCCGGTGTACCAAGAGAGGGACACAGAACC 5580

CAGGGCCTCAAACGCATCACGTCTCCTCCCCTCCAAAGAGAAGCCCACAATGCACTCTCT 5640

CAGGCTCGTCATAGAGAGCAGTCCCCTAAGCAGAGCTGAGAAAGTAGCATATGTGAAATC 5700

ATTATCCAAGTGCAAGACAGACCAAGAGGTTAAGGCAGTCATGGAACTCGTAGAAGAGGA 5760

CATAGAGTCACTGACCAACTAGATCCCGGGTGAGGCATCCTACCATCCTCAGTCATAGAG 5820

AGATCCAATCTACCATCAGCATCAGCCAGTAAAGATTAAGAAAAACTTAGGGTGAAAGAA 5880

ATTTCACCTAACACGGCGCAATGGCAGATATCTATAGATTCCCTAAGTTCTCATATGAGG 5940

ATAACGGTACTGTGGAGCCCCTGCCTCTGAGAACTGGTCCGGATAAGAAAGCCATCCCCC 6000

ACATCAGGATTGTCAAGGTAGGAGACCCTCCTAAACATGGAGTGAGATACCTAGATTTAT 6060

TGCTCTTGGGTTTCTTTGAGACACCGAAACAAACAACCAATCTAGGGAGCGTATCTGACT 6120

TGACAGAGCCGACCAGCTACTCAATATGCGGCTCCGGGTCGTTACCCATAGGTGTGGCCA 6180

AATACTACGGGACTGATCAGGAACTCTTAAAGGCCTGCACCGATCTCAGAATTACGGTGA 6240

GGAGGACTGTTCGAGCAGGAGAGATGATCGTATACATGGTGGATTCGATTGGTGCTCCAC 6300

TCCTACCATGGTCAGGCAGGCTGAGACAGGGAATGATATTTAATGCAAACAAGGTCGCAC 6360

TAGCTCCCCAATGCCTCCCTGTGGACAAGGACATAAGACTCAGAGTGGTGTTTGTCAATG 6420

GGACATCTCTAGGGGCAATCACCATAGCCAAGATCCCAAAGACCCTTGCAGACCTTGCAT 6480

TGCCCAACTCTATATCTGTTAATTTACTGGTGACACTCAAGACCGGGATCTCCACAGAAC 6540

AAAAGGGGGTACTCCCAGTACTTGATGATCAAGGGGAGAAAAAGCTCAATTTTATGGTGC 6600

ACCTCGGGTTGATCAGGAGAAAGGTCGGGAAGATATACTCTGTTGAGTACTGCAAGAGCA 6660

AGATTGAGAGAATGCGGCTGATTTTCTCACTTGGGTTAATCGGCGGTATAAGCTTCCATG 6720

TTCAGGTTAATGGGACACTATCTAAGACATTCATGAGTCAGCTCGCATGGAAGAGGGCAG 6780

TCTGCTTCCCATTAATGGATGTGAATCCCCATATGAACATGGTGATTTGGGCGGCATCTG 6840

TAGAAATCACAGGCGTCGATGCGGTGTTCCAACCGGCCATCCCTCGTGATTTCCGCTACT 6900

ACCCTAATGTTGTGGCTAAGAACATCGGAAGGATCAGAAAGCTGTAAATGTGCACCCATC 6960

AGAGACCTGCGACAATGCCCCAAGCAGACACCACCTGGCAGTCGGAGCCACCGGGTCACT 7020

CCTTGTCTTAAATAAGAAAAACTTAGGGATAAAGTCCCTTGTGAGTGCTTGGTTGCAAAA 7080

CTCTCCCCTTGGGAAACATGACAGCATATATCCAGAGATCACAGTGCATCTCAACATCAC 7140

-> F

TACTGGTTGTTCTCACCACATTGGTCTCGTGTCAGATTCCCAGGGATAGGCTCTCTAACA 7200

TAGGGGTCATAGTCGATGAAGGGAAATCACTGAAGATAGCTGGATCCCACGAATCGAGGT 7260

ACATAGTACTGAGTCTAGTTCCGGGGGTAGACTTTGAGAATGGGTGCGGAACAGCCCAGG 7320

TTATCCAGTACAAGAGCCTACTGAACAGGCTGGTTAATCCCATTGAGGGATGCCTTAGATC 7380

TTCAGGAGGCTCTGATAACTGTCACCAATGATACGACACAAAATGCCGGTGCTCCCCAGT 7440

CGAGATTCTTCGGTGCTGTGATTGGTACTATCGCACTTGGAGTGGCGACATCAGCACAAA 7500

TCACCGCAGGGATTGCACTAGCCGAAGCGAGGGAGGCCAAAAGAGACATAGCGCTCATCA 7560

AAGAATCGATGACAAAAACACACAAGTCTATAGAACTGCTGCAAAACGCTGTGGGGGAAC 7620

AAATTCTTGCTCTAAAGACACTCCAGGATTTCGTGAATGATGAGATCAAACCCGCAATAA 7680

GCGAATTAGGCTGTGAGACTGCTGCCTTAAGACTGGGTATAAAATTGACACAGCATTACT 7740

CCGAGCTGTTAACTGCGTTCGGCTCGAATTTCGGAACCATCGGAGAGAAGAGCCTCACGC 7800

FIG. 8V

TGCAGGCGCTGTCTTCACTTTACTCTGCTAACATTACTGAGATTATGACCACAATCAGGA 7860

CAGGGCAGTCTAACATCTATGATGTCATTTATACAGAACAGATCAAAGGAACGGTGATAG 7920

ATGTGGATCTAGAGAGATACATGGTCACCCTGTCTGTGAAGATCCCTATTCTTTCTGAAG 7980

TCCCAGGTGTGCTCATACACAAGGCATCATCTATTTCTTACAACATAGACGGGGAGGAAT 8040

GGTATGTGACTGTCCCCAGCCATATACTCAGTCGTGCTTCTTTCTTAGGGGGTGCAGACA 8100

TAACCGATTGTGTTGAGTCCAGATTGACCTATATATGCCCCAGGGATCCCGCACAACTGA 8160

TACCTGACAGCCAGCAAAAGTGTATCCTGGGGGACACAACAAGGTGTCCTGTCACAAAAG 8220

TTGTGGACAGCCTTATCCCCAAGTTTGCTTTTGTGAATGGGGGCGTTGTTGCTAACTGCA 8280

TAGCATCCACATGTACCTGCGGGACAGGCCGAAGACCAATCAGTCAGGATCGCTCTAAAG 8340

GTGTAGTATTCCTAACCCATGACAACTGTGGTCTTATAGGTGTCAATGGGGTAGAATTGT 8400

ATGCTAACCGGAGAGGGCACGATGCCACTTGGGGGGTCCAGAACTTGACAGTCGGTCCTG 8460

CAATTGCTATCAGACCCGTTGATATTTCTCTCAACCTTGCTGATGCTACGAATTTCTTGC 8520

AAGACTCTAAGGCTGAGCTTGAGAAAGCACGGAAAATCCTCTCGGAGGTAGGTAGATGGT 8580

ACAACTCAAGAGAGACTGTGATTACGATCATAGTAGTTATGGTCGTAATATTGGTGGTCA 8640

TTATAGTGATCATCATCGTGCTTTATAGACTCAGAAGGTCAATGCTAATGGGTAATCCAG 8700

ATGACCGTATACCGAGGGACACATACACATTAGAGCCGAAGATCAGACATATGTACACAA 8760

ACGGTGGGTTTGATGCAATGGCTGAGAAAAGATGATCACGACCATTATCAGATGTCTTGT 8820

AAAGCAGGCATAGTATCCGTTGAGATCTGTATATAATAAGAAAAACTTAGGGTGAAAGTG 8880

AGGTCGCGCGGTACTTTAGCTTTCACCTCAAACAAGCACAGATCATGGATGGTGATAGGG 8940

-> HN

GCAAACGTGACTCGTACTGGTCTACTTCTCCTAGTGGTAGCACCACAAAACCAGCATCAG 9000

GTTGGGAGAGGTCAAGTAAAGCCGACACATGGTTGCTGATTCTCTCATTCACCCAGTGGG 9060

CTTTGTCAATTGCCACAGTGATCATCTGTATCATAATTTCTGCTAGACAAGGGTATAGTA 9120

TGAAAGAGTACTCAATGACTGTAGAGGCATTGAACATGAGCAGCAGGGAGGTGAAAGAGT 9180

CACTTACCAGTCTAATAAGGCAAGAGGTTATAGCAAGGGCTGTCAACATTCAGAGCTCTG 9240

TGCAAACCGGAATCCCAGTCTTGTTGAACAAAAACAGCAGGGATGTCATCCAGATGATTG 9300

ATAAGTCGTGCAGCAGACAAGAGCTCACTCAGCACTGTGAGAGTACGATCGCAGTCCACC 9360

ATGCCGATGGAATTGCCCCACTTGAGCCACATAGTTTCTGGAGATGCCCTGTCGGAGAAC 9420

CGTATCTTAGCTCAGATCCTGAAATCTCATTGCTGCCTGGTCCGAGCTTGTTATCTGGTT 9480

CTACAACGATCTCTGGATGTGTTAGGCTCCCTTCACTCTCAATTGGCGAGGCAATCTATG 9540

CCTATTCATCAAATCTCATTACACAAGGTTGTGCTGACATAGGGAAATCATATCAGGTCC 9600

TGCAGCTAGGGTACATATCACTCAATTCAGATATGTTCCCTGATCTTAACCCCGTAGTGT 9660

CCCACACTTATGACATCAACGACAATCGGAAATCATGCTCTGTGGTGGCAACCGGGACTA 9720

FIG. 8W

GGGGTTATCAGCTTTGCTCCATGCCGACTGTAGACGAAAGAACCGACTACTCTAGTGATG 9780

GTATTGAGGATCTGGTCCTTGATGTCCTGGATCTCAAAGGGAGAACTAAGTCTCACCGGT 9840

ATCGCAACAGCGAGGTAGATCTTGATCACCCGTTCTCTGCACTATACCCCAGTGTAGGCA 9900

ACGGCATTGCAACAGAAGGCTCATTGATATTTCTTGGGTATGGTGGACTAACCACCCCTC 9960

TGCAGGGTGATACAAAATGTAGGACCCAAGGATGCCAACAGGTGTCGCAAGACACATGCA 10020

ATGAGGCTCTGAAAATTACATGGCTAGGAGGGAAACAGGTGGTCAGCGTGATCATCCAGG 10080

TCAATGACTATCTCTCAGAGAGGCCAAAGATAAGAGTCACAACCATTCCAATCACTCAAA 10140

ACTATCTCGGGGCGGAAGGTAGATTATTAAAATTGGGTGATCGGGTGTACATCTATACAA 10200

GATCATCAGGCTGGCACTCTCAACTGCAGATAGGAGTACTTGATGTCAGCCACCCTTTGA 10260

CTATCAACTGGACACCTCATGAAGCCTTGTCTAGACCAGGAAATAAAGAGTGCAATTGGT 10320

ACAATAAGTGTCCGAAGGAATGCATATCAGGCGTATACACTGATGCTTATCCATTGTCCC 10380

CTGATGCAGCTAACGTCGCTACCGTCACGCTATATGCCAATACATCGCGTGTCAACCCAA 10440

CAATCATGTATTCTAACACTACTAACATTATAAATATGTTAAGGATAAAGGATGTTCAAT 10500

TAGAGGCTGCATATACCACGACATCGTGTATCACGCATTTTGGTAAAGGCTACTGCTTTC 10560

ACATCATCGAGATCAATCAGAAGAGCCTGAATACCTTACAGCCGATGCTCTTTAAGACTA 10620

GCATCCCTAAATTATGCAAGGCCGAGTCTTAAATTTAACTGACTAGCAGGCTTGTCGGCC 10680

TTGCTGACACTAGAGTCATCTCCGAACATCCACAATATCTCTCAGTCTCTTACGTCTCTC 10740

ACAGTATTAAGAAAAACCCAGGGTGAATGGGAAGCTTGCCATAGGTCATGGATGGGCAGG 10800

-> L

AGTCCTCCCAAAACCCTTCTGACATACTCTATCCAGAATGCCACCTGAACTCTCCCATAG 10860

TCAGGGGGAAGATAGCACAGTTGCACGTCTTGTTAGATGTGAACCAGCCCTACAGACTGA 10920

AGGACGACAGCATAATAAATATTACAAAGCACAAAATTAGGAACGGAGGATTGTCCCCCC 10980

GTCAAATTAAGATCAGGTCTCTGGGTAAGGCTCTTCAACGCACAATAAAGGATTTAGACC 11040

GATACACGTTTGAACCGTACCCAACCTACTCTCAGGAATTACTTAGGCTTGATATACCAG 11100

AGATATGTGACAAAATCCGATCCGTCTTCGCGGTCTCGGATCGGCTGACCAGGGAGTTAT 11160

CTAGTGGGTTCCAGGATCTTTGGTTGAATATCTTCAAGCAACTAGGCAATATAGAAGGAA 11220

GAGAGGGGTACGATCCGTTGCAGGATATCGGCACCATCCCGGAGATAACTGATAAGTACA 11280

GCAGGAATAGATGGTATAGGCCATTCCTAACTTGGTTCAGCATCAAATATGACATGCGGT 11340

GGATGCAGAAGACCAGACCGGGGGGACCCCTCGATACCTCTAATTCACATAACCTCCTAG 11400

AATGCAAATCATACACTCTAGTAACATACGGAGATCTTGTCATGATACTGAACAAGTTGA 11460

CATTGACAGGGTATATCCTAACCCCTGAGCTGGTCTTGATGTATTGTGATGTTGTAGAAG 11520

GAAGGTGGAATATGTCTGCTGCAGGGCATCTAGATAAGAAGTCCATTGGGATAACAAGCA 11580

FIG. 8X

AAGGTGAGGAATTATGGGAACTAGTGGATTCCCTCTTCTCAAGTCTTGGAGAGGAAATAT 11640
ACAATGTCATCGCACTATTGGAGCCCCTATCACTTGCTCTCATACAACTAAATGATCCTG 11700
TTATACCTCTACGTGGGGCATTTATGAGGCATGTGTTGACAGAGCTACAGACTGTTTTAA 11760
CAAGTAGAGACGTGTACACAGATGCTGAAGCAGACACTATTGTGGAGTCGTTACTCGCCA 11820
TTTTCCATGGAACCTCTATTGATGAGAAAGCAGAGATCTTTTCCTTCTTTAGGACATTTG 11880
GCCACCCCAGCTTAGAGGCTGTCACTGCCGCCGACAAGGTAAGGGCCCATATGTATGCAC 11940
AAAAGGCAATAAAGCTTAAGACCCTATACGAGTGTCATGCAGTTTTTTGCACTATCATCA 12000
TAAATGGGTATAGAGAGAGGCATGGCGGACAGTGGCCCCCCTGTGACTTCCCTGATCACG 12060
TGTGTCTAGAACTAAGGAACGCTCAAGGGTCCAATACGGCAATCTCTTATGAATGTGCTG 12120
TAGACAACTATACAAGTTTCATAGGCTTCAAGTTTCGGAAGTTTATAGAACCACAACTAG 12180
ATGAAGATCTCACAATATATATGAAAGACAAAGCACTATCCCCCAGGAAGGAGGCATGGG 12240
ACTCTGTATACCCGGATAGTAATCTGTACTATAAAGCCCCAGAGTCTGAAGAGACCCGGC 12300
GGCTTATTGAAGTGTTCATAAATGATGAGAATTTCAACCCAGAAGAAATTATCAATTATG 12360
TGGAGTCAGGAGATTGGTTGAAAGACGAGGAGTTCAACATCTCGTACAGTCTCAAAGAGA 12420
AAGAGATCAAGCAAGAGGGTCGTCTATTCGCAAAAATGACTTATAAGATGCGAGCCGTAC 12480
AGGTGCTGGCAGAGACACTACTGGCTAAAGGAATAGGAGAGCTATTCAGCGAAAATGGGA 12540
TGGTTAAAGGAGAGATAGACCTACTTAAAAGATTGACTACTCTTTCTGTCTCAGGCGTCC 12600
CCAGGACTGATTCAGTGTACAATAACTCTAAATCATCAGAGAAGAGAAACGAAGGCATGG 12660
AAAATAAGAACTCTGGGGGGTACTGGGACGAAAAGAAGAGGTCCAGACATGAATTCAAGG 12720
CAACAGATTCATCAACAGACGGCTATGAAACGTTAAGTTGCTTCCTCACAACAGACCTCA 12780
AGAAATACTGCTTAAACTGGAGATTTGAGAGTACTGCATTGTTTGGTCAGAGATGCAACG 12840
AGATATTTGGCTTCAAGACCTTCTTTAACTGGATGCATCCAGTCCTTGAAAGGTGTACAA 12900
TATATGTTGGAGATCCTTACTGTCCAGTCGCCGACCGGATGCATCGACAACTCCAGGATC 12960
ATGCAGACTCTGGCATTTTCATACATAATCCTAGGGGGGGCATAGAAGGTTACTGCCAGA 13020
AGCTGTGGACCTTAATCTCAATCAGTGCAATCCACCTAGCAGCTGTGAGAGTGGGTGTCA 13080
GGGTCTCTGCAATGGTTCAGGGTGACAATCAAGCTATAGCCGTGACATCAAGAGTACCTG 13140
TAGCTCAGACTTACAAGCAGAAGAAAAATCATGTCTATGAGGAGATCACCAAATATTTCG 13200
GTGCTCTAAGACACGTCATGTTTGATGTAGGGCACGAGCTAAAATTGAACGAGACCATCA 13260
TTAGTAGCAAGATGTTTGTCTATAGTAAAAGGATATACTATGATGGGAAGATTTTACCAC 13320
AGTGCCTGAAAGCCTTGACCAAGTGTGTATTCTGGTCCGAGACACTGGTAGATGAAAACA 13380
GATCTGCTTGTTCGAACATCTCAACATCCATAGCAAAAGCTATCGAAAATGGGTATTCTC 13440

FIG. 8Y

CTATACTAGGCTACTGCATTGCGTTGTATAAGACCTGTCAGCAGGTGTGCATATCACTAG 13500
GGATGACTATAAATCCAACTATCAGCCCGACCGTAAGAGATCAATACTTTAAGGGTAAGA 13560
ATTGGCTGAGATGTGCAGTGTTGATTCCAGCAAATGTTGGAGGATTCAACTACATGTCTA 13620
CATCTAGATGCTTTGTTAGAAATATTGGAGACCCCGCAGTAGCAGCCCTAGCTGATCTCA 13680
AAAGATTCATCAGAGCGGATCTGTTAGACAAGCAGGTATTATACAGGGTCATGAATCAAG 13740
AACCCGGTGACTCTAGTTTTCTAGATTGGGCTTCAGACCCTTATTCGTGTAACCTCCCGC 13800
ATTCTCAGAGTATAACTACGATTATAAAGAATATCACTGCTAGATCTGTGCTGCAGGAAT 13860
CCCCGAATCCTCTACTGTCTGGTCTCTTCACCGAGACTAGTGGAGAAGAGGATCTCAACC 13920
TGGCCTCGTTCCTTATGGACCGGAAAGTCATCCTGCCGAGAGTGGCTCATGAGATCCTGG 13980
GTAATTCCTTAACTGGAGTTAGGGAGGCGATTGCAGGGATGCTTGATACGACCAAGTCTC 14040
TAGTGAGAGCCAGCGTTAGGAAAGGAGGATTATCATATGGGATATTGAGGAGGCTTGTCA 14100
ATTATGATCTATTGCAGTACGAGACACTGACTAGAACTCTCAGGAAACCGGTGAAAGACA 14160
ACATCGAATATGAGTATATGTGTTCAGTTGAGCTAGCTGTCGGTCTAAGGCAGAAAATGT 14220
GGATCCACCTGACTTACGGGAGACCCATACATGGGCTAGAAACACCAGACCCTTTAGAGC 14280
TCTTGAGGGGAATATTTATCGAAGGTTCAGAGGTGTGCAAGCTTTGCAGGTCTGAAGGAG 14340
CAGACCCCATCTATACATGGTTCTATCTTCCTGACAATATAGACCTGGACACGCTTACAA 14400
ACGGATGTCCGGCTATAAGAATCCCCTATTTTGGATCAGCCACTGATGAAAGGTCGGAAG 14460
CCCAACTCGGGTATGTAAGAAATCTAAGCAAACCCGCAAAGGCGGCCATCCGGATAGCTA 14520
TGGTGTATACGTGGGCCTACGGGACTGATGAGATATCGTGGATGGAAGCCGCTCTTATAG 14580
CCCAAACAAGAGCTAATCTGAGCTTAGAGAATCTAAAGCTGCTGACTCCTGTTTCAACCT 14640
CCACTAATCTATCTCATAGGTTGAAAGATACGGCAACCCAGATGAAGTTCTCTAGTGCAA 14700
CACTAGTCCGTGCAAGTCGGTTCATAACAATATCAAATGATAACATGGCACTCAAAGAAG 14760
CAGGGGAGTCGAAGGATACTAATCTCGTGTATCAGCAGATTATGCTAACTGGGCTAAGCT 14820
TGTTCGAGTTCAATATGAGATATAAGAAAGGTTCCTTAGGGAAGCCACTGATATTGCACT 14880
TACATCTTAATAACGGGTGCTGTATAATGGAGTCCCCACAGGAGGCGAATATCCCCCCAA 14940
GGTCCACATTAGATTTAGAGATTACACAAGAGAACAATAAATTGATCTATGATCCTGATC 15000
CACTCAAGGATGTGGACCTTGAGCTATTTAGCAAGGTCAGAGATGTTGTACACACAGTTG 15060
ACATGACTTATTGGTCAGATGATGAAGTTATCAGAGCAACCAGTATCTGTACTGCAATGA 15120
CGATAGCTGATACAATGTCTCAATTAGATAGAGACAACTTAAAAGAGATGATCGCACTAG 15180
TAAATGACGATGATGTCAACAGCTTGATTACTGAGTTTATGGTGATTGATGTTCCTTTAT 15240
TTTGCTCAACGTTCGGGGGTATTCTAGTCAATCAGTTTGCATACTCACTCTACGGCTTAA 15300

FIG. 8Z

ACATCAGAGGAAGGGAAGAAATATGGGGACATGTAGTCCGGATTCTTAAAGATACCTCCC 15360
ACGCAGTTTTAAAAGTCTTATCTAATGCTCTATCTCATCCCAAAATCTTCAAACGATTCT 15420
GGAATGCAGGTGTCGTGGAACCTGTGTATGGGCCTAACCTCTCAAATCAGGATAAGATAC 15480
TCTTGGCCCTCTCTGTCTGTGAATATTCTGTGGATCTATTCATGCACGATTGGCAAGGGG 15540
GTGTACCGCTTGAGATCTTTATCTGTGACAATGACCCAGATGTGGCCGACATGAGGAGGT 15600
CCTCTTTCTTGGCAAGACATCTTGCATACCTATGCAGCTTGGCAGAGATATCTAGGGATG 15660
GGCCAAGATTAGAATCAATGAACTCTCTAGAGAGGCTCGAGTCACTAAAGAGTTACCTGG 15720
AACTCACATTTCTTGATGACCCGGTACTGAGGTACAGTCAGTTGACTGGCCTAGTCATCA 15780
AAGTATTCCCATCTACTTTGACCTATATCCGGAAGTCATCTATAAAAGTGTTAAGGACAA 15840
GAGGTATAGGAGTCCCTGAAGTCTTAGAAGATTGGGATCCCGAGGCAGATAATGCACTGT 15900
TAGATGGTATCGCGGCAGAAATACAACAGAATATTCCTTTGGGACATCAGACTAGAGCCC 15960
CTTTTTGGGGGTTGAGAGTATCCAAGTCACAGGTACTGCGTCTCCGGGGGTACAAGGAGA 16020
TCACAAGAGGTGAGATAGGCAGATCAGGTGTTGGTCTGACGTTACCATTCGATGGAAGAT 16080
ATCTATCTCACCAGCTGAGGCTCTTTGGCATCAACAGTACTAGCTGCTTGAAAGCACTTG 16140
AACTTACCTACCTATTGAGCCCCTTAGTTGACAAGGATAAAGATAGGCTATATTTAGGGG 16200
AAGGAGCTGGGGCCATGCTTTCCTGTTATGACGCTACTCTTGGCCCATGCATCAACTATT 16260
ATAACTCAGGGGTATACTCTTGTGATGTCAATGGGCAGAGAGAGTTAAATATATATCCTG 16320
CTGAGGTGGCACTAGTGGGAAAGAAATTAAACAATGTTACTAGTCTGGGTCAAAGAGTTA 16380
AAGTGTTATTCAACGGGAATCCTGGCTCGACATGGATTGGGAATGATGAGTGTGAGGCTT 16440
TGATTTGGAATGAATTACAGAATAGCTCGATAGGCCTAGTCCACTGTGACATGGAGGGAG 16500
GAGATCATAAGGATGATCAAGTTGTACTGCATGAGCATTACAGTGTAATCCGGATCGCGT 16560
ATCTGGTGGGGGATCGAGACGTTGTGCTTATAAGCAAGATTGCTCCCAGGCTGGGCACGG 16620
ATTGGACCAGGCAGCTCAGCCTATATCTGAGATACTGGGACGAGGTTAACCTAATAGTGC 16680
TTAAAACATCTAACCCTGCTTCCACAGAGATGTATCTCCTATCGAGGCACCCCAAATCTG 16740
ACATTATAGAGGACAGCAAGACAGTGTTAGCTAGTCTCCTCCCTTTGTCAAAAGAAGATA 16800
GCATCAAGATAGAAAAGTGGATCTTAATAGAGAAGGCAAAGGCTCACGAATGGGTTACTC 16860
GGGAATTGAGAGAAGGAAGCTCTTCATCAGGGATGCTTAGACCTTACCATCAAGCACTGC 16920
AGACGTTTGGCTTTGAACCAAACTTGTATAAATTGAGCAGAGATTTCTTGTCCACCATGA 16980
ACATAGCTGATACACACAACTGCATGATAGCTTTCAACAGGGTTTTGAAGGATACAATCT 17040
TCGAATGGGCTAGAATAACTGAGTCAGATAAAAGGCTTAAACTAACTGGTAAGTATGACC 17100
TGTATCCTGTGAGAGATTCAGGCAAGTTGAAGACAATTTCTAGAAGACTTGTGCTATCTT 17160

FIG. 8AA

GGATATCTTTATCTATGTCCACAAGATTGGTAACTGGGTCATTCCCTGACCAGAAGTTTG 17220

AAGCAAGACTTCAATTGGGAATAGTTTCATTATCATCCCGTGAAATCAGGAACCTGAGGG 17280

TTATCACAAAAACTTTATTAGACAGGTTTGAGGATATTATACATAGTATAACGTATAGAT 17340

TCCTCACCAAAGAAATAAAGATTTTGATGAAGATTTTAGGGGCAGTCAAGATGTTCGGGG 17400

CCAGGCAAAATGAATACACGACCGTGATTGATGATGGATCACTAGGTGATATCGAGCCAT 17460

ATGACAGCTCGTAATAATTAGTCCCTATCGTGCAGAACGATCGAAGCTCCGCGGTACCTG 17520

GAAGTCTTGGACTTGTCCATATGACAATAGTAAGAAAAACTTACAAGAAGACAAGAAAAT 17580

TTAAAAGGATACATATCTCTTAAACTCTTGTCTGGT 17616 sgEnvG: Red characters
NP: Blue characters, P: Green characters, M: Brown characters, F: Orange characters, HN: Pink characters, L: Violet characters The nucleotide sequence of SeV-HIVconC5(NP)

ACCAAACAAGAGAAAAAACATGTATGGGATATGTAATGAAGTTATACAGGATTTTAGGGT 60

CAAAGTATCCACCCTGAGGAGCAGGTTCCAGACCCTTTGCTTTGCTGCCAAAGTTCACGC 120

GGCCGCCAAGGTTCAATGGAGGAGAAAGCATTCTCACCTGAAGTGATCCCTATGTTCACA 180
NotI -> HIVconC5
GCATTATCTGAGGGAGCTACTCCTCAAGATCTTAACACAATGCTTAACACAGTCGGAGGA 240

CATCAAGCAGCAATGCAAATGTTGAAAGATACAATTAACGAGGAAGCAGCAGAATGGGAT 300

AGAATCTATAAGAGATGGATAATATTAGGATTGAACAAGATTGTTAGAATGTATTCTCCT 360

GTGTCAATCCTTGATATAAGACAAGGACCTAAAGAGCCTTTCAGAGATTACGTCGATAGA 420

TTTGCAAGAAATTGTAGAGCACCTAGAAAGAAGGGATGTTGGAAATGTGGGAAAGAAGGA 480

CATCAAATGAAAGATTGTACTGAGAGACAAGCTAACTTCTTGGGAAAGATATGGCCTTCA 540

AGATGGAAACCTAAGATGATAGGAGGAATAGGAGGATTTATTAAAGTCAGACAATATGAT 600

CAAATATTGATTGAAATATGTGGACATAAAGCTATTGGAACAGTCCTAGTGGGTCCAACA 660

CCTGTCAACATCATTGGTAGAAATCTTCTCACTCAAATCGGATGTACACTCAATTTCCCA 720

ATATCACCTATTGAGACCGTGCCTGTCAAATTGAAACCTGGAATGGATGGACCTAAAGTC 780

AAACAATGGCCATTAACTGAGGAGAAGATTAAAGCACTGGTAGAAATTTGTACAGAGATG 840

GAGAAAGAAGGAAAGATTTCCAAGATTGGTCCTGAGAATCCTTATAATACTCCTGTCTTT 900

GCTATTAAGAAGAAGGATAGTACCAAATGGAGGAAATTAGTCGATTTCAGAGAACTTAAC 960

AAGAGGACTCAAGACTTCTGGGAAGTGCAATTGGGAATCCCACACCCTGCAGGATTGAAG 1020

AAGAAGAAGTCTGTCACTGTCCTAGATGTGGGAGATGCATATTTCAGTGTCCCACTGGAT 1080

GAAGGTTTCAGAAAGTATACAGCATTCACAATCCCTTCCATTAATAATGAAACACCTGGA 1140

ATAAGATATCAATATAATGTCTTACCTCAAGGGTGGAAAGGATCTCCAGCAATATTCCAA 1200

FIG. 8BB

```
TCATCAATGACAAAGATCTTGGAGCCTTTCAGAGCTCAGAATCCAGAGATAGTTATTTAC 1260
CAATACATGGATGATTTGTATGTTGGGTCAGATCTCGAGATCGGACAGCACAGGATGGAG 1320
AATAGATGGCAAGTAATGATTGTCTGGCAAGTCGATAGAATGAGAATAAGAACATGGAAA 1380
TCCTTGGTGAAACATCACCTTACAGAGGAGGCAGAACTGGAACTGGCAGAGAATAGGGAA 1440
ATATTGAAAGATCCAGTGCATGGTGTCTATTACGATCCTTCTAAAGATCTGATAGCAGAG 1500
ATCCAGTACTGGCAAGCAACATGGATTCCTGAGTGGGAATTCGTCAACACACCTCCATTA 1560
GTGAAACTATGGTACCAATTAGAGAAGAATGTCACCGAGAACTTCAACATGTGGAAGAAC 1620
GATATGGTAGATCAAATGCACGAAGATATCATCTCCTTGTGGGATCAATCACTTAAACCT 1680
TGTGTTAAATTGACACCTTGGGTACCTGCTCATAAAGGGATAGGAGGAAACGAACAAGTG 1740
GATAAATTGGTGTCCCAAGGGATCAGGAAAGTCTTGTTCCTAGATGGAATTGATAAAGCT 1800
CAAGCAAAGGAAATTGTCGCAAGCTGTGATAAGTGTCAATTAAAGGGAGAGGCAATGCAC 1860
GGACAAGTCGATTGTTCACCTGGTATTTGGCAACTTGATTGTACACATTTGGAGGGTAAA 1920
GTTATTCTAGTAGCAGTACATGTCGCTTCTGGTTATATTGAGGCAGAAGTGATACCTGCT 1980
GAGACAGGACAGGAGACCGCATACTTTCTACTTAAGTTAGCTATGAATAAGGAGCTCAAG 2040
AAGATAATAGGACAAGTTAGAGATCAAGCAGAGCACCTTAAGACAGCTGTCCAAATGGCA 2100
GTGTTTATACACAACTTTAAGAGAAAGGGTGGAATCGGAGGATATTCCGCAGGAGAGAGA 2160
ATCTGGAAAGGTCCTGCTAAATTGTTATGGAAAGGAGAAGGAGCAGTTGTAATACAAGAT 2220
AATTCTGATATAAAAGTAGTCCCTAGAAGGAAAGCTAAGATTATTAGAGATTATGGGAAA 2280
CAAATGGCAGGAGCTGATTGTGTGTTTCTAGGAGCAGCAGGATCCACTATGGGAGCTGCA 2340
TCAATGACACTTACCGTGCAGGCTAGACAGCTTCTTTCAGGAATTGTACAGCAACAGAAT 2400
AATTTGCTAAGAGCAATTGAAGCTCAACAACACTTACTTCAACTTACAGTCTGGGGAATC 2460
AAGCAAGCACCTACAAAAGCAAAGAGAAGAGTCGTCCAAAGAGAGAAAAAGATAACCGTAG 2520
TAAGAAAAACTTAGGGTGAAAGTTCATC[redacted]AGATCTTCACGATGGCCGGGTTGT 2580
                            NotI            -> NP
TGAGCACCTTCGATACATTTAGCTCTAGGAGGAGCGAAAGTATTAATAAGTCGGGAGGAG 2640
GTGCTGTTATCCCCGGCCAGAGGAGCACAGTCTCAGTGTTCGTACTAGGCCCAAGTGTGA 2700
CTGATGATGCAGACAAGTTATTCATTGCAACTACCTTCCTAGCTCACTCATTGGACACAG 2760
ATAAGCAGCACTCTCAGAGAGGGGGGTTCCTCGTCTCTCTGCTTGCCATGGCTTACAGTA 2820
GTCCAGAATTGTACTTGACAACAAACGGAGTAAACGCCGATGTCAAATATGTGATCTACA 2880
ACATAGAGAAAGACCCTAAGAGGACGAAGACAGACGGATTCATTGTGAAGACGAGAGATA 2940
TGGAATATGAGAGGACCACAGAATGGCTGTTTGGACCTATGGTCAACAAGAGCCCACTCT 3000
TCCAGGGTCAACGGGATGCTGCAGACCCTGACACACTCCTTCAAATCTATGGGTATCCTG 3060
```

FIG. 8CC

CATGCCTAGGAGCAATAATTGTCCAAGTCTGGATTGTGCTGGTGAAGGCCATCACAAGCA 3120

GCGCCGGCTTAAGGAAAGGGTTCTTCAACAGGTTAGAGGCGTTCAGACAAGACGGCACCG 3180

TGAAAGGTGCCTTAGTTTTCACTGGGGAGACAGTTGAGGGGATAGGCTCGGTTATGAGAT 3240

CTCAGCAAAGCCTTGTATCTCTCATGGTTGAGACCCTTGTGACTATGAATACTGCAAGAT 3300

CTGATCTCACCACATTAGAGAAGAACATCCAGATCGTTGGGAACTACATCCGAGATGCAG 3360

GGCTGGCTTCCTTCATGAACACTATTAAATATGGGGTGGAAACAAAGATGGCAGCTCTAA 3420

CGTTGTCAAACCTGAGGCCCGATATTAATAAGCTTAGAAGCCTCATAGACACCTACCTGT 3480

CAAAAGGCCCCAGAGCTCCCTTTATCTGTATCCTCAAGGACCCTGTTCATGGTGAATTTG 3540

CTCCAGGCAATTATCCTGCACTATGGAGTTACGCCATGGGAGTCGCCGTCGTACAGAACA 3600

AGGCAATGCAGCAGTACGTCACAGGGAGGACATACCTTGATATGGAAATGTTCTTACTAG 3660

GACAAGCCGTGGCAAAGGATGCTGAATCGAAGATCAGCAGTGCCTTGGAAGATGAGTTAG 3720

GAGTGACGGATACAGCCAAGGGGAGGCTCAGACATCATCTGGCAAACTTGTCCGGTGGGG 3780

ATGGTGCTTACCACAAACCAACAGGCGGTGGTGCAATTGAGGTAGCTCTAGACAATGCCG 3840

ACATCGACCTAGAAACAAAAGCCCATGCGGACCAGGACGCTAGGGGTTGGGGTGGAGATA 3900

GTGGTGAAAGATGGGCACGTCAGGTGAGTGGTGGCCACTTTGTCACACTACATGGGGCTG 3960

AACGGTTAGAGGAGGAAACCAATGATGAGGATGTATCAGACATAGAGAGAAGAATAGCCA 4020

TGAGACTCGCAGAGAGACGGCAAGAGGATTCTGCAACCCATGGAGATGAAGGCCGCAATA 4080

ACGGTGTCGATCATGACGAAGATGACGATGCCGCAGCAGTAGCTGGGATAGGAGGAATCT 4140

AGGATCATACGAGGCTTCAAGGTACTTGATCCGTAGTAAGAAAAACTTAGGGTGAAAGTT 4200

CATCCACCGATCGGCTCAGGCAAGGCCACACCCAACCCCACCGACCACACCCAGCAGTCG 4260

AGACAGCCACGGCTTCGGCTACACTTACCGCATGGATCAAGATGCCTTCATTCTTAAAGA 4320

-> P

AGATTCTGAAGTTGAGAGGGAGGCGCCAGGAGGACGAGAGTCGCTCTCGGATGTTATCGG 4380

ATTCCTCGATGCTGTCCTGTCGAGTGAACCAACTGACATCGGAGGGGACAGAAGCTGGCT 4440

CCACAACACCATCAACACTCCCCAAGGACCAGGCTCTGCTCATAGAGCCAAAAGTGAGGG 4500

CGAAGGAGAAGTCTCAACACCGTCGACCCAAGATAATCGATCAGGTGAGGAGAGTAGAGT 4560

CTCTGGGAGAACAAGCAAGCCAGAGGCAGAAGCACATGCTGGAAACCTTGATAAACAAAA 4620

TATACACCGGGCCTTTGGGGGAAGAACTGGTACAAACTCTGTATCTCAGGATCTGGGCGA 4680

TGGAGGAGACTCCGGAATCCTTGAAAATCCTCCAAATGAGAGAGGATATCCGAGATCAGG 4740

TATTGAAGATGAAAACAGAGAGATGGCTGCGCACCCTGATAAGAGGGGAGAAGACCAAGC 4800

TGAAGGACTTCCAGAAGAGGTACGAGGAAGTACATCCCTACCTGATGAAGGAGAAGGTGG 4860

AGCAAGTAATAATGGAAGAAGCATGGAGCCTGGCAGCTCACATAGTGCAAGAGTAACTGG 4920

GGTCCTGGTGATTCCTAGCCCCGAACTTGAAGAGGCTGTGCTACGGAGGAACAAAAGAAG 4980

FIG. 8DD

ACCTACCAACAGTGGGTCCAAACCTCTTACTCCAGCAACCGTGCCTGGCACCCGGTCCCC 5040

ACCGCTGAATCGTTACAACAGCACAGGGTCACCACCAGGAAAACCCCCATCTACACAGGA 5100

TGAGCACATCAACTCTGGGGACACCCCCGCCGTCAGGGTCAAAGACCGGAAACCACCAAT 5160

AGGGACCCGCTCTGTCTCAGATTGTCCAGCCAACGGCCGCCCAATCCACCCGGGTCTAGA 5220

GACCGACTCAACAAAAAAGGGCATAGGAGAGAACACATCATCTATGAAAGAGATGGCTAC 5280

ATTGTTGACGAGTCTTGGTGTAATCCAGTCTGCTCAAGAATTCGAATCATCCCGAGACGC 5340

GAGTTATGTGTTTGCAAGACGTGCCCTAAAGTCTGCAAACTATGCAGAGATGACATTCAA 5400

TGTATGCGGCCTGATCCTTTCTGCCGAGAAATCTTCCGCTCGTAAGGTAGATGAGAACAA 5460

ACAACTGCTCAAACAGATCCAAGAGAGCGTGGAATCATTCCGGGATATTTACAAGAGATT 5520

CTCTGAGTATCAGAAAGAACAGAACTCATTGCTGATGTCCAACCTATCTACACTTCATAT 5580

CATCACAGATAGAGGTGGCAAGACTGACAACACAGACTCCCTTACAAGGTCCCCCTCCGT 5640

TTTTGCAAAATCAAAAGAGAACAAGACTAAGGCTACCAGGTTTGACCCATCTATGGAGAC 5700

CCTAGAAGATATGAAGTACAAACCGGACCTAATCCGAGAGGATGAATTTAGAGATGAGAT 5760

CCGCAACCCGGTGTACCAAGAGAGGGACACAGAACCCAGGGCCTCAAACGCATCACGTCT 5820

CCTCCCCTCCAAAGAGAAGCCCACAATGCACTCTCTCAGGCTCGTCATAGAGAGCAGTCC 5880

CCTAAGCAGAGCTGAGAAAGTAGCATATGTGAAATCATTATCCAAGTGCAAGACAGACCA 5940

AGAGGTTAAGGCAGTCATGGAACTCGTAGAAGAGGACATAGAGTCACTGACCAACTAGAT 6000

CCCGGGTGAGGCATCCTACCATCCTCAGTCATAGAGAGATCCAATCTACCATCAGCATCA 6060

GCCAGTAAAGATTAAGAAAAACTTAGGGTGAAAGAAATTTCACCTAACACGGCGCAATGG 6120

~> M

CAGATATCTATAGATTCCCTAAGTTCTCATATGAGGATAACGGTACTGTGGAGCCCCTGC 6180

CTCTGAGAACTGGTCCGGATAAGAAAGCCATCCCCCACATCAGGATTGTCAAGGTAGGAG 6240

ACCCTCCTAAACATGGAGTGAGATACCTAGATTTATTGCTCTTGGGTTTCTTTGAGACAC 6300

CGAAACAAACAACCAATCTAGGGAGCGTATCTGACTTGACAGAGCCGACCAGCTACTCAA 6360

TATGCGGCTCCGGGTCGTTACCCATAGGTGTGGCCAAATACTACGGGACTGATCAGGAAC 6420

TCTTAAAGGCCTGCACCGATCTCAGAATTACGGTGAGGAGGACTGTTCGAGCAGGAGAGA 6480

TGATCGTATACATGGTGGATTCGATTGGTGCTCCACTCCTACCATGGTCAGGCAGGCTGA 6540

GACAGGGAATGATATTTAATGCAAACAAGGTCGCACTAGCTCCCCAATGCCTCCCTGTGG 6600

ACAAGGACATAAGACTCAGAGTGGTGTTTGTCAATGGGACATCTCTAGGGGCAATCACCA 6660

TAGCCAAGATCCCAAAGACCCTTGCAGACCTTGCATTGCCCAACTCTATATCTGTTAATT 6720

TACTGGTGACACTCAAGACCGGGATCTCCACAGAACAAAAGGGGGTACTCCCAGTACTTG 6780

ATGATCAAGGGGAGAAAAAGCTCAATTTTATGGTGCACCTCGGGTTGATCAGGAGAAAGG 6840

FIG. 8EE

TCGGGAAGATATACTCTGTTGAGTACTGCAAGAGCAAGATTGAGAGAATGCGGCTGATTT 6900

TCTCACTTGGGTTAATCGGCGGTATAAGCTTCCATGTTCAGGTTAATGGGACACTATCTA 6960

AGACATTCATGAGTCAGCTCGCATGGAAGAGGGCAGTCTGCTTCCCATTAATGGATGTGA 7020

ATCCCCATATGAACATGGTGATTTGGGCGGCATCTGTAGAAATCACAGGCGTCGATGCGG 7080

TGTTCCAACCGGCCATCCCTCGTGATTTCCGCTACTACCCTAATGTTGTGGCTAAGAACA 7140

TCGGAAGGATCAGAAAGCTGTAAATGTGCACCCATCAGAGACCTGCGACAATGCCCCAAG 7200

CAGACACCACCTGGCAGTCGGAGCCACCGGGTCACTCCTTGTCTTAAATAAGAAAAACTT 7260

AGGGATAAAGTCCCTTGTGAGTGCTTGGTTGCAAAACTCTCCCCTTGGGAAACATGACAG 7320

-> F

CATATATCCAGAGATCACAGTGCATCTCAACATCACTACTGGTTGTTCTCACCACATTGG 7380

TCTCGTGTCAGATTCCCAGGGATAGGCTCTCTAACATAGGGGTCATAGTCGATGAAGGGA 7440

AATCACTGAAGATAGCTGGATCCCACGAATCGAGGTACATAGTACTGAGTCTAGTTCCGG 7500

GGGTAGACTTTGAGAATGGGTGCGGAACAGCCCAGGTTATCCAGTACAAGAGCCTACTGA 7560

ACAGGCTGTTAATCCCATTGAGGGATGCCTTAGATCTTCAGGAGGCTCTGATAACTGTCA 7620

CCAATGATACGACACAAAATGCCGGTGCTCCCCAGTCGAGATTCTTCGGTGCTGTGATTG 7680

GTACTATCGCACTTGGAGTGGCGACATCAGCACAAATCACCGCAGGGATTGCACTAGCCG 7740

AAGCGAGGGAGGCCAAAAGAGACATAGCGCTCATCAAAGAATCGATGACAAAAACACACA 7800

AGTCTATAGAACTGCTGCAAAACGCTGTGGGGGAACAAATTCTTGCTCTAAAGACACTCC 7860

AGGATTTCGTGAATGATGAGATCAAACCCGCAATAAGCGAATTAGGCTGTGAGACTGCTG 7920

CCTTAAGACTGGGTATAAAATTGACACAGCATTACTCCGAGCTGTTAACTGCGTTCGGCT 7980

CGAATTTCGGAACCATCGGAGAGAAGAGCCTCACGCTGCAGGCGCTGTCTTCACTTTACT 8040

CTGCTAACATTACTGAGATTATGACCACAATCAGGACAGGGCAGTCTAACATCTATGATG 8100

TCATTTATACAGAACAGATCAAAGGAACGGTGATAGATGTGGATCTAGAGAGATACATGG 8160

TCACCCTGTCTGTGAAGATCCCTATTCTTTCTGAAGTCCCAGGTGTGCTCATACACAAGG 8220

CATCATCTATTTCTTACAACATAGACGGGGAGGAATGGTATGTGACTGTCCCCAGCCATA 8280

TACTCAGTCGTGCTTCTTTCTTAGGGGGTGCAGACATAACCGATTGTGTTGAGTCCAGAT 8340

TGACCTATATATGCCCCAGGGATCCCGCACAACTGATACCTGACAGCCAGCAAAAGTGTA 8400

TCCTGGGGGACACAACAAGGTGTCCTGTCACAAAAGTTGTGGACAGCCTTATCCCCAAGT 8460

TTGCTTTTGTGAATGGGGGCGTTGTTGCTAACTGCATAGCATCCACATGTACCTGCGGGA 8520

CAGGCCGAAGACCAATCAGTCAGGATCGCTCTAAAGGTGTAGTATTCCTAACCCATGACA 8580

ACTGTGGTCTTATAGGTGTCAATGGGGTAGAATTGTATGCTAACCGGAGAGGGCACGATT 8640

GCACTTGGGGGGTCCAGAACTTGACAGTCGGTCCTGCAATTGCTATCAGACCCGTTGATA 8700

TTTCTCTCAACCTTGCTGATGCTACGAATTTCTTGCAAGACTCTAAGGCTGAGCTTGAGA 8760

FIG. 8FF

AAGCACGGAAAATCCTCTCGGAGGTAGGTAGATGGTACAACTCAAGAGAGACTGTGATTA 8820

CGATCATAGTAGTTATGGTCGTAATATTGGTGGTCATTATAGTGATCATCATCGTGCTTT 8880

ATAGACTCAGAAGGTCAATGCTAATGGGTAATCCAGATGACCGTATACCGAGGGACACAT 8940

ACACATTAGAGCCGAAGATCAGACATATGTACACAAACGGTGGGTTTGATGCAATGGCTG 9000

AGAAAAGATGATCACGACCATTATCAGATGTCTTGTAAAGCAGGCATAGTATCCGTTGAG 9060

ATCTGTATATAATAAGAAAAACTTAGGGTGAAAGTGAGGTCGCGCGGTACTTTAGCTTTC 9120

ACCTCAAACAAGCACAGATCATGGATGGTGATAGGGGCAAACGTGACTCGTACTGGTCTA 9180
-> HN

CTTCTCCTAGTGGTAGCACCACAAAACCAGCATCAGGTTGGGAGAGGTCAAGTAAAGCCG 9240

ACACATGGTTGCTGATTCTCTCATTCACCCAGTGGGCTTTGTCAATTGCCACAGTGATCA 9300

TCTGTATCATAATTTCTGCTAGACAAGGGTATAGTATGAAAGAGTACTCAATGACTGTAG 9360

AGGCATTGAACATGAGCAGCAGGGAGGTGAAAGAGTCACTTACCAGTCTAATAAGGCAAG 9420

AGGTTATAGCAAGGGCTGTCAACATTCAGAGCTCTGTGCAAACCGGAATCCCAGTCTTGT 9480

TGAACAAAAACAGCAGGGATGTCATCCAGATGATTGATAAGTCGTGCAGCAGACAAGAGC 9540

TCACTCAGCACTGTGAGAGTACGATCGCAGTCCACCATGCCGATGGAATTGCCCCACTTG 9600

AGCCACATAGTTTCTGGAGATGCCCTGTCGGAGAACCGTATCTTAGCTCAGATCCTGAAA 9660

TCTCATTGCTGCCTGGTCCGAGCTTGTTATCTGGTTCTACAACGATCTCTGGATGTGTTA 9720

GGCTCCCTTCACTCTCAATTGGCGAGGCAATCTATGCCTATTCATCAAATCTCATTACAC 9780

AAGGTTGTGCTGACATAGGGAAATCATATCAGGTCCTGCAGCTAGGGTACATATCACTCA 9840

ATTCAGATATGTTCCCTGATCTTAACCCCGTAGTGTCCCACACTTATGACATCAACGACA 9900

ATCGGAAATCATGCTCTGTGGTGGCAACCGGGACTAGGGGTTATCAGCTTTGCTCCATGC 9960

CGACTGTAGACGAAAGAACCGACTACTCTAGTGATGGTATTGAGGATCTGGTCCTTGATG 10020

TCCTGGATCTCAAAGGGAGAACTAAGTCTCACCGGTATCGCAACAGCGAGGTAGATCTTG 10080

ATCACCCGTTCTCTGCACTATACCCCAGTGTAGGCAACGGCATTGCAACAGAAGGCTCAT 10140

TGATATTTCTTGGGTATGGTGGACTAACCACCCCTCTGCAGGGTGATACAAAATGTAGGA 10200

CCCAAGGATGCCAACAGGTGTCGCAAGACACATGCAATGAGGCTCTGAAAATTACATGGC 10260

TAGGAGGGAAACAGGTGGTCAGCGTGATCATCCAGGTCAATGACTATCTCTCAGAGAGGC 10320

CAAAGATAAGAGTCACAACCATTCCAATCACTCAAAACTATCTCGGGGCGGAAGGTAGAT 10380

TATTAAAATTGGGTGATCGGGTGTACATCTATACAAGATCATCAGGCTGGCACTCTCAAC 10440

TGCAGATAGGAGTACTTGATGTCAGCCACCCTTTGACTATCAACTGGACACCTCATGAAG 10500

CCTTGTCTAGACCAGGAAATAAAGAGTGCAATTGGTACAATAAGTGTCCGAAGGAATGCA 10560

TATCAGGCGTATACACTGATGCTTATCCATTGTCCCCTGATGCAGCTAACGTCGCTACCG 10620

TCACGCTATATGCCAATACATCGCGTGTCAACCCAACAATCATGTATTCTAACACTACTA 10680

FIG. 8GG

ACATTATAAATATGTTAAGGATAAAGGATGTTCAATTAGAGGCTGCATATACCACGACAT 10740

CGTGTATCACGCATTTTGGTAAAGGCTACTGCTTTCACATCATCGAGATCAATCAGAAGA 10800

GCCTGAATACCTTACAGCCGATGCTCTTTAAGACTAGCATCCCTAAATTATGCAAGGCCG 10860

AGTCTTAAATTTAACTGACTAGCAGGCTTGTCGGCCTTGCTGACACTAGAGTCATCTCCG 10920

AACATCCACAATATCTCTCAGTCTCTTACGTCTCTCACAGTATTAAGAAAAACCCAGGGT 10980

GAATGGGAAGCTTGCCATAGGTCATGGATGGGCAGGAGTCCTCCCAAAACCCTTCTGACA 11040

~> L

TACTCTATCCAGAATGCCACCTGAACTCTCCCATAGTCAGGGGGAAGATAGCACAGTTGC 11100

ACGTCTTGTTAGATGTGAACCAGCCCTACAGACTGAAGGACGACAGCATAATAAATATTA 11160

CAAAGCACAAAATTAGGAACGGAGGATTGTCCCCCCGTCAAATTAAGATCAGGTCTCTGG 11220

GTAAGGCTCTTCAACGCACAATAAAGGATTTAGACCGATACACGTTTGAACCGTACCCAA 11280

CCTACTCTCAGGAATTACTTAGGCTTGATATACCAGAGATATGTGACAAAATCCGATCCG 11340

TCTTCGCGGTCTCGGATCGGCTGACCAGGGAGTTATCTAGTGGGTTCCAGGATCTTTGGT 11400

TGAATATCTTCAAGCAACTAGGCAATATAGAAGGAAGAGAGGGGTACGATCCGTTGCAGG 11460

ATATCGGCACCATCCCGGAGATAACTGATAAGTACAGCAGGAATAGATGGTATAGGCCAT 11520

TCCTAACTTGGTTCAGCATCAAATATGACATGCGGTGGATGCAGAAGACCAGACCGGGGG 11580

GACCCCTCGATACCTCTAATTCACATAACCTCCTAGAATGCAAATCATACACTCTAGTAA 11640

CATACGGAGATCTTGTCATGATACTGAACAAGTTGACATTGACAGGGTATATCCTAACCC 11700

CTGAGCTGGTCTTGATGTATTGTGATGTTGTAGAAGGAAGGTGGAATATGTCTGCTGCAG 11760

GGCATCTAGATAAGAAGTCCATTGGGATAACAAGCAAAGGTGAGGAATTATGGGAACTAG 11820

TGGATTCCCTCTTCTCAAGTCTTGGAGAGGAAATATACAATGTCATCGCACTATTGGAGC 11880

CCCTATCACTTGCTCTCATACAACTAAATGATCCTGTTATACCTCTACGTGGGGCATTTA 11940

TGAGGCATGTGTTGACAGAGCTACAGACTGTTTTAACAAGTAGAGACGTGTACACAGATG 12000

CTGAAGCAGACACTATTGTGGAGTCGTTACTCGCCATTTTCCATGGAACCTCTATTGATG 12060

AGAAAGCAGAGATCTTTTCCTTCTTTAGGACATTTGGCCACCCCAGCTTAGAGGCTGTCA 12120

CTGCCGCCGACAAGGTAAGGGCCCATATGTATGCACAAAAGGCAATAAAGCTTAAGACCC 12180

TATACGAGTGTCATGCAGTTTTTTGCACTATCATCATAAATGGGTATAGAGAGAGGCATG 12240

GCGGACAGTGGCCCCCCTGTGACTTCCCTGATCACGTGTGTCTAGAACTAAGGAACGCTC 12300

AAGGGTCCAATACGGCAATCTCTTATGAATGTGCTGTAGACAACTATACAAGTTTCATAG 12360

GCTTCAAGTTTCGGAAGTTTATAGAACCACAACTAGATGAAGATCTCACAATATATATGA 12420

AAGACAAAGCACTATCCCCCAGGAAGGAGGCATGGGACTCTGTATACCCGGATAGTAATC 12480

TGTACTATAAAGCCCCAGAGTCTGAAGAGACCCGGCGGCTTATTGAAGTGTTCATAAATG 12540

ATGAGAATTTCAACCCAGAAGAAATTATCAATTATGTGGAGTCAGGAGATTGGTTGAAAG 12600

FIG. 8HH

ACGAGGAGTTCAACATCTCGTACAGTCTCAAAGAGAAAGAGATCAAGCAAGAGGGTCGTC 12660
TATTCGCAAAAATGACTTATAAGATGCGAGCCGTACAGGTGCTGGCAGAGACACTACTGG 12720
CTAAAGGAATAGGAGAGCTATTCAGCGAAAATGGGATGGTTAAAGGAGAGATAGACCTAC 12780
TTAAAAGATTGACTACTCTTTCTGTCTCAGGCGTCCCCAGGACTGATTCAGTGTACAATA 12840
ACTCTAAATCATCAGAGAAGAGAAACGAAGGCATGGAAAATAAGAACTCTGGGGGTACT 12900
GGGACGAAAAGAAGAGGTCCAGACATGAATTCAAGGCAACAGATTCATCAACAGACGGCT 12960
ATGAAACGTTAAGTTGCTTCCTCACAACAGACCTCAAGAAATACTGCTTAAACTGGAGAT 13020
TTGAGAGTACTGCATTGTTTGGTCAGAGATGCAACGAGATATTTGGCTTCAAGACCTTCT 13080
TTAACTGGATGCATCCAGTCCTTGAAAGGTGTACAATATATGTTGGAGATCCTTACTGTC 13140
CAGTCGCCGACCGGATGCATCGACAACTCCAGGATCATGCAGACTCTGGCATTTTCATAC 13200
ATAATCCTAGGGGGGCATAGAAGGTTACTGCCAGAAGCTGTGGACCTTAATCTCAATCA 13260
GTGCAATCCACCTAGCAGCTGTGAGAGTGGGTGTCAGGGTCTCTGCAATGGTTCAGGGTG 13320
ACAATCAAGCTATAGCCGTGACATCAAGAGTACCTGTAGCTCAGACTTACAAGCAGAAGA 13380
AAAATCATGTCTATGAGGAGATCACCAAATATTTCGGTGCTCTAAGACACGTCATGTTTG 13440
ATGTAGGGCACGAGCTAAAATTGAACGAGACCATCATTAGTAGCAAGATGTTTGTCTATA 13500
GTAAAAGGATATACTATGATGGGAAGATTTTACCACAGTGCCTGAAAGCCTTGACCAAGT 13560
GTGTATTCTGGTCCGAGACACTGGTAGATGAAAACAGATCTGCTTGTTCGAACATCTCAA 13620
CATCCATAGCAAAAGCTATCGAAAATGGGTATTCTCCTATACTAGGCTACTGCATTGCGT 13680
TGTATAAGACCTGTCAGCAGGTGTGCATATCACTAGGGATGACTATAAATCCAACTATCA 13740
GCCCGACCGTAAGAGATCAATACTTTAAGGGTAAGAATTGGCTGAGATGTGCAGTGTTGA 13800
TTCCAGCAAATGTTGGAGGATTCAACTACATGTCTACATCTAGATGCTTTGTTAGAAATA 13860
TTGGAGACCCCGCAGTAGCAGCCCTAGCTGATCTCAAAAGATTCATCAGAGCGGATCTGT 13920
TAGACAAGCAGGTATTATACAGGGTCATGAATCAAGAACCCGGTGACTCTAGTTTTCTAG 13980
ATTGGGCTTCAGACCCTTATTCGTGTAACCTCCCGCATTCTCAGAGTATAACTACGATTA 14040
TAAAGAATATCACTGCTAGATCTGTGCTGCAGGAATCCCCGAATCCTCTACTGTCTGGTC 14100
TCTTCACCGAGACTAGTGGAGAAGAGGATCTCAACCTGGCCTCGTTCCTTATGGACCGGA 14160
AAGTCATCCTGCCGAGAGTGGCTCATGAGATCCTGGGTAATTCCTTAACTGGAGTTAGGG 14220
AGGCGATTGCAGGGATGCTTGATACGACCAAGTCTCTAGTGAGAGCCAGCGTTAGGAAAG 14280
GAGGATTATCATATGGGATATTGAGGAGGCTTGTCAATTATGATCTATTGCAGTACGAGA 14340
CACTGACTAGAACTCTCAGGAAACCGGTGAAAGACAACATCGAATATGAGTATATGTGTT 14400
CAGTTGAGCTAGCTGTCGGTCTAAGGCAGAAAATGTGGATCCACCTGACTTACGGGAGAC 14460
CCATACATGGGCTAGAAACACCAGACCCTTTAGAGCTCTTGAGGGGAATATTTATCGAAG 14520

FIG. 8H

GTTCAGAGGTGTGCAAGCTTTGCAGGTCTGAAGGAGCAGACCCCATCTATACATGGTTCT 14580
ATCTTCCTGACAATATAGACCTGGACACGCTTACAAACGGATGTCCGGCTATAAGAATCC 14640
CCTATTTTGGATCAGCCACTGATGAAAGGTCGGAAGCCCAACTCGGGTATGTAAGAAATC 14700
TAAGCAAACCCGCAAAGGCGGCCATCCGGATAGCTATGGTGTATACGTGGGCCTACGGGA 14760
CTGATGAGATATCGTGGATGGAAGCCGCTCTTATAGCCCAAACAAGAGCTAATCTGAGCT 14820
TAGAGAATCTAAAGCTGCTGACTCCTGTTTCAACCTCCACTAATCTATCTCATAGGTTGA 14880
AAGATACGGCAACCCAGATGAAGTTCTCTAGTGCAACACTAGTCCGTGCAAGTCGGTTCA 14940
TAACAATATCAAATGATAACATGGCACTCAAAGAAGCAGGGGAGTCGAAGGATACTAATC 15000
TCGTGTATCAGCAGATTATGCTAACTGGGCTAAGCTTGTTCGAGTTCAATATGAGATATA 15060
AGAAAGGTTCCTTAGGGAAGCCACTGATATTGCACTTACATCTTAATAACGGGTGCTGTA 15120
TAATGGAGTCCCCACAGGAGGCGAATATCCCCCCAAGGTCCACATTAGATTTAGAGATTA 15180
CACAAGAGAACAATAAATTGATCTATGATCCTGATCCACTCAAGGATGTGGACCTTGAGC 15240
TATTTAGCAAGGTCAGAGATGTTGTACACACAGTTGACATGACTTATTGGTCAGATGATG 15300
AAGTTATCAGAGCAACCAGTATCTGTACTGCAATGACGATAGCTGATACAATGTCTCAAT 15360
TAGATAGAGACAACTTAAAAGAGATGATCGCACTAGTAAATGACGATGATGTCAACAGCT 15420
TGATTACTGAGTTTATGGTGATTGATGTTCCTTTATTTTGCTCAACGTTCGGGGGTATTC 15480
TAGTCAATCAGTTTGCATACTCACTCTACGGCTTAAACATCAGAGGAAGGGAAGAAATAT 15540
GGGGACATGTAGTCCGGATTCTTAAAGATACCTCCCACGCAGTTTTAAAAGTCTTATCTA 15600
ATGCTCTATCTCATCCCAAAATCTTCAAACGATTCTGGAATGCAGGTGTCGTGGAACCTG 15660
TGTATGGGCCTAACCTCTCAAATCAGGATAAGATACTCTTGGCCCTCTCTGTCTGTGAAT 15720
ATTCTGTGGATCTATTCATGCACGATTGGCAAGGGGGTGTACCGCTTGAGATCTTTATCT 15780
GTGACAATGACCCAGATGTGGCCGACATGAGGAGGTCCTCTTTCTTGGCAAGACATCTTG 15840
CATACCTATGCAGCTTGGCAGAGATATCTAGGGATGGGCCAAGATTAGAATCAATGAACT 15900
CTCTAGAGAGGCTCGAGTCACTAAAGAGTTACCTGGAACTCACATTTCTTGATGACCCGG 15960
TACTGAGGTACAGTCAGTTGACTGGCCTAGTCATCAAAGTATTCCCATCTACTTTGACCT 16020
ATATCCGGAAGTCATCTATAAAAGTGTTAAGGACAAGAGGTATAGGAGTCCCTGAAGTCT 16080
TAGAAGATTGGGATCCCGAGGCAGATAATGCACTGTTAGATGGTATCGCGGCAGAAATAC 16140
AACAGAATATTCCTTTGGGACATCAGACTAGAGCCCCTTTTTGGGGGTTGAGAGTATCCA 16200
AGTCACAGGTACTGCGTCTCCGGGGGTACAAGGAGATCACAAGAGGTGAGATAGGCAGAT 16260
CAGGTGTTGGTCTGACGTTACCATTCGATGGAAGATATCTATCTCACCAGCTGAGGCTCT 16320
TTGGCATCAACAGTACTAGCTGCTTGAAAGCACTTGAACTTACCTACCTATTGAGCCCCT 16380
TAGTTGACAAGGATAAAGATAGGCTATATTTAGGGGAAGGAGCTGGGGCCATGCTTTCCT 16440

FIG. 8JJ

GTTATGACGCTACTCTTGGCCCATGCATCAACTATTATAACTCAGGGGTATACTCTTGTG 16500

ATGTCAATGGGCAGAGAGAGTTAAATATATATCCTGCTGAGGTGGCACTAGTGGGAAAGA 16560

AATTAAACAATGTTACTAGTCTGGGTCAAAGAGTTAAAGTGTTATTCAACGGGAATCCTG 16620

GCTCGACATGGATTGGGAATGATGAGTGTGAGGCTTTGATTTGGAATGAATTACAGAATA 16680

GCTCGATAGGCCTAGTCCACTGTGACATGGAGGGAGGAGATCATAAGGATGATCAAGTTG 16740

TACTGCATGAGCATTACAGTGTAATCCGGATCGCGTATCTGGTGGGGGATCGAGACGTTG 16800

TGCTTATAAGCAAGATTGCTCCCAGGCTGGGCACGGATTGGACCAGGCAGCTCAGCCTAT 16860

ATCTGAGATACTGGGACGAGGTTAACCTAATAGTGCTTAAAACATCTAACCCTGCTTCCA 16920

CAGAGATGTATCTCCTATCGAGGCACCCCAAATCTGACATTATAGAGGACAGCAAGACAG 16980

TGTTAGCTAGTCTCCTCCCTTTGTCAAAAGAAGATAGCATCAAGATAGAAAAGTGGATCT 17040

TAATAGAGAAGGCAAAGGCTCACGAATGGGTTACTCGGGAATTGAGAGAAGGAAGCTCTT 17100

CATCAGGGATGCTTAGACCTTACCATCAAGCACTGCAGACGTTTGGCTTTGAACCAAACT 17160

TGTATAAATTGAGCAGAGATTTCTTGTCCACCATGAACATAGCTGATACACACAACTGCA 17220

TGATAGCTTTCAACAGGGTTTTGAAGGATACAATCTTCGAATGGGCTAGAATAACTGAGT 17280

CAGATAAAAGGCTTAAACTAACTGGTAAGTATGACCTGTATCCTGTGAGAGATTCAGGCA 17340

AGTTGAAGACAATTTCTAGAAGACTTGTGCTATCTTGGATATCTTTATCTATGTCCACAA 17400

GATTGGTAACTGGGTCATTCCCTGACCAGAAGTTTGAAGCAAGACTTCAATTGGGAATAG 17460

TTTCATTATCATCCCGTGAAATCAGGAACCTGAGGGTTATCACAAAAACTTTATTAGACA 17520

GGTTTGAGGATATTATACATAGTATAACGTATAGATTCCTCACCAAAGAAATAAAGATTT 17580

TGATGAAGATTTTAGGGGCAGTCAAGATGTTCGGGGCCAGGCAAAATGAATACACGACCG 17640

TGATTGATGATGGATCACTAGGTGATATCGAGCCATATGACAGCTCGTAATAATTAGTCC 17700

CTATCGTGCAGAACGATCGAAGCTCCGCGGTACCTGGAAGTCTTGGACTTGTCCATATGA 17760

CAATAGTAAGAAAAACTTACAAGAAGACAAGAAAATTTAAAAGGATACATATCTCTTAAA 17820

CTCTTGTCTGGT 17832

HIVCONC5: Red characters
NP: Blue characters, P: Green characters, M: Brown characters, F: Orange characters, HN: Pink characters, L: Violet characters

FIG. 8KK

A Gag Insert PCR

PCR →
■ Gag ■ NP ■ P
← PCR

B PCR

Gag insert >

C Western blot p55 Gag >

---

Pre-MVS
↓
Conduct 5 rounds of expansion with virus from Pre-MVS exceeding amplification need to manufacture clinical trial material
↓
Derive 50 clonal isolates from amplified preMVS(p5)
↓
Confirm gene insert integrity by PCR and protein expression by Western blotting

```
   1 ATGGCCGCCA GAGCCAGCAT CCTGAGCGGG GGCAAGCTGG ACGCCTGGGA GAAGATCAGA
  61 CTGAGGCCTG GCGGCAAGAA GAAGTACCGG CTGAAGCACC TGGTGTGGGC CAGCAGAGAG
 121 CTGGATCGCT TCGCCCTGAA TCCTAGCCTG CTGGAGACCA CCGAGGGCTG CCAGCAGATC
 181 ATGAACCAGC TGCAGCCCGC CGTGAAAACC GGCACCGAGG AGATCAAGAG CCTGTTCAAC
 241 ACCGTGGCCA CCCTGTACTG CGTGCACCAG CGGATCGACG TGAAGGATAC CAAGGAGGCC
 301 CTGGACAAGA TCGAGGAGAT CCAGAACAAG AGCAAGCAGA AAACCCAGCA GGCCGCTGCC
 361 GACACCGGCG ACAGCAGCAA AGTGAGCCAG AACTACCCCA TCATCCAGAA TGCCCAGGGC
 421 CAGATGATCC ACCAGAACCT GAGCCCCAGA ACCCTGAATG CCTGGGTGAA AGTGATCGAG
 481 GAAAAGGCCT TCAGCCCCGA AGTGATCCCT ATGTTCAGCG CCCTGAGCGA GGGCGCCACC
 541 CCCCAGGACC TGAACGTGAT GCTGAACATT GTGGGCGGAC ACCAGGCCGC CATGCAGATG
 601 CTGAAGGACA CCATCAATGA GGAGGCCGCC GAGTGGGACA GACTGCACCC CGTGCAGGCC
 661 GGACCCATCC CCCCTGGCCA GATCAGAGAG CCCAGAGGCA GCGACATCGC CGGCACCACC
 721 TCCACCCCTC AAGAACAGCT GCAGTGGATG ACCGGCAACC CTCCCATCCC TGTGGGCAAC
 781 ATCTACAAGC GGTGGATCAT CCTGGGCCTG AACAAGATTG TGCGGATGTA CAGCCCCGTG
 841 TCCATCCTGG ATATCAAGCA GGGCCCCAAG GAGCCCTTCA GAGACTACGT GGACCGGTTC
 901 TTCAAGGCCC TGAGAGCCGA GCAGGCCACC CAGGACGTGA AGGGCTGGAT GACCGAGACC
 961 CTGCTGGTGC AGAACGCCAA CCCCGACTGC AAGAGCATCC TGAAGGCCCT GGGCAGCGGC
1021 GCCACACTGG AGGAGATGAT GACCGCCTGC CAGGGAGTGG GCGGACCCGG CCACAAGGCC
1081 AGAGTGCTGG CCGAGGCCAT GAGCCAGGCC CAGCAGACCA ACATCATGAT GCAGCGGGGC
1141 AACTTCAGAG GCCAGAAGCG GATCAAGTGC TTCAACTGCG GCAAGGAGGG CCACCTGGCC
1201 AGAAACTGCA GAGCCCCCAG GAAGAAGGGC TGCTGGAAGT GTGGCAAGGA AGGGCACCAG
1261 ATGAAGGACT GCACCGAGAG GCAGGCCAAT TTCCTGGGCA AGATTTGGCC TAGCAGCAAG
1321 GGCAGACCCG GCAATTTCCC CCAGAGCAGA CCCGAGCCCA CCGCCCCTCC CGCCGAGCTG
1381 TTCGGCATGG GCGAGGGCAT CGCCAGCCTG CCCAAGCAGG AGCAGAAGGA CAGAGAGCAG
1441 GTGCCCCCCC TGGTGTCCCT GAAGTCCCTG TTCGGCAACG ATCCTCTGAG CCAGGGATCC
1501 TGA
```

FIG. 23

```
   1 ATGAAGTGCC TTTTGTACTT AGCTTTCTTA TTCATCGGGG TGAATTGCAA GGCTAGCGCA
  61 GAGAATTTGT GGGTAACAGT CTACTATGGA GTCCCTGTAT GGAAGGATGC AGAGACAACA
 121 TTGTTCTGTG CTAGTGACGC AAAGGCTTAC GAGACGGAGA AGCACAATGT GTGGGCAACT
 181 CACGCATGTG TCCCAACCGA TCCAAATCCT CAAGAGATTC ATCTAGAGAA TGTGACTGAA
 241 GAATTCAATA TGTGGAAGAA TAATATGGTA GAGCAAATGC ATACAGATAT CATTAGTTTA
 301 TGGGACCAGT CACTTAAACC CTGCGTTAAA TTGACGCCTC TATGTGTGAC ACTTCAATGT
 361 ACTAATGTTA CAAACAACAT AACAGATGAT ATGAGAGGAG AACTGAAGAA CTGTAGTTTC
 421 AACATGACGA CAGAGTTGCG TGACAAGAAA CAGAAAGTGT ATTCACTATT CTATCGGTTG
 481 GATGTAGTAC AGATAAATGA GAATCAAGGA AACAGGTCCA ACAACTCTAA CAAAGAGTAC
 541 AGACTTATTA ATTGCAATAC CAGTGCTATC ACGCAAGCCT GCCCAAAGGT TTCATTTGAA
 601 CCAATACCTA TTCATTATTG TGCACCTGCT GGATTCGCCA TCCTCAAATG TAAAGACAAG
 661 AAGTTCAATG GAACAGGACC CTGCCCATCA GTTTCAACCG TTCAGTGCAC CCACGGAATC
 721 AAGCCTGTAG TTAGTACTCA ATTATTGTTA AATGGGAGCT TAGCTGAAGA AGAAGTTATG
 781 ATTAGATCAG AGAATATTAC CAATAATGCG AAGAACATCT TGGTTCAATT CAATACTCCA
 841 GTCCAGATCA ATTGCACAAG GCCTAATAAT AATACCAGAA AGAGTATAAG AATTGGGCCA
 901 GGACAGGCAT TCTATGCAAC AGGAGATATA ATCGGAGACA TTCGACAAGC GCACTGCACT
 961 GTTTCTAAGG CCACTTGGAA TGAAACATTG GGTAAAGTTG TAAAGCAACT TCGGAAGCAT
1021 TTCGGAAATA ACACAATTAT TAGATTTGCG AACTCATCTG GAGGGGATCT GGAAGTGACA
1081 ACACACTCTT TCAATTGCGG TGGCGAGTTC TTCTATTGTA ATACAAGTGG ATTATTTAAC
1141 TCTACTTGGA TTTCAAATAC CTCAGTCCAA GGATCTAATT CAACAGGGTC TAACGATTCT
1201 ATAACATTAC CTTGCCGTAT AAAGCAAATT ATTAATATGT GGCAAAGAAT CGGGCAAGCG
1261 ATGTATGCTC CACCTATTCA AGGCGTGATT CGTTGCGTTT CAAACATAAC AGGGTTGATC
1321 CTGACCAGGG ATGGAGGCTC TACCAATTCC ACCACCGAGA CCTTCCGTCC CGGTGGCGGA
1381 GATATGCGGG ATAACTGGAG ATCAGAGCTC TATAAGTATA AGGTTGTGAA GATTGAACCT
1441 CTTGGAGTTG CCCCTACAAG AGCAAAGAGA AGGGTGGTTG GCCGAGAGAA GAGAGCAGTT
1501 GGCATCGGTG CTGTCTTTCT CGGATTTCTT GGAGCAGCTG GATCCACTAT GGGAGCAGCA
1561 TCAATGACAC TAACAGTGCA GGCTAGAAAT TTGCTTAGCG GAATCGTTCA GCAGCAGAGC
1621 AATTTACTAA GAGCAATTGA AGCACAGCAA CATCTCTTAA AGTTGACGGT GTGGGGCATT
1681 AAACAACTAC AAGCGAGAGT GCTTGCCGTC GAAAGATATT TGCGAGACCA ACAGCTATTG
1741 GGTATTTGGG GTTGTTCTGG GAAATTAATT TGCACAACAA ATGTTCCATG GAACTCCTCC
1801 TGGAGTAATA GGAATTTAAG TGAGATATGG GACAACATGA CATGGTTGCA GTGGGACAAG
1861 GAAATCTCAA ATTATACACA GATAATCTAT GGATTATTAG AAGAGTCTCA GAATCAGCAA
1921 GAGAAGAATG AACAGGATTT GCTTGCATTG GATAAGTGGG CTTCTCTATG GAACTGGTTC
1981 GATATTAGTA ATTGGCTCTG GTATATTAAG AGCTCTATTG CCTCTTTTTT CTTTATCATA
2041 GGGTTAATCA TTGGACTATT CTTGGTTCTC CGAGTTGGTA TTTATCTTTG CATTAAATTA
2101 AAGCACACCA AGAAAAGACA GATTTATACA GACATAGAGA TGAACCGACT TGGAAAGTAA
```

FIG. 24

```
   1 ATGACAGCAT ATATCCAGAG ATCACAGTGC ATCTCAACAT CACTACTGGT TGTTCTCACC
  61 ACATTGGTCT CGTGTCAGGC TAGCGCAGAG AATTTGTGGG TAACAGTCTA CTATGGAGTC
 121 CCTGTATGGA AGGATGCAGA GACAACATTG TTCTGTGCTA GTGACGCAAA GGCTTACGAG
 181 ACGGAGAAGC ACAATGTGTG GGCAACTCAC GCATGTGTCC CAACCGATCC AAATCCTCAA
 241 GAGATTCATC TAGAGAATGT GACTGAAGAA TTCAATATGT GGAAGAATAA TATGGTAGAG
 301 CAAATGCATA CAGATATCAT TAGTTTATGG GACCAGTCAC TTAAACCCTG CGTTAAATTG
 361 ACGCCTCTAT GTGTGACACT TCAATGTACT AATGTTACAA ACAACATAAC AGATGATATG
 421 AGAGGAGAAC TGAAGAACTG TAGTTTCAAC ATGACGACAG AGTTGCGTGA CAAGAAACAG
 481 AAAGTGTATT CACTATTCTA TCGGTTGGAT GTAGTACAGA TAAATGAGAA TCAAGGAAAC
 541 AGGTCCAACA ACTCTAACAA AGAGTACAGA CTTATTAATT GCAATACCAG TGCTATCACG
 601 CAAGCCTGCC CAAAGGTTTC ATTTGAACCA ATACCTATTC ATTATTGTGC ACCTGCTGGA
 661 TTCGCCATCC TCAAATGTAA AGACAAGAAG TTCAATGGAA CAGGACCCTG CCCATCAGTT
 721 TCAACCGTTC AGTGCACCCA CGGAATCAAG CCTGTAGTTA GTACTCAATT ATTGTTAAAT
 781 GGGAGCTTAG CTGAAGAAGA AGTTATGATT AGATCAGAGA ATATTACCAA TAATGCGAAG
 841 AACATCTTGG TTCAATTCAA TACTCCAGTC CAGATCAATT GCACAAGGCC TAATAATAAT
 901 ACCAGAAAGA GTATAAGAAT TGGGCCAGGA CAGGCATTCT ATGCAACAGG AGATATAATC
 961 GGAGACATTC GACAAGCGCA CTGCACTGTT TCTAAGGCCA CTTGGAATGA AACATTGGGT
1021 AAAGTTGTAA AGCAACTTCG GAAGCATTTC GGAAATAACA CAATTATTAG ATTTGCGAAC
1081 TCATCTGGAG GGGATCTGGA AGTGACAACA CACTCTTTCA ATTGCGGTGG CGAGTTCTTC
1141 TATTGTAATA CAAGTGGATT ATTTAACTCT ACTTGGATTT CAAATACCTC AGTCCAAGGA
1201 TCTAATTCAA CAGGGTCTAA CGATTCTATA ACATTACCTT GCCGTATAAA GCAAATTATT
1261 AATATGTGGC AAAGAATCGG GCAAGCGATG TATGCTCCAC CTATTCAAGG CGTGATTCGT
1321 TGCGTTTCAA ACATAACAGG GTTGATCCTG ACCAGGGATG GAGGCTCTAC CAATTCCACC
1381 ACCGAGACCT TCCGTCCCGG TGGCGGAGAT ATGCGGGATA ACTGGAGATC AGAGCTCTAT
1441 AAGTATAAGG TTGTGAAGAT TGAACCTCTT GGAGTTGCCC CTACAAGAGC AAAGAGAAGG
1501 GTGGTTGGCC GAGAGAAGAG AGCAGTTGGC ATCGGTGCTG TCTTTCTCGG ATTTCTTGGA
1561 GCAGCTGGAT CCACTATGGG AGCAGCATCA ATGACACTAA CAGTGCAGGC TAGAAATTTG
1621 CTTAGCGGAA TCGTTCAGCA GCAGAGCAAT TTACTAAGAG CAATTGAAGC ACAGCAACAT
1681 CTCTTAAAGT TGACGGTGTG GGGCATTAAA CAACTACAAG CGAGAGTGCT TGCCGTCGAA
1741 AGATATTTGC GAGACCAACA GCTATTGGGT ATTTGGGGTT GTTCTGGGAA ATTAATTTGC
1801 ACAACAAATG TTCCATGGAA CTCCTCCTGG AGTAATAGGA ATTTAAGTGA GATATGGGAC
1861 AACATGACAT GGTTGCAGTG GGACAAGGAA ATCTCAAATT ATACACAGAT AATCTATGGA
1921 TTATTAGAAG AGTCTCAGAA TCAGCAAGAG AAGAATGAAC AGGATTTGCT TGCATTGGAT
1981 AAGTGGGCTT CTCTATGGAA CTGGTTCGAT ATTAGTAATT GGCTCTGGTA TATTAAGAAC
2041 TCAAGAGAGA CTGTGATTAC GATCATAGTA GTTATGGTCG TAATATTGGT GGTCATTATA
2101 GTGATCATCA TCGTGCTTTA TAGACTCAGA AGGTCAATGC TAATGGGTAA TCCAGATGAC
2161 CGTATACCGA GGGACACATA CACATTAGAG CCGAAGATCA GACATATGTA CACAAACGGT
2221 GGGTTTGATG CAATGGCTGA GAAAAGATGA
```

FIG. 25

```
   1 ATGGAGGAGA AAGCATTCTC ACCTGAAGTG ATCCCTATGT TCACAGCATT ATCTGAGGGA
  61 GCTACTCCTC AAGATCTTAA CACAATGCTT AACACAGTCG GAGGACATCA AGCAGCAATG
 121 CAAATGTTGA AAGATACAAT TAACGAGGAA GCAGCAGAAT GGGATAGAAT CTATAAGAGA
 181 TGGATAATAT TAGGATTGAA CAAGATTGTT AGAATGTATT CTCCTGTGTC AATCCTTGAT
 241 ATAAGACAAG GACCTAAAGA GCCTTTCAGA GATTACGTCG ATAGATTTGC AAGAAATTGT
 301 AGAGCACCTA GAAAGAAGGG ATGTTGGAAA TGTGGGAAAG AAGGACATCA AATGAAAGAT
 361 TGTACTGAGA GACAAGCTAA CTTCTTGGGA AAGATATGGC CTTCAAGATG GAAACCTAAG
 421 ATGATAGGAG GAATAGGAGG ATTTATTAAA GTCAGACAAT ATGATCAAAT ATTGATTGAA
 481 ATATGTGGAC ATAAAGCTAT TGGAACAGTC CTAGTGGGTC CAACACCTGT CAACATCATT
 541 GGTAGAAATC TTCTCACTCA AATCGGATGT ACACTCAATT TCCCAATATC ACCTATTGAG
 601 ACCGTGCCTG TCAAATTGAA ACCTGGAATG GATGGACCTA AAGTCAAACA ATGGCCATTA
 661 ACTGAGGAGA AGATTAAAGC ACTGGTAGAA ATTTGTACAG AGATGGAGAA AGAAGGAAAG
 721 ATTTCCAAGA TTGGTCCTGA GAATCCTTAT AATACTCCTG TCTTTGCTAT TAAGAAGAAG
 781 GATAGTACCA AATGGAGGAA ATTAGTCGAT TTCAGAGAAC TTAACAAGAG GACTCAAGAC
 841 TTCTGGGAAG TGCAATTGGG AATCCCACAC CCTGCAGGAT TGAAGAAGAA GAAGTCTGTC
 901 ACTGTCCTAG ATGTGGGAGA TGCATATTTC AGTGTCCCAC TGGATGAAGG TTTCAGAAAG
 961 TATACAGCAT TCACAATCCC TTCCATTAAT AATGAAACAC CTGGAATAAG ATATCAATAT
1021 AATGTCTTAC CTCAAGGGTG GAAAGGATCT CCAGCAATAT TCCAATCATC AATGACAAAG
1081 ATCTTGGAGC CTTTCAGAGC TCAGAATCCA GAGATAGTTA TTTACCAATA CATGGATGAT
1141 TTGTATGTTG GGTCAGATCT CGAGATCGGA CAGCACAGGA TGGAGAATAG ATGGCAAGTA
1201 ATGATTGTCT GGCAAGTCGA TAGAATGAGA ATAAGAACAT GGAAATCCTT GGTGAAACAT
1261 CACCTTACAG AGGAGGCAGA ACTGGAACTG GCAGAGAATA GGGAAATATT GAAAGATCCA
1321 GTGCATGGTG TCTATTACGA TCCTTCTAAA GATCTGATAG CAGAGATCCA GTACTGGCAA
1381 GCAACATGGA TTCCTGAGTG GGAATTCGTC AACACACCTC CATTAGTGAA ACTATGGTAC
1441 CAATTAGAGA AGAATGTCAC CGAGAACTTC AACATGTGGA AGAACGATAT GGTAGATCAA
1501 ATGCACGAAG ATATCATCTC CTTGTGGGAT CAATCACTTA AACCTTGTGT TAAATTGACA
1561 CCTTGGGTAC CTGCTCATAA AGGGATAGGA GGAAACGAAC AAGTGGATAA ATTGGTGTCC
1621 CAAGGGATCA GGAAAGTCTT GTTCCTAGAT GGAATTGATA AAGCTCAAGC AAAGGAAATT
1681 GTCGCAAGCT GTGATAAGTG TCAATTAAAG GGAGAGGCAA TGCACGGACA AGTCGATTGT
1741 TCACCTGGTA TTTGGCAACT TGATTGTACA CATTTGGAGG GTAAAGTTAT TCTAGTAGCA
1801 GTACATGTCG CTTCTGGTTA TATTGAGGCA GAAGTGATAC CTGCTGAGAC AGGACAGGAG
1861 ACCGCATACT TTCTACTTAA GTTAGCTATG AATAAGGAGC TCAAGAAGAT AATAGGACAA
1921 GTTAGAGATC AAGCAGAGCA CCTTAAGACA GCTGTCCAAA TGGCAGTGTT TATACACAAC
1981 TTTAAGAGAA AGGGTGGAAT CGGAGGATAT TCCGCAGGAG AGAGAATCTG GAAAGGTCCT
2041 GCTAAATTGT TATGGAAAGG AGAAGGAGCA GTTGTAATAC AAGATAATTC TGATATAAAA
2101 GTAGTCCCTA GAAGGAAAGC TAAGATTATT AGAGATTATG GGAAACAAAT GGCAGGAGCT
2161 GATTGTGTGT TTCTAGGAGC AGCAGGATCC ACTATGGGAG CTGCATCAAT GACACTTACC
2221 GTGCAGGCTA GACAGCTTCT TTCAGGAATT GTACAGCAAC AGAATAATTT GCTAAGAGCA
2281 ATTGAAGCTC AACAACACTT ACTTCAACTT ACAGTCTGGG GAATCAAGCA AGCACCTACA
2341 AAAGCAAAGA GAAGAGTCGT CCAAAGAGAG AAAAGATAA
```

FIG. 26

OPTIMIZED HIV ENVELOPE GENE AND EXPRESSION THEREOF

RELATED APPLICATIONS AND INCORPORATION BY REFERENCE

This application is a Continuation of U.S. application Ser. No. 15/498,556 filed Apr. 27, 2017, now U.S. Pat. No. 10,220,087, which application is a Continuation-in-Part Application of International Patent Application Number PCT/US15/57452 filed Oct. 27, 2015, which published as PCT Publication No. WO 2016/069521 on May 6, 2016 and claims benefit of and priority to U.S. Provisional Patent Application Ser. No. 62/069,022 filed Oct. 27, 2014. Reference also is made to U.S. patent application Ser. Nos. 13/792,103 and 13/792,106 both filed Mar. 10, 2013.

The foregoing applications, and all documents cited therein or during their prosecution ("appin cited documents") and all documents cited or referenced in the appin cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant No. AID-OAA-A-11-00020 awarded by the USAID. The government has certain rights in the invention.

SEQUENCE LISTING

The instant application contains a Sequence Listing which has been submitted electronically in ASCII format and is hereby incorporated by reference in its entirety. Said ASCII copy, created on Nov. 17, 2015, is named 43094992040_SL.txt and is 176,525 bytes in size.

FIELD OF THE INVENTION

The present invention encompasses optimized HIV genes and expression thereof.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally-encoded membrane proteins (Abbas et al., Cellular and Molecular Immunology, 4th edition, W.B. Saunders Company, 2000, p. 454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that are transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Research on the Env glycoprotein has shown that the virus has many effective protective mechanisms with few vulnerabilities (Wyatt & Sodroski, Science. 1998 Jun. 19;

280(5371):1884-8). For fusion with its target cells, HIV-1 uses a trimeric Env complex containing gp120 and gp41 subunits (Burton et al., Nat. Immunol. 2004 March; 5(3): 233-6). The fusion potential of the Env complex is triggered by engagement of the CD4 receptor and a coreceptor, usually CCRS or CXCR4. Neutralizing antibodies seem to work either by binding to the mature trimer on the virion surface and preventing initial receptor engagement events, or by binding after virion attachment and inhibiting the fusion process (Parren & Burton, Adv Immunol. 2001; 77:195-262). In the latter case, neutralizing antibodies may bind to epitopes whose exposure is enhanced or triggered by receptor binding. However, given the potential antiviral effects of neutralizing antibodies, it is not unexpected that HIV-1 has evolved multiple mechanisms to protect it from antibody binding (Johnson & Desrosiers, Annu Rev Med. 2002; 53:499-518).

Problems encountered frequently during vaccine delivery vector development include poor foreign protein expression, inefficient or incomplete post-translational processing of the immunogen, diminished vector propagation, and gene insert instability. These problems are often related to the foreign gene being nonessential for vector propagation and the negative effect on replicative fitness that often is conferred by the biological or physical characteristics of the nucleotide sequence or the encoded protein.

Earlier 'gene optimization' procedures used to develop gene inserts for vaccine vectors focused primarily on designing synthetic coding sequences with the characteristics of highly expressed cellular mRNAs (Andre et al. 1998. J Virol 72:1497-1503, Barouch 2006. The Journal of pathology 208:283-289, Donnelly et al. 1997. DNA vaccines Annu Rev Immunol 15:617-648 and Haas et al. 1996. Codon usage limitation in the expression of HIV-1 envelope glycoprotein. Current biology: CB 6:315-324). Although this general optimization approach often increases expression of the encoded polypeptide, it also can result in a gene insert that is poorly compatible with the vector because the expressed protein is cytotoxic and/or the engineered nucleotide sequence is difficult to replicate and unstable. Accordingly, there is a need to develop a gene design approach that makes it possible to abundantly express foreign proteins while also reducing the negative effect caused by introducing foreign gene sequences into a vector genetic background.

Citation or identification of any document in this application is not an admission that such document is available as prior art to the present invention.

SUMMARY OF THE INVENTION

The present invention relates to viral vector which may contain and express a nucleic acid encoding an optimized human immunodeficiency virus (HIV) immunogen, wherein the HIV immunogen is a Env-F hybrid based on BG505 optimized for use in negative-strand RNA virus vectors and plasmid DNA vectors.

The present invention also relates to cells transfected with DNA to generate recombinant viral vectors of the invention. Advantageously, the cell is a Vero cell.

The present invention also relates to optimized HIV immunogens, which may be contained and expressed in the vectors of the present invention. Advantageously, the HIV immunogens are Env-F hybrids based on BG505, optimized for a negative strand RNA virus vector, such as a CDV vector, and also may be used for efficient expression in pDNA vectors.

The present invention also relates to the proteins expressed as optimized HIV immunogens, which may be contained and expressed in the vectors of the present invention.

The present invention also relates to vaccines, which may comprise the vectors of the present invention as well as methods for eliciting an immune response.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1. Amino acid sequence of the Clade A Env-G hybrid based on HIV isolate BG505 (SEQ ID NO: 2).

FIG. 2. Nucleotide sequence for the Clade A Env-G hybrid based on HIV isolate BG505 Env (SEQ ID NO: 3). Color-coding refers to features in FIG. 1. The nucleotide sequence was designed to resemble a VSV gene, but Applicants have found that it also is expressed efficiently from transfected plasmid DNA. A 5-nucleotide Kozak sequence is added before the ATG (5'-gccacc) (Kozak (1991) J Biol Chem 266, 19867-19870) before insertion into expression vectors.

FIG. 4. HIVCON coding sequence modified for use in negative-strand RNA virus vectors (SEQ ID NO: 4). The coding sequence was designed to resemble a negative-strand RNA virus genomic sequence. Specifically, the sequence was designed to resemble a gene from CDV. The 3' end includes coding sequence for an epitope tag described by Letourneau et al ((2007) *PLoS One* 2, e984). In this version of the synthetic gene, the 5' end includes coding sequence for the VSV signal peptide. The signal peptide coding sequence was added to provide the option for developing a gene that would direct synthesis of the HIVCON protein to the endoplasmic reticulum, which has been shown to stimulate both B and T cell responses for some immunogens (Kim et al. (2003) Gene Ther 10, 1268-1273; Kim et al. (2003) Virology 314, 84-91 and Fu et al. (1998) J Virol 72, 1469-1481). Sequences coding for the signal peptide and/or epitope tag can be removed by amplifying subregions of the gene by PCR. The epitope tag includes a strong T cell epitope recognized by rhesus macaques, a murine T cell epitope, and an antibody tag (V5 epitope) as described in Letourneau et al ((2007) *PLoS One* 2, e984). Also see Genbank DM059276.1 and FW556903.1.

FIG. 5. HIVCON polypeptide sequence (SEQ ID NO: 5). The HIVCON amino acid sequence is described by Letourneau et al. ((2007) PLoS One 2, e984) Also see GEnbank: DM059276.1 and FW556903.1. The C-terminal multi-epitope tag is highlighted in grey.

FIG. 6A. Nucleotide sequence of $HIV_{CON}$ with C5 env-tag (optimized for pDNA vector) (SEQ ID NO: 6).

FIG. 6B-6E. Translation of nucleotide sequence of FIG. 6A. FIG. 6B discloses the nucleotide sequence as SEQ ID NO: 6 and the protein sequence as SEQ ID NO: 7.

FIG. 6F. Amino acid sequence of $HIV_{CON}$C5 (SEQ ID NO: 7).

FIG. 7A. $HIV_{CON}$C5 nucleotide sequence optimized for CDV (SEQ ID NO: 8).

FIG. 7B-7F. Translation of nucleotide sequence of FIG. 7A. FIG. 7B discloses the nucleotide sequence as SEQ ID NO: 8 and the protein sequence as SEQ ID NO: 9.

FIG. 7G. Protein sequence of nucleotide sequence of 7A (Residues 2-792 of SEQ ID NO: 9).

FIG. 8A-8KK. Nucleotide sequence of SeV(NP) (SEQ ID NO: 10), SeV-sfEnvF(NP) (SEQ ID NO: 11), SeV-sgEnvG (NP) (SEQ ID NO: 12) and SeV-HIVconC5(NP) (SEQ ID NO: 13).

FIG. 23. Gag(NP) sequence (SEQ ID NO: 14).

FIG. 24. EnvG sequence used in SeV (SEQ ID NO: 15).

FIG. 25. EnvF sequence used in SeV (SEQ ID NO: 16).

FIG. 26. HIVcon sequence used in SeV (SEQ ID NO: 17).

DETAILED DESCRIPTION OF THE INVENTION

Figure 3:
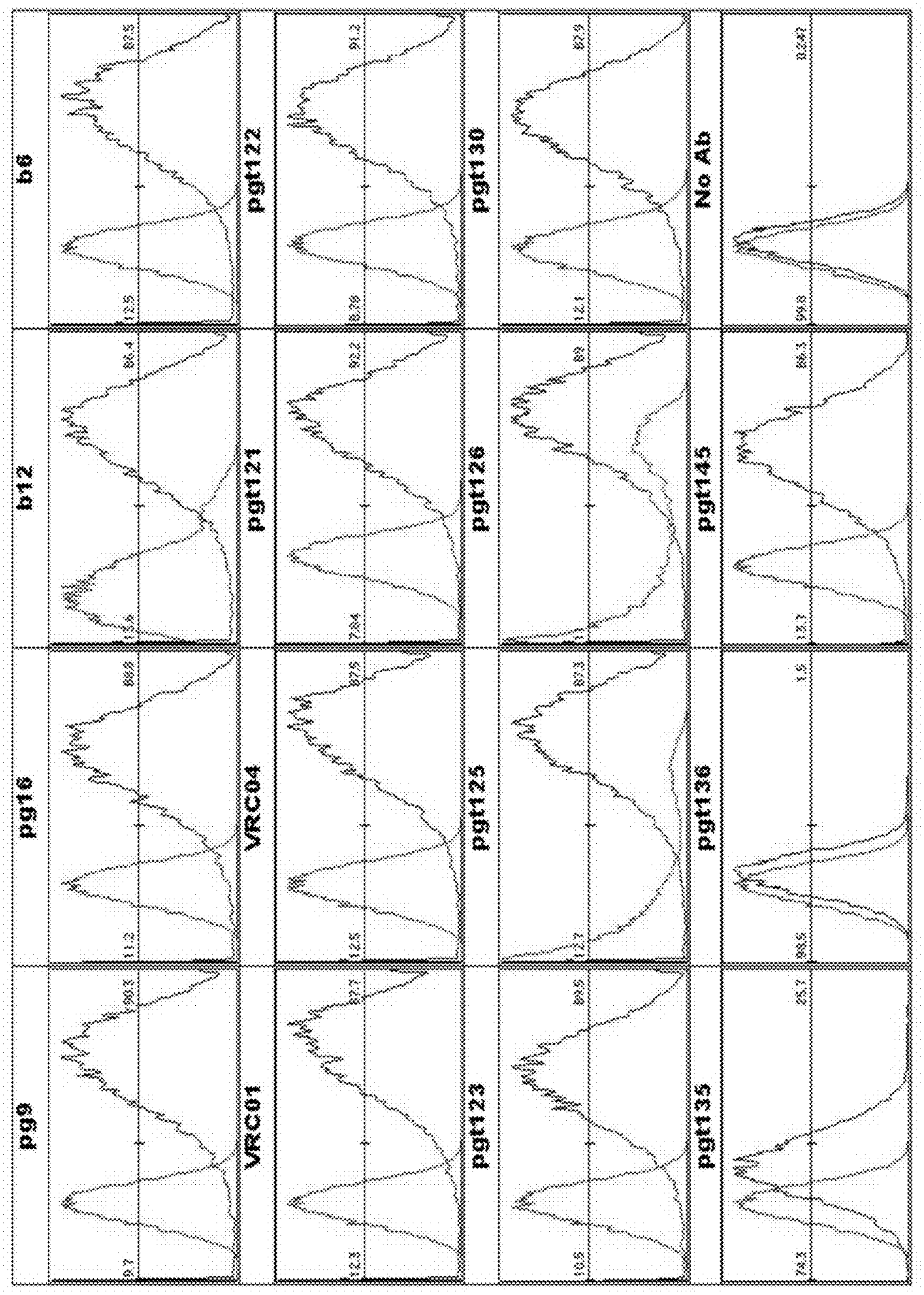
FIG. 3. FACS analysis on 293T cells transfected with plasmid encoding EnvG (BG505). Antibodies used for detection are identified in each panel. Note that the plasmid DNA vector contained the EnvG nucleotide sequence included in FIG. 2.

Genetically stable Sendai virus (SeV) vectors expressing membrane-anchored HIV Env trimer and the HIVconsv T cell immunogen were developed using Vero cells qualified for vaccine production and processes that comply with future cGMP vaccine manufacturing. The new vectors expressing HIV Gag or modified HIV trimers (EnvG or EnvF) or the modified HIVconsv immunogen (HIV-consvC5) were generated with rare or no observation of genetic instability. The observed genetic stability may be attributed to: 1) the foreign gene design, and 2) revised procedures used to generate virus from cloned DNA and subsequent methods used to select and verify clonal isolates.

The Env trimer immunogens expressed from the SeV vector are hybrid immunogens in which the signal peptide, transmembrane, and cytoplasmic regions were replaced with analogous sequences from VSV G or SeV F. The EnvG immunogen was described in U.S. patent application Ser. Nos. 13/792,103 and 13/792,106 both filed Mar. 10, 2013. EnvF is a novel immunogen generated by replacing the SS, TMR, and CT coding sequence in the EnvG coding region with nucleotide sequence directly from the SeV F gene. SeV vector genomic DNA clones subsequently were generated with the optimized EnvG or EnvF genes located upstream of NP (FIGS. 9G and H) in the most highly transcribed transcription unit. The modified HIVconsvC5 gene is related to the original HIVconsv sequence (Létourneau S. et al. PLoS One. 2007 Oct. 3; 2(10):e984. PMID: 17912361). The c-terminal epitope tag used in the original HIVconsv was replaced with the 'C5 tag', which is s peptide sequence from HIV Env. The genes encoding EnvG, EnvF, and HIV-consvC5 were optimized for used in negative-strand RNA virus vectors as described in US patent application Ser. Nos. 13,792,103 and 13/792,106 both filed Mar. 10, 2013.

The SeV vector rescue and propagation methods were developed for use with qualified Vero cells. Rescue of the SeV-EnvF, SeV-EnvG, and SeV-HIVconsv initially was conducted successfully using commercial DNA transfection reagents and human 293T cells or LLCMK2 (a monkey kidney cell line), but application of these protocols to virus rescue using qualified Vero cells failed. Applicants utilized a protocol based on electroporation of DNA and heat shock treatment resulted in rescue of recombinant SeV-EnvF, SeV-EnvG, and SeV-HIVconsvC5 from qualified Vero cells. Genetically-stable clonal isolates also were prepared and expanded using Vero cells under serum-free conditions producing master virus seeds.

The present invention also encompasses a vector rescue of the SeV-GOI (gene of interest: EnvF, EnvG, HIVcon etc.) on Vero cells by an electropration method. For example, Vero cells are transfected with the pSeV-GOI plasmid and supporting plasmids (NP, P, L, F, and T7) using an electroporator and cultured. The HA test is performed a few days after transfection to assess vector rescue. The culture media containing the rescued vector (Virus Seed: VS) is harvested, aliquoted into cryotubes, quickly frozen with dry-ice/ethanol, and stored at −80° C.

SeV-G(NP) Virus Rescue and Generation of Virus Seed (VS): To rescue recombinant SeV encoding HIV Gag, (SeV-G(NP)), the pSeV-G(NP) genomic clone along with the supporting plasmids expressing SeV NP, P, and L and bacteriophage T7 RNA polymerase were co-transfected into qualified Vero cells using a commercially available transfection reagent Lipofectamine 2000 CD. Lipofectamine 2000 CD is free of animal-derived material. Recombinant SeV-G(NP) produced from transfected cell monolayers was then amplified in Vero cells to generate the Virus Seed (VS). The VS was analyzed to determine virus titer by CIU assay, confirm integrity of the gag gene insert by RT/PCR, verify the nucleotide sequence of the gag insert, and evaluate Gag protein expression by Western blot analysis.

pMVS Production: The SeV-G(NP) VS was subjected to three sequential rounds of clonal purification by the limiting dilution clonal isolation method to generate a Cloned Virus Seed (CVS). Four Cloned Virus Seeds (CVSs) were selected and used to produce four separate pre-Master Virus Seeds (pMVSs). Each of the pMVSs was found to meet specifications as determined by virus productivity, HIV Gag protein expression by Western blot, and gag gene insert integrity by RT/PCR.

pMVS Genetic Stability Testing: The four pMVSs were subjected to genetic stability assessment by conducting five serial passages (P5) of each pMVSs on Vero cells and testing the pMVS+p5 (plus five passages) for virus productivity, HIV Gag protein expression by Western blot, and gene insert integrity by RT/PCR. The purpose of this study was to simulate virus amplification three passages beyond the level needed for production of clinical trial material (CTM). One SeV-G(NP) pMVS (clone FAA) was selected for MVS production based on titer, gene insert integrity, Gag protein expression, and results from complete genomic nucleotide sequencing. Additionally, 50 individual subclones were isolated at the pMVS+p5 level that were analyzed to confirm genetic integrity of the insert by RT/PCR and Gag protein expression by Western blot analysis. All the pMVSs were additionally tested for sterility and *mycoplasma* (PCR) at DNAVEC. Vials of the selected SeV-G(NP) pMVS (clone FAA) were transferred to BioReliance (BREL) for additional testing (Sterility, *Mycoplasma* and Adventitious Agents by the in-vitro Method—Points to Consider-FDA Guidance). All the test results met specifications. Data has been compiled as a Certificate of Analysis for the pMVS Lot.

Rescue of SeV expressing sfEnvF, sgEnvG, or HIV-conC5: Plasmid solution was prepared by mixing the pCAGGS-NP, pCAGGS-P, pCAGGS-L, pCAGGS-T7, and the SeV vector genomic clone containing the gene of interest (pSeV-GOI). Around 0.7 mL of cell suspension in Medium 2 (Iscove's modified MEM [IMEM] supplemented with 10% FBS, 220 uM 2-mercaptoethanol, 2 mM glutamine, 1 mM sodium pyruvate, and 0.1 mM nonessential amino acids from Life Technologies) was dispensed in 3 cryovials and 100 μL of plasmid solution prepared earlier was added to the cell suspension. The DNA and cells suspension was mixed gently before transfer to an electroporation cuvette. The Electroporator (BTX T820, Harvard Instruments) was set to low voltage mode (LV) to deliver 3 140-volt pulses of 70 msec with an interval between pulses 200 ms. After electroporation the cells subsequently were transferred to a sterile 50 mL conical centrifuge tube by pipetting. Around 10 mL of room temperature Medium 1 (DMEM supplemented with 10% FBS, 220 uM 2-mercaptoethanol, 2 mM glutamine, 1 mM sodium pyruvate, and 0.1 mM nonessential amino acids from Life Technologies) was added to the cells and mixed. The cells were collected by centrifugation for 5 minutes (1000 rpm, room temperature) after which the supernatant was discarded and the cells were resuspended in 48 mL of Medium 1. A uniform cell suspension was created and 2 mL cell suspension added per well into 4×6-well plates (24 wells). The cells were incubated at 37° C. for 4 hours before heat shock was performed at 42° C. for 2 hour. The 6-well plates were then incubated at 37° C. for 15 to 24 hr and examined microscopically to ensure good attachment and no contamination. The medium was collected from the wells every 15 to 24 hours to test for HA activity and the monolayer was fed with fresh 2 mL Medium 4 (Medium 1 supplemented with containing 50 ug/ml gentamicin and TrypLE Select) and incubation was continued at 37° C. with 5% $CO_2$ in air atmosphere. The supernatant was distributed and stored (−80° C.) in 0.2 mL aliquots and supernatant from wells exhibiting HA activity were also tested for infectivity and expressed as Cell Infectious Units (CIU)/mL.

SeV-sfEnvF(NP), SeV-sfEnvG(NP) and SeV-HIVconC5 (NP) pMVS Production: The sSeV-fEnvF(NP) and SeV-HIVconC5(NP) virus seeds (VS) was subjected to three sequential rounds of clonal purification by the limiting dilution cloning method to generate a Cloned Virus Seed (CVS). Between three and five CVSs were selected and used to produce separate pre-Master Virus Seeds (pMVSs). Each of the pMVSs was found to meet specifications as determined by virus productivity, HIV Gag protein expression by Western blot, and gag gene insert integrity by RT/PCR. All the pMVSs were additionally tested for sterility and *mycoplasma* (PCR).

The pMVSs were subjected to genetic stability assessment by conducting five serial passages of each pMVSs on Vero cells and testing the pMVS+p5 (plus five passages) for virus productivity, HIV Gag protein expression by Western blot, and gene insert integrity by RT/PCR. The purpose of this study was to simulate virus amplification three passages beyond the CTM production level. One pMVS was selected for MVS production based on titer, gene insert integrity, Gag protein expression, and results from complete genomic nucleotide sequencing. Virus from the selected preMVS also was serially passaged 5 times (preMVS+p5) to simulate amplification beyond that needed for manufacturing after which 50 individual subclones were isolated from the pMVS+p5. The virus subclones were analyzed to confirm genetic integrity of the insert by RT/PCR and Gag protein expression by Western blot analysis. RT/PCR for the SeV-sfEnvF(NP) and SeV-sfEnvG(NP) vectors produced a single PCR band at the expected size (sfEnvF at approximately 2.5 kb, sgEnvG at approximately 2.4 kb) was detected. EnvF and EnvG proteins were detected at the expected molecular mass (a precursor protein of about 160 kDa and the product of proteolytic processing of approximately 120 kDa). Greater than 90% of individual clones expressed a full-length EnvF or EnvG protein. RT/PCR conducted with clones of the HIVconC5 vector also produced a single band at the expected size (approximately 2.6 kb). HIVconC5 protein was detected at the expected molecular mass (approximately 90 kDa). Greater than 90% of individual clones expressed a full-length HIVconC5 protein.

Generation of recombinant SeV vectors may be applicable for vaccine and gene therapy application. Methods can be applied to vectors based on other paramyxoviruses such as animal or human parainfluenza viruses, measles virus, canine distemper virus, and bovine and human respiratory syncytial virus.

The Sendai virus vectors disclosed in U.S. Pat. Nos. 8,741,650; 8,217,019; 7,442,544; 7,314,614; 7,241,617; 7,226,786; 7,144,579; 7,101,685; 6,828,138; 6,746,860; 6,723,532 and 6,645,760 are also contemplated for the present invention.

Clade A Env trimer immunongen. Applicants conducted a computational analysis to identify potential ancestral virus sequences in HIV databases that were related to specimens collected from the IAVI Protocol G clinical trial. The results indicated that there was a high probability that HIV-1 strain BG505 (Subtype A; Genbank accession: ABA61516.1) was closely related to the progenitor virus that infected the patient from which PG9 and PG16 were isolated. Thus, for vaccine vector development, HIV Env BG505 has been used to develop a gene encoding a new membrane-bound timeric Env imunogen.

To efficiently express a membrane-bound Env trimer from vesicular stomatitis virus (VSV) it was necessary to make a hybrid Env protein in which the signal peptide, transmembrane domain, and cytoplasmic tail were replaced with sequence from VSV G. This hybrid protein (called EnvG, see FIGS. 1 and 2) expressed from VSV or plasmid DNA vectors retains Env function and is recognized on the cell surface by antibodies specific for multiple determinants (FIG. 3) including those formed by the CD4 binding site (b12, PGV04), V3 and carbohydrate (PGT126), the MPER (2F5 and 4E10), the glycan shield (2G12), and structures formed by V1/V2 and carbohydrate (PG9, PG16, PGT145).

In addition to the protein domain swaps, VSV vector replication and genetic stability was improved significantly by developing an EnvG(BG505) gene insert with a nucleotide sequence that resembles the genome of a negative-strand RNA virus (FIG. 2). Features of the modified gene sequence include codon bias and guanine-plus-cytosine content that is more consistent with VSV and other viruses in the mononegavirales family, and elimination of sequences found to promote instability in VSV and canine distemper virus (CDV) such as homopolymeric regions of greater than 4 (AAAA or TTTT) or 5 (GGGGG or CCCCC).

Applicants worked primarily on developing Env trimer immunogens that retain function. This strategy was followed to produce an immunogen that closely mimics the authentic trimeric Env spike on the HIV particle. If it is necessary to diminish Env function, we propose evaluating amino acid substitutions in the fusion peptide domain (Lay et al. (2011) J Biol Chem 286, 41331-41343). This will impair membrane fusion, but should limit effects on the overall trimeric structure of the immunogen.

The immunogen expressed on the cell surface following SeV-Env vector infection is analyzed comprehensively with a panel of monoclonal antibodies to confirm that the expected antigenic determinants are present. This is particularly important if Env function must be inactivated by amino acid substitutions. Applicants have standardized FACS analysis using a panel of monoclonal antibodies (see FIG. 3).

HIVCON Immunogen. The HIVCON immunogen is a fusion protein composed of highly conserved amino acid sequence motifs identified by comparing protein sequences from numerous isolates of HIV-1 subtypes A-D (Letourneau et al. (2007) PLoS One 2, e984). Applicants introduce the HIVCON into several vectors including pDNA and CDV. The original nucleotide sequence developed by Hanke and colleagues was optimized for expression from DNA vectors including Adenovirus, MVA, and plasmid (Genbank accession: DM059276.1 and FW556903.1). Because Applicants had difficulty using this type of optimized gene insert in negative-strand RNA virus vectors, Applicants developed a modified nucleotide sequence that resembles the sequence of RNA viruses. The modified HIVCON nucleotide sequence is provided in FIG. 4. The original HIVCON polypeptide sequence (Letourneau et al. (2007) PLoS One 2, e984) is in FIG. 5.

Reference is made to U.S. Pat. No. 8,119,114 B2 granted on Feb. 21, 2012 titled HIV-1 CLADE A CONSENSUS SEQUENCES, ANTIGENS, AND TRANSGENES; US Patent publication No. 20100215691 titled RECOMBINANT VIRAL VECTORS, filed Aug. 26, 2010; U.S. Provisional Patent Applications No. 61/617,368 titled METHODS TO IMPROVE VECTOR EXPRESSION AND GENETIC STABILITY filed Mar. 29, 2012 and U.S. Provisional Patent Applications No. 61/614,584 titled RECOMBINANT VIRAL VECTORS. Filed Mar. 23, 2012, the disclosures of which are incorporated by reference.

The invention also provides sequences for a modified $HIV_{CON}$ protein sequence which may comprise a C-terminal epitope tag derived from HIV Env (the C5 epitope tag: APTKAKRRVVQREKR (SEQ ID NO: 1)). This tag amino acid sequence corresponds to amino acid numbers 497-511 (HIV-1 BH-10 stain) located in the C-terminus of the gp120 Env subunit. An antibody available from Aalto Bio Reagents (ref. # D7324) recognizes the epitope. An example publication in which the antibody was used is Eggink et al. Virology. 2010 Jun. 5; 401(2):236-47. Epub 2010 Mar. 21. Erratum in: Virology. 2010 Oct. 10; 406(1):162-3. PubMed PMID: 20304457.

Two sequences provided are: A gene optimized for plasmid DNA vectors, which was modified from the nucleotide sequence published by Letourneau et al. PLoS One. 2007 Oct. 3; 2(10):e984. Erratum in: PLoS One. 2011; 6(3). doi: 10.1371/annotation/fca26a4f-42c1-4772-a19e-aa9d96c4eeb2. PubMedPMID: 17912361; PubMed Central PMCID: PMC1991584 (see FIGS. 6A, 6B and 6C) and A gene optimized for incorporation into negative strand RNA virus vectors such as CDV vectors (see FIGS. 7A, 7B and 7C).

The present invention also relates to protocols based on electroporation of DNA and heat shock treatment resulted in rescue of recombinant SeV-EnvF, SeV-EnvG, and SeV-HIVconsvC5 from qualified Vero cells.

One protocol for virus rescue is based on a BTX ECM830 electroporation device. The BTX and Gene Pulser II are fundamentally different devices. The BTX delivers DNA with a square-wave electrical pulse. The Gene Pulser delivers DNA with an exponential-decay electrical pulse. The square-wave device makes it possible to deliver multiple rapid electrical pulses which Applicants find helpful for Vero cells. Applicant's protocol uses 3 electrical pulses. Unfortunately, the difference in devices also means that the protocols cannot be directly applied to the Gene Pulser. To test the Applicants' protocol directly requires a square-wave electroporator.

For VSV Applicants cotransfect T7, genomic DNA, and plasmids encoding all other VSV genes (N, P, M, G, and L). For CDV, Applicants also cotransfect T7, genomic, N, P, M, F, H, and L.

Enveloped negative-strand RNA viruses are used to generate experimental vaccine vectors, because this class of viruses has multiple biological properties that are advantageous for vaccine development (Bukreyev et al. 2006. J Virol 80:10293-10306, Parks et al. 2013. Curr Opin HIV AIDS 8:402-411). Notable among their common features is the relatively small single-stranded nonsegmented RNA genome, which provides several practical advantages (Conzelmann 2004. Curr Top Microbiol Immunol 283:1-41, Clarke et al. 2006. Springer seminars in immunopathology 28:239-253). Importantly, gene exchange between genetically modified viral vectors and circulating wild-type viruses is not a significant risk, because the negative-strand RNA genome does not undergo homologous recombination. Furthermore, gene transfer through gene segment reassortment is not possible because of the nonsegmented structure of the genome. The RNA genome also cannot integrate into DNA, thus vectors based on these viruses do not modify the host cell chromosome. Their unique genome structure also can be modified to modulate vector replicative capacity and foreign gene expression (Conzelmann 2004. Curr Top Microbiol Immunol 283:1-41, Clarke et al. 2006. Springer seminars in immunopathology 28:239-253).

Although the nonsegmented negative-sense RNA genome provides important advantages, the ability of RNA viruses to mutate and evolve can make vector development challenging. The most common hurdle is nucleotide substitutions caused by the relatively low fidelity of virus-encoded RNA-dependent RNA polymerase, which lacks a proofreading and repair function analogous to DNA polymerases (Novella 2003. Curr Opin Microbiol 6:399-405). Nucleotide misincorporations occur at a frequency that produces about 1 base substitution per replicated genome. This generates minor nucleotide heterogeneity at the level of individual genomic RNAs, but across the total population of replicated genomes a very stable consensus sequence is established when virus is propagated under constant conditions. The stability of the consensus sequence reflects the fact that viruses most fit to replicate under the applied growth conditions have a selective advantage and remain dominant in the population, but if growth conditions change base substitution variants existing in the virus pool may have a replicative advantage that allows them to emerge as a more predominant element of the population.

Sequence deletion also can occur in negative-strand RNA genomes. These were originally observed by studying defective interfering particles, which form most readily when virus is serially amplified under conditions in which infection is initiated with large quantities of virus per cell (Blumberg et al. 1983. J Gen Virol 64 (Pt 9):1839-1847). Under these conditions, defective interfering particles will amplify rapidly because most cells are coinfected with wild-type virus, which provides the requisite replication machinery to propagate the defective particles. Analysis of defective interfering particle genomic RNA structures showed that some contain large internal deletions spanning much of the genome that likely are formed when a polymerase engaged in replication jumps to a downstream position on the replication template (Epstein et al. 1980. J Virol 33:818-829). The structure of some defective interfering particle genomes also indicates that the polymerase can jump from the template to the growing genome being synthesized, and as a result, copy back along the nascent genomic RNA (Calain et al. 1992. Virology 191:62-71). Deletions resulting from polymerase jumping rarely generate a viable mutant virus, because there is very little dispensable sequence in negative-strand RNA virus genomes. On the other hand, vectors that contain a foreign gene do have nonessential sequence that can be a target for deletion events.

Figure 9:
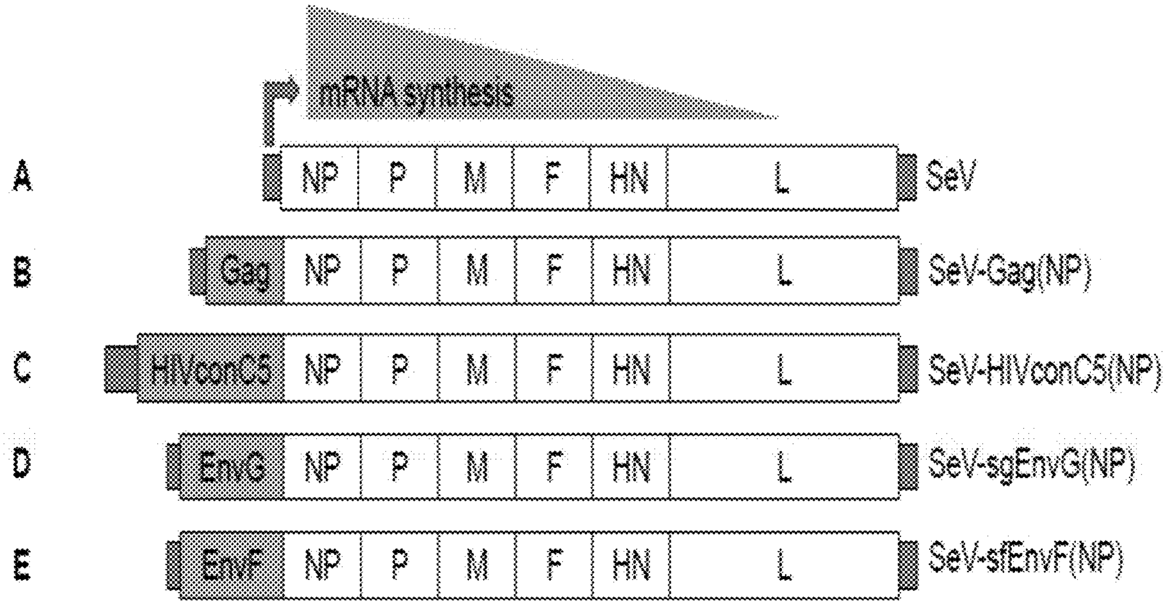
FIG. 9. Structure of the SeV vector genome.

The mutation mechanisms described above can be problematic for vector development if steps are not taken to minimize the replicative fitness cost associated with adding a foreign protein-coding gene into the small negative strand RNA virus genome. Because the foreign gene usually is nonessential for virus replication, it can accrue mutations without loss of virus functions required for propagation. Although mutations that provide a significant growth advantage might be rare, the extensive amplification needed to generate a recombinant vector and produce vaccine for use in preclinical and clinical studies provides ample opportunity for emergence of mutant viruses. Studies conducted with vesicular stomatitis virus (VSV) vectors illustrate that nucleotide substitutions in the foreign gene or in associated transcriptional control regions will accrue as the virus attempts to offset any negative fitness cost of the gene insert (Quinones-Kochs et al. 2001. Virology 287:427-435, Wertz et al. 2002. J Virol 76:7642-7650). The effect of deletions on vector development has not been described in the literature, but was observed during development of live attenuated respiratory syncytial virus vaccines (Karron et al. 1997. Proceedings of the National Academy of Sciences of the United States of America 94:13961-13966) indicating that it also can be problematic. As described below, both nucleotide substitutions and deletion mutations were encountered during development and large-scale production of some prototype Sendai virus (SeV) vaccine vectors encoding HIV immunogens (FIG. 9). Based in part on this experience with the SeV vector, a gene insert optimization approach and procedures for vector production and genetic stability analysis were developed that have supported development of several cGMP-compliant SeV-HIV vaccine candidates.

During negative-strand RNA virus vector development, Applicants and others have found that some gene inserts prevent vector rescue, inhibit virus propagation, or are subject to mutation at a frequency that may be problematic (Zhang et al. 2013. Virology 446:25-36, Wertz et al. 2002. J Virol 76:7642-7650, Yang et al. 2013. Vaccine 31:2822-2827, Nelson et al. 2013. Vaccine 31:3756-3762, Liang et al. 2014. J Virol 88:4237-4250, Quinones-Kochs et al. 2001. Virology 287:427-435). Remarkably, deletion mutations were observed when developing vectors based on paramyxoviruses, such as canine distemper virus (not shown), even though the deletion must maintain a genome length that is evenly divisible by units of 6 nucleotides to generate a viable virus (Kolakofsky et al. 1998. J Virol 72:891-899). This indicates that the extensive virus expansion needed to generate a vector and prepare vaccines to support large preclinical experiments or clinical trials provides opportunity for even very rare mutations to affect vaccine production. Therefore, generating and testing vector and insert designs that minimize the frequency of mutations and/or lessens the negative fitness cost of adding an extra gene is essential for advancing vaccine candidates beyond small-scale laboratory investigation.

Stable SeV vectors were generated encoding four different HIV vaccine immunogens (FIGS. 9 E-H) and their genetic stability was evaluated rigorously. Three of the vectors were advanced to the stage where cGMP-compliant virus seed banks were prepared and one encoding HIV Gag was used to prepare vaccine for Phase 1 clinical trial. During the course of developing these vectors, several advances were made in different phases of vector design, development, and testing, including: 1) definition of a gene insert design approach tailored to negative-strand RNA viruses; 2) processes for rescue and expansion of recombinant virus under conditions that comply with cGMP; and 3) a rigorous genetic stability testing approach designed to determine if a new vaccine candidate is capable expansion on a scale to support manufacturing. This is exemplified by development of the stable vectors described below, which encode HIV Gag, the HIVconC5 immunogen, and two different HIV Env glycoprotein variants (FIG. 9).

Figure 10:
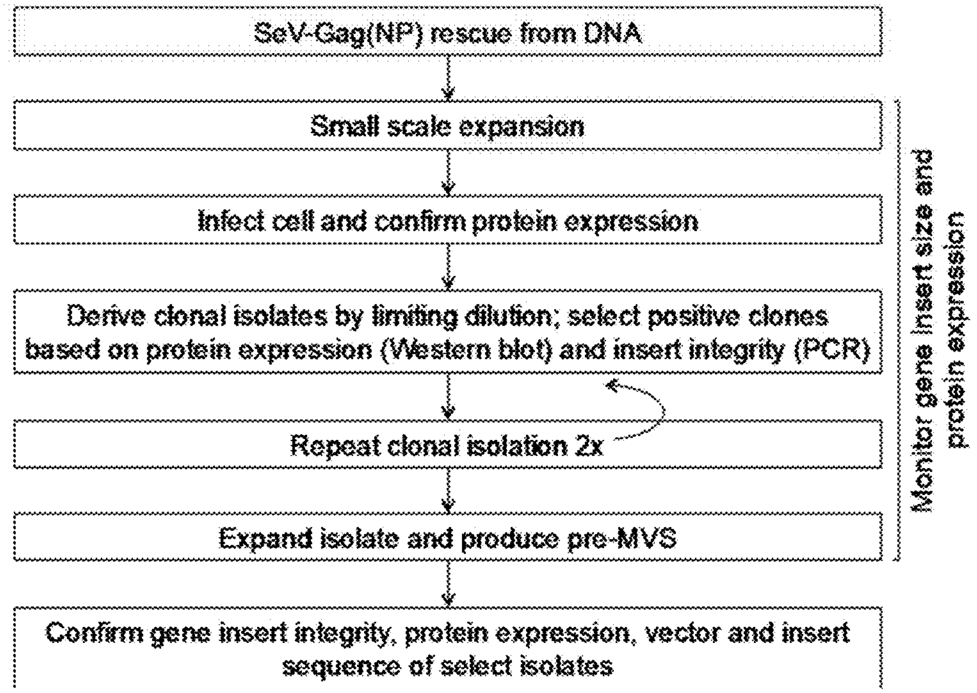
FIG. 10. Development of SeV-Gag(NP).
Figure 11:
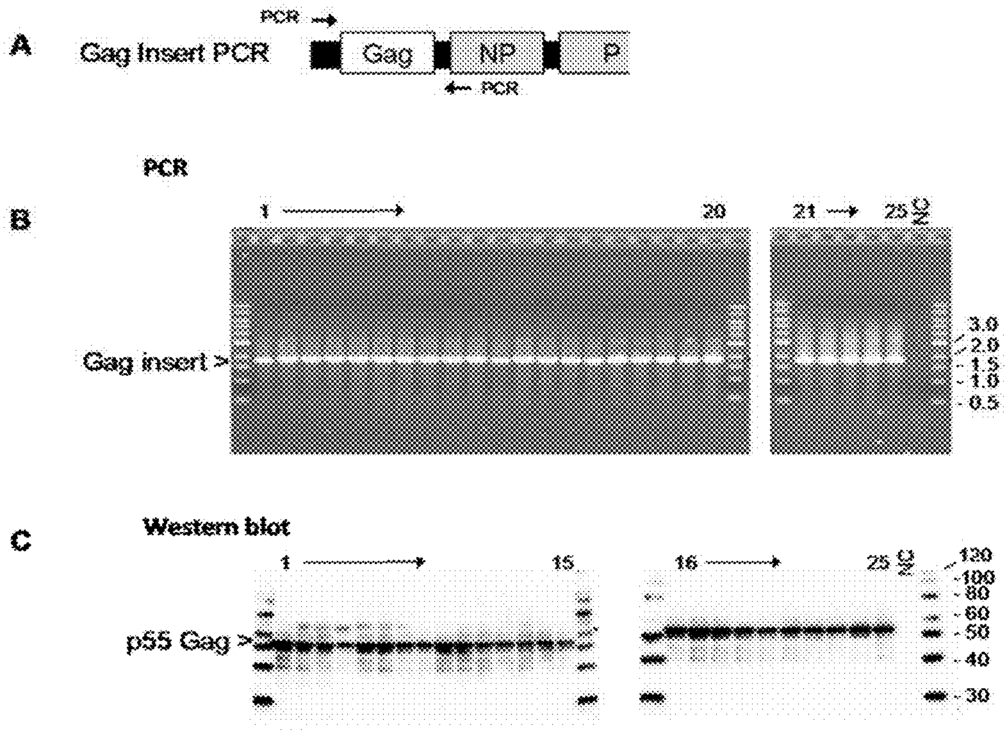
FIG. 11. Selection of clonal isolates. PCR and Western blot analysis of SeV-Gag(NP) following the 3rd round of limiting dilution prior to amplifying select isolates for generation of pMVS.

Potential contributors to the genetic instability of some gene inserts in negative-strand RNA viruses have been proposed including: 1) large gene insert size, 2) location of the insert in the viral genome; 3) the nucleotide sequence of the insert, which may have a high percentage of guanine and cytosine (61% G+C), and/or 4) a protein activity that was inhibitory to replication. The authors developed and applied a number of gene design approaches to maximize stability of gene inserts and then developed an approach to rigorously confirm that genetically stable vectors were produced and could support vaccine manufacturing. An SeV genomic clone was generated in which only the Gag coding sequence (1.5 kb, FIG. 9E) derived from the GRIN gene (U.S. Pat. Nos. 8,119,144 and 8,735,542 and Keefer et al. 2012. PLoS ONE 7:e41936) was inserted upstream of NP. Recombinant virus called SeV-Gag(NP) was generated from DNA using procedures (Kato et al. 1996. Genes to cells: devoted to molecular & cellular mechanisms 1:569-579, Hasan et al. 1997. J Gen Virol 78 (Pt 11):2813-2820) that were modified to ensure compliance with cGMP. In brief, key elements of this virus rescue procedure included using only plasmid DNA to initiate rescue and no complementing helper virus, recovery of recombinant SeV-Gag(NP) from transfected Vero cells that were qualified for vaccine production, use of transfection reagent that was free of animal-derived materials, and culture medium containing documented fetal bovine serum. This made it possible to use qualified Vero cells throughout the entire process of developing SeV-Gag (NP) (FIG. 10) including virus rescue, clonal isolation by limiting dilution and virus expansion to produce a pre-Master Virus Seed bank (Pre-MVS). Gag gene insert stability was monitored continuously during the process by a combination of RT/PCR and Western blotting to confirm integrity of the inserted nucleotide sequence and the size of the expressed polypeptide as illustrated in FIG. 11, which shows analysis of virus isolates after the third round of clonal isolation by limiting dilution.

Figure 12:
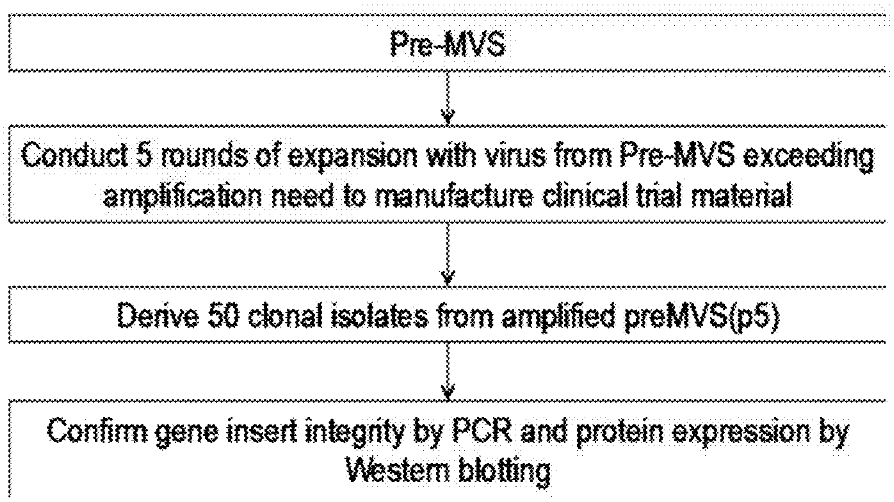
FIG. 12. Genetic stability testing summary.
Figure 13:
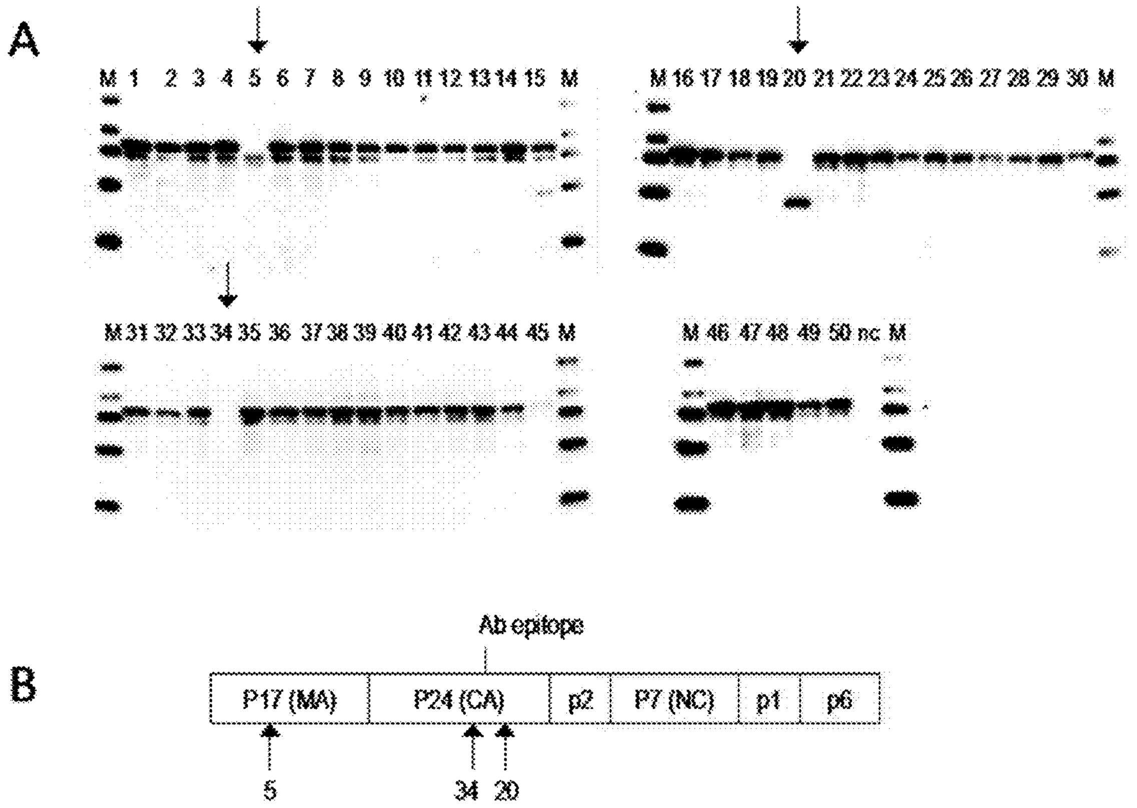
FIG. 13. Analysis of expanded pMVS.

To rigorously evaluate if SeV-Gag(NP) genetic stability was adequate to support production of vaccine for clinical trial, virus from the pre-MVS was subjected to 5 additional serial amplifications (pre-MVSp5) in Vero cells, which was estimated to exceed the magnitude of expansion needed for a manufacturing run (FIG. 12). To analyze the composition of the expanded virus in detail, 50 clonal isolates were derived from the pre-MVSp5 by limiting dilution and each was analyzed to confirm integrity of the gene insert (FIG. 12). RT/PCR was conducted with primers specific for SeV sequence flanking the Gag insert (FIG. 11A), and the results showed that all clonal isolates had a full-length Gag gene (FIG. 15A). Western blotting demonstrated that 47 of 50 (94%) clonal isolates expressed full-length Gag protein (FIG. 11A). Analysis of the 3 clonal isolates that did not express full-length Gag showed that point mutations were present, which introduced premature stop codons that truncated the Gag polypeptide (FIG. 11B). Overall the results demonstrated that the 1.5 kb Gag gene in SeV-Gag(NP) was not subject to deletion mutations and that the majority of virus in the population encoded a full-length Gag immunogen. This result also provided confidence that the preMVS would support production of a larger master virus seed (MVS) bank and subsequent cGMP manufacturing.

A portion of the preMVS was transferred to a contract manufacturer and a MVS bank was prepared and clinical trial material was manufactured. Analysis of the bulk vaccine material showed that the gene insert was intact, Gag protein was expressed from infected cells, and the consensus nucleotide sequence of the Gag gene was correct. From these results, it can be concluded that SeV-Gag(NP) was genetically stable through cGMP manufacturing and that the genetic stability testing approach (FIG. 12) provided a reliable predictor of the results during manufacturing.

Plans for further development of the SeV-HIV vaccine required use of foreign genes (FIGS. 1F-H) that were larger than the gag coding sequence, and in some cases, encoded immunogens known to promote vector genetic instability such as a trimeric HIV Env (Wyatt et al. 2008. Virology 372:260-272, Wyatt et al. 2009. J Virol 83:7176-7184). Therefore, it was essential to develop gene design strategies that would minimize accrual of mutations in the foreign nucleotide sequence and reduce any inhibitory effects associated with expression of the polypeptide encoded by the transgene. To achieve this, two gene design strategies were applied during development of SeV vectors encoding the Env and HIVconC5 immuongens (FIGS. 9F-H).

One involved a sequence optimization method that designs foreign genes to have a nucleotide content that is similar to negative-strand RNA virus genomic RNA. This gene optimization method was applied to the Env and HIVconC5 genes. The second approach involved modifying the Env gene to have it encode a hybrid polypeptide in which several Env functional domains were replaced with analogous regions of heterologous transmembrane glycoproteins.

Part of the rationale for developing a new gene optimization approach came from observing that a SIV Gag with a high G+C content (>60%) was unstable when cloned into a CDV vector. Gene deletions initially prevented rescue of vector with an intact Gag gene. Notably, the high G+C content differed substantially from negative-stranded RNA virus genomes, which generally have relatively low percentage of G+C (i.e. SeV G+C is 46% and VSV Indiana serotype is 42%). The high G+C content of the SIV Gag sequence was due to the gene optimization process used to design the gene (Schneider et al. 1997. J Virol 71:4892-4903). Genes optimized to achieve maximum expression in mammalian cells typically have a codon bias that results in high G+C content (Kudla et al. 2006. PLoS Biol 4:e180). In addition to generating a nucleotide content and codon bias that is not typical of a negative-strand RNA virus, standard gene optimization methods do not survey the designer gene for sequence motifs that might have a negative effect on RNA genome replication or viral mRNA synthesis. Example of sequence motifs that might cause instability include: 1) regions rich in G+C that may form secondary structures that inhibit the viral RNA-dependent RNA polymerase; 2) sequence elements that resemble the natural cis-acting signals that direct template-independent addition of nucleotides by the viral RNA-dependent RNA polymerase during mRNA editing or polyadenylation (Lamb et al. 2007. Paramyxoviridae: the viruses and thier replication, p. 1449-1496. In Knipe et al. (ed.), Fields Virology, vol. 2. Wolters Kluwer, Philadelphia, Lyles et al. 2007. Rhabdoviridae, p. 1363-1408. In Knipe et al. (ed.), Fields virology, vol. 1. Wolters Kluwer, Philadelphia); 3) sequences that resemble conserved transcription initiation or termination signals specific for the viral polymerase (Sakai et al. 1999. FEBS letters 456:221-226, Lamb et al. 2007. Paramyxoviridae: the viruses and thier replication, p. 1449-1496. In Knipe et al. (ed.), Fields Virology, vol. 2. Wolters Kluwer, Philadelphia, Lyles et al. 2007. Rhabdoviridae, p. 1363-1408. In Knipe et al. (ed.), Fields virology, vol. 1. Wolters Kluwer, Philadelphia, Zhang et al. 2012. PLoS ONE 7:e51633); and homopolymeric sequence motifs that might cause RNA polymerase stuttering (Skiadopoulos et al. 2003. J Virol 77:270-279, Hausmann et al. 1999. J Virol 73:5568-5576, Bilsel et al. 1990. J Virol 64:4873-4883). Nucleotide sequence elements like these if present in a foreign gene can promote genetic instability by interfering with RNA genome replication or promoting a higher frequency of nucleotide misincorporation.

A new gene optimization process was developed specifically to make genes resemble a negative-strand viral genomic RNA while omitting sequence motifs that might interfere with RNA replication or promote greater rates of nucleotide misincorporation. The end result is a foreign protein coding sequence that has a codon bias similar to negative-strand viruses, a lower overall G+C content, no sequences resembling cis-acting viral RNA polymerase control elements, and very few or no homopolymeric nucleotide stretches greater than 4-5 nucleotides in length. This gene optimization process has been used during generation of genetically stable SeV vectors expressing HIV Env (2.1 to 2.3 kb, FIGS. 9G and H) or containing the 2.2 Kb HIVconC5 gene (FIG. 9F).

Figure 14:
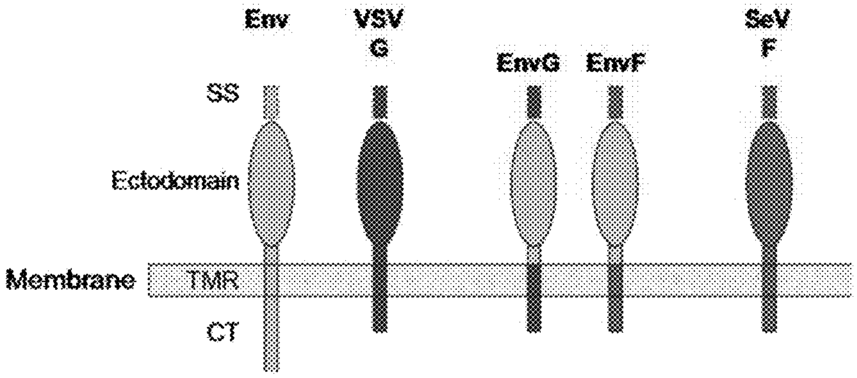
FIG. 14. HIV Env modification.

In addition to applying the gene optimization process described above, additional steps were taken to make HIV Env protein more compatible with negative-strand RNA viruses and reduce its known negative effect on virus replicative fitness. The vaccine design goal was to express an Env immunogen that closely resembled the authentic HIV glycoprotein. This meant expressing Env as a trimeric transmembrane glycoprotein, but vector delivery of Env as a transmembrane glycoprotein was known to be problematic, because it is expressed poorly at the cell surface, it is cytotoxic, and the Env gene tends to promote vector instability (Wyatt et al. 2008. Virology 372:260-272, Wyatt et al. 2009. J Virol 83:7176-7184, Postler et al. 2013. J Virol 87:2-15). To lessen the negative effect of the transgene while improving Env expression, protein domain substitutions were introduced in regions that control cell surface incorporation. Hybrid Envs were developed in which the Env signal sequence (SS), transmembrane region (TMR), and the cytoplasmic tail (CT) were replaced with analogous sequence from VSV G or SeV F (FIG. 14). These domains were exchanged because they were expected to have little effect on the native structure of the trimeric Env ectodomain, and earlier studies had shown that replacement of the SS or CT could modulate Env expression (Haas et al. 1996. Current biology: CB 6:315-324, Owens et al. 1993 J Virol 67:360-365), and TMR substitution had been shown to affect surface expression of a variety of different transmembrane glycoproteins including HIV Env (Garrone et al. 2011. Sci Transl Med 3:94ra71, Kirchmeier et al. 2014. Clin Vaccine Immunol 21:174-180, Wang et al. 2007. J Virol 81:10869-10878, Schmidt et al. 2014. J Virol 88:10165-10176, Gravel et al. 2011. J Virol 85:3486-3497, Zimmer et al. 2005. J Virol 79:10467-10477).

Two chimeric Envs were generated for testing in the SeV-Env vector. In one, Glade A HIV Env from strain BG505 (Genbank ABA61516.1) (Hoffenberg et al. 2013. J Virol 87:5372-5383, Wu et al. 2006. J Virol 80:835-844) was modified by replacing the SS, CT, and TMR regions with analogous sequence from VSV G to generate a hybrid called EnvG. A second gene was designed to encode a hybrid in which the same domains were replaced with sequence from the SeV fusion protein (F), which was called EnvF. To generate the EnvF gene, the SS, TMR, and CT coding sequence in the EnvG coding region was replaced with nucleotide sequence directly from the SeV F gene. SeV vector genomic DNA clones subsequently were generated with the optimized EnvG or EnvF genes located upstream of NP (FIGS. 9G and H) in the most highly transcribed transcription unit.

Figure 15:
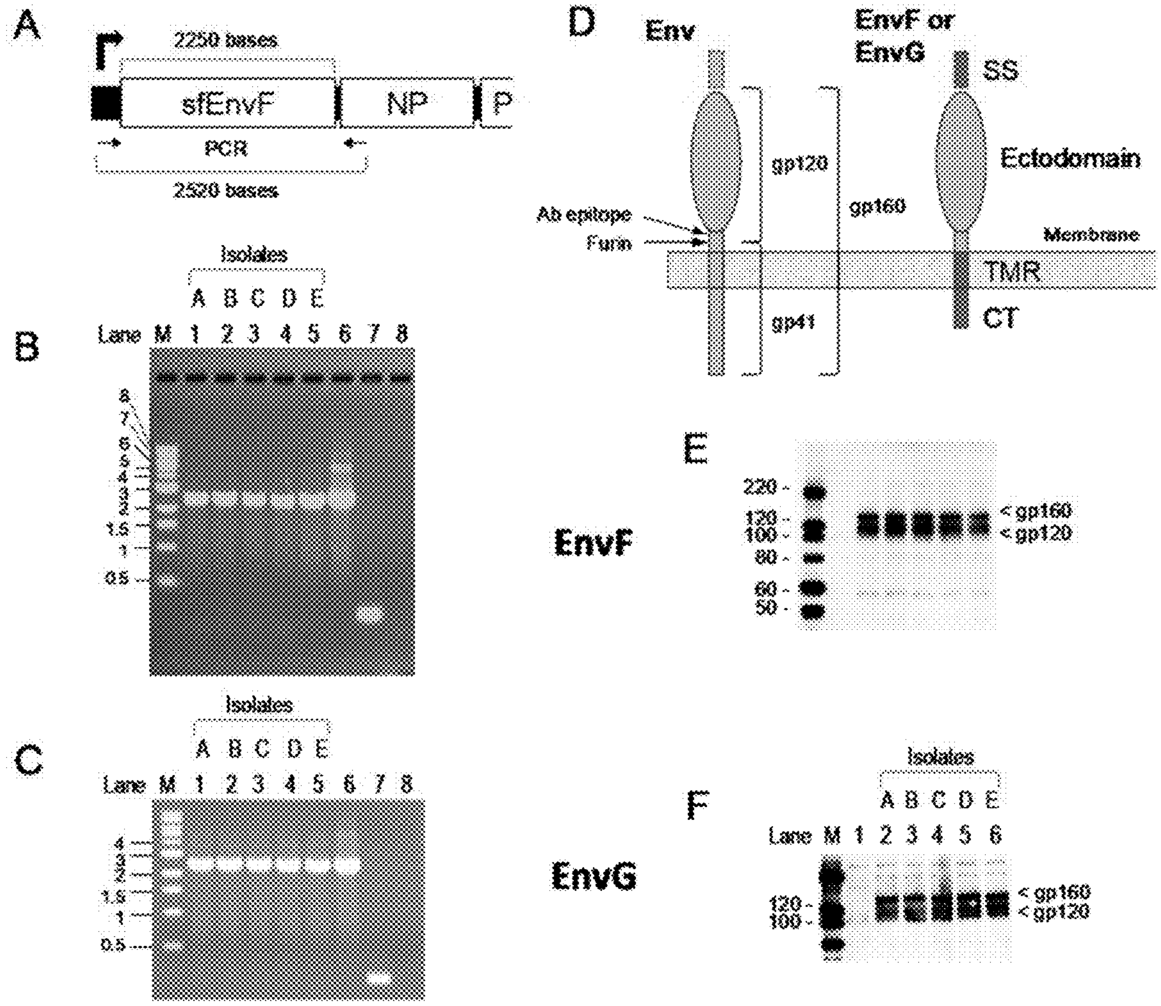
FIG. 15. Rescue of SeV-sfEnvF and SeV-sgEnvG.

Multiple attempts to rescue the SeV-sfEnvF(NP) or SeV-sgEnvG (NP) failed to produce infectious SeV vectors when using the Vero cell-based protocol that was successful with SeV-Gag (NP). Investigation of transfection variables such as using different DNA quantities or alternative transfection reagents also failed indicating that recovery of vectors expressing Env, particularly from a gene inserted in the promoter-proximal transcription unit, would require a more robust virus rescue procedure. Accordingly, a new Vero cell-based SeV rescue method was developed based on earlier approaches shown to work with other negative strand viruses in which DNA is delivered by electroporation and recovery of recombinant virus is enhanced by induction of the cellular heat shock response (Witko et al. 2010. J Virol Methods 164:43-50, Witko et al. 2006. J Virol Methods 135:91-101). Using this new SeV rescue method under research laboratory conditions, infectious recombinants were recovered from Vero cells after which three rounds of limiting dilution was performed to generate multiple clonal isolates of SeV-sfEnvF(NP) and SeV-sgEnvG(NP). Analysis by RT/PCR and Western blotting demonstrated that all clonal isolates contained an intact gene insert and expressed the expected Env immunogen (FIG. 15). This result indicated that SeV-sfEnvF(NP) and SeV-sfEnvG(NP) produced by this method would enable development of vector seeds under cGMP-compliant conditions.

Figure 16:
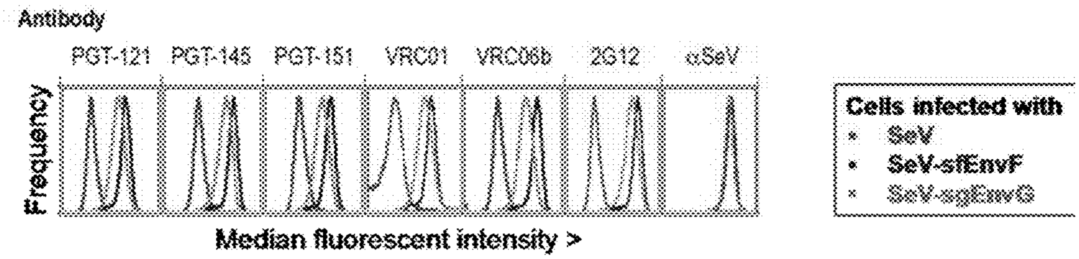
FIG. 16. Flow cytometry.
Figure 17:
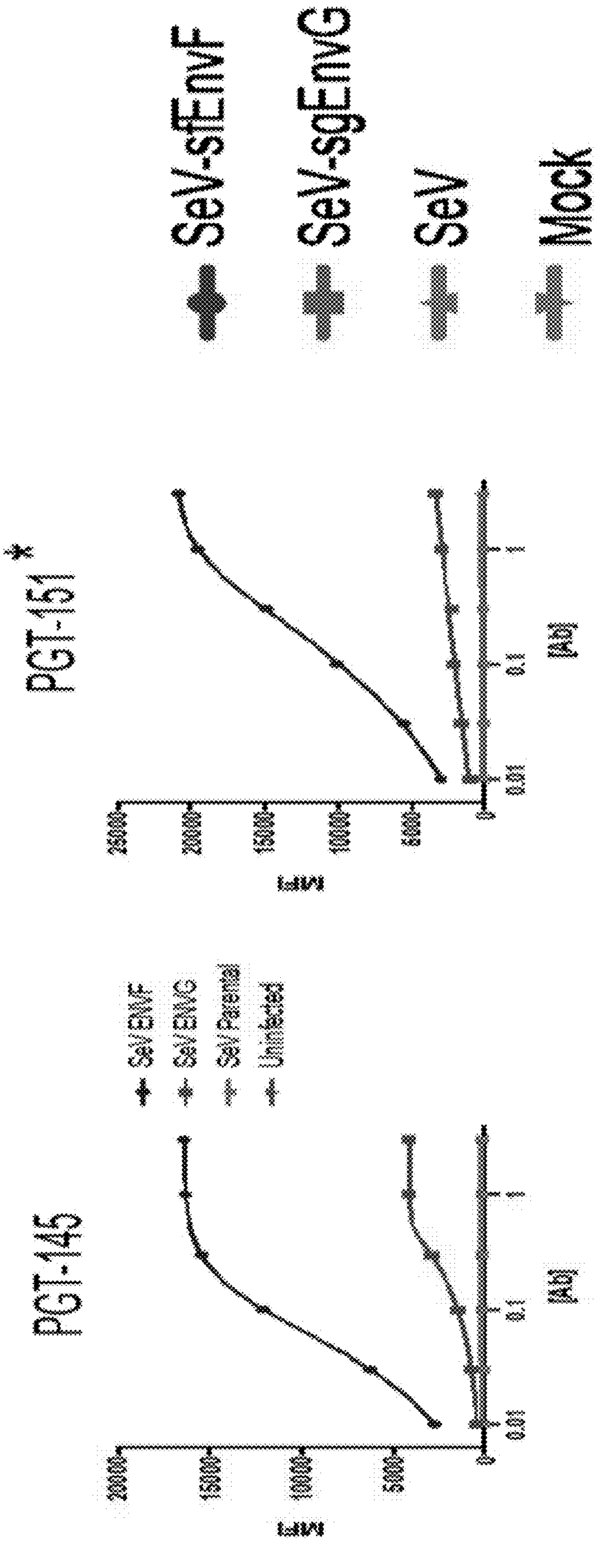
FIG. 17. Antibody binding curves.
Figure 17:
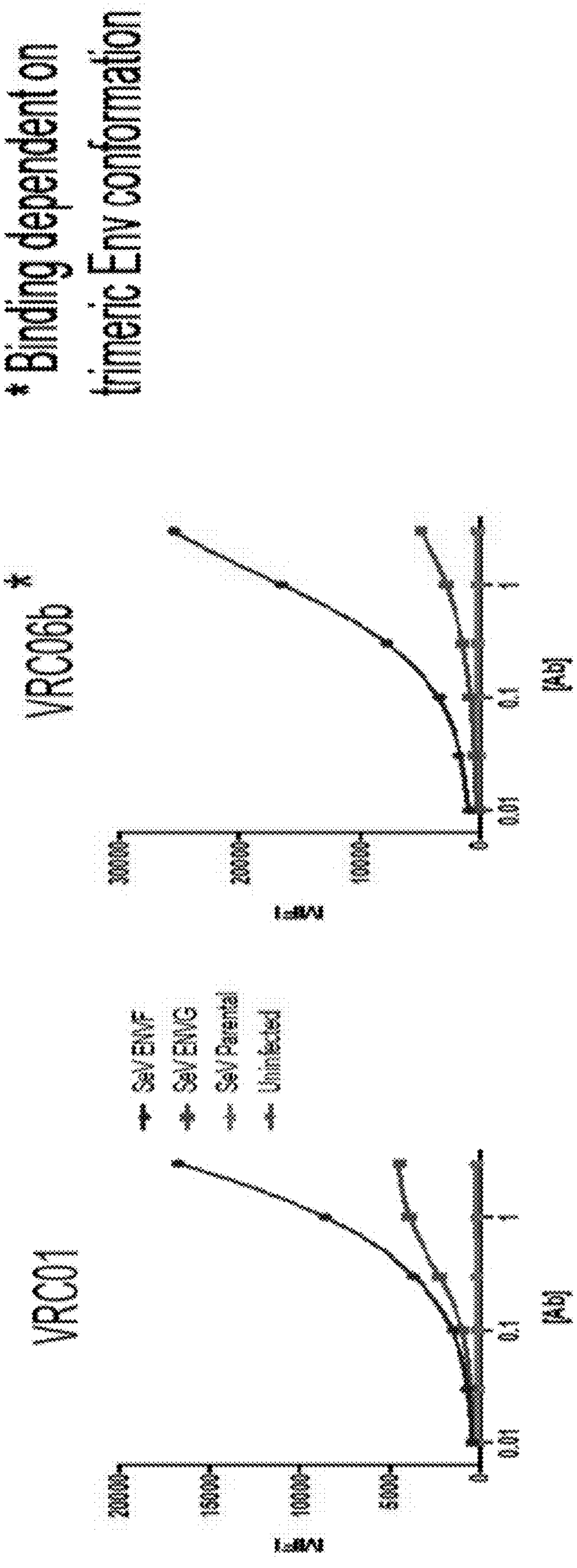
Figure 17:
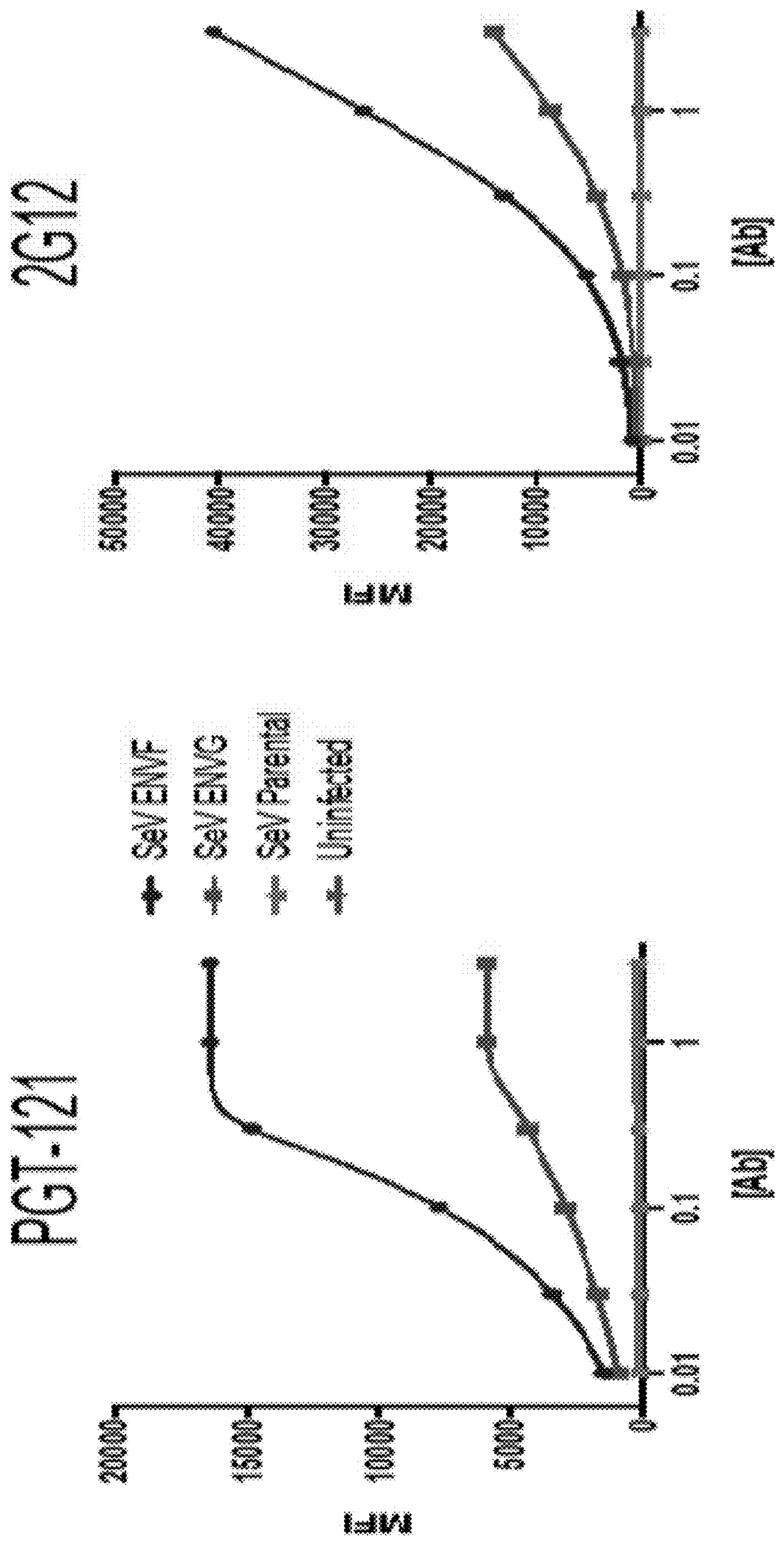

Because the vaccine design objective was to develop a vector that expressed an immunogen that mimicked the native HIV Env spike incorporated in the cell membrane, flow cytometry was conducted with cells infected with SeV-sfEnvF(NP) or SeV-sfEnvG(NP) to evaluate surface expression of the Env immunogens. Vero cells were infected with an SeV-sfEnvF(NP) or SeV-sfEnvG(NP) clonal isolate and stained 48 hours later with monoclonal antibodies specific for a number of different Env epitopes (Kwong et al. 2012. Immunity 37:412-425, Haynes et al. 2011. Trends Mol Med 17:108-116, Burton et al. 2012. Science 337:183-186). The results showed (FIG. 16) that EnvF or EnvG was detected on the cell surface by multiple broadly neutralizing monoclonal antibodies (bnAbs) specific for Env, and importantly, this included bnAbs PGT151 and VRC06b, which preferentially bind to mature trimeric Env spikes (Falkowska et al. 2014. Immunity, Blattner et al. 2014. Immunity, Li et al. 2012. J Virol 86:11231-11241).

To evaluate the relative abundance of EnvF and EnvG expressed on the cell surface, infected cells were reacted with increasing quantities of antibodies to assess binding over a range of concentrations and estimate the point at which antibody binding plateaued. The antibody titrations clearly showed that cells infected with SeV-sfEnvF(NP) bound to increased quantities of antibody indicating that EnvF was expressed in greater quantities on the cells surface; therefore, SeV-sfEnvF(NP) was selected for further development.

Figures 18A, 18B:
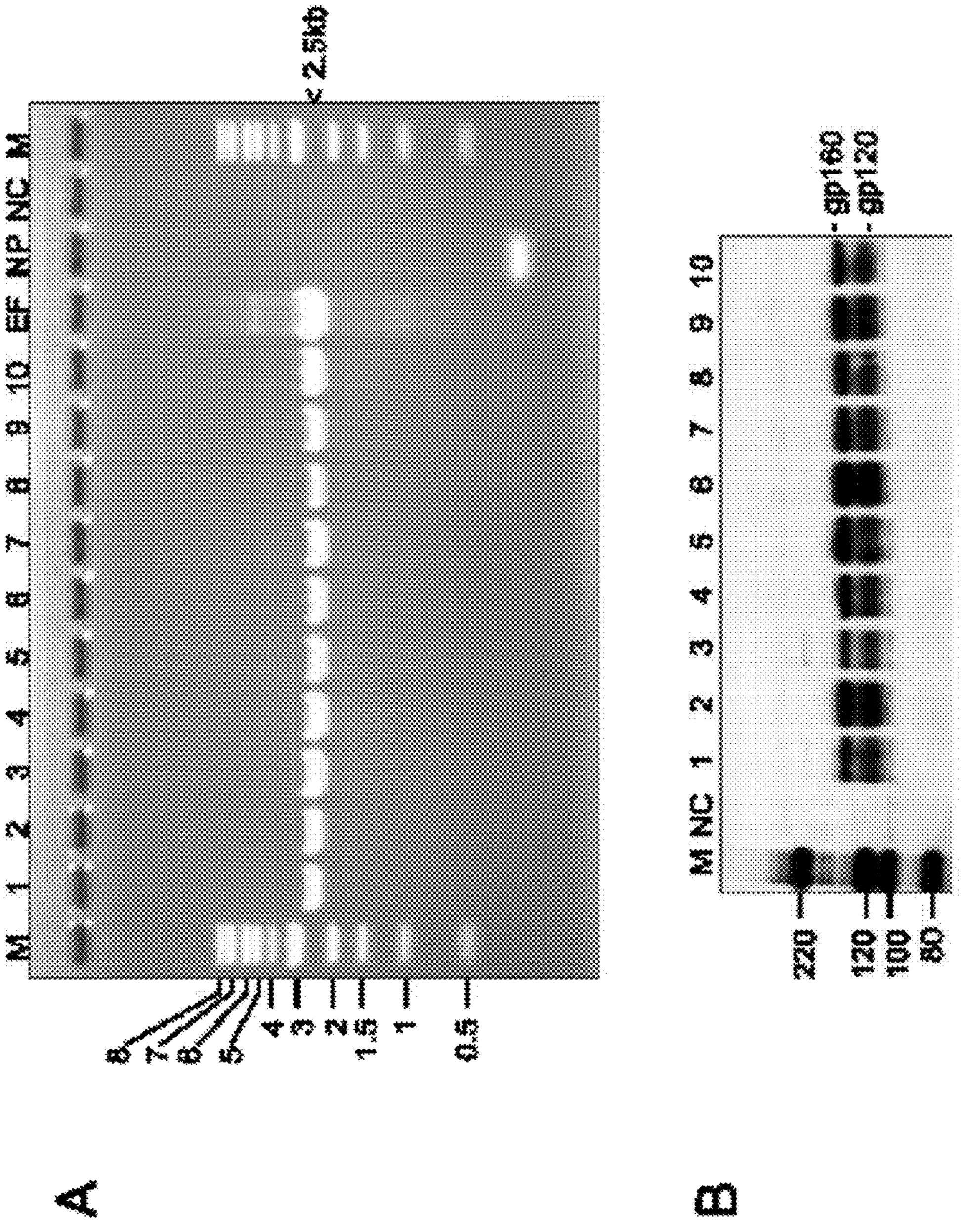
FIG. 18A-18B. Monitoring protein expression and gene insert integrity during clonal isolation.

Using the electroporation-based SeV rescue method, infectious SeV-sfEnvF(NP) was produced under conditions that complied with cGMP. Afterward, three rounds of clonal isolation was performed by limiting dilution during which EnvF(NP) insert integrity and protein expression were monitored (FIG. 18). A SeV-sfEnvF clonal isolate was then selected and amplified in Vero cells to produce a preMVS. Virus from the preMVS was shown to express EnvF and the complete nucleotide sequence of vector genome was confirmed (data not shown).

Figures 19A, 19B:
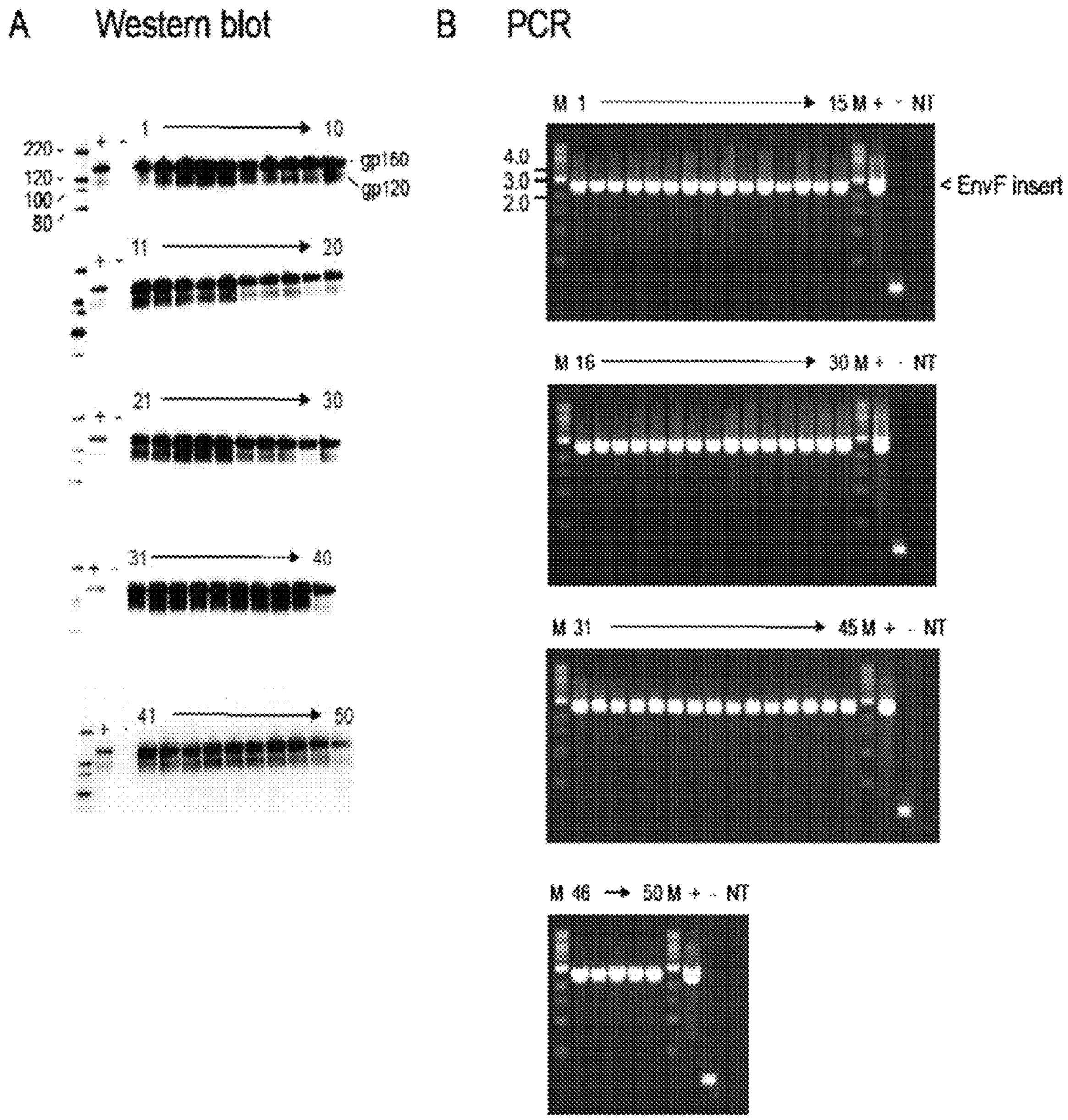
FIG. 19A-19B. Genetic stability analysis conducted with SeV-EnvF pre-MVS.

To establish that the SeV-sfEnvF(NP) preMVS would support cGMP manufacturing, virus from the preMVS was serially amplified 5 times (preMVSp5) to mimic expansion during vaccine manufacturing. As described above for SeV-Gag(NP) (FIG. 11), 50 clonal isolates were then derived from the pMVSp5 and analyzed. Western blot analysis showed (FIG. 19A) that cells infected with the clonal isolates all contained the expected EnvF species equivalent to Env gp160 precursor and the gp120 subunit produced by proteolytic processing by furin protease. Consistent with this data, all of the clonal isolates also had an intact EnvF gene insert as shown by RT/PCR (FIG. 19B). These results indicate that the genetic stability of SeV-sfEnvF(NP) supports manufacturing of clinical trial material.

Using the cGMP-complaint virus rescue and clonal isolation process described above for SeV-sfEnvF, a genetically stable vector called SeV-HIVconC5 also was rescued and advanced to produce a pMVS. The HIVconC5 immunogen (FIG. 12A) is related to HIVCONSV developed by Letourneau et al. (Letourneau et al. 2007 PLoS ONE 2:e984). The HIVCONSV immunogen is a fusion protein composed of 14 highly conserved HIV polypeptide sequence elements plus a C-terminal epitope tag. The original HIVCONSV nucleotide sequence was optimized by a commercial vendor (GeneArt, Inc; Genbank DM059276.1) resulting in 64% G+C. The 2.4 kbp HIVconC5 was using the nucleotide optimization process described above and in Appendix 6. Additionally, the C-terminal epitope tag in HIVCONSV was replaced a known antibody epitope from clade B HIV Env (C5 epitope recognized by antiserum D7324, see reference (Eggink et al. 2010. Virology 401: 236-247). The new HIVconC5 gene optimization process significantly reduced the G+C content down to 40%.

Figures 20A, 20B, 20C:
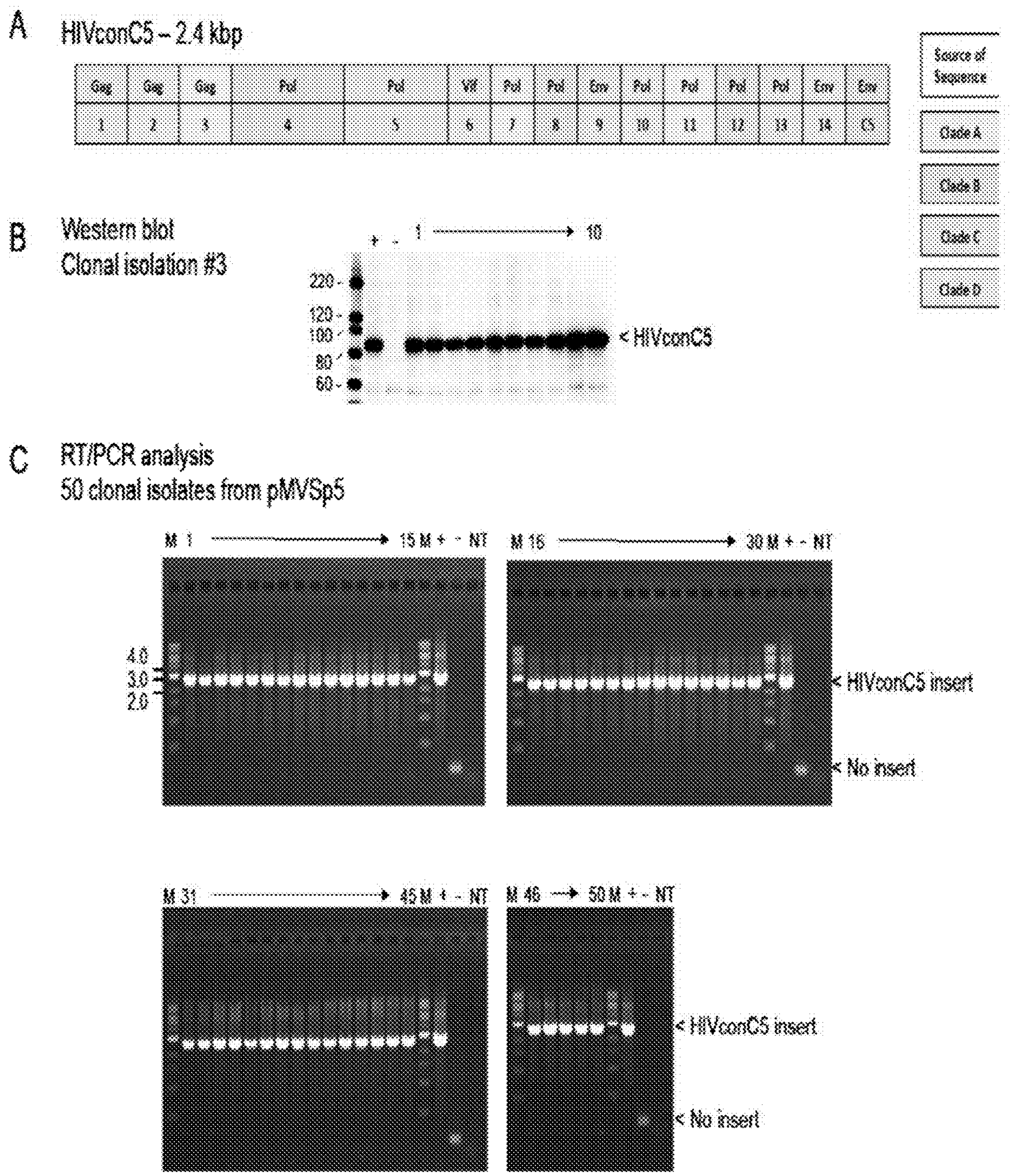
FIG. 20A-20C. Development of SeV-HIVconC5.

SeV-HIVconC5(NP) with the foreign gene inserted upstream of the NP transcription unit (FIG. 9F) was rescued from Vero cells under conditions that complied with cGMP standards as described above for SeV-sfEnvF(NP). Rescued virus was subjected to three rounds of clonal isolation by limiting dilution, and as shown by Western blotting (FIG. 20B), all clonal isolates consistently expressed the expected ~90 kd HIVconC5 fusion protein. A clonal isolate was expanded to generate a preMVS bank after which virus from the bank was expanded further to confirm genetic stability. Analysis of pre-MVSp5 by RT/PCR (FIG. 12C) and Western blotting (data not shown) showed that all 50 clonal isolates derived from the expanded pre-MVSp5 contained an intact HIVconC5 gene.

An improved and detailed process for generating genetically stable SeV vaccine vectors suitable for cGMP manufacturing was developed. Many elements of the process were exemplified by development of SeV-Gag(NP) vaccine, which was subsequently manufactured and evaluated in a Phase 1 clinical trial. Improvements in gene design and recombinant virus rescue enabled development of SeV vectors encoding Env trimer immunogens and a fusion protein composed of multiple conserved epitopes for eliciting T lymphocyte responses (HIVconC5). Notably, the SeV vectors encoding EnvF, EnvG, and HIVconC5 were highly stable even with the foreign gene inserted upstream of the NP transcription unit. Foreign genes inserted in positions closer to the promoter tend to be more difficult to rescue and propagate as shown by others working with different negative-strand RNA viruses (Wertz et al. 2002. J Virol 76:7642-7650, Carnero et al. 2009. J Virol 83:584-597, Zhang et al. 2013. Virology 446:25-36).

The final vector development process included: development of rigorous procedures for genetic stability testing that reliably predicted whether a vaccine can be manufactured, processes for rescue of recombinant virus, clonal isolation, and preMVS production that support subsequent cGMP manufacturing, a method for optimizing nucleotide sequences of gene inserts specifically for use in negative-strand RNA viruses and a strategy based on protein domain substitution that enhances transmembrane glycoprotein immunogen expression and vector genetic stability as shown during development of the SeV-sfEnvG(NP) and SeV-sfEnvF(NP).

In one embodiment, the present invention encompasses the use of immunogens expressed in recombinant SeV vectors, advantageously as HIV-1 vaccine components.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

$F(ab')_2$, the fragment of the antibody that can be obtained by treating whole antibody with the enzyme pepsin without subsequent reduction; $F(ab')_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a Glade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an HIV epitope. In an advantageous embodiment, the HIV epitope is a soluble envelope glycoprotein, however, the present invention may encompass additional HIV antigens, epitopes or immunogens. Advantageously, the HIV epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329,807; 7,323,553; 7,320,859; 7,311,920; 7,306,798; 7,285,646; 7,285,289; 7,285,271; 7,282,364; 7,273,695; 7,270,997; 7,262,270; 7,244,819; 7,244,575; 7,232,567; 7,232,566; 7,223,844; 7,223,739; 7,223,534; 7,223,368; 7,220, 554; 7,214,530; 7,211,659; 7,211,432; 7,205,159; 7,198,934; 7,195,768; 7,192,555; 7,189,826; 7,189,522; 7,186,507; 7,179,645; 7,175,843; 7,172,761; 7,169,550; 7,157,083; 7,153,509; 7,147,862; 7,141,550; 7,129,219; 7,122,188; 7,118,859; 7,118,855; 7,118,751; 7,118,742; 7,105,655; 7,101,552; 7,097,971; 7,097,842; 7,094,405; 7,091,049; 7,090,648; 7,087,377; 7,083,787; 7,070,787; 7,070,781; 7,060,273; 7,056,521; 7,056,519; 7,049,136; 7,048,929; 7,033,593; 7,030,094; 7,022,326; 7,009,037; 7,008,622; 7,001,759; 6,997,863; 6,995,008; 6,979,535; 6,974,574; 6,972,126; 6,969,609; 6,964,769; 6,964,762; 6,958,158; 6,956,059; 6,953,689; 6,951,648; 6,946,075; 6,927,031; 6,919,319; 6,919,318; 6,919,077; 6,913,752; 6,911,315; 6,908,617; 6,908,612; 6,902,743; 6,900,010; 6,893,869; 6,884,785; 6,884,435; 6,875,435; 6,867,005; 6,861,234; 6,855,539; 6,841,381; 6,841,345; 6,838,477; 6,821,955; 6,818,392; 6,818,222; 6,815,217; 6,815,201; 6,812,026; 6,812,025; 6,812,024; 6,808,923; 6,806,055; 6,803,231; 6,800,613; 6,800,288; 6,797,811; 6,780,967; 6,780,598; 6,773,920; 6,764,682; 6,761,893; 6,753,015; 6,750,005; 6,737,239; 6,737,067; 6,730,304; 6,720,310; 6,716,823; 6,713,301; 6,713,070; 6,706,859; 6,699,722; 6,699,656; 6,696,291; 6,692,745; 6,670,181; 6,670,115; 6,664,406; 6,657,055; 6,657,050; 6,656,471; 6,653,066; 6,649,409; 6,649,372; 6,645,732; 6,641,816; 6,635,469; 6,613,530; 6,605,427; 6,602,709; 6,602,705; 6,600,023; 6,596,477; 6,596,172; 6,593,103; 6,593,079; 6,579,673; 6,576,758; 6,573,245; 6,573,040; 6,569,418; 6,569,340; 6,562,800; 6,558,961; 6,551,828; 6,551,824; 6,548,275; 6,544,780; 6,544,752; 6,544,728; 6,534,482; 6,534,312; 6,534,064; 6,531,572; 6,531,313; 6,525,179; 6,525,028; 6,524,582; 6,521,449; 6,518,030; 6,518,015; 6,514,691; 6,514,503; 6,511,845; 6,511,812; 6,511,801; 6,509,313; 6,506,384; 6,503,882; 6,495,676; 6,495,526; 6,495,347; 6,492,123; 6,489,131; 6,489,129; 6,482,614; 6,479,286; 6,479,284; 6,465,634; 6,461,615; 6,458,560; 6,458,527; 6,458,370; 6,451,601; 6,451,592; 6,451,323; 6,436,407; 6,432,633; 6,428,970; 6,428,952; 6,428,790; 6,420,139; 6,416,997; 6,410,318; 6,410,028; 6,410,014; 6,407,221; 6,406,710; 6,403,092; 6,399,295; 6,392,013; 6,391,657; 6,384,198; 6,380,170; 6,376,170; 6,372,426; 6,365,187; 6,358,739; 6,355,248; 6,355,247; 6,348,450; 6,342,372; 6,342,228; 6,338,952; 6,337,179; 6,335,183; 6,335,017; 6,331,404; 6,329,202; 6,329,173; 6,328,976; 6,322,964; 6,319,666; 6,319,665; 6,319,500; 6,319,494; 6,316,205; 6,316,003; 6,309,633; 6,306,625; 6,296,807; 6,294,322; 6,291,239; 6,291,157; 6,287,568; 6,284,456; 6,284,194; 6,274,337; 6,270,956; 6,270,769; 6,268,484; 6,265,562; 6,265,149; 6,262,029; 6,261,762; 6,261,571; 6,261,569; 6,258,599; 6,258,358; 6,248,332; 6,245,331; 6,242,461; 6,241,986; 6,235,526; 6,235,466; 6,232,120; 6,228,361; 6,221,579; 6,214,862; 6,214,804; 6,210,963; 6,210,873; 6,207,185; 6,203,974; 6,197,755; 6,197,531; 6,197,496; 6,194,142; 6,190,871; 6,190,666; 6,168,923; 6,156,302; 6,153,408; 6,153,393; 6,153,392; 6,153,378; 6,153,377; 6,146,635; 6,146,614; 6,143,876; 6,140,059; 6,140,043; 6,139,746; 6,132,992; 6,124,306; 6,124,132; 6,121,006; 6,120,990; 6,114,507; 6,114,143; 6,110,466; 6,107,020; 6,103,521; 6,100,234; 6,099,848; 6,099,847; 6,096,291; 6,093,405; 6,090,392; 6,087,476; 6,083,903; 6,080,846; 6,080,725; 6,074,650; 6,074,646; 6,070,126; 6,063,905; 6,063,564; 6,060,256; 6,060,064; 6,048,530; 6,045,788; 6,043,347; 6,043,248; 6,042,831; 6,037,165; 6,033,672; 6,030,772; 6,030,770; 6,030,618; 6,025,141; 6,025,125; 6,020,468; 6,019,979; 6,017,543; 6,017,537; 6,015,694; 6,015,661; 6,013,484; 6,013,432; 6,007,838; 6,004,811; 6,004,807; 6,004,763; 5,998,132; 5,993,819; 5,989,806; 5,985,926; 5,985,641; 5,985,545; 5,981,537; 5,981,505; 5,981,170; 5,976,551; 5,972,339; 5,965,371; 5,962,428; 5,962,318; 5,961,979; 5,961,970; 5,958,765; 5,958,422; 5,955,647; 5,955,342; 5,951,986; 5,951,975; 5,942,237; 5,939,277; 5,939,074; 5,935,580; 5,928,930; 5,928,913; 5,928,644; 5,928,642; 5,925,513; 5,922,550; 5,922,325; 5,919,458; 5,916,806; 5,916,563; 5,914,395; 5,914,109; 5,912,338; 5,912,176; 5,912,170; 5,906,936; 5,895,650; 5,891,623; 5,888,726; 5,885,580; 5,885,578; 5,879,685; 5,876,731; 5,876,716; 5,874,226; 5,872,012; 5,871,747; 5,869,058; 5,866,694; 5,866,341; 5,866,320; 5,866,319; 5,866,137; 5,861,290; 5,858,740; 5,858,647; 5,858,646; 5,858,369; 5,858,368; 5,858,366; 5,856,185; 5,854,400; 5,853,736; 5,853,725; 5,853,724; 5,852,186; 5,851,829; 5,851,529; 5,849,475; 5,849,288; 5,843,728; 5,843,723; 5,843,640; 5,843,635; 5,840,480; 5,837,510; 5,837,250; 5,837,242; 5,834,599; 5,834,441; 5,834,429; 5,834,256; 5,830,876; 5,830,641; 5,830,475; 5,830,458; 5,830,457; 5,827,749; 5,827,723; 5,824,497; 5,824,304; 5,821,047; 5,817,767; 5,817,754; 5,817,637; 5,817,470; 5,817,318; 5,814,482; 5,807,707; 5,804,604; 5,804,371; 5,800,822; 5,795,955; 5,795,743; 5,795,572; 5,789,388; 5,780,279; 5,780,038; 5,776,703; 5,773,260; 5,770,572; 5,766,844; 5,766,842; 5,766,625; 5,763,574; 5,763,190; 5,762,965; 5,759,769; 5,756,666; 5,753,258; 5,750,373; 5,747,641; 5,747,526; 5,747,028; 5,736,320; 5,736,146; 5,733,760; 5,731,189; 5,728,385; 5,721,095; 5,716,826; 5,716,637; 5,716,613; 5,714,374; 5,709,879; 5,709,860; 5,709,843; 5,705,331; 5,703,057; 5,702,707; 5,698,178; 5,688,914; 5,686,078; 5,681,831; 5,679,784; 5,674,984; 5,672,472; 5,667,964; 5,667,783; 5,665,536; 5,665,355; 5,660,990; 5,658,745; 5,658,569; 5,643,756; 5,641,624; 5,639,854; 5,639,598; 5,637,677; 5,637,455; 5,633,234; 5,629,153; 5,627,025; 5,622,705; 5,614,413; 5,610,035; 5,607,831; 5,606,026; 5,601,819; 5,597,688; 5,593,972; 5,591,829; 5,591,823; 5,589,466; 5,587,285; 5,585,254; 5,585,250; 5,580,773; 5,580,739; 5,580,563; 5,573,916; 5,571,667; 5,569,468; 5,558,865; 5,556,745; 5,550,052; 5,543,328; 5,541,100; 5,541,057; 5,534,406; 5,529,765; 5,523,232; 5,516,895; 5,514,541; 5,510,264; 5,500,161; 5,480,967; 5,480,966; 5,470,701; 5,468,606; 5,462,852; 5,459,127; 5,449,601; 5,447,838; 5,447,837; 5,439,809; 5,439,792; 5,418,136; 5,399,501; 5,397,695; 5,391,479; 5,384,240; 5,374,519; 5,374,518; 5,374,516; 5,364,933; 5,359,046; 5,356,772; 5,354,654; 5,344,755; 5,335,673; 5,332,567; 5,320,940; 5,317,009; 5,312,902; 5,304,466; 5,296,347; 5,286,852; 5,268,265; 5,264,356; 5,264,342; 5,260,308; 5,256,767; 5,256,561; 5,252,556; 5,230,998; 5,230,887; 5,227,159; 5,225,347; 5,221,610; 5,217,861; 5,208,321; 5,206,136; 5,198,346; 5,185,147; 5,178,865; 5,173,400; 5,173,399; 5,166,050; 5,156,951; 5,135,864; 5,122,446; 5,120,662; 5,103,836; 5,100,777; 5,100,662; 5,093,230; 5,077,284; 5,070,010; 5,068,174; 5,066,782; 5,055,391; 5,043,262; 5,039,604; 5,039,522; 5,030,718; 5,030,555; 5,030,449; 5,019,387; 5,013,556; 5,008,183; 5,004,697; 4,997,772; 4,983,529; 4,983,387; 4,965,069; 4,945,082; 4,921,787; 4,918,166; 4,900,548; 4,888,290; 4,886,742; 4,885,235; 4,870,003; 4,869,903; 4,861,707; 4,853,326; 4,839,288; 4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,949,337, 6,900,010, 6,821,744, 6,768,004, 6,613,743, 6,534,312, 6,511,830, 6,489,131, 6,242,197, 6,114,143, 6,074,646, 6,063,564, 6,060,254, 5,919,457, 5,916,806, 5,871,732, 5,824,304, 5,773,247, 5,736,320, 5,637,455, 5,587,285, 5,514,541, 5,317,009, 4,983,529, 4,886,742, 4,870,003 and 4,795,739 are useful for the present invention. Furthermore, monoclonal anti-HIV antibodies of U.S. Pat. Nos. 7,074,556, 7,074,554, 7,070,787, 7,060,273, 7,045,130, 7,033,593, RE39,057, 7,008,622, 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Sendai virus vectors are preferred. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors. Such viruses are also contemplated for the expression of the herein disclosed proteins, such as EnvF and EnvG.

The nucleotide sequences and vectors of the invention can be delivered to cells, for example if aim is to express and the HIV-1 antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the $34^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from *Mycobacterium tuberculosis*, substances found in *Cornyebacterium parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, GM-CSF, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with “other” immunological, antigenic or vaccine or therapeutic compositions thereby providing multivalent or “cocktail” or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1: Clinical Safety and Immunogenicity of Two HIV Vaccines SeV-G(NP) and Ad35-GRIN in HIV-Uninfected, Healthy Adult Volunteers Development of vaccines that stimulate sustained humoral and/or cellular immunity at mucosal HIV entry points is critical in the quest for an HIV vaccine. To achieve this goal, Applicants investigate replication-competent viral vectors for mucosal delivery that might mimic the efficacy of live-attenuated viral vaccines (Excler et al 2009). Sendai virus (SeV) is a mouse paramyxovirus, not pathogenic in humans, but can infect cells in the primate upper respiratory tract and replicates in human nasal epithelial cells in vitro. Applicants hypothesize that intranasal (IN) administration of SeV-G(NP) will stimulate a mucosal immune response. In addition, IN administration could minimize the effect of pre-existing immunity to the vaccine carrier. Sendai virus is genetically and antigenically related to human parainfluenza virus type 1 (hPIV-1).

SeV-G(NP) was administered IN in heterologous prime boost (PB) combinations with an Adenovirus-35 encoding subtype A Gag, RT, Integrase and Nef (Ad35-GRIN at 1×10^10 vp (Keefer et al 2012) given intramuscularly (IM) (Groups A-C) or in a homologous regimen (Group D), all at 0 and 4 months as shown in Table 1. Sixty-five HIV uninfected adults (20 females; 45 males) were enrolled at three sites; Kenya Vaccine Initiative (KAVI), Nairobi, Kenya; Projet San Francisco (PSF), Kigali, Rwanda and St Stephen's AIDS Trust (SSAT), London, UK (Table 2). Safety, tolerability and immunogenicity were assessed at predetermined time points. Peripheral blood mononuclear cells (PBMCs) were processed at each clinical site and cryopreserved PBMCs were assessed in an IFN-y ELISPOT assay using 4 peptide pools matched to GRIN (1 each for Gag, RT, Int and Nef). An ELISA was used to assess Gag-p24 binding in serum and mucosal samples. SeV-NAbs were assessed as described (Hara et al 2011). Mucosal samples were collected for detection of secreted antibodies in nasal swabs (midturbinate flocked swabs), parotid and transudated saliva, rectal secretions (Merocel sponges) and in females cervicovaginal secretions (Softcup and Merocel sponges). Shedding was assessed in nasal swabs, active parotid saliva and urine samples in Groups A, B and D at five time points following Sendai vaccination: Days 2±1, 5±1, 6±1, 7±1 and 9±1. Virus foci were detected with an anti-Sendai Ab in an infectious cell infectivity assay (CIU) assay. CIU-positive samples were then tested by SeV-specific-qPCR to confirm the presence of SeV followed by Gag-specific-RT-PCR testing to confirm the presence of an intact Gag insert.

TABLE 1

Study Schedule

| Group | Vaccine/Placebo | Month 0 | Month 4 |
|---|---|---|---|
| Part I | | | |
| A | 12/4 | SeV-G(NP) $2 \times 10^7$ CIU-i.n. | Ad35-GRIN $1 \times 10^{10}$ vp-i.m |
| Part II | | | |
| B | 12/4 | SeV-G(NP) $2 \times 10^8$ CIU-i.n. | Ad35-GRIN $1 \times 10^{10}$ vp-i.m |
| C | 12/4 | Ad35-GRIN $1 \times 10^{10}$ vp-i.m | SeV-G(NP) $2 \times 10^8$ CIU-i.n. |
| D | 12/4 | SeV-G(NP) $2 \times 10^8$ CIU-i.n. | SeV-G(NP) $2 \times 10^8$ CIU-i.n. |

Safety data are currently blinded with volunteers being followed for serious adverse events (SAEs) through their last study visit (12 months after last study vaccination; 1Q.2015). No related SAEs have been reported. Local and systemic reactogenicity events were mild (Grade 1) or moderate (Grade 2). No unusual adverse event or upper/lower respiratory illness patterns have been reported. No incident HIV infections have been reported and no pregnancies have been reported through the protocol-specified 4-month period following last study vaccination.

TABLE 2

Volunteer Enrollment

| Site | A | B | C | D | Total |
|---|---|---|---|---|---|
| PSF-(Rwanda) | 16 | 6 | 7 | 7 | 36 |
| KAVI (Kenya) | N/A | 7 | 7 | 7 | 21 |
| SSAT (UK) | N/A | 3 | 3 | 2 | 8 |
| Total | 16 | 16 | 17 | 16 | 65 |

Figure 21:
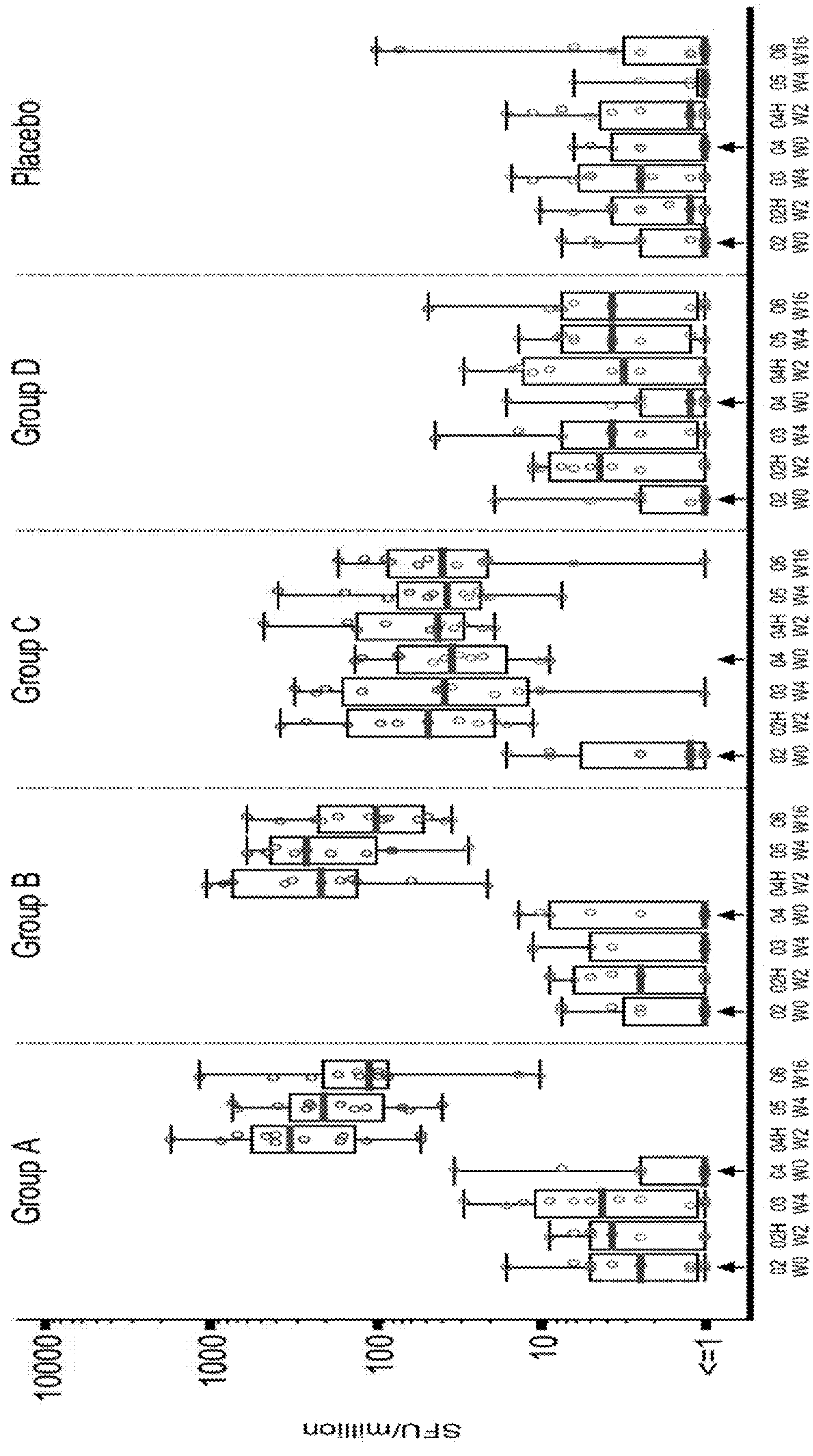
FIG. 21. Gag-specific IFN-g ELISPOT. Responses are to clade A Gag peptide pool after prime and boost (indicated by arrows ↑) for each group. The red line represents median and the box and whiskers are 1st and 3rd quartiles and minimum/maximum. ⭘ are responders, ○ non-responders.

FIG. 21 shows that systemic HIV-Gag specific IFN-y ELISPOT responses were seen in all recipients of the heterologous P/B regimen of SeV-G(NP) followed by Ad35-GRIN except for one volunteer in group B. Gag responses were similar in groups A and B, indicating no clear dose response. No Gag responses were seen in group D [SeV-G (NP) homologous] after one or two immunizations with the SeV-G(NP). In group C, Gag responses were seen after the Ad35-GRIN prime but did not appear to be boosted by SeV-G(NP). The magnitude of the response to Gag was greatest in Groups A and B after prime boost compared with responses to RT, Int and Nef indicating that the SeV-G(NP) provided a strong priming effect ('hidden prime'). Gag ELISPOT responses start to decline by 8 months after the last vaccine.

Figure 22:
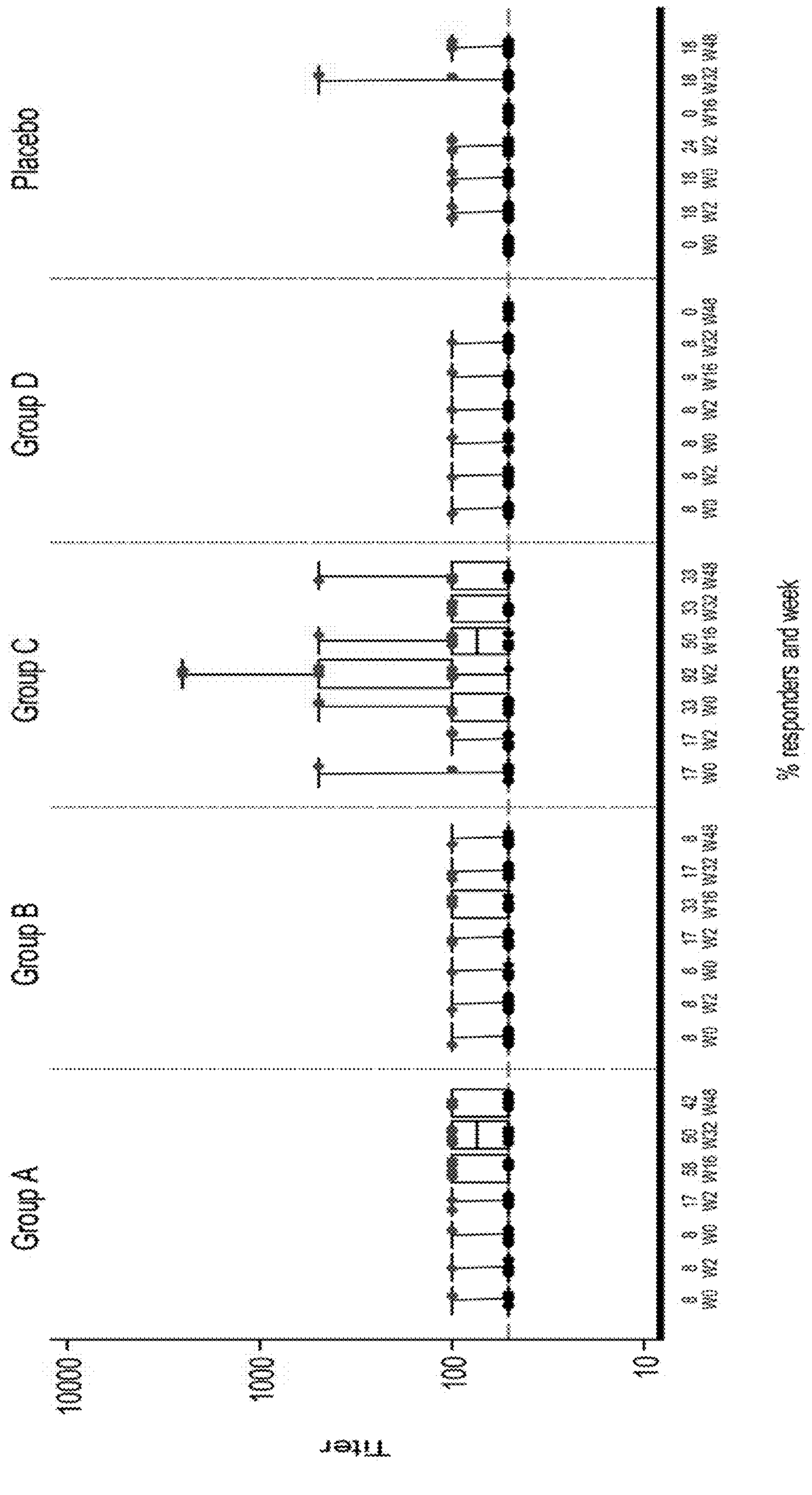
FIG. 22. Gag-ELISA. A positive Gag-p14 titer response was defined as a titer ≥100. All values below the cut-off are displayed as 50 (half the cutoff). The x-axis shows the group ID and % response rate.

FIG. 22 shows that systemic IgG Gag-p24 antibody responses were detected in 92% of recipients of the heterologous P/B regimen (Group C) of Ad35-GRIN followed by SeV-G(NP) but less frequently in Groups A, B and D. Systemic IgA Gag-p24 antibody responses were sporadic and of low titer (data not shown). Gag-p24 antibody IgG and IgA responses were also sporadically detected and of low titer in mucosal secretions. Gag ELISA titers rapidly decline after the second immunization in group C.

SeV-neutralizing antibodies magnitude and response rates were similar across all groups. Five volunteers seroconverted, 19/53 (36%) volunteers had 2 or more fold increase in SeV-NAbs titer post SeV vaccine (including some placebos). No direct correlation between pre-existing hPIV1/SeVNAbs titer and CMI or Humoral immune response was observed.

SeV Shedding. 141/703 (20%) samples were positive by the CIU assay. All SeV positive samples (17/141, 12%) bore the HIVgag insert, demonstrating in vivo genetic stability. These 17 samples were from 15 of 36 (42%) eligible volunteers receiving active product and were only from nasal swab sampling. Two of the volunteers were positive at two time points.

The combination of IN SeV-G(NP) and IM Ad35-GRIN was well tolerated. Immunogenicity data to date shows that a single SeV-G(NP) is a potent prime for Gag-specific T-cell responses and conversely SeV-G(NP) boosts Ad35-GRIN systemic IgG Gag-specific antibody responses. The order of vaccination thus appears to determine which arm of the immune response is stimulated. No mucosal immune responses were observed in the tested conditions. Pre-existing hPIV1/SeVNAbs did not impact T-cell or antibody responses.

TABLE 3

Summary Table of Immunogenicity

| Immune Responses Measured | Outcome | Peak Immune responses (2-4 weeks post second vaccination) | Durability of response |
|---|---|---|---|
| Interferon-gamma (IFN-γ) secreting T-cells | Evaluates the numbers of antigen specific cells producing IFN-γ. Measures the Magnitude of IFN-γ response to vaccine antigens and frequency of responders | In groups A and B (SeV-G(NP)/Ad35-GRIN), the HIV-Gag IFN-γ ELISPOT response rate was 100 and 91% respectively. In Group C, (Ad35-GRIN/SeV-G(NP)) the response rate was 55% and in group D (SeV-G(NP) /SeV-G(NP)) 0%. Both the magnitude and response rates of Gag IFN-γ ELISPOT were higher in groups A and B compared with C and D. | HIV-specific T-cell responses decrease over time, though still present at one year (8 months post last vaccine) |
| Intracellular cytokine staining (ICS) | Defines the phenotype (CD4+ or CD8+ T-cells), and measures the magnitude and frequency of cytokines: IFN-γ, Interleukin-2 (IL-2) and Tumor necrosis factor-alpha(TNF-α) producing cells | ICS magnitude and response rates showed a similar pattern to ELISPOT. Both CD4 and CD8 T-cells were induced by the prime boost combinations of SeV-G(NP) and Ad35-GRIN and secreted multiple cytokines: IFN-γ, IL-2 and TNF-α | |
| Viral Inhibition assay (VIA) | Detects magnitude and frequency of CD8 T cell mediated reduction in viral replication in-vitro. | Viral inhibition was detected in Groups A-C, the magnitude, breadth and response rates were higher in Groups A and B (SeV-G(NP)/Ad35-GRIN) compared to C (Ad35-GRIN/SeV-G(NP)) | Not tested |

TABLE 3-continued

| Summary Table of Immunogenicity | | | |
|---|---|---|---|
| Immune Responses Measured | Outcome | Peak Immune responses (2-4 weeks post second vaccination) | Durability of response |
| Anti-Gag antibodies | Measures Antigen-specific antibodies generated in response to the vaccine insert (Gag) in serum. Measures Antibody titer to vaccine antigens and frequency of responders. | Sporadic weak Gag-specific antibodies were detected in volunteers in about one third of volunteers in Groups A & B (SeV-G(NP)/Ad35-GRIN). In Group C Gag-specific antibody responses rates were detected in about one third of volunteers after the Ad35-GRIN prime and in 92% after the SeV-G(NP). Gag-specific antibody titers were modest overall. | Gag antibody responses in group C decreased over time and absent at one year |
| Mucosal anti-Gag antibodies | Measures the Presence of anti-Gag (IgG and IgA) antibodies at mucosal surfaces (nasal, oral, rectal and vaginal) | Weak, sporadic Gag-specific antibodies were detected in mucosal samples | Not tested |
| SeV neutralization | Measures vector-specific neutralizing antibodies | There were no overall differences in the magnitude and response rates of SeV neutralization in vaccine vs placebo and baseline vs post vaccine samples | Not tested |

Example 2: VSV-EnvF Construction and Antigenicity

Figure 27A:
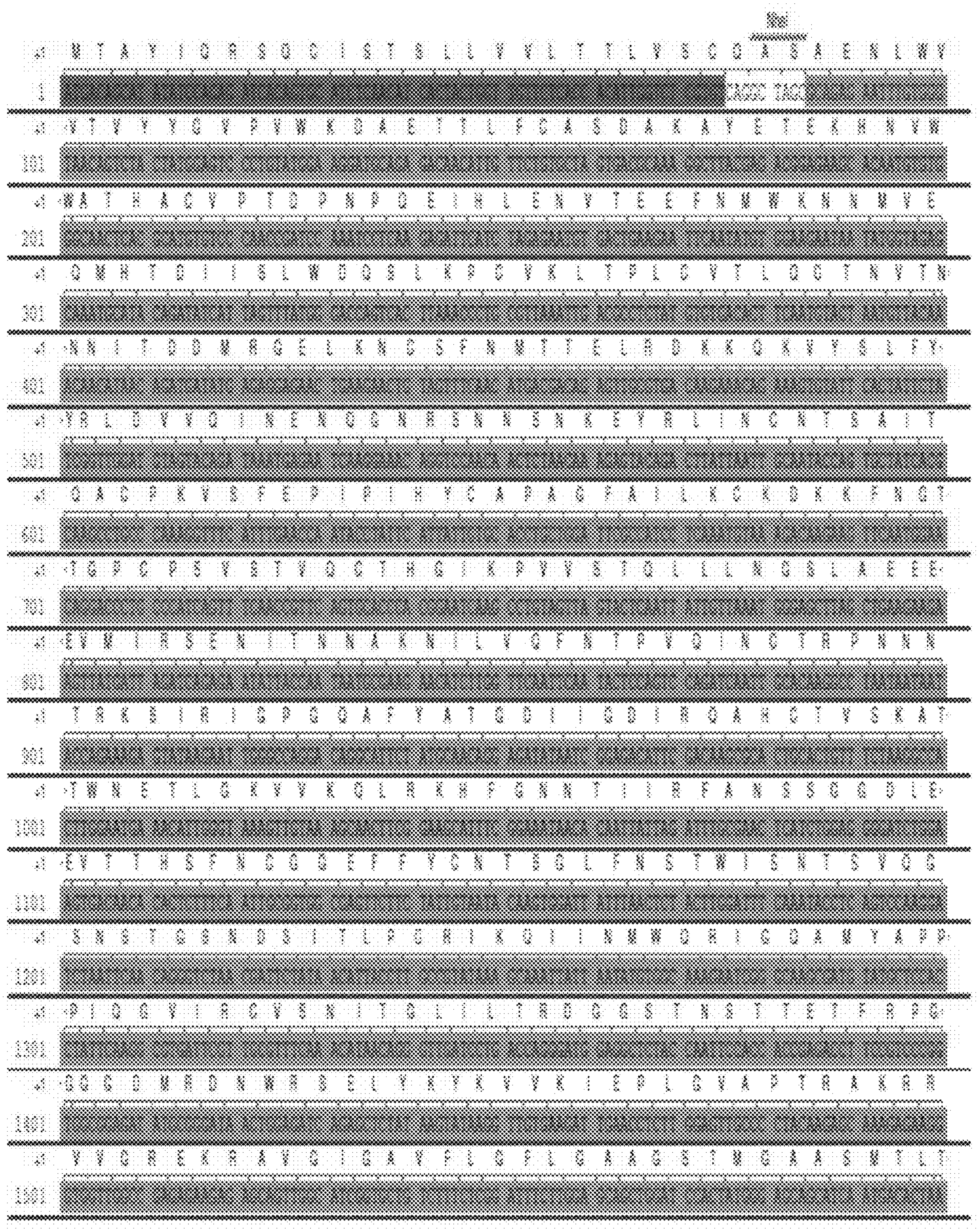
FIG. 27A-27B. EnvF DNA (SEQ ID NO: 18) and protein sequence (SEQ ID NO: 19).
Figure 27B:
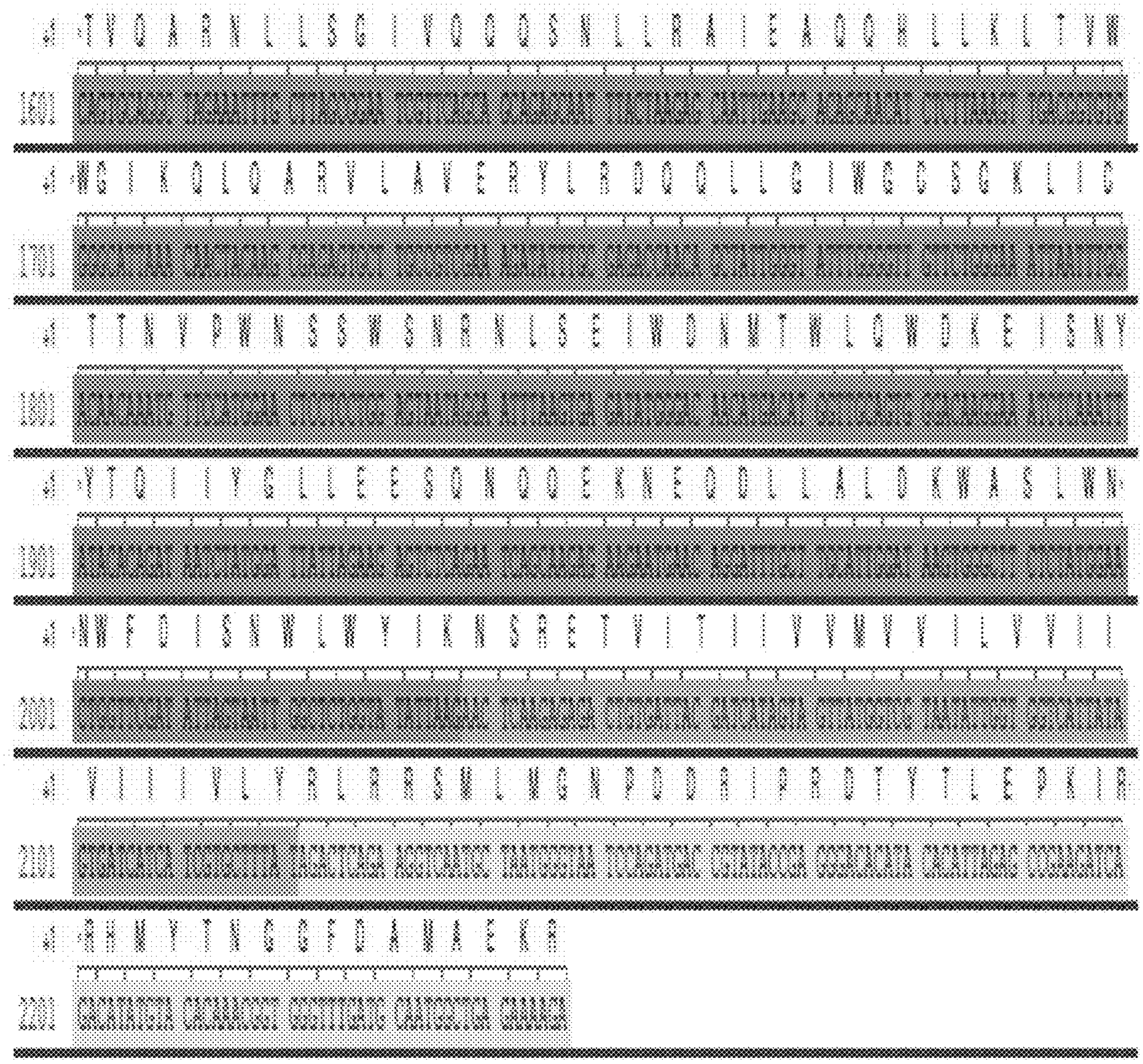

FIG. 27 depicts an EnvF DNA and protein sequence.

Figure 28:
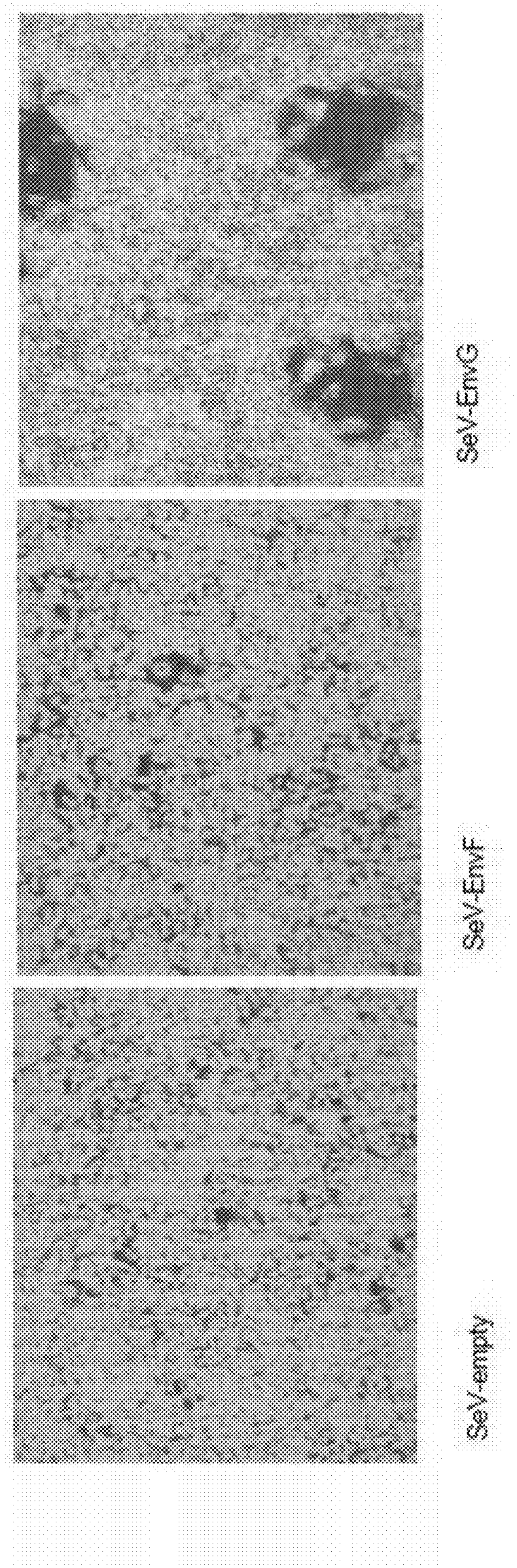
FIG. 28. EnvF lacks fusion function. SeV vector infection on human CD4+/CCR5+ GHOST cells. The SeV vector lacking an Env insert (SeV-empty) infection typically doesn't induce cell-cell fusion when culture medium contains no trypsin-like protease. SeV-EnvF infection did not cause visible fusion while SeV-EnvG induced large syncytium formation, indicating EnvF is not fusogenic like EnvG. Lack of fusion function may be a safety advantage for SeVEnvF since it cannot propagate.

FIG. 28 shows that an EnvF lacks fusion function. SeV vector infection on human CD4+/CCR5+ GHOST cells. The SeV vector lacking an Env insert (SeV-empty) infection typically doesn't induce cell-cell fusion when culture medium contains no trypsin-like protease. SeV-EnvF infection did not cause visible fusion while SeV-EnvG induced large syncytium formation, indicating EnvF is not fusogenic like EnvG. Lack of fusion function may be a safety advantage for SeVEnvF since it cannot propagate.

Figure 29:
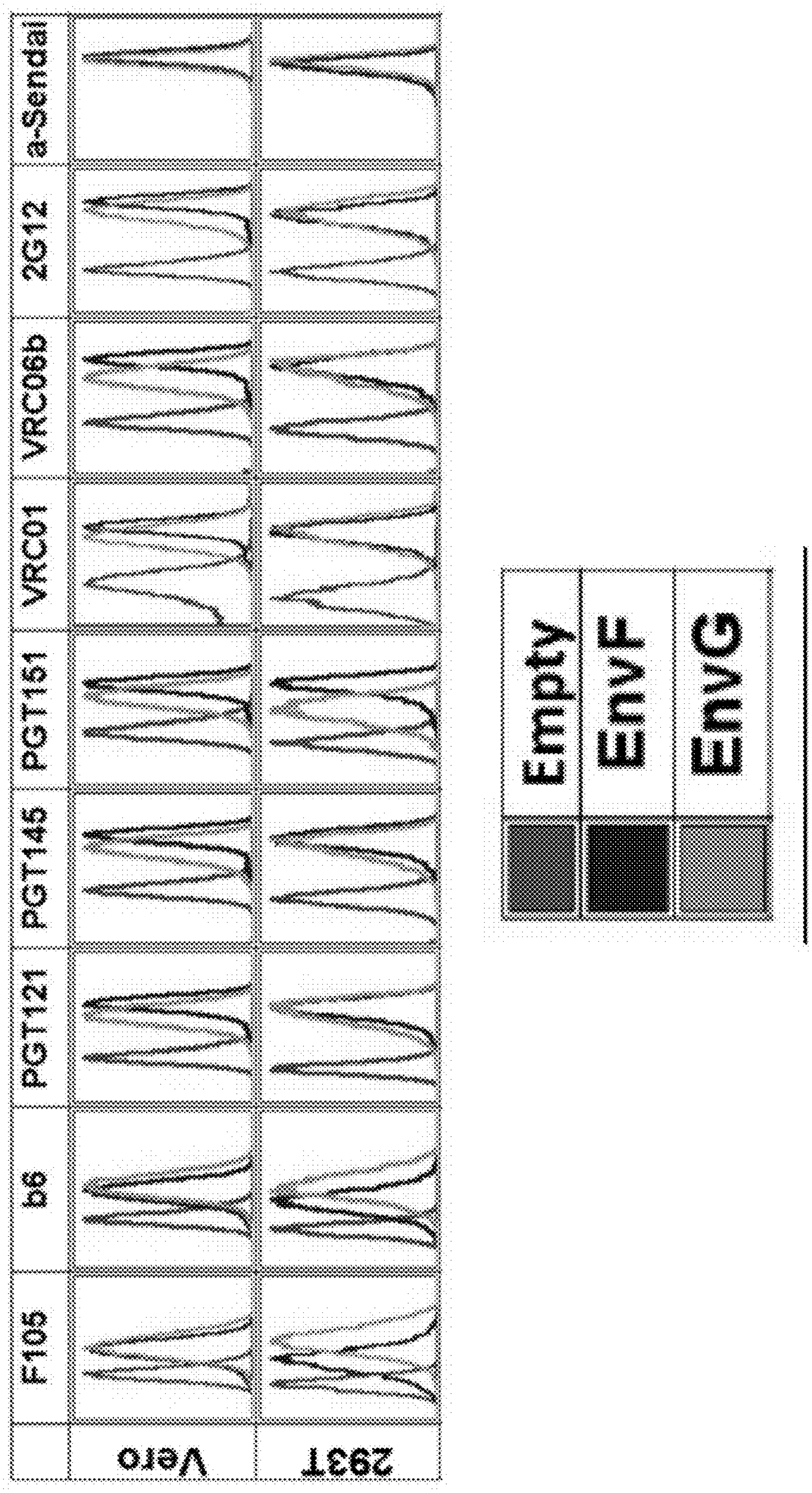
FIG. 29. Better antigenicity of EnvF than EnvG when expressed from SeV Vector. Vero or 293T cells were infected with SeV-empty, SeV-EnvF or SeV-EnvG at comparable MOI of 5. Three days post infection, cells were harvested and cell membrane Env was stained with a panel of Env-specific antibodies. Positive signal by anti-SeV antibody confirmed that all cells were infected. Only SeV-EnvF and SeV-EnvG infected cells were positive for Env staining. Compared to EnvG, the EnvF showed better antigenicity for bnAbs especially for trimer specific antibodies (PGT145, PGT151, and VRC06b), while less interactivity to non neutralizing antibodies like F105 and b6.

FIG. 29 shows better antigenicity of EnvF than EnvG when expressed from SeV Vector. Vero or 293T cells were infected with SeV-empty, SeV-EnvF or SeV-EnvG at comparable MOI of 5. Three days post infection, cells were harvested and cell membrane Env was stained with a panel of Env-specific antibodies. Positive signal by anti-SeV antibody confirmed that all cells were infected. Only SeV-EnvF and SeV-EnvG infected cells were positive for Env staining. Compared to EnvG, the EnvF showed better antigenicity for bnAbs especially for trimer specific antibodies (PGT145, PGT151, and VRC06b), while less interactivity to non neutralizing antibodies like F105 and b6.

Figure 30:
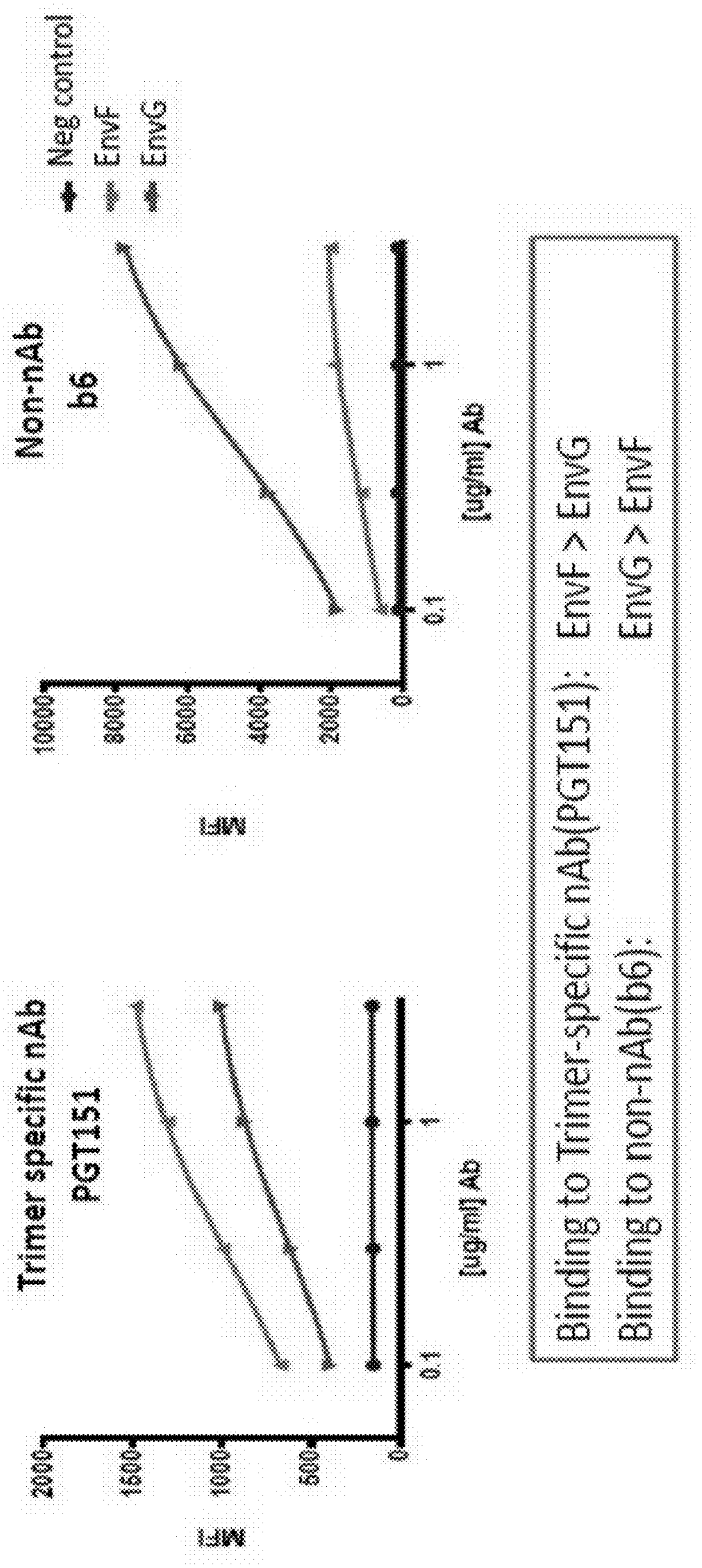
FIG. 30. Better EnvF antigenicity than EnvG when expressed from DNA plasmid transfection. 293T cells were transfected with pClneo plasmids expressing EnvG or EnvF gene. 48 h post transfection, cells were collected, fixed, and then stained with PGT151 and b6. Cell surface protein expression were measured as Mean Fluorescent Intensity (MFI) by Flow cytometry.

FIG. 30 shows better EnvF antigenicity than EnvG when expressed from DNA plasmid transfection. 293T cells were transfected with pClneo plasmids expressing EnvG or EnvF gene. 48 h post transfection, cells were collected, fixed, and then stained with PGT151 and b6. Cell surface protein expression were measured as Mean Fluorescent Intensity (MFI) by Flow cytometry.

Figure 31:
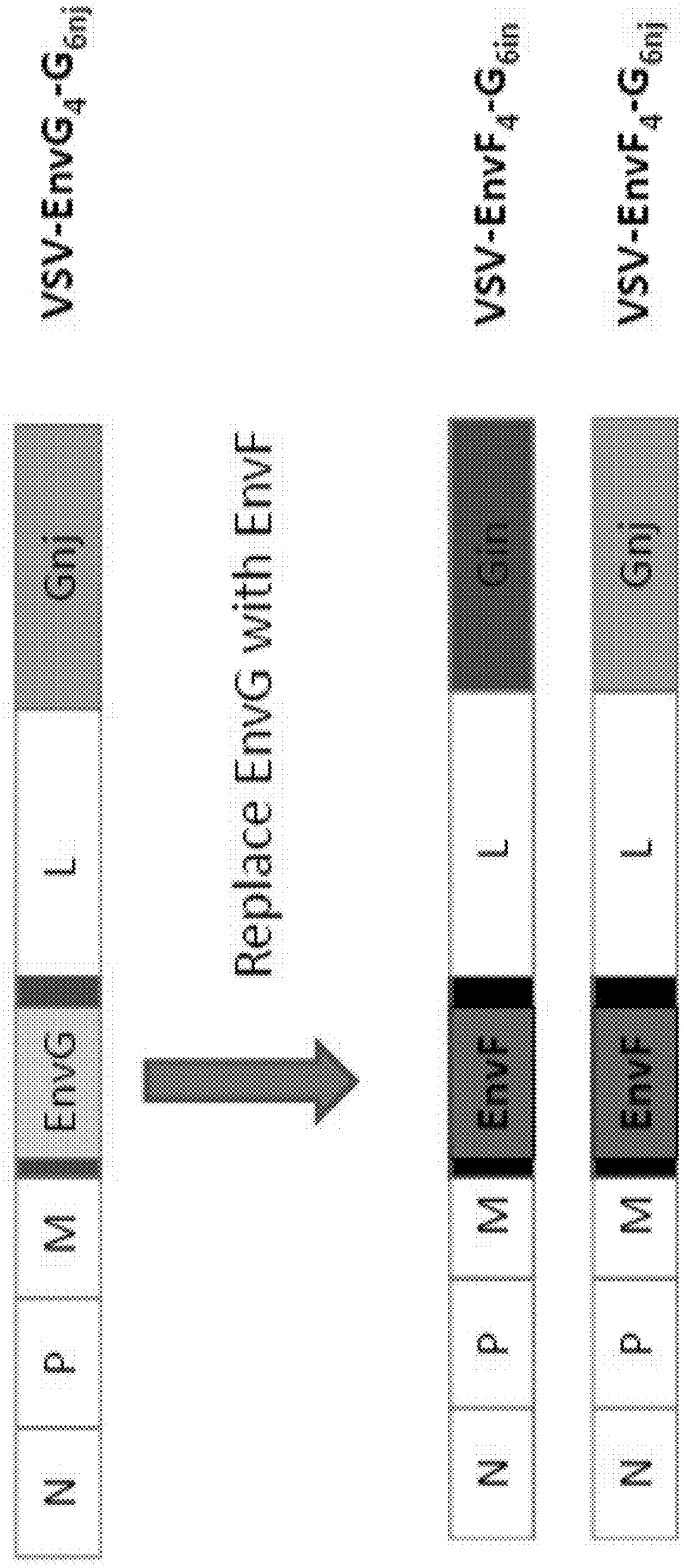
FIG. 31. The same EnvF and EnvG were inserted into VSV vectors.

FIG. 31 shows the same EnvF and EnvG were inserted into VSV vectors.

Figure 32:
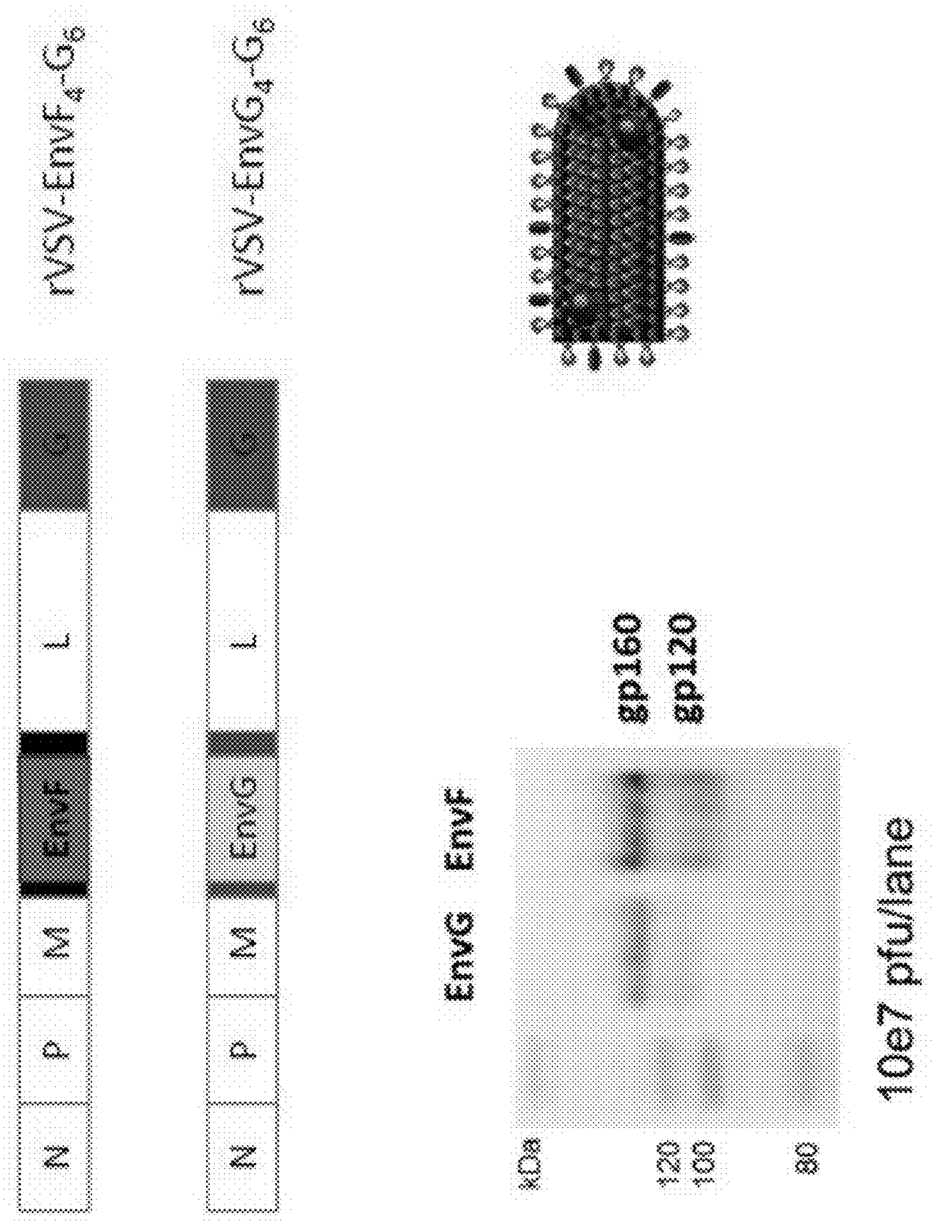
FIG. 32. EnvG and EnvF are detectable in mature VSV particles released from infected Vero cells.

FIG. 32 shows that EnvG and EnvF are detectable in mature VSV particles released from infected Vero cells.

Figure 33:
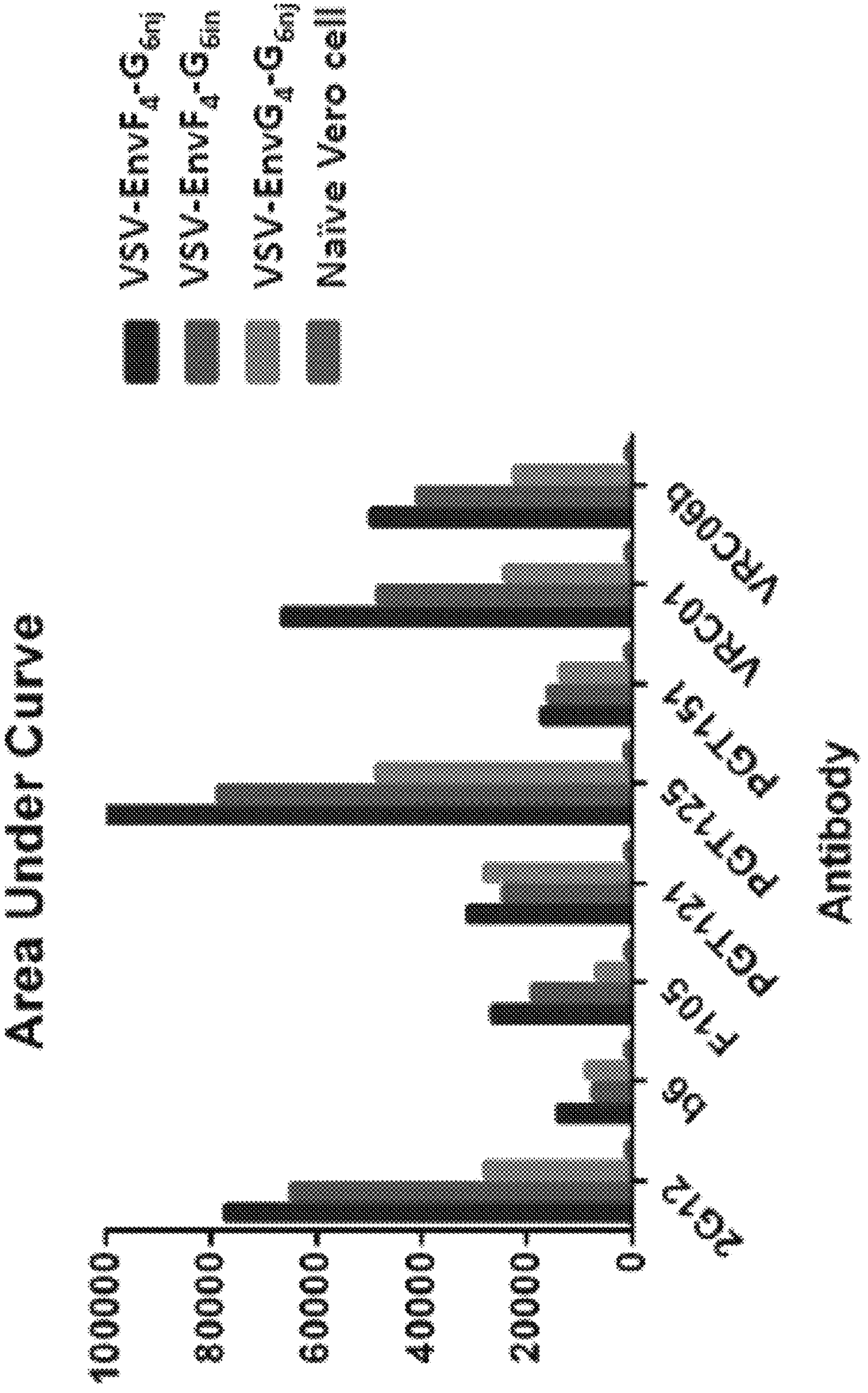
FIG. 33. Better EnvF antigenicity than EnvG detected in the VSV vector infected Vero cell. Vero cells were infected at MOI=0.1 by the three VSV vectors. 24 h post infection, cells were harvested and cell membrane Env stained with a panel of the Env-specific nAb followed by flow cytometric detection. Level of Env expression is represented by mean fluorescent intensity (MFI).

FIG. 33 shows better EnvF antigenicity than EnvG detected in the VSV vector infected Vero cell. Vero cells were infected at MOI=0.1 by the three VSV vectors. 24 h post infection, cells were harvested and cell membrane Env stained with a panel of the Env-specific nAb followed by flow cytometric detection. Level of Env expression is represented by mean fluorescent intensity (MFI).

Figure 34:
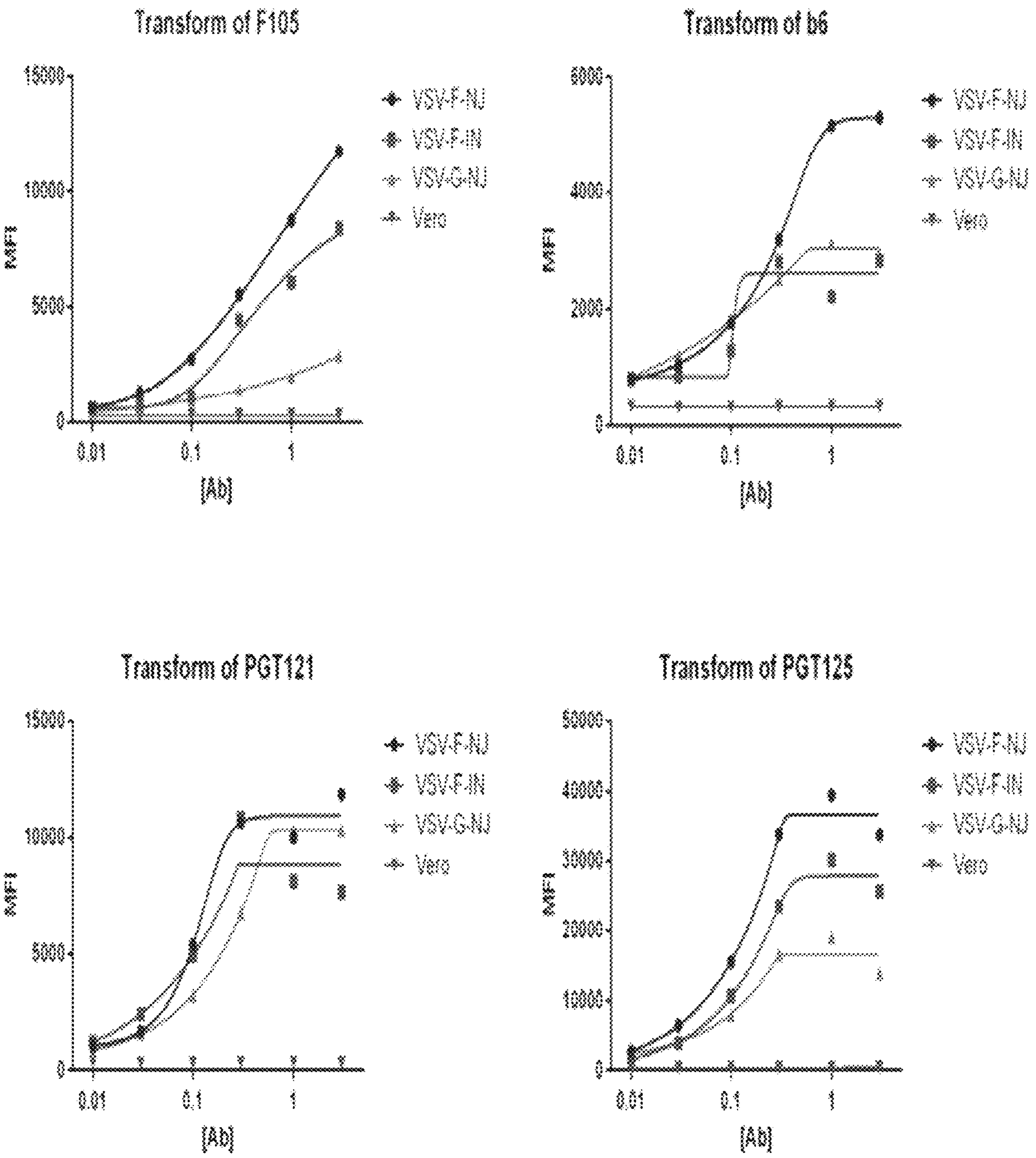
FIG. 34. Antibody titration curve of the three VSV vectors. Same experiment as in FIG. 35 but data presented in different format.
Figure 34:
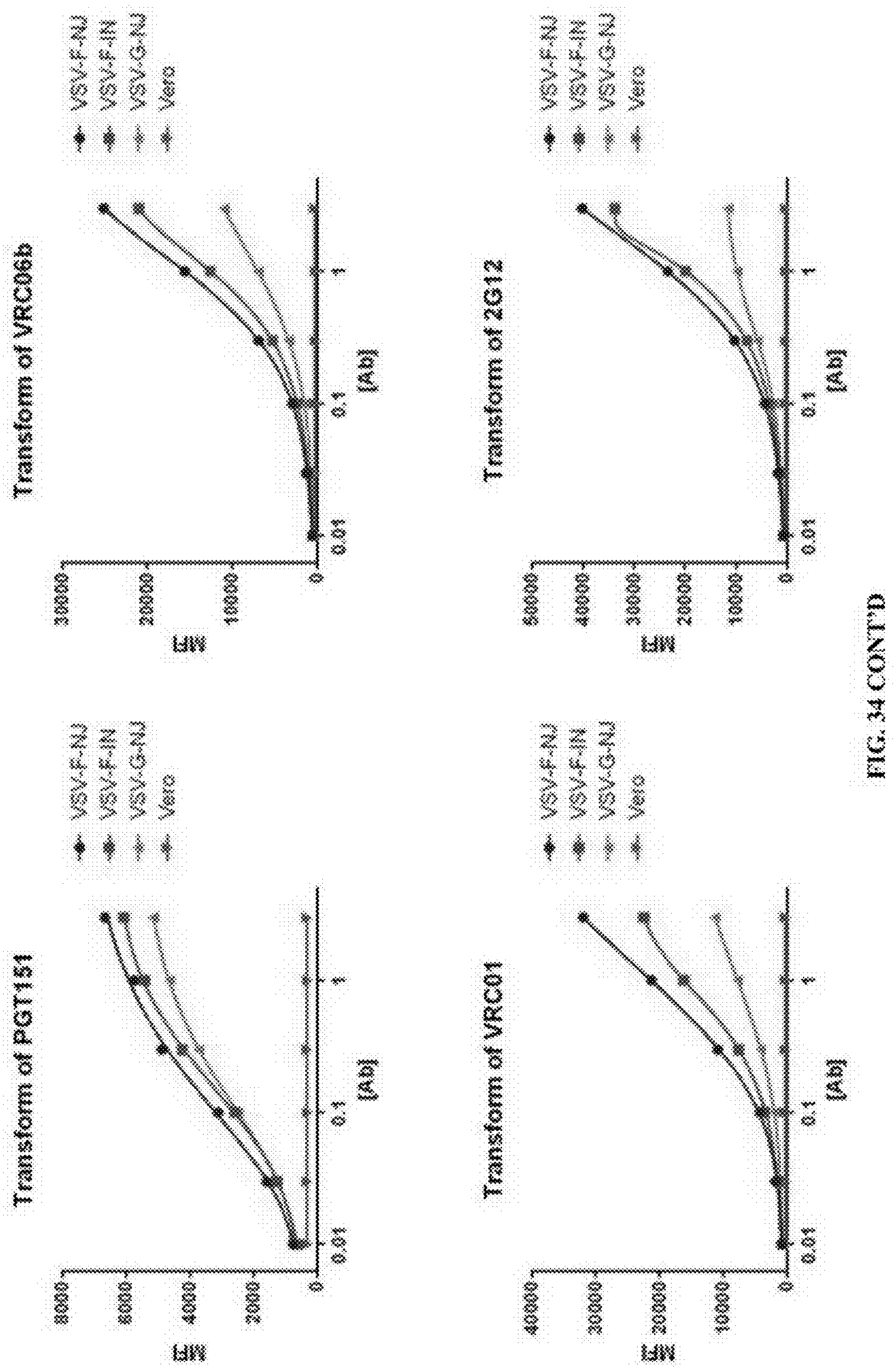

FIG. 34 shows antibody titration curve of the three VSV vectors. Same experiment as in FIG. 35 but data presented in different format.

Figure 35:
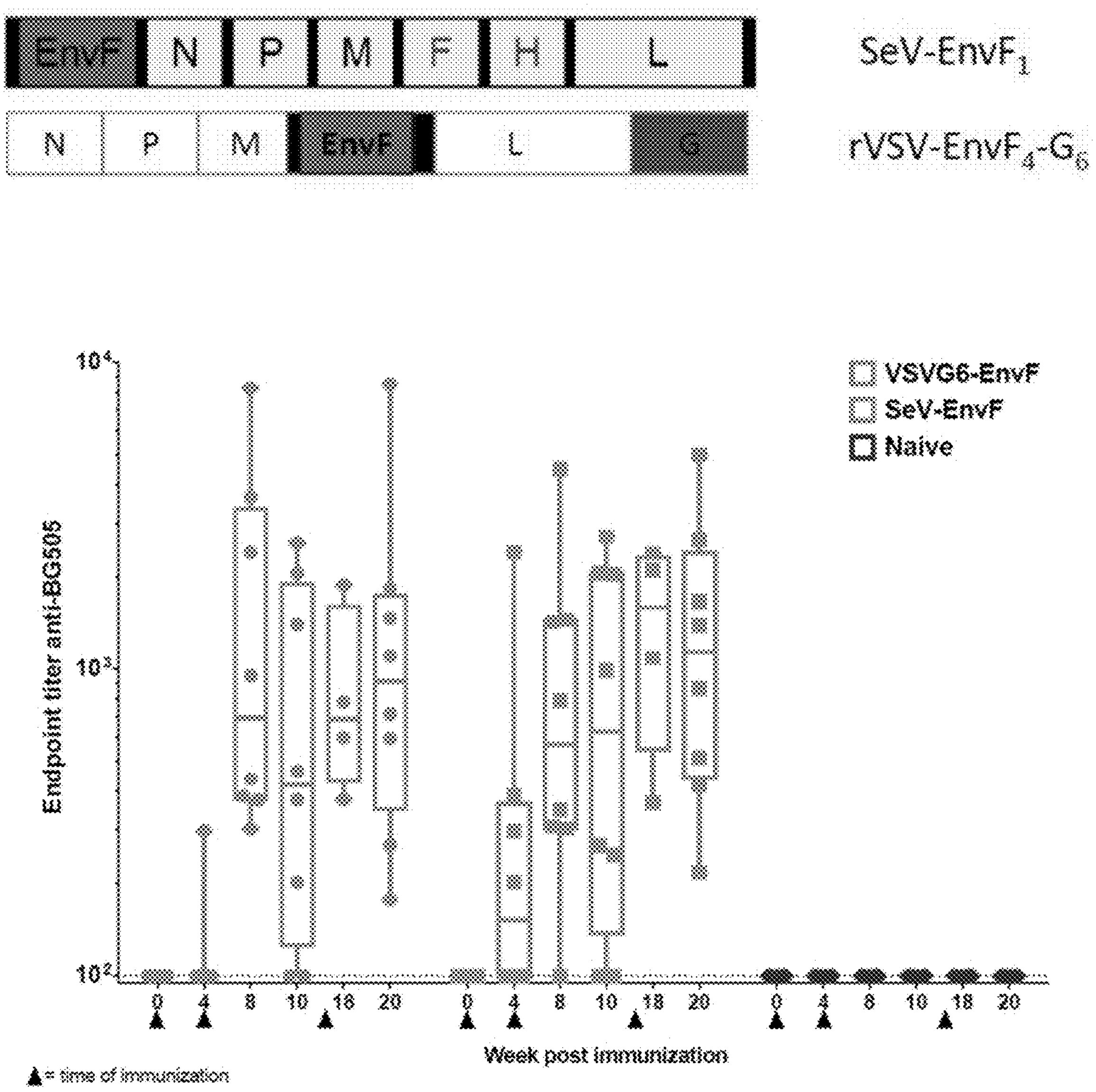
FIG. 35. EnvF is immunogenic in both SeV and VSV vector vaccinated NHPs: Env antibodies are detected in vaccinated animal serum. $2\times10^8$ pfu VSVG6-EnvF delivered by combined intranasal/oral route. $2\times10^7$ cell-infectious units (CIU) SeV-EnvF delivered by intranasal route. Both vectors administered at weeks 0, 4 and 16. BG505 gp120 ELISA to detect the generation of anti-BG505 antibodies in response to immunization.

FIG. 35 shows that EnvF is immunogenic in both SeV and VSV vector vaccinated NHPs: Env antibodies are detected in vaccinated animal serum. $2\times10^8$ pfu VSVG6-EnvF delivered by combined intranasal/oral route. $2\times10^7$ CIUSeV-EnvF delivered by intranasal route. Both vectors administered at weeks 0, 4 and 16. BG505 gp120 ELISA to detect the generation of anti-BG505 antibodies in response to immunization.

Figure 36:
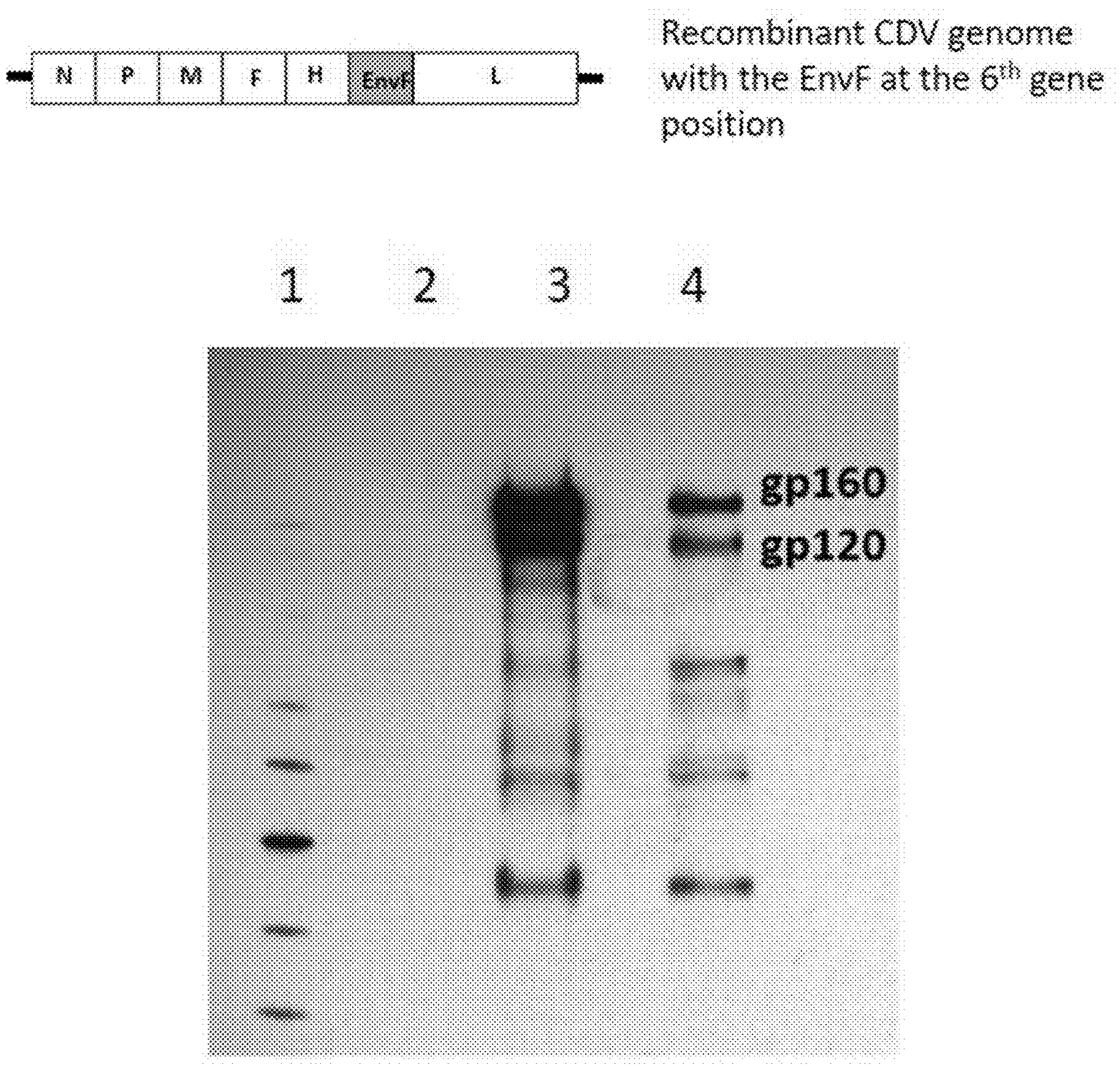
FIG. 36. The EnvF can be inserted into recombinant CDV vector and the vector expresses EnvF protein in infected cells. EnvF can be detected on rCDV-EnvF infected cell surface by Env trimer specific bnAbs including PGT and VRC06b antibodies similar to SeVEnvF and VSV-EnvF infections. EnvF detection in rCDVEnvF vector infected Vero cells: lanes 1, protein ladder; 2, uninfected Vero control; 3, BG505 Env positive control; 4, rCDV-EnvF infected Vero cell lysate.

FIG. 36 shows that the EnvF can be inserted into recombinant CDV vector and the vector expresses EnvF protein in infected cells. EnvF can be detected on rCDV-EnvF infected cell surface by Env trimer specific bnAbs including PGT and VRC06b antibodies similar to SeVEnvF and VSV-EnvF infections. EnvF detection in rCDVEnvF vector infected Vero cells: lanes 1, protein ladder; 2, uninfected Vero control; 3, BG505 Env positive control; 4, rCDV-EnvF infected Vero cell lysate.

The invention is further described by the following numbered paragraphs:

1. A viral vector containing and expressing a nucleic acid encoding an optimized human immunodeficiency virus (HIV) immunogen, wherein the HIV immunogen is a Clade A Env-F hybrid based on BG505.

2. The vector of paragraph 1, wherein the nucleic acid comprises the nucleic acid sequence of FIG. 27.

3. The vector of paragraph 1, wherein the nucleic acid encodes an amino acid sequence of the HIV immunogen comprises the amino acid sequence of FIG. 27.

4. The vector of any one of paragraphs 1-3, wherein the vector is a canine distemper virus (CDV) or a vesicular stomatitis virus (VSV) vector.

5. A cell transfected with the vector of any one of paragraphs 1-4.

6. The cell of paragraph 5 wherein the cell is a Vero cell.

7. A method for eliciting an immune response against HIV comprising administering an effective amount of the vector of any one of paragraphs 1-4 or the cell of paragraph 6 to a mammal in need thereof.

8. The method of paragraph 7 further comprising administering an adjuvant.

9. The method of paragraph 8, wherein the adjuvant is comprised of an acrylic polymer.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
<110> INTERNATIONAL AIDS VACCINE INITIATIVE

<120> OPTIMIZED HIV ENVELOPE GENE AND EXPRESSION THEREOF

<130> 43094.99.2040

<140> PCT/US2015/057452
<141> 2015-10-27

<150> 62/069,022
<151> 2014 Oct. 27

<160>     19

<170> PatentIn version 3.5

<210>     1
<211>    15
<212> PRT
<213> Artificial Sequence

<220>
<223> Description of Artificial Sequence: Synthetic
peptide

<400>     1
Ala Pro Thr Lys Ala Lys Arg Arg Val Val Gln Arg Glu Lys Arg
1         5           10          15

<210>     2
<211>   719
<212> PRT
<213> Artificial Sequence

<220>
<223> Description of Artificial Sequence: Synthetic
polypeptide

<400>     2
Met Lys Cys Leu Leu Tyr Leu Ala Phe Leu Phe Ile Gly Val Asn Cys
1        5           10           15
Lys Ala Ser Ala Glu Asn Leu Trp Val Thr Val Tyr Tyr Gly Val Pro
      20            25          30
Val Trp Lys Asp Ala Glu Thr Thr Leu Phe Cys Ala Ser Asp Ala Lys
     35           40          45
Ala Tyr Glu Thr Glu Lys His Asn Val Trp Ala Thr His Ala Cys Val
  50           55          60
Pro Thr Asp Pro Asn Pro Gln Glu Ile His Leu Glu Asn Val Thr Glu
65           70           75           80
Glu Phe Asn Met Trp Lys Asn Asn Met Val Glu Gln Met His Thr Asp
         85           90          95
Ile Ile Ser Leu Trp Asp Gln Ser Leu Lys Pro Cys Val Lys Leu Thr
         100           105          110
Pro Leu Cys Val Thr Leu Gln Cys Thr Asn Val Thr Asn Asn Ile Thr
     115           120          125
Asp Asp Met Arg Gly Glu Leu Lys Asn Cys Ser Phe Asn Met Thr Thr
  130          135          140
Glu Leu Arg Asp Lys Lys Gln Lys Val Tyr Ser Leu Phe Tyr Arg Leu
145          150          155          160
Asp Val Val Gln Ile Asn Glu Asn Gln Gly Asn Arg Ser Asn Asn Ser
         165           170          175
Asn Lys Glu Tyr Arg Leu Ile Asn Cys Asn Thr Ser Ala Ile Thr Gln
      180           185          190
Ala Cys Pro Lys Val Ser Phe Glu Pro Ile Pro Ile His Tyr Cys Ala
    195           200          205
Pro Ala Gly Phe Ala Ile Leu Lys Cys Lys Asp Lys Lys Phe Asn Gly
  210           215           220
```

-continued

SEQUENCE LISTING

```
Thr Gly Pro Cys Pro Ser Val Ser Thr Val Gln Cys Thr His Gly Ile
225             230             235             240
Lys Pro Val Val Ser Thr Gln Leu Leu Leu Asn Gly Ser Leu Ala Glu
            245             250             255
Glu Glu Val Met Ile Arg Ser Glu Asn Ile Thr Asn Asn Ala Lys Asn
        260             265             270
Ile Leu Val Gln Phe Asn Thr Pro Val Gln Ile Asn Cys Thr Arg Pro
    275             280             285
Asn Asn Asn Thr Arg Lys Ser Ile Arg Ile Gly Pro Gly Gln Ala Phe
    290             295             300
Tyr Ala Thr Gly Asp Ile Ile Gly Asp Ile Arg Gln Ala His Cys Thr
305             310             315             320
Val Ser Lys Ala Thr Trp Asn Glu Thr Leu Gly Lys Val Val Lys Gln
            325             330             335
Leu Arg Lys His Phe Gly Asn Asn Thr Ile Ile Arg Phe Ala Asn Ser
        340             345             350
Ser Gly Gly Asp Leu Glu Val Thr Thr His Ser Phe Asn Cys Gly Gly
    355             360             365
Glu Phe Phe Tyr Cys Asn Thr Ser Gly Leu Phe Asn Ser Thr Trp Ile
    370             375             380
Ser Asn Thr Ser Val Gln Gly Ser Asn Ser Thr Gly Ser Asn Asp Ser
385             390             395             400
Ile Thr Leu Pro Cys Arg Ile Lys Gln Ile Ile Asn Met Trp Gln Arg
            405             410             415
Ile Gly Gln Ala Met Tyr Ala Pro Pro Ile Gln Gly Val Ile Arg Cys
        420             425             430
Val Ser Asn Ile Thr Gly Leu Ile Leu Thr Arg Asp Gly Gly Ser Thr
    435             440             445
Asn Ser Thr Thr Glu Thr Phe Arg Pro Gly Gly Gly Asp Met Arg Asp
    450             455             460
Asn Trp Arg Ser Glu Leu Tyr Lys Tyr Lys Val Val Lys Ile Glu Pro
465             470             475             480
Leu Gly Val Ala Pro Thr Arg Ala Lys Arg Arg Val Val Gly Arg Glu
            485             490             495
Lys Arg Ala Val Gly Ile Gly Ala Val Phe Leu Gly Phe Leu Gly Ala
        500             505             510
Ala Gly Ser Thr Met Gly Ala Ala Ser Met Thr Leu Thr Val Gln Ala
    515             520             525
Arg Asn Leu Leu Ser Gly Ile Val Gln Gln Gln Ser Asn Leu Leu Arg
    530             535             540
Ala Ile Glu Ala Gln Gln His Leu Leu Lys Leu Thr Val Trp Gly Ile
545             550             555             560
Lys Gln Leu Gln Ala Arg Val Leu Ala Val Glu Arg Tyr Leu Arg Asp
            565             570             575
Gln Gln Leu Leu Gly Ile Trp Gly Cys Ser Gly Lys Leu Ile Cys Thr
        580             585             590
Thr Asn Val Pro Trp Asn Ser Ser Trp Ser Asn Arg Asn Leu Ser Glu
    595             600             605
Ile Trp Asp Asn Met Thr Trp Leu Gln Trp Asp Lys Glu Ile Ser Asn
    610             615             620
Tyr Thr Gln Ile Ile Tyr Gly Leu Leu Glu Glu Ser Gln Asn Gln Gln
625             630             635             640
Glu Lys Asn Glu Gln Asp Leu Leu Ala Leu Asp Lys Trp Ala Ser Leu
            645             650             655
Trp Asn Trp Phe Asp Ile Ser Asn Trp Leu Trp Tyr Ile Lys Ser Ser
        660             665             670
Ile Ala Ser Phe Phe Phe Ile Ile Gly Leu Ile Ile Gly Leu Phe Leu
    675             680             685
Val Leu Arg Val Gly Ile Tyr Leu Cys Ile Lys Leu Lys His Thr Lys
    690             695             700
Lys Arg Gln Ile Tyr Thr Asp Ile Glu Met Asn Arg Leu Gly Lys
705             710             715

<210> 3
<211> 2162
<212> DNA
<213> Artificial Sequence

<220>
<223> Description of Artificial Sequence: Synthetic
      polynucleotide

<400> 3
atgaagtgcc ttttgtactt agctttctta ttcatcgggg tgaattgcaa ggctagcgca     60
gagaatttgt gggtaacagt ctactatgga gtccctgtat ggaaggatgc agagacaaca    120
ttgttctgtg ctagtgacgc aaaggcttac gagacggaga agcacaatgt gtgggcaact    180
cacgcatgtg tcccaaccga tccaaatcct caagagattc atctagagaa tgtgactgaa    240
```

-continued

SEQUENCE LISTING

```
gaattcaata tgtggaagaa taatatggta gagcaaatgc atacagatat cattagttta    300
tgggaccagt cacttaaacc ctgcgttaaa ttgacgcctc tatgtgtgac acttcaatgt    360
actaatgtta caaacaacat aacagatgat atgagaggag aactgaagaa ctgtagtttc    420
aacatgacga cagagttgcg tgacaagaaa cagaaagtgt attcactatt ctatcggttg    480
gatgtagtac agataaatga gaatcaagga aacaggtcca acaactctaa caaagagtac    540
agacttatta attgcaatac cagtgctatc acgcaagcct gcccaaaggt ttcatttgaa    600
ccaataccta ttcattattg tgcacctgct ggattcgcca tcctcaaatg taaagacaag    660
aagttcaatg gaacaggacc ctgcccatca gtttcaaccg ttcagtgcac ccacggaatc    720
aagcctgtag ttagtactca attattgtta aatgggagct tagctgaaga agaagttatg    780
attagatcag agaatattac caataatgcg aagaacatct tggttcaatt caatactcca    840
gtccagatca attgcacaag gcctaataat aataccagaa agagtataag aattgggcca    900
ggacaggcat tctatgcaac aggagatata atcggagaca ttcgacaagc gcactgcact    960
gtttctaagg ccacttggaa tgaaacattg ggtaaagttg taaagcaact tcggaagcat   1020
ttcggaaata acacaattat tagatttgcg aactcatctg gaggggatct ggaagtgaca   1080
acacactctt tcaattgcgg tggcgagttc ttctattgta atacaagtgg attatttaac   1140
tctacttgga tttcaaatac ctcagtccaa ggatctaatt caacagggtc taacgattct   1200
ataacattac cttgccgtat aaagcaaatt attaatatgt ggcaaagaat cgggcaagcg   1260
atgtatgctc cacctattca aggcgtgatt cgttgcgttt caaacataac agggttgatc   1320
ctgaccaggg atggaggctc taccaattcc accaccgaga ccttccgtcc cggtggcgga   1380
gatatgcggg ataactggag atcagagctc tataagtata aggttgtgaa gattgaacct   1440
cttggagttg cccctacaag agcaaagaga agggtggttg gccgagagaa gagagcagtt   1500
ggcatcggtg ctgtctttct cggatttctt ggagcagctg gatccactat gggagcagca   1560
tcaatgacac taacagtgca ggctagaaat ttgcttagcg gaatcgttca gcagcagagc   1620
aatttactaa gagcaattga agcacagcaa catctcttaa agttgacggt gtggggcatt   1680
aaacaactac aagcgagagt gcttgccgtc gaaagatatt tgcgagacca acagctattg   1740
ggtatttggg gttgttctgg gaaattaatt tgcacaacaa atgttccatg gaactcctcc   1800
tggagtaata ggaatttaag tgagatatgg gacaacatga catggttgca gtgggacaag   1860
gaaatctcaa attatacaca gataatctat ggattattag aagagtctca gaatcagcaa   1920
gagaagaatg aacaggattt gcttgcattg gataagtggg cttctctatg gaactggttc   1980
gatattagta attggctctg gtatattaag agctctattg cctctttttt ctttatcata   2040
gggttaatca ttggactatt cttggttctc cgagttggta tttatctttg cattaaatta   2100
aagcacacca agaaaagaca gatttataca gacatagaga tgaaccgact tggaaagtaa   2160
ag                                                                  2162

<210>   4
<211>  2475
<212> DNA
<213> Artificial Sequence

<220>
<223> Description of Artificial Sequence: Synthetic
polynucleotide

<400>   4
ggagccacca tgaagtgttt gttgtatttg gcattcttat tcatcggagt gaattgtaag     60
gaggagaaag cattctcacc tgaagtgatc cctatgttca cagcattatc tgagggagct    120
actcctcaag atcttaacac aatgcttaac acagtcggag gacatcaagc agcaatgcaa    180
atgttgaaag atacaattaa cgaggaagca gcagaatggg atagaatcta taagagatgg    240
ataatattag gattgaacaa gattgttaga atgtattctc ctgtgtcaat ccttgatata    300
agacaaggac ctaaagagcc tttcagagat tacgtcgata gatttgcaag aaattgtaga    360
gcacctagaa agaagggatg ttggaaatgt gggaaagaag gacatcaaat gaaagattgt    420
actgagagac aagctaactt cttgggaaag atatggcctt caagatggaa acctaagatg    480
ataggaggaa taggaggatt tattaaagtc agacaatatg atcaaatatt gattgaaata    540
tgtggacata aagctattgg aacagtccta gtgggtccaa cacctgtcaa catcattggt    600
agaaatcttc tcactcaaat cggatgtaca ctcaatttcc caatatcacc tattgagacc    660
gtgcctgtca aattgaaacc tggaatggat ggacctaaag tcaaacaatg gccattaact    720
gaggagaaga ttaaagcact ggtagaaatt tgtacagaga tggagaaaga aggaaagatt    780
tccaagattg gtcctgagaa tccttataat actcctgtct ttgctattaa gaagaaggat    840
agtaccaaat ggaggaaatt agtcgatttc agagaactta acaagaggac tcaagacttc    900
tgggaagtgc aattgggaat cccacaccct gcaggattga agaagaagaa gtctgtcact    960
gtcctagatg tgggagatgc atatttcagt gtcccactgg atgaaggttt cagaaagtat   1020
acagcattca caatcccttc cattaataat gaaacacctg gaataagata tcaatataat   1080
gtcttacctc aagggtggaa aggatctcca gcaatattcc aatcatcaat gacaaagatc   1140
ttggagcctt tcagagctca gaatccagag atagttattt accaatacat ggatgatttg   1200
tatgttgggt cagatctcga gatcggacag cacaggatgg agaatagatg gcaagtaatg   1260
attgtctggc aagtcgatag aatgagaata agaacatgga aatccttggt gaaacatcac   1320
cttacagagg aggcagaact ggaactggca gagaataggg aaatattgaa agatccagtg   1380
catggtgtct attacgatcc ttctaaagat ctgatagcag agatccagta ctggcaagca   1440
acatggattc ctgagtggga attcgtcaac acacctccat tagtgaaact atggtaccaa   1500
ttagagaaga atgtcaccga gaacttcaac atgtggaaga acgatatggt agatcaaatg   1560
cacgaagata tcatctcctt gtgggatcaa tcacttaaac cttgtgttaa attgacacct   1620
tgggtacctg ctcataaagg gataggagga aacgaacaag tggataaatt ggtgtcccaa   1680
gggatcagga aagtcttgtt cctagatgga attgataaag ctcaagcaaa ggaaattgtc   1740
gcaagctgtg ataagtgtca attaaaggga gaggcaatgc acggacaagt cgattgttca   1800
cctggtattt ggcaacttga ttgtacacat ttggagggta aagttattct agtagcagta   1860
catgtcgctt ctggttatat tgaggcagaa gtgatacctg ctgagacagg acaggagacc   1920
gcatactttc tacttaagtt agctatgaat aaggagctca agaagataat aggacaagtt   1980
```

-continued

SEQUENCE LISTING

```
agagatcaag cagagcacct taagacagct gtccaaatgg cagtgtttat acacaacttt   2040
aagagaaagg gtggaatcgg aggatattcc gcaggagaga gaatctggaa aggtcctgct   2100
aaattgttat ggaaaggaga aggagcagtt gtaatacaag ataattctga tataaaagta   2160
gtccctagaa ggaaagctaa gattattaga gattatggga aacaaatggc aggagctgat   2220
tgtgtgtttc taggagcagc aggatccact atgggagctg catcaatgac acttaccgtg   2280
caggctagac agcttctttc aggaattgta cagcaacaga ataatttgct aagagcaatt   2340
gaagctcaac aacacttact tcaacttaca gtctggggaa tcaagcaagc atgtacacct   2400
tatgatatca accaaatgct gagaggacca ggaagagcat ttgtaacaat ccctaatcct   2460
ttattgggtc tggat                                                     2475

<210>    5
<211>   806
<212> PRT
<213> Artificial Sequence

<220>
<223> Description of Artificial Sequence: Synthetic
polypeptide

<400>    5
Met Glu Glu Lys Ala Phe Ser Pro Glu Val Ile Pro Met Phe Thr Ala
1               5                   10                  15
Leu Ser Glu Gly Ala Thr Pro Gln Asp Leu Asn Thr Met Leu Asn Thr
            20                  25                  30
Val Gly Gly His Gln Ala Ala Met Gln Met Leu Lys Asp Thr Ile Asn
        35                  40                  45
Glu Glu Ala Ala Glu Trp Asp Arg Ile Tyr Lys Arg Trp Ile Ile Leu
    50                  55                  60
Gly Leu Asn Lys Ile Val Arg Met Tyr Ser Pro Val Ser Ile Leu Asp
65                  70                  75                  80
Ile Arg Gln Gly Pro Lys Glu Pro Phe Arg Asp Tyr Val Asp Arg Phe
                85                  90                  95
Ala Arg Asn Cys Arg Ala Pro Arg Lys Lys Gly Cys Trp Lys Cys Gly
            100                 105                 110
Lys Glu Gly His Gln Met Lys Asp Cys Thr Glu Arg Gln Ala Asn Phe
        115                 120                 125
Leu Gly Lys Ile Trp Pro Ser Arg Trp Lys Pro Lys Met Ile Gly Gly
    130                 135                 140
Ile Gly Gly Phe Ile Lys Val Arg Gln Tyr Asp Gln Ile Leu Ile Glu
145                 150                 155                 160
Ile Cys Gly His Lys Ala Ile Gly Thr Val Leu Val Gly Pro Thr Pro
                165                 170                 175
Val Asn Ile Ile Gly Arg Asn Leu Leu Thr Gln Ile Gly Cys Thr Leu
            180                 185                 190
Asn Phe Pro Ile Ser Pro Ile Glu Thr Val Pro Val Lys Leu Lys Pro
        195                 200                 205
Gly Met Asp Gly Pro Lys Val Lys Gln Trp Pro Leu Thr Glu Glu Lys
    210                 215                 220
Ile Lys Ala Leu Val Glu Ile Cys Thr Glu Met Glu Lys Glu Gly Lys
225                 230                 235                 240
Ile Ser Lys Ile Gly Pro Glu Asn Pro Tyr Asn Thr Pro Val Phe Ala
                245                 250                 255
Ile Lys Lys Lys Asp Ser Thr Lys Trp Arg Lys Leu Val Asp Phe Arg
            260                 265                 270
Glu Leu Asn Lys Arg Thr Gln Asp Phe Trp Glu Val Gln Leu Gly Ile
        275                 280                 285
Pro His Pro Ala Gly Leu Lys Lys Lys Lys Ser Val Thr Val Leu Asp
    290                 295                 300
Val Gly Asp Ala Tyr Phe Ser Val Pro Leu Asp Glu Gly Phe Arg Lys
305                 310                 315                 320
Tyr Thr Ala Phe Thr Ile Pro Ser Ile Asn Asn Glu Thr Pro Gly Ile
                325                 330                 335
Arg Tyr Gln Tyr Asn Val Leu Pro Gln Gly Trp Lys Gly Ser Pro Ala
            340                 345                 350
Ile Phe Gln Ser Ser Met Thr Lys Ile Leu Glu Pro Phe Arg Ala Gln
        355                 360                 365
Asn Pro Glu Ile Val Ile Tyr Gln Tyr Met Asp Asp Leu Tyr Val Gly
    370                 375                 380
Ser Asp Leu Glu Ile Gly Gln His Arg Met Glu Asn Arg Trp Gln Val
385                 390                 395                 400
Met Ile Val Trp Gln Val Asp Arg Met Arg Ile Arg Thr Trp Lys Ser
                405                 410                 415
Leu Val Lys His His Leu Thr Glu Glu Ala Glu Leu Glu Leu Ala Glu
            420                 425                 430
Asn Arg Glu Ile Leu Lys Asp Pro Val His Gly Val Tyr Tyr Asp Pro
        435                 440                 445
Ser Lys Asp Leu Ile Ala Glu Ile Gln Tyr Trp Gln Ala Thr Trp Ile
```

-continued

SEQUENCE LISTING

```
 450                 455                 460
Pro Glu Trp Glu Phe Val Asn Thr Pro Pro Leu Val Lys Leu Trp Tyr
465                 470                 475                 480
Gln Leu Glu Lys Asn Val Thr Glu Asn Phe Asn Met Trp Lys Asn Asp
                485                 490                 495
Met Val Asp Gln Met His Glu Asp Ile Ile Ser Leu Trp Asp Gln Ser
            500                 505                 510
Leu Lys Pro Cys Val Lys Leu Thr Pro Trp Val Pro Ala His Lys Gly
        515                 520                 525
Ile Gly Gly Asn Glu Gln Val Asp Lys Leu Val Ser Gln Gly Ile Arg
    530                 535                 540
Lys Val Leu Phe Leu Asp Gly Ile Asp Lys Ala Gln Ala Lys Glu Ile
545                 550                 555                 560
Val Ala Ser Cys Asp Lys Cys Gln Leu Lys Gly Glu Ala Met His Gly
                565                 570                 575
Gln Val Asp Cys Ser Pro Gly Ile Trp Gln Leu Asp Cys Thr His Leu
            580                 585                 590
Glu Gly Lys Val Ile Leu Val Ala Val His Val Ala Ser Gly Tyr Ile
        595                 600                 605
Glu Ala Glu Val Ile Pro Ala Glu Thr Gly Gln Glu Thr Ala Tyr Phe
    610                 615                 620
Leu Leu Lys Leu Ala Met Asn Lys Glu Leu Lys Lys Ile Ile Gly Gln
625                 630                 635                 640
Val Arg Asp Gln Ala Glu His Leu Lys Thr Ala Val Gln Met Ala Val
                645                 650                 655
Phe Ile His Asn Phe Lys Arg Lys Gly Gly Ile Gly Gly Tyr Ser Ala
            660                 665                 670
Gly Glu Arg Ile Trp Lys Gly Pro Ala Lys Leu Leu Trp Lys Gly Glu
        675                 680                 685
Gly Ala Val Val Ile Gln Asp Asn Ser Asp Ile Lys Val Val Pro Arg
    690                 695                 700
Arg Lys Ala Lys Ile Ile Arg Asp Tyr Gly Lys Gln Met Ala Gly Ala
705                 710                 715                 720
Asp Cys Val Phe Leu Gly Ala Ala Gly Ser Thr Met Gly Ala Ala Ser
                725                 730                 735
Met Thr Leu Thr Val Gln Ala Arg Gln Leu Leu Ser Gly Ile Val Gln
            740                 745                 750
Gln Gln Asn Asn Leu Leu Arg Ala Ile Glu Ala Gln Gln His Leu Leu
        755                 760                 765
Gln Leu Thr Val Trp Gly Ile Lys Gln Ala Cys Thr Pro Tyr Asp Ile
    770                 775                 780
Asn Gln Met Leu Arg Gly Pro Gly Arg Ala Phe Val Thr Ile Pro Asn
785                 790                 795                 800
Pro Leu Leu Gly Leu Asp
                805

<210> 6
<211> 2391
<212> DNA
<213> Artificial Sequence

<220>
<223> Description of Artificial Sequence: Synthetic
      polynucleotide

<220>
<221> CDS
<222> (10) . . . (2385)

<400> 6
gccgccacc atg gag gag aag gcc ttc agc cct gag gtg atc ccc atg ttc      51
          Met Glu Glu Lys Ala Phe Ser Pro Glu Val Ile Pro Met Phe
          1               5                   10
acc gcc ctg tcc gag ggc gcc acc ccc cag gac ctg aac acc atg ctg        99
Thr Ala Leu Ser Glu Gly Ala Thr Pro Gln Asp Leu Asn Thr Met Leu
15                  20                  25                  30
aac acc gtg ggc ggc cac cag gcc gcc atg cag atg ctg aag gac acc       147
Asn Thr Val Gly Gly His Gln Ala Ala Met Gln Met Leu Lys Asp Thr
                35                  40                  45
atc aac gag gag gcc gcc gag tgg gac cgc atc tac aag cgc tgg atc       195
Ile Asn Glu Glu Ala Ala Glu Trp Asp Arg Ile Tyr Lys Arg Trp Ile
            50                  55                  60
atc ctg ggc ctg aac aag atc gtg cgc atg tac tcc ccc gtg tcc atc       243
Ile Leu Gly Leu Asn Lys Ile Val Arg Met Tyr Ser Pro Val Ser Ile
        65                  70                  75
ctg gac atc cgc cag ggc ccc aag gag ccc ttc cgc gac tac gtg gac       291
Leu Asp Ile Arg Gln Gly Pro Lys Glu Pro Phe Arg Asp Tyr Val Asp
```

```
                    SEQUENCE LISTING
       80         85         90
cgc ttc gcc cgc aac tgc cgc gcc cct cgc aag aag ggc tgc tgg aag      339
Arg Phe Ala Arg Asn Cys Arg Ala Pro Arg Lys Lys Gly Cys Trp Lys
 95             100            105             110
tgc ggc aag gag ggc cac cag atg aag gac tgc acc gag cgc cag gcc      387
Cys Gly Lys Glu Gly His Gln Met Lys Asp Cys Thr Glu Arg Gln Ala
         115            120            125
aac ttc ctg ggc aag atc tgg ccc tcc cgc tgg aag ccc aag atg att      435
Asn Phe Leu Gly Lys Ile Trp Pro Ser Arg Trp Lys Pro Lys Met Ile
     130            135            140
ggg ggc atc ggc ggc ttc atc aag gtg cgc cag tac gac cag atc ctg      483
Gly Gly Ile Gly Gly Phe Ile Lys Val Arg Gln Tyr Asp Gln Ile Leu
 145            150            155
atc gag atc tgc ggc cac aag gcc atc ggc acc gtg ctc gtg ggc ccc      531
Ile Glu Ile Cys Gly His Lys Ala Ile Gly Thr Val Leu Val Gly Pro
         160            165            170
acc ccc gtg aac atc atc ggc cgc aac ctg ctg acc cag atc ggc tgc      579
Thr Pro Val Asn Ile Ile Gly Arg Asn Leu Leu Thr Gln Ile Gly Cys
175            180            185            190
acc ctg aac ttc ccc atc tcc ccc atc gag acc gtg ccc gtg aag ctg      627
Thr Leu Asn Phe Pro Ile Ser Pro Ile Glu Thr Val Pro Val Lys Leu
             195            200            205
aag ccc ggc atg gac ggc ccc aag gtg aag cag tgg ccc ctg acc gag      675
Lys Pro Gly Met Asp Gly Pro Lys Val Lys Gln Trp Pro Leu Thr Glu
         210            215            220
gag aag atc aag gcc ctg gtg gag atc tgc acc gag atg gag aag gag      723
Glu Lys Ile Lys Ala Leu Val Glu Ile Cys Thr Glu Met Glu Lys Glu
     225            230            235
ggc aag atc tcc aag atc ggc ccc gag aac ccc tac aac acc ccc gtg      771
Gly Lys Ile Ser Lys Ile Gly Pro Glu Asn Pro Tyr Asn Thr Pro Val
 240            245            250
ttc gcc atc aag aag aag gac tcc acc aag tgg cgc aaa ctg gtg gac      819
Phe Ala Ile Lys Lys Lys Asp Ser Thr Lys Trp Arg Lys Leu Val Asp
255            260            265            270
ttc cgc gag ctg aac aag cgc acc cag gac ttc tgg gag gtg cag ctg      867
Phe Arg Glu Leu Asn Lys Arg Thr Gln Asp Phe Trp Glu Val Gln Leu
             275            280            285
ggc atc ccc cac cct gcc ggc ctg aag aag aag aag tcc gtg acc gtg      915
Gly Ile Pro His Pro Ala Gly Leu Lys Lys Lys Lys Ser Val Thr Val
         290            295            300
ctg gac gtg ggc gac gcc tac ttc tcc gtg ccc ctg gac gag ggc ttc      963
Leu Asp Val Gly Asp Ala Tyr Phe Ser Val Pro Leu Asp Glu Gly Phe
     305            310            315
cgc aag tac acc gcc ttc acc atc ccc tcc atc aac aac gag acc ccc     1011
Arg Lys Tyr Thr Ala Phe Thr Ile Pro Ser Ile Asn Asn Glu Thr Pro
 320            325            330
ggc atc cgc tac cag tac aac gtg ctg ccc cag ggc tgg aag ggc tcc     1059
Gly Ile Arg Tyr Gln Tyr Asn Val Leu Pro Gln Gly Trp Lys Gly Ser
335            340            345            350
ccc gcc atc ttc cag tcc tcc atg acc aag atc ctg gag ccc ttc cgc     1107
Pro Ala Ile Phe Gln Ser Ser Met Thr Lys Ile Leu Glu Pro Phe Arg
             355            360            365
gcc cag aac ccc gag atc gtg atc tac cag tac atg gac gac ctg tac     1155
Ala Gln Asn Pro Glu Ile Val Ile Tyr Gln Tyr Met Asp Asp Leu Tyr
         370            375            380
gtg ggc tcc gac ctg gag atc ggc cag cac cgc atg gag aac cgc tgg     1203
Val Gly Ser Asp Leu Glu Ile Gly Gln His Arg Met Glu Asn Arg Trp
     385            390            395
cag gtg atg atc gtg tgg cag gtg gac cgc atg cgc atc cgc acc tgg     1251
Gln Val Met Ile Val Trp Gln Val Asp Arg Met Arg Ile Arg Thr Trp
 400            405            410
aag tcc ctg gtg aag cac cac ctg acc gag gag gcc gag ctg gag ctg     1299
Lys Ser Leu Val Lys His His Leu Thr Glu Glu Ala Glu Leu Glu Leu
415            420            425            430
gcc gag aac cgc gag atc ctg aag gac ccc gtg cac ggc gtg tac tac     1347
Ala Glu Asn Arg Glu Ile Leu Lys Asp Pro Val His Gly Val Tyr Tyr
             435            440            445
gac ccc tcc aag gac ctg atc gcc gag atc cag tac tgg cag gcc acc     1395
Asp Pro Ser Lys Asp Leu Ile Ala Glu Ile Gln Tyr Trp Gln Ala Thr
         450            455            460
tgg atc ccc gag tgg gag ttc gtg aac acc cca ccc ctg gtg aag ctg     1443
Trp Ile Pro Glu Trp Glu Phe Val Asn Thr Pro Pro Leu Val Lys Leu
     465            470            475
tgg tac cag ctg gag aag aac gtg acc gag aac ttc aac atg tgg aag     1491
Trp Tyr Gln Leu Glu Lys Asn Val Thr Glu Asn Phe Asn Met Trp Lys
 480            485            490
aac gac atg gtg gac cag atg cac gag gac atc atc tcc ctg tgg gac     1539
```

-continued

SEQUENCE LISTING

```
Asn Asp Met Val Asp Gln Met His Glu Asp Ile Ile Ser Leu Trp Asp
495             500             505             510
cag tcc ctg aag ccc tgc gtg aag ctg acc ccc tgg gtg ccc gcc cac      1587
Gln Ser Leu Lys Pro Cys Val Lys Leu Thr Pro Trp Val Pro Ala His
            515             520             525
aag ggc atc ggc ggc aac gag cag gtg gac aag ctg gtg tcc cag ggc      1635
Lys Gly Ile Gly Gly Asn Glu Gln Val Asp Lys Leu Val Ser Gln Gly
        530             535             540
atc cgc aag gtg ctg ttc ctg gac ggc atc gac aag gcc cag gcc aag      1683
Ile Arg Lys Val Leu Phe Leu Asp Gly Ile Asp Lys Ala Gln Ala Lys
    545             550             555
gag atc gtg gcc tcc tgc gac aag tgc cag ctg aag ggc gag gcc atg      1731
Glu Ile Val Ala Ser Cys Asp Lys Cys Gln Leu Lys Gly Glu Ala Met
560             565             570
cac ggc cag gtg gac tgc tcc ccc ggc atc tgg cag ctg gac tgc acc      1779
His Gly Gln Val Asp Cys Ser Pro Gly Ile Trp Gln Leu Asp Cys Thr
575             580             585             590
cac ctg gag ggc aag gtg atc ctg gtg gcc gtg cac gtg gcc tcc ggc      1827
His Leu Glu Gly Lys Val Ile Leu Val Ala Val His Val Ala Ser Gly
            595             600             605
tac atc gag gcc gaa gtg att ccc gcc gag acc ggc cag gag acc gcc      1875
Tyr Ile Glu Ala Glu Val Ile Pro Ala Glu Thr Gly Gln Glu Thr Ala
            610             615             620
tac ttc ctg ctg aag ctg gcc atg aac aag gag ctg aag aag atc atc      1923
Tyr Phe Leu Leu Lys Leu Ala Met Asn Lys Glu Leu Lys Lys Ile Ile
    625             630             635
ggc cag gtg cgc gac cag gcc gag cac ctg aag acc gcc gtg cag atg      1971
Gly Gln Val Arg Asp Gln Ala Glu His Leu Lys Thr Ala Val Gln Met
640             645             650
gcc gtg ttc atc cac aac ttc aag cgc aag ggc gga atc ggc ggc tac      2019
Ala Val Phe Ile His Asn Phe Lys Arg Lys Gly Gly Ile Gly Gly Tyr
655             660             665             670
tcc gcc ggc gag cgc atc tgg aag ggc ccc gcc aag ctg ctg tgg aag      2067
Ser Ala Gly Glu Arg Ile Trp Lys Gly Pro Ala Lys Leu Leu Trp Lys
            675             680             685
ggc gag ggc gcc gtg gtg atc cag gac aac tcc gac atc aag gtg gtg      2115
Gly Glu Gly Ala Val Val Ile Gln Asp Asn Ser Asp Ile Lys Val Val
        690             695             700
ccc cgc cgc aag gcc aag atc atc cgc gac tac ggc aag cag atg gcc      2163
Pro Arg Arg Lys Ala Lys Ile Ile Arg Asp Tyr Gly Lys Gln Met Ala
    705             710             715
ggt gcc gac tgc gtg ttc ctg ggc gct gcc ggc tcc acc atg ggc gcc      2211
Gly Ala Asp Cys Val Phe Leu Gly Ala Ala Gly Ser Thr Met Gly Ala
720             725             730
gcc tcc atg acc ctg acc gtg cag gcc cgc cag ctg ctg tcc ggc atc      2259
Ala Ser Met Thr Leu Thr Val Gln Ala Arg Gln Leu Leu Ser Gly Ile
735             740             745             750
gtg cag cag cag aac aac ctg ctg cgc gcc atc gag gcc cag cag cac      2307
Val Gln Gln Gln Asn Asn Leu Leu Arg Ala Ile Glu Ala Gln Gln His
            755             760             765
ctg ctg cag ctg acc gtg tgg ggc atc aag cag gca ccc acc aag gca      2355
Leu Leu Gln Leu Thr Val Trp Gly Ile Lys Gln Ala Pro Thr Lys Ala
        770             775             780
aag aga aga gtg gtg cag aga gaa aag aga tag taa                      2391
Lys Arg Arg Val Val Gln Arg Glu Lys Arg
    785             790

<210> 7
<211> 792
<212> PRT
<213> Artificial Sequence

<220>
<223> Description of Artificial Sequence: Synthetic
polypeptide

<400> 7
Met Glu Glu Lys Ala Phe Ser Pro Glu Val Ile Pro Met Phe Thr Ala
1               5                   10                  15
Leu Ser Glu Gly Ala Thr Pro Gln Asp Leu Asn Thr Met Leu Asn Thr
        20                  25                  30
Val Gly Gly His Gln Ala Ala Met Gln Met Leu Lys Asp Thr Ile Asn
    35                  40                  45
Glu Glu Ala Ala Glu Trp Asp Arg Ile Tyr Lys Arg Trp Ile Ile Leu
  50                  55                  60
Gly Leu Asn Lys Ile Val Arg Met Tyr Ser Pro Val Ser Ile Leu Asp
65                  70                  75                  80
```

-continued

SEQUENCE LISTING

```
Ile Arg Gln Gly Pro Lys Glu Pro Phe Arg Asp Tyr Val Asp Arg Phe
         85                  90                  95
Ala Arg Asn Cys Arg Ala Pro Arg Lys Lys Gly Cys Trp Lys Cys Gly
        100                 105                 110
Lys Glu Gly His Gln Met Lys Asp Cys Thr Glu Arg Gln Ala Asn Phe
    115                 120                 125
Leu Gly Lys Ile Trp Pro Ser Arg Trp Lys Pro Lys Met Ile Gly Gly
  130                 135                 140
Ile Gly Gly Phe Ile Lys Val Arg Gln Tyr Asp Gln Ile Leu Ile Glu
145                 150                 155                 160
Ile Cys Gly His Lys Ala Ile Gly Thr Val Leu Val Gly Pro Thr Pro
         165                 170                 175
Val Asn Ile Ile Gly Arg Asn Leu Leu Thr Gln Ile Gly Cys Thr Leu
      180                 185                 190
Asn Phe Pro Ile Ser Pro Ile Glu Thr Val Pro Val Lys Leu Lys Pro
    195                 200                 205
Gly Met Asp Gly Pro Lys Val Lys Gln Trp Pro Leu Thr Glu Glu Lys
  210                 215                 220
Ile Lys Ala Leu Val Glu Ile Cys Thr Glu Met Glu Lys Glu Gly Lys
225                 230                 235                 240
Ile Ser Lys Ile Gly Pro Glu Asn Pro Tyr Asn Thr Pro Val Phe Ala
         245                 250                 255
Ile Lys Lys Lys Asp Ser Thr Lys Trp Arg Lys Leu Val Asp Phe Arg
        260                 265                 270
Glu Leu Asn Lys Arg Thr Gln Asp Phe Trp Glu Val Gln Leu Gly Ile
    275                 280                 285
Pro His Pro Ala Gly Leu Lys Lys Lys Lys Ser Val Thr Val Leu Asp
  290                 295                 300
Val Gly Asp Ala Tyr Phe Ser Val Pro Leu Asp Glu Gly Phe Arg Lys
305                 310                 315                 320
Tyr Thr Ala Phe Thr Ile Pro Ser Ile Asn Asn Glu Thr Pro Gly Ile
        325                 330                 335
Arg Tyr Gln Tyr Asn Val Leu Pro Gln Gly Trp Lys Gly Ser Pro Ala
      340                 345                 350
Ile Phe Gln Ser Ser Met Thr Lys Ile Leu Glu Pro Phe Arg Ala Gln
     355                 360                 365
Asn Pro Glu Ile Val Ile Tyr Gln Tyr Met Asp Asp Leu Tyr Val Gly
  370                 375                 380
Ser Asp Leu Glu Ile Gly Gln His Arg Met Glu Asn Arg Trp Gln Val
385                 390                 395                 400
Met Ile Val Trp Gln Val Asp Arg Met Arg Ile Arg Thr Trp Lys Ser
        405                 410                 415
Leu Val Lys His His Leu Thr Glu Glu Ala Glu Leu Glu Leu Ala Glu
       420                 425                 430
Asn Arg Glu Ile Leu Lys Asp Pro Val His Gly Val Tyr Tyr Asp Pro
    435                 440                 445
Ser Lys Asp Leu Ile Ala Glu Ile Gln Tyr Trp Gln Ala Thr Trp Ile
  450                 455                 460
Pro Glu Trp Glu Phe Val Asn Thr Pro Pro Leu Val Lys Leu Trp Tyr
465                 470                 475                 480
Gln Leu Glu Lys Asn Val Thr Glu Asn Phe Asn Met Trp Lys Asn Asp
        485                 490                 495
Met Val Asp Gln Met His Glu Asp Ile Ile Ser Leu Trp Asp Gln Ser
       500                 505                 510
Leu Lys Pro Cys Val Lys Leu Thr Pro Trp Val Pro Ala His Lys Gly
    515                 520                 525
Ile Gly Gly Asn Glu Gln Val Asp Lys Leu Val Ser Gln Gly Ile Arg
   530                 535                 540
Lys Val Leu Phe Leu Asp Gly Ile Asp Lys Ala Gln Ala Lys Glu Ile
545                 550                 555                 560
Val Ala Ser Cys Asp Lys Cys Gln Leu Lys Gly Glu Ala Met His Gly
        565                 570                 575
Gln Val Asp Cys Ser Pro Gly Ile Trp Gln Leu Asp Cys Thr His Leu
       580                 585                 590
Glu Gly Lys Val Ile Leu Val Ala Val His Val Ala Ser Gly Tyr Ile
    595                 600                 605
Glu Ala Glu Val Ile Pro Ala Glu Thr Gly Gln Glu Thr Ala Tyr Phe
  610                 615                 620
Leu Leu Lys Leu Ala Met Asn Lys Glu Leu Lys Lys Ile Ile Gly Gln
625                 630                 635                 640
Val Arg Asp Gln Ala Glu His Leu Lys Thr Ala Val Gln Met Ala Val
        645                 650                 655
Phe Ile His Asn Phe Lys Arg Lys Gly Gly Ile Gly Gly Tyr Ser Ala
        660                 665                 670
Gly Glu Arg Ile Trp Lys Gly Pro Ala Lys Leu Leu Trp Lys Gly Glu
    675                 680                 685
Gly Ala Val Val Ile Gln Asp Asn Ser Asp Ile Lys Val Val Pro Arg
```

-continued

SEQUENCE LISTING

```
  690           695           700
Arg Lys Ala Lys Ile Ile Arg Asp Tyr Gly Lys Gln Met Ala Gly Ala
705           710           715           720
Asp Cys Val Phe Leu Gly Ala Ala Gly Ser Thr Met Gly Ala Ala Ser
        725           730           735
Met Thr Leu Thr Val Gln Ala Arg Gln Leu Leu Ser Gly Ile Val Gln
       740           745           750
Gln Gln Asn Asn Leu Leu Arg Ala Ile Glu Ala Gln Gln His Leu Leu
    755           760           765
Gln Leu Thr Val Trp Gly Ile Lys Gln Ala Pro Thr Lys Ala Lys Arg
  770           775           780
Arg Val Val Gln Arg Glu Lys Arg
785           790

<210>     8
<211>  2391
<212> DNA
<213> Artificial Sequence

<220>
<223> Description of Artificial Sequence: Synthetic
polynucleotide

<220>
<221> CDS
<222> (10) . . . (2385)

<400>     8
ggagccacc atg gag gag aaa gca ttc tca cct gaa gtg atc cct atg ttc  51
          Met Glu Glu Lys Ala Phe Ser Pro Glu Val Ile Pro Met Phe
          1        5           10
aca gca tta tct gag gga gct act cct caa gat ctt aac aca atg ctt    99
Thr Ala Leu Ser Glu Gly Ala Thr Pro Gln Asp Leu Asn Thr Met Leu
15           20           25           30
aac aca gtc gga gga cat caa gca gca atg caa atg ttg aaa gat aca    147
Asn Thr Val Gly Gly His Gln Ala Ala Met Gln Met Leu Lys Asp Thr
         35           40           45
att aac gag gaa gca gca gaa tgg gat aga atc tat aag aga tgg ata    195
Ile Asn Glu Glu Ala Ala Glu Trp Asp Arg Ile Tyr Lys Arg Trp Ile
        50           55           60
ata tta gga ttg aac aag att gtt aga atg tat tct cct gtg tca atc    243
Ile Leu Gly Leu Asn Lys Ile Val Arg Met Tyr Ser Pro Val Ser Ile
     65           70           75
ctt gat ata aga caa gga cct aaa gag cct ttc aga gat tac gtc gat    291
Leu Asp Ile Arg Gln Gly Pro Lys Glu Pro Phe Arg Asp Tyr Val Asp
  80           85           90
aga ttt gca aga aat tgt aga gca cct aga aag aag gga tgt tgg aaa    339
Arg Phe Ala Arg Asn Cys Arg Ala Pro Arg Lys Lys Gly Cys Trp Lys
95           100           105           110
tgt ggg aaa gaa gga cat caa atg aaa gat tgt act gag aga caa gct    387
Cys Gly Lys Glu Gly His Gln Met Lys Asp Cys Thr Glu Arg Gln Ala
        115           120           125
aac ttc ttg gga aag ata tgg cct tca aga tgg aaa cct aag atg ata    435
Asn Phe Leu Gly Lys Ile Trp Pro Ser Arg Trp Lys Pro Lys Met Ile
      130           135           140
gga gga ata gga gga ttt att aaa gtc aga caa tat gat caa ata ttg    483
Gly Gly Ile Gly Gly Phe Ile Lys Val Arg Gln Tyr Asp Gln Ile Leu
    145           150           155
att gaa ata tgt gga cat aaa gct att gga aca gtc cta gtg ggt cca    531
Ile Glu Ile Cys Gly His Lys Ala Ile Gly Thr Val Leu Val Gly Pro
   160           165           170
aca cct gtc aac atc att ggt aga aat ctt ctc act caa atc gga tgt    579
Thr Pro Val Asn Ile Ile Gly Arg Asn Leu Leu Thr Gln Ile Gly Cys
175           180           185           190
aca ctc aat ttc cca ata tca cct att gag acc gtg cct gtc aaa ttg    627
Thr Leu Asn Phe Pro Ile Ser Pro Ile Glu Thr Val Pro Val Lys Leu
        195           200           205
aaa cct gga atg gat gga cct aaa gtc aaa caa tgg cca tta act gag    675
Lys Pro Gly Met Asp Gly Pro Lys Val Lys Gln Trp Pro Leu Thr Glu
       210           215           220
gag aag att aaa gca ctg gta gaa att tgt aca gag atg gag aaa gaa    723
Glu Lys Ile Lys Ala Leu Val Glu Ile Cys Thr Glu Met Glu Lys Glu
    225           230           235
gga aag att tcc aag att ggt cct gag aat cct tat aat act cct gtc    771
Gly Lys Ile Ser Lys Ile Gly Pro Glu Asn Pro Tyr Asn Thr Pro Val
  240           245           250
ttt gct att aag aag aag gat agt acc aaa tgg agg aaa tta gtc gat    819
```

-continued

SEQUENCE LISTING

```
Phe Ala Ile Lys Lys Lys Asp Ser Thr Lys Trp Arg Lys Leu Val Asp
255             260             265             270
ttc aga gaa ctt aac aag agg act caa gac ttc tgg gaa gtg caa ttg    867
Phe Arg Glu Leu Asn Lys Arg Thr Gln Asp Phe Trp Glu Val Gln Leu
        275             280             285
gga atc cca cac cct gca gga ttg aag aag aag aag tct gtc act gtc    915
Gly Ile Pro His Pro Ala Gly Leu Lys Lys Lys Lys Ser Val Thr Val
        290             295             300
cta gat gtg gga gat gca tat ttc agt gtc cca ctg gat gaa ggt ttc    963
Leu Asp Val Gly Asp Ala Tyr Phe Ser Val Pro Leu Asp Glu Gly Phe
    305             310             315
aga aag tat aca gca ttc aca atc cct tcc att aat aat gaa aca cct    1011
Arg Lys Tyr Thr Ala Phe Thr Ile Pro Ser Ile Asn Asn Glu Thr Pro
  320             325             330
gga ata aga tat caa tat aat gtc tta cct caa ggg tgg aaa gga tct    1059
Gly Ile Arg Tyr Gln Tyr Asn Val Leu Pro Gln Gly Trp Lys Gly Ser
335             340             345             350
cca gca ata ttc caa tca tca atg aca aag atc ttg gag cct ttc aga    1107
Pro Ala Ile Phe Gln Ser Ser Met Thr Lys Ile Leu Glu Pro Phe Arg
            355             360             365
gct cag aat cca gag ata gtt att tac caa tac atg gat gat ttg tat    1155
Ala Gln Asn Pro Glu Ile Val Ile Tyr Gln Tyr Met Asp Asp Leu Tyr
        370             375             380
gtt ggg tca gat ctc gag atc gga cag cac agg atg gag aat aga tgg    1203
Val Gly Ser Asp Leu Glu Ile Gly Gln His Arg Met Glu Asn Arg Trp
    385             390             395
caa gta atg att gtc tgg caa gtc gat aga atg aga ata aga aca tgg    1251
Gln Val Met Ile Val Trp Gln Val Asp Arg Met Arg Ile Arg Thr Trp
  400             405             410
aaa tcc ttg gtg aaa cat cac ctt aca gag gag gca gaa ctg gaa ctg    1299
Lys Ser Leu Val Lys His His Leu Thr Glu Glu Ala Glu Leu Glu Leu
415             420             425             430
gca gag aat agg gaa ata ttg aaa gat cca gtg cat ggt gtc tat tac    1347
Ala Glu Asn Arg Glu Ile Leu Lys Asp Pro Val His Gly Val Tyr Tyr
            435             440             445
gat cct tct aaa gat ctg ata gca gag atc cag tac tgg caa gca aca    1395
Asp Pro Ser Lys Asp Leu Ile Ala Glu Ile Gln Tyr Trp Gln Ala Thr
        450             455             460
tgg att cct gag tgg gaa ttc gtc aac aca cct cca tta gtg aaa cta    1443
Trp Ile Pro Glu Trp Glu Phe Val Asn Thr Pro Pro Leu Val Lys Leu
      465             470             475
tgg tac caa tta gag aag aat gtc acc gag aac ttc aac atg tgg aag    1491
Trp Tyr Gln Leu Glu Lys Asn Val Thr Glu Asn Phe Asn Met Trp Lys
  480             485             490
aac gat atg gta gat caa atg cac gaa gat atc atc tcc ttg tgg gat    1539
Asn Asp Met Val Asp Gln Met His Glu Asp Ile Ile Ser Leu Trp Asp
495             500             505             510
caa tca ctt aaa cct tgt gtt aaa ttg aca cct tgg gta cct gct cat    1587
Gln Ser Leu Lys Pro Cys Val Lys Leu Thr Pro Trp Val Pro Ala His
            515             520             525
aaa ggg ata gga gga aac gaa caa gtg gat aaa ttg gtg tcc caa ggg    1635
Lys Gly Ile Gly Gly Asn Glu Gln Val Asp Lys Leu Val Ser Gln Gly
        530             535             540
atc agg aaa gtc ttg ttc cta gat gga att gat aaa gct caa gca aag    1683
Ile Arg Lys Val Leu Phe Leu Asp Gly Ile Asp Lys Ala Gln Ala Lys
      545             550             555
gaa att gtc gca agc tgt gat aag tgt caa tta aag gga gag gca atg    1731
Glu Ile Val Ala Ser Cys Asp Lys Cys Gln Leu Lys Gly Glu Ala Met
  560             565             570
cac gga caa gtc gat tgt tca cct ggt att tgg caa ctt gat tgt aca    1779
His Gly Gln Val Asp Cys Ser Pro Gly Ile Trp Gln Leu Asp Cys Thr
575             580             585             590
cat ttg gag ggt aaa gtt att cta gta gca gta cat gtc gct tct ggt    1827
His Leu Glu Gly Lys Val Ile Leu Val Ala Val His Val Ala Ser Gly
        595             600             605
tat att gag gca gaa gtg ata cct gct gag aca gga cag gag acc gca    1875
Tyr Ile Glu Ala Glu Val Ile Pro Ala Glu Thr Gly Gln Glu Thr Ala
        610             615             620
tac ttt cta ctt aag tta gct atg aat aag gag ctc aag aag ata ata    1923
Tyr Phe Leu Leu Lys Leu Ala Met Asn Lys Glu Leu Lys Lys Ile Ile
    625             630             635
gga caa gtt aga gat caa gca gag cac ctt aag aca gct gtc caa atg    1971
Gly Gln Val Arg Asp Gln Ala Glu His Leu Lys Thr Ala Val Gln Met
  640             645             650
gca gtg ttt ata cac aac ttt aag aga aag ggt gga atc gga gga tat    2019
Ala Val Phe Ile His Asn Phe Lys Arg Lys Gly Gly Ile Gly Gly Tyr
655             660             665             670
```

-continued

SEQUENCE LISTING

```
tcc gca gga gag aga atc tgg aaa ggt cct gct aaa ttg tta tgg aaa    2067
Ser Ala Gly Glu Arg Ile Trp Lys Gly Pro Ala Lys Leu Leu Trp Lys
          675             680             685
gga gaa gga gca gtt gta ata caa gat aat tct gat ata aaa gta gtc    2115
Gly Glu Gly Ala Val Val Ile Gln Asp Asn Ser Asp Ile Lys Val Val
       690             695             700
cct aga agg aaa gct aag att att aga gat tat ggg aaa caa atg gca    2163
Pro Arg Arg Lys Ala Lys Ile Ile Arg Asp Tyr Gly Lys Gln Met Ala
    705             710             715
gga gct gat tgt gtg ttt cta gga gca gca gga tcc act atg gga gct    2211
Gly Ala Asp Cys Val Phe Leu Gly Ala Ala Gly Ser Thr Met Gly Ala
  720             725             730
gca tca atg aca ctt acc gtg cag gct aga cag ctt ctt tca gga att    2259
Ala Ser Met Thr Leu Thr Val Gln Ala Arg Gln Leu Leu Ser Gly Ile
735             740             745             750
gta cag caa cag aat aat ttg cta aga gca att gaa gct caa caa cac    2307
Val Gln Gln Gln Asn Asn Leu Leu Arg Ala Ile Glu Ala Gln Gln His
          755             760             765
tta ctt caa ctt aca gtc tgg gga atc aag caa gca cct aca aaa gca    2355
Leu Leu Gln Leu Thr Val Trp Gly Ile Lys Gln Ala Pro Thr Lys Ala
       770             775             780
aag aga aga gtc gtc caa aga gag aaa aga tag taa                    2391
Lys Arg Arg Val Val Gln Arg Glu Lys Arg
    785             790

<210>     9
<211>   792
<212> PRT
<213> Artificial Sequence

<220>
<223> Description of Artificial Sequence: Synthetic
polypeptide

<400>     9
Met Glu Glu Lys Ala Phe Ser Pro Glu Val Ile Pro Met Phe Thr Ala
1               5                   10                  15
Leu Ser Glu Gly Ala Thr Pro Gln Asp Leu Asn Thr Met Leu Asn Thr
            20                  25                  30
Val Gly Gly His Gln Ala Ala Met Gln Met Leu Lys Asp Thr Ile Asn
        35                  40                  45
Glu Glu Ala Ala Glu Trp Asp Arg Ile Tyr Lys Arg Trp Ile Ile Leu
    50                  55                  60
Gly Leu Asn Lys Ile Val Arg Met Tyr Ser Pro Val Ser Ile Leu Asp
65                  70                  75                  80
Ile Arg Gln Gly Pro Lys Glu Pro Phe Arg Asp Tyr Val Asp Arg Phe
                85                  90                  95
Ala Arg Asn Cys Arg Ala Pro Arg Lys Lys Gly Cys Trp Lys Cys Gly
            100                 105                 110
Lys Glu Gly His Gln Met Lys Asp Cys Thr Glu Arg Gln Ala Asn Phe
        115                 120                 125
Leu Gly Lys Ile Trp Pro Ser Arg Trp Lys Pro Lys Met Ile Gly Gly
    130                 135                 140
Ile Gly Gly Phe Ile Lys Val Arg Gln Tyr Asp Gln Ile Leu Ile Glu
145                 150                 155                 160
Ile Cys Gly His Lys Ala Ile Gly Thr Val Leu Val Gly Pro Thr Pro
                165                 170                 175
Val Asn Ile Ile Gly Arg Asn Leu Leu Thr Gln Ile Gly Cys Thr Leu
            180                 185                 190
Asn Phe Pro Ile Ser Pro Ile Glu Thr Val Pro Val Lys Leu Lys Pro
        195                 200                 205
Gly Met Asp Gly Pro Lys Val Lys Gln Trp Pro Leu Thr Glu Glu Lys
    210                 215                 220
Ile Lys Ala Leu Val Glu Ile Cys Thr Glu Met Glu Lys Glu Gly Lys
225                 230                 235                 240
Ile Ser Lys Ile Gly Pro Glu Asn Pro Tyr Asn Thr Pro Val Phe Ala
                245                 250                 255
Ile Lys Lys Lys Asp Ser Thr Lys Trp Arg Lys Leu Val Asp Phe Arg
            260                 265                 270
Glu Leu Asn Lys Arg Thr Gln Asp Phe Trp Glu Val Gln Leu Gly Ile
        275                 280                 285
Pro His Pro Ala Gly Leu Lys Lys Lys Lys Ser Val Thr Val Leu Asp
    290                 295                 300
Val Gly Asp Ala Tyr Phe Ser Val Pro Leu Asp Glu Gly Phe Arg Lys
305                 310                 315                 320
Tyr Thr Ala Phe Thr Ile Pro Ser Ile Asn Asn Glu Thr Pro Gly Ile
                325                 330                 335
```

-continued

SEQUENCE LISTING

```
Arg Tyr Gln Tyr Asn Val Leu Pro Gln Gly Trp Lys Gly Ser Pro Ala
        340                 345                 350
Ile Phe Gln Ser Ser Met Thr Lys Ile Leu Glu Pro Phe Arg Ala Gln
    355                 360                 365
Asn Pro Glu Ile Val Ile Tyr Gln Tyr Met Asp Asp Leu Tyr Val Gly
  370                 375                 380
Ser Asp Leu Glu Ile Gly Gln His Arg Met Glu Asn Arg Trp Gln Val
385                 390                 395                 400
Met Ile Val Trp Gln Val Asp Arg Met Arg Ile Arg Thr Trp Lys Ser
            405                 410                 415
Leu Val Lys His His Leu Thr Glu Glu Ala Glu Leu Glu Leu Ala Glu
        420                 425                 430
Asn Arg Glu Ile Leu Lys Asp Pro Val His Gly Val Tyr Tyr Asp Pro
    435                 440                 445
Ser Lys Asp Leu Ile Ala Glu Ile Gln Tyr Trp Gln Ala Thr Trp Ile
   450                 455                 460
Pro Glu Trp Glu Phe Val Asn Thr Pro Pro Leu Val Lys Leu Trp Tyr
465                 470                 475                 480
Gln Leu Glu Lys Asn Val Thr Glu Asn Phe Asn Met Trp Lys Asn Asp
          485                 490                 495
Met Val Asp Gln Met His Glu Asp Ile Ile Ser Leu Trp Asp Gln Ser
        500                 505                 510
Leu Lys Pro Cys Val Lys Leu Thr Pro Trp Val Pro Ala His Lys Gly
    515                 520                 525
Ile Gly Gly Asn Glu Gln Val Asp Lys Leu Val Ser Gln Gly Ile Arg
   530                 535                 540
Lys Val Leu Phe Leu Asp Gly Ile Asp Lys Ala Gln Ala Lys Glu Ile
545                 550                 555                 560
Val Ala Ser Cys Asp Lys Cys Gln Leu Lys Gly Glu Ala Met His Gly
            565                 570                 575
Gln Val Asp Cys Ser Pro Gly Ile Trp Gln Leu Asp Cys Thr His Leu
        580                 585                 590
Glu Gly Lys Val Ile Leu Val Ala Val His Val Ala Ser Gly Tyr Ile
    595                 600                 605
Glu Ala Glu Val Ile Pro Ala Glu Thr Gly Gln Glu Thr Ala Tyr Phe
  610                 615                 620
Leu Leu Lys Leu Ala Met Asn Lys Glu Leu Lys Lys Ile Ile Gly Gln
625                 630                 635                 640
Val Arg Asp Gln Ala Glu His Leu Lys Thr Ala Val Gln Met Ala Val
            645                 650                 655
Phe Ile His Asn Phe Lys Arg Lys Gly Gly Ile Gly Gly Tyr Ser Ala
            660                 665                 670
Gly Glu Arg Ile Trp Lys Gly Pro Ala Lys Leu Leu Trp Lys Gly Glu
    675                 680                 685
Gly Ala Val Val Ile Gln Asp Asn Ser Asp Ile Lys Val Val Pro Arg
  690                 695                 700
Arg Lys Ala Lys Ile Ile Arg Asp Tyr Gly Lys Gln Met Ala Gly Ala
705                 710                 715                 720
Asp Cys Val Phe Leu Gly Ala Ala Gly Ser Thr Met Gly Ala Ala Ser
            725                 730                 735
Met Thr Leu Thr Val Gln Ala Arg Gln Leu Leu Ser Gly Ile Val Gln
        740                 745                 750
Gln Gln Asn Asn Leu Leu Arg Ala Ile Glu Ala Gln Gln His Leu Leu
    755                 760                 765
Gln Leu Thr Val Trp Gly Ile Lys Gln Ala Pro Thr Lys Ala Lys Arg
  770                 775                 780
Arg Val Val Gln Arg Glu Lys Arg
785                 790
```

<210> 10
<211> 15402
<212> DNA
<213> Artificial Sequence

<220>
<223> Description of Artificial Sequence: Synthetic polynucleotide

<400> 10

```
accaaacaag agaaaaaaca tgtatgggat atgtaatgaa gttatacagg attttagggt     60
caaagtatcc accctgagga gcaggttcca gacccttttgc tttgctgcca aagttcacgc    120
ggccgcagat cttcacgatg gccgggttgt tgagcacctt cgatacattt agctctagga    180
ggagcgaaag tattaataag tcgggaggag gtgctgttat ccccggccag aggagcacag    240
tctcagtgtt cgtactaggc ccaagtgtga ctgatgatgc agacaagtta ttcattgcaa    300
ctaccttcct agctcactca ttggacacag ataagcagca ctctcagaga ggggggttcc    360
tcgtctctct gcttgccatg gcttacagta gtccagaatt gtacttgaca acaaacggag    420
taaacgccga tgtcaaatat gtgatctaca acatagagaa agaccctaag aggacgaaga    480
```

-continued

SEQUENCE LISTING

```
cagacggatt cattgtgaag acgagagata tggaatatga gaggaccaca gaatggctgt    540
ttggacctat ggtcaacaag agcccactct tccagggtca acgggatgct gcagaccctg    600
acacactcct tcaaatctat gggtatcctg catgcctagg agcaataatt gtccaagtct    660
ggattgtgct ggtgaaggcc atcacaagca gcgccggctt aaggaaaggg ttcttcaaca    720
ggttagaggc gttcagacaa gacggcaccg tgaaaggtgc cttagttttc actggggaga    780
cagttgaggg gataggctcg gttatgagat ctcagcaaag ccttgtatct ctcatggttg    840
agacccttgt gactatgaat actgcaagat ctgatctcac cacattagag aagaacatcc    900
agatcgttgg gaactacatc cgagatgcag ggctggcttc cttcatgaac actattaaat    960
atggggtgga aacaaagatg gcagctctaa cgttgtcaaa cctgaggccc gatattaata   1020
agcttagaag cctcatagac acctacctgt caaaaggccc cagagctccc tttatctgta   1080
tcctcaagga ccctgttcat ggtgaatttg ctccaggcaa ttatcctgca ctatggagtt   1140
acgccatggg agtcgccgtc gtacagaaca aggcaatgca gcagtacgtc acagggagga   1200
cataccttga tatggaaatg ttcttactag gacaagccgt ggcaaaggat gctgaatcga   1260
agatcagcag tgccttggaa gatgagttag gagtgacgga tacagccaag ggaggctca    1320
gacatcatct ggcaaacttg tccggtgggg atggtgctta ccacaaacca acaggcggtg   1380
gtgcaattga ggtagctcta gacaatgccg acatcgacct agaaacaaaa gcccatgcgg   1440
accaggacgc tagggggttgg ggtggagata gtggtgaaag atgggcacgt caggtgagtg   1500
gtggccactt tgtcacacta catggggctg aacggttaga ggaggaaacc aatgatgagg   1560
atgtatcaga catagagaga agaatagcca tgagactcgc agagagacgg caagaggatt   1620
ctgcaaccca tggagatgaa ggccgcaata acggtgtcga tcatgacgaa gatgacgatg   1680
ccgcagcagt agctgggata ggaggaatct aggatcatac gaggcttcaa ggtacttgat   1740
ccgtagtaag aaaaacttag ggtgaaagtt catccaccga tcggctcagg caaggccaca   1800
cccaacccca ccgaccacac ccagcagtcg agacagccac ggcttcggct acacttaccg   1860
catggatcaa gatgccttca ttcttaaaga agattctgaa gttgagaggg aggcgccagg   1920
aggacgagag tcgctctcgg atgttatcgg attcctcgat gctgtcctgt cgagtgaacc   1980
aactgacatc ggaggggaca gaagctggct ccacaacacc atcaacactc cccaaggacc   2040
aggctctgct catagagcca aaagtgaggg cgaaggagaa gtctcaacac cgtcgaccca   2100
agataatcga tcaggtgagg agagtagagt ctctgggaga acaagcaagc cagaggcaga   2160
agcacatgct ggaaaccttg ataaacaaaa tatacaccgg gcctttgggg gaagaactgg   2220
tacaaactct gtatctcagg atctgggcga tggaggagac tccggaatcc ttgaaaatcc   2280
tccaaatgag agaggatatc cgagatcagg tattgaagat gaaaacagag agatggctgc   2340
gcaccctgat aagaggggag aagaccaagc tgaaggactt ccagaagagg tacgaggaag   2400
tacatcccta cctgatgaag gagaaggtgg agcaagtaat aatggaagaa gcatggagcc   2460
tggcagctca catagtgcaa gagtaactgg ggtcctggtg attcctagcc ccgaacttga   2520
agaggctgtg ctacggagga acaaaagaag acctaccaac agtgggtcca aacctcttac   2580
tccagcaacc gtgcctggca cccggtcccc accgctgaat cgttacaaca gcacagggtc   2640
accaccagga aaacccccat ctacacagga tgagcacatc aactctgggg acacccccgc   2700
cgtcagggtc aaagaccgga aaccaccaat agggacccgc tctgtctcag attgtccagc   2760
caacggccgc ccaatccacc cgggtctaga gaccgactca acaaaaaagg gcataggaga   2820
gaacacatca tctatgaaag agatggctac attgttgacg agtcttggtg taatccagtc   2880
tgctcaagaa ttcgaatcat cccgagacgc gagttatgtg tttgcaagac gtgccctaaa   2940
gtctgcaaac tatgcagaga tgacattcaa tgtatgcggc ctgatccttt ctgccgagaa   3000
atcttccgct cgtaaggtag atgagaacaa acaactgctc aaacagatcc aagagagcgt   3060
ggaatcattc cgggatattt acaagagatt ctctgagtat cagaaagaac agaactcatt   3120
gctgatgtcc aacctatcta cacttcatat catcacagat agaggtggca agactgacaa   3180
cacagactcc cttacaaggt ccccctccgt ttttgcaaaa tcaaaagaga acaagactaa   3240
ggctaccagg tttgacccat ctatggagac cctagaagat atgaagtaca aaccggacct   3300
aatccgagag gatgaattta gagatgagat ccgcaacccg gtgtaccaag agagggacac   3360
agaacccagg gcctcaaacg catcacgtct cctcccctcc aaagagaagc ccacaatgca   3420
ctctctcagg ctcgtcatag agagcagtcc cctaagcaga gctgagaaag tagcatatgt   3480
gaaatcatta tccaagtgca agacagacca agaggttaag gcagtcatgg aactcgtaga   3540
agaggacata gagtcactga ccaactagat cccgggtgag gcatcctacc atcctcagtc   3600
atagagagat ccaatctacc atcagcatca gccagtaaag attaagaaaa acttagggtg   3660
aaagaaattt cacctaacac ggcgcaatgg cagatatcta tagattccct aagttctcat   3720
atgaggataa cggtactgtg gagcccctgc ctctgagaac tggtccggat aagaaagcca   3780
tcccccacat caggattgtc aaggtaggag accctcctaa acatggagtg agatacctag   3840
atttattgct cttgggtttc tttgagacac cgaaacaaac aaccaatcta gggagcgtat   3900
ctgacttgac agagccgacc agctactcaa tatgcggctc cgggtcgtta cccataggtg   3960
tggccaaata ctacgggact gatcaggaac tcttaaaggc ctgcaccgat ctcagaatta   4020
cggtgaggag gactgttcga gcaggagaga tgatcgtata catggtggat tcgattggtg   4080
ctccactcct accatggtca ggcaggctga gacagggaat gatatttaat gcaaacaagg   4140
tcgcactagc tccccaatgc ctccctgtgg acaaggacat aagactcaga gtggtgtttg   4200
tcaatgggac atctctaggg gcaatcacca tagccaagat cccaaagacc cttgcagacc   4260
ttgcattgcc caactctata tctgttaatt tactggtgac actcaagacc gggatctcca   4320
cagaacaaaa gggggtactc ccagtacttg atgatcaagg ggagaaaaag ctcaatttta   4380
tggtgcacct cgggttgatc aggagaaagg tcgggaagat atactctgtt gagtactgca   4440
agagcaagat tgagagaatg cggctgattt tctcacttgg gttaatcggc ggtataagct   4500
tccatgttca ggttaatggg acactatcta agacattcat gagtcagctc gcatggaaga   4560
gggcagtctg cttcccatta atggatgtga atccccatat gaacatggtg atttgggcgg   4620
catctgtaga aatcacaggc gtcgatgcgg tgttccaacc ggccatccct cgtgatttcc   4680
gctactaccc taatgttgtg gctaagaaca tcggaaggat cagaaagctg taaatgtgca   4740
cccatcagag acctgcgaca atgccccaag cagacaccac ctggcagtcg gagccaccgg   4800
gtcactcctt gtcttaaata agaaaaactt agggataaag tcccttgtga gtgcttggtt   4860
gcaaaactct ccccttggga aacatgacag catatatcca gagatcacag tgcatctcaa   4920
catcactact ggttgttctc accacattgg tctcgtgtca gattcccagg gataggctct   4980
ctaacatagg ggtcatagtc gatgaaggga aatcactgaa gatagctgga tcccacgaat   5040
cgaggtacat agtactgagt ctagttccgg gggtagactt tgagaatggg tgcggaacag   5100
```

-continued

SEQUENCE LISTING

```
cccaggttat ccagtacaag agcctactga acaggctgtt aatcccattg agggatgcct   5160
tagatcttca ggaggctctg ataactgtca ccaatgatac gacacaaaat gccggtgctc   5220
cccagtcgag attcttcggt gctgtgattg gtactatcgc acttggagtg gcgacatcag   5280
cacaaatcac cgcagggatt gcactagccg aagcgaggga ggccaaaaga gacatagcgc   5340
tcatcaaaga atcgatgaca aaaacacaca agtctataga actgctgcaa aacgctgtgg   5400
gggaacaaat tcttgctcta aagacactcc aggatttcgt gaatgatgag atcaaacccg   5460
caataagcga attaggctgt gagactgctg ccttaagact gggtataaaa ttgacacagc   5520
attactccga gctgttaact gcgttcggct cgaatttcgg aaccatcgga gagaagagcc   5580
tcacgctgca ggcgctgtct tcactttact ctgctaacat tactgagatt atgaccacaa   5640
tcaggacagg gcagtctaac atctatgatg tcatttatac agaacagatc aaaggaacgg   5700
tgatagatgt ggatctagag agatacatgg tcaccctgtc tgtgaagatc cctattcttt   5760
ctgaagtccc aggtgtgctc atacacaagg catcatctat ttcttacaac atagacgggg   5820
aggaatggta tgtgactgtc cccagccata tactcagtcg tgcttctttc ttagggggtg   5880
cagacataac cgattgtgtt gagtccagat tgacctatat atgccccagg gatcccgcac   5940
aactgatacc tgacagccag caaaagtgta tcctggggga cacaacaagg tgtcctgtca   6000
caaaagttgt ggacagcctt atccccaagt ttgcttttgt gaatgggggc gttgttgcta   6060
actgcatagc atccacatgt acctgcggga caggccgaag accaatcagt caggatcgct   6120
ctaaaggtgt agtattccta acccatgaca actgtggtct tataggtgtc aatggggtag   6180
aattgtatgc taaccggaga gggcacgatg ccacttgggg ggtccagaac ttgacagtcg   6240
gtcctgcaat tgctatcaga cccgttgata tttctctcaa ccttgctgat gctacgaatt   6300
tcttgcaaga ctctaaggct gagcttgaga aagcacggaa aatcctctcg gaggtaggta   6360
gatggtacaa ctcaagagag actgtgatta cgatcatagt agttatggtc gtaatattgg   6420
tggtcattat agtgatcatc atcgtgcttt atagactcag aaggtcaatg ctaatgggta   6480
atccagatga ccgtataccg agggacacat acacattaga gccgaagatc agacatatgt   6540
acacaaacgg tgggtttgat gcaatggctg agaaaagatg atcacgacca ttatcagatg   6600
tcttgtaaag caggcatagt atccgttgag atctgtatat aataagaaaa acttagggtg   6660
aaagtgaggt cgcgcggtac tttagctttc acctcaaaca agcacagatc atggatggtg   6720
atagggggcaa acgtgactcg tactggtcta cttctcctag tggtagcacc acaaaaccag   6780
catcaggttg ggagaggtca agtaaagccg acacatggtt gctgattctc tcattcaccc   6840
agtgggcttt gtcaattgcc acagtgatca tctgtatcat aatttctgct agacaagggt   6900
atagtatgaa agagtactca atgactgtag aggcattgaa catgagcagc agggaggtga   6960
aagagtcact taccagtcta ataaggcaag aggttatagc aagggctgtc aacattcaga   7020
gctctgtgca aaccggaatc ccagtcttgt tgaacaaaaa cagcagggat gtcatccaga   7080
tgattgataa gtcgtgcagc agacaagagc tcactcagca ctgtgagagt acgatcgcag   7140
tccaccatgc cgatggaatt gccccacttg agccacatag tttctggaga tgccctgtcg   7200
gagaaccgta tcttagctca gatcctgaaa tctcattgct gcctggtccg agcttgttat   7260
ctggttctac aacgatctct ggatgtgtta ggctcccttc actctcaatt ggcgaggcaa   7320
tctatgccta ttcatcaaat ctcattacac aaggttgtgc tgacataggg aaatcatatc   7380
aggtcctgca gctagggtac atatcactca attcagatat gttccctgat cttaaccccg   7440
tagtgtccca cacttatgac atcaacgaca atcggaaatc atgctctgtg gtggcaaccg   7500
ggactagggg ttatcagctt tgctccatgc cgactgtaga cgaaagaacc gactactcta   7560
gtgatggtat tgaggatctg gtccttgatg tcctggatct caaagggaga actaagtctc   7620
accggtatcg caacagcgag gtagatcttg atcacccgtt ctctgcacta taccccagtg   7680
taggcaacgg cattgcaaca gaaggctcat tgatatttct tgggtatggt ggactaacca   7740
cccctctgca gggtgataca aaatgtagga cccaaggatg ccaacaggtg tcgcaagaca   7800
catgcaatga ggctctgaaa attacatggc taggagggaa acaggtggtc agcgtgatca   7860
tccaggtcaa tgactatctc tcagagaggc caaagataag agtcacaacc attccaatca   7920
ctcaaaacta tctcggggcg gaaggtagat tattaaaatt gggtgatcgg gtgtacatct   7980
atacaagatc atcaggctgg cactctcaac tgcagatagg agtacttgat gtcagccacc   8040
ctttgactat caactggaca cctcatgaag ccttgtctag accaggaaat aaagagtgca   8100
attggtacaa taagtgtccg aaggaatgca tatcaggcgt atacactgat gcttatccat   8160
tgtcccctga tgcagctaac gtcgctaccg tcacgctata tgccaataca tcgcgtgtca   8220
acccaacaat catgtattct aacactacta acattataaa tatgttaagg ataaaggatg   8280
ttcaattaga ggctgcatat accacgacat cgtgtatcac gcattttggt aaaggctact   8340
gctttcacat catcgagatc aatcagaaga gcctgaatac cttacagccg atgctcttta   8400
agactagcat ccctaaatta tgcaaggccg agtcttaaat ttaactgact agcaggcttg   8460
tcggccttgc tgacactaga gtcatctccg aacatccaca atatctctca gtctcttacg   8520
tctctcacag tattaagaaa aacccagggt gaatgggaag cttgccatag gtcatggatg   8580
ggcaggagtc ctcccaaaac ccttctgaca tactctatcc agaatgccac ctgaactctc   8640
ccatagtcag gggaagagta gcacagttgc acgtcttgtt agatgtgaac cagccctaca   8700
gactgaagga cgacagcata ataaatatta caaagcacaa aattaggaac ggaggattgt   8760
ccccccgtca aattaagatc aggtctctgg gtaaggctct tcaacgcaca ataaaggatt   8820
tagaccgata cacgtttgaa ccgtacccaa cctactctca ggaattactt aggcttgata   8880
taccagagat atgtgacaaa atccgatccg tcttcgcggt ctcggatcgg ctgaccaggg   8940
agttatctag tgggttccag gatctttggt tgaatatctt caagcaacta ggcaatatag   9000
aaggaagaga ggggtacgat ccgttgcagg atatcggcac catcccggag ataactgata   9060
agtacagcag gaatagatgg tataggccat tcctaacttg gttcagcatc aaatatgaca   9120
tgcggtggat gcagaagacc agaccggggg gacccctcga tacctctaat tcacataacc   9180
tcctagaatg caaatcatac actctagtaa catacggaga tcttgtcatg atactgaaca   9240
agttgacatt gacagggtat atcctaaccc ctgagctggt cttgatgtat tgtgatgttg   9300
tagaaggaag gtggaatatg tctgctgcag ggcatctaga taagaagtcc attgggataa   9360
caagcaaagg tgaggaatta tgggaactag tggattccct cttctcaagt cttggagagg   9420
aaatatacaa tgtcatcgca ctattggagc ccctatcact tgctctcata caactaaatg   9480
atcctgttat acctctacgt ggggcattta tgaggcatgt gttgacagag ctacagactg   9540
ttttaacaag tagagacgtg tacacagatg ctgaagcaga cactattgtg gagtcgttac   9600
tcgccatttt ccatggaacc tctattgatg agaaagcaga gatcttttcc ttctttagga   9660
catttggcca ccccagctta gaggctgtca ctgccgccga caaggtaagg gcccatatgt   9720
```

-continued

SEQUENCE LISTING

```
atgcacaaaa ggcaataaag cttaagaccc tatacgagtg tcatgcagtt ttttgcacta    9780
tcatcataaa tgggtataga gagaggcatg gcggacagtg gccccctgt gacttccctg    9840
atcacgtgtg tctagaacta aggaacgctc aagggtccaa tacggcaatc tcttatgaat    9900
gtgctgtaga caactataca agtttcatag gcttcaagtt tcggaagttt atagaaccac    9960
aactagatga agatctcaca atatatatga aagacaaagc actatccccc aggaaggagg   10020
catgggactc tgtatacccg gatagtaatc tgtactataa agccccagag tctgaagaga   10080
cccggcggct tattgaagtg ttcataaatg atgagaattt caacccagaa gaaattatca   10140
attatgtgga gtcaggagat tggttgaaag acgaggagtt caacatctcg tacagtctca   10200
aagagaaaga gatcaagcaa gagggtcgtc tattcgcaaa aatgacttat aagatgcgag   10260
ccgtacaggt gctggcagag acactactgg ctaaaggaat aggagagcta ttcagcgaaa   10320
atgggatggt taaaggagag atagacctac ttaaaagatt gactactctt tctgtctcag   10380
gcgtccccag gactgattca gtgtacaata actctaaatc atcagagaag agaaacgaag   10440
gcatggaaaa taagaactct gggggggtact gggacgaaaa gaagaggtcc agacatgaat   10500
tcaaggcaac agattcatca acagacggct atgaaacgtt aagttgcttc ctcacaacag   10560
acctcaagaa atactgctta aactggagat ttgagagtac tgcattgttt ggtcagagat   10620
gcaacgagat atttggcttc aagaccttct ttaactggat gcatccagtc cttgaaaggt   10680
gtacaatata tgttggagat ccttactgtc cagtcgccga ccggatgcat cgacaactcc   10740
aggatcatgc agactctggc attttcatac ataatcctag gggggggcata gaaggttact   10800
gccagaagct gtggacctta atctcaatca gtgcaatcca cctagcagct gtgagagtgg   10860
gtgtcagggt ctctgcaatg gttcagggtg acaatcaagc tatagccgtg acatcaagag   10920
tacctgtagc tcagacttac aagcagaaga aaaatcatgt ctatgaggag atcaccaaat   10980
atttcggtgc tctaagacac gtcatgtttg atgtagggca cgagctaaaa ttgaacgaga   11040
ccatcattag tagcaagatg tttgtctata gtaaaaggat atactatgat gggaagattt   11100
taccacagtg cctgaaagcc ttgaccaagt gtgtattctg gtccgagaca ctggtagatg   11160
aaaacagatc tgcttgttcg aacatctcaa catccatagc aaaagctatc gaaaatgggt   11220
attctcctat actaggctac tgcattgcgt tgtataagac ctgtcagcag gtgtgcatat   11280
cactagggat gactataaat ccaactatca gcccgaccgt aagagatcaa tactttaagg   11340
gtaagaattg gctgagatgt gcagtgttga ttccagcaaa tgttggagga ttcaactaca   11400
tgtctacatc tagatgcttt gttagaaata ttggagaccc cgcagtagca gccctagctg   11460
atctcaaaag attcatcaga gcggatctgt tagacaagca ggtattatac agggtcatga   11520
atcaagaacc cggtgactct agttttctag attgggcttc agaccctat tcgtgtaacc   11580
tcccgcattc tcagagtata actacgatta taaagaatat cactgctaga tctgtgctgc   11640
aggaatcccc gaatcctcta ctgtctggtc tcttcaccga gactagtgga gaagaggatc   11700
tcaacctggc ctcgttcctt atggaccgga aagtcatcct gccgagagtg gctcatgaga   11760
tcctgggtaa ttccttaact ggagttaggg aggcgattgc agggatgctt gatacgacca   11820
agtctctagt gagagccagc gttaggaaag gaggattatc atatgggata ttgaggaggc   11880
ttgtcaatta tgatctattg cagtacgaga cactgactag aactctcagg aaaccggtga   11940
aagacaacat cgaatatgag tatatgtgtt cagttgagct agctgtcggt ctaaggcaga   12000
aaatgtggat ccacctgact tacgggagac ccatacatgg gctagaaaca ccagaccctt   12060
tagagctctt gaggggaata tttatcgaag gttcagaggt gtgcaagctt tgcaggtctg   12120
aaggagcaga ccccatctat acatggttct atcttcctga caatatagac ctggacacgc   12180
ttacaaacgg atgtccggct ataagaatcc cctattttgg atcagccact gatgaaaggt   12240
cggaagccca actcgggtat gtaagaaatc taagcaaacc cgcaaaggcg gccatccgga   12300
tagctatggt gtatacgtgg gcctacggga ctgatgagat atcgtggatg gaagccgctc   12360
ttatagccca aacaagagct aatctgagct tagagaatct aaagctgctg actcctgttt   12420
caacctccac taatctatct cataggttga aagatacggc aacccagatg aagttctcta   12480
gtgcaacact agtccgtgca agtcggttca taacaatatc aaatgataac atggcactca   12540
aagaagcagg ggagtcgaag gatactaatc tcgtgtatca gcagattatg ctaactgggc   12600
taagcttgtt cgagttcaat atgagatata agaaaggttc cttagggaag ccactgatat   12660
tgcacttaca tcttaataac gggtgctgta taatggagtc cccacaggag gcgaatatcc   12720
ccccaaggtc cacattagat ttagagatta cacaagagaa caataaattg atctatgatc   12780
ctgatccact caaggatgtg gaccttgagc tatttagcaa ggtcagagat gttgtacaca   12840
cagttgacat gacttattgg tcagatgatg aagttatcag agcaaccagt atctgtactg   12900
caatgacgat agctgataca atgtctcaat tagatagaga caacttaaaa gagatgatcg   12960
cactagtaaa tgacgatgat gtcaacagct tgattactga gtttatggtg attgatgttc   13020
ctttattttg ctcaacgttc gggggtattc tagtcaatca gtttgcatac tcactctacg   13080
gcttaaacat cagaggaagg gaagaaatat ggggacatgt agtccggatt cttaaagata   13140
cctcccacgc agttttaaaa gtcttatcta atgctctatc tcatcccaaa atcttcaaac   13200
gattctggaa tgcaggtgtc gtggaacctg tgtatgggcc taacctctca aatcaggata   13260
agatactctt ggccctctct gtctgtgaat attctgtgga tctattcatg cacgattggc   13320
aagggggtgt accgcttgag atctttatct gtgacaatga cccagatgtg gccgacatga   13380
ggaggtcctc tttcttggca agacatcttg catacctatg cagcttggca gagatatcta   13440
gggatgggcc aagattagaa tcaatgaact ctctagagag gctcgagtca ctaaagagtt   13500
acctggaact cacatttctt gatgacccgg tactgaggta cagtcagttg actggcctag   13560
tcatcaaagt attcccatct actttgacct atatccggaa gtcatctata aaagtgttaa   13620
ggacaagagg tataggagtc cctgaagtct tagaagattg ggatcccgag gcagataatg   13680
cactgttaga tggtatcgcg gcagaaatac aacagaatat tccifiggga catcagacta   13740
gagccccttt ttgggggttg agagtatcca agtcacaggt actgcgtctc cgggggtaca   13800
aggagatcac aagaggtgag ataggcagat caggtgttgg tctgacgtta ccattcgatg   13860
gaagatatct atctcaccag ctgaggctct ttggcatcaa cagtactagc tgcttgaaag   13920
cacttgaact tacctaccta ttgagcccct tagttgacaa ggataaagat aggctatatt   13980
taggggaagg agctggggcc atgctttcct gttatgacgc tactcttggc ccatgcatca   14040
actattataa ctcaggggta tactcttgtg atgtcaatgg gcagagagag ttaaatatat   14100
atcctgctga ggtggcacta gtgggaaaga aattaaacaa tgttactagt ctgggtcaaa   14160
gagttaaagt gttattcaac gggaatcctg gctcgacatg gattgggaat gatgagtgtg   14220
aggctttgat ttggaatgaa ttacagaata gctcgatagg cctagtccac tgtgacatgg   14280
agggaggaga tcataaggat gatcaagttg tactgcatga gcattacagt gtaatccgga   14340
```

-continued

SEQUENCE LISTING

```
tcgcgtatct ggtgggggat cgagacgttg tgcttataag caagattgct cccaggctgg  14400
gcacggattg gaccaggcag ctcagcctat atctgagata ctgggacgag gttaacctaa  14460
tagtgcttaa aacatctaac cctgcttcca cagagatgta tctcctatcg aggcaccccca  14520
aatctgacat tatagaggac agcaagacag tgttagctag tctcctccct ttgtcaaaag  14580
aagatagcat caagatagaa aagtggatct taatagagaa ggcaaaggct cacgaatggg  14640
ttactcggga attgagagaa ggaagctctt catcagggat gcttagacct taccatcaag  14700
cactgcagac gtttggcttt gaaccaaact tgtataaatt gagcagagat ttcttgtcca  14760
ccatgaacat agctgataca cacaactgca tgatagcttt caacagggtt ttgaaggata  14820
caatcttcga atgggctaga ataactgagt cagataaaag gcttaaacta actggtaagt  14880
atgacctgta tcctgtgaga gattcaggca agttgaagac aatttctaga agacttgtgc  14940
tatcttggat atctttatct atgtccacaa gattggtaac tgggtcattc cctgaccaga  15000
agtttgaagc aagacttcaa ttgggaatag tttcattatc atcccgtgaa atcaggaacc  15060
tgagggttat cacaaaaact ttattagaca ggtttgagga tattatacat agtataacgt  15120
atagattcct caccaaagaa ataaagattt tgatgaagat tttaggggca gtcaagatgt  15180
tcggggccag gcaaaatgaa tacacgaccg tgattgatga tggatcacta ggtgatatcg  15240
agccatatga cagctcgtaa taattagtcc ctatcgtgca gaacgatcga agctccgcgg  15300
tacctggaag tcttggactt gtccatatga caatagtaag aaaaacttac aagaagacaa  15360
gaaaatttaa aaggatacat atctcttaaa ctcttgtctg gt                     15402

<210>    11
<211> 17706
<212> DNA
<213> Artificial Sequence

<220>
<223> Description of Artificial Sequence: Synthetic
polynucleotide

<400>    11
accaaacaag agaaaaaaca tgtatgggat atgtaatgaa gttatacagg attttagggt     60
caaagtatcc accctgagga gcaggttcca gaccctttgc tttgctgcca aagttcacgc    120
ggccgccaag gttcacttat gacagcatat atccagagat cacagtgcat ctcaacatca    180
ctactggttg ttctcaccac attggtctcg tgtcaggcta gcgcagagaa tttgtgggta    240
acagtctact atggagtccc tgtatggaag gatgcagaga caacattgtt ctgtgctagt    300
gacgcaaagg cttacgagac ggagaagcac aatgtgtggg caactcacgc atgtgtccca    360
accgatccaa atcctcaaga gattcatcta gagaatgtga ctgaagaatt caatatgtgg    420
aagaataata tggtagagca aatgcataca gatatcatta gtttatggga ccagtcactt    480
aaaccctgcg ttaaattgac gcctctatgt gtgacacttc aatgtactaa tgttacaaac    540
aacataacag atgatatgag aggagaactg aagaactgta gtttcaacat gacgacagag    600
ttgcgtgaca agaaacagaa agtgtattca ctattctatc ggttggatgt agtacagata    660
aatgagaatc aaggaaacag gtccaacaac tctaacaaag agtacagact tattaattgc    720
aataccagtg ctatcacgca agcctgccca aaggtttcat ttgaaccaat acctattcat    780
tattgtgcac ctgctggatt cgccatcctc aaatgtaaag acaagaagtt caatggaaca    840
ggaccctgcc catcagtttc aaccgttcag tgcacccacg gaatcaagcc tgtagttagt    900
actcaattat tgttaaatgg gagcttagct gaagaagaag ttatgattag atcagagaat    960
attaccaata atgcgaagaa catcttggtt caattcaata ctccagtcca gatcaattgc   1020
acaaggccta ataataatac cagaaagagt ataagaattg ggccaggaca ggcattctat   1080
gcaacaggag atataatcgg agacattcga caagcgcact gcactgtttc taaggccact   1140
tggaatgaaa cattgggtaa agttgtaaag caacttcgga agcatttcgg aaataacaca   1200
attattagat ttgcgaactc atctggaggg gatctggaag tgacaacaca ctctttcaat   1260
tgcggtggcg agttcttcta ttgtaataca agtggattat ttaactctac ttggatttca   1320
aatacctcag tccaaggatc taattcaaca gggtctaacg attctataac attaccttgc   1380
cgtataaagc aaattattaa tatgtggcaa agaatcgggc aagcgatgta tgctccacct   1440
attcaaggcg tgattcgttg cgtttcaaac ataacagggt tgatcctgac cagggatgga   1500
ggctctacca attccaccac cgagaccttc cgtcccggtg gcggagatat gcgggataac   1560
tggagatcag agctctataa gtataaggtt gtgaagattg aacctcttgg agttgcccct   1620
acaagagcaa agagaagggt ggttggccga gagaagagag cagttggcat cggtgctgtc   1680
tttctcggat ttcttggagc agctggatcc actatgggag cagcatcaat gacactaaca   1740
gtgcaggcta gaaatttgct tagcggaatc gttcagcagc agagcaattt actaagagca   1800
attgaagcac agcaacatct cttaaagttg acggtgtggg gcattaaaca actacaagcg   1860
agagtgcttg ccgtcgaaag atatttgcga gaccaacagc tattgggtat ttggggttgt   1920
tctgggaaat taatttgcac aacaaatgtt ccatggaact cctcctggag taataggaat   1980
ttaagtgaga tatgggacaa catgacatgg ttgcagtggg acaaggaaat ctcaaattat   2040
acacagataa tctatggatt attagaagag tctcagaatc agcaagagaa gaatgaacag   2100
gatttgcttg cattggataa gtgggcttct ctatggaact ggttcgatat tagtaattgg   2160
ctctggtata ttaagaactc aagagagact gtgattacga tcatagtagt tatggtcgta   2220
atattggtgg tcattatagt gatcatcatc gtgctttata gactcagaag gtcaatgcta   2280
atgggtaatc cagatgaccg tataccgagg gacacataca cattagagcc gaagatcaga   2340
catatgtaca caaacggtgg gtttgatgca atggctgaga aaagatgacc gtagtaagaa   2400
aaacttaggg tgaaagttca tcgcggccgc agatcttcac gatggccggg ttgttgagca   2460
ccttcgatac atttagctct aggaggagcg aaagtattaa taagtcggga ggaggtgctg   2520
ttatccccgg ccagaggagc acagtctcag tgttcgtact aggcccaagt gtgactgatg   2580
atgcagacaa gttattcatt gcaactacct tcctagctca ctcattggac acagataagc   2640
agcactctca gagagggggg ttcctcgtct ctctgcttgc catggcttac agtagtccag   2700
aattgtactt gacaacaaac ggagtaaacg ccgatgtcaa atatgtgatc tacaacatag   2760
agaaagaccc taagaggacg aagacagacg gattcattgt gaagacgaga gatatggaat   2820
atgagaggac cacagaatgg ctgtttggac ctatggtcaa caagagccca ctcttccagg   2880
```

-continued

SEQUENCE LISTING

```
gtcaacggga tgctgcagac cctgacacac tccttcaaat ctatgggtat cctgcatgcc   2940
taggagcaat aattgtccaa gtctggattg tgctggtgaa ggccatcaca agcagcgccg   3000
gcttaaggaa agggttcttc aacaggttag aggcgttcag acaagacggc accgtgaaag   3060
gtgccttagt tttcactggg gagacagttg aggggatagg ctcggttatg agatctcagc   3120
aaagccttgt atctctcatg gttgagaccc ttgtgactat gaatactgca agatctgatc   3180
tcaccacatt agagaagaac atccagatcg ttgggaacta catccgagat gcagggctgg   3240
cttccttcat gaacactatt aaatatgggg tggaaacaaa gatggcagct ctaacgttgt   3300
caaacctgag gcccgatatt aataagctta gaagcctcat agacacctac ctgtcaaaag   3360
gccccagagc tccctttatc tgtatcctca aggaccctgt tcatggtgaa tttgctccag   3420
gcaattatcc tgcactatgg agttacgcca tgggagtcgc cgtcgtacag aacaaggcaa   3480
tgcagcagta cgtcacaggg aggacatacc ttgatatgga aatgttctta ctaggacaag   3540
ccgtggcaaa ggatgctgaa tcgaagatca gcagtgcctt ggaagatgag ttaggagtga   3600
cggatacagc caaggggagg ctcagacatc atctggcaaa cttgtccggt ggggatggtg   3660
cttaccacaa accaacaggc ggtggtgcaa ttgaggtagc tctagacaat gccgacatcg   3720
acctagaaac aaaagcccat gcggaccagg acgctagggg ttggggtgga gatagtggtg   3780
aaagatgggc acgtcaggtg agtggtggcc actttgtcac actacatggg gctgaacggt   3840
tagaggagga aaccaatgat gaggatgtat cagacataga gagaagaata gccatgagac   3900
tcgcagagag acggcaagag gattctgcaa cccatggaga tgaaggccgc aataacggtg   3960
tcgatcatga cgaagatgac gatgccgcag cagtagctgg gataggagga atctaggatc   4020
atacgaggct tcaaggtact tgatccgtag taagaaaaac ttagggtgaa agttcatcca   4080
ccgatcggct caggcaaggc cacacccaac cccaccgacc acacccagca gtcgagacag   4140
ccacggcttc ggctacactt accgcatgga tcaagatgcc ttcattctta aagaagattc   4200
tgaagttgag agggaggcgc caggaggacg agagtcgctc tcggatgtta tcggattcct   4260
cgatgctgtc ctgtcgagtg aaccaactga catcggaggg gacagaagct ggctccacaa   4320
caccatcaac actccccaag gaccaggctc tgctcataga gccaaaagtg agggcgaagg   4380
agaagtctca acaccgtcga cccaagataa tcgatcaggt gaggagagta gagtctctgg   4440
gagaacaagc aagccagagg cagaagcaca tgctggaaac cttgataaac aaaatataca   4500
ccgggccttt gggggaagaa ctggtacaaa ctctgtatct caggatctgg gcgatggagg   4560
agactccgga atccttgaaa atcctccaaa tgagagagga tatccgagat caggtattga   4620
agatgaaaac agagagatgg ctgcgcaccc tgataagagg ggagaagacc aagctgaagg   4680
acttccagaa gaggtacgag gaagtacatc cctacctgat gaaggagaag gtggagcaag   4740
taataatgga agaagcatgg agcctggcag ctcacatagt gcaagagtaa ctggggtcct   4800
ggtgattcct agccccgaac ttgaagaggc tgtgctacgg aggaacaaaa gaagacctac   4860
caacagtggg tccaaacctc ttactccagc aaccgtgcct ggcacccggt ccccaccgct   4920
gaatcgttac aacagcacag ggtcaccacc aggaaaaccc ccatctacac aggatgagca   4980
catcaactct ggggacaccc ccgccgtcag ggtcaaagac cggaaaccac caatagggac   5040
ccgctctgtc tcagattgtc cagccaacgg ccgcccaatc cacccgggtc tagagaccga   5100
ctcaacaaaa aagggcatag gagagaacac atcatctatg aaagagatgg ctacattgtt   5160
gacgagtctt ggtgtaatcc agtctgctca agaattcgaa tcatcccgag acgcgagtta   5220
tgtgtttgca agacgtgccc taaagtctgc aaactatgca gagatgacat tcaatgtatg   5280
cggcctgatc ctttctgccg agaaatcttc cgctcgtaag gtagatgaga acaaacaact   5340
gctcaaacag atccaagaga gcgtggaatc attccgggat atttacaaga gattctctga   5400
gtatcagaaa gaacagaact cattgctgat gtccaaccta tctacacttc atatcatcac   5460
agatagaggt ggcaagactg acaacacaga ctcccttaca aggtccccct ccgtttttgc   5520
aaaatcaaaa gagaacaaga ctaaggctac caggtttgac ccatctatgg agaccctaga   5580
agatatgaag tacaaaccgg acctaatccg agaggatgaa tttagagatg agatccgcaa   5640
cccggtgtac caagagaggg acacagaacc cagggcctca aacgcatcac gtctcctccc   5700
ctccaaagag aagcccacaa tgcactctct caggctcgtc atagagagca gtcccctaag   5760
cagagctgag aaagtagcat atgtgaaatc attatccaag tgcaagacag accaagaggt   5820
taaggcagtc atggaactcg tagaagagga catagagtca ctgaccaact agatcccggg   5880
tgaggcatcc taccatcctc agtcatagag agatccaatc taccatcagc atcagccagt   5940
aaagattaag aaaaacttag ggtgaaagaa atttcaccta acacggcgca atggcagata   6000
tctatagatt ccctaagttc tcatatgagg ataacggtac tgtggagccc ctgcctctga   6060
gaactggtcc ggataagaaa gccatccccc acatcaggat tgtcaaggta ggagaccctc   6120
ctaaacatgg agtgagatac ctagatttat tgctcttggg tttctttgag acaccgaaac   6180
aaacaaccaa tctagggagc gtatctgact tgacagagcc gaccagctac tcaatatgcg   6240
gctccgggtc gttacccata ggtgtggcca aatactacgg gactgatcag gaactcttaa   6300
aggcctgcac cgatctcaga attacggtga ggaggactgt tcgagcagga gagatgatcg   6360
tatacatggt ggattcgatt ggtgctccac tcctaccatg gtcaggcagg ctgagacagg   6420
gaatgatatt taatgcaaac aaggtcgcac tagctcccca atgcctccct gtggacaagg   6480
acataagact cagagtggtg tttgtcaatg ggacatctct aggggcaatc accatagcca   6540
agatcccaaa gacccttgca gaccttgcat tgcccaactc tatatctgtt aatttactgg   6600
tgacactcaa gaccgggatc tccacagaac aaaagggggt actcccagta cttgatgatc   6660
aaggggagaa aaagctcaat tttatggtgc acctcgggtt gatcaggaga aaggtcggga   6720
agatatactc tgttgagtac tgcaagagca agattgagag aatgcggctg attttctcac   6780
ttgggttaat cggcggtata agcttccatg ttcaggttaa tgggacacta tctaagacat   6840
tcatgagtca gctcgcatgg aagagggcag tctgcttccc attaatggat gtgaatcccc   6900
atatgaacat ggtgatttgg gcggcatctg tagaaatcac aggcgtcgat gcggtgttcc   6960
aaccggccat ccctcgtgat ttccgctact accctaatgt tgtggctaag aacatcggaa   7020
ggatcagaaa gctgtaaatg tgcacccatc agagacctgc gacaatgccc caagcagaca   7080
ccacctggca gtcggagcca ccgggtcact ccttgtctta aataagaaaa acttagggat   7140
aaagtccctt gtgagtgctt ggttgcaaaa ctctcccctt gggaaacatg acagcatata   7200
tccagagatc acagtgcatc tcaacatcac tactggttgt tctcaccaca ttggtctcgt   7260
gtcagattcc cagggatagg ctctctaaca taggggtcat agtcgatgaa gggaaatcac   7320
tgaagatagc tggatcccac gaatcgaggt acatagtact gagtctagtt ccgggggtag   7380
actttgagaa tgggtgcgga acagcccagg ttatccagta caagagccta ctgaacaggc   7440
tgttaatccc attgagggat gccttagatc ttcaggaggc tctgataact gtcaccaatg   7500
```

-continued

SEQUENCE LISTING atacgacaca aaatgccggt gctccccagt cgagattctt cggtgctgtg attggtacta 7560
tcgcacttgg agtggcgaca tcagcacaaa tcaccgcagg gattgcacta gccgaagcga 7620
gggaggccaa aagagacata gcgctcatca aagaatcgat gacaaaaaca cacaagtcta 7680
tagaactgct gcaaaacgct gtgggggaac aaattcttgc tctaaagaca ctccaggatt 7740
tcgtgaatga tgagatcaaa cccgcaataa gcgaattagg ctgtgagact gctgccttaa 7800
gactgggtat aaaattgaca cagcattact ccgagctgtt aactgcgttc ggctcgaatt 7860
tcggaaccat cggagagaag agcctcacgc tgcaggcgct gtcttcactt tactctgcta 7920
acattactga gattatgacc acaatcagga cagggcagtc taacatctat gatgtcattt 7980
atacagaaca gatcaaagga acggtgatag atgtggatct agagagatac atggtcaccc 8040
tgtctgtgaa gatccctatt ctttctgaag tcccaggtgt gctcatacac aaggcatcat 8100
ctatttctta caacatagac ggggaggaat ggtatgtgac tgtccccagc catatactca 8160
gtcgtgcttc tttcttaggg ggtgcagaca taaccgattg tgttgagtcc agattgacct 8220
atatatgccc cagggatccc gcacaactga tacctgacag ccagcaaaag tgtatcctgg 8280
gggacacaac aaggtgtcct gtcacaaaag ttgtggacag ccttatcccc aagtttgctt 8340
ttgtgaatgg gggcgttgtt gctaactgca tagcatccac atgtacctgc gggacaggcc 8400
gaagaccaat cagtcaggat cgctctaaag gtgtagtatt cctaacccat gacaactgtg 8460
gtcttatagg tgtcaatggg gtagaattgt atgctaaccg gagagggcac gatgccactt 8520
ggggggtcca gaacttgaca gtcggtcctg caattgctat cagacccgtt gatatttctc 8580
tcaaccttgc tgatgctacg aatttcttgc aagactctaa ggctgagctt gagaaagcac 8640
ggaaaatcct ctcggaggta ggtagatggt acaactcaag agagactgtg attacgatca 8700
tagtagttat ggtcgtaata ttggtggtca ttatagtgat catcatcgtg ctttatagac 8760
tcagaaggtc aatgctaatg ggtaatccag atgaccgtat accgagggac acatacacat 8820
tagagccgaa gatcagacat atgtacacaa acggtgggtt tgatgcaatg gctgagaaaa 8880
gatgatcacg accattatca gatgtcttgt aaagcaggca tagtatccgt tgagatctgt 8940
atataataag aaaaacttag ggtgaaagtg aggtcgcgcg gtactttagc tttcacctca 9000
aacaagcaca gatcatggat ggtgataggg gcaaacgtga ctcgtactgg tctacttctc 9060
ctagtggtag caccacaaaa ccagcatcag gttgggagag gtcaagtaaa gccgacacat 9120
ggttgctgat tctctcattc acccagtggg ctttgtcaat tgccacagtg atcatctgta 9180
tcataatttc tgctagacaa gggtatagta tgaaagagta ctcaatgact gtagaggcat 9240
tgaacatgag cagcagggag gtgaaagagt cacttaccag tctaataagg caagaggtta 9300
tagcaagggc tgtcaacatt cagagctctg tgcaaaccgg aatcccagtc ttgttgaaca 9360
aaaacagcag ggatgtcatc cagatgattg ataagtcgtg cagcagacaa gagctcactc 9420
agcactgtga gagtacgatc gcagtccacc atgccgatgg aattgcccca cttgagccac 9480
atagtttctg gagatgccct gtcggagaac cgtatcttag ctcagatcct gaaatctcat 9540
tgctgcctgg tccgagcttg ttatctggtt ctacaacgat ctctggatgt gttaggctcc 9600
cttcactctc aattggcgag gcaatctatg cctattcatc aaatctcatt acacaaggtt 9660
gtgctgacat agggaaatca tatcaggtcc tgcagctagg gtacatatca ctcaattcag 9720
atatgttccc tgatcttaac cccgtagtgt cccacactta tgacatcaac gacaatcgga 9780
aatcatgctc tgtggtggca accgggacta ggggttatca gctttgctcc atgccgactg 9840
tagacgaaag aaccgactac tctagtgatg gtattgagga tctggtcctt gatgtcctgg 9900
atctcaaagg gagaactaag tctcaccggt atcgcaacag cgaggtagat cttgatcacc 9960
cgttctctgc actatacccc agtgtaggca acggcattgc aacagaaggc tcattgatat 10020
ttcttgggta tggtggacta accacccctc tgcagggtga tacaaaatgt aggacccaag 10080
gatgccaaca ggtgtcgcaa gacacatgca atgaggctct gaaaattaca tggctaggag 10140
ggaaacaggt ggtcagcgtg atcatccagg tcaatgacta tctctcagag aggccaaaga 10200
taagagtcac aaccattcca atcactcaaa actatctcgg ggcggaaggt agattattaa 10260
aattgggtga tcgggtgtac atctatacaa gatcatcagg ctggcactct caactgcaga 10320
taggagtact tgatgtcagc caccctttga ctatcaactg gacacctcat gaagccttgt 10380
ctagaccagg aaataaagag tgcaattggt acaataagtg tccgaaggaa tgcatatcag 10440
gcgtatacac tgatgcttat ccattgtccc ctgatgcagc taacgtcgct accgtcacgc 10500
tatatgccaa tacatcgcgt gtcaacccaa caatcatgta ttctaacact actaacatta 10560
taaatatgtt aaggataaag gatgttcaat tagaggctgc atataccacg acatcgtgta 10620
tcacgcattt tggtaaaggc tactgctttc acatcatcga gatcaatcag aagagcctga 10680
ataccttaca gccgatgctc tttaagacta gcatccctaa attatgcaag gccgagtctt 10740
aaatttaact gactagcagg cttgtcggcc ttgctgacac tagagtcatc tccgaacatc 10800
cacaatatct ctcagtctct tacgtctctc acagtattaa gaaaaaccca gggtgaatgg 10860
gaagcttgcc ataggtcatg gatgggcagg agtcctccca aaacccttct gacatactct 10920
atccagaatg ccacctgaac tctcccatag tcagggggaa gatagcacag ttgcacgtct 10980
tgttagatgt gaaccagccc tacagactga aggacgacag cataataaat attacaaagc 11040
acaaaattag gaacggagga ttgtccccccc gtcaaattaa gatcaggtct ctgggtaagg 11100
ctcttcaacg cacaataaag gatttagacc gatacacgtt tgaaccgtac ccaacctact 11160
ctcaggaatt acttaggctt gatataccag agatatgtga caaaatccga tccgtcttcg 11220
cggtctcgga tcggctgacc agggagttat ctagtgggtt ccaggatctt tggttgaata 11280
tcttcaagca actaggcaat atagaaggaa gagaggggta cgatccgttg caggatatcg 11340
gcaccatccc ggagataact gataagtaca gcaggaatag atggtatagg ccattcctaa 11400
cttggttcag catcaaatat gacatgcggt ggatgcagaa gaccagaccg gggggacccc 11460
tcgatacctc taattcacat aacctcctag aatgcaaatc atacactcta gtaacatacg 11520
gagatcttgt catgatactg aacaagttga cattgacagg gtatatccta acccctgagc 11580
tggtcttgat gtattgtgat gttgtagaag gaaggtggaa tatgtctgct gcagggcatc 11640
tagataagaa gtccattggg ataacaagca aaggtgagga attatgggaa ctagtggatt 11700
ccctcttctc aagtcttgga gaggaaatat acaatgtcat cgcactattg gagcccctat 11760
cacttgctct catacaacta aatgatcctg ttatacctct acgtggggca tttatgaggc 11820
atgtgttgac agagctacag actgttttaa caagtagaga cgtgtacaca gatgctgaag 11880
cagacactat tgtggagtcg ttactcgcca ttttccatgg aacctctatt gatgagaaag 11940
cagagatctt ttccttcttt aggacatttg gccaccccag cttagaggct gtcactgccg 12000
ccgacaaggt aagggcccat atgtatgcac aaaaggcaat aaagcttaag accctatacg 12060
agtgtcatgc agttttttgc actatcatca taaatgggta tagagagagg catggcggac 12120

-continued

SEQUENCE LISTING

```
agtggccccc ctgtgacttc cctgatcacg tgtgtctaga actaaggaac gctcaagggt   12180
ccaatacggc aatctcttat gaatgtgctg tagacaacta tacaagtttc ataggcttca   12240
agtttcggaa gtttatagaa ccacaactag atgaagatct cacaatatat atgaaagaca   12300
aagcactatc ccccaggaag gaggcatggg actctgtata cccggatagt aatctgtact   12360
ataaagcccc agagtctgaa gagacccggc ggcttattga agtgttcata aatgatgaga   12420
atttcaaccc agaagaaatt atcaattatg tggagtcagg agattggttg aaagacgagg   12480
agttcaacat ctcgtacagt ctcaaagaga aagagatcaa gcaagagggt cgtctattcg   12540
caaaaatgac ttataagatg cgagccgtac aggtgctggc agagacacta ctggctaaag   12600
gaataggaga gctattcagc gaaaatggga tggttaaagg agagatagac ctacttaaaa   12660
gattgactac tctttctgtc tcaggcgtcc ccaggactga ttcagtgtac aataactcta   12720
aatcatcaga gaagagaaac gaaggcatgg aaaataagaa ctctgggggg tactgggacg   12780
aaaagaagag gtccagacat gaattcaagg caacagattc atcaacagac ggctatgaaa   12840
cgttaagttg cttcctcaca acagacctca agaaatactg cttaaactgg agatttgaga   12900
gtactgcatt gtttggtcag agatgcaacg agatatttgg cttcaagacc ttctttaact   12960
ggatgcatcc agtccttgaa aggtgtacaa tatatgttgg agatccttac tgtccagtcg   13020
ccgaccggat gcatcgacaa ctccaggatc atgcagactc tggcattttc atacataatc   13080
ctaggggggg catagaaggt tactgccaga agctgtggac cttaatctca atcagtgcaa   13140
tccacctagc agctgtgaga gtgggtgtca gggtctctgc aatggttcag ggtgacaatc   13200
aagctatagc cgtgacatca agagtacctg tagctcagac ttacaagcag aagaaaaatc   13260
atgtctatga ggagatcacc aaatatttcg gtgctctaag acacgtcatg tttgatgtag   13320
ggcacgagct aaaattgaac gagaccatca ttagtagcaa gatgtttgtc tatagtaaaa   13380
ggatatacta tgatgggaag attttaccac agtgcctgaa agccttgacc aagtgtgtat   13440
tctggtccga gacactggta gatgaaaaca gatctgcttg ttcgaacatc tcaacatcca   13500
tagcaaaagc tatcgaaaat gggtattctc ctatactagg ctactgcatt gcgttgtata   13560
agacctgtca gcaggtgtgc atatcactag ggatgactat aaatccaact atcagcccga   13620
ccgtaagaga tcaatacttt aagggtaaga attggctgag atgtgcagtg ttgattccag   13680
caaatgttgg aggattcaac tacatgtcta catctagatg ctttgttaga aatattggag   13740
accccgcagt agcagcccta gctgatctca aaagattcat cagagcggat ctgttagaca   13800
agcaggtatt atacagggtc atgaatcaag aacccggtga ctctagtttt ctagattggg   13860
cttcagaccc ttattcgtgt aacctcccgc attctcagag tataactacg attataaaga   13920
atatcactgc tagatctgtg ctgcaggaat ccccgaatcc tctactgtct ggtctcttca   13980
ccgagactag tggagaagag gatctcaacc tggcctcgtt ccttatggac cggaaagtca   14040
tcctgccgag agtggctcat gagatcctgg gtaattcctt aactggagtt agggaggcga   14100
ttgcagggat gcttgatacg accaagtctc tagtgagagc cagcgttagg aaaggaggat   14160
tatcatatgg gatattgagg aggcttgtca attatgatct attgcagtac gagacactga   14220
ctagaactct caggaaaccg gtgaaagaca acatcgaata tgagtatatg tgttcagttg   14280
agctagctgt cggtctaagg cagaaaatgt ggatccacct gacttacggg agacccatac   14340
atgggctaga aacaccagac cctttagagc tcttgagggg aatatttatc gaaggttcag   14400
aggtgtgcaa gctttgcagg tctgaaggag cagaccccat ctatacatgg ttctatcttc   14460
ctgacaatat agacctggac acgcttacaa acggatgtcc ggctataaga atcccctatt   14520
ttggatcagc cactgatgaa aggtcggaag cccaactcgg gtatgtaaga aatctaagca   14580
aacccgcaaa ggcggccatc cggatagcta tggtgtatac gtgggcctac gggactgatg   14640
agatatcgtg gatggaagcc gctcttatag cccaaacaag agctaatctg agcttagaga   14700
atctaaagct gctgactcct gtttcaacct ccactaatct atctcatagg ttgaaagata   14760
cggcaaccca gatgaagttc tctagtgcaa cactagtccg tgcaagtcgg ttcataacaa   14820
tatcaaatga taacatggca ctcaaagaag caggggagtc gaaggatact aatctcgtgt   14880
atcagcagat tatgctaact gggctaagct tgttcgagtt caatatgaga tataagaaag   14940
gttccttagg gaagccactg atattgcact tacatcttaa taacgggtgc tgtataatgg   15000
agtccccaca ggaggcgaat atcccccaa ggtccacatt agatttagag attacacaag   15060
agaacaataa attgatctat gatcctgatc cactcaagga tgtggacctt gagctattta   15120
gcaaggtcag agatgttgta cacacagttg acatgactta ttggtcagat gatgaagtta   15180
tcagagcaac cagtatctgt actgcaatga cgatagctga tacaatgtct caattagata   15240
gagacaactt aaaagagatg atcgcactag taaatgacga tgatgtcaac agcttgatta   15300
ctgagtttat ggtgattgat gttcctttat tttgctcaac gttcgggggt attctagtca   15360
atcagtttgc atactcactc tacggcttaa acatcagagg aagggaagaa atatggggac   15420
atgtagtccg gattcttaaa gatacctccc acgcagtttt aaaagtctta tctaatgctc   15480
tatctcatcc caaaatcttc aaacgattct ggaatgcagg tgtcgtggaa cctgtgtatg   15540
ggcctaacct ctcaaatcag gataagatac tcttggccct ctctgtctgt gaatattctg   15600
tggatctatt catgcacgat tggcaagggg gtgtaccgct tgagatcttt atctgtgaca   15660
atgacccaga tgtggccgac atgaggaggt cctctttctt ggcaagacat cttgcatacc   15720
tatgcagctt ggcagagata tctagggatg ggccaagatt agaatcaatg aactctctag   15780
agaggctcga gtcactaaag agttacctgg aactcacatt tcttgatgac ccggtactga   15840
ggtacagtca gttgactggc ctagtcatca aagtattccc atctactttg acctatatcc   15900
ggaagtcatc tataaaagtg ttaaggacaa gaggtatagg agtccctgaa gtcttagaag   15960
attgggatcc cgaggcagat aatgcactgt tagatggtat cgcggcagaa atacaacaga   16020
atattccttt gggacatcag actagagccc ctttttgggg gttgagagta tccaagtcac   16080
aggtactgcg tctccggggg tacaaggaga tcacaagagg tgagataggc agatcaggtg   16140
ttggtctgac gttaccattc gatggaagat atctatctca ccagctgagg ctctttggca   16200
tcaacagtac tagctgcttg aaagcacttg aacttaccta cctattgagc cccttagttg   16260
acaaggataa agataggcta tatttagggg aaggagctgg ggccatgctt tcctgttatg   16320
acgctactct tggcccatgc atcaactatt ataactcagg ggtatactct tgtgatgtca   16380
atgggcagag agagttaaat atatatcctg ctgaggtggc actagtggga aagaaattaa   16440
acaatgttac tagtctgggt caaagagtta aagtgttatt caacgggaat cctggctcga   16500
catggattgg gaatgatgag tgtgaggctt tgatttggaa tgaattacag aatagctcga   16560
taggcctagt ccactgtgac atggagggag gagatcataa ggatgatcaa gttgtactgc   16620
atgagcatta cagtgtaatc cggatcgcgt atctggtggg ggatcgagac gttgtgctta   16680
taagcaagat tgctcccagg ctgggcacgg attggaccag gcagctcagc ctatatctga   16740
```

-continued

SEQUENCE LISTING gatactggga cgaggttaac ctaatagtgc ttaaaacatc taaccctgct tccacagaga 16800
tgtatctcct atcgaggcac cccaaatctg acattataga ggacagcaag acagtgttag 16860
ctagtctcct ccctttgtca aaagaagata gcatcaagat agaaaagtgg atcttaatag 16920
agaaggcaaa ggctcacgaa tggggttactc gggaattgag agaaggaagc tcttcatcag 16980
ggatgcttag accttaccat caagcactgc agacgtttgg ctttgaacca aacttgtata 17040
aattgagcag agatttcttg tccaccatga acatagctga tacacacaac tgcatgatag 17100
ctttcaacag ggttttgaag gatacaatct tcgaatgggc tagaataact gagtcagata 17160
aaaggcttaa actaactggt aagtatgacc tgtatcctgt gagagattca ggcaagttga 17220
agacaatttc tagaagactt gtgctatctt ggatatcttt atctatgtcc acaagattgg 17280
taactgggtc attccctgac cagaagtttg aagcaagact tcaattggga atagtttcat 17340
tatcatcccg tgaaatcagg aacctgaggg ttatcacaaa aactttatta gacaggtttg 17400
aggatattat acatagtata acgtatagat tcctcaccaa agaaataaag attttgatga 17460
agattttagg ggcagtcaag atgttcgggg ccaggcaaaa tgaatacacg accgtgattg 17520
atgatggatc actaggtgat atcgagccat atgacagctc gtaataatta gtccctatcg 17580
tgcagaacga tcgaagctcc gcggtacctg gaagtcttgg acttgtccat atgacaatag 17640
taagaaaaac ttacaagaag acaagaaaat ttaaaaggat acatatctct taaactcttg 17700
tctggt 17706

<210> 12
<211> 17616
<212> DNA
<213> Artificial Sequence

<220>
<223> Description of Artificial Sequence: Synthetic
polynucleotide

<400> 12
accaaacaag agaaaaaaca tgtatgggat atgtaatgaa gttatacagg attttagggt 60
caaagtatcc accctgagga gcaggttcca gaccctttgc tttgctgcca aagttcacgc 120
ggccgccaag gttcacttat gaagtgcctt ttgtacttag ctttcttatt catcggggtg 180
aattgcaagg ctagcgcaga gaatttgtgg gtaacagtct actatggagt ccctgtatgg 240
aaggatgcag agacaacatt gttctgtgct agtgacgcaa aggcttacga gacggagaag 300
cacaatgtgt gggcaactca cgcatgtgtc ccaaccgatc caaatcctca agagattcat 360
ctagagaatg tgactgaaga attcaatatg tggaagaata atatggtaga gcaaatgcat 420
acagatatca ttagtttatg ggaccagtca cttaaaccct gcgttaaatt gacgcctcta 480
tgtgtgacac ttcaatgtac taatgttaca aacaacataa cagatgatat gagaggagaa 540
ctgaagaact gtagtttcaa catgacgaca gagttgcgtg acaagaaaca gaaagtgtat 600
tcactattct atcggttgga tgtagtacag ataaatgaga atcaaggaaa caggtccaac 660
aactctaaca aagagtacag acttattaat tgcaatacca gtgctatcac gcaagcctgc 720
ccaaaggttt catttgaacc aatacctatt cattattgtg cacctgctgg attcgccatc 780
ctcaaatgta aagacaagaa gttcaatgga acaggaccct gcccatcagt ttcaaccgtt 840
cagtgcaccc acggaatcaa gcctgtagtt agtactcaat tattgttaaa tgggagctta 900
gctgaagaag aagttatgat tagatcagag aatattacca ataatgcgaa gaacatcttg 960
gttcaattca atactccagt ccagatcaat tgcacaaggc ctaataataa taccagaaag 1020
agtataagaa ttgggccagg acaggcattc tatgcaacag gagatataat cggagacatt 1080
cgacaagcgc actgcactgt ttctaaggcc acttggaatg aaacattggg taaagttgta 1140
aagcaacttc ggaagcattt cggaaataac acaattatta gatttgcgaa ctcatctgga 1200
ggggatctgg aagtgacaac acactctttc aattgcggtg gcgagttctt ctattgtaat 1260
acaagtggat tatttaactc tacttggatt tcaaatacct cagtccaagg atctaattca 1320
acagggtcta acgattctat aacattacct tgccgtataa agcaaattat taatatgtgg 1380
caaagaatcg ggcaagcgat gtatgctcca cctattcaag gcgtgattcg ttgcgtttca 1440
aacataacag ggttgatcct gaccagggat ggaggctcta ccaattccac caccgagacc 1500
ttccgtcccg gtggcggaga tatgcgggat aactggagat cagagctcta taagtataag 1560
gttgtgaaga ttgaacctct tggagttgcc cctacaagag caaagagaag ggtggttggc 1620
cgagagaaga gagcagttgg catcggtgct gtctttctcg gatttcttgg agcagctgga 1680
tccactatgg gagcagcatc aatgacacta acagtgcagg ctagaaattt gcttagcgga 1740
atcgttcagc agcagagcaa tttactaaga gcaattgaag cacagcaaca tctcttaaag 1800
ttgacggtgt ggggcattaa acaactacaa gcgagagtgc ttgccgtcga aagatatttg 1860
cgagaccaac agctattggg tatttggggt tgttctggga aattaatttg cacaacaaat 1920
gttccatgga actcctcctg gagtaatagg aatttaagtg agatatggga caacatgaca 1980
tggttgcagt gggacaagga aatctcaaat tatacacaga taatctatgg attattagaa 2040
gagtctcaga atcagcaaga gaagaatgaa caggatttgc ttgcattgga taagtgggct 2100
tctctatgga actggttcga tattagtaat tggctctggt atattaagag ctctattgcc 2160
tcttttttct ttatcatagg gttaatcatt ggactattct tggttctccg agttggtatt 2220
tatctttgca ttaaattaaa gcacaccaag aaaagacaga tttatacaga catagagatg 2280
aaccgacttg gaaagtaacc gtagtaagaa aaacttaggg tgaaagttca tcgcggccgc 2340
agatcttcac gatggccggg ttgttgagca ccttcgatac atttagctct aggaggagcg 2400
aaagtattaa taagtcggga ggaggtgctg ttatccccgg ccagaggagc acagtctcag 2460
tgttcgtact aggcccaagt gtgactgatg atgcagacaa gttattcatt gcaactacct 2520
tcctagctca ctcattggac acagataagc agcactctca gagagggggg ttcctcgtct 2580
ctctgcttgc catggcttac agtagtccag aattgtactt gacaacaaac ggagtaaacg 2640
ccgatgtcaa atatgtgatc tacaacatag agaaagaccc taagaggacg aagacagacg 2700
gattcattgt gaagacgaga gatatggaat atgagaggac cacagaatgg ctgtttggac 2760
ctatggtcaa caagagccca ctcttccagg gtcaacggga tgctgcagac cctgacacac 2820
tccttcaaat ctatgggtat cctgcatgcc taggagcaat aattgtccaa gtctggattg 2880
tgctggtgaa ggccatcaca agcagcgccg gcttaaggaa agggttcttc aacaggttag 2940

-continued

SEQUENCE LISTING

```
aggcgttcag acaagacggc accgtgaaag gtgccttagt tttcactggg gagacagttg   3000
aggggatagg ctcggttatg agatctcagc aaagccttgt atctctcatg gttgagaccc   3060
ttgtgactat gaatactgca agatctgatc tcaccacatt agagaagaac atccagatcg   3120
ttgggaacta catccgagat gcagggctgg cttccttcat gaacactatt aaatatgggg   3180
tggaaacaaa gatggcagct ctaacgttgt caaacctgag gcccgatatt aataagctta   3240
gaagcctcat agacacctac ctgtcaaaag gccccagagc tccctttatc tgtatcctca   3300
aggaccctgt tcatggtgaa tttgctccag gcaattatcc tgcactatgg agttacgcca   3360
tgggagtcgc cgtcgtacag aacaaggcaa tgcagcagta cgtcacaggg aggacatacc   3420
ttgatatgga aatgttctta ctaggacaag ccgtggcaaa ggatgctgaa tcgaagatca   3480
gcagtgcctt ggaagatgag ttaggagtga cggatacagc caaggggagg ctcagacatc   3540
atctggcaaa cttgtccggt ggggatggtg cttaccacaa accaacaggc ggtggtgcaa   3600
ttgaggtagc tctagacaat gccgacatcg acctagaaac aaaagcccat gcggaccagg   3660
acgctagggg ttggggtgga gatagtggtg aaagatgggc acgtcaggtg agtggtggcc   3720
actttgtcac actacatggg gctgaacggt tagaggagga aaccaatgat gaggatgtat   3780
cagacataga gagaagaata gccatgagac tcgcagagag acggcaagag gattctgcaa   3840
cccatggaga tgaaggccgc aataacggtg tcgatcatga cgaagatgac gatgccgcag   3900
cagtagctgg gataggagga atctaggatc atacgaggct tcaaggtact tgatccgtag   3960
taagaaaaac ttagggtgaa agttcatcca ccgatcggct caggcaaggc cacacccaac   4020
cccaccgacc acacccagca gtcgagacag ccacggcttc ggctacactt accgcatgga   4080
tcaagatgcc ttcattctta aagaagattc tgaagttgag agggaggcgc caggaggacg   4140
agagtcgctc tcggatgtta tcggattcct cgatgctgtc ctgtcgagtg aaccaactga   4200
catcggaggg gacagaagct ggctccacaa caccatcaac actccccaag gaccaggctc   4260
tgctcataga gccaaaagtg agggcgaagg agaagtctca acaccgtcga cccaagataa   4320
tcgatcaggt gaggagagta gagtctctgg gagaacaagc aagccagagg cagaagcaca   4380
tgctggaaac cttgataaac aaaatataca ccgggccttt gggggaagaa ctggtacaaa   4440
ctctgtatct caggatctgg gcgatggagg agactccgga atccttgaaa atcctccaaa   4500
tgagagagga tatccgagat caggtattga agatgaaaac agagagatgg ctgcgcaccc   4560
tgataagagg ggagaagacc aagctgaagg acttccagaa gaggtacgag gaagtacatc   4620
cctacctgat gaaggagaag gtggagcaag taataatgga agaagcatgg agcctggcag   4680
ctcacatagt gcaagagtaa ctggggtcct ggtgattcct agccccgaac ttgaagaggc   4740
tgtgctacgg aggaacaaaa gaagacctac caacagtggg tccaaacctc ttactccagc   4800
aaccgtgcct ggcacccggt ccccaccgct gaatcgttac aacagcacag ggtcaccacc   4860
aggaaaaccc ccatctacac aggatgagca catcaactct ggggacaccc ccgccgtcag   4920
ggtcaaagac cggaaaccac caatagggac ccgctctgtc tcagattgtc cagccaacgg   4980
ccgcccaatc cacccgggtc tagagaccga ctcaacaaaa aagggcatag gagagaacac   5040
atcatctatg aaagagatgg ctacattgtt gacgagtctt ggtgtaatcc agtctgctca   5100
agaattcgaa tcatcccgag acgcgagtta tgtgtttgca agacgtgccc taaagtctgc   5160
aaactatgca gagatgacat tcaatgtatg cggcctgatc ctttctgccg agaaatcttc   5220
cgctcgtaag gtagatgaga acaaacaact gctcaaacag atccaagaga gcgtggaatc   5280
attccgggat atttacaaga gattctctga gtatcagaaa gaacagaact cattgctgat   5340
gtccaaccta tctacacttc atatcatcac agatagaggt ggcaagactg acaacacaga   5400
ctcccttaca aggtccccct ccgtttttgc aaaatcaaaa gagaacaaga ctaaggctac   5460
caggtttgac ccatctatgg agaccctaga agatatgaag tacaaaccgg acctaatccg   5520
agaggatgaa tttagagatg agatccgcaa cccggtgtac caagagaggg acacagaacc   5580
cagggcctca aacgcatcac gtctcctccc ctccaaagag aagcccacaa tgcactctct   5640
caggctcgtc atagagagca gtcccctaag cagagctgag aaagtagcat atgtgaaatc   5700
attatccaag tgcaagacag accaagaggt taaggcagtc atggaactcg tagaagagga   5760
catagagtca ctgaccaact agatcccggg tgaggcatcc taccatcctc agtcatagag   5820
agatccaatc taccatcagc atcagccagt aaagattaag aaaaacttag ggtgaaagaa   5880
atttcaccta acacggcgca atggcagata tctatagatt ccctaagttc tcatatgagg   5940
ataacggtac tgtggagccc ctgcctctga gaactggtcc ggataagaaa gccatccccc   6000
acatcaggat tgtcaaggta ggagaccctc ctaaacatgg agtgagatac ctagatttat   6060
tgctcttggg tttctttgag acaccgaaac aaacaaccaa tctagggagc gtatctgact   6120
tgacagagcc gaccagctac tcaatatgcg gctccgggtc gttacccata ggtgtggcca   6180
aatactacgg gactgatcag gaactcttaa aggcctgcac cgatctcaga attacggtga   6240
ggaggactgt tcgagcagga gagatgatcg tatacatggt ggattcgatt ggtgctccac   6300
tcctaccatg gtcaggcagg ctgagacagg gaatgatatt taatgcaaac aaggtcgcac   6360
tagctcccca atgcctccct gtggacaagg acataagact cagagtggtg tttgtcaatg   6420
ggacatctct aggggcaatc accatagcca agatcccaaa gacccttgca gaccttgcat   6480
tgcccaactc tatatctgtt aatttactgg tgacactcaa gaccgggatc tccacagaac   6540
aaaagggggt actcccagta cttgatgatc aaggggagaa aaagctcaat tttatggtgc   6600
acctcgggtt gatcaggaga aaggtcggga agatatactc tgttgagtac tgcaagagca   6660
agattgagag aatgcggctg attttctcac ttgggttaat cggcggtata agcttccatg   6720
ttcaggttaa tgggacacta tctaagacat tcatgagtca gctcgcatgg aagagggcag   6780
tctgcttccc attaatggat gtgaatcccc atatgaacat ggtgatttgg gcggcatctg   6840
tagaaatcac aggcgtcgat gcggtgttcc aaccggccat ccctcgtgat ttccgctact   6900
accctaatgt tgtggctaag aacatcggaa ggatcagaaa gctgtaaatg tgcacccatc   6960
agagacctgc gacaatgccc caagcagaca ccacctggca gtcggagcca ccgggtcact   7020
ccttgtctta aataagaaaa acttagggat aaagtccctt gtgagtgctt ggttgcaaaa   7080
ctctcccctt gggaaacatg acagcatata tccagagatc acagtgcatc tcaacatcac   7140
tactggttgt tctcaccaca ttggtctcgt gtcagattcc cagggatagg ctctctaaca   7200
taggggtcat agtcgatgaa gggaaatcac tgaagatagc tggatcccac gaatcgaggt   7260
acatagtact gagtctagtt ccgggggtag actttgagaa tgggtgcgga acagcccagg   7320
ttatccagta caagagccta ctgaacaggc tgttaatccc attgagggat gccttagatc   7380
ttcaggaggc tctgataact gtcaccaatg atacgacaca aaatgccggt gctccccagt   7440
cgagattctt cggtgctgtg attggtacta tcgcacttgg agtggcgaca tcagcacaaa   7500
tcaccgcagg gattgcacta gccgaagcga gggaggccaa aagagacata gcgctcatca   7560
```

-continued

SEQUENCE LISTING

```
aagaatcgat gacaaaaaca cacaagtcta tagaactgct gcaaaacgct gtgggggaac    7620
aaattcttgc tctaaagaca ctccaggatt tcgtgaatga tgagatcaaa cccgcaataa    7680
gcgaattagg ctgtgagact gctgccttaa gactgggtat aaaattgaca cagcattact    7740
ccgagctgtt aactgcgttc ggctcgaatt tcggaaccat cggagagaag agcctcacgc    7800
tgcaggcgct gtcttcactt tactctgcta acattactga gattatgacc acaatcagga    7860
cagggcagtc taacatctat gatgtcattt atacagaaca gatcaaagga acggtgatag    7920
atgtggatct agagagatac atggtcaccc tgtctgtgaa gatccctatt ctttctgaag    7980
tcccaggtgt gctcatacac aaggcatcat ctatttctta caacatagac ggggaggaat    8040
ggtatgtgac tgtccccagc catatactca gtcgtgcttc tttcttaggg ggtgcagaca    8100
taaccgattg tgttgagtcc agattgacct atatatgccc cagggatccc gcacaactga    8160
tacctgacag ccagcaaaag tgtatcctgg gggacacaac aaggtgtcct gtcacaaaag    8220
ttgtggacag ccttatcccc aagtttgctt ttgtgaatgg gggcgttgtt gctaactgca    8280
tagcatccac atgtacctgc gggacaggcc gaagaccaat cagtcaggat cgctctaaag    8340
gtgtagtatt cctaacccat gacaactgtg gtcttatagg tgtcaatggg gtagaattgt    8400
atgctaaccg gagagggcac gatgccactt ggggggtcca gaacttgaca gtcggtcctg    8460
caattgctat cagacccgtt gatatttctc tcaaccttgc tgatgctacg aatttcttgc    8520
aagactctaa ggctgagctt gagaaagcac ggaaaatcct ctcggaggta ggtagatggt    8580
acaactcaag agagactgtg attacgatca tagtagttat ggtcgtaata ttggtggtca    8640
ttatagtgat catcatcgtg ctttatagac tcagaaggtc aatgctaatg ggtaatccag    8700
atgaccgtat accgagggac acatacacat tagagccgaa gatcagacat atgtacacaa    8760
acggtgggtt tgatgcaatg gctgagaaaa gatgatcacg accattatca gatgtcttgt    8820
aaagcaggca tagtatccgt tgagatctgt atataataag aaaaacttag ggtgaaagtg    8880
aggtcgcgcg gtactttagc tttcacctca aacaagcaca gatcatggat ggtgataggg    8940
gcaaacgtga ctcgtactgg tctacttctc ctagtggtag caccacaaaa ccagcatcag    9000
gttgggagag gtcaagtaaa gccgacacat ggttgctgat tctctcattc acccagtggg    9060
ctttgtcaat tgccacagtg atcatctgta tcataatttc tgctagacaa gggtatagta    9120
tgaaagagta ctcaatgact gtagaggcat tgaacatgag cagcagggag gtgaaagagt    9180
cacttaccag tctaataagg caagaggtta tagcaagggc tgtcaacatt cagagctctg    9240
tgcaaaccgg aatcccagtc ttgttgaaca aaaacagcag ggatgtcatc cagatgattg    9300
ataagtcgtg cagcagacaa gagctcactc agcactgtga gagtacgatc gcagtccacc    9360
atgccgatgg aattgcccca cttgagccac atagtttctg gagatgccct gtcggagaac    9420
cgtatcttag ctcagatcct gaaatctcat tgctgcctgg tccgagcttg ttatctggtt    9480
ctacaacgat ctctggatgt gttaggctcc cttcactctc aattggcgag gcaatctatg    9540
cctattcatc aaatctcatt acacaaggtt gtgctgacat agggaaatca tatcaggtcc    9600
tgcagctagg gtacatatca ctcaattcag atatgttccc tgatcttaac cccgtagtgt    9660
cccacactta tgacatcaac gacaatcgga aatcatgctc tgtggtggca accgggacta    9720
ggggttatca gctttgctcc atgccgactg tagacgaaag aaccgactac tctagtgatg    9780
gtattgagga tctggtcctt gatgtcctgg atctcaaagg gagaactaag tctcaccggt    9840
atcgcaacag cgaggtagat cttgatcacc cgttctctgc actatacccc agtgtaggca    9900
acggcattgc aacagaaggc tcattgatat ttcttgggta tggtggacta accacccctc    9960
tgcagggtga tacaaaatgt aggacccaag gatgccaaca ggtgtcgcaa gacacatgca   10020
atgaggctct gaaaattaca tggctaggag ggaaacaggt ggtcagcgtg atcatccagg   10080
tcaatgacta tctctcagag aggccaaaga taagagtcac aaccattcca atcactcaaa   10140
actatctcgg ggcggaaggt agattattaa aattgggtga tcgggtgtac atctatacaa   10200
gatcatcagg ctggcactct caactgcaga taggagtact tgatgtcagc caccctttga   10260
ctatcaactg gacacctcat gaagccttgt ctagaccagg aaataaagag tgcaattggt   10320
acaataagtg tccgaaggaa tgcatatcag gcgtatacac tgatgcttat ccattgtccc   10380
ctgatgcagc taacgtcgct accgtcacgc tatatgccaa tacatcgcgt gtcaacccaa   10440
caatcatgta ttctaacact actaacatta taaatatgtt aaggataaag gatgttcaat   10500
tagaggctgc atataccacg acatcgtgta tcacgcattt tggtaaaggc tactgctttc   10560
acatcatcga gatcaatcag aagagcctga ataccttaca gccgatgctc tttaagacta   10620
gcatccctaa attatgcaag gccgagtctt aaatttaact gactagcagg cttgtcggcc   10680
ttgctgacac tagagtcatc tccgaacatc cacaatatct ctcagtctct tacgtctctc   10740
acagtattaa gaaaaaccca gggtgaatgg gaagcttgcc ataggtcatg gatgggcagg   10800
agtcctccca aaacccttct gacatactct atccagaatg ccacctgaac tctcccatag   10860
tcagggggaa gatagcacag ttgcacgtct tgttagatgt gaaccagccc tacagactga   10920
aggacgacag cataataaat attacaaagc acaaaattag gaacggagga ttgtcccccc   10980
gtcaaattaa gatcaggtct ctgggtaagg ctcttcaacg cacaataaag gatttagacc   11040
gatacacgtt tgaaccgtac ccaacctact ctcaggaatt acttaggctt gatataccag   11100
agatatgtga caaaatccga tccgtcttcg cggtctcgga tcggctgacc agggagttat   11160
ctagtgggtt ccaggatctt tggttgaata tcttcaagca actaggcaat atagaaggaa   11220
gagaggggta cgatccgttg caggatatcg gcaccatccc ggagataact gataagtaca   11280
gcaggaatag atggtatagg ccattcctaa cttggttcag catcaaatat gacatgcggt   11340
ggatgcagaa gaccagaccg gggggacccc tcgatacctc taattcacat aacctcctag   11400
aatgcaaatc atacactcta gtaacatacg gagatcttgt catgatactg aacaagttga   11460
cattgacagg gtatatccta acccctgagc tggtcttgat gtattgtgat gttgtagaag   11520
gaaggtggaa tatgtctgct gcagggcatc tagataagaa gtccattggg ataacaagca   11580
aaggtgagga attatgggaa ctagtggatt ccctcttctc aagtcttgga gaggaaatat   11640
acaatgtcat cgcactattg gagcccctat cacttgctct catacaacta aatgatcctg   11700
ttatacctct acgtggggca tttatgaggc atgtgttgac agagctacag actgttttaa   11760
caagtagaga cgtgtacaca gatgctgaag cagacactat tgtggagtcg ttactcgcca   11820
ttttccatgg aacctctatt gatgagaaag cagagatctt ttccttcttt aggacatttg   11880
gccaccccag cttagaggct gtcactgccg ccgacaaggt aagggcccat atgtatgcac   11940
aaaaggcaat aaagcttaag accctatacg agtgtcatgc agttttttgc actatcatca   12000
taaatgggta tagagagagg catggcggac agtggccccc ctgtgacttc cctgatcacg   12060
tgtgtctaga actaaggaac gctcaagggt ccaatacggc aatctcttat gaatgtgctg   12120
tagacaacta tacaagtttc ataggcttca agtttcggaa gtttatagaa ccacaactag   12180
```

-continued

SEQUENCE LISTING atgaagatct cacaatatat atgaaagaca aagcactatc ccccaggaag gaggcatggg 12240
actctgtata cccggatagt aatctgtact ataaagcccc agagtctgaa gagacccggc 12300
ggcttattga agtgttcata aatgatgaga atttcaaccc agaagaaatt atcaattatg 12360
tggagtcagg agattggttg aaagacgagg agttcaacat ctcgtacagt ctcaaagaga 12420
aagagatcaa gcaagagggt cgtctattcg caaaaatgac ttataagatg cgagccgtac 12480
aggtgctggc agagacacta ctggctaaag gaataggaga gctattcagc gaaaatggga 12540
tggttaaagg agagatagac ctacttaaaa gattgactac tctttctgtc tcaggcgtcc 12600
ccaggactga ttcagtgtac aataactcta aatcatcaga gaagagaaac gaaggcatgg 12660
aaaataagaa ctctgggggg tactgggacg aaaagaagag gtccagacat gaattcaagg 12720
caacagattc atcaacagac ggctatgaaa cgttaagttg cttcctcaca acagacctca 12780
agaaatactg cttaaactgg agatttgaga gtactgcatt gtttggtcag agatgcaacg 12840
agatatttgg cttcaagacc ttctttaact ggatgcatcc agtccttgaa aggtgtacaa 12900
tatatgttgg agatccttac tgtccagtcg ccgaccggat gcatcgacaa ctccaggatc 12960
atgcagactc tggcattttc atacataatc ctaggggggg catagaaggt tactgccaga 13020
agctgtggac cttaatctca atcagtgcaa tccacctagc agctgtgaga gtgggtgtca 13080
gggtctctgc aatggttcag ggtgacaatc aagctatagc cgtgacatca agagtacctg 13140
tagctcagac ttacaagcag aagaaaaatc atgtctatga ggagatcacc aaatatttcg 13200
gtgctctaag acacgtcatg tttgatgtag ggcacgagct aaaattgaac gagaccatca 13260
ttagtagcaa gatgtttgtc tatagtaaaa ggatatacta tgatgggaag attttaccac 13320
agtgcctgaa agccttgacc aagtgtgtat tctggtccga gacactggta gatgaaaaca 13380
gatctgcttg ttcgaacatc tcaacatcca tagcaaaagc tatcgaaaat gggtattctc 13440
ctatactagg ctactgcatt gcgttgtata agacctgtca gcaggtgtgc atatcactag 13500
ggatgactat aaatccaact atcagcccga ccgtaagaga tcaatacttt aagggtaaga 13560
attggctgag atgtgcagtg ttgattccag caaatgttgg aggattcaac tacatgtcta 13620
catctagatg ctttgttaga aatattggag accccgcagt agcagcccta gctgatctca 13680
aaagattcat cagagcggat ctgttagaca agcaggtatt atacagggtc atgaatcaag 13740
aacccggtga ctctagtttt ctagattggg cttcagaccc ttattcgtgt aacctcccgc 13800
attctcagag tataactacg attataaaga atatcactgc tagatctgtg ctgcaggaat 13860
ccccgaatcc tctactgtct ggtctcttca ccgagactag tggagaagag gatctcaacc 13920
tggcctcgtt ccttatggac cggaaagtca tcctgccgag agtggctcat gagatcctgg 13980
gtaattcctt aactggagtt agggaggcga ttgcagggat gcttgatacg accaagtctc 14040
tagtgagagc cagcgttagg aaaggaggat tatcatatgg gatattgagg aggcttgtca 14100
attatgatct attgcagtac gagacactga ctagaactct caggaaaccg gtgaaagaca 14160
acatcgaata tgagtatatg tgttcagttg agctagctgt cggtctaagg cagaaaatgt 14220
ggatccacct gacttacggg agacccatac atgggctaga aacaccagac cctttagagc 14280
tcttgagggg aatatttatc gaaggttcag aggtgtgcaa gctttgcagg tctgaaggag 14340
cagaccccat ctatacatgg ttctatcttc ctgacaatat agacctggac acgcttacaa 14400
acggatgtcc ggctataaga atcccctatt ttggatcagc cactgatgaa aggtcggaag 14460
cccaactcgg gtatgtaaga aatctaagca aacccgcaaa ggcggccatc cggatagcta 14520
tggtgtatac gtgggcctac gggactgatg agatatcgtg gatggaagcc gctcttatag 14580
cccaaacaag agctaatctg agcttagaga atctaaagct gctgactcct gificaacct 14640
ccactaatct atctcatagg ttgaaagata cggcaaccca gatgaagttc tctagtgcaa 14700
cactagtccg tgcaagtcgg ttcataacaa tatcaaatga taacatggca ctcaaagaag 14760
caggggagtc gaaggatact aatctcgtgt atcagcagat tatgctaact gggctaagct 14820
tgttcgagtt caatatgaga tataagaaag gttccttagg gaagccactg atattgcact 14880
tacatcttaa taacgggtgc tgtataatgg agtccccaca ggaggcgaat atccccccaa 14940
ggtccacatt agatttagag attacacaag agaacaataa attgatctat gatcctgatc 15000
cactcaagga tgtggacctt gagctattta gcaaggtcag agatgttgta cacacagttg 15060
acatgactta ttggtcagat gatgaagtta tcagagcaac cagtatctgt actgcaatga 15120
cgatagctga tacaatgtct caattagata gagacaactt aaaagagatg atcgcactag 15180
taaatgacga tgatgtcaac agcttgatta ctgagtttat ggtgattgat gttcctttat 15240
tttgctcaac gttcgggggt attctagtca atcagtttgc atactcactc tacggcttaa 15300
acatcagagg aagggaagaa atatggggac atgtagtccg gattcttaaa gatacctccc 15360
acgcagtttt aaaagtctta tctaatgctc tatctcatcc caaaatcttc aaacgattct 15420
ggaatgcagg tgtcgtggaa cctgtgtatg ggcctaacct ctcaaatcag gataagatac 15480
tcttggccct ctctgtctgt gaatattctg tggatctatt catgcacgat tggcaagggg 15540
gtgtaccgct tgagatcttt atctgtgaca atgacccaga tgtggccgac atgaggaggt 15600
cctctttctt ggcaagacat cttgcatacc tatgcagctt ggcagagata tctagggatg 15660
ggccaagatt agaatcaatg aactctctag agaggctcga gtcactaaag agttacctgg 15720
aactcacatt tcttgatgac ccggtactga ggtacagtca gttgactggc ctagtcatca 15780
aagtattccc atctactttg acctatatcc ggaagtcatc tataaaagtg ttaaggacaa 15840
gaggtatagg agtccctgaa gtcttagaag attgggatcc cgaggcagat aatgcactgt 15900
tagatggtat cgcggcagaa atacaacaga atattccttt gggacatcag actagagccc 15960
ctttttgggg gttgagagta tccaagtcac aggtactgcg tctccggggg tacaaggaga 16020
tcacaagagg tgagataggc agatcaggtg ttggtctgac gttaccattc gatggaagat 16080
atctatctca ccagctgagg ctctttggca tcaacagtac tagctgcttg aaagcacttg 16140
aacttaccta cctattgagc cccttagttg acaaggataa agataggcta tatttagggg 16200
aaggagctgg ggccatgctt tcctgttatg acgctactct tggcccatgc atcaactatt 16260
ataactcagg ggtatactct tgtgatgtca atgggcagag agagttaaat atatatcctg 16320
ctgaggtggc actagtggga aagaaattaa acaatgttac tagtctgggt caaagagtta 16380
aagtgttatt caacgggaat cctggctcga catggattgg gaatgatgag tgtgaggctt 16440
tgatttggaa tgaattacag aatagctcga taggcctagt ccactgtgac atggagggag 16500
gagatcataa ggatgatcaa gttgtactgc atgagcatta cagtgtaatc cggatcgcgt 16560
atctggtggg ggatcgagac gttgtgctta taagcaagat tgctcccagg ctgggcacgg 16620
attggaccag gcagctcagc ctatatctga gatactggga cgaggttaac ctaatagtgc 16680
ttaaaacatc taaccctgct tccacagaga tgtatctcct atcgaggcac cccaaatctg 16740
acattataga ggacagcaag acagtgttag ctagtctcct ccctttgtca aaagaagata 16800

-continued

SEQUENCE LISTING

```
gcatcaagat agaaaagtgg atcttaatag agaaggcaaa ggctcacgaa tgggttactc   16860
gggaattgag agaaggaagc tcttcatcag ggatgcttag accttaccat caagcactgc   16920
agacgtttgg ctttgaacca aacttgtata aattgagcag agatttcttg tccaccatga   16980
acatagctga tacacacaac tgcatgatag ctttcaacag ggttttgaag gatacaatct   17040
tcgaatgggc tagaataact gagtcagata aaaggcttaa actaactggt aagtatgacc   17100
tgtatcctgt gagagattca ggcaagttga agacaatttc tagaagactt gtgctatctt   17160
ggatatcttt atctatgtcc acaagattgg taactgggtc attccctgac cagaagtttg   17220
aagcaagact tcaattggga atagtttcat tatcatcccg tgaaatcagg aacctgaggg   17280
ttatcacaaa aactttatta gacaggtttg aggatattat acatagtata acgtatagat   17340
tcctcaccaa agaaataaag attttgatga agattttagg ggcagtcaag atgttcgggg   17400
ccaggcaaaa tgaatacacg accgtgattg atgatggatc actaggtgat atcgagccat   17460
atgacagctc gtaataatta gtccctatcg tgcagaacga tcgaagctcc gcggtacctg   17520
gaagtcttgg acttgtccat atgacaatag taagaaaaac ttacaagaag acaagaaaat   17580
ttaaaaggat acatatctct taaactcttg tctggt                             17616

<210>   13
<211> 17832
<212> DNA
<213> Artificial Sequence

<220>
<223> Description of Artificial Sequence: Synthetic
polynucleotide

<400>   13
accaaacaag agaaaaaaca tgtatgggat atgtaatgaa gttatacagg attttagggt     60
caaagtatcc accctgagga gcaggttcca gaccctttgc tttgctgcca aagttcacgc    120
ggccgccaag gttcaatgga ggagaaagca ttctcacctg aagtgatccc tatgttcaca    180
gcattatctg agggagctac tcctcaagat cttaacacaa tgcttaacac agtcggagga    240
catcaagcag caatgcaaat gttgaaagat acaattaacg aggaagcagc agaatgggat    300
agaatctata agagatggat aatattagga ttgaacaaga ttgttagaat gtattctcct    360
gtgtcaatcc ttgatataag acaaggacct aaagagcctt tcagagatta cgtcgataga    420
tttgcaagaa attgtagagc acctagaaag aagggatgtt ggaaatgtgg gaaagaagga    480
catcaaatga aagattgtac tgagagacaa gctaacttct tgggaaagat atggccttca    540
agatggaaac ctaagatgat aggaggaata ggaggattta ttaaagtcag acaatatgat    600
caaatattga ttgaaatatg tggacataaa gctattggaa cagtcctagt gggtccaaca    660
cctgtcaaca tcattggtag aaatcttctc actcaaatcg gatgtacact caatttccca    720
atatcaccta ttgagaccgt gcctgtcaaa ttgaaacctg gaatggatgg acctaaagtc    780
aaacaatggc cattaactga ggagaagatt aaagcactgg tagaaatttg tacagagatg    840
gagaaagaag gaaagatttc caagattggt cctgagaatc cttataatac tcctgtcttt    900
gctattaaga agaaggatag taccaaatgg aggaaattag tcgatttcag agaacttaac    960
aagaggactc aagacttctg ggaagtgcaa ttgggaatcc cacaccctgc aggattgaag   1020
aagaagaagt ctgtcactgt cctagatgtg ggagatgcat atttcagtgt ccccactggat   1080
gaaggtttca gaaagtatac agcattcaca atcccttcca ttaataatga aacacctgga   1140
ataagatatc aatataatgt cttacctcaa gggtggaaag gatctccagc aatattccaa   1200
tcatcaatga caaagatctt ggagcctttc agagctcaga atccagagat agttatttac   1260
caatacatgg atgatttgta tgttgggtca gatctcgaga tcggacagca caggatggag   1320
aatagatggc aagtaatgat tgtctggcaa gtcgatagaa tgagaataag aacatggaaa   1380
tccttggtga aacatcacct tacagaggag gcagaactgg aactggcaga gaatagggaa   1440
atattgaaag atccagtgca tggtgtctat tacgatcctt ctaaagatct gatagcagag   1500
atccagtact ggcaagcaac atggattcct gagtgggaat tcgtcaacac acctccatta   1560
gtgaaactat ggtaccaatt agagaagaat gtcaccgaga acttcaacat gtggaagaac   1620
gatatggtag atcaaatgca cgaagatatc atctccttgt gggatcaatc acttaaacct   1680
tgtgttaaat tgacaccttg ggtacctgct cataaaggga taggaggaaa cgaacaagtg   1740
gataaattgg tgtcccaagg gatcaggaaa gtcttgttcc tagatggaat tgataaagct   1800
caagcaaagg aaattgtcgc aagctgtgat aagtgtcaat taaagggaga ggcaatgcac   1860
ggacaagtcg attgttcacc tggtatttgg caacttgatt gtacacattt ggagggtaaa   1920
gttattctag tagcagtaca tgtcgcttct ggttatattg aggcagaagt gatacctgct   1980
gagacaggac aggagaccgc atactttcta cttaagttag ctatgaataa ggagctcaag   2040
aagataatag gacaagttag agatcaagca gagcacctta agacagctgt ccaaatggca   2100
gtgtttatac acaactttaa gagaaagggt ggaatcggag gatattccgc aggagagaga   2160
atctggaaag gtcctgctaa attgttatgg aaaggagaag gagcagttgt aatacaagat   2220
aattctgata taaaagtagt ccctagaagg aaagctaaga ttattagaga ttatgggaaa   2280
caaatggcag gagctgattg tgtgtttcta ggagcagcag gatccactat gggagctgca   2340
tcaatgacac ttaccgtgca ggctagacag cttctttcag gaattgtaca gcaacagaat   2400
aatttgctaa gagcaattga agctcaacaa cacttacttc aacttacagt ctggggaatc   2460
aagcaagcac ctacaaaagc aaagagaaga gtcgtccaaa gagagaaaag ataaccgtag   2520
taagaaaaac ttagggtgaa agttcatcgc ggccgcagat cttcacgatg gccgggttgt   2580
tgagcacctt cgatacattt agctctagga ggagcgaaag tattaataag tcgggaggag   2640
gtgctgttat ccccggccag aggagcacag tctcagtgtt cgtactaggc ccaagtgtga   2700
ctgatgatgc agacaagtta ttcattgcaa ctaccttcct agctcactca ttggacacag   2760
ataagcagca ctctcagaga ggggggttcc tcgtctctct gcttgccatg gcttacagta   2820
gtccagaatt gtacttgaca acaaacggag taaacgccga tgtcaaatat gtgatctaca   2880
acatagagaa agaccctaag aggacgaaga cagacggatt cattgtgaag acgagagata   2940
tggaatatga gaggaccaca gaatggctgt ttggacctat ggtcaacaag agcccactct   3000
tccagggtca acgggatgct gcagaccctg acacactcct tcaaatctat gggtatcctg   3060
catgcctagg agcaataatt gtccaagtct ggattgtgct ggtgaaggcc atcacaagca   3120
```

-continued

SEQUENCE LISTING

```
gcgccggctt aaggaaaggg ttcttcaaca ggttagaggc gttcagacaa gacggcaccg   3180
tgaaaggtgc cttagttttc actggggaga cagttgaggg gataggctcg gttatgagat   3240
ctcagcaaag ccttgtatct ctcatggttg agacccttgt gactatgaat actgcaagat   3300
ctgatctcac cacattagag aagaacatcc agatcgttgg gaactacatc cgagatgcag   3360
ggctggcttc cttcatgaac actattaaat atggggtgga aacaaagatg gcagctctaa   3420
cgttgtcaaa cctgaggccc gatattaata agcttagaag cctcatagac acctacctgt   3480
caaaaggccc cagagctccc tttatctgta tcctcaagga ccctgttcat ggtgaatttg   3540
ctccaggcaa ttatcctgca ctatggagtt acgccatggg agtcgccgtc gtacagaaca   3600
aggcaatgca gcagtacgtc acagggagga catacttgga tatggaaatg ttcttactag   3660
gacaagccgt ggcaaaggat gctgaatcga agatcagcag tgccttggaa gatgagttag   3720
gagtgacgga tacagccaag ggaggctca gacatcatct ggcaaacttg tccggtgggg   3780
atggtgctta ccacaaacca acaggcggtg gtgcaattga ggtagctcta gacaatgccg   3840
acatcgacct agaaacaaaa gcccatgcgg accaggacgc taggggttgg ggtggagata   3900
gtggtgaaag atgggcacgt caggtgagtg gtggccactt tgtcacacta catggggctg   3960
aacggttaga ggaggaaacc aatgatgagg atgtatcaga catagagaga agaatagcca   4020
tgagactcgc agagagacgg caagaggatt ctgcaaccca tggagatgaa ggccgcaata   4080
acggtgtcga tcatgacgaa gatgacgatg ccgcagcagt agctgggata ggaggaatct   4140
aggatcatac gaggcttcaa ggtacttgat ccgtagtaag aaaaacttag ggtgaaagtt   4200
catccaccga tcggctcagg caaggccaca cccaacccca ccgaccacac ccagcagtcg   4260
agacagccac ggcttcggct acacttaccg catggatcaa gatgccttca ttcttaaaga   4320
agattctgaa gttgagaggg aggcgccagg aggacgagag tcgctctcgg atgttatcgg   4380
attcctcgat gctgtcctgt cgagtgaacc aactgacatc ggaggggaca gaagctggct   4440
ccacaacacc atcaacactc cccaaggacc aggctctgct catagagcca aaagtgaggg   4500
cgaaggagaa gtctcaacac cgtcgaccca agataatcga tcaggtgagg agagtagagt   4560
ctctgggaga acaagcaagc cagaggcaga agcacatgct ggaaaccttg ataaacaaaa   4620
tatacaccgg gcctttgggg gaagaactgg tacaaactct gtatctcagg atctgggcga   4680
tggaggagac tccggaatcc ttgaaaatcc tccaaatgag agaggatatc cgagatcagg   4740
tattgaagat gaaaacagag agatggctgc gcaccctgat aagaggggag aagaccaagc   4800
tgaaggactt ccagaagagg tacgaggaag tacatcccta cctgatgaag gagaaggtgg   4860
agcaagtaat aatggaagaa gcatggagcc tggcagctca catagtgcaa gagtaactgg   4920
ggtcctggtg attcctagcc ccgaacttga agaggctgtg ctacggagga acaaaagaag   4980
acctaccaac agtgggtcca aacctcttac tccagcaacc gtgcctggca cccggtcccc   5040
accgctgaat cgttacaaca gcacagggtc accaccagga aaacccccat ctacacagga   5100
tgagcacatc aactctgggg acaccccgc cgtcagggtc aaagaccgga aaccaccaat   5160
agggacccgc tctgtctcag attgtccagc caacggccgc ccaatccacc cgggtctaga   5220
gaccgactca acaaaaaagg gcataggaga gaacacatca tctatgaaag agatggctac   5280
attgttgacg agtcttggtg taatccagtc tgctcaagaa ttcgaatcat cccgagacgc   5340
gagttatgtg tttgcaagac gtgccctaaa gtctgcaaac tatgcagaga tgacattcaa   5400
tgtatgcggc ctgatccttt ctgccgagaa atcttccgct cgtaaggtag atgagaacaa   5460
acaactgctc aaacagatcc aagagagcgt ggaatcattc cgggatattt acaagagatt   5520
ctctgagtat cagaaagaac agaactcatt gctgatgtcc aacctatcta cacttcatat   5580
catcacagat agaggtggca agactgacaa cacagactcc cttacaaggt ccccctccgt   5640
ttttgcaaaa tcaaaagaga acaagactaa ggctaccagg tttgacccat ctatggagac   5700
cctagaagat atgaagtaca aaccggacct aatccgagag gatgaattta gagatgagat   5760
ccgcaacccg gtgtaccaag agagggacac agaacccagg gcctcaaacg catcacgtct   5820
cctcccctcc aaagagaagc ccacaatgca ctctctcagg ctcgtcatag agagcagtcc   5880
cctaagcaga gctgagaaag tagcatatgt gaaatcatta tccaagtgca agacagacca   5940
agaggttaag gcagtcatgg aactcgtaga agaggacata gagtcactga ccaactagat   6000
cccgggtgag gcatcctacc atcctcagtc atagagagat ccaatctacc atcagcatca   6060
gccagtaaag attaagaaaa acttagggtg aaagaaattt cacctaacac ggcgcaatgg   6120
cagatatcta tagattccct aagttctcat atgaggataa cggtactgtg gagcccctgc   6180
ctctgagaac tggtccggat aagaaagcca tcccccacat caggattgtc aaggtaggag   6240
accctcctaa acatggagtg agatacctag atttattgct cttgggtttc tttgagacac   6300
cgaaacaaac aaccaatcta gggagcgtat ctgacttgac agagccgacc agctactcaa   6360
tatgcggctc cgggtcgtta cccataggtg tggccaaata ctacgggact gatcaggaac   6420
tcttaaaggc ctgcaccgat ctcagaatta cggtgaggag gactgttcga gcaggagaga   6480
tgatcgtata catggtggat tcgattggtg ctccactcct accatggtca ggcaggctga   6540
gacagggaat gatatttaat gcaaacaagg tcgcactagc tccccaatgc ctccctgtgg   6600
acaaggacat aagactcaga gtggtgtttg tcaatgggac atctctaggg gcaatcacca   6660
tagccaagat cccaaagacc cttgcagacc ttgcattgcc caactctata tctgttaatt   6720
tactggtgac actcaagacc gggatctcca cagaacaaaa gggggtactc ccagtacttg   6780
atgatcaagg ggagaaaaag ctcaatttta tggtgcacct cgggttgatc aggagaaagg   6840
tcgggaagat atactctgtt gagtactgca agagcaagat tgagagaatg cggctgattt   6900
tctcacttgg gttaatcggc ggtataagct tccatgttca ggttaatggg acactatcta   6960
agacattcat gagtcagctc gcatggaaga gggcagtctg cttcccatta atggatgtga   7020
atccccatat gaacatggtg atttgggcgg catctgtaga aatcacaggc gtcgatgcgg   7080
tgttccaacc ggccatccct cgtgatttcc gctactaccc taatgttgtg gctaagaaca   7140
tcggaaggat cagaaagctg taaatgtgca cccatcagag acctgcgaca atgccccaag   7200
cagacaccac ctggcagtcg gagccaccgg gtcactcctt gtcttaaata agaaaaactt   7260
agggataaag tcccttgtga gtgcttggtt gcaaaactct ccccttggga aacatgacag   7320
catatatcca gagatcacag tgcatctcaa catcactact ggttgttctc accacattgg   7380
tctcgtgtca gattcccagg gataggctct ctaacatagg ggtcatagtc gatgaaggga   7440
aatcactgaa gatagctgga tcccacgaat cgaggtacat agtactgagt ctagttccgg   7500
gggtagactt tgagaatggg tgcggaacag cccaggttat ccagtacaag agcctactga   7560
acaggctgtt aatcccattg agggatgcct tagatcttca ggaggctctg ataactgtca   7620
ccaatgatac gacacaaaat gccggtgctc cccagtcgag attcttcggt gctgtgattg   7680
gtactatcgc acttggagtg gcgacatcag cacaaatcac cgcagggatt gcactagccg   7740
```

-continued

SEQUENCE LISTING

```
aagcgaggga ggccaaaaga gacatagcgc tcatcaaaga atcgatgaca aaaacacaca    7800
agtctataga actgctgcaa aacgctgtgg gggaacaaat tcttgctcta aagacactcc    7860
aggatttcgt gaatgatgag atcaaacccg caataagcga attaggctgt gagactgctg    7920
ccttaagact gggtataaaa ttgacacagc attactccga gctgttaact gcgttcggct    7980
cgaatttcgg aaccatcgga gagaagagcc tcacgctgca ggcgctgtct tcactttact    8040
ctgctaacat tactgagatt atgaccacaa tcaggacagg gcagtctaac atctatgatg    8100
tcatttatac agaacagatc aaaggaacgg tgatagatgt ggatctagag agatacatgg    8160
tcaccctgtc tgtgaagatc cctattcttt ctgaagtccc aggtgtgctc atacacaagg    8220
catcatctat ttcttacaac atagacgggg aggaatggta tgtgactgtc cccagccata    8280
tactcagtcg tgcttctttc ttagggggtg cagacataac cgattgtgtt gagtccagat    8340
tgacctatat atgccccagg gatcccgcac aactgatacc tgacagccag caaaagtgta    8400
tcctggggga cacaacaagg tgtcctgtca caaaagttgt ggacagcctt atccccaagt    8460
ttgcttttgt gaatgggggc gttgttgcta actgcatagc atccacatgt acctgcggga    8520
caggccgaag accaatcagt caggatcgct ctaaaggtgt agtattccta acccatgaca    8580
actgtggtct tataggtgtc aatggggtag aattgtatgc taaccggaga gggcacgatg    8640
ccacttgggg ggtccagaac ttgacagtcg gtcctgcaat tgctatcaga cccgttgata    8700
tttctctcaa ccttgctgat gctacgaatt tcttgcaaga ctctaaggct gagcttgaga    8760
aagcacggaa aatcctctcg gaggtaggta gatggtacaa ctcaagagag actgtgatta    8820
cgatcatagt agttatggtc gtaatattgg tggtcattat agtgatcatc atcgtgcttt    8880
atagactcag aaggtcaatg ctaatgggta atccagatga ccgtataccg agggacacat    8940
acacattaga gccgaagatc agacatatgt acacaaacgg tgggtttgat gcaatggctg    9000
agaaaagatg atcacgacca ttatcagatg tcttgtaaag caggcatagt atccgttgag    9060
atctgtatat aataagaaaa acttagggtg aaagtgaggt cgcgcggtac tttagctttc    9120
acctcaaaca agcacagatc atggatggtg ataggggcaa acgtgactcg tactggtcta    9180
cttctcctag tggtagcacc acaaaaccag catcaggttg ggagaggtca agtaaagccg    9240
acacatggtt gctgattctc tcattcaccc agtgggcttt gtcaattgcc acagtgatca    9300
tctgtatcat aatttctgct agacaagggt atagtatgaa agagtactca atgactgtag    9360
aggcattgaa catgagcagc agggaggtga aagagtcact taccagtcta ataaggcaag    9420
aggttatagc aagggctgtc aacattcaga gctctgtgca aaccggaatc ccagtcttgt    9480
tgaacaaaaa cagcagggat gtcatccaga tgattgataa gtcgtgcagc agacaagagc    9540
tcactcagca ctgtgagagt acgatcgcag tccaccatgc cgatggaatt gccccacttg    9600
agccacatag tttctggaga tgccctgtcg gagaaccgta tcttagctca gatcctgaaa    9660
tctcattgct gcctggtccg agcttgttat ctggttctac aacgatctct ggatgtgtta    9720
ggctcccttc actctcaatt ggcgaggcaa tctatgccta ttcatcaaat ctcattacac    9780
aaggttgtgc tgacataggg aaatcatatc aggtcctgca gctagggtac atatcactca    9840
attcagatat gttccctgat cttaaccccg tagtgtccca cacttatgac atcaacgaca    9900
atcggaaatc atgctctgtg gtggcaaccg ggactagggg ttatcagctt tgctccatgc    9960
cgactgtaga cgaaagaacc gactactcta gtgatggtat tgaggatctg gtccttgatg   10020
tcctggatct caaagggaga actaagtctc accggtatcg caacagcgag gtagatcttg   10080
atcacccgtt ctctgcacta taccccagtg taggcaacgg cattgcaaca gaaggctcat   10140
tgatatttct tgggtatggt ggactaacca cccctctgca gggtgataca aaatgtagga   10200
cccaaggatg ccaacaggtg tcgcaagaca catgcaatga ggctctgaaa attacatggc   10260
taggagggaa acaggtggtc agcgtgatca tccaggtcaa tgactatctc tcagagaggc   10320
caaagataag agtcacaacc attccaatca ctcaaaacta tctcggggcg gaaggtagat   10380
tattaaaatt gggtgatcgg gtgtacatct atacaagatc atcaggctgg cactctcaac   10440
tgcagatagg agtacttgat gtcagccacc ctttgactat caactggaca cctcatgaag   10500
ccttgtctag accaggaaat aaagagtgca attggtacaa taagtgtccg aaggaatgca   10560
tatcaggcgt atacactgat gcttatccat tgtcccctga tgcagctaac gtcgctaccg   10620
tcacgctata tgccaataca tcgcgtgtca acccaacaat catgtattct aacactacta   10680
acattataaa tatgttaagg ataaaggatg ttcaattaga ggctgcatat accacgacat   10740
cgtgtatcac gcattttggt aaaggctact gctttcacat catcgagatc aatcagaaga   10800
gcctgaatac cttacagccg atgctcttta agactagcat ccctaaatta tgcaaggccg   10860
agtcttaaat ttaactgact agcaggcttg tcggccttgc tgacactaga gtcatctccg   10920
aacatccaca atatctctca gtctcttacg tctctcacag tattaagaaa aacccagggt   10980
gaatgggaag cttgccatag gtcatggatg ggcaggagtc ctcccaaaac ccttctgaca   11040
tactctatcc agaatgccac ctgaactctc ccatagtcag gggaagata gcacagttgc     11100
acgtcttgtt agatgtgaac cagccctaca gactgaagga cgacagcata ataaatatta   11160
caaagcacaa aattaggaac ggaggattgt ccccccgtca aattaagatc aggtctctgg   11220
gtaaggctct tcaacgcaca ataaaggatt tagaccgata cacgtttgaa ccgtacccaa   11280
cctactctca ggaattactt aggcttgata taccagagat atgtgacaaa atccgatccg   11340
tcttcgcggt ctcggatcgg ctgaccaggg agttatctag tgggttccag gatctttggt   11400
tgaatatctt caagcaacta ggcaatatag aaggaagaga ggggtacgat ccgttgcagg   11460
atatcggcac catcccggag ataactgata agtacagcag gaatagatgg tataggccat   11520
tcctaacttg gttcagcatc aaatatgaca tgcggtggat gcagaagacc agaccggggg   11580
gacccctcga tacctctaat tcacataacc tcctagaatg caaatcatac actctagtaa   11640
catacggaga tcttgtcatg atactgaaca agttgacatt gacagggtat atcctaaccc   11700
ctgagctggt cttgatgtat tgtgatgttg tagaaggaag gtggaatatg tctgctgcag   11760
ggcatctaga taagaagtcc attgggataa caagcaaagg tgaggaatta tgggaactag   11820
tggattccct cttctcaagt cttggagagg aaatatacaa tgtcatcgca ctattggagc   11880
ccctatcact tgctctcata caactaaatg atcctgttat acctctacgt ggggcattta   11940
tgaggcatgt gttgacagag ctacagactg ttttaacaag tagagacgtg tacacagatg   12000
ctgaagcaga cactattgtg gagtcgttac tcgccatttt ccatggaacc tctattgatg   12060
agaaagcaga gatcttttcc ttctttagga catttggcca ccccagctta gaggctgtca   12120
ctgccgccga caaggtaagg gcccatatgt atgcacaaaa ggcaataaag cttaagaccc   12180
tatacgagtg tcatgcagtt ttttgcacta tcatcataaa tgggtataga gagaggcatg   12240
gcggacagtg gccccctgt gacttccctg atcacgtgtg tctagaacta aggaacgctc    12300
aagggtccaa tacggcaatc tcttatgaat gtgctgtaga caactataca agtttcatag   12360
```

-continued

SEQUENCE LISTING

```
gcttcaagtt tcggaagttt atagaaccac aactagatga agatctcaca atatatatga   12420
aagacaaagc actatccccc aggaaggagg catgggactc tgtatacccg gatagtaatc   12480
tgtactataa agccccagag tctgaagaga cccggcggct tattgaagtg ttcataaatg   12540
atgagaattt caacccagaa gaaattatca attatgtgga gtcaggagat tggttgaaag   12600
acgaggagtt caacatctcg tacagtctca aagagaaaga gatcaagcaa gagggtcgtc   12660
tattcgcaaa aatgacttat aagatgcgag ccgtacaggt gctggcagag acactactgg   12720
ctaaaggaat aggagagcta ttcagcgaaa atgggatggt taaaggagag atagacctac   12780
ttaaaagatt gactactctt tctgtctcag gcgtccccag gactgattca gtgtacaata   12840
actctaaatc atcagagaag agaaacgaag gcatggaaaa taagaactct ggggggtact   12900
gggacgaaaa gaagaggtcc agacatgaat tcaaggcaac agattcatca acagacggct   12960
atgaaacgtt aagttgcttc ctcacaacag acctcaagaa atactgctta aactggagat   13020
ttgagagtac tgcattgttt ggtcagagat gcaacgagat atttggcttc aagaccttct   13080
ttaactggat gcatccagtc cttgaaaggt gtacaatata tgttggagat ccttactgtc   13140
cagtcgccga ccggatgcat cgacaactcc aggatcatgc agactctggc attttcatac   13200
ataatcctag ggggggcata gaaggttact gccagaagct gtggacctta atctcaatca   13260
gtgcaatcca cctagcagct gtgagagtgg gtgtcagggt ctctgcaatg gttcagggtg   13320
acaatcaagc tatagccgtg acatcaagag tacctgtagc tcagacttac aagcagaaga   13380
aaaatcatgt ctatgaggag atcaccaaat atttcggtgc tctaagacac gtcatgtttg   13440
atgtagggca cgagctaaaa ttgaacgaga ccatcattag tagcaagatg tttgtctata   13500
gtaaaaggat atactatgat gggaagattt taccacagtg cctgaaagcc ttgaccaagt   13560
gtgtattctg gtccgagaca ctggtagatg aaaacagatc tgcttgttcg aacatctcaa   13620
catccatagc aaaagctatc gaaaatgggt attctcctat actaggctac tgcattgcgt   13680
tgtataagac ctgtcagcag gtgtgcatat cactagggat gactataaat ccaactatca   13740
gcccgaccgt aagagatcaa tactttaagg gtaagaattg gctgagatgt gcagtgttga   13800
ttccagcaaa tgttggagga ttcaactaca tgtctacatc tagatgcttt gttagaaata   13860
ttggagaccc cgcagtagca gccctagctg atctcaaaag attcatcaga gcggatctgt   13920
tagacaagca ggtattatac agggtcatga atcaagaacc cggtgactct agttttctag   13980
attgggcttc agacccttat tcgtgtaacc tcccgcattc tcagagtata actacgatta   14040
taaagaatat cactgctaga tctgtgctgc aggaatcccc gaatcctcta ctgtctggtc   14100
tcttcaccga gactagtgga gaagaggatc tcaacctggc ctcgttcctt atggaccgga   14160
aagtcatcct gccgagagtg gctcatgaga tcctgggtaa ttccttaact ggagttaggg   14220
aggcgattgc agggatgctt gatacgacca agtctctagt gagagccagc gttaggaaag   14280
gaggattatc atatgggata ttgaggaggc ttgtcaatta tgatctattg cagtacgaga   14340
cactgactag aactctcagg aaaccggtga aagacaacat cgaatatgag tatatgtgtt   14400
cagttgagct agctgtcggt ctaaggcaga aaatgtggat ccacctgact tacgggagac   14460
ccatacatgg gctagaaaca ccagaccctt tagagctctt gaggggaata tttatcgaag   14520
gttcagaggt gtgcaagctt tgcaggtctg aaggagcaga ccccatctat acatggttct   14580
atcttcctga caatatagac ctggacacgc ttacaaacgg atgtccggct ataagaatcc   14640
cctattttgg atcagccact gatgaaaggt cggaagccca actcgggtat gtaagaaatc   14700
taagcaaacc cgcaaaggcg gccatccgga tagctatggt gtatacgtgg gcctacggga   14760
ctgatgagat atcgtggatg gaagccgctc ttatagccca aacaagagct aatctgagct   14820
tagagaatct aaagctgctg actcctgttt caacctccac taatctatct cataggttga   14880
aagatacggc aacccagatg aagttctcta gtgcaacact agtccgtgca agtcggttca   14940
taacaatatc aaatgataac atggcactca aagaagcagg ggagtcgaag gatactaatc   15000
tcgtgtatca gcagattatg ctaactgggc taagcttgtt cgagttcaat atgagatata   15060
agaaaggttc cttagggaag ccactgatat tgcacttaca tcttaataac gggtgctgta   15120
taatggagtc cccacaggag gcgaatatcc ccccaaggtc cacattagat ttagagatta   15180
cacaagagaa caataaattg atctatgatc ctgatccact caaggatgtg gaccttgagc   15240
tatttagcaa ggtcagagat gttgtacaca cagttgacat gacttattgg tcagatgatg   15300
aagttatcag agcaaccagt atctgtactg caatgacgat agctgataca atgtctcaat   15360
tagatagaga caacttaaaa gagatgatcg cactagtaaa tgacgatgat gtcaacagct   15420
tgattactga gtttatggtg attgatgttc ctttattttg ctcaacgttc ggggggtattc   15480
tagtcaatca gtttgcatac tcactctacg gcttaaacat cagaggaagg gaagaaatat   15540
ggggacatgt agtccggatt cttaaagata cctcccacgc agttttaaaa gtcttatcta   15600
atgctctatc tcatcccaaa atcttcaaac gattctggaa tgcaggtgtc gtggaacctg   15660
tgtatgggcc taacctctca aatcaggata agatactctt ggccctctct gtctgtgaat   15720
attctgtgga tctattcatg cacgattggc aagggggtgt accgcttgag atctttatct   15780
gtgacaatga cccagatgtg gccgacatga ggaggtcctc tttcttggca agacatcttg   15840
catacctatg cagcttggca gagatatcta gggatgggcc aagattagaa tcaatgaact   15900
ctctagagag gctcgagtca ctaaagagtt acctggaact cacatttctt gatgacccgg   15960
tactgaggta cagtcagttg actggcctag tcatcaaagt attcccatct actttgacct   16020
atatccggaa gtcatctata aaagtgttaa ggacaagagg tataggagtc cctgaagtct   16080
tagaagattg ggatcccgag gcagataatg cactgttaga tggtatcgcg gcagaaatac   16140
aacagaatat tcctttggga catcagacta gagccccttt ttgggggttg agagtatcca   16200
agtcacaggt actgcgtctc cgggggtaca aggagatcac aagaggtgag atagcagat   16260
caggtgttgg tctgacgtta ccattcgatg gaagatatct atctcaccag ctgaggctct   16320
ttggcatcaa cagtactagc tgcttgaaag cacttgaact tacctaccta ttgagcccct   16380
tagttgacaa ggataaagat aggctatatt taggggaagg agctggggcc atgctttcct   16440
gttatgacgc tactcttggc ccatgcatca actattataa ctcaggggta tactcttgtg   16500
atgtcaatgg gcagagagag ttaaatatat atcctgctga ggtggcacta gtgggaaaga   16560
aattaaacaa tgttactagt ctgggtcaaa gagttaaagt gttattcaac gggaatcctg   16620
gctcgacatg gattgggaat gatgagtgtg aggctttgat ttggaatgaa ttacagaata   16680
gctcgatagg cctagtccac tgtgacatgg agggaggaga tcataaggat gatcaagttg   16740
tactgcatga gcattacagt gtaatccgga tcgcgtatct ggtgggggat cgagacgttg   16800
tgcttataag caagattgct cccaggctgg gcacggattg gaccaggcag ctcagcctat   16860
atctgagata ctgggacgag gttaacctaa tagtgcttaa aacatctaac cctgcttcca   16920
cagagatgta tctcctatcg aggcacccca aatctgacat tatagaggac agcaagacag   16980
```

-continued

SEQUENCE LISTING

```
tgttagctag tctcctccct ttgtcaaaag aagatagcat caagatagaa aagtggatct  17040
taatagagaa ggcaaaggct cacgaatggg ttactcggga attgagagaa ggaagctctt  17100
catcagggat gcttagacct taccatcaag cactgcagac gtttggcttt gaaccaaact  17160
tgtataaatt gagcagagat ttcttgtcca ccatgaacat agctgataca cacaactgca  17220
tgatagcttt caacagggtt ttgaaggata caatcttcga atgggctaga ataactgagt  17280
cagataaaag gcttaaacta actggtaagt atgacctgta tcctgtgaga gattcaggca  17340
agttgaagac aatttctaga agacttgtgc tatcttggat atctttatct atgtccacaa  17400
gattggtaac tgggtcattc cctgaccaga agtttgaagc aagacttcaa ttgggaatag  17460
tttcattatc atcccgtgaa atcaggaacc tgagggttat cacaaaaact ttattagaca  17520
ggtttgagga tattatacat agtataacgt atagattcct caccaaagaa ataaagattt  17580
tgatgaagat tttaggggca gtcaagatgt tcggggccag gcaaaatgaa tacacgaccg  17640
tgattgatga tggatcacta ggtgatatcg agccatatga cagctcgtaa taattagtcc  17700
ctatcgtgca gaacgatcga agctccgcgg tacctggaag tcttggactt gtccatatga  17760
caatagtaag aaaaacttac aagaagacaa gaaaatttaa aaggatacat atctcttaaa  17820
ctcttgtctg gt                                                      17832
```

<210> 14
<211> 1503
<212> DNA
<213> Artificial Sequence

<220>
<223> Description of Artificial Sequence: Synthetic
polynucleotide

<400> 14

```
atggccgcca gagccagcat cctgagcggg ggcaagctgg acgcctggga gaagatcaga    60
ctgaggcctg gcggcaagaa gaagtaccgg ctgaagcacc tggtgtgggc cagcagagag   120
ctggatcgct tcgccctgaa tcctagcctg ctggagacca ccgagggctg ccagcagatc   180
atgaaccagc tgcagcccgc cgtgaaaacc ggcaccgagg agatcaagag cctgttcaac   240
accgtggcca ccctgtactg cgtgcaccag cggatcgacg tgaaggatac caaggaggcc   300
ctggacaaga tcgaggagat ccagaacaag agcaagcaga aaacccagca ggccgctgcc   360
gacaccggcg acagcagcaa agtgagccag aactacccca tcatccagaa tgcccagggc   420
cagatgatcc accagaacct gagccccaga accctgaatg cctgggtgaa agtgatcgag   480
gaaaaggcct tcagccccga agtgatccct atgttcagcg ccctgagcga gggcgccacc   540
ccccaggacc tgaacgtgat gctgaacatt gtgggcggac accaggccgc catgcagatg   600
ctgaaggaca ccatcaatga ggaggccgcc gagtgggaca gactgcaccc cgtgcaggcc   660
ggacccatcc cccctggcca gatcagagag cccagaggca gcgacatcgc cggcaccacc   720
tccacccctc aagaacagct gcagtggatg accggcaacc ctcccatccc tgtgggcaac   780
atctacaagc ggtggatcat cctgggcctg aacaagattg tgcggatgta cagccccgtg   840
tccatcctgg atatcaagca gggccccaag gagcccttca gagactacgt ggaccggttc   900
ttcaaggccc tgagagccga gcaggccacc caggacgtga agggctggat gaccgagacc   960
ctgctggtgc agaacgccaa ccccgactgc aagagcatcc tgaaggccct gggcagcggc  1020
gccacactgg aggagatgat gaccgcctgc cagggagtgg gcggacccgg ccacaaggcc  1080
agagtgctgg ccgaggccat gagccaggcc cagcagacca acatcatgat gcagcggggc  1140
aacttcagag gccagaagcg gatcaagtgc ttcaactgcg gcaaggaggg ccacctggcc  1200
agaaactgca gagcccccag gaagaagggc tgctggaagt gtggcaagga agggcaccag  1260
atgaaggact gcaccgagag gcaggccaat ttcctgggca agatttggcc tagcagcaag  1320
ggcagacccg gcaatttccc ccagagcaga cccgagccca ccgcccctcc cgccgagctg  1380
ttcggcatgg gcgagggcat cgccagcctg cccaagcagg agcagaagga cagagagcag  1440
gtgccccccc tggtgtccct gaagtccctg ttcggcaacg atcctctgag ccagggatcc  1500
tga                                                                1503
```

<210> 15
<211> 2160
<212> DNA
<213> Artificial Sequence

<220>
<223> Description of Artificial Sequence: Synthetic
polynucleotide

<400> 15

```
atgaagtgcc ttttgtactt agctttctta ttcatcgggg tgaattgcaa ggctagcgca    60
gagaatttgt gggtaacagt ctactatgga gtccctgtat ggaaggatgc agagacaaca   120
ttgttctgtg ctagtgacgc aaaggcttac gagacggaga agcacaatgt gtgggcaact   180
cacgcatgtg tcccaaccga tccaaatcct caagagattc atctagagaa tgtgactgaa   240
gaattcaata tgtggaagaa taatatggta gagcaaatgc atacagatat cattagttta   300
tgggaccagt cacttaaacc ctgcgttaaa ttgacgcctc tatgtgtgac acttcaatgt   360
actaatgtta caaacaacat aacagatgat atgagaggag aactgaagaa ctgtagtttc   420
aacatgacga cagagttgcg tgacaagaaa cagaaagtgt attcactatt ctatcggttg   480
gatgtagtac agataaatga gaatcaagga aacaggtcca acaactctaa caaagagtac   540
agacttatta attgcaatac cagtgctatc acgcaagcct gcccaaaggt ttcatttgaa   600
ccaataccta ttcattattg tgcacctgct ggattcgcca tcctcaaatg taaagacaag   660
aagttcaatg gaacaggacc ctgcccatca gtttcaaccg ttcagtgcac ccacggaatc   720
aagcctgtag ttagtactca attattgtta aatgggagct tagctgaaga agaagttatg   780
attagatcag agaatattac caataatgcg aagaacatct tggttcaatt caatactcca   840
```

SEQUENCE LISTING

```
gtccagatca attgcacaag gcctaataat aataccagaa agagtataag aattgggcca     900
ggacaggcat tctatgcaac aggagatata atcggagaca ttcgacaagc gcactgcact     960
gtttctaagg ccacttggaa tgaaacattg ggtaaagttg taaagcaact tcggaagcat    1020
ttcggaaata acacaattat tagatttgcg aactcatctg gaggggatct ggaagtgaca    1080
acacactctt tcaattgcgg tggcgagttc ttctattgta atacaagtgg attatttaac    1140
tctacttgga tttcaaatac ctcagtccaa ggatctaatt caacagggtc taacgattct    1200
ataacattac cttgccgtat aaagcaaatt attaatatgt ggcaaagaat cgggcaagcg    1260
atgtatgctc cacctattca aggcgtgatt cgttgcgttt caaacataac agggttgatc    1320
ctgaccaggg atggaggctc taccaattcc accaccgaga ccttccgtcc cggtggcgga    1380
gatatgcggg ataactggag atcagagctc tataagtata aggttgtgaa gattgaacct    1440
cttggagttg cccctacaag agcaaagaga agggtggttg gccgagagaa gagagcagtt    1500
ggcatcggtg ctgtctttct cggatttctt ggagcagctg gatccactat gggagcagca    1560
tcaatgacac taacagtgca ggctagaaat ttgcttagcg gaatcgttca gcagcagagc    1620
aatttactaa gagcaattga agcacagcaa catctcttaa agttgacggt gtggggcatt    1680
aaacaactac aagcgagagt gcttgccgtc gaaagatatt tgcgagacca acagctattg    1740
ggtatttggg gttgttctgg gaaattaatt tgcacaacaa atgttccatg gaactcctcc    1800
tggagtaata ggaatttaag tgagatatgg gacaacatga catggttgca gtgggacaag    1860
gaaatctcaa attatacaca gataatctat ggattattag aagagtctca gaatcagcaa    1920
gagaagaatg aacaggattt gcttgcattg gataagtggg cttctctatg gaactggttc    1980
gatattagta attggctctg gtatattaag agctctattg cctctttttt ctttatcata    2040
gggttaatca ttggactatt cttggttctc cgagttggta tttatctttg cattaaatta    2100
aagcacacca agaaaagaca gatttataca gacatagaga tgaaccgact tggaaagtaa    2160

<210>    16
<211>  2250
<212> DNA
<213> Artificial Sequence

<220>
<223> Description of Artificial Sequence: Synthetic
polynucleotide

<400>    16
atgacagcat atatccagag atcacagtgc atctcaacat cactactggt tgttctcacc      60
acattggtct cgtgtcaggc tagcgcagag aatttgtggg taacagtcta ctatggagtc     120
cctgtatgga aggatgcaga gacaacattg ttctgtgcta gtgacgcaaa ggcttacgag     180
acggagaagc acaatgtgtg ggcaactcac gcatgtgtcc caaccgatcc aaatcctcaa     240
gagattcatc tagagaatgt gactgaagaa ttcaatatgt ggaagaataa tatggtagag     300
caaatgcata cagatatcat tagtttatgg gaccagtcac ttaaaccctg cgttaaattg     360
acgcctctat gtgtgacact tcaatgtact aatgttacaa acaacataac agatgatatg     420
agaggagaac tgaagaactg tagtttcaac atgacgacag agttgcgtga caagaaacag     480
aaagtgtatt cactattcta tcggttggat gtagtacaga taaatgagaa tcaaggaaac     540
aggtccaaca actctaacaa agagtacaga cttattaatt gcaataccag tgctatcacg     600
caagcctgcc caaaggtttc atttgaacca atacctattc attattgtgc acctgctgga     660
ttcgccatcc tcaaatgtaa agacaagaag ttcaatggaa caggaccctg cccatcagtt     720
tcaaccgttc agtgcaccca cggaatcaag cctgtagtta gtactcaatt attgttaaat     780
gggagcttag ctgaagaaga agttatgatt agatcagaga atattaccaa taatgcgaag     840
aacatcttgg ttcaattcaa tactccagtc cagatcaatt gcacaaggcc taataataat     900
accagaaaga gtataagaat tgggccagga caggcattct atgcaacagg agatataatc     960
ggagacattc gacaagcgca ctgcactgtt tctaaggcca cttggaatga aacattgggt    1020
aaagttgtaa agcaacttcg gaagcatttc ggaaataaca caattattag atttgcgaac    1080
tcatctggag gggatctgga agtgacaaca cactctttca attgcggtgg cgagttcttc    1140
tattgtaata caagtggatt atttaactct acttggattt caaatacctc agtccaagga    1200
tctaattcaa cagggtctaa cgattctata acattacctt gccgtataaa gcaaattatt    1260
aatatgtggc aaagaatcgg gcaagcgatg tatgctccac ctattcaagg cgtgattcgt    1320
tgcgtttcaa acataacagg gttgatcctg accagggatg gaggctctac caattccacc    1380
accgagacct tccgtcccgg tggcggagat atgcgggata actggagatc agagctctat    1440
aagtataagg ttgtgaagat tgaacctctt ggagttgccc ctacaagagc aaagagaagg    1500
gtggttggcc gagagaagag agcagttggc atcggtgctg tctttctcgg atttcttgga    1560
gcagctggat ccactatggg agcagcatca atgacactaa cagtgcaggc tagaaatttg    1620
cttagcggaa tcgttcagca gcagagcaat ttactaagag caattgaagc acagcaacat    1680
ctcttaaagt tgacggtgtg gggcattaaa caactacaag cgagagtgct tgccgtcgaa    1740
agatatttgc gagaccaaca gctattgggt atttggggtt gttctgggaa attaatttgc    1800
acaacaaatg ttccatggaa ctcctcctgg agtaatagga atttaagtga gatatgggac    1860
aacatgacat ggttgcagtg ggacaaggaa atctcaaatt atacacagat aatctatgga    1920
ttattagaag agtctcagaa tcagcaagag aagaatgaac aggatttgct tgcattggat    1980
aagtgggctt ctctatggaa ctggttcgat attagtaatt ggctctggta tattaagaac    2040
tcaagagaga ctgtgattac gatcatagta gttatggtcg taatattggt ggtcattata    2100
gtgatcatca tcgtgcttta tagactcaga aggtcaatgc taatgggtaa tccagatgac    2160
cgtataccga gggacacata cacattagag ccgaagatca gacatatgta cacaaacggt    2220
gggtttgatg caatggctga gaaaagatga                                    2250

<210>    17
<211>  2379
<212> DNA
<213> Artificial Sequence
```

-continued

SEQUENCE LISTING

<220>
<223> Description of Artificial Sequence: Synthetic polynucleotide

<400> 17
atggaggaga aagcattctc acctgaagtg atccctatgt tcacagcatt atctgaggga 60
gctactcctc aagatcttaa cacaatgctt aacacagtcg gaggacatca agcagcaatg 120
caaatgttga aagatacaat taacgaggaa gcagcagaat gggatagaat ctataagaga 180
tggataatat taggattgaa caagattgtt agaatgtatt ctcctgtgtc aatccttgat 240
ataagacaag gacctaaaga gcctttcaga gattacgtcg atagatttgc aagaaattgt 300
agagcaccta gaaagaaggg atgttggaaa tgtgggaaag aaggacatca aatgaaagat 360
tgtactgaga gacaagctaa cttcttggga aagatatggc cttcaagatg gaaacctaag 420
atgataggag gaataggagg atttattaaa gtcagacaat atgatcaaat attgattgaa 480
atatgtggac ataaagctat tggaacagtc ctagtgggtc caacacctgt caacatcatt 540
ggtagaaatc ttctcactca aatcggatgt acactcaatt tcccaatatc acctattgag 600
accgtgcctg tcaaattgaa acctggaatg gatggaccta aagtcaaaca atggccatta 660
actgaggaga agattaaagc actggtagaa atttgtacag agatggagaa agaaggaaag 720
atttccaaga ttggtcctga gaatccttat aatactcctg tctttgctat taagaagaag 780
gatagtacca aatggaggaa attagtcgat ttcagagaac ttaacaagag gactcaagac 840
ttctgggaag tgcaattggg aatcccacac cctgcaggat tgaagaagaa gaagtctgtc 900
actgtcctag atgtgggaga tgcatatttc agtgtcccac tggatgaagg tttcagaaag 960
tatacagcat tcacaatccc ttccattaat aatgaaacac ctggaataag atatcaatat 1020
aatgtcttac ctcaagggtg gaaaggatct ccagcaatat tccaatcatc aatgacaaag 1080
atcttggagc ctttcagagc tcagaatcca gagatagtta tttaccaata catggatgat 1140
ttgtatgttg ggtcagatct cgagatcgga cagcacagga tggagaatag atggcaagta 1200
atgattgtct ggcaagtcga tagaatgaga ataagaacat ggaaatcctt ggtgaaacat 1260
caccttacag aggaggcaga actggaactg gcagagaata gggaaatatt gaaagatcca 1320
gtgcatggtg tctattacga tccttctaaa gatctgatag cagagatcca gtactggcaa 1380
gcaacatgga ttcctgagtg ggaattcgtc aacacacctc cattagtgaa actatggtac 1440
caattagaga agaatgtcac cgagaacttc aacatgtgga agaacgatat ggtagatcaa 1500
atgcacgaag atatcatctc cttgtgggat caatcactta aaccttgtgt taaattgaca 1560
ccttgggtac ctgctcataa agggatagga ggaaacgaac aagtggataa attggtgtcc 1620
caagggatca ggaaagtctt gttcctagat ggaattgata aagctcaagc aaaggaaatt 1680
gtcgcaagct gtgataagtg tcaattaaag ggagaggcaa tgcacggaca agtcgattgt 1740
tcacctggta tttggcaact tgattgtaca catttggagg gtaaagttat tctagtagca 1800
gtacatgtcg cttctggtta tattgaggca gaagtgatac ctgctgagac aggacaggag 1860
accgcatact ttctacttaa gttagctatg aataaggagc tcaagaagat aataggacaa 1920
gttagagatc aagcagagca ccttaagaca gctgtccaaa tggcagtgtt tatacacaac 1980
tttaagagaa agggtggaat cggaggatat tccgcaggag agagaatctg gaaaggtcct 2040
gctaaattgt tatggaaagg agaaggagca gttgtaatac aagataattc tgatataaaa 2100
gtagtcccta gaaggaaagc taagattatt agagattatg ggaaacaaat ggcaggagct 2160
gattgtgtgt ttctaggagc agcaggatcc actatgggag ctgcatcaat gacacttacc 2220
gtgcaggcta gacagcttct ttcaggaatt gtacagcaac agaataattt gctaagagca 2280
attgaagctc aacaacactt acttcaactt acagtctggg gaatcaagca agcacctaca 2340
aaagcaaaga gaagagtcgt ccaaagagag aaaagataa 2379

<210> 18
<211> 2247
<212> DNA
<213> Artificial Sequence

<220>
<223> Description of Artificial Sequence: Synthetic polynucleotide

<220>
<221> CDS
<222> (1) . . . (2247)

<400> 18
atg aca gca tat atc cag aga tca cag tgc atc tca aca tca cta ctg 48
Met Thr Ala Tyr Ile Gln Arg Ser Gln Cys Ile Ser Thr Ser Leu Leu
1 5 10 15
gtt gtt ctc acc aca ttg gtc tcg tgt cag gct agc gca gag aat ttg 96
Val Val Leu Thr Thr Leu Val Ser Cys Gln Ala Ser Ala Glu Asn Leu
20 25 30
tgg gta aca gtc tac tat gga gtc cct gta tgg aag gat gca gag aca 144
Trp Val Thr Val Tyr Tyr Gly Val Pro Val Trp Lys Asp Ala Glu Thr
35 40 45
aca ttg ttc tgt gct agt gac gca aag gct tac gag acg gag aag cac 192
Thr Leu Phe Cys Ala Ser Asp Ala Lys Ala Tyr Glu Thr Glu Lys His
50 55 60
aat gtg tgg gca act cac gca tgt gtc cca acc gat cca aat cct caa 240
Asn Val Trp Ala Thr His Ala Cys Val Pro Thr Asp Pro Asn Pro Gln
65 70 75 80
gag att cat cta gag aat gtg act gaa gaa ttc aat atg tgg aag aat 288
Glu Ile His Leu Glu Asn Val Thr Glu Glu Phe Asn Met Trp Lys Asn -continued

SEQUENCE LISTING

```
          85          90          95
aat atg gta gag caa atg cat aca gat atc att agt tta tgg gac cag      336
Asn Met Val Glu Gln Met His Thr Asp Ile Ile Ser Leu Trp Asp Gln
      100         105         110
tca ctt aaa ccc tgc gtt aaa ttg acg cct cta tgt gtg aca ctt caa      384
Ser Leu Lys Pro Cys Val Lys Leu Thr Pro Leu Cys Val Thr Leu Gln
     115         120         125
tgt act aat gtt aca aac aac ata aca gat gat atg aga gga gaa ctg      432
Cys Thr Asn Val Thr Asn Asn Ile Thr Asp Asp Met Arg Gly Glu Leu
  130         135         140
aag aac tgt agt ttc aac atg acg aca gag ttg cgt gac aag aaa cag      480
Lys Asn Cys Ser Phe Asn Met Thr Thr Glu Leu Arg Asp Lys Lys Gln
145         150         155         160
aaa gtg tat tca cta ttc tat cgg ttg gat gta gta cag ata aat gag      528
Lys Val Tyr Ser Leu Phe Tyr Arg Leu Asp Val Val Gln Ile Asn Glu
        165         170         175
aat caa gga aac agg tcc aac aac tct aac aaa gag tac aga ctt att      576
Asn Gln Gly Asn Arg Ser Asn Asn Ser Asn Lys Glu Tyr Arg Leu Ile
      180         185         190
aat tgc aat acc agt gct atc acg caa gcc tgc cca aag gtt tca ttt      624
Asn Cys Asn Thr Ser Ala Ile Thr Gln Ala Cys Pro Lys Val Ser Phe
    195         200         205
gaa cca ata cct att cat tat tgt gca cct gct gga ttc gcc atc ctc      672
Glu Pro Ile Pro Ile His Tyr Cys Ala Pro Ala Gly Phe Ala Ile Leu
  210         215         220
aaa tgt aaa gac aag aag ttc aat gga aca gga ccc tgc cca tca gtt      720
Lys Cys Lys Asp Lys Lys Phe Asn Gly Thr Gly Pro Cys Pro Ser Val
225         230         235         240
tca acc gtt cag tgc acc cac gga atc aag cct gta gtt agt act caa      768
Ser Thr Val Gln Cys Thr His Gly Ile Lys Pro Val Val Ser Thr Gln
        245         250         255
tta ttg tta aat ggg agc tta gct gaa gaa gaa gtt atg att aga tca      816
Leu Leu Leu Asn Gly Ser Leu Ala Glu Glu Glu Val Met Ile Arg Ser
      260         265         270
gag aat att acc aat aat gcg aag aac atc ttg gtt caa ttc aat act      864
Glu Asn Ile Thr Asn Asn Ala Lys Asn Ile Leu Val Gln Phe Asn Thr
    275         280         285
cca gtc cag atc aat tgc aca agg cct aat aat aat acc aga aag agt      912
Pro Val Gln Ile Asn Cys Thr Arg Pro Asn Asn Asn Thr Arg Lys Ser
  290         295         300
ata aga att ggg cca gga cag gca ttc tat gca aca gga gat ata atc      960
Ile Arg Ile Gly Pro Gly Gln Ala Phe Tyr Ala Thr Gly Asp Ile Ile
305         310         315         320
gga gac att cga caa gcg cac tgc act gtt tct aag gcc act tgg aat     1008
Gly Asp Ile Arg Gln Ala His Cys Thr Val Ser Lys Ala Thr Trp Asn
        325         330         335
gaa aca ttg ggt aaa gtt gta aag caa ctt cgg aag cat ttc gga aat     1056
Glu Thr Leu Gly Lys Val Val Lys Gln Leu Arg Lys His Phe Gly Asn
      340         345         350
aac aca att att aga ttt gcg aac tca tct gga ggg gat ctg gaa gtg     1104
Asn Thr Ile Ile Arg Phe Ala Asn Ser Ser Gly Gly Asp Leu Glu Val
    355         360         365
aca aca cac tct ttc aat tgc ggt ggc gag ttc ttc tat tgt aat aca     1152
Thr Thr His Ser Phe Asn Cys Gly Gly Glu Phe Phe Tyr Cys Asn Thr
  370         375         380
agt gga tta ttt aac tct act tgg att tca aat acc tca gtc caa gga     1200
Ser Gly Leu Phe Asn Ser Thr Trp Ile Ser Asn Thr Ser Val Gln Gly
385         390         395         400
tct aat tca aca ggg tct aac gat tct ata aca tta cct tgc cgt ata     1248
Ser Asn Ser Thr Gly Ser Asn Asp Ser Ile Thr Leu Pro Cys Arg Ile
        405         410         415
aag caa att att aat atg tgg caa aga atc ggg caa gcg atg tat gct     1296
Lys Gln Ile Ile Asn Met Trp Gln Arg Ile Gly Gln Ala Met Tyr Ala
      420         425         430
cca cct att caa ggc gtg att cgt tgc gtt tca aac ata aca ggg ttg     1344
Pro Pro Ile Gln Gly Val Ile Arg Cys Val Ser Asn Ile Thr Gly Leu
    435         440         445
atc ctg acc agg gat gga ggc tct acc aat tcc acc acc gag acc ttc     1392
Ile Leu Thr Arg Asp Gly Gly Ser Thr Asn Ser Thr Thr Glu Thr Phe
  450         455         460
cgt ccc ggt ggc gga gat atg cgg gat aac tgg aga tca gag ctc tat     1440
Arg Pro Gly Gly Gly Asp Met Arg Asp Asn Trp Arg Ser Glu Leu Tyr
465         470         475         480
aag tat aag gtt gtg aag att gaa cct ctt gga gtt gcc cct aca aga     1488
Lys Tyr Lys Val Val Lys Ile Glu Pro Leu Gly Val Ala Pro Thr Arg
        485         490         495
gca aag aga agg gtg gtt ggc cga gag aag aga gca gtt ggc atc ggt     1536
```

-continued

SEQUENCE LISTING

```
Ala Lys Arg Arg Val Val Gly Arg Glu Lys Arg Ala Val Gly Ile Gly
        500           505           510
gct gtc ttt ctc gga ttt ctt gga gca gct gga tcc act atg gga gca     1584
Ala Val Phe Leu Gly Phe Leu Gly Ala Ala Gly Ser Thr Met Gly Ala
    515           520           525
gca tca atg aca cta aca gtg cag gct aga aat ttg ctt agc gga atc     1632
Ala Ser Met Thr Leu Thr Val Gln Ala Arg Asn Leu Leu Ser Gly Ile
  530           535           540
gtt cag cag cag agc aat tta cta aga gca att gaa gca cag caa cat     1680
Val Gln Gln Gln Ser Asn Leu Leu Arg Ala Ile Glu Ala Gln Gln His
545           550           555           560
ctc tta aag ttg acg gtg tgg ggc att aaa caa cta caa gcg aga gtg     1728
Leu Leu Lys Leu Thr Val Trp Gly Ile Lys Gln Leu Gln Ala Arg Val
         565           570           575
ctt gcc gtc gaa aga tat ttg cga gac caa cag cta ttg ggt att tgg     1776
Leu Ala Val Glu Arg Tyr Leu Arg Asp Gln Gln Leu Leu Gly Ile Trp
        580           585           590
ggt tgt tct ggg aaa tta att tgc aca aca aat gtt cca tgg aac tcc     1824
Gly Cys Ser Gly Lys Leu Ile Cys Thr Thr Asn Val Pro Trp Asn Ser
    595           600           605
tcc tgg agt aat agg aat tta agt gag ata tgg gac aac atg aca tgg     1872
Ser Trp Ser Asn Arg Asn Leu Ser Glu Ile Trp Asp Asn Met Thr Trp
  610           615           620
ttg cag tgg gac aag gaa atc tca aat tat aca cag ata atc tat gga     1920
Leu Gln Trp Asp Lys Glu Ile Ser Asn Tyr Thr Gln Ile Ile Tyr Gly
625           630           635           640
tta tta gaa gag tct cag aat cag caa gag aag aat gaa cag gat ttg     1968
Leu Leu Glu Glu Ser Gln Asn Gln Gln Glu Lys Asn Glu Gln Asp Leu
         645           650           655
ctt gca ttg gat aag tgg gct tct cta tgg aac tgg ttc gat att agt     2016
Leu Ala Leu Asp Lys Trp Ala Ser Leu Trp Asn Trp Phe Asp Ile Ser
        660           665           670
aat tgg ctc tgg tat att aag aac tca aga gag act gtg att acg atc     2064
Asn Trp Leu Trp Tyr Ile Lys Asn Ser Arg Glu Thr Val Ile Thr Ile
    675           680           685
ata gta gtt atg gtc gta ata ttg gtg gtc att ata gtg atc atc atc     2112
Ile Val Val Met Val Val Ile Leu Val Val Ile Ile Val Ile Ile Ile
   690           695           700
gtg ctt tat aga ctc aga agg tca atg cta atg ggt aat cca gat gac     2160
Val Leu Tyr Arg Leu Arg Arg Ser Met Leu Met Gly Asn Pro Asp Asp
705           710           715           720
cgt ata ccg agg gac aca tac aca tta gag ccg aag atc aga cat atg     2208
Arg Ile Pro Arg Asp Thr Tyr Thr Leu Glu Pro Lys Ile Arg His Met
          725           730           735
tac aca aac ggt ggg ttt gat gca atg gct gag aaa aga                 2247
Tyr Thr Asn Gly Gly Phe Asp Ala Met Ala Glu Lys Arg
        740           745

<210>    19
<211>   749
<212> PRT
<213> Artificial Sequence

<220>
<223> Description of Artificial Sequence: Synthetic
polypeptide

<400>    19
Met Thr Ala Tyr Ile Gln Arg Ser Gln Cys Ile Ser Thr Ser Leu Leu
1       5           10           15
Val Val Leu Thr Thr Leu Val Ser Cys Gln Ala Ser Ala Glu Asn Leu
       20           25           30
Trp Val Thr Val Tyr Tyr Gly Val Pro Val Trp Lys Asp Ala Glu Thr
    35           40           45
Thr Leu Phe Cys Ala Ser Asp Ala Lys Ala Tyr Glu Thr Glu Lys His
  50           55           60
Asn Val Trp Ala Thr His Ala Cys Val Pro Thr Asp Pro Asn Pro Gln
65           70           75           80
Glu Ile His Leu Glu Asn Val Thr Glu Glu Phe Asn Met Trp Lys Asn
          85           90           95
Asn Met Val Glu Gln Met His Thr Asp Ile Ile Ser Leu Trp Asp Gln
       100           105           110
Ser Leu Lys Pro Cys Val Lys Leu Thr Pro Leu Cys Val Thr Leu Gln
      115           120           125
Cys Thr Asn Val Thr Asn Asn Ile Thr Asp Asp Met Arg Gly Glu Leu
  130           135           140
Lys Asn Cys Ser Phe Asn Met Thr Thr Glu Leu Arg Asp Lys Lys Gln
```

-continued

SEQUENCE LISTING

```
145                 150                 155                 160
Lys Val Tyr Ser Leu Phe Tyr Arg Leu Asp Val Val Gln Ile Asn Glu
                165                 170                 175
Asn Gln Gly Asn Arg Ser Asn Asn Ser Asn Lys Glu Tyr Arg Leu Ile
            180                 185                 190
Asn Cys Asn Thr Ser Ala Ile Thr Gln Ala Cys Pro Lys Val Ser Phe
        195                 200                 205
Glu Pro Ile Pro Ile His Tyr Cys Ala Pro Ala Gly Phe Ala Ile Leu
    210                 215                 220
Lys Cys Lys Asp Lys Lys Phe Asn Gly Thr Gly Pro Cys Pro Ser Val
225                 230                 235                 240
Ser Thr Val Gln Cys Thr His Gly Ile Lys Pro Val Val Ser Thr Gln
                245                 250                 255
Leu Leu Leu Asn Gly Ser Leu Ala Glu Glu Glu Val Met Ile Arg Ser
            260                 265                 270
Glu Asn Ile Thr Asn Asn Ala Lys Asn Ile Leu Val Gln Phe Asn Thr
        275                 280                 285
Pro Val Gln Ile Asn Cys Thr Arg Pro Asn Asn Asn Thr Arg Lys Ser
    290                 295                 300
Ile Arg Ile Gly Pro Gly Gln Ala Phe Tyr Ala Thr Gly Asp Ile Ile
305                 310                 315                 320
Gly Asp Ile Arg Gln Ala His Cys Thr Val Ser Lys Ala Thr Trp Asn
                325                 330                 335
Glu Thr Leu Gly Lys Val Val Lys Gln Leu Arg Lys His Phe Gly Asn
            340                 345                 350
Asn Thr Ile Ile Arg Phe Ala Asn Ser Ser Gly Gly Asp Leu Glu Val
        355                 360                 365
Thr Thr His Ser Phe Asn Cys Gly Gly Glu Phe Phe Tyr Cys Asn Thr
    370                 375                 380
Ser Gly Leu Phe Asn Ser Thr Trp Ile Ser Asn Thr Ser Val Gln Gly
385                 390                 395                 400
Ser Asn Ser Thr Gly Ser Asn Asp Ser Ile Thr Leu Pro Cys Arg Ile
                405                 410                 415
Lys Gln Ile Ile Asn Met Trp Gln Arg Ile Gly Gln Ala Met Tyr Ala
            420                 425                 430
Pro Pro Ile Gln Gly Val Ile Arg Cys Val Ser Asn Ile Thr Gly Leu
        435                 440                 445
Ile Leu Thr Arg Asp Gly Gly Ser Thr Asn Ser Thr Thr Glu Thr Phe
    450                 455                 460
Arg Pro Gly Gly Gly Asp Met Arg Asp Asn Trp Arg Ser Glu Leu Tyr
465                 470                 475                 480
Lys Tyr Lys Val Val Lys Ile Glu Pro Leu Gly Val Ala Pro Thr Arg
                485                 490                 495
Ala Lys Arg Arg Val Val Gly Arg Glu Lys Arg Ala Val Gly Ile Gly
            500                 505                 510
Ala Val Phe Leu Gly Phe Leu Gly Ala Ala Gly Ser Thr Met Gly Ala
        515                 520                 525
Ala Ser Met Thr Leu Thr Val Gln Ala Arg Asn Leu Leu Ser Gly Ile
    530                 535                 540
Val Gln Gln Gln Ser Asn Leu Leu Arg Ala Ile Glu Ala Gln Gln His
545                 550                 555                 560
Leu Leu Lys Leu Thr Val Trp Gly Ile Lys Gln Leu Gln Ala Arg Val
                565                 570                 575
Leu Ala Val Glu Arg Tyr Leu Arg Asp Gln Gln Leu Leu Gly Ile Trp
            580                 585                 590
Gly Cys Ser Gly Lys Leu Ile Cys Thr Thr Asn Val Pro Trp Asn Ser
        595                 600                 605
Ser Trp Ser Asn Arg Asn Leu Ser Glu Ile Trp Asp Asn Met Thr Trp
    610                 615                 620
Leu Gln Trp Asp Lys Glu Ile Ser Asn Tyr Thr Gln Ile Ile Tyr Gly
625                 630                 635                 640
Leu Leu Glu Glu Ser Gln Asn Gln Gln Glu Lys Asn Glu Gln Asp Leu
                645                 650                 655
Leu Ala Leu Asp Lys Trp Ala Ser Leu Trp Asn Trp Phe Asp Ile Ser
            660                 665                 670
Asn Trp Leu Trp Tyr Ile Lys Asn Ser Arg Glu Thr Val Ile Thr Ile
        675                 680                 685
Ile Val Val Met Val Val Ile Leu Val Val Ile Ile Val Ile Ile Ile
    690                 695                 700
Val Leu Tyr Arg Leu Arg Arg Ser Met Leu Met Gly Asn Pro Asp Asp
705                 710                 715                 720
Arg Ile Pro Arg Asp Thr Tyr Thr Leu Glu Pro Lys Ile Arg His Met
                725                 730                 735
Tyr Thr Asn Gly Gly Phe Asp Ala Met Ala Glu Lys Arg
            740                 745
```

```
                              SEQUENCE LISTING


<160> NUMBER OF SEQ ID NOS: 19

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Pro Thr Lys Ala Lys Arg Arg Val Val Gln Arg Glu Lys Arg
1               5                   10                  15


<210> SEQ ID NO 2
<211> LENGTH: 719
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Cys Leu Leu Tyr Leu Ala Phe Leu Phe Ile Gly Val Asn Cys
1               5                   10                  15

Lys Ala Ser Ala Glu Asn Leu Trp Val Thr Val Tyr Tyr Gly Val Pro
            20                  25                  30

Val Trp Lys Asp Ala Glu Thr Thr Leu Phe Cys Ala Ser Asp Ala Lys
        35                  40                  45

Ala Tyr Glu Thr Glu Lys His Asn Val Trp Ala Thr His Ala Cys Val
    50                  55                  60

Pro Thr Asp Pro Asn Pro Gln Glu Ile His Leu Glu Asn Val Thr Glu
65                  70                  75                  80

Glu Phe Asn Met Trp Lys Asn Asn Met Val Glu Gln Met His Thr Asp
                85                  90                  95

Ile Ile Ser Leu Trp Asp Gln Ser Leu Lys Pro Cys Val Lys Leu Thr
            100                 105                 110

Pro Leu Cys Val Thr Leu Gln Cys Thr Asn Val Thr Asn Asn Ile Thr
        115                 120                 125

Asp Asp Met Arg Gly Glu Leu Lys Asn Cys Ser Phe Asn Met Thr Thr
    130                 135                 140

Glu Leu Arg Asp Lys Lys Gln Lys Val Tyr Ser Leu Phe Tyr Arg Leu
145                 150                 155                 160

Asp Val Val Gln Ile Asn Glu Asn Gln Gly Asn Arg Ser Asn Asn Ser
                165                 170                 175

Asn Lys Glu Tyr Arg Leu Ile Asn Cys Asn Thr Ser Ala Ile Thr Gln
            180                 185                 190

Ala Cys Pro Lys Val Ser Phe Glu Pro Ile Pro Ile His Tyr Cys Ala
        195                 200                 205

Pro Ala Gly Phe Ala Ile Leu Lys Cys Lys Asp Lys Lys Phe Asn Gly
    210                 215                 220

Thr Gly Pro Cys Pro Ser Val Ser Thr Val Gln Cys Thr His Gly Ile
225                 230                 235                 240

Lys Pro Val Val Ser Thr Gln Leu Leu Leu Asn Gly Ser Leu Ala Glu
                245                 250                 255

Glu Glu Val Met Ile Arg Ser Glu Asn Ile Thr Asn Asn Ala Lys Asn
            260                 265                 270

Ile Leu Val Gln Phe Asn Thr Pro Val Gln Ile Asn Cys Thr Arg Pro
```

-continued

```
        275                 280                 285

Asn Asn Asn Thr Arg Lys Ser Ile Arg Ile Gly Pro Gly Gln Ala Phe
    290                 295                 300

Tyr Ala Thr Gly Asp Ile Ile Gly Asp Ile Arg Gln Ala His Cys Thr
305                 310                 315                 320

Val Ser Lys Ala Thr Trp Asn Glu Thr Leu Gly Lys Val Val Lys Gln
                325                 330                 335

Leu Arg Lys His Phe Gly Asn Asn Thr Ile Ile Arg Phe Ala Asn Ser
            340                 345                 350

Ser Gly Gly Asp Leu Glu Val Thr Thr His Ser Phe Asn Cys Gly Gly
        355                 360                 365

Glu Phe Phe Tyr Cys Asn Thr Ser Gly Leu Phe Asn Ser Thr Trp Ile
    370                 375                 380

Ser Asn Thr Ser Val Gln Gly Ser Asn Ser Thr Gly Ser Asn Asp Ser
385                 390                 395                 400

Ile Thr Leu Pro Cys Arg Ile Lys Gln Ile Ile Asn Met Trp Gln Arg
                405                 410                 415

Ile Gly Gln Ala Met Tyr Ala Pro Pro Ile Gln Gly Val Ile Arg Cys
            420                 425                 430

Val Ser Asn Ile Thr Gly Leu Ile Leu Thr Arg Asp Gly Gly Ser Thr
        435                 440                 445

Asn Ser Thr Thr Glu Thr Phe Arg Pro Gly Gly Gly Asp Met Arg Asp
    450                 455                 460

Asn Trp Arg Ser Glu Leu Tyr Lys Tyr Lys Val Val Lys Ile Glu Pro
465                 470                 475                 480

Leu Gly Val Ala Pro Thr Arg Ala Lys Arg Arg Val Val Gly Arg Glu
                485                 490                 495

Lys Arg Ala Val Gly Ile Gly Ala Val Phe Leu Gly Phe Leu Gly Ala
            500                 505                 510

Ala Gly Ser Thr Met Gly Ala Ala Ser Met Thr Leu Thr Val Gln Ala
        515                 520                 525

Arg Asn Leu Leu Ser Gly Ile Val Gln Gln Gln Ser Asn Leu Leu Arg
    530                 535                 540

Ala Ile Glu Ala Gln Gln His Leu Leu Lys Leu Thr Val Trp Gly Ile
545                 550                 555                 560

Lys Gln Leu Gln Ala Arg Val Leu Ala Val Glu Arg Tyr Leu Arg Asp
                565                 570                 575

Gln Gln Leu Leu Gly Ile Trp Gly Cys Ser Gly Lys Leu Ile Cys Thr
            580                 585                 590

Thr Asn Val Pro Trp Asn Ser Ser Trp Ser Asn Arg Asn Leu Ser Glu
        595                 600                 605

Ile Trp Asp Asn Met Thr Trp Leu Gln Trp Asp Lys Glu Ile Ser Asn
    610                 615                 620

Tyr Thr Gln Ile Ile Tyr Gly Leu Leu Glu Glu Ser Gln Asn Gln Gln
625                 630                 635                 640

Glu Lys Asn Glu Gln Asp Leu Leu Ala Leu Asp Lys Trp Ala Ser Leu
                645                 650                 655

Trp Asn Trp Phe Asp Ile Ser Asn Trp Leu Trp Tyr Ile Lys Ser Ser
            660                 665                 670

Ile Ala Ser Phe Phe Phe Ile Ile Gly Leu Ile Ile Gly Leu Phe Leu
        675                 680                 685

Val Leu Arg Val Gly Ile Tyr Leu Cys Ile Lys Leu Lys His Thr Lys
    690                 695                 700
```

Lys Arg Gln Ile Tyr Thr Asp Ile Glu Met Asn Arg Leu Gly Lys
705 710 715

<210> SEQ ID NO 3
<211> LENGTH: 2162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3
atgaagtgcc ttttgtactt agctttctta ttcatcgggg tgaattgcaa ggctagcgca 60
gagaatttgt gggtaacagt ctactatgga gtccctgtat ggaaggatgc agagacaaca 120
ttgttctgtg ctagtgacgc aaaggcttac gagacggaga agcacaatgt gtgggcaact 180
cacgcatgtg tcccaaccga tccaaatcct caagagattc atctagagaa tgtgactgaa 240
gaattcaata tgtggaagaa taatatggta gagcaaatgc atacagatat cattagttta 300
tgggaccagt cacttaaacc ctgcgttaaa ttgacgcctc tatgtgtgac acttcaatgt 360
actaatgtta caaacaacat aacagatgat atgagaggag aactgaagaa ctgtagtttc 420
aacatgacga cagagttgcg tgacaagaaa cagaaagtgt attcactatt ctatcggttg 480
gatgtagtac agataaatga gaatcaagga aacaggtcca acaactctaa caaagagtac 540
agacttatta attgcaatac cagtgctatc acgcaagcct gcccaaaggt ttcatttgaa 600
ccaataccta ttcattattg tgcacctgct ggattcgcca tcctcaaatg taaagacaag 660
aagttcaatg gaacaggacc ctgcccatca gtttcaaccg ttcagtgcac ccacggaatc 720
aagcctgtag ttagtactca attattgtta aatgggagct tagctgaaga agaagttatg 780
attagatcag agaatattac caataatgcg aagaacatct tggttcaatt caatactcca 840
gtccagatca attgcacaag gcctaataat aataccagaa agagtataag aattgggcca 900
ggacaggcat tctatgcaac aggagatata atcggagaca ttcgacaagc gcactgcact 960
gtttctaagg ccacttggaa tgaaacattg ggtaaagttg taaagcaact tcggaagcat 1020
ttcggaaata acacaattat tagatttgcg aactcatctg gaggggatct ggaagtgaca 1080
acacactctt tcaattgcgg tggcgagttc ttctattgta atacaagtgg attatttaac 1140
tctacttgga tttcaaatac ctcagtccaa ggatctaatt caacagggtc taacgattct 1200
ataacattac cttgccgtat aaagcaaatt attaatatgt ggcaaagaat cgggcaagcg 1260
atgtatgctc cacctattca aggcgtgatt cgttgcgttt caaacataac agggttgatc 1320
ctgaccaggg atggaggctc taccaattcc accaccgaga ccttccgtcc cggtggcgga 1380
gatatgcggg ataactggag atcagagctc tataagtata aggttgtgaa gattgaacct 1440
cttggagttg cccctacaag agcaaagaga agggtggttg gccgagagaa gagagcagtt 1500
ggcatcggtg ctgtctttct cggatttctt ggagcagctg gatccactat gggagcagca 1560
tcaatgacac taacagtgca ggctagaaat ttgcttagcg gaatcgttca gcagcagagc 1620
aatttactaa gagcaattga agcacagcaa catctcttaa agttgacggt gtggggcatt 1680
aaacaactac aagcgagagt gcttgccgtc gaaagatatt tgcgagacca acagctattg 1740
ggtatttggg gttgttctgg gaaattaatt tgcacaacaa atgttccatg gaactcctcc 1800
tggagtaata ggaatttaag tgagatatgg gacaacatga catggttgca gtgggacaag 1860
gaaatctcaa attatacaca gataatctat ggattattag aagagtctca gaatcagcaa 1920

-continued

```
gagaagaatg aacaggattt gcttgcattg gataagtggg cttctctatg gaactggttc   1980

gatattagta attggctctg gtatattaag agctctattg cctctttttt ctttatcata   2040

gggttaatca ttggactatt cttggttctc cgagttggta tttatctttg cattaaatta   2100

aagcacacca agaaaagaca gatttataca gacatagaga tgaaccgact tggaaagtaa   2160

ag                                                                  2162


<210> SEQ ID NO 4
<211> LENGTH: 2475
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

ggagccacca tgaagtgttt gttgtatttg gcattcttat tcatcggagt gaattgtaag     60

gaggagaaag cattctcacc tgaagtgatc cctatgttca cagcattatc tgagggagct    120

actcctcaag atcttaacac aatgcttaac acagtcggag gacatcaagc agcaatgcaa    180

atgttgaaag atacaattaa cgaggaagca gcagaatggg atagaatcta taagagatgg    240

ataatattag gattgaacaa gattgttaga atgtattctc ctgtgtcaat ccttgatata    300

agacaaggac ctaaagagcc tttcagagat tacgtcgata gatttgcaag aaattgtaga    360

gcacctagaa agaagggatg ttggaaatgt gggaaagaag gacatcaaat gaaagattgt    420

actgagagac aagctaactt cttgggaaag atatggcctt caagatggaa acctaagatg    480

ataggaggaa taggaggatt tattaaagtc agacaatatg atcaaatatt gattgaaata    540

tgtggacata aagctattgg aacagtccta gtgggtccaa cacctgtcaa catcattggt    600

agaaatcttc tcactcaaat cggatgtaca ctcaatttcc caatatcacc tattgagacc    660

gtgcctgtca aattgaaacc tggaatggat ggacctaaag tcaaacaatg gccattaact    720

gaggagaaga ttaaagcact ggtagaaatt tgtacagaga tggagaaaga aggaaagatt    780

tccaagattg gtcctgagaa tccttataat actcctgtct ttgctattaa gaagaaggat    840

agtaccaaat ggaggaaatt agtcgatttc agagaactta acaagaggac tcaagacttc    900

tgggaagtgc aattgggaat cccacaccct gcaggattga agaagaagaa gtctgtcact    960

gtcctagatg tgggagatgc atatttcagt gtcccactgg atgaaggttt cagaaagtat   1020

acagcattca caatcccttc cattaataat gaaacacctg gaataagata tcaatataat   1080

gtcttacctc aagggtggaa aggatctcca gcaatattcc aatcatcaat gacaaagatc   1140

ttggagcctt tcagagctca gaatccagag atagttattt accaatacat ggatgatttg   1200

tatgttgggt cagatctcga gatcggacag cacaggatgg agaatagatg gcaagtaatg   1260

attgtctggc aagtcgatag aatgagaata agaacatgga aatccttggt gaaacatcac   1320

cttacagagg aggcagaact ggaactggca gagaataggg aaatattgaa agatccagtg   1380

catggtgtct attacgatcc ttctaaagat ctgatagcag agatccagta ctggcaagca   1440

acatggattc ctgagtggga attcgtcaac acacctccat tagtgaaact atggtaccaa   1500

ttagagaaga atgtcaccga gaacttcaac atgtggaaga acgatatggt agatcaaatg   1560

cacgaagata tcatctcctt gtgggatcaa tcacttaaac cttgtgttaa attgacacct   1620

tgggtacctg ctcataaagg gataggagga aacgaacaag tggataaatt ggtgtcccaa   1680

gggatcagga aagtcttgtt cctagatgga attgataaag ctcaagcaaa ggaaattgtc   1740
```

gcaagctgtg ataagtgtca attaaaggga gaggcaatgc acggacaagt cgattgttca 1800
cctggtattt ggcaacttga ttgtacacat ttggagggta aagttattct agtagcagta 1860
catgtcgctt ctggttatat tgaggcagaa gtgatacctg ctgagacagg acaggagacc 1920
gcatactttc tacttaagtt agctatgaat aaggagctca agaagataat aggacaagtt 1980
agagatcaag cagagcacct taagacagct gtccaaatgg cagtgtttat acacaacttt 2040
aagagaaagg gtggaatcgg aggatattcc gcaggagaga gaatctggaa aggtcctgct 2100
aaattgttat ggaaaggaga aggagcagtt gtaatacaag ataattctga tataaaagta 2160
gtccctagaa ggaaagctaa gattattaga gattatggga aacaaatggc aggagctgat 2220
tgtgtgtttc taggagcagc aggatccact atgggagctg catcaatgac acttaccgtg 2280
caggctagac agcttctttc aggaattgta cagcaacaga ataatttgct aagagcaatt 2340
gaagctcaac aacacttact tcaacttaca gtctggggaa tcaagcaagc atgtacacct 2400
tatgatatca accaaatgct gagaggacca ggaagagcat ttgtaacaat ccctaatcct 2460
ttattgggtc tggat 2475

<210> SEQ ID NO 5
<211> LENGTH: 806
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 5

Met Glu Glu Lys Ala Phe Ser Pro Glu Val Ile Pro Met Phe Thr Ala
1 5 10 15

Leu Ser Glu Gly Ala Thr Pro Gln Asp Leu Asn Thr Met Leu Asn Thr
20 25 30

Val Gly Gly His Gln Ala Ala Met Gln Met Leu Lys Asp Thr Ile Asn
35 40 45

Glu Glu Ala Ala Glu Trp Asp Arg Ile Tyr Lys Arg Trp Ile Ile Leu
50 55 60

Gly Leu Asn Lys Ile Val Arg Met Tyr Ser Pro Val Ser Ile Leu Asp
65 70 75 80

Ile Arg Gln Gly Pro Lys Glu Pro Phe Arg Asp Tyr Val Asp Arg Phe
85 90 95

Ala Arg Asn Cys Arg Ala Pro Arg Lys Lys Gly Cys Trp Lys Cys Gly
100 105 110

Lys Glu Gly His Gln Met Lys Asp Cys Thr Glu Arg Gln Ala Asn Phe
115 120 125

Leu Gly Lys Ile Trp Pro Ser Arg Trp Lys Pro Lys Met Ile Gly Gly
130 135 140

Ile Gly Gly Phe Ile Lys Val Arg Gln Tyr Asp Gln Ile Leu Ile Glu
145 150 155 160

Ile Cys Gly His Lys Ala Ile Gly Thr Val Leu Val Gly Pro Thr Pro
165 170 175

Val Asn Ile Ile Gly Arg Asn Leu Leu Thr Gln Ile Gly Cys Thr Leu
180 185 190

Asn Phe Pro Ile Ser Pro Ile Glu Thr Val Pro Val Lys Leu Lys Pro
195 200 205

Gly Met Asp Gly Pro Lys Val Lys Gln Trp Pro Leu Thr Glu Glu Lys
210 215 220

-continued

```
Ile Lys Ala Leu Val Glu Ile Cys Thr Glu Met Glu Lys Glu Gly Lys
225                 230                 235                 240

Ile Ser Lys Ile Gly Pro Glu Asn Pro Tyr Asn Thr Pro Val Phe Ala
                245                 250                 255

Ile Lys Lys Lys Asp Ser Thr Lys Trp Arg Lys Leu Val Asp Phe Arg
            260                 265                 270

Glu Leu Asn Lys Arg Thr Gln Asp Phe Trp Glu Val Gln Leu Gly Ile
        275                 280                 285

Pro His Pro Ala Gly Leu Lys Lys Lys Lys Ser Val Thr Val Leu Asp
    290                 295                 300

Val Gly Asp Ala Tyr Phe Ser Val Pro Leu Asp Glu Gly Phe Arg Lys
305                 310                 315                 320

Tyr Thr Ala Phe Thr Ile Pro Ser Ile Asn Asn Glu Thr Pro Gly Ile
                325                 330                 335

Arg Tyr Gln Tyr Asn Val Leu Pro Gln Gly Trp Lys Gly Ser Pro Ala
            340                 345                 350

Ile Phe Gln Ser Ser Met Thr Lys Ile Leu Glu Pro Phe Arg Ala Gln
        355                 360                 365

Asn Pro Glu Ile Val Ile Tyr Gln Tyr Met Asp Asp Leu Tyr Val Gly
    370                 375                 380

Ser Asp Leu Glu Ile Gly Gln His Arg Met Glu Asn Arg Trp Gln Val
385                 390                 395                 400

Met Ile Val Trp Gln Val Asp Arg Met Arg Ile Arg Thr Trp Lys Ser
                405                 410                 415

Leu Val Lys His His Leu Thr Glu Glu Ala Glu Leu Glu Leu Ala Glu
            420                 425                 430

Asn Arg Glu Ile Leu Lys Asp Pro Val His Gly Val Tyr Tyr Asp Pro
        435                 440                 445

Ser Lys Asp Leu Ile Ala Glu Ile Gln Tyr Trp Gln Ala Thr Trp Ile
    450                 455                 460

Pro Glu Trp Glu Phe Val Asn Thr Pro Pro Leu Val Lys Leu Trp Tyr
465                 470                 475                 480

Gln Leu Glu Lys Asn Val Thr Glu Asn Phe Asn Met Trp Lys Asn Asp
                485                 490                 495

Met Val Asp Gln Met His Glu Asp Ile Ile Ser Leu Trp Asp Gln Ser
            500                 505                 510

Leu Lys Pro Cys Val Lys Leu Thr Pro Trp Val Pro Ala His Lys Gly
        515                 520                 525

Ile Gly Gly Asn Glu Gln Val Asp Lys Leu Val Ser Gln Gly Ile Arg
    530                 535                 540

Lys Val Leu Phe Leu Asp Gly Ile Asp Lys Ala Gln Ala Lys Glu Ile
545                 550                 555                 560

Val Ala Ser Cys Asp Lys Cys Gln Leu Lys Gly Glu Ala Met His Gly
                565                 570                 575

Gln Val Asp Cys Ser Pro Gly Ile Trp Gln Leu Asp Cys Thr His Leu
            580                 585                 590

Glu Gly Lys Val Ile Leu Val Ala Val His Val Ala Ser Gly Tyr Ile
        595                 600                 605

Glu Ala Glu Val Ile Pro Ala Glu Thr Gly Gln Glu Thr Ala Tyr Phe
    610                 615                 620

Leu Leu Lys Leu Ala Met Asn Lys Glu Leu Lys Lys Ile Ile Gly Gln
625                 630                 635                 640

Val Arg Asp Gln Ala Glu His Leu Lys Thr Ala Val Gln Met Ala Val
```

```
                645                 650                 655

Phe Ile His Asn Phe Lys Arg Lys Gly Gly Ile Gly Gly Tyr Ser Ala
            660                 665                 670

Gly Glu Arg Ile Trp Lys Gly Pro Ala Lys Leu Leu Trp Lys Gly Glu
        675                 680                 685

Gly Ala Val Val Ile Gln Asp Asn Ser Asp Ile Lys Val Val Pro Arg
    690                 695                 700

Arg Lys Ala Lys Ile Ile Arg Asp Tyr Gly Lys Gln Met Ala Gly Ala
705                 710                 715                 720

Asp Cys Val Phe Leu Gly Ala Ala Gly Ser Thr Met Gly Ala Ala Ser
                725                 730                 735

Met Thr Leu Thr Val Gln Ala Arg Gln Leu Leu Ser Gly Ile Val Gln
            740                 745                 750

Gln Gln Asn Asn Leu Leu Arg Ala Ile Glu Ala Gln Gln His Leu Leu
        755                 760                 765

Gln Leu Thr Val Trp Gly Ile Lys Gln Ala Cys Thr Pro Tyr Asp Ile
    770                 775                 780

Asn Gln Met Leu Arg Gly Pro Gly Arg Ala Phe Val Thr Ile Pro Asn
785                 790                 795                 800

Pro Leu Leu Gly Leu Asp
                805


<210> SEQ ID NO 6
<211> LENGTH: 2391
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(2385)

<400> SEQUENCE: 6

gccgccacc atg gag gag aag gcc ttc agc cct gag gtg atc ccc atg ttc      51
          Met Glu Glu Lys Ala Phe Ser Pro Glu Val Ile Pro Met Phe
          1               5                   10

acc gcc ctg tcc gag ggc gcc acc ccc cag gac ctg aac acc atg ctg       99
Thr Ala Leu Ser Glu Gly Ala Thr Pro Gln Asp Leu Asn Thr Met Leu
15                  20                  25                  30

aac acc gtg ggc ggc cac cag gcc gcc atg cag atg ctg aag gac acc      147
Asn Thr Val Gly Gly His Gln Ala Ala Met Gln Met Leu Lys Asp Thr
                35                  40                  45

atc aac gag gag gcc gcc gag tgg gac cgc atc tac aag cgc tgg atc      195
Ile Asn Glu Glu Ala Ala Glu Trp Asp Arg Ile Tyr Lys Arg Trp Ile
            50                  55                  60

atc ctg ggc ctg aac aag atc gtg cgc atg tac tcc ccc gtg tcc atc      243
Ile Leu Gly Leu Asn Lys Ile Val Arg Met Tyr Ser Pro Val Ser Ile
        65                  70                  75

ctg gac atc cgc cag ggc ccc aag gag ccc ttc cgc gac tac gtg gac      291
Leu Asp Ile Arg Gln Gly Pro Lys Glu Pro Phe Arg Asp Tyr Val Asp
    80                  85                  90

cgc ttc gcc cgc aac tgc cgc gcc cct cgc aag aag ggc tgc tgg aag      339
Arg Phe Ala Arg Asn Cys Arg Ala Pro Arg Lys Lys Gly Cys Trp Lys
95                  100                 105                 110

tgc ggc aag gag ggc cac cag atg aag gac tgc acc gag cgc cag gcc      387
Cys Gly Lys Glu Gly His Gln Met Lys Asp Cys Thr Glu Arg Gln Ala
                115                 120                 125

aac ttc ctg ggc aag atc tgg ccc tcc cgc tgg aag ccc aag atg att      435
```

-continued

```
Asn Phe Leu Gly Lys Ile Trp Pro Ser Arg Trp Lys Pro Lys Met Ile
            130                 135                 140

ggc ggg atc ggc ggc ttc atc aag gtg cgc cag tac gac cag atc ctg      483
Gly Gly Ile Gly Gly Phe Ile Lys Val Arg Gln Tyr Asp Gln Ile Leu
        145                 150                 155

atc gag atc tgc ggc cac aag gcc atc ggc acc gtg ctc gtg ggc ccc      531
Ile Glu Ile Cys Gly His Lys Ala Ile Gly Thr Val Leu Val Gly Pro
    160                 165                 170

acc ccc gtg aac atc atc ggc cgc aac ctg ctg acc cag atc ggc tgc      579
Thr Pro Val Asn Ile Ile Gly Arg Asn Leu Leu Thr Gln Ile Gly Cys
175                 180                 185                 190

acc ctg aac ttc ccc atc tcc ccc atc gag acc gtg ccc gtg aag ctg      627
Thr Leu Asn Phe Pro Ile Ser Pro Ile Glu Thr Val Pro Val Lys Leu
                195                 200                 205

aag ccc ggc atg gac ggc ccc aag gtg aag cag tgg ccc ctg acc gag      675
Lys Pro Gly Met Asp Gly Pro Lys Val Lys Gln Trp Pro Leu Thr Glu
            210                 215                 220

gag aag atc aag gcc ctg gtg gag atc tgc acc gag atg gag aag gag      723
Glu Lys Ile Lys Ala Leu Val Glu Ile Cys Thr Glu Met Glu Lys Glu
        225                 230                 235

ggc aag atc tcc aag atc ggc ccc gag aac ccc tac aac acc ccc gtg      771
Gly Lys Ile Ser Lys Ile Gly Pro Glu Asn Pro Tyr Asn Thr Pro Val
    240                 245                 250

ttc gcc atc aag aag aag gac tcc acc aag tgg cgc aaa ctg gtg gac      819
Phe Ala Ile Lys Lys Lys Asp Ser Thr Lys Trp Arg Lys Leu Val Asp
255                 260                 265                 270

ttc cgc gag ctg aac aag cgc acc cag gac ttc tgg gag gtg cag ctg      867
Phe Arg Glu Leu Asn Lys Arg Thr Gln Asp Phe Trp Glu Val Gln Leu
                275                 280                 285

ggc atc ccc cac cct gcc ggc ctg aag aag aag aag tcc gtg acc gtg      915
Gly Ile Pro His Pro Ala Gly Leu Lys Lys Lys Lys Ser Val Thr Val
            290                 295                 300

ctg gac gtg ggc gac gcc tac ttc tcc gtg ccc ctg gac gag ggc ttc      963
Leu Asp Val Gly Asp Ala Tyr Phe Ser Val Pro Leu Asp Glu Gly Phe
        305                 310                 315

cgc aag tac acc gcc ttc acc atc ccc tcc atc aac aac gag acc ccc     1011
Arg Lys Tyr Thr Ala Phe Thr Ile Pro Ser Ile Asn Asn Glu Thr Pro
    320                 325                 330

ggc atc cgc tac cag tac aac gtg ctg ccc cag ggc tgg aag ggc tcc     1059
Gly Ile Arg Tyr Gln Tyr Asn Val Leu Pro Gln Gly Trp Lys Gly Ser
335                 340                 345                 350

ccc gcc atc ttc cag tcc tcc atg acc aag atc ctg gag ccc ttc cgc     1107
Pro Ala Ile Phe Gln Ser Ser Met Thr Lys Ile Leu Glu Pro Phe Arg
                355                 360                 365

gcc cag aac ccc gag atc gtg atc tac cag tac atg gac gac ctg tac     1155
Ala Gln Asn Pro Glu Ile Val Ile Tyr Gln Tyr Met Asp Asp Leu Tyr
            370                 375                 380

gtg ggc tcc gac ctg gag atc ggc cag cac cgc atg gag aac cgc tgg     1203
Val Gly Ser Asp Leu Glu Ile Gly Gln His Arg Met Glu Asn Arg Trp
        385                 390                 395

cag gtg atg atc gtg tgg cag gtg gac cgc atg cgc atc cgc acc tgg     1251
Gln Val Met Ile Val Trp Gln Val Asp Arg Met Arg Ile Arg Thr Trp
    400                 405                 410

aag tcc ctg gtg aag cac cac ctg acc gag gag gcc gag ctg gag ctg     1299
Lys Ser Leu Val Lys His His Leu Thr Glu Glu Ala Glu Leu Glu Leu
415                 420                 425                 430

gcc gag aac cgc gag atc ctg aag gac ccc gtg cac ggc gtg tac tac     1347
Ala Glu Asn Arg Glu Ile Leu Lys Asp Pro Val His Gly Val Tyr Tyr
                435                 440                 445
```

-continued

```
gac ccc tcc aag gac ctg atc gcc gag atc cag tac tgg cag gcc acc      1395
Asp Pro Ser Lys Asp Leu Ile Ala Glu Ile Gln Tyr Trp Gln Ala Thr
            450                 455                 460

tgg atc ccc gag tgg gag ttc gtg aac acc cca ccc ctg gtg aag ctg      1443
Trp Ile Pro Glu Trp Glu Phe Val Asn Thr Pro Pro Leu Val Lys Leu
        465                 470                 475

tgg tac cag ctg gag aag aac gtg acc gag aac ttc aac atg tgg aag      1491
Trp Tyr Gln Leu Glu Lys Asn Val Thr Glu Asn Phe Asn Met Trp Lys
    480                 485                 490

aac gac atg gtg gac cag atg cac gag gac atc atc tcc ctg tgg gac      1539
Asn Asp Met Val Asp Gln Met His Glu Asp Ile Ile Ser Leu Trp Asp
495                 500                 505                 510

cag tcc ctg aag ccc tgc gtg aag ctg acc ccc tgg gtg ccc gcc cac      1587
Gln Ser Leu Lys Pro Cys Val Lys Leu Thr Pro Trp Val Pro Ala His
                515                 520                 525

aag ggc atc ggc ggc aac gag cag gtg gac aag ctg gtg tcc cag ggc      1635
Lys Gly Ile Gly Gly Asn Glu Gln Val Asp Lys Leu Val Ser Gln Gly
            530                 535                 540

atc cgc aag gtg ctg ttc ctg gac ggc atc gac aag gcc cag gcc aag      1683
Ile Arg Lys Val Leu Phe Leu Asp Gly Ile Asp Lys Ala Gln Ala Lys
        545                 550                 555

gag atc gtg gcc tcc tgc gac aag tgc cag ctg aag ggc gag gcc atg      1731
Glu Ile Val Ala Ser Cys Asp Lys Cys Gln Leu Lys Gly Glu Ala Met
    560                 565                 570

cac ggc cag gtg gac tgc tcc ccc ggc atc tgg cag ctg gac tgc acc      1779
His Gly Gln Val Asp Cys Ser Pro Gly Ile Trp Gln Leu Asp Cys Thr
575                 580                 585                 590

cac ctg gag ggc aag gtg atc ctg gtg gcc gtg cac gtg gcc tcc ggc      1827
His Leu Glu Gly Lys Val Ile Leu Val Ala Val His Val Ala Ser Gly
                595                 600                 605

tac atc gag gcc gaa gtg att ccc gcc gag acc ggc cag gag acc gcc      1875
Tyr Ile Glu Ala Glu Val Ile Pro Ala Glu Thr Gly Gln Glu Thr Ala
            610                 615                 620

tac ttc ctg ctg aag ctg gcc atg aac aag gag ctg aag aag atc atc      1923
Tyr Phe Leu Leu Lys Leu Ala Met Asn Lys Glu Leu Lys Lys Ile Ile
        625                 630                 635

ggc cag gtg cgc gac cag gcc gag cac ctg aag acc gcc gtg cag atg      1971
Gly Gln Val Arg Asp Gln Ala Glu His Leu Lys Thr Ala Val Gln Met
    640                 645                 650

gcc gtg ttc atc cac aac ttc aag cgc aag ggc gga atc ggc ggc tac      2019
Ala Val Phe Ile His Asn Phe Lys Arg Lys Gly Gly Ile Gly Gly Tyr
655                 660                 665                 670

tcc gcc ggc gag cgc atc tgg aag ggc ccc gcc aag ctg ctg tgg aag      2067
Ser Ala Gly Glu Arg Ile Trp Lys Gly Pro Ala Lys Leu Leu Trp Lys
                675                 680                 685

ggc gag ggc gcc gtg gtg atc cag gac aac tcc gac atc aag gtg gtg      2115
Gly Glu Gly Ala Val Val Ile Gln Asp Asn Ser Asp Ile Lys Val Val
            690                 695                 700

ccc cgc cgc aag gcc aag atc atc cgc gac tac ggc aag cag atg gcc      2163
Pro Arg Arg Lys Ala Lys Ile Ile Arg Asp Tyr Gly Lys Gln Met Ala
        705                 710                 715

ggt gcc gac tgc gtg ttc ctg ggc gct gcc ggc tcc acc atg ggc gcc      2211
Gly Ala Asp Cys Val Phe Leu Gly Ala Ala Gly Ser Thr Met Gly Ala
    720                 725                 730

gcc tcc atg acc ctg acc gtg cag gcc cgc cag ctg ctg tcc ggc atc      2259
Ala Ser Met Thr Leu Thr Val Gln Ala Arg Gln Leu Leu Ser Gly Ile
735                 740                 745                 750

gtg cag cag cag aac aac ctg ctg cgc gcc atc gag gcc cag cag cac      2307
Val Gln Gln Gln Asn Asn Leu Leu Arg Ala Ile Glu Ala Gln Gln His
                755                 760                 765
```

```
ctg ctg cag ctg acc gtg tgg ggc atc aag cag gca ccc acc aag gca      2355
Leu Leu Gln Leu Thr Val Trp Gly Ile Lys Gln Ala Pro Thr Lys Ala
            770                 775                 780

aag aga aga gtg gtg cag aga gaa aag aga tagtaa                      2391
Lys Arg Arg Val Val Gln Arg Glu Lys Arg
        785                 790


<210> SEQ ID NO 7
<211> LENGTH: 792
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Glu Lys Ala Phe Ser Pro Glu Val Ile Pro Met Phe Thr Ala
1               5                   10                  15

Leu Ser Glu Gly Ala Thr Pro Gln Asp Leu Asn Thr Met Leu Asn Thr
            20                  25                  30

Val Gly Gly His Gln Ala Ala Met Gln Met Leu Lys Asp Thr Ile Asn
        35                  40                  45

Glu Glu Ala Ala Glu Trp Asp Arg Ile Tyr Lys Arg Trp Ile Ile Leu
    50                  55                  60

Gly Leu Asn Lys Ile Val Arg Met Tyr Ser Pro Val Ser Ile Leu Asp
65                  70                  75                  80

Ile Arg Gln Gly Pro Lys Glu Pro Phe Arg Asp Tyr Val Asp Arg Phe
                85                  90                  95

Ala Arg Asn Cys Arg Ala Pro Arg Lys Lys Gly Cys Trp Lys Cys Gly
            100                 105                 110

Lys Glu Gly His Gln Met Lys Asp Cys Thr Glu Arg Gln Ala Asn Phe
        115                 120                 125

Leu Gly Lys Ile Trp Pro Ser Arg Trp Lys Pro Lys Met Ile Gly Gly
    130                 135                 140

Ile Gly Gly Phe Ile Lys Val Arg Gln Tyr Asp Gln Ile Leu Ile Glu
145                 150                 155                 160

Ile Cys Gly His Lys Ala Ile Gly Thr Val Leu Val Gly Pro Thr Pro
                165                 170                 175

Val Asn Ile Ile Gly Arg Asn Leu Leu Thr Gln Ile Gly Cys Thr Leu
            180                 185                 190

Asn Phe Pro Ile Ser Pro Ile Glu Thr Val Pro Val Lys Leu Lys Pro
        195                 200                 205

Gly Met Asp Gly Pro Lys Val Lys Gln Trp Pro Leu Thr Glu Glu Lys
    210                 215                 220

Ile Lys Ala Leu Val Glu Ile Cys Thr Glu Met Glu Lys Glu Gly Lys
225                 230                 235                 240

Ile Ser Lys Ile Gly Pro Glu Asn Pro Tyr Asn Thr Pro Val Phe Ala
                245                 250                 255

Ile Lys Lys Lys Asp Ser Thr Lys Trp Arg Lys Leu Val Asp Phe Arg
            260                 265                 270

Glu Leu Asn Lys Arg Thr Gln Asp Phe Trp Glu Val Gln Leu Gly Ile
        275                 280                 285

Pro His Pro Ala Gly Leu Lys Lys Lys Lys Ser Val Thr Val Leu Asp
    290                 295                 300

Val Gly Asp Ala Tyr Phe Ser Val Pro Leu Asp Glu Gly Phe Arg Lys
305                 310                 315                 320
```

-continued

```
Tyr Thr Ala Phe Thr Ile Pro Ser Ile Asn Asn Glu Thr Pro Gly Ile
                325                 330                 335

Arg Tyr Gln Tyr Asn Val Leu Pro Gln Gly Trp Lys Gly Ser Pro Ala
            340                 345                 350

Ile Phe Gln Ser Ser Met Thr Lys Ile Leu Glu Pro Phe Arg Ala Gln
        355                 360                 365

Asn Pro Glu Ile Val Ile Tyr Gln Tyr Met Asp Asp Leu Tyr Val Gly
    370                 375                 380

Ser Asp Leu Glu Ile Gly Gln His Arg Met Glu Asn Arg Trp Gln Val
385                 390                 395                 400

Met Ile Val Trp Gln Val Asp Arg Met Arg Ile Arg Thr Trp Lys Ser
                405                 410                 415

Leu Val Lys His His Leu Thr Glu Glu Ala Glu Leu Glu Leu Ala Glu
            420                 425                 430

Asn Arg Glu Ile Leu Lys Asp Pro Val His Gly Val Tyr Tyr Asp Pro
        435                 440                 445

Ser Lys Asp Leu Ile Ala Glu Ile Gln Tyr Trp Gln Ala Thr Trp Ile
    450                 455                 460

Pro Glu Trp Glu Phe Val Asn Thr Pro Pro Leu Val Lys Leu Trp Tyr
465                 470                 475                 480

Gln Leu Glu Lys Asn Val Thr Glu Asn Phe Asn Met Trp Lys Asn Asp
                485                 490                 495

Met Val Asp Gln Met His Glu Asp Ile Ile Ser Leu Trp Asp Gln Ser
            500                 505                 510

Leu Lys Pro Cys Val Lys Leu Thr Pro Trp Val Pro Ala His Lys Gly
        515                 520                 525

Ile Gly Gly Asn Glu Gln Val Asp Lys Leu Val Ser Gln Gly Ile Arg
    530                 535                 540

Lys Val Leu Phe Leu Asp Gly Ile Asp Lys Ala Gln Ala Lys Glu Ile
545                 550                 555                 560

Val Ala Ser Cys Asp Lys Cys Gln Leu Lys Gly Glu Ala Met His Gly
                565                 570                 575

Gln Val Asp Cys Ser Pro Gly Ile Trp Gln Leu Asp Cys Thr His Leu
            580                 585                 590

Glu Gly Lys Val Ile Leu Val Ala Val His Val Ala Ser Gly Tyr Ile
        595                 600                 605

Glu Ala Glu Val Ile Pro Ala Glu Thr Gly Gln Glu Thr Ala Tyr Phe
    610                 615                 620

Leu Leu Lys Leu Ala Met Asn Lys Glu Leu Lys Lys Ile Ile Gly Gln
625                 630                 635                 640

Val Arg Asp Gln Ala Glu His Leu Lys Thr Ala Val Gln Met Ala Val
                645                 650                 655

Phe Ile His Asn Phe Lys Arg Lys Gly Gly Ile Gly Gly Tyr Ser Ala
            660                 665                 670

Gly Glu Arg Ile Trp Lys Gly Pro Ala Lys Leu Leu Trp Lys Gly Glu
        675                 680                 685

Gly Ala Val Val Ile Gln Asp Asn Ser Asp Ile Lys Val Val Pro Arg
    690                 695                 700

Arg Lys Ala Lys Ile Ile Arg Asp Tyr Gly Lys Gln Met Ala Gly Ala
705                 710                 715                 720

Asp Cys Val Phe Leu Gly Ala Ala Gly Ser Thr Met Gly Ala Ala Ser
                725                 730                 735
```

-continued

```
Met Thr Leu Thr Val Gln Ala Arg Gln Leu Leu Ser Gly Ile Val Gln
            740                 745                 750

Gln Gln Asn Asn Leu Leu Arg Ala Ile Glu Ala Gln Gln His Leu Leu
        755                 760                 765

Gln Leu Thr Val Trp Gly Ile Lys Gln Ala Pro Thr Lys Ala Lys Arg
    770                 775                 780

Arg Val Val Gln Arg Glu Lys Arg
785                 790


<210> SEQ ID NO 8
<211> LENGTH: 2391
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (10)..(2385)

<400> SEQUENCE: 8

ggagccacc atg gag gag aaa gca ttc tca cct gaa gtg atc cct atg ttc      51
          Met Glu Glu Lys Ala Phe Ser Pro Glu Val Ile Pro Met Phe
          1               5                   10

aca gca tta tct gag gga gct act cct caa gat ctt aac aca atg ctt        99
Thr Ala Leu Ser Glu Gly Ala Thr Pro Gln Asp Leu Asn Thr Met Leu
15                  20                  25                  30

aac aca gtc gga gga cat caa gca gca atg caa atg ttg aaa gat aca       147
Asn Thr Val Gly Gly His Gln Ala Ala Met Gln Met Leu Lys Asp Thr
                35                  40                  45

att aac gag gaa gca gca gaa tgg gat aga atc tat aag aga tgg ata       195
Ile Asn Glu Glu Ala Ala Glu Trp Asp Arg Ile Tyr Lys Arg Trp Ile
            50                  55                  60

ata tta gga ttg aac aag att gtt aga atg tat tct cct gtg tca atc       243
Ile Leu Gly Leu Asn Lys Ile Val Arg Met Tyr Ser Pro Val Ser Ile
        65                  70                  75

ctt gat ata aga caa gga cct aaa gag cct ttc aga gat tac gtc gat       291
Leu Asp Ile Arg Gln Gly Pro Lys Glu Pro Phe Arg Asp Tyr Val Asp
    80                  85                  90

aga ttt gca aga aat tgt aga gca cct aga aag aag gga tgt tgg aaa       339
Arg Phe Ala Arg Asn Cys Arg Ala Pro Arg Lys Lys Gly Cys Trp Lys
95                  100                 105                 110

tgt ggg aaa gaa gga cat caa atg aaa gat tgt act gag aga caa gct       387
Cys Gly Lys Glu Gly His Gln Met Lys Asp Cys Thr Glu Arg Gln Ala
                115                 120                 125

aac ttc ttg gga aag ata tgg cct tca aga tgg aaa cct aag atg ata       435
Asn Phe Leu Gly Lys Ile Trp Pro Ser Arg Trp Lys Pro Lys Met Ile
            130                 135                 140

gga gga ata gga gga ttt att aaa gtc aga caa tat gat caa ata ttg       483
Gly Gly Ile Gly Gly Phe Ile Lys Val Arg Gln Tyr Asp Gln Ile Leu
        145                 150                 155

att gaa ata tgt gga cat aaa gct att gga aca gtc cta gtg ggt cca       531
Ile Glu Ile Cys Gly His Lys Ala Ile Gly Thr Val Leu Val Gly Pro
    160                 165                 170

aca cct gtc aac atc att ggt aga aat ctt ctc act caa atc gga tgt       579
Thr Pro Val Asn Ile Ile Gly Arg Asn Leu Leu Thr Gln Ile Gly Cys
175                 180                 185                 190

aca ctc aat ttc cca ata tca cct att gag acc gtg cct gtc aaa ttg       627
Thr Leu Asn Phe Pro Ile Ser Pro Ile Glu Thr Val Pro Val Lys Leu
                195                 200                 205

aaa cct gga atg gat gga cct aaa gtc aaa caa tgg cca tta act gag       675
```

-continued

```
Lys Pro Gly Met Asp Gly Pro Lys Val Lys Gln Trp Pro Leu Thr Glu
            210                 215                 220

gag aag att aaa gca ctg gta gaa att tgt aca gag atg gag aaa gaa      723
Glu Lys Ile Lys Ala Leu Val Glu Ile Cys Thr Glu Met Glu Lys Glu
        225                 230                 235

gga aag att tcc aag att ggt cct gag aat cct tat aat act cct gtc      771
Gly Lys Ile Ser Lys Ile Gly Pro Glu Asn Pro Tyr Asn Thr Pro Val
    240                 245                 250

ttt gct att aag aag aag gat agt acc aaa tgg agg aaa tta gtc gat      819
Phe Ala Ile Lys Lys Lys Asp Ser Thr Lys Trp Arg Lys Leu Val Asp
255                 260                 265                 270

ttc aga gaa ctt aac aag agg act caa gac ttc tgg gaa gtg caa ttg      867
Phe Arg Glu Leu Asn Lys Arg Thr Gln Asp Phe Trp Glu Val Gln Leu
                275                 280                 285

gga atc cca cac cct gca gga ttg aag aag aag aag tct gtc act gtc      915
Gly Ile Pro His Pro Ala Gly Leu Lys Lys Lys Lys Ser Val Thr Val
            290                 295                 300

cta gat gtg gga gat gca tat ttc agt gtc cca ctg gat gaa ggt ttc      963
Leu Asp Val Gly Asp Ala Tyr Phe Ser Val Pro Leu Asp Glu Gly Phe
        305                 310                 315

aga aag tat aca gca ttc aca atc cct tcc att aat aat gaa aca cct     1011
Arg Lys Tyr Thr Ala Phe Thr Ile Pro Ser Ile Asn Asn Glu Thr Pro
    320                 325                 330

gga ata aga tat caa tat aat gtc tta cct caa ggg tgg aaa gga tct     1059
Gly Ile Arg Tyr Gln Tyr Asn Val Leu Pro Gln Gly Trp Lys Gly Ser
335                 340                 345                 350

cca gca ata ttc caa tca tca atg aca aag atc ttg gag cct ttc aga     1107
Pro Ala Ile Phe Gln Ser Ser Met Thr Lys Ile Leu Glu Pro Phe Arg
                355                 360                 365

gct cag aat cca gag ata gtt att tac caa tac atg gat gat ttg tat     1155
Ala Gln Asn Pro Glu Ile Val Ile Tyr Gln Tyr Met Asp Asp Leu Tyr
            370                 375                 380

gtt ggg tca gat ctc gag atc gga cag cac agg atg gag aat aga tgg     1203
Val Gly Ser Asp Leu Glu Ile Gly Gln His Arg Met Glu Asn Arg Trp
        385                 390                 395

caa gta atg att gtc tgg caa gtc gat aga atg aga ata aga aca tgg     1251
Gln Val Met Ile Val Trp Gln Val Asp Arg Met Arg Ile Arg Thr Trp
    400                 405                 410

aaa tcc ttg gtg aaa cat cac ctt aca gag gag gca gaa ctg gaa ctg     1299
Lys Ser Leu Val Lys His His Leu Thr Glu Glu Ala Glu Leu Glu Leu
415                 420                 425                 430

gca gag aat agg gaa ata ttg aaa gat cca gtg cat ggt gtc tat tac     1347
Ala Glu Asn Arg Glu Ile Leu Lys Asp Pro Val His Gly Val Tyr Tyr
                435                 440                 445

gat cct tct aaa gat ctg ata gca gag atc cag tac tgg caa gca aca     1395
Asp Pro Ser Lys Asp Leu Ile Ala Glu Ile Gln Tyr Trp Gln Ala Thr
            450                 455                 460

tgg att cct gag tgg gaa ttc gtc aac aca cct cca tta gtg aaa cta     1443
Trp Ile Pro Glu Trp Glu Phe Val Asn Thr Pro Pro Leu Val Lys Leu
        465                 470                 475

tgg tac caa tta gag aag aat gtc acc gag aac ttc aac atg tgg aag     1491
Trp Tyr Gln Leu Glu Lys Asn Val Thr Glu Asn Phe Asn Met Trp Lys
    480                 485                 490

aac gat atg gta gat caa atg cac gaa gat atc atc tcc ttg tgg gat     1539
Asn Asp Met Val Asp Gln Met His Glu Asp Ile Ile Ser Leu Trp Asp
495                 500                 505                 510

caa tca ctt aaa cct tgt gtt aaa ttg aca cct tgg gta cct gct cat     1587
Gln Ser Leu Lys Pro Cys Val Lys Leu Thr Pro Trp Val Pro Ala His
                515                 520                 525
```

```
aaa ggg ata gga gga aac gaa caa gtg gat aaa ttg gtg tcc caa ggg     1635
Lys Gly Ile Gly Gly Asn Glu Gln Val Asp Lys Leu Val Ser Gln Gly
            530                 535                 540

atc agg aaa gtc ttg ttc cta gat gga att gat aaa gct caa gca aag     1683
Ile Arg Lys Val Leu Phe Leu Asp Gly Ile Asp Lys Ala Gln Ala Lys
        545                 550                 555

gaa att gtc gca agc tgt gat aag tgt caa tta aag gga gag gca atg     1731
Glu Ile Val Ala Ser Cys Asp Lys Cys Gln Leu Lys Gly Glu Ala Met
    560                 565                 570

cac gga caa gtc gat tgt tca cct ggt att tgg caa ctt gat tgt aca     1779
His Gly Gln Val Asp Cys Ser Pro Gly Ile Trp Gln Leu Asp Cys Thr
575                 580                 585                 590

cat ttg gag ggt aaa gtt att cta gta gca gta cat gtc gct tct ggt     1827
His Leu Glu Gly Lys Val Ile Leu Val Ala Val His Val Ala Ser Gly
                595                 600                 605

tat att gag gca gaa gtg ata cct gct gag aca gga cag gag acc gca     1875
Tyr Ile Glu Ala Glu Val Ile Pro Ala Glu Thr Gly Gln Glu Thr Ala
            610                 615                 620

tac ttt cta ctt aag tta gct atg aat aag gag ctc aag aag ata ata     1923
Tyr Phe Leu Leu Lys Leu Ala Met Asn Lys Glu Leu Lys Lys Ile Ile
        625                 630                 635

gga caa gtt aga gat caa gca gag cac ctt aag aca gct gtc caa atg     1971
Gly Gln Val Arg Asp Gln Ala Glu His Leu Lys Thr Ala Val Gln Met
    640                 645                 650

gca gtg ttt ata cac aac ttt aag aga aag ggt gga atc gga gga tat     2019
Ala Val Phe Ile His Asn Phe Lys Arg Lys Gly Gly Ile Gly Gly Tyr
655                 660                 665                 670

tcc gca gga gag aga atc tgg aaa ggt cct gct aaa ttg tta tgg aaa     2067
Ser Ala Gly Glu Arg Ile Trp Lys Gly Pro Ala Lys Leu Leu Trp Lys
                675                 680                 685

gga gaa gga gca gtt gta ata caa gat aat tct gat ata aaa gta gtc     2115
Gly Glu Gly Ala Val Val Ile Gln Asp Asn Ser Asp Ile Lys Val Val
            690                 695                 700

cct aga agg aaa gct aag att att aga gat tat ggg aaa caa atg gca     2163
Pro Arg Arg Lys Ala Lys Ile Ile Arg Asp Tyr Gly Lys Gln Met Ala
        705                 710                 715

gga gct gat tgt gtg ttt cta gga gca gca gga tcc act atg gga gct     2211
Gly Ala Asp Cys Val Phe Leu Gly Ala Ala Gly Ser Thr Met Gly Ala
    720                 725                 730

gca tca atg aca ctt acc gtg cag gct aga cag ctt ctt tca gga att     2259
Ala Ser Met Thr Leu Thr Val Gln Ala Arg Gln Leu Leu Ser Gly Ile
735                 740                 745                 750

gta cag caa cag aat aat ttg cta aga gca att gaa gct caa caa cac     2307
Val Gln Gln Gln Asn Asn Leu Leu Arg Ala Ile Glu Ala Gln Gln His
                755                 760                 765

tta ctt caa ctt aca gtc tgg gga atc aag caa gca cct aca aaa gca     2355
Leu Leu Gln Leu Thr Val Trp Gly Ile Lys Gln Ala Pro Thr Lys Ala
            770                 775                 780

aag aga aga gtc gtc caa aga gag aaa aga tagtaa                      2391
Lys Arg Arg Val Val Gln Arg Glu Lys Arg
        785                 790
```

<210> SEQ ID NO 9
<211> LENGTH: 792
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

-continued

```
Met Glu Glu Lys Ala Phe Ser Pro Glu Val Ile Pro Met Phe Thr Ala
1               5                   10                  15

Leu Ser Glu Gly Ala Thr Pro Gln Asp Leu Asn Thr Met Leu Asn Thr
            20                  25                  30

Val Gly Gly His Gln Ala Ala Met Gln Met Leu Lys Asp Thr Ile Asn
        35                  40                  45

Glu Glu Ala Ala Glu Trp Asp Arg Ile Tyr Lys Arg Trp Ile Ile Leu
    50                  55                  60

Gly Leu Asn Lys Ile Val Arg Met Tyr Ser Pro Val Ser Ile Leu Asp
65                  70                  75                  80

Ile Arg Gln Gly Pro Lys Glu Pro Phe Arg Asp Tyr Val Asp Arg Phe
                85                  90                  95

Ala Arg Asn Cys Arg Ala Pro Arg Lys Lys Gly Cys Trp Lys Cys Gly
            100                 105                 110

Lys Glu Gly His Gln Met Lys Asp Cys Thr Glu Arg Gln Ala Asn Phe
        115                 120                 125

Leu Gly Lys Ile Trp Pro Ser Arg Trp Lys Pro Lys Met Ile Gly Gly
    130                 135                 140

Ile Gly Gly Phe Ile Lys Val Arg Gln Tyr Asp Gln Ile Leu Ile Glu
145                 150                 155                 160

Ile Cys Gly His Lys Ala Ile Gly Thr Val Leu Val Gly Pro Thr Pro
                165                 170                 175

Val Asn Ile Ile Gly Arg Asn Leu Leu Thr Gln Ile Gly Cys Thr Leu
            180                 185                 190

Asn Phe Pro Ile Ser Pro Ile Glu Thr Val Pro Val Lys Leu Lys Pro
        195                 200                 205

Gly Met Asp Gly Pro Lys Val Lys Gln Trp Pro Leu Thr Glu Glu Lys
    210                 215                 220

Ile Lys Ala Leu Val Glu Ile Cys Thr Glu Met Glu Lys Glu Gly Lys
225                 230                 235                 240

Ile Ser Lys Ile Gly Pro Glu Asn Pro Tyr Asn Thr Pro Val Phe Ala
                245                 250                 255

Ile Lys Lys Lys Asp Ser Thr Lys Trp Arg Lys Leu Val Asp Phe Arg
            260                 265                 270

Glu Leu Asn Lys Arg Thr Gln Asp Phe Trp Glu Val Gln Leu Gly Ile
        275                 280                 285

Pro His Pro Ala Gly Leu Lys Lys Lys Lys Ser Val Thr Val Leu Asp
    290                 295                 300

Val Gly Asp Ala Tyr Phe Ser Val Pro Leu Asp Glu Gly Phe Arg Lys
305                 310                 315                 320

Tyr Thr Ala Phe Thr Ile Pro Ser Ile Asn Asn Glu Thr Pro Gly Ile
                325                 330                 335

Arg Tyr Gln Tyr Asn Val Leu Pro Gln Gly Trp Lys Gly Ser Pro Ala
            340                 345                 350

Ile Phe Gln Ser Ser Met Thr Lys Ile Leu Glu Pro Phe Arg Ala Gln
        355                 360                 365

Asn Pro Glu Ile Val Ile Tyr Gln Tyr Met Asp Asp Leu Tyr Val Gly
    370                 375                 380

Ser Asp Leu Glu Ile Gly Gln His Arg Met Glu Asn Arg Trp Gln Val
385                 390                 395                 400

Met Ile Val Trp Gln Val Asp Arg Met Arg Ile Arg Thr Trp Lys Ser
                405                 410                 415

Leu Val Lys His His Leu Thr Glu Glu Ala Glu Leu Glu Leu Ala Glu
```

```
            420                 425                 430

Asn Arg Glu Ile Leu Lys Asp Pro Val His Gly Val Tyr Tyr Asp Pro
        435                 440                 445

Ser Lys Asp Leu Ile Ala Glu Ile Gln Tyr Trp Gln Ala Thr Trp Ile
    450                 455                 460

Pro Glu Trp Glu Phe Val Asn Thr Pro Pro Leu Val Lys Leu Trp Tyr
465                 470                 475                 480

Gln Leu Glu Lys Asn Val Thr Glu Asn Phe Asn Met Trp Lys Asn Asp
                485                 490                 495

Met Val Asp Gln Met His Glu Asp Ile Ile Ser Leu Trp Asp Gln Ser
            500                 505                 510

Leu Lys Pro Cys Val Lys Leu Thr Pro Trp Val Pro Ala His Lys Gly
        515                 520                 525

Ile Gly Gly Asn Glu Gln Val Asp Lys Leu Val Ser Gln Gly Ile Arg
    530                 535                 540

Lys Val Leu Phe Leu Asp Gly Ile Asp Lys Ala Gln Ala Lys Glu Ile
545                 550                 555                 560

Val Ala Ser Cys Asp Lys Cys Gln Leu Lys Gly Glu Ala Met His Gly
                565                 570                 575

Gln Val Asp Cys Ser Pro Gly Ile Trp Gln Leu Asp Cys Thr His Leu
            580                 585                 590

Glu Gly Lys Val Ile Leu Val Ala Val His Val Ala Ser Gly Tyr Ile
        595                 600                 605

Glu Ala Glu Val Ile Pro Ala Glu Thr Gly Gln Glu Thr Ala Tyr Phe
    610                 615                 620

Leu Leu Lys Leu Ala Met Asn Lys Glu Leu Lys Lys Ile Ile Gly Gln
625                 630                 635                 640

Val Arg Asp Gln Ala Glu His Leu Lys Thr Ala Val Gln Met Ala Val
                645                 650                 655

Phe Ile His Asn Phe Lys Arg Lys Gly Gly Ile Gly Gly Tyr Ser Ala
            660                 665                 670

Gly Glu Arg Ile Trp Lys Gly Pro Ala Lys Leu Leu Trp Lys Gly Glu
        675                 680                 685

Gly Ala Val Val Ile Gln Asp Asn Ser Asp Ile Lys Val Val Pro Arg
    690                 695                 700

Arg Lys Ala Lys Ile Ile Arg Asp Tyr Gly Lys Gln Met Ala Gly Ala
705                 710                 715                 720

Asp Cys Val Phe Leu Gly Ala Ala Gly Ser Thr Met Gly Ala Ala Ser
                725                 730                 735

Met Thr Leu Thr Val Gln Ala Arg Gln Leu Leu Ser Gly Ile Val Gln
            740                 745                 750

Gln Gln Asn Asn Leu Leu Arg Ala Ile Glu Ala Gln Gln His Leu Leu
        755                 760                 765

Gln Leu Thr Val Trp Gly Ile Lys Gln Ala Pro Thr Lys Ala Lys Arg
    770                 775                 780

Arg Val Val Gln Arg Glu Lys Arg
785                 790
```

<210> SEQ ID NO 10
<211> LENGTH: 15402
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
accaaacaag agaaaaaaca tgtatgggat atgtaatgaa gttatacagg attttagggt     60
caaagtatcc accctgagga gcaggttcca gaccctttgc tttgctgcca aagttcacgc    120
ggccgcagat cttcacgatg gccgggttgt tgagcacctt cgatacattt agctctagga    180
ggagcgaaag tattaataag tcgggaggag gtgctgttat ccccggccag aggagcacag    240
tctcagtgtt cgtactaggc ccaagtgtga ctgatgatgc agacaagtta ttcattgcaa    300
ctaccttcct agctcactca ttggacacag ataagcagca ctctcagaga ggggggttcc    360
tcgtctctct gcttgccatg gcttacagta gtccagaatt gtacttgaca acaaacggag    420
taaacgccga tgtcaaatat gtgatctaca acatagagaa agaccctaag aggacgaaga    480
cagacggatt cattgtgaag acgagagata tggaatatga gaggaccaca gaatggctgt    540
ttggacctat ggtcaacaag agcccactct tccagggtca acgggatgct gcagaccctg    600
acacactcct tcaaatctat gggtatcctg catgcctagg agcaataatt gtccaagtct    660
ggattgtgct ggtgaaggcc atcacaagca gcgccggctt aaggaaaggg ttcttcaaca    720
ggttagaggc gttcagacaa gacggcaccg tgaaaggtgc cttagttttc actggggaga    780
cagttgaggg gataggctcg gttatgagat ctcagcaaag ccttgtatct ctcatggttg    840
agacccttgt gactatgaat actgcaagat ctgatctcac cacattagag aagaacatcc    900
agatcgttgg gaactacatc cgagatgcag ggctggcttc cttcatgaac actattaaat    960
atggggtgga aacaaagatg gcagctctaa cgttgtcaaa cctgaggccc gatattaata   1020
agcttagaag cctcatagac acctacctgt caaaaggccc cagagctccc tttatctgta   1080
tcctcaagga ccctgttcat ggtgaatttg ctccaggcaa ttatcctgca ctatggagtt   1140
acgccatggg agtcgccgtc gtacagaaca aggcaatgca gcagtacgtc acagggagga   1200
cataccttga tatggaaatg ttcttactag gacaagccgt ggcaaaggat gctgaatcga   1260
agatcagcag tgccttggaa gatgagttag gagtgacgga tacagccaag gggaggctca   1320
gacatcatct ggcaaacttg tccggtgggg atggtgctta ccacaaacca acaggcggtg   1380
gtgcaattga ggtagctcta gacaatgccg acatcgacct agaaacaaaa gcccatgcgg   1440
accaggacgc taggggttgg ggtggagata gtggtgaaag atgggcacgt caggtgagtg   1500
gtggccactt tgtcacacta catggggctg aacggttaga ggaggaaacc aatgatgagg   1560
atgtatcaga catagagaga agaatagcca tgagactcgc agagagacgg caagaggatt   1620
ctgcaaccca tggagatgaa ggccgcaata acggtgtcga tcatgacgaa gatgacgatg   1680
ccgcagcagt agctgggata ggaggaatct aggatcatac gaggcttcaa ggtacttgat   1740
ccgtagtaag aaaaacttag ggtgaaagtt catccaccga tcggctcagg caaggccaca   1800
cccaacccca ccgaccacac ccagcagtcg agacagccac ggcttcggct acacttaccg   1860
catggatcaa gatgccttca ttcttaaaga agattctgaa gttgagaggg aggcgccagg   1920
aggacgagag tcgctctcgg atgttatcgg attcctcgat gctgtcctgt cgagtgaacc   1980
aactgacatc ggaggggaca gaagctggct ccacaacacc atcaacactc cccaaggacc   2040
aggctctgct catagagcca aaagtgaggg cgaaggagaa gtctcaacac cgtcgaccca   2100
agataatcga tcaggtgagg agagtagagt ctctgggaga acaagcaagc cagaggcaga   2160
agcacatgct ggaaaccttg ataaacaaaa tatacaccgg gcctttgggg gaagaactgg   2220
tacaaactct gtatctcagg atctgggcga tggaggagac tccggaatcc ttgaaaatcc   2280
```

```
tccaaatgag agaggatatc cgagatcagg tattgaagat gaaaacagag agatggctgc   2340
gcaccctgat aagaggggag aagaccaagc tgaaggactt ccagaagagg tacgaggaag   2400
tacatcccta cctgatgaag gagaaggtgg agcaagtaat aatggaagaa gcatggagcc   2460
tggcagctca catagtgcaa gagtaactgg ggtcctggtg attcctagcc ccgaacttga   2520
agaggctgtg ctacggagga acaaaagaag acctaccaac agtgggtcca aacctcttac   2580
tccagcaacc gtgcctggca cccggtcccc accgctgaat cgttacaaca gcacagggtc   2640
accaccagga aaacccccat ctacacagga tgagcacatc aactctgggg acacccccgc   2700
cgtcagggtc aaagaccgga aaccaccaat agggacccgc tctgtctcag attgtccagc   2760
caacggccgc ccaatccacc cgggtctaga gaccgactca acaaaaaagg gcataggaga   2820
gaacacatca tctatgaaag agatggctac attgttgacg agtcttggtg taatccagtc   2880
tgctcaagaa ttcgaatcat cccgagacgc gagttatgtg tttgcaagac gtgccctaaa   2940
gtctgcaaac tatgcagaga tgacattcaa tgtatgcggc ctgatccttt ctgccgagaa   3000
atcttccgct cgtaaggtag atgagaacaa acaactgctc aaacagatcc aagagagcgt   3060
ggaatcattc cgggatattt acaagagatt ctctgagtat cagaaagaac agaactcatt   3120
gctgatgtcc aacctatcta cacttcatat catcacagat agaggtggca agactgacaa   3180
cacagactcc cttacaaggt ccccctccgt tttgcaaaa tcaaaagaga acaagactaa   3240
ggctaccagg tttgacccat ctatggagac cctagaagat atgaagtaca aaccggacct   3300
aatccgagag gatgaattta gagatgagat ccgcaacccg gtgtaccaag agagggacac   3360
agaacccagg gcctcaaacg catcacgtct cctcccctcc aaagagaagc ccacaatgca   3420
ctctctcagg ctcgtcatag agagcagtcc cctaagcaga gctgagaaag tagcatatgt   3480
gaaatcatta tccaagtgca agacagacca agaggttaag gcagtcatgg aactcgtaga   3540
agaggacata gagtcactga ccaactagat cccgggtgag gcatcctacc atcctcagtc   3600
atagagagat ccaatctacc atcagcatca gccagtaaag attaagaaaa acttagggtg   3660
aaagaaattt cacctaacac ggcgcaatgg cagatatcta tagattccct aagttctcat   3720
atgaggataa cggtactgtg gagcccctgc ctctgagaac tggtccggat aagaaagcca   3780
tcccccacat caggattgtc aaggtaggag accctcctaa acatggagtg agatacctag   3840
atttattgct cttgggtttc tttgagacac cgaaacaaac aaccaatcta gggagcgtat   3900
ctgacttgac agagccgacc agctactcaa tatgcggctc cgggtcgtta cccataggtg   3960
tggccaaata ctacgggact gatcaggaac tcttaaaggc ctgcaccgat ctcagaatta   4020
cggtgaggag gactgttcga gcaggagaga tgatcgtata catggtggat tcgattggtg   4080
ctccactcct accatggtca ggcaggctga gacagggaat gatatttaat gcaaacaagg   4140
tcgcactagc tccccaatgc ctccctgtgg acaaggacat aagactcaga gtggtgtttg   4200
tcaatgggac atctctaggg gcaatcacca tagccaagat cccaaagacc cttgcagacc   4260
ttgcattgcc caactctata tctgttaatt tactggtgac actcaagacc gggatctcca   4320
cagaacaaaa gggggtactc ccagtacttg atgatcaagg ggagaaaaag ctcaatttta   4380
tggtgcacct cgggttgatc aggagaaagg tcgggaagat atactctgtt gagtactgca   4440
agagcaagat tgagagaatg cggctgattt tctcacttgg gttaatcggc ggtataagct   4500
tccatgttca ggttaatggg acactatcta agacattcat gagtcagctc gcatggaaga   4560
gggcagtctg cttcccatta atggatgtga atccccatat gaacatggtg atttgggcgg   4620
catctgtaga aatcacaggc gtcgatgcgg tgttccaacc ggccatccct cgtgatttcc   4680
```

```
gctactaccc taatgttgtg gctaagaaca tcggaaggat cagaaagctg taaatgtgca   4740
cccatcagag acctgcgaca atgccccaag cagacaccac ctggcagtcg gagccaccgg   4800
gtcactcctt gtcttaaata agaaaaactt agggataaag tcccttgtga gtgcttggtt   4860
gcaaaactct ccccttggga aacatgacag catatatcca gagatcacag tgcatctcaa   4920
catcactact ggttgttctc accacattgg tctcgtgtca gattcccagg gataggctct   4980
ctaacatagg ggtcatagtc gatgaaggga aatcactgaa gatagctgga tcccacgaat   5040
cgaggtacat agtactgagt ctagttccgg gggtagactt tgagaatggg tgcggaacag   5100
cccaggttat ccagtacaag agcctactga acaggctgtt aatcccattg agggatgcct   5160
tagatcttca ggaggctctg ataactgtca ccaatgatac gacacaaaat gccggtgctc   5220
cccagtcgag attcttcggt gctgtgattg gtactatcgc acttggagtg gcgacatcag   5280
cacaaatcac cgcagggatt gcactagccg aagcgaggga ggccaaaaga gacatagcgc   5340
tcatcaaaga atcgatgaca aaaacacaca agtctataga actgctgcaa aacgctgtgg   5400
gggaacaaat tcttgctcta aagacactcc aggatttcgt gaatgatgag atcaaacccg   5460
caataagcga attaggctgt gagactgctg ccttaagact gggtataaaa ttgacacagc   5520
attactccga gctgttaact gcgttcggct cgaatttcgg aaccatcgga gagaagagcc   5580
tcacgctgca ggcgctgtct tcactttact ctgctaacat tactgagatt atgaccacaa   5640
tcaggacagg gcagtctaac atctatgatg tcatttatac agaacagatc aaaggaacgg   5700
tgatagatgt ggatctagag agatacatgg tcaccctgtc tgtgaagatc cctattcttt   5760
ctgaagtccc aggtgtgctc atacacaagg catcatctat ttcttacaac atagacgggg   5820
aggaatggta tgtgactgtc cccagccata tactcagtcg tgcttctttc ttagggggtg   5880
cagacataac cgattgtgtt gagtccagat tgacctatat atgccccagg gatcccgcac   5940
aactgatacc tgacagccag caaaagtgta tcctgggggga cacaacaagg tgtcctgtca   6000
caaaagttgt ggacagcctt atccccaagt ttgcttttgt gaatgggggc gttgttgcta   6060
actgcatagc atccacatgt acctgcggga caggccgaag accaatcagt caggatcgct   6120
ctaaaggtgt agtattccta acccatgaca actgtggtct tataggtgtc aatggggtag   6180
aattgtatgc taaccggaga gggcacgatg ccacttgggg ggtccagaac ttgacagtcg   6240
gtcctgcaat tgctatcaga cccgttgata tttctctcaa ccttgctgat gctacgaatt   6300
tcttgcaaga ctctaaggct gagcttgaga aagcacggaa aatcctctcg gaggtaggta   6360
gatggtacaa ctcaagagag actgtgatta cgatcatagt agttatggtc gtaatattgg   6420
tggtcattat agtgatcatc atcgtgcttt atagactcag aaggtcaatg ctaatgggta   6480
atccagatga ccgtataccg agggacacat acacattaga gccgaagatc agacatatgt   6540
acacaaacgg tgggtttgat gcaatggctg agaaaagatg atcacgacca ttatcagatg   6600
tcttgtaaag caggcatagt atccgttgag atctgtatat aataagaaaa acttagggtg   6660
aaagtgaggt cgcgcggtac tttagctttc acctcaaaca agcacagatc atggatggtg   6720
ataggggcaa acgtgactcg tactggtcta cttctcctag tggtagcacc acaaaaccag   6780
catcaggttg ggagaggtca agtaaagccg acacatggtt gctgattctc tcattcaccc   6840
agtgggcttt gtcaattgcc acagtgatca tctgtatcat aatttctgct agacaagggt   6900
atagtatgaa agagtactca atgactgtag aggcattgaa catgagcagc agggaggtga   6960
aagagtcact taccagtcta ataaggcaag aggttatagc aagggctgtc aacattcaga   7020
```

-continued

```
gctctgtgca aaccggaatc ccagtcttgt tgaacaaaaa cagcagggat gtcatccaga   7080
tgattgataa gtcgtgcagc agacaagagc tcactcagca ctgtgagagt acgatcgcag   7140
tccaccatgc cgatggaatt gccccacttg agccacatag tttctggaga tgccctgtcg   7200
gagaaccgta tcttagctca gatcctgaaa tctcattgct gcctggtccg agcttgttat   7260
ctggttctac aacgatctct ggatgtgtta ggctcccttc actctcaatt ggcgaggcaa   7320
tctatgccta ttcatcaaat ctcattacac aaggttgtgc tgacataggg aaatcatatc   7380
aggtcctgca gctagggtac atatcactca attcagatat gttccctgat cttaaccccg   7440
tagtgtccca cacttatgac atcaacgaca atcggaaatc atgctctgtg gtggcaaccg   7500
ggactagggg ttatcagctt tgctccatgc cgactgtaga cgaaagaacc gactactcta   7560
gtgatggtat tgaggatctg gtccttgatg tcctggatct caaagggaga actaagtctc   7620
accggtatcg caacagcgag gtagatcttg atcacccgtt ctctgcacta taccccagtg   7680
taggcaacgg cattgcaaca gaaggctcat tgatatttct tgggtatggt ggactaacca   7740
cccctctgca gggtgataca aaatgtagga cccaaggatg ccaacaggtg tcgcaagaca   7800
catgcaatga ggctctgaaa attacatggc taggagggaa acaggtggtc agcgtgatca   7860
tccaggtcaa tgactatctc tcagagaggc caaagataag agtcacaacc attccaatca   7920
ctcaaaacta tctcggggcg gaaggtagat tattaaaatt gggtgatcgg gtgtacatct   7980
atacaagatc atcaggctgg cactctcaac tgcagatagg agtacttgat gtcagccacc   8040
ctttgactat caactggaca cctcatgaag ccttgtctag accaggaaat aaagagtgca   8100
attggtacaa taagtgtccg aaggaatgca tatcaggcgt atacactgat gcttatccat   8160
tgtcccctga tgcagctaac gtcgctaccg tcacgctata tgccaataca tcgcgtgtca   8220
acccaacaat catgtattct aacactacta acattataaa tatgttaagg ataaaggatg   8280
ttcaattaga ggctgcatat accacgacat cgtgtatcac gcattttggt aaaggctact   8340
gctttcacat catcgagatc aatcagaaga gcctgaatac cttacagccg atgctcttta   8400
agactagcat ccctaaatta tgcaaggccg agtcttaaat ttaactgact agcaggcttg   8460
tcggccttgc tgacactaga gtcatctccg aacatccaca atatctctca gtctcttacg   8520
tctctcacag tattaagaaa aacccagggt gaatgggaag cttgccatag gtcatggatg   8580
ggcaggagtc ctcccaaaac ccttctgaca tactctatcc agaatgccac ctgaactctc   8640
ccatagtcag ggggaagata gcacagttgc acgtcttgtt agatgtgaac cagccctaca   8700
gactgaagga cgacagcata ataaatatta caaagcacaa aattaggaac ggaggattgt   8760
ccccccgtca aattaagatc aggtctctgg gtaaggctct tcaacgcaca ataaaggatt   8820
tagaccgata cacgtttgaa ccgtacccaa cctactctca ggaattactt aggcttgata   8880
taccagagat atgtgacaaa atccgatccg tcttcgcggt ctcggatcgg ctgaccaggg   8940
agttatctag tgggttccag gatctttggt tgaatatctt caagcaacta ggcaatatag   9000
aaggaagaga ggggtacgat ccgttgcagg atatcggcac catcccggag ataactgata   9060
agtacagcag gaatagatgg tataggccat tcctaacttg gttcagcatc aaatatgaca   9120
tgcggtggat gcagaagacc agaccggggg gacccctcga tacctctaat tcacataacc   9180
tcctagaatg caaatcatac actctagtaa catacggaga tcttgtcatg atactgaaca   9240
agttgacatt gacagggtat atcctaaccc ctgagctggt cttgatgtat tgtgatgttg   9300
tagaaggaag gtggaatatg tctgctgcag ggcatctaga taagaagtcc attgggataa   9360
caagcaaagg tgaggaatta tgggaactag tggattccct cttctcaagt cttggagagg   9420
```

aaatatacaa tgtcatcgca ctattggagc ccctatcact tgctctcata caactaaatg 9480
atcctgttat acctctacgt ggggcattta tgaggcatgt gttgacagag ctacagactg 9540
ttttaacaag tagagacgtg tacacagatg ctgaagcaga cactattgtg gagtcgttac 9600
tcgccatttt ccatggaacc tctattgatg agaaagcaga gatcttttcc ttctttagga 9660
catttggcca ccccagctta gaggctgtca ctgccgccga caaggtaagg gcccatatgt 9720
atgcacaaaa ggcaataaag cttaagaccc tatacgagtg tcatgcagtt ttttgcacta 9780
tcatcataaa tgggtataga gagaggcatg gcggacagtg gcccccctgt gacttccctg 9840
atcacgtgtg tctagaacta aggaacgctc aagggtccaa tacggcaatc tcttatgaat 9900
gtgctgtaga caactataca agtttcatag gcttcaagtt tcggaagttt atagaaccac 9960
aactagatga agatctcaca atatatatga aagacaaagc actatccccc aggaaggagg 10020
catgggactc tgtatacccg gatagtaatc tgtactataa agccccagag tctgaagaga 10080
cccggcggct tattgaagtg ttcataaatg atgagaattt caacccagaa gaaattatca 10140
attatgtgga gtcaggagat tggttgaaag acgaggagtt caacatctcg tacagtctca 10200
aagagaaaga gatcaagcaa gagggtcgtc tattcgcaaa aatgacttat aagatgcgag 10260
ccgtacaggt gctggcagag acactactgg ctaaaggaat aggagagcta ttcagcgaaa 10320
atgggatggt taaaggagag atagacctac ttaaaagatt gactactctt tctgtctcag 10380
gcgtccccag gactgattca gtgtacaata actctaaatc atcagagaag agaaacgaag 10440
gcatggaaaa taagaactct ggggggtact gggacgaaaa gaagaggtcc agacatgaat 10500
tcaaggcaac agattcatca acagacggct atgaaacgtt aagttgcttc ctcacaacag 10560
acctcaagaa atactgctta aactggagat ttgagagtac tgcattgttt ggtcagagat 10620
gcaacgagat atttggcttc aagaccttct ttaactggat gcatccagtc cttgaaaggt 10680
gtacaatata tgttggagat ccttactgtc cagtcgccga ccggatgcat cgacaactcc 10740
aggatcatgc agactctggc attttcatac ataatcctag ggggggcata gaaggttact 10800
gccagaagct gtggacctta atctcaatca gtgcaatcca cctagcagct gtgagagtgg 10860
gtgtcagggt ctctgcaatg gttcagggtg acaatcaagc tatagccgtg acatcaagag 10920
tacctgtagc tcagacttac aagcagaaga aaaatcatgt ctatgaggag atcaccaaat 10980
atttcggtgc tctaagacac gtcatgtttg atgtagggca cgagctaaaa ttgaacgaga 11040
ccatcattag tagcaagatg tttgtctata gtaaaaggat atactatgat gggaagattt 11100
taccacagtg cctgaaagcc ttgaccaagt gtgtattctg gtccgagaca ctggtagatg 11160
aaaacagatc tgcttgttcg aacatctcaa catccatagc aaaagctatc gaaaatgggt 11220
attctcctat actaggctac tgcattgcgt tgtataagac ctgtcagcag gtgtgcatat 11280
cactagggat gactataaat ccaactatca gcccgaccgt aagagatcaa tactttaagg 11340
gtaagaattg gctgagatgt gcagtgttga ttccagcaaa tgttggagga ttcaactaca 11400
tgtctacatc tagatgcttt gttagaaata ttggagaccc cgcagtagca gccctagctg 11460
atctcaaaag attcatcaga gcggatctgt tagacaagca ggtattatac agggtcatga 11520
atcaagaacc cggtgactct agttttctag attgggcttc agacccttat tcgtgtaacc 11580
tcccgcattc tcagagtata actacgatta taaagaatat cactgctaga tctgtgctgc 11640
aggaatcccc gaatcctcta ctgtctggtc tcttcaccga gactagtgga gaagaggatc 11700
tcaacctggc ctcgttcctt atggaccgga aagtcatcct gccgagagtg gctcatgaga 11760

-continued

```
tcctgggtaa ttccttaact ggagttaggg aggcgattgc agggatgctt gatacgacca  11820
agtctctagt gagagccagc gttaggaaag gaggattatc atatgggata ttgaggaggc  11880
ttgtcaatta tgatctattg cagtacgaga cactgactag aactctcagg aaaccggtga  11940
aagacaacat cgaatatgag tatatgtgtt cagttgagct agctgtcggt ctaaggcaga  12000
aaatgtggat ccacctgact tacgggagac ccatacatgg gctagaaaca ccagaccctt  12060
tagagctctt gaggggaata tttatcgaag gttcagaggt gtgcaagctt tgcaggtctg  12120
aaggagcaga ccccatctat acatggttct atcttcctga caatatagac ctggacacgc  12180
ttacaaacgg atgtccggct ataagaatcc cctattttgg atcagccact gatgaaaggt  12240
cggaagccca actcgggtat gtaagaaatc taagcaaacc cgcaaaggcg gccatccgga  12300
tagctatggt gtatacgtgg gcctacggga ctgatgagat atcgtggatg gaagccgctc  12360
ttatagccca aacaagagct aatctgagct tagagaatct aaagctgctg actcctgttt  12420
caacctccac taatctatct cataggttga aagatacggc aacccagatg aagttctcta  12480
gtgcaacact agtccgtgca agtcggttca taacaatatc aaatgataac atggcactca  12540
aagaagcagg ggagtcgaag gatactaatc tcgtgtatca gcagattatg ctaactgggc  12600
taagcttgtt cgagttcaat atgagatata agaaaggttc cttagggaag ccactgatat  12660
tgcacttaca tcttaataac gggtgctgta taatggagtc cccacaggag gcgaatatcc  12720
ccccaaggtc cacattagat ttagagatta cacaagagaa caataaattg atctatgatc  12780
ctgatccact caaggatgtg gaccttgagc tatttagcaa ggtcagagat gttgtacaca  12840
cagttgacat gacttattgg tcagatgatg aagttatcag agcaaccagt atctgtactg  12900
caatgacgat agctgataca atgtctcaat tagatagaga caacttaaaa gagatgatcg  12960
cactagtaaa tgacgatgat gtcaacagct tgattactga gtttatggtg attgatgttc  13020
ctttattttg ctcaacgttc gggggtattc tagtcaatca gtttgcatac tcactctacg  13080
gcttaaacat cagaggaagg gaagaaatat ggggacatgt agtccggatt cttaaagata  13140
cctcccacgc agttttaaaa gtcttatcta atgctctatc tcatcccaaa atcttcaaac  13200
gattctggaa tgcaggtgtc gtggaacctg tgtatgggcc taacctctca aatcaggata  13260
agatactctt ggccctctct gtctgtgaat attctgtgga tctattcatg cacgattggc  13320
aagggggtgt accgcttgag atctttatct gtgacaatga cccagatgtg gccgacatga  13380
ggaggtcctc tttcttggca agacatcttg catacctatg cagcttggca gagatatcta  13440
gggatgggcc aagattagaa tcaatgaact ctctagagag gctcgagtca ctaaagagtt  13500
acctggaact cacatttctt gatgacccgg tactgaggta cagtcagttg actggcctag  13560
tcatcaaagt attcccatct actttgacct atatccggaa gtcatctata aaagtgttaa  13620
ggacaagagg tataggagtc cctgaagtct tagaagattg ggatcccgag gcagataatg  13680
cactgttaga tggtatcgcg gcagaaatac aacagaatat tcctttggga catcagacta  13740
gagccccttt ttgggggttg agagtatcca agtcacaggt actgcgtctc cgggggtaca  13800
aggagatcac aagaggtgag ataggcagat caggtgttgg tctgacgtta ccattcgatg  13860
gaagatatct atctcaccag ctgaggctct ttggcatcaa cagtactagc tgcttgaaag  13920
cacttgaact tacctaccta ttgagcccct tagttgacaa ggataaagat aggctatatt  13980
taggggaagg agctggggcc atgctttcct gttatgacgc tactcttggc ccatgcatca  14040
actattataa ctcaggggta tactcttgtg atgtcaatgg gcagagagag ttaaatatat  14100
atcctgctga ggtggcacta gtgggaaaga aattaaacaa tgttactagt ctgggtcaaa  14160
```

gagttaaagt gttattcaac gggaatcctg gctcgacatg gattgggaat gatgagtgtg 14220
aggctttgat ttggaatgaa ttacagaata gctcgatagg cctagtccac tgtgacatgg 14280
agggaggaga tcataaggat gatcaagttg tactgcatga gcattacagt gtaatccgga 14340
tcgcgtatct ggtgggggat cgagacgttg tgcttataag caagattgct cccaggctgg 14400
gcacggattg gaccaggcag ctcagcctat atctgagata ctgggacgag gttaacctaa 14460
tagtgcttaa aacatctaac cctgcttcca cagagatgta tctcctatcg aggcacccca 14520
aatctgacat tatagaggac agcaagacag tgttagctag tctcctccct ttgtcaaaag 14580
aagatagcat caagatagaa aagtggatct taatagagaa ggcaaaggct cacgaatggg 14640
ttactcggga attgagagaa ggaagctctt catcagggat gcttagacct taccatcaag 14700
cactgcagac gtttggcttt gaaccaaact tgtataaatt gagcagagat ttcttgtcca 14760
ccatgaacat agctgataca cacaactgca tgatagcttt caacagggtt ttgaaggata 14820
caatcttcga atgggctaga ataactgagt cagataaaag gcttaaacta actggtaagt 14880
atgacctgta tcctgtgaga gattcaggca agttgaagac aatttctaga agacttgtgc 14940
tatcttggat atctttatct atgtccacaa gattggtaac tgggtcattc cctgaccaga 15000
agtttgaagc aagacttcaa ttgggaatag tttcattatc atcccgtgaa atcaggaacc 15060
tgagggttat cacaaaaact ttattagaca ggtttgagga tattatacat agtataacgt 15120
atagattcct caccaaagaa ataaagattt tgatgaagat tttaggggca gtcaagatgt 15180
tcggggccag gcaaaatgaa tacacgaccg tgattgatga tggatcacta ggtgatatcg 15240
agccatatga cagctcgtaa taattagtcc ctatcgtgca gaacgatcga agctccgcgg 15300
tacctggaag tcttggactt gtccatatga caatagtaag aaaaacttac aagaagacaa 15360
gaaaatttaa aaggatacat atctcttaaa ctcttgtctg gt 15402

<210> SEQ ID NO 11
<211> LENGTH: 17706
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11
accaaacaag agaaaaaaca tgtatgggat atgtaatgaa gttatacagg attttagggt 60
caaagtatcc accctgagga gcaggttcca gaccctttgc tttgctgcca aagttcacgc 120
ggccgccaag gttcacttat gacagcatat atccagagat cacagtgcat ctcaacatca 180
ctactggttg ttctcaccac attggtctcg tgtcaggcta gcgcagagaa tttgtgggta 240
acagtctact atggagtccc tgtatggaag gatgcagaga caacattgtt ctgtgctagt 300
gacgcaaagg cttacgagac ggagaagcac aatgtgtggg caactcacgc atgtgtccca 360
accgatccaa atcctcaaga gattcatcta gagaatgtga ctgaagaatt caatatgtgg 420
aagaataata tggtagagca aatgcataca gatatcatta gtttatggga ccagtcactt 480
aaaccctgcg ttaaattgac gcctctatgt gtgacacttc aatgtactaa tgttacaaac 540
aacataacag atgatatgag aggagaactg aagaactgta gtttcaacat gacgacagag 600
ttgcgtgaca agaaacagaa agtgtattca ctattctatc ggttggatgt agtacagata 660
aatgagaatc aaggaaacag gtccaacaac tctaacaaag agtacagact tattaattgc 720
aataccagtg ctatcacgca agcctgccca aaggtttcat ttgaaccaat acctattcat 780

```
tattgtgcac ctgctggatt cgccatcctc aaatgtaaag acaagaagtt caatggaaca    840
ggaccctgcc catcagtttc aaccgttcag tgcacccacg gaatcaagcc tgtagttagt    900
actcaattat tgttaaatgg gagcttagct gaagaagaag ttatgattag atcagagaat    960
attaccaata atgcgaagaa catcttggtt caattcaata ctccagtcca gatcaattgc   1020
acaaggccta ataataatac cagaaagagt ataagaattg ggccaggaca ggcattctat   1080
gcaacaggag atataatcgg agacattcga caagcgcact gcactgtttc taaggccact   1140
tggaatgaaa cattgggtaa agttgtaaag caacttcgga agcatttcgg aaataacaca   1200
attattagat ttgcgaactc atctggaggg gatctggaag tgacaacaca ctctttcaat   1260
tgcggtggcg agttcttcta ttgtaataca agtggattat ttaactctac ttggatttca   1320
aatacctcag tccaaggatc taattcaaca gggtctaacg attctataac attaccttgc   1380
cgtataaagc aaattattaa tatgtggcaa agaatcgggc aagcgatgta tgctccacct   1440
attcaaggcg tgattcgttg cgtttcaaac ataacagggt tgatcctgac cagggatgga   1500
ggctctacca attccaccac cgagaccttc cgtcccggtg gcggagatat gcgggataac   1560
tggagatcag agctctataa gtataaggtt gtgaagattg aacctcttgg agttgcccct   1620
acaagagcaa agagaagggt ggttggccga gagaagagag cagttggcat cggtgctgtc   1680
tttctcggat ttcttggagc agctggatcc actatgggag cagcatcaat gacactaaca   1740
gtgcaggcta gaaatttgct tagcggaatc gttcagcagc agagcaattt actaagagca   1800
attgaagcac agcaacatct cttaaagttg acggtgtggg gcattaaaca actacaagcg   1860
agagtgcttg ccgtcgaaag atatttgcga gaccaacagc tattgggtat ttggggttgt   1920
tctgggaaat taatttgcac aacaaatgtt ccatggaact cctcctggag taataggaat   1980
ttaagtgaga tatgggacaa catgacatgg ttgcagtggg acaaggaaat ctcaaattat   2040
acacagataa tctatggatt attagaagag tctcagaatc agcaagagaa gaatgaacag   2100
gatttgcttg cattggataa gtgggcttct ctatggaact ggttcgatat tagtaattgg   2160
ctctggtata ttaagaactc aagagagact gtgattacga tcatagtagt tatggtcgta   2220
atattggtgg tcattatagt gatcatcatc gtgctttata gactcagaag gtcaatgcta   2280
atgggtaatc cagatgaccg tataccgagg gacacataca cattagagcc gaagatcaga   2340
catatgtaca caaacggtgg gtttgatgca atggctgaga aaagatgacc gtagtaagaa   2400
aaacttaggg tgaaagttca tcgcggccgc agatcttcac gatggccggg ttgttgagca   2460
ccttcgatac atttagctct aggaggagcg aaagtattaa taagtcggga ggaggtgctg   2520
ttatccccgg ccagaggagc acagtctcag tgttcgtact aggcccaagt gtgactgatg   2580
atgcagacaa gttattcatt gcaactacct tcctagctca ctcattggac acagataagc   2640
agcactctca gagagggggg ttcctcgtct ctctgcttgc catggcttac agtagtccag   2700
aattgtactt gacaacaaac ggagtaaacg ccgatgtcaa atatgtgatc tacaacatag   2760
agaaagaccc taagaggacg aagacagacg gattcattgt gaagacgaga gatatggaat   2820
atgagaggac cacagaatgg ctgtttggac ctatggtcaa caagagccca ctcttccagg   2880
gtcaacggga tgctgcagac cctgacacac tccttcaaat ctatgggtat cctgcatgcc   2940
taggagcaat aattgtccaa gtctggattg tgctggtgaa ggccatcaca agcagcgccg   3000
gcttaaggaa agggttcttc aacaggttag aggcgttcag acaagacggc accgtgaaag   3060
gtgccttagt tttcactggg gagacagttg aggggatagg ctcggttatg agatctcagc   3120
```

-continued

```
aaagccttgt atctctcatg gttgagaccc ttgtgactat gaatactgca agatctgatc   3180
tcaccacatt agagaagaac atccagatcg ttgggaacta catccgagat gcagggctgg   3240
cttccttcat gaacactatt aaatatgggg tggaaacaaa gatggcagct ctaacgttgt   3300
caaacctgag gcccgatatt aataagctta gaagcctcat agacacctac ctgtcaaaag   3360
gccccagagc tccctttatc tgtatcctca aggaccctgt tcatggtgaa tttgctccag   3420
gcaattatcc tgcactatgg agttacgcca tgggagtcgc cgtcgtacag aacaaggcaa   3480
tgcagcagta cgtcacaggg aggacatacc ttgatatgga aatgttctta ctaggacaag   3540
ccgtggcaaa ggatgctgaa tcgaagatca gcagtgcctt ggaagatgag ttaggagtga   3600
cggatacagc caaggggagg ctcagacatc atctggcaaa cttgtccggt ggggatggtg   3660
cttaccacaa accaacaggc ggtggtgcaa ttgaggtagc tctagacaat gccgacatcg   3720
acctagaaac aaaagcccat gcggaccagg acgctagggg ttggggtgga gatagtggtg   3780
aaagatgggc acgtcaggtg agtggtggcc actttgtcac actacatggg gctgaacggt   3840
tagaggagga aaccaatgat gaggatgtat cagacataga gagaagaata gccatgagac   3900
tcgcagagag acggcaagag gattctgcaa cccatggaga tgaaggccgc aataacggtg   3960
tcgatcatga cgaagatgac gatgccgcag cagtagctgg gataggagga atctaggatc   4020
atacgaggct tcaaggtact tgatccgtag taagaaaaac ttagggtgaa agttcatcca   4080
ccgatcggct caggcaaggc cacacccaac cccaccgacc acacccagca gtcgagacag   4140
ccacggcttc ggctacactt accgcatgga tcaagatgcc ttcattctta aagaagattc   4200
tgaagttgag agggaggcgc caggaggacg agagtcgctc tcggatgtta tcggattcct   4260
cgatgctgtc ctgtcgagtg aaccaactga catcggaggg gacagaagct ggctccacaa   4320
caccatcaac actccccaag gaccaggctc tgctcataga gccaaaagtg agggcgaagg   4380
agaagtctca acaccgtcga cccaagataa tcgatcaggt gaggagagta gagtctctgg   4440
gagaacaagc aagccagagg cagaagcaca tgctggaaac cttgataaac aaaatataca   4500
ccgggccttt gggggaagaa ctggtacaaa ctctgtatct caggatctgg gcgatggagg   4560
agactccgga atccttgaaa atcctccaaa tgagagagga tatccgagat caggtattga   4620
agatgaaaac agagagatgg ctgcgcaccc tgataagagg ggagaagacc aagctgaagg   4680
acttccagaa gaggtacgag gaagtacatc cctacctgat gaaggagaag gtggagcaag   4740
taataatgga agaagcatgg agcctggcag ctcacatagt gcaagagtaa ctggggtcct   4800
ggtgattcct agccccgaac ttgaagaggc tgtgctacgg aggaacaaaa gaagacctac   4860
caacagtggg tccaaacctc ttactccagc aaccgtgcct ggcacccggt ccccaccgct   4920
gaatcgttac aacagcacag ggtcaccacc aggaaaaccc ccatctacac aggatgagca   4980
catcaactct ggggacaccc ccgccgtcag ggtcaaagac cggaaaccac caatagggac   5040
ccgctctgtc tcagattgtc cagccaacgg ccgcccaatc cacccgggtc tagagaccga   5100
ctcaacaaaa aagggcatag gagagaacac atcatctatg aaagagatgg ctacattgtt   5160
gacgagtctt ggtgtaatcc agtctgctca agaattcgaa tcatcccgag acgcgagtta   5220
tgtgtttgca agacgtgccc taaagtctgc aaactatgca gagatgacat tcaatgtatg   5280
cggcctgatc ctttctgccg agaaatcttc cgctcgtaag gtagatgaga acaaacaact   5340
gctcaaacag atccaagaga gcgtggaatc attccgggat atttacaaga gattctctga   5400
gtatcagaaa gaacagaact cattgctgat gtccaaccta tctacacttc atatcatcac   5460
agatagaggt ggcaagactg acaacacaga ctcccttaca aggtccccct ccgtttttgc   5520
```

```
aaaatcaaaa gagaacaaga ctaaggctac caggtttgac ccatctatgg agaccctaga   5580
agatatgaag tacaaaccgg acctaatccg agaggatgaa tttagagatg agatccgcaa   5640
cccggtgtac caagagaggg acacagaacc cagggcctca aacgcatcac gtctcctccc   5700
ctccaaagag aagcccacaa tgcactctct caggctcgtc atagagagca gtcccctaag   5760
cagagctgag aaagtagcat atgtgaaatc attatccaag tgcaagacag accaagaggt   5820
taaggcagtc atggaactcg tagaagagga catagagtca ctgaccaact agatcccggg   5880
tgaggcatcc taccatcctc agtcatagag agatccaatc taccatcagc atcagccagt   5940
aaagattaag aaaaacttag ggtgaaagaa atttcaccta acacggcgca atggcagata   6000
tctatagatt ccctaagttc tcatatgagg ataacggtac tgtggagccc ctgcctctga   6060
gaactggtcc ggataagaaa gccatccccc acatcaggat tgtcaaggta ggagaccctc   6120
ctaaacatgg agtgagatac ctagatttat tgctcttggg tttctttgag acaccgaaac   6180
aaacaaccaa tctagggagc gtatctgact tgacagagcc gaccagctac tcaatatgcg   6240
gctccgggtc gttacccata ggtgtggcca aatactacgg gactgatcag gaactcttaa   6300
aggcctgcac cgatctcaga attacggtga ggaggactgt tcgagcagga gagatgatcg   6360
tatacatggt ggattcgatt ggtgctccac tcctaccatg gtcaggcagg ctgagacagg   6420
gaatgatatt taatgcaaac aaggtcgcac tagctcccca atgcctccct gtggacaagg   6480
acataagact cagagtggtg tttgtcaatg ggacatctct aggggcaatc accatagcca   6540
agatcccaaa gacccttgca gaccttgcat tgcccaactc tatatctgtt aatttactgg   6600
tgacactcaa gaccgggatc tccacagaac aaaagggggt actcccagta cttgatgatc   6660
aaggggagaa aaagctcaat tttatggtgc acctcgggtt gatcaggaga aaggtcggga   6720
agatatactc tgttgagtac tgcaagagca agattgagag aatgcggctg attttctcac   6780
ttgggttaat cggcggtata agcttccatg ttcaggttaa tgggacacta tctaagacat   6840
tcatgagtca gctcgcatgg aagagggcag tctgcttccc attaatggat gtgaatcccc   6900
atatgaacat ggtgatttgg gcggcatctg tagaaatcac aggcgtcgat gcggtgttcc   6960
aaccggccat ccctcgtgat ttccgctact accctaatgt tgtggctaag aacatcggaa   7020
ggatcagaaa gctgtaaatg tgcacccatc agagacctgc gacaatgccc caagcagaca   7080
ccacctggca gtcggagcca ccgggtcact ccttgtctta aataagaaaa acttagggat   7140
aaagtccctt gtgagtgctt ggttgcaaaa ctctcccctt gggaaacatg acagcatata   7200
tccagagatc acagtgcatc tcaacatcac tactggttgt tctcaccaca ttggtctcgt   7260
gtcagattcc cagggatagg ctctctaaca taggggtcat agtcgatgaa gggaaatcac   7320
tgaagatagc tggatcccac gaatcgaggt acatagtact gagtctagtt ccgggggtag   7380
actttgagaa tgggtgcgga acagcccagg ttatccagta caagagccta ctgaacaggc   7440
tgttaatccc attgagggat gccttagatc ttcaggaggc tctgataact gtcaccaatg   7500
atacgacaca aaatgccggt gctccccagt cgagattctt cggtgctgtg attggtacta   7560
tcgcacttgg agtggcgaca tcagcacaaa tcaccgcagg gattgcacta gccgaagcga   7620
gggaggccaa aagagacata gcgctcatca aagaatcgat gacaaaaaca cacaagtcta   7680
tagaactgct gcaaaacgct gtgggggaac aaattcttgc tctaaagaca ctccaggatt   7740
tcgtgaatga tgagatcaaa cccgcaataa gcgaattagg ctgtgagact gctgccttaa   7800
gactgggtat aaaattgaca cagcattact ccgagctgtt aactgcgttc ggctcgaatt   7860
```

-continued

```
tcggaaccat cggagagaag agcctcacgc tgcaggcgct gtcttcactt tactctgcta   7920
acattactga gattatgacc acaatcagga cagggcagtc taacatctat gatgtcattt   7980
atacagaaca gatcaaagga acggtgatag atgtggatct agagagatac atggtcaccc   8040
tgtctgtgaa gatccctatt ctttctgaag tcccaggtgt gctcatacac aaggcatcat   8100
ctatttctta caacatagac ggggaggaat ggtatgtgac tgtccccagc catatactca   8160
gtcgtgcttc tttcttaggg ggtgcagaca taaccgattg tgttgagtcc agattgacct   8220
atatatgccc cagggatccc gcacaactga tacctgacag ccagcaaaag tgtatcctgg   8280
gggacacaac aaggtgtcct gtcacaaaag ttgtggacag ccttatcccc aagtttgctt   8340
ttgtgaatgg gggcgttgtt gctaactgca tagcatccac atgtacctgc gggacaggcc   8400
gaagaccaat cagtcaggat cgctctaaag gtgtagtatt cctaacccat gacaactgtg   8460
gtcttatagg tgtcaatggg gtagaattgt atgctaaccg gagagggcac gatgccactt   8520
ggggggtcca gaacttgaca gtcggtcctg caattgctat cagacccgtt gatatttctc   8580
tcaaccttgc tgatgctacg aatttcttgc aagactctaa ggctgagctt gagaaagcac   8640
ggaaaatcct ctcggaggta ggtagatggt acaactcaag agagactgtg attacgatca   8700
tagtagttat ggtcgtaata ttggtggtca ttatagtgat catcatcgtg ctttatagac   8760
tcagaaggtc aatgctaatg ggtaatccag atgaccgtat accgagggac acatacacat   8820
tagagccgaa gatcagacat atgtacacaa acggtgggtt tgatgcaatg gctgagaaaa   8880
gatgatcacg accattatca gatgtcttgt aaagcaggca tagtatccgt tgagatctgt   8940
atataataag aaaaacttag ggtgaaagtg aggtcgcgcg gtactttagc tttcacctca   9000
aacaagcaca gatcatggat ggtgataggg gcaaacgtga ctcgtactgg tctacttctc   9060
ctagtggtag caccacaaaa ccagcatcag gttgggagag gtcaagtaaa gccgacacat   9120
ggttgctgat tctctcattc acccagtggg ctttgtcaat tgccacagtg atcatctgta   9180
tcataatttc tgctagacaa gggtatagta tgaaagagta ctcaatgact gtagaggcat   9240
tgaacatgag cagcagggag gtgaaagagt cacttaccag tctaataagg caagaggtta   9300
tagcaagggc tgtcaacatt cagagctctg tgcaaaccgg aatcccagtc ttgttgaaca   9360
aaaacagcag ggatgtcatc cagatgattg ataagtcgtg cagcagacaa gagctcactc   9420
agcactgtga gagtacgatc gcagtccacc atgccgatgg aattgcccca cttgagccac   9480
atagtttctg gagatgccct gtcggagaac cgtatcttag ctcagatcct gaaatctcat   9540
tgctgcctgg tccgagcttg ttatctggtt ctacaacgat ctctggatgt gttaggctcc   9600
cttcactctc aattggcgag gcaatctatg cctattcatc aaatctcatt acacaaggtt   9660
gtgctgacat agggaaatca tatcaggtcc tgcagctagg gtacatatca ctcaattcag   9720
atatgttccc tgatcttaac cccgtagtgt cccacactta tgacatcaac gacaatcgga   9780
aatcatgctc tgtggtggca accgggacta ggggttatca gctttgctcc atgccgactg   9840
tagacgaaag aaccgactac tctagtgatg gtattgagga tctggtcctt gatgtcctgg   9900
atctcaaagg gagaactaag tctcaccggt atcgcaacag cgaggtagat cttgatcacc   9960
cgttctctgc actatacccc agtgtaggca acggcattgc aacagaaggc tcattgatat  10020
ttcttgggta tggtggacta accacccctc tgcagggtga tacaaaatgt aggacccaag  10080
gatgccaaca ggtgtcgcaa gacacatgca atgaggctct gaaaattaca tggctaggag  10140
ggaaacaggt ggtcagcgtg atcatccagg tcaatgacta tctctcagag aggccaaaga  10200
taagagtcac aaccattcca atcactcaaa actatctcgg ggcggaaggt agattattaa  10260
```

```
aattgggtga tcgggtgtac atctatacaa gatcatcagg ctggcactct caactgcaga  10320
taggagtact tgatgtcagc caccctttga ctatcaactg gacacctcat gaagccttgt  10380
ctagaccagg aaataaagag tgcaattggt acaataagtg tccgaaggaa tgcatatcag  10440
gcgtatacac tgatgcttat ccattgtccc ctgatgcagc taacgtcgct accgtcacgc  10500
tatatgccaa tacatcgcgt gtcaacccaa caatcatgta ttctaacact actaacatta  10560
taaatatgtt aaggataaag gatgttcaat tagaggctgc atataccacg acatcgtgta  10620
tcacgcattt tggtaaaggc tactgctttc acatcatcga gatcaatcag aagagcctga  10680
ataccttaca gccgatgctc tttaagacta gcatccctaa attatgcaag gccgagtctt  10740
aaatttaact gactagcagg cttgtcggcc ttgctgacac tagagtcatc tccgaacatc  10800
cacaatatct ctcagtctct tacgtctctc acagtattaa gaaaaaccca gggtgaatgg  10860
gaagcttgcc ataggtcatg gatgggcagg agtcctccca aaacccttct gacatactct  10920
atccagaatg ccacctgaac tctcccatag tcagggggaa gatagcacag ttgcacgtct  10980
tgttagatgt gaaccagccc tacagactga aggacgacag cataataaat attacaaagc  11040
acaaaattag gaacggagga ttgtcccccc gtcaaattaa gatcaggtct ctgggtaagg  11100
ctcttcaacg cacaataaag gatttagacc gatacacgtt tgaaccgtac ccaacctact  11160
ctcaggaatt acttaggctt gatataccag agatatgtga caaaatccga tccgtcttcg  11220
cggtctcgga tcggctgacc agggagttat ctagtgggtt ccaggatctt tggttgaata  11280
tcttcaagca actaggcaat atagaaggaa gagaggggta cgatccgttg caggatatcg  11340
gcaccatccc ggagataact gataagtaca gcaggaatag atggtatagg ccattcctaa  11400
cttggttcag catcaaatat gacatgcggt ggatgcagaa gaccagaccg gggggacccc  11460
tcgatacctc taattcacat aacctcctag aatgcaaatc atacactcta gtaacatacg  11520
gagatcttgt catgatactg aacaagttga cattgacagg gtatatccta acccctgagc  11580
tggtcttgat gtattgtgat gttgtagaag gaaggtggaa tatgtctgct gcagggcatc  11640
tagataagaa gtccattggg ataacaagca aaggtgagga attatgggaa ctagtggatt  11700
ccctcttctc aagtcttgga gaggaaatat acaatgtcat cgcactattg gagcccctat  11760
cacttgctct catacaacta aatgatcctg ttatacctct acgtggggca tttatgaggc  11820
atgtgttgac agagctacag actgttttaa caagtagaga cgtgtacaca gatgctgaag  11880
cagacactat tgtggagtcg ttactcgcca ttttccatgg aacctctatt gatgagaaag  11940
cagagatctt ttccttcttt aggacatttg gccaccccag cttagaggct gtcactgccg  12000
ccgacaaggt aagggcccat atgtatgcac aaaaggcaat aaagcttaag accctatacg  12060
agtgtcatgc agtttttttgc actatcatca taaatgggta tagagagagg catggcggac  12120
agtggccccc ctgtgacttc cctgatcacg tgtgtctaga actaaggaac gctcaagggt  12180
ccaatacggc aatctcttat gaatgtgctg tagacaacta tacaagtttc ataggcttca  12240
agtttcggaa gtttatagaa ccacaactag atgaagatct cacaatatat atgaaagaca  12300
aagcactatc ccccaggaag gaggcatggg actctgtata cccggatagt aatctgtact  12360
ataaagcccc agagtctgaa gagacccggc ggcttattga agtgttcata aatgatgaga  12420
atttcaaccc agaagaaatt atcaattatg tggagtcagg agattggttg aaagacgagg  12480
agttcaacat ctcgtacagt ctcaaagaga aagagatcaa gcaagagggt cgtctattcg  12540
caaaaatgac ttataagatg cgagccgtac aggtgctggc agagacacta ctggctaaag  12600
```

-continued

```
gaataggaga gctattcagc gaaaatggga tggttaaagg agagatagac ctacttaaaa  12660
gattgactac tctttctgtc tcaggcgtcc ccaggactga ttcagtgtac aataactcta  12720
aatcatcaga gaagagaaac gaaggcatgg aaaataagaa ctctgggggg tactgggacg  12780
aaaagaagag gtccagacat gaattcaagg caacagattc atcaacagac ggctatgaaa  12840
cgttaagttg cttcctcaca acagacctca agaaatactg cttaaactgg agatttgaga  12900
gtactgcatt gtttggtcag agatgcaacg agatatttgg cttcaagacc ttctttaact  12960
ggatgcatcc agtccttgaa aggtgtacaa tatatgttgg agatccttac tgtccagtcg  13020
ccgaccggat gcatcgacaa ctccaggatc atgcagactc tggcattttc atacataatc  13080
ctaggggggg catagaaggt tactgccaga agctgtggac cttaatctca atcagtgcaa  13140
tccacctagc agctgtgaga gtgggtgtca gggtctctgc aatggttcag ggtgacaatc  13200
aagctatagc cgtgacatca agagtacctg tagctcagac ttacaagcag aagaaaaatc  13260
atgtctatga ggagatcacc aaatatttcg gtgctctaag acacgtcatg tttgatgtag  13320
ggcacgagct aaaattgaac gagaccatca ttagtagcaa gatgtttgtc tatagtaaaa  13380
ggatatacta tgatgggaag attttaccac agtgcctgaa agccttgacc aagtgtgtat  13440
tctggtccga gacactggta gatgaaaaca gatctgcttg ttcgaacatc tcaacatcca  13500
tagcaaaagc tatcgaaaat gggtattctc ctatactagg ctactgcatt gcgttgtata  13560
agacctgtca gcaggtgtgc atatcactag ggatgactat aaatccaact atcagcccga  13620
ccgtaagaga tcaatacttt aagggtaaga attggctgag atgtgcagtg ttgattccag  13680
caaatgttgg aggattcaac tacatgtcta catctagatg ctttgttaga aatattggag  13740
accccgcagt agcagcccta gctgatctca aaagattcat cagagcggat ctgttagaca  13800
agcaggtatt atacagggtc atgaatcaag aacccggtga ctctagtttt ctagattggg  13860
cttcagaccc ttattcgtgt aacctcccgc attctcagag tataactacg attataaaga  13920
atatcactgc tagatctgtg ctgcaggaat ccccgaatcc tctactgtct ggtctcttca  13980
ccgagactag tggagaagag gatctcaacc tggcctcgtt ccttatggac cggaaagtca  14040
tcctgccgag agtggctcat gagatcctgg gtaattcctt aactggagtt agggaggcga  14100
ttgcagggat gcttgatacg accaagtctc tagtgagagc cagcgttagg aaaggaggat  14160
tatcatatgg gatattgagg aggcttgtca attatgatct attgcagtac gagacactga  14220
ctagaactct caggaaaccg gtgaaagaca acatcgaata tgagtatatg tgttcagttg  14280
agctagctgt cggtctaagg cagaaaatgt ggatccacct gacttacggg agacccatac  14340
atgggctaga aacaccagac cctttagagc tcttgagggg aatatttatc gaaggttcag  14400
aggtgtgcaa gctttgcagg tctgaaggag cagaccccat ctatacatgg ttctatcttc  14460
ctgacaatat agacctggac acgcttacaa acggatgtcc ggctataaga atcccctatt  14520
ttggatcagc cactgatgaa aggtcggaag cccaactcgg gtatgtaaga aatctaagca  14580
aacccgcaaa ggcggccatc cggatagcta tggtgtatac gtgggcctac gggactgatg  14640
agatatcgtg gatggaagcc gctcttatag cccaaacaag agctaatctg agcttagaga  14700
atctaaagct gctgactcct gtttcaacct ccactaatct atctcatagg ttgaaagata  14760
cggcaaccca gatgaagttc tctagtgcaa cactagtccg tgcaagtcgg ttcataacaa  14820
tatcaaatga taacatggca ctcaaagaag caggggagtc gaaggatact aatctcgtgt  14880
atcagcagat tatgctaact gggctaagct tgttcgagtt caatatgaga tataagaaag  14940
gttccttagg gaagccactg atattgcact tacatcttaa taacgggtgc tgtataatgg  15000
```

agtccccaca ggaggcgaat atccccccaa ggtccacatt agatttagag attacacaag 15060
agaacaataa attgatctat gatcctgatc cactcaagga tgtggacctt gagctattta 15120
gcaaggtcag agatgttgta cacacagttg acatgactta ttggtcagat gatgaagtta 15180
tcagagcaac cagtatctgt actgcaatga cgatagctga tacaatgtct caattagata 15240
gagacaactt aaaagagatg atcgcactag taaatgacga tgatgtcaac agcttgatta 15300
ctgagtttat ggtgattgat gttcctttat tttgctcaac gttcgggggt attctagtca 15360
atcagtttgc atactcactc tacggcttaa acatcagagg aagggaagaa atatggggac 15420
atgtagtccg gattcttaaa gatacctccc acgcagtttt aaaagtctta tctaatgctc 15480
tatctcatcc caaaatcttc aaacgattct ggaatgcagg tgtcgtggaa cctgtgtatg 15540
ggcctaacct ctcaaatcag gataagatac tcttggccct ctctgtctgt gaatattctg 15600
tggatctatt catgcacgat tggcaagggg gtgtaccgct tgagatcttt atctgtgaca 15660
atgacccaga tgtggccgac atgaggaggt cctctttctt ggcaagacat cttgcatacc 15720
tatgcagctt ggcagagata tctagggatg ggccaagatt agaatcaatg aactctctag 15780
agaggctcga gtcactaaag agttacctgg aactcacatt tcttgatgac ccggtactga 15840
ggtacagtca gttgactggc ctagtcatca aagtattccc atctactttg acctatatcc 15900
ggaagtcatc tataaaagtg ttaaggacaa gaggtatagg agtccctgaa gtcttagaag 15960
attgggatcc cgaggcagat aatgcactgt tagatggtat cgcggcagaa atacaacaga 16020
atattccttt gggacatcag actagagccc ctttttgggg gttgagagta tccaagtcac 16080
aggtactgcg tctccggggg tacaaggaga tcacaagagg tgagataggc agatcaggtg 16140
ttggtctgac gttaccattc gatggaagat atctatctca ccagctgagg ctctttggca 16200
tcaacagtac tagctgcttg aaagcacttg aacttaccta cctattgagc cccttagttg 16260
acaaggataa agataggcta tatttagggg aaggagctgg ggccatgctt tcctgttatg 16320
acgctactct tggcccatgc atcaactatt ataactcagg ggtatactct tgtgatgtca 16380
atgggcagag agagttaaat atatatcctg ctgaggtggc actagtggga aagaaattaa 16440
acaatgttac tagtctgggt caaagagtta aagtgttatt caacgggaat cctggctcga 16500
catggattgg gaatgatgag tgtgaggctt tgatttggaa tgaattacag aatagctcga 16560
taggcctagt ccactgtgac atggagggag gagatcataa ggatgatcaa gttgtactgc 16620
atgagcatta cagtgtaatc cggatcgcgt atctggtggg ggatcgagac gttgtgctta 16680
taagcaagat tgctcccagg ctgggcacgg attggaccag gcagctcagc ctatatctga 16740
gatactggga cgaggttaac ctaatagtgc ttaaaacatc taaccctgct tccacagaga 16800
tgtatctcct atcgaggcac cccaaatctg acattataga ggacagcaag acagtgttag 16860
ctagtctcct ccctttgtca aaagaagata gcatcaagat agaaaagtgg atcttaatag 16920
agaaggcaaa ggctcacgaa tgggttactc gggaattgag agaaggaagc tcttcatcag 16980
ggatgcttag accttaccat caagcactgc agacgtttgg ctttgaacca aacttgtata 17040
aattgagcag agatttcttg tccaccatga acatagctga tacacacaac tgcatgatag 17100
ctttcaacag ggttttgaag gatacaatct tcgaatgggc tagaataact gagtcagata 17160
aaaggcttaa actaactggt aagtatgacc tgtatcctgt gagagattca ggcaagttga 17220
agacaatttc tagaagactt gtgctatctt ggatatcttt atctatgtcc acaagattgg 17280
taactgggtc attccctgac cagaagtttg aagcaagact tcaattggga atagtttcat 17340

-continued

```
tatcatcccg tgaaatcagg aacctgaggg ttatcacaaa aactttatta gacaggtttg  17400

aggatattat acatagtata acgtatagat tcctcaccaa agaaataaag attttgatga  17460

agattttagg ggcagtcaag atgttcgggg ccaggcaaaa tgaatacacg accgtgattg  17520

atgatggatc actaggtgat atcgagccat atgacagctc gtaataatta gtccctatcg  17580

tgcagaacga tcgaagctcc gcggtacctg gaagtcttgg acttgtccat atgacaatag  17640

taagaaaaac ttacaagaag acaagaaaat ttaaaaggat acatatctct taaactcttg  17700

tctggt                                                             17706
```

<210> SEQ ID NO 12
<211> LENGTH: 17616
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 12

```
accaaacaag agaaaaaaca tgtatgggat atgtaatgaa gttatacagg attttagggt     60

caaagtatcc accctgagga gcaggttcca gaccctttgc tttgctgcca aagttcacgc    120

ggccgccaag gttcacttat gaagtgcctt ttgtacttag ctttcttatt catcggggtg    180

aattgcaagg ctagcgcaga gaatttgtgg gtaacagtct actatggagt ccctgtatgg    240

aaggatgcag agacaacatt gttctgtgct agtgacgcaa aggcttacga gacggagaag    300

cacaatgtgt gggcaactca cgcatgtgtc ccaaccgatc caaatcctca agagattcat    360

ctagagaatg tgactgaaga attcaatatg tggaagaata atatggtaga gcaaatgcat    420

acagatatca ttagtttatg ggaccagtca cttaaaccct gcgttaaatt gacgcctcta    480

tgtgtgacac ttcaatgtac taatgttaca aacaacataa cagatgatat gagaggagaa    540

ctgaagaact gtagtttcaa catgacgaca gagttgcgtg acaagaaaca gaaagtgtat    600

tcactattct atcggttgga tgtagtacag ataaatgaga atcaaggaaa caggtccaac    660

aactctaaca aagagtacag acttattaat tgcaatacca gtgctatcac gcaagcctgc    720

ccaaaggttt catttgaacc aatacctatt cattattgtg cacctgctgg attcgccatc    780

ctcaaatgta aagacaagaa gttcaatgga acaggaccct gcccatcagt ttcaaccgtt    840

cagtgcaccc acggaatcaa gcctgtagtt agtactcaat tattgttaaa tgggagctta    900

gctgaagaag aagttatgat tagatcagag aatattacca ataatgcgaa gaacatcttg    960

gttcaattca atactccagt ccagatcaat tgcacaaggc ctaataataa taccagaaag   1020

agtataagaa ttgggccagg acaggcattc tatgcaacag gagatataat cggagacatt   1080

cgacaagcgc actgcactgt ttctaaggcc acttggaatg aaacattggg taaagttgta   1140

aagcaacttc ggaagcattt cggaaataac acaattatta gatttgcgaa ctcatctgga   1200

ggggatctgg aagtgacaac acactctttc aattgcggtg gcgagttctt ctattgtaat   1260

acaagtggat tatttaactc tacttggatt tcaaatacct cagtccaagg atctaattca   1320

acagggtcta acgattctat aacattacct tgccgtataa agcaaattat taatatgtgg   1380

caaagaatcg ggcaagcgat gtatgctcca cctattcaag gcgtgattcg ttgcgtttca   1440

aacataacag ggttgatcct gaccagggat ggaggctcta ccaattccac caccgagacc   1500

ttccgtcccg gtggcggaga tatgcgggat aactggagat cagagctcta taagtataag   1560

gttgtgaaga ttgaacctct tggagttgcc cctacaagag caaagagaag ggtggttggc   1620
```

```
cgagagaaga gagcagttgg catcggtgct gtctttctcg gatttcttgg agcagctgga   1680
tccactatgg gagcagcatc aatgacacta acagtgcagg ctagaaattt gcttagcgga   1740
atcgttcagc agcagagcaa tttactaaga gcaattgaag cacagcaaca tctcttaaag   1800
ttgacggtgt ggggcattaa acaactacaa gcgagagtgc ttgccgtcga aagatatttg   1860
cgagaccaac agctattggg tatttggggt tgttctggga aattaatttg cacaacaaat   1920
gttccatgga actcctcctg gagtaatagg aatttaagtg agatatggga caacatgaca   1980
tggttgcagt gggacaagga aatctcaaat tatacacaga taatctatgg attattagaa   2040
gagtctcaga atcagcaaga gaagaatgaa caggatttgc ttgcattgga taagtgggct   2100
tctctatgga actggttcga tattagtaat tggctctggt atattaagag ctctattgcc   2160
tctttttct ttatcatagg gttaatcatt ggactattct tggttctccg agttggtatt   2220
tatctttgca ttaaattaaa gcacaccaag aaaagacaga tttatacaga catagagatg   2280
aaccgacttg gaaagtaacc gtagtaagaa aaacttaggg tgaaagttca tcgcggccgc   2340
agatcttcac gatggccggg ttgttgagca ccttcgatac atttagctct aggaggagcg   2400
aaagtattaa taagtcggga ggaggtgctg ttatccccgg ccagaggagc acagtctcag   2460
tgttcgtact aggcccaagt gtgactgatg atgcagacaa gttattcatt gcaactacct   2520
tcctagctca ctcattggac acagataagc agcactctca gagagggggg ttcctcgtct   2580
ctctgcttgc catggcttac agtagtccag aattgtactt gacaacaaac ggagtaaacg   2640
ccgatgtcaa atatgtgatc tacaacatag agaaagaccc taagaggacg aagacagacg   2700
gattcattgt gaagacgaga gatatggaat atgagaggac cacagaatgg ctgtttggac   2760
ctatggtcaa caagagccca ctcttccagg gtcaacggga tgctgcagac cctgacacac   2820
tccttcaaat ctatgggtat cctgcatgcc taggagcaat aattgtccaa gtctggattg   2880
tgctggtgaa ggccatcaca agcagcgccg gcttaaggaa agggttcttc aacaggttag   2940
aggcgttcag acaagacggc accgtgaaag gtgccttagt tttcactggg gagacagttg   3000
aggggatagg ctcggttatg agatctcagc aaagccttgt atctctcatg gttgagaccc   3060
ttgtgactat gaatactgca agatctgatc tcaccacatt agagaagaac atccagatcg   3120
ttgggaacta catccgagat gcagggctgg cttccttcat gaacactatt aaatatgggg   3180
tggaaacaaa gatggcagct ctaacgttgt caaacctgag gcccgatatt aataagctta   3240
gaagcctcat agacacctac ctgtcaaaag gccccagagc tccctttatc tgtatcctca   3300
aggaccctgt tcatggtgaa tttgctccag gcaattatcc tgcactatgg agttacgcca   3360
tgggagtcgc cgtcgtacag aacaaggcaa tgcagcagta cgtcacaggg aggacatacc   3420
ttgatatgga aatgttctta ctaggacaag ccgtggcaaa ggatgctgaa tcgaagatca   3480
gcagtgcctt ggaagatgag ttaggagtga cggatacagc caaggggagg ctcagacatc   3540
atctggcaaa cttgtccggt ggggatggtg cttaccacaa accaacaggc ggtggtgcaa   3600
ttgaggtagc tctagacaat gccgacatcg acctagaaac aaaagcccat gcggaccagg   3660
acgctagggg ttggggtgga gatagtggtg aaagatgggc acgtcaggtg agtggtggcc   3720
actttgtcac actacatggg gctgaacggt tagaggagga aaccaatgat gaggatgtat   3780
cagacataga gagaagaata gccatgagac tcgcagagag acggcaagag gattctgcaa   3840
cccatggaga tgaaggccgc aataacggtg tcgatcatga cgaagatgac gatgccgcag   3900
cagtagctgg gataggagga atctaggatc atacgaggct tcaaggtact tgatccgtag   3960
taagaaaaac ttagggtgaa agttcatcca ccgatcggct caggcaaggc cacacccaac   4020
```

```
cccaccgacc acacccagca gtcgagacag ccacggcttc ggctacactt accgcatgga   4080
tcaagatgcc ttcattctta aagaagattc tgaagttgag agggaggcgc caggaggacg   4140
agagtcgctc tcggatgtta tcggattcct cgatgctgtc ctgtcgagtg aaccaactga   4200
catcggaggg gacagaagct ggctccacaa caccatcaac actccccaag gaccaggctc   4260
tgctcataga gccaaaagtg agggcgaagg agaagtctca acaccgtcga cccaagataa   4320
tcgatcaggt gaggagagta gagtctctgg gagaacaagc aagccagagg cagaagcaca   4380
tgctggaaac cttgataaac aaaatataca ccgggccttt gggggaagaa ctggtacaaa   4440
ctctgtatct caggatctgg gcgatggagg agactccgga atccttgaaa atcctccaaa   4500
tgagagagga tatccgagat caggtattga agatgaaaac agagagatgg ctgcgcaccc   4560
tgataagagg ggagaagacc aagctgaagg acttccagaa gaggtacgag gaagtacatc   4620
cctacctgat gaaggagaag gtggagcaag taataatgga agaagcatgg agcctggcag   4680
ctcacatagt gcaagagtaa ctggggtcct ggtgattcct agccccgaac ttgaagaggc   4740
tgtgctacgg aggaacaaaa gaagacctac caacagtggg tccaaacctc ttactccagc   4800
aaccgtgcct ggcacccggt ccccaccgct gaatcgttac aacagcacag ggtcaccacc   4860
aggaaaaccc ccatctacac aggatgagca catcaactct ggggacaccc ccgccgtcag   4920
ggtcaaagac cggaaaccac caatagggac ccgctctgtc tcagattgtc cagccaacgg   4980
ccgcccaatc cacccgggtc tagagaccga ctcaacaaaa aagggcatag gagagaacac   5040
atcatctatg aaagagatgg ctacattgtt gacgagtctt ggtgtaatcc agtctgctca   5100
agaattcgaa tcatcccgag acgcgagtta tgtgtttgca agacgtgccc taaagtctgc   5160
aaactatgca gagatgacat tcaatgtatg cggcctgatc ctttctgccg agaaatcttc   5220
cgctcgtaag gtagatgaga acaaacaact gctcaaacag atccaagaga gcgtggaatc   5280
attccgggat atttacaaga gattctctga gtatcagaaa gaacagaact cattgctgat   5340
gtccaaccta tctacacttc atatcatcac agatagaggt ggcaagactg acaacacaga   5400
ctcccttaca aggtccccct ccgtttttgc aaaatcaaaa gagaacaaga ctaaggctac   5460
caggtttgac ccatctatgg agaccctaga agatatgaag tacaaaccgg acctaatccg   5520
agaggatgaa tttagagatg agatccgcaa cccggtgtac caagagaggg acacagaacc   5580
cagggcctca aacgcatcac gtctcctccc ctccaaagag aagcccacaa tgcactctct   5640
caggctcgtc atagagagca gtcccctaag cagagctgag aaagtagcat atgtgaaatc   5700
attatccaag tgcaagacag accaagaggt taaggcagtc atggaactcg tagaagagga   5760
catagagtca ctgaccaact agatcccggg tgaggcatcc taccatcctc agtcatagag   5820
agatccaatc taccatcagc atcagccagt aaagattaag aaaaacttag ggtgaaagaa   5880
atttcaccta acacggcgca atggcagata tctatagatt ccctaagttc tcatatgagg   5940
ataacggtac tgtggagccc ctgcctctga gaactggtcc ggataagaaa gccatccccc   6000
acatcaggat tgtcaaggta ggagaccctc ctaaacatgg agtgagatac ctagatttat   6060
tgctcttggg tttctttgag acaccgaaac aaacaaccaa tctagggagc gtatctgact   6120
tgacagagcc gaccagctac tcaatatgcg gctccgggtc gttacccata ggtgtggcca   6180
aatactacgg gactgatcag gaactcttaa aggcctgcac cgatctcaga attacggtga   6240
ggaggactgt tcgagcagga gagatgatcg tatacatggt ggattcgatt ggtgctccac   6300
tcctaccatg gtcaggcagg ctgagacagg gaatgatatt taatgcaaac aaggtcgcac   6360
```

-continued

```
tagctcccca atgcctccct gtggacaagg acataagact cagagtggtg tttgtcaatg   6420
ggacatctct aggggcaatc accatagcca agatcccaaa gacccttgca gaccttgcat   6480
tgcccaactc tatatctgtt aatttactgg tgacactcaa gaccgggatc tccacagaac   6540
aaaagggggt actcccagta cttgatgatc aaggggagaa aaagctcaat tttatggtgc   6600
acctcgggtt gatcaggaga aaggtcggga agatatactc tgttgagtac tgcaagagca   6660
agattgagag aatgcggctg attttctcac ttgggttaat cggcggtata agcttccatg   6720
ttcaggttaa tgggacacta tctaagacat tcatgagtca gctcgcatgg aagagggcag   6780
tctgcttccc attaatggat gtgaatcccc atatgaacat ggtgatttgg gcggcatctg   6840
tagaaatcac aggcgtcgat gcggtgttcc aaccggccat ccctcgtgat ttccgctact   6900
accctaatgt tgtggctaag aacatcggaa ggatcagaaa gctgtaaatg tgcacccatc   6960
agagacctgc gacaatgccc caagcagaca ccacctggca gtcggagcca ccgggtcact   7020
ccttgtctta aataagaaaa acttagggat aaagtccctt gtgagtgctt ggttgcaaaa   7080
ctctcccctt gggaaacatg acagcatata tccagagatc acagtgcatc tcaacatcac   7140
tactggttgt tctcaccaca ttggtctcgt gtcagattcc cagggatagg ctctctaaca   7200
taggggtcat agtcgatgaa gggaaatcac tgaagatagc tggatcccac gaatcgaggt   7260
acatagtact gagtctagtt ccgggggtag actttgagaa tgggtgcgga acagcccagg   7320
ttatccagta caagagccta ctgaacaggc tgttaatccc attgagggat gccttagatc   7380
ttcaggaggc tctgataact gtcaccaatg atacgacaca aaatgccggt gctccccagt   7440
cgagattctt cggtgctgtg attggtacta tcgcacttgg agtggcgaca tcagcacaaa   7500
tcaccgcagg gattgcacta gccgaagcga gggaggccaa aagagacata gcgctcatca   7560
aagaatcgat gacaaaaaca cacaagtcta tagaactgct gcaaaacgct gtgggggaac   7620
aaattcttgc tctaaagaca ctccaggatt tcgtgaatga tgagatcaaa cccgcaataa   7680
gcgaattagg ctgtgagact gctgccttaa gactgggtat aaaattgaca cagcattact   7740
ccgagctgtt aactgcgttc ggctcgaatt tcggaaccat cggagagaag agcctcacgc   7800
tgcaggcgct gtcttcactt tactctgcta acattactga gattatgacc acaatcagga   7860
cagggcagtc taacatctat gatgtcattt atacagaaca gatcaaagga acggtgatag   7920
atgtggatct agagagatac atggtcaccc tgtctgtgaa gatccctatt ctttctgaag   7980
tcccaggtgt gctcatacac aaggcatcat ctatttctta caacatagac ggggaggaat   8040
ggtatgtgac tgtccccagc catatactca gtcgtgcttc tttcttaggg ggtgcagaca   8100
taaccgattg tgttgagtcc agattgacct atatatgccc cagggatccc gcacaactga   8160
tacctgacag ccagcaaaag tgtatcctgg gggacacaac aaggtgtcct gtcacaaaag   8220
ttgtggacag ccttatcccc aagtttgctt ttgtgaatgg gggcgttgtt gctaactgca   8280
tagcatccac atgtacctgc gggacaggcc gaagaccaat cagtcaggat cgctctaaag   8340
gtgtagtatt cctaacccat gacaactgtg gtcttatagg tgtcaatggg gtagaattgt   8400
atgctaaccg gagagggcac gatgccactt ggggggtcca gaacttgaca gtcggtcctg   8460
caattgctat cagacccgtt gatatttctc tcaaccttgc tgatgctacg aatttcttgc   8520
aagactctaa ggctgagctt gagaaagcac ggaaaatcct ctcggaggta ggtagatggt   8580
acaactcaag agagactgtg attacgatca tagtagttat ggtcgtaata ttggtggtca   8640
ttatagtgat catcatcgtg ctttatagac tcagaaggtc aatgctaatg ggtaatccag   8700
atgaccgtat accgagggac acatacacat tagagccgaa gatcagacat atgtacacaa   8760
```

-continued

```
acggtgggtt tgatgcaatg gctgagaaaa gatgatcacg accattatca gatgtcttgt   8820
aaagcaggca tagtatccgt tgagatctgt atataataag aaaaacttag ggtgaaagtg   8880
aggtcgcgcg gtactttagc tttcacctca aacaagcaca gatcatggat ggtgataggg   8940
gcaaacgtga ctcgtactgg tctacttctc ctagtggtag caccacaaaa ccagcatcag   9000
gttgggagag gtcaagtaaa gccgacacat ggttgctgat tctctcattc acccagtggg   9060
ctttgtcaat tgccacagtg atcatctgta tcataatttc tgctagacaa gggtatagta   9120
tgaaagagta ctcaatgact gtagaggcat tgaacatgag cagcagggag gtgaaagagt   9180
cacttaccag tctaataagg caagaggtta tagcaagggc tgtcaacatt cagagctctg   9240
tgcaaaccgg aatcccagtc ttgttgaaca aaaacagcag ggatgtcatc cagatgattg   9300
ataagtcgtg cagcagacaa gagctcactc agcactgtga gagtacgatc gcagtccacc   9360
atgccgatgg aattgcccca cttgagccac atagtttctg gagatgccct gtcggagaac   9420
cgtatcttag ctcagatcct gaaatctcat tgctgcctgg tccgagcttg ttatctggtt   9480
ctacaacgat ctctggatgt gttaggctcc cttcactctc aattggcgag gcaatctatg   9540
cctattcatc aaatctcatt acacaaggtt gtgctgacat agggaaatca tatcaggtcc   9600
tgcagctagg gtacatatca ctcaattcag atatgttccc tgatcttaac cccgtagtgt   9660
cccacactta tgacatcaac gacaatcgga aatcatgctc tgtggtggca accgggacta   9720
ggggttatca gctttgctcc atgccgactg tagacgaaag aaccgactac tctagtgatg   9780
gtattgagga tctggtcctt gatgtcctgg atctcaaagg gagaactaag tctcaccggt   9840
atcgcaacag cgaggtagat cttgatcacc cgttctctgc actatacccc agtgtaggca   9900
acggcattgc aacagaaggc tcattgatat ttcttgggta tggtggacta accacccctc   9960
tgcagggtga tacaaaatgt aggacccaag gatgccaaca ggtgtcgcaa gacacatgca  10020
atgaggctct gaaaattaca tggctaggag ggaaacaggt ggtcagcgtg atcatccagg  10080
tcaatgacta tctctcagag aggccaaaga taagagtcac aaccattcca atcactcaaa  10140
actatctcgg ggcggaaggt agattattaa aattgggtga tcgggtgtac atctatacaa  10200
gatcatcagg ctggcactct caactgcaga taggagtact tgatgtcagc cacccctttga 10260
ctatcaactg gacacctcat gaagccttgt ctagaccagg aaataaagag tgcaattggt  10320
acaataagtg tccgaaggaa tgcatatcag gcgtatacac tgatgcttat ccattgtccc  10380
ctgatgcagc taacgtcgct accgtcacgc tatatgccaa tacatcgcgt gtcaacccaa  10440
caatcatgta ttctaacact actaacatta taaatatgtt aaggataaag gatgttcaat  10500
tagaggctgc atataccacg acatcgtgta tcacgcattt tggtaaaggc tactgctttc  10560
acatcatcga gatcaatcag aagagcctga ataccttaca gccgatgctc tttaagacta  10620
gcatccctaa attatgcaag gccgagtctt aaatttaact gactagcagg cttgtcggcc  10680
ttgctgacac tagagtcatc tccgaacatc cacaatatct ctcagtctct tacgtctctc  10740
acagtattaa gaaaaaccca gggtgaatgg gaagcttgcc ataggtcatg gatgggcagg  10800
agtcctccca aaacccttct gacatactct atccagaatg ccacctgaac tctcccatag  10860
tcagggggaa gatagcacag ttgcacgtct tgttagatgt gaaccagccc tacagactga  10920
aggacgacag cataataaat attacaaagc acaaaattag gaacggagga ttgtcccccc  10980
gtcaaattaa gatcaggtct ctgggtaagg ctcttcaacg cacaataaag gatttagacc  11040
gatacacgtt tgaaccgtac ccaacctact ctcaggaatt acttaggctt gatataccag  11100
```

agatatgtga caaaatccga tccgtcttcg cggtctcgga tcggctgacc agggagttat 11160
ctagtgggtt ccaggatctt tggttgaata tcttcaagca actaggcaat atagaaggaa 11220
gagaggggta cgatccgttg caggatatcg gcaccatccc ggagataact gataagtaca 11280
gcaggaatag atggtatagg ccattcctaa cttggttcag catcaaatat gacatgcggt 11340
ggatgcagaa gaccagaccg gggggacccc tcgatacctc taattcacat aacctcctag 11400
aatgcaaatc atacactcta gtaacatacg gagatcttgt catgatactg aacaagttga 11460
cattgacagg gtatatccta acccctgagc tggtcttgat gtattgtgat gttgtagaag 11520
gaaggtggaa tatgtctgct gcagggcatc tagataagaa gtccattggg ataacaagca 11580
aaggtgagga attatgggaa ctagtggatt ccctcttctc aagtcttgga gaggaaatat 11640
acaatgtcat cgcactattg gagcccctat cacttgctct catacaacta aatgatcctg 11700
ttatacctct acgtggggca tttatgaggc atgtgttgac agagctacag actgttttaa 11760
caagtagaga cgtgtacaca gatgctgaag cagacactat tgtggagtcg ttactcgcca 11820
ttttccatgg aacctctatt gatgagaaag cagagatctt ttccttcttt aggacatttg 11880
gccaccccag cttagaggct gtcactgccg ccgacaaggt aagggcccat atgtatgcac 11940
aaaaggcaat aaagcttaag accctatacg agtgtcatgc agttttttgc actatcatca 12000
taaatgggta tagagagagg catggcggac agtggccccc ctgtgacttc cctgatcacg 12060
tgtgtctaga actaaggaac gctcaagggt ccaatacggc aatctcttat gaatgtgctg 12120
tagacaacta tacaagtttc ataggcttca agtttcggaa gtttatagaa ccacaactag 12180
atgaagatct cacaatatat atgaaagaca aagcactatc ccccaggaag gaggcatggg 12240
actctgtata cccggatagt aatctgtact ataaagcccc agagtctgaa gagacccggc 12300
ggcttattga agtgttcata aatgatgaga atttcaaccc agaagaaatt atcaattatg 12360
tggagtcagg agattggttg aaagacgagg agttcaacat ctcgtacagt ctcaaagaga 12420
aagagatcaa gcaagagggt cgtctattcg caaaaatgac ttataagatg cgagccgtac 12480
aggtgctggc agagacacta ctggctaaag gaataggaga gctattcagc gaaaatggga 12540
tggttaaagg agagatagac ctacttaaaa gattgactac tctttctgtc tcaggcgtcc 12600
ccaggactga ttcagtgtac aataactcta aatcatcaga gaagagaaac gaaggcatgg 12660
aaaataagaa ctctgggggg tactgggacg aaaagaagag gtccagacat gaattcaagg 12720
caacagattc atcaacagac ggctatgaaa cgttaagttg cttcctcaca acagacctca 12780
agaaatactg cttaaactgg agatttgaga gtactgcatt gtttggtcag agatgcaacg 12840
agatatttgg cttcaagacc ttctttaact ggatgcatcc agtccttgaa aggtgtacaa 12900
tatatgttgg agatccttac tgtccagtcg ccgaccggat gcatcgacaa ctccaggatc 12960
atgcagactc tggcattttc atacataatc ctaggggggg catagaaggt tactgccaga 13020
agctgtggac cttaatctca atcagtgcaa tccacctagc agctgtgaga gtgggtgtca 13080
gggtctctgc aatggttcag ggtgacaatc aagctatagc cgtgacatca agagtacctg 13140
tagctcagac ttacaagcag aagaaaaatc atgtctatga ggagatcacc aaatatttcg 13200
gtgctctaag acacgtcatg tttgatgtag ggcacgagct aaaattgaac gagaccatca 13260
ttagtagcaa gatgtttgtc tatagtaaaa ggatatacta tgatgggaag attttaccac 13320
agtgcctgaa agccttgacc aagtgtgtat tctggtccga gacactggta gatgaaaaca 13380
gatctgcttg ttcgaacatc tcaacatcca tagcaaaagc tatcgaaaat gggtattctc 13440
ctatactagg ctactgcatt gcgttgtata agacctgtca gcaggtgtgc atatcactag 13500

```
ggatgactat aaatccaact atcagcccga ccgtaagaga tcaatacttt aagggtaaga  13560
attggctgag atgtgcagtg ttgattccag caaatgttgg aggattcaac tacatgtcta  13620
catctagatg ctttgttaga aatattggag accccgcagt agcagcccta gctgatctca  13680
aaagattcat cagagcggat ctgttagaca agcaggtatt atacagggtc atgaatcaag  13740
aacccggtga ctctagtttt ctagattggg cttcagaccc ttattcgtgt aacctcccgc  13800
attctcagag tataactacg attataaaga atatcactgc tagatctgtg ctgcaggaat  13860
ccccgaatcc tctactgtct ggtctcttca ccgagactag tggagaagag gatctcaacc  13920
tggcctcgtt ccttatggac cggaaagtca tcctgccgag agtggctcat gagatcctgg  13980
gtaattcctt aactggagtt agggaggcga ttgcagggat gcttgatacg accaagtctc  14040
tagtgagagc cagcgttagg aaaggaggat tatcatatgg gatattgagg aggcttgtca  14100
attatgatct attgcagtac gagacactga ctagaactct caggaaaccg gtgaaagaca  14160
acatcgaata tgagtatatg tgttcagttg agctagctgt cggtctaagg cagaaaatgt  14220
ggatccacct gacttacggg agacccatac atgggctaga aacaccagac cctttagagc  14280
tcttgagggg aatatttatc gaaggttcag aggtgtgcaa gctttgcagg tctgaaggag  14340
cagaccccat ctatacatgg ttctatcttc ctgacaatat agacctggac acgcttacaa  14400
acggatgtcc ggctataaga atcccctatt ttggatcagc cactgatgaa aggtcggaag  14460
cccaactcgg gtatgtaaga aatctaagca aacccgcaaa ggcggccatc cggatagcta  14520
tggtgtatac gtgggcctac gggactgatg agatatcgtg gatggaagcc gctcttatag  14580
cccaaacaag agctaatctg agcttagaga atctaaagct gctgactcct gtttcaacct  14640
ccactaatct atctcatagg ttgaaagata cggcaaccca gatgaagttc tctagtgcaa  14700
cactagtccg tgcaagtcgg ttcataacaa tatcaaatga taacatggca ctcaaagaag  14760
caggggagtc gaaggatact aatctcgtgt atcagcagat tatgctaact gggctaagct  14820
tgttcgagtt caatatgaga tataagaaag gttccttagg gaagccactg atattgcact  14880
tacatcttaa taacgggtgc tgtataatgg agtccccaca ggaggcgaat atcccccCaa  14940
ggtccacatt agatttagag attacacaag agaacaataa attgatctat gatcctgatc  15000
cactcaagga tgtggacctt gagctattta gcaaggtcag agatgttgta cacacagttg  15060
acatgactta ttggtcagat gatgaagtta tcagagcaac cagtatctgt actgcaatga  15120
cgatagctga tacaatgtct caattagata gagacaactt aaaagagatg atcgcactag  15180
taaatgacga tgatgtcaac agcttgatta ctgagtttat ggtgattgat gttcctttat  15240
tttgctcaac gttcgggggt attctagtca atcagtttgc atactcactc tacggcttaa  15300
acatcagagg aagggaagaa atatggggac atgtagtccg gattcttaaa gatacctccc  15360
acgcagtttt aaaagtctta tctaatgctc tatctcatcc caaaatcttc aaacgattct  15420
ggaatgcagg tgtcgtggaa cctgtgtatg ggcctaacct ctcaaatcag gataagatac  15480
tcttggccct ctctgtctgt gaatattctg tggatctatt catgcacgat tggcaagggg  15540
gtgtaccgct tgagatcttt atctgtgaca atgacccaga tgtggccgac atgaggaggt  15600
cctctttctt ggcaagacat cttgcatacc tatgcagctt ggcagagata tctagggatg  15660
ggccaagatt agaatcaatg aactctctag agaggctcga gtcactaaag agttacctgg  15720
aactcacatt tcttgatgac ccggtactga ggtacagtca gttgactggc ctagtcatca  15780
aagtattccc atctactttg acctatatcc ggaagtcatc tataaaagtg ttaaggacaa  15840
```

gaggtatagg agtccctgaa gtcttagaag attgggatcc cgaggcagat aatgcactgt 15900
tagatggtat cgcggcagaa atacaacaga atattccttt gggacatcag actagagccc 15960
ctttttgggg gttgagagta tccaagtcac aggtactgcg tctccggggg tacaaggaga 16020
tcacaagagg tgagataggc agatcaggtg ttggtctgac gttaccattc gatggaagat 16080
atctatctca ccagctgagg ctctttggca tcaacagtac tagctgcttg aaagcacttg 16140
aacttaccta cctattgagc cccttagttg acaaggataa agataggcta tatttagggg 16200
aaggagctgg ggccatgctt tcctgttatg acgctactct tggcccatgc atcaactatt 16260
ataactcagg ggtatactct tgtgatgtca atgggcagag agagttaaat atatatcctg 16320
ctgaggtggc actagtggga aagaaattaa acaatgttac tagtctgggt caaagagtta 16380
aagtgttatt caacgggaat cctggctcga catggattgg gaatgatgag tgtgaggctt 16440
tgatttggaa tgaattacag aatagctcga taggcctagt ccactgtgac atggagggag 16500
gagatcataa ggatgatcaa gttgtactgc atgagcatta cagtgtaatc cggatcgcgt 16560
atctggtggg ggatcgagac gttgtgctta taagcaagat tgctcccagg ctgggcacgg 16620
attggaccag gcagctcagc ctatatctga gatactggga cgaggttaac ctaatagtgc 16680
ttaaaacatc taaccctgct tccacagaga tgtatctcct atcgaggcac cccaaatctg 16740
acattataga ggacagcaag acagtgttag ctagtctcct ccctttgtca aaagaagata 16800
gcatcaagat agaaaagtgg atcttaatag agaaggcaaa ggctcacgaa tgggttactc 16860
gggaattgag agaaggaagc tcttcatcag ggatgcttag accttaccat caagcactgc 16920
agacgtttgg ctttgaacca aacttgtata aattgagcag agatttcttg tccaccatga 16980
acatagctga tacacacaac tgcatgatag ctttcaacag ggttttgaag gatacaatct 17040
tcgaatgggc tagaataact gagtcagata aaaggcttaa actaactggt aagtatgacc 17100
tgtatcctgt gagagattca ggcaagttga agacaatttc tagaagactt gtgctatctt 17160
ggatatcttt atctatgtcc acaagattgg taactgggtc attccctgac cagaagtttg 17220
aagcaagact tcaattggga atagtttcat tatcatcccg tgaaatcagg aacctgaggg 17280
ttatcacaaa aactttatta gacaggtttg aggatattat acatagtata acgtatagat 17340
tcctcaccaa agaaataaag attttgatga agattttagg ggcagtcaag atgttcgggg 17400
ccaggcaaaa tgaatacacg accgtgattg atgatggatc actaggtgat atcgagccat 17460
atgacagctc gtaataatta gtccctatcg tgcagaacga tcgaagctcc gcggtacctg 17520
gaagtcttgg acttgtccat atgacaatag taagaaaaac ttacaagaag acaagaaaat 17580
ttaaaaggat acatatctct taaactcttg tctggt 17616

<210> SEQ ID NO 13
<211> LENGTH: 17832
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13
accaaacaag agaaaaaaca tgtatgggat atgtaatgaa gttatacagg attttagggt 60
caaagtatcc accctgagga gcaggttcca gaccctttgc tttgctgcca aagttcacgc 120
ggccgccaag gttcaatgga ggagaaagca ttctcacctg aagtgatccc tatgttcaca 180
gcattatctg agggagctac tcctcaagat cttaacacaa tgcttaacac agtcggagga 240
catcaagcag caatgcaaat gttgaaagat acaattaacg aggaagcagc agaatgggat 300
agaatctata agagatggat aatattagga ttgaacaaga ttgttagaat gtattctcct 360
gtgtcaatcc ttgatataag acaaggacct aaagagcctt tcagagatta cgtcgataga 420
tttgcaagaa attgtagagc acctagaaag aagggatgtt ggaaatgtgg gaaagaagga 480
catcaaatga aagattgtac tgagagacaa gctaacttct tgggaaagat atggccttca 540
agatggaaac ctaagatgat aggaggaata ggaggattta ttaaagtcag acaatatgat 600
caaatattga ttgaaatatg tggacataaa gctattggaa cagtcctagt gggtccaaca 660
cctgtcaaca tcattggtag aaatcttctc actcaaatcg gatgtacact caatttccca 720
atatcaccta ttgagaccgt gcctgtcaaa ttgaaacctg gaatggatgg acctaaagtc 780
aaacaatggc cattaactga ggagaagatt aaagcactgg tagaaatttg tacagagatg 840
gagaaagaag gaaagatttc caagattggt cctgagaatc cttataatac tcctgtcttt 900
gctattaaga agaaggatag taccaaatgg aggaaattag tcgatttcag agaacttaac 960
aagaggactc aagacttctg ggaagtgcaa ttgggaatcc cacaccctgc aggattgaag 1020
aagaagaagt ctgtcactgt cctagatgtg ggagatgcat atttcagtgt cccactggat 1080
gaaggtttca gaaagtatac agcattcaca atcccttcca ttaataatga aacacctgga 1140
ataagatatc aatataatgt cttacctcaa gggtggaaag gatctccagc aatattccaa 1200
tcatcaatga caaagatctt ggagcctttc agagctcaga atccagagat agttatttac 1260
caatacatgg atgatttgta tgttgggtca gatctcgaga tcggacagca caggatggag 1320
aatagatggc aagtaatgat tgtctggcaa gtcgatagaa tgagaataag aacatggaaa 1380
tccttggtga aacatcacct tacagaggag gcagaactgg aactggcaga gaatagggaa 1440
atattgaaag atccagtgca tggtgtctat tacgatcctt ctaaagatct gatagcagag 1500
atccagtact ggcaagcaac atggattcct gagtgggaat tcgtcaacac acctccatta 1560
gtgaaactat ggtaccaatt agagaagaat gtcaccgaga acttcaacat gtggaagaac 1620
gatatggtag atcaaatgca cgaagatatc atctccttgt gggatcaatc acttaaacct 1680
tgtgttaaat tgacaccttg ggtacctgct cataaaggga taggaggaaa cgaacaagtg 1740
gataaattgg tgtcccaagg gatcaggaaa gtcttgttcc tagatggaat tgataaagct 1800
caagcaaagg aaattgtcgc aagctgtgat aagtgtcaat taaagggaga ggcaatgcac 1860
ggacaagtcg attgttcacc tggtatttgg caacttgatt gtacacattt ggagggtaaa 1920
gttattctag tagcagtaca tgtcgcttct ggttatattg aggcagaagt gatacctgct 1980
gagacaggac aggagaccgc atactttcta cttaagttag ctatgaataa ggagctcaag 2040
aagataatag gacaagttag agatcaagca gagcacctta agacagctgt ccaaatggca 2100
gtgtttatac acaactttaa gagaaagggt ggaatcggag gatattccgc aggagagaga 2160
atctggaaag gtcctgctaa attgttatgg aaaggagaag gagcagttgt aatacaagat 2220
aattctgata taaaagtagt ccctagaagg aaagctaaga ttattagaga ttatgggaaa 2280
caaatggcag gagctgattg tgtgtttcta ggagcagcag gatccactat gggagctgca 2340
tcaatgacac ttaccgtgca ggctagacag cttctttcag gaattgtaca gcaacagaat 2400
aatttgctaa gagcaattga agctcaacaa cacttacttc aacttacagt ctggggaatc 2460
aagcaagcac ctacaaaagc aaagagaaga gtcgtccaaa gagagaaaag ataaccgtag 2520
taagaaaaac ttagggtgaa agttcatcgc ggccgcagat cttcacgatg gccgggttgt 2580
tgagcacctt cgatacattt agctctagga ggagcgaaag tattaataag tcgggaggag 2640

-continued

```
gtgctgttat ccccggccag aggagcacag tctcagtgtt cgtactaggc ccaagtgtga   2700
ctgatgatgc agacaagtta ttcattgcaa ctaccttcct agctcactca ttggacacag   2760
ataagcagca ctctcagaga ggggggttcc tcgtctctct gcttgccatg gcttacagta   2820
gtccagaatt gtacttgaca acaaacggag taaacgccga tgtcaaatat gtgatctaca   2880
acatagagaa agaccctaag aggacgaaga cagacggatt cattgtgaag acgagagata   2940
tggaatatga gaggaccaca gaatggctgt ttggacctat ggtcaacaag agcccactct   3000
tccagggtca acgggatgct gcagaccctg acacactcct tcaaatctat gggtatcctg   3060
catgcctagg agcaataatt gtccaagtct ggattgtgct ggtgaaggcc atcacaagca   3120
gcgccggctt aaggaaaggg ttcttcaaca ggttagaggc gttcagacaa gacggcaccg   3180
tgaaaggtgc cttagttttc actggggaga cagttgaggg gataggctcg gttatgagat   3240
ctcagcaaag ccttgtatct ctcatggttg agacccttgt gactatgaat actgcaagat   3300
ctgatctcac cacattagag aagaacatcc agatcgttgg gaactacatc cgagatgcag   3360
ggctggcttc cttcatgaac actattaaat atggggtgga aacaaagatg gcagctctaa   3420
cgttgtcaaa cctgaggccc gatattaata agcttagaag cctcatagac acctacctgt   3480
caaaaggccc cagagctccc tttatctgta tcctcaagga ccctgttcat ggtgaatttg   3540
ctccaggcaa ttatcctgca ctatggagtt acgccatggg agtcgccgtc gtacagaaca   3600
aggcaatgca gcagtacgtc acagggagga cataccttga tatggaaatg ttcttactag   3660
gacaagccgt ggcaaaggat gctgaatcga agatcagcag tgccttggaa gatgagttag   3720
gagtgacgga tacagccaag gggaggctca gacatcatct ggcaaacttg tccggtgggg   3780
atggtgctta ccacaaacca acaggcggtg gtgcaattga ggtagctcta gacaatgccg   3840
acatcgacct agaaacaaaa gcccatgcgg accaggacgc taggggttgg ggtggagata   3900
gtggtgaaag atgggcacgt caggtgagtg gtggccactt tgtcacacta catggggctg   3960
aacggttaga ggaggaaacc aatgatgagg atgtatcaga catagagaga agaatagcca   4020
tgagactcgc agagagacgg caagaggatt ctgcaaccca tggagatgaa ggccgcaata   4080
acggtgtcga tcatgacgaa gatgacgatg ccgcagcagt agctgggata ggaggaatct   4140
aggatcatac gaggcttcaa ggtacttgat ccgtagtaag aaaaacttag ggtgaaagtt   4200
catccaccga tcggctcagg caaggccaca cccaacccca ccgaccacac ccagcagtcg   4260
agacagccac ggcttcggct acacttaccg catggatcaa gatgccttca ttcttaaaga   4320
agattctgaa gttgagaggg aggcgccagg aggacgagag tcgctctcgg atgttatcgg   4380
attcctcgat gctgtcctgt cgagtgaacc aactgacatc ggaggggaca gaagctggct   4440
ccacaacacc atcaacactc cccaaggacc aggctctgct catagagcca aaagtgaggg   4500
cgaaggagaa gtctcaacac cgtcgaccca agataatcga tcaggtgagg agagtagagt   4560
ctctgggaga acaagcaagc cagaggcaga agcacatgct ggaaaccttg ataaacaaaa   4620
tatacaccgg gcctttgggg gaagaactgg tacaaactct gtatctcagg atctgggcga   4680
tggaggagac tccggaatcc ttgaaaatcc tccaaatgag agaggatatc cgagatcagg   4740
tattgaagat gaaaacagag agatggctgc gcaccctgat aagaggggag aagaccaagc   4800
tgaaggactt ccagaagagg tacgaggaag tacatcccta cctgatgaag gagaaggtgg   4860
agcaagtaat aatggaagaa gcatggagcc tggcagctca catagtgcaa gagtaactgg   4920
ggtcctggtg attcctagcc ccgaacttga agaggctgtg ctacggagga acaaaagaag   4980
```

```
acctaccaac agtgggtcca aacctcttac tccagcaacc gtgcctggca cccggtcccc   5040
accgctgaat cgttacaaca gcacagggtc accaccagga aaacccccat ctacacagga   5100
tgagcacatc aactctgggg acaccccgc cgtcagggtc aaagaccgga aaccaccaat   5160
agggacccgc tctgtctcag attgtccagc caacggccgc ccaatccacc cgggtctaga   5220
gaccgactca acaaaaaagg gcataggaga gaacacatca tctatgaaag agatggctac   5280
attgttgacg agtcttggtg taatccagtc tgctcaagaa ttcgaatcat cccgagacgc   5340
gagttatgtg tttgcaagac gtgccctaaa gtctgcaaac tatgcagaga tgacattcaa   5400
tgtatgcggc ctgatccttt ctgccgagaa atcttccgct cgtaaggtag atgagaacaa   5460
acaactgctc aaacagatcc aagagagcgt ggaatcattc cgggatattt acaagagatt   5520
ctctgagtat cagaaagaac agaactcatt gctgatgtcc aacctatcta cacttcatat   5580
catcacagat agaggtggca agactgacaa cacagactcc cttacaaggt ccccctccgt   5640
ttttgcaaaa tcaaaagaga acaagactaa ggctaccagg tttgacccat ctatggagac   5700
cctagaagat atgaagtaca aaccggacct aatccgagag gatgaattta gagatgagat   5760
ccgcaacccg gtgtaccaag agagggacac agaacccagg gcctcaaacg catcacgtct   5820
cctcccctcc aaagagaagc ccacaatgca ctctctcagg ctcgtcatag agagcagtcc   5880
cctaagcaga gctgagaaag tagcatatgt gaaatcatta tccaagtgca agacagacca   5940
agaggttaag gcagtcatgg aactcgtaga agaggacata gagtcactga ccaactagat   6000
cccgggtgag gcatcctacc atcctcagtc atagagagat ccaatctacc atcagcatca   6060
gccagtaaag attaagaaaa acttagggtg aaagaaattt cacctaacac ggcgcaatgg   6120
cagatatcta tagattccct aagttctcat atgaggataa cggtactgtg gagcccctgc   6180
ctctgagaac tggtccggat aagaaagcca tcccccacat caggattgtc aaggtaggag   6240
accctcctaa acatggagtg agatacctag atttattgct cttgggtttc tttgagacac   6300
cgaaacaaac aaccaatcta gggagcgtat ctgacttgac agagccgacc agctactcaa   6360
tatgcggctc cgggtcgtta cccataggtg tggccaaata ctacgggact gatcaggaac   6420
tcttaaaggc ctgcaccgat ctcagaatta cggtgaggag gactgttcga gcaggagaga   6480
tgatcgtata catggtggat tcgattggtg ctccactcct accatggtca ggcaggctga   6540
gacagggaat gatatttaat gcaaacaagg tcgcactagc tccccaatgc ctccctgtgg   6600
acaaggacat aagactcaga gtggtgtttg tcaatgggac atctctaggg gcaatcacca   6660
tagccaagat cccaaagacc cttgcagacc ttgcattgcc caactctata tctgttaatt   6720
tactggtgac actcaagacc gggatctcca cagaacaaaa gggggtactc ccagtacttg   6780
atgatcaagg ggagaaaaag ctcaatttta tggtgcacct cgggttgatc aggagaaagg   6840
tcgggaagat atactctgtt gagtactgca agagcaagat tgagagaatg cggctgattt   6900
tctcacttgg gttaatcggc ggtataagct tccatgttca ggttaatggg acactatcta   6960
agacattcat gagtcagctc gcatggaaga gggcagtctg cttcccatta atggatgtga   7020
atccccatat gaacatggtg atttgggcgg catctgtaga aatcacaggc gtcgatgcgg   7080
tgttccaacc ggccatccct cgtgatttcc gctactaccc taatgttgtg gctaagaaca   7140
tcggaaggat cagaaagctg taaatgtgca cccatcagag acctgcgaca atgccccaag   7200
cagacaccac ctggcagtcg gagccaccgg gtcactcctt gtcttaaata agaaaaactt   7260
agggataaag tcccttgtga gtgcttggtt gcaaaactct ccccttggga aacatgacag   7320
catatatcca gagatcacag tgcatctcaa catcactact ggttgttctc accacattgg   7380
```

-continued

```
tctcgtgtca gattcccagg gataggctct ctaacatagg ggtcatagtc gatgaaggga   7440
aatcactgaa gatagctgga tcccacgaat cgaggtacat agtactgagt ctagttccgg   7500
gggtagactt tgagaatggg tgcggaacag cccaggttat ccagtacaag agcctactga   7560
acaggctgtt aatcccattg agggatgcct tagatcttca ggaggctctg ataactgtca   7620
ccaatgatac gacacaaaat gccggtgctc cccagtcgag attcttcggt gctgtgattg   7680
gtactatcgc acttggagtg gcgacatcag cacaaatcac cgcagggatt gcactagccg   7740
aagcgaggga ggccaaaaga gacatagcgc tcatcaaaga atcgatgaca aaaacacaca   7800
agtctataga actgctgcaa aacgctgtgg gggaacaaat tcttgctcta aagacactcc   7860
aggatttcgt gaatgatgag atcaaacccg caataagcga attaggctgt gagactgctg   7920
ccttaagact gggtataaaa ttgacacagc attactccga gctgttaact gcgttcggct   7980
cgaatttcgg aaccatcgga gagaagagcc tcacgctgca ggcgctgtct tcactttact   8040
ctgctaacat tactgagatt atgaccacaa tcaggacagg gcagtctaac atctatgatg   8100
tcatttatac agaacagatc aaaggaacgg tgatagatgt ggatctagag agatacatgg   8160
tcaccctgtc tgtgaagatc cctattcttt ctgaagtccc aggtgtgctc atacacaagg   8220
catcatctat ttcttacaac atagacgggg aggaatggta tgtgactgtc cccagccata   8280
tactcagtcg tgcttctttc ttagggggtg cagacataac cgattgtgtt gagtccagat   8340
tgacctatat atgccccagg gatcccgcac aactgatacc tgacagccag caaaagtgta   8400
tcctggggga cacaacaagg tgtcctgtca caaaagttgt ggacagcctt atccccaagt   8460
ttgcttttgt gaatgggggc gttgttgcta actgcatagc atccacatgt acctgcggga   8520
caggccgaag accaatcagt caggatcgct ctaaaggtgt agtattccta acccatgaca   8580
actgtggtct tataggtgtc aatggggtag aattgtatgc taaccggaga gggcacgatg   8640
ccacttgggg ggtccagaac ttgacagtcg gtcctgcaat tgctatcaga cccgttgata   8700
tttctctcaa ccttgctgat gctacgaatt tcttgcaaga ctctaaggct gagcttgaga   8760
aagcacggaa aatcctctcg gaggtaggta gatggtacaa ctcaagagag actgtgatta   8820
cgatcatagt agttatggtc gtaatattgg tggtcattat agtgatcatc atcgtgcttt   8880
atagactcag aaggtcaatg ctaatgggta atccagatga ccgtataccg agggacacat   8940
acacattaga gccgaagatc agacatatgt acacaaacgg tgggtttgat gcaatggctg   9000
agaaaagatg atcacgacca ttatcagatg tcttgtaaag caggcatagt atccgttgag   9060
atctgtatat aataagaaaa acttagggtg aaagtgaggt cgcgcggtac tttagctttc   9120
acctcaaaca agcacagatc atggatggtg ataggggcaa acgtgactcg tactggtcta   9180
cttctcctag tggtagcacc acaaaaccag catcaggttg ggagaggtca agtaaagccg   9240
acacatggtt gctgattctc tcattcaccc agtgggcttt gtcaattgcc acagtgatca   9300
tctgtatcat aatttctgct agacaagggt atagtatgaa agagtactca atgactgtag   9360
aggcattgaa catgagcagc agggaggtga aagagtcact taccagtcta ataaggcaag   9420
aggttatagc aagggctgtc aacattcaga gctctgtgca aaccggaatc ccagtcttgt   9480
tgaacaaaaa cagcagggat gtcatccaga tgattgataa gtcgtgcagc agacaagagc   9540
tcactcagca ctgtgagagt acgatcgcag tccaccatgc cgatggaatt gccccacttg   9600
agccacatag tttctggaga tgccctgtcg gagaaccgta tcttagctca gatcctgaaa   9660
tctcattgct gcctggtccg agcttgttat ctggttctac aacgatctct ggatgtgtta   9720
```

-continued

```
ggctcccttc actctcaatt ggcgaggcaa tctatgccta ttcatcaaat ctcattacac   9780
aaggttgtgc tgacataggg aaatcatatc aggtcctgca gctagggtac atatcactca   9840
attcagatat gttccctgat cttaaccccg tagtgtccca cacttatgac atcaacgaca   9900
atcggaaatc atgctctgtg gtggcaaccg ggactagggg ttatcagctt tgctccatgc   9960
cgactgtaga cgaaagaacc gactactcta gtgatggtat tgaggatctg gtccttgatg  10020
tcctggatct caaagggaga actaagtctc accggtatcg caacagcgag gtagatcttg  10080
atcacccgtt ctctgcacta taccccagtg taggcaacgg cattgcaaca gaaggctcat  10140
tgatatttct tgggtatggt ggactaacca cccctctgca gggtgataca aaatgtagga  10200
cccaaggatg ccaacaggtg tcgcaagaca catgcaatga ggctctgaaa attacatggc  10260
taggagggaa acaggtggtc agcgtgatca tccaggtcaa tgactatctc tcagagaggc  10320
caaagataag agtcacaacc attccaatca ctcaaaacta tctcggggcg gaaggtagat  10380
tattaaaatt gggtgatcgg gtgtacatct atacaagatc atcaggctgg cactctcaac  10440
tgcagatagg agtacttgat gtcagccacc ctttgactat caactggaca cctcatgaag  10500
ccttgtctag accaggaaat aaagagtgca attggtacaa taagtgtccg aaggaatgca  10560
tatcaggcgt atacactgat gcttatccat tgtcccctga tgcagctaac gtcgctaccg  10620
tcacgctata tgccaataca tcgcgtgtca acccaacaat catgtattct aacactacta  10680
acattataaa tatgttaagg ataaaggatg ttcaattaga ggctgcatat accacgacat  10740
cgtgtatcac gcattttggt aaaggctact gctttcacat catcgagatc aatcagaaga  10800
gcctgaatac cttacagccg atgctcttta agactagcat ccctaaatta tgcaaggccg  10860
agtcttaaat ttaactgact agcaggcttg tcggccttgc tgacactaga gtcatctccg  10920
aacatccaca atatctctca gtctcttacg tctctcacag tattaagaaa aacccagggt  10980
gaatgggaag cttgccatag gtcatggatg ggcaggagtc ctcccaaaac ccttctgaca  11040
tactctatcc agaatgccac ctgaactctc ccatagtcag ggggaagata gcacagttgc  11100
acgtcttgtt agatgtgaac cagccctaca gactgaagga cgacagcata ataaatatta  11160
caaagcacaa aattaggaac ggaggattgt ccccccgtca aattaagatc aggtctctgg  11220
gtaaggctct tcaacgcaca ataaaggatt tagaccgata cacgtttgaa ccgtacccaa  11280
cctactctca ggaattactt aggcttgata taccagagat atgtgacaaa atccgatccg  11340
tcttcgcggt ctcggatcgg ctgaccaggg agttatctag tgggttccag gatctttggt  11400
tgaatatctt caagcaacta ggcaatatag aaggaagaga ggggtacgat ccgttgcagg  11460
atatcggcac catcccggag ataactgata agtacagcag gaatagatgg tataggccat  11520
tcctaacttg gttcagcatc aaatatgaca tgcggtggat gcagaagacc agaccggggg  11580
gacccctcga tacctctaat tcacataacc tcctagaatg caaatcatac actctagtaa  11640
catacggaga tcttgtcatg atactgaaca agttgacatt gacagggtat atcctaaccc  11700
ctgagctggt cttgatgtat tgtgatgttg tagaaggaag gtggaatatg tctgctgcag  11760
ggcatctaga taagaagtcc attgggataa caagcaaagg tgaggaatta tgggaactag  11820
tggattccct cttctcaagt cttggagagg aaatatacaa tgtcatcgca ctattggagc  11880
ccctatcact tgctctcata caactaaatg atcctgttat acctctacgt ggggcattta  11940
tgaggcatgt gttgacagag ctacagactg ttttaacaag tagagacgtg tacacagatg  12000
ctgaagcaga cactattgtg gagtcgttac tcgccatttt ccatggaacc tctattgatg  12060
agaaagcaga gatcttttcc ttctttagga catttggcca ccccagctta gaggctgtca  12120
```

-continued ctgccgccga caaggtaagg gcccatatgt atgcacaaaa ggcaataaag cttaagaccc 12180
tatacgagtg tcatgcagtt ttttgcacta tcatcataaa tgggtataga gagaggcatg 12240
gcggacagtg gcccccctgt gacttccctg atcacgtgtg tctagaacta aggaacgctc 12300
aagggtccaa tacggcaatc tcttatgaat gtgctgtaga caactataca agtttcatag 12360
gcttcaagtt tcggaagttt atagaaccac aactagatga agatctcaca atatatatga 12420
aagacaaagc actatccccc aggaaggagg catgggactc tgtatacccg gatagtaatc 12480
tgtactataa agccccagag tctgaagaga cccggcggct tattgaagtg ttcataaatg 12540
atgagaattt caacccagaa gaaattatca attatgtgga gtcaggagat tggttgaaag 12600
acgaggagtt caacatctcg tacagtctca aagagaaaga gatcaagcaa gagggtcgtc 12660
tattcgcaaa aatgacttat aagatgcgag ccgtacaggt gctggcagag acactactgg 12720
ctaaaggaat aggagagcta ttcagcgaaa atgggatggt taaaggagag atagacctac 12780
ttaaaagatt gactactctt tctgtctcag gcgtccccag gactgattca gtgtacaata 12840
actctaaatc atcagagaag agaaacgaag gcatggaaaa taagaactct gggggtact 12900
gggacgaaaa gaagaggtcc agacatgaat tcaaggcaac agattcatca acagacggct 12960
atgaaacgtt aagttgcttc ctcacaacag acctcaagaa atactgctta aactggagat 13020
ttgagagtac tgcattgttt ggtcagagat gcaacgagat atttggcttc aagaccttct 13080
ttaactggat gcatccagtc cttgaaaggt gtacaatata tgttggagat ccttactgtc 13140
cagtcgccga ccggatgcat cgacaactcc aggatcatgc agactctggc attttcatac 13200
ataatcctag ggggggcata gaaggttact gccagaagct gtggacctta atctcaatca 13260
gtgcaatcca cctagcagct gtgagagtgg gtgtcagggt ctctgcaatg gttcagggtg 13320
acaatcaagc tatagccgtg acatcaagag tacctgtagc tcagacttac aagcagaaga 13380
aaaatcatgt ctatgaggag atcaccaaat atttcggtgc tctaagacac gtcatgtttg 13440
atgtagggca cgagctaaaa ttgaacgaga ccatcattag tagcaagatg tttgtctata 13500
gtaaaaggat atactatgat gggaagattt taccacagtg cctgaaagcc ttgaccaagt 13560
gtgtattctg gtccgagaca ctggtagatg aaaacagatc tgcttgttcg aacatctcaa 13620
catccatagc aaaagctatc gaaaatgggt attctcctat actaggctac tgcattgcgt 13680
tgtataagac ctgtcagcag gtgtgcatat cactagggat gactataaat ccaactatca 13740
gcccgaccgt aagagatcaa tactttaagg gtaagaattg gctgagatgt gcagtgttga 13800
ttccagcaaa tgttggagga ttcaactaca tgtctacatc tagatgcttt gttagaaata 13860
ttggagaccc cgcagtagca gccctagctg atctcaaaag attcatcaga gcggatctgt 13920
tagacaagca ggtattatac agggtcatga atcaagaacc cggtgactct agttttctag 13980
attgggcttc agacccttat tcgtgtaacc tcccgcattc tcagagtata actacgatta 14040
taaagaatat cactgctaga tctgtgctgc aggaatcccc gaatcctcta ctgtctggtc 14100
tcttcaccga gactagtgga gaagaggatc tcaacctggc ctcgttcctt atggaccgga 14160
aagtcatcct gccgagagtg gctcatgaga tcctgggtaa ttccttaact ggagttaggg 14220
aggcgattgc agggatgctt gatacgacca agtctctagt gagagccagc gttaggaaag 14280
gaggattatc atatgggata ttgaggaggc ttgtcaatta tgatctattg cagtacgaga 14340
cactgactag aactctcagg aaaccggtga aagacaacat cgaatatgag tatatgtgtt 14400
cagttgagct agctgtcggt ctaaggcaga aaatgtggat ccacctgact tacgggagac 14460

-continued

```
ccatacatgg gctagaaaca ccagaccctt tagagctctt gaggggaata tttatcgaag  14520
gttcagaggt gtgcaagctt tgcaggtctg aaggagcaga ccccatctat acatggttct  14580
atcttcctga caatatagac ctggacacgc ttacaaacgg atgtccggct ataagaatcc  14640
cctattttgg atcagccact gatgaaaggt cggaagccca actcgggtat gtaagaaatc  14700
taagcaaacc cgcaaaggcg gccatccgga tagctatggt gtatacgtgg gcctacggga  14760
ctgatgagat atcgtggatg gaagccgctc ttatagccca aacaagagct aatctgagct  14820
tagagaatct aaagctgctg actcctgttt caacctccac taatctatct cataggttga  14880
aagatacggc aacccagatg aagttctcta gtgcaacact agtccgtgca agtcggttca  14940
taacaatatc aaatgataac atggcactca aagaagcagg ggagtcgaag gatactaatc  15000
tcgtgtatca gcagattatg ctaactgggc taagcttgtt cgagttcaat atgagatata  15060
agaaaggttc cttagggaag ccactgatat tgcacttaca tcttaataac gggtgctgta  15120
taatggagtc cccacaggag gcgaatatcc ccccaaggtc cacattagat ttagagatta  15180
cacaagagaa caataaattg atctatgatc ctgatccact caaggatgtg gaccttgagc  15240
tatttagcaa ggtcagagat gttgtacaca cagttgacat gacttattgg tcagatgatg  15300
aagttatcag agcaaccagt atctgtactg caatgacgat agctgataca atgtctcaat  15360
tagatagaga caacttaaaa gagatgatcg cactagtaaa tgacgatgat gtcaacagct  15420
tgattactga gtttatggtg attgatgttc ctttattttg ctcaacgttc gggggtattc  15480
tagtcaatca gtttgcatac tcactctacg gcttaaacat cagaggaagg gaagaaatat  15540
ggggacatgt agtccggatt cttaaagata cctcccacgc agttttaaaa gtcttatcta  15600
atgctctatc tcatcccaaa atcttcaaac gattctggaa tgcaggtgtc gtggaacctg  15660
tgtatgggcc taacctctca aatcaggata agatactctt ggccctctct gtctgtgaat  15720
attctgtgga tctattcatg cacgattggc aagggggtgt accgcttgag atctttatct  15780
gtgacaatga cccagatgtg gccgacatga ggaggtcctc tttcttggca agacatcttg  15840
catacctatg cagcttggca gagatatcta gggatgggcc aagattagaa tcaatgaact  15900
ctctagagag gctcgagtca ctaaagagtt acctggaact cacatttctt gatgacccgg  15960
tactgaggta cagtcagttg actggcctag tcatcaaagt attcccatct actttgacct  16020
atatccggaa gtcatctata aaagtgttaa ggacaagagg tataggagtc cctgaagtct  16080
tagaagattg ggatcccgag gcagataatg cactgttaga tggtatcgcg gcagaaatac  16140
aacagaatat tcctttggga catcagacta gagccccttt ttgggggttg agagtatcca  16200
agtcacaggt actgcgtctc cgggggtaca aggagatcac aagaggtgag ataggcagat  16260
caggtgttgg tctgacgtta ccattcgatg gaagatatct atctcaccag ctgaggctct  16320
ttggcatcaa cagtactagc tgcttgaaag cacttgaact tacctaccta ttgagcccct  16380
tagttgacaa ggataaagat aggctatatt taggggaagg agctggggcc atgctttcct  16440
gttatgacgc tactcttggc ccatgcatca actattataa ctcaggggta tactcttgtg  16500
atgtcaatgg gcagagagag ttaaatatat atcctgctga ggtggcacta gtgggaaaga  16560
aattaaacaa tgttactagt ctgggtcaaa gagttaaagt gttattcaac gggaatcctg  16620
gctcgacatg gattgggaat gatgagtgtg aggctttgat ttggaatgaa ttacagaata  16680
gctcgatagg cctagtccac tgtgacatgg agggaggaga tcataaggat gatcaagttg  16740
tactgcatga gcattacagt gtaatccgga tcgcgtatct ggtgggggat cgagacgttg  16800
tgcttataag caagattgct cccaggctgg gcacggattg gaccaggcag ctcagcctat  16860
```

-continued atctgagata ctgggacgag gttaacctaa tagtgcttaa aacatctaac cctgcttcca 16920
cagagatgta tctcctatcg aggcacccca aatctgacat tatagaggac agcaagacag 16980
tgttagctag tctcctccct ttgtcaaaag aagatagcat caagatagaa aagtggatct 17040
taatagagaa ggcaaaggct cacgaatggg ttactcggga attgagagaa ggaagctctt 17100
catcagggat gcttagacct taccatcaag cactgcagac gtttggcttt gaaccaaact 17160
tgtataaatt gagcagagat ttcttgtcca ccatgaacat agctgataca cacaactgca 17220
tgatagcttt caacagggtt ttgaaggata caatcttcga atgggctaga ataactgagt 17280
cagataaaag gcttaaacta actggtaagt atgacctgta tcctgtgaga gattcaggca 17340
agttgaagac aatttctaga agacttgtgc tatcttggat atctttatct atgtccacaa 17400
gattggtaac tgggtcattc cctgaccaga agtttgaagc aagacttcaa ttgggaatag 17460
tttcattatc atcccgtgaa atcaggaacc tgagggttat cacaaaaact ttattagaca 17520
ggtttgagga tattatacat agtataacgt atagattcct caccaaagaa ataaagattt 17580
tgatgaagat tttaggggca gtcaagatgt tcggggccag gcaaaatgaa tacacgaccg 17640
tgattgatga tggatcacta ggtgatatcg agccatatga cagctcgtaa taattagtcc 17700
ctatcgtgca gaacgatcga agctccgcgg tacctggaag tcttggactt gtccatatga 17760
caatagtaag aaaaacttac aagaagacaa gaaaatttaa aaggatacat atctcttaaa 17820
ctcttgtctg gt 17832

<210> SEQ ID NO 14
<211> LENGTH: 1503
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggccgcca gagccagcat cctgagcggg ggcaagctgg acgcctggga gaagatcaga 60
ctgaggcctg gcggcaagaa gaagtaccgg ctgaagcacc tggtgtgggc cagcagagag 120
ctggatcgct tcgccctgaa tcctagcctg ctggagacca ccgagggctg ccagcagatc 180
atgaaccagc tgcagcccgc cgtgaaaacc ggcaccgagg agatcaagag cctgttcaac 240
accgtggcca ccctgtactg cgtgcaccag cggatcgacg tgaaggatac caaggaggcc 300
ctggacaaga tcgaggagat ccagaacaag agcaagcaga aaacccagca ggccgctgcc 360
gacaccggcg acagcagcaa agtgagccag aactacccca tcatccagaa tgcccagggc 420
cagatgatcc accagaacct gagccccaga accctgaatg cctgggtgaa agtgatcgag 480
gaaaaggcct tcagccccga agtgatccct atgttcagcg ccctgagcga gggcgccacc 540
ccccaggacc tgaacgtgat gctgaacatt gtgggcggac accaggccgc catgcagatg 600
ctgaaggaca ccatcaatga ggaggccgcc gagtgggaca gactgcaccc cgtgcaggcc 660
ggacccatcc cccctggcca gatcagagag cccagaggca gcgacatcgc cggcaccacc 720
tccacccctc aagaacagct gcagtggatg accggcaacc ctcccatccc tgtgggcaac 780
atctacaagc ggtggatcat cctgggcctg aacaagattg tgcggatgta cagccccgtg 840
tccatcctgg atatcaagca gggccccaag gagcccttca gagactacgt ggaccggttc 900
ttcaaggccc tgagagccga gcaggccacc caggacgtga agggctggat gaccgagacc 960
ctgctggtgc agaacgccaa ccccgactgc aagagcatcc tgaaggccct gggcagcggc 1020

```
gccacactgg aggagatgat gaccgcctgc cagggagtgg gcggacccgg ccacaaggcc   1080

agagtgctgg ccgaggccat gagccaggcc cagcagacca acatcatgat gcagcggggc   1140

aacttcagag gccagaagcg gatcaagtgc ttcaactgcg gcaaggaggg ccacctggcc   1200

agaaactgca gagcccccag gaagaagggc tgctggaagt gtggcaagga agggcaccag   1260

atgaaggact gcaccgagag gcaggccaat ttcctgggca agatttggcc tagcagcaag   1320

ggcagacccg gcaatttccc ccagagcaga cccgagccca ccgcccctcc cgccgagctg   1380

ttcggcatgg gcgagggcat cgccagcctg cccaagcagg agcagaagga cagagagcag   1440

gtgccccccc tggtgtccct gaagtccctg ttcggcaacg atcctctgag ccagggatcc   1500

tga                                                                 1503
```

<210> SEQ ID NO 15
<211> LENGTH: 2160
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
atgaagtgcc ttttgtactt agctttctta ttcatcgggg tgaattgcaa ggctagcgca     60

gagaatttgt gggtaacagt ctactatgga gtccctgtat ggaaggatgc agagacaaca    120

ttgttctgtg ctagtgacgc aaaggcttac gagacggaga agcacaatgt gtgggcaact    180

cacgcatgtg tcccaaccga tccaaatcct caagagattc atctagagaa tgtgactgaa    240

gaattcaata tgtggaagaa taatatggta gagcaaatgc atacagatat cattagttta    300

tgggaccagt cacttaaacc ctgcgttaaa ttgacgcctc tatgtgtgac acttcaatgt    360

actaatgtta caaacaacat aacagatgat atgagaggag aactgaagaa ctgtagtttc    420

aacatgacga cagagttgcg tgacaagaaa cagaaagtgt attcactatt ctatcggttg    480

gatgtagtac agataaatga gaatcaagga aacaggtcca acaactctaa caaagagtac    540

agacttatta attgcaatac cagtgctatc acgcaagcct gcccaaaggt ttcatttgaa    600

ccaataccta ttcattattg tgcacctgct ggattcgcca tcctcaaatg taaagacaag    660

aagttcaatg gaacaggacc ctgcccatca gtttcaaccg ttcagtgcac ccacggaatc    720

aagcctgtag ttagtactca attattgtta aatgggagct tagctgaaga agaagttatg    780

attagatcag agaatattac caataatgcg aagaacatct tggttcaatt caatactcca    840

gtccagatca attgcacaag gcctaataat aataccagaa agagtataag aattgggcca    900

ggacaggcat tctatgcaac aggagatata atcggagaca ttcgacaagc gcactgcact    960

gtttctaagg ccacttggaa tgaaacattg ggtaaagttg taaagcaact tcggaagcat   1020

ttcggaaata acacaattat tagatttgcg aactcatctg gaggggatct ggaagtgaca   1080

acacactctt tcaattgcgg tggcgagttc ttctattgta atacaagtgg attatttaac   1140

tctacttgga tttcaaatac ctcagtccaa ggatctaatt caacagggtc taacgattct   1200

ataacattac cttgccgtat aaagcaaatt attaatatgt ggcaaagaat cgggcaagcg   1260

atgtatgctc cacctattca aggcgtgatt cgttgcgttt caaacataac agggttgatc   1320

ctgaccaggg atggaggctc taccaattcc accaccgaga ccttccgtcc cggtggcgga   1380

gatatgcggg ataactggag atcagagctc tataagtata aggttgtgaa gattgaacct   1440

cttggagttg cccctacaag agcaaagaga agggtggttg gccgagagaa gagagcagtt   1500
```

```
ggcatcggtg ctgtctttct cggatttctt ggagcagctg gatccactat gggagcagca   1560

tcaatgacac taacagtgca ggctagaaat ttgcttagcg gaatcgttca gcagcagagc   1620

aatttactaa gagcaattga agcacagcaa catctcttaa agttgacggt gtggggcatt   1680

aaacaactac aagcgagagt gcttgccgtc gaaagatatt tgcgagacca acagctattg   1740

ggtatttggg gttgttctgg gaaattaatt tgcacaacaa atgttccatg gaactcctcc   1800

tggagtaata ggaatttaag tgagatatgg gacaacatga catggttgca gtgggacaag   1860

gaaatctcaa attatacaca gataatctat ggattattag aagagtctca gaatcagcaa   1920

gagaagaatg aacaggattt gcttgcattg gataagtggg cttctctatg gaactggttc   1980

gatattagta attggctctg gtatattaag agctctattg cctctttttt ctttatcata   2040

gggttaatca ttggactatt cttggttctc cgagttggta tttatctttg cattaaatta   2100

aagcacacca agaaaagaca gatttataca gacatagaga tgaaccgact tggaaagtaa   2160
```

```
<210> SEQ ID NO 16
<211> LENGTH: 2250
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

atgacagcat atatccagag atcacagtgc atctcaacat cactactggt tgttctcacc     60

acattggtct cgtgtcaggc tagcgcagag aatttgtggg taacagtcta ctatggagtc    120

cctgtatgga aggatgcaga gacaacattg ttctgtgcta gtgacgcaaa ggcttacgag    180

acggagaagc acaatgtgtg ggcaactcac gcatgtgtcc caaccgatcc aaatcctcaa    240

gagattcatc tagagaatgt gactgaagaa ttcaatatgt ggaagaataa tatggtagag    300

caaatgcata cagatatcat tagtttatgg gaccagtcac ttaaaccctg cgttaaattg    360

acgcctctat gtgtgacact tcaatgtact aatgttacaa acaacataac agatgatatg    420

agaggagaac tgaagaactg tagtttcaac atgacgacag agttgcgtga caagaaacag    480

aaagtgtatt cactattcta tcggttggat gtagtacaga taaatgagaa tcaaggaaac    540

aggtccaaca actctaacaa agagtacaga cttattaatt gcaataccag tgctatcacg    600

caagcctgcc caaaggtttc atttgaacca atacctattc attattgtgc acctgctgga    660

ttcgccatcc tcaaatgtaa agacaagaag ttcaatggaa caggaccctg cccatcagtt    720

tcaaccgttc agtgcaccca cggaatcaag cctgtagtta gtactcaatt attgttaaat    780

gggagcttag ctgaagaaga agttatgatt agatcagaga atattaccaa taatgcgaag    840

aacatcttgg ttcaattcaa tactccagtc cagatcaatt gcacaaggcc taataataat    900

accagaaaga gtataagaat tgggccagga caggcattct atgcaacagg agatataatc    960

ggagacattc gacaagcgca ctgcactgtt tctaaggcca cttggaatga aacattgggt   1020

aaagttgtaa agcaacttcg gaagcatttc ggaaataaca caattattag atttgcgaac   1080

tcatctggag gggatctgga agtgacaaca cactctttca attgcggtgg cgagttcttc   1140

tattgtaata caagtggatt atttaactct acttggattt caaataccta agtccaagga   1200

tctaattcaa cagggtctaa cgattctata acattacctt gccgtataaa gcaaattatt   1260

aatatgtggc aaagaatcgg gcaagcgatg tatgctccac ctattcaagg cgtgattcgt   1320

tgcgtttcaa acataacagg gttgatcctg accagggatg gaggctctac caattccacc   1380
```

```
accgagacct tccgtcccgg tggcggagat atgcgggata actggagatc agagctctat   1440

aagtataagg ttgtgaagat tgaacctctt ggagttgccc ctacaagagc aaagagaagg   1500

gtggttggcc gagagaagag agcagttggc atcggtgctg tctttctcgg atttcttgga   1560

gcagctggat ccactatggg agcagcatca atgacactaa cagtgcaggc tagaaatttg   1620

cttagcggaa tcgttcagca gcagagcaat ttactaagag caattgaagc acagcaacat   1680

ctcttaaagt tgacggtgtg gggcattaaa caactacaag cgagagtgct tgccgtcgaa   1740

agatatttgc gagaccaaca gctattgggt atttggggtt gttctgggaa attaatttgc   1800

acaacaaatg ttccatggaa ctcctcctgg agtaatagga atttaagtga gatatgggac   1860

aacatgacat ggttgcagtg ggacaaggaa atctcaaatt atacacagat aatctatgga   1920

ttattagaag agtctcagaa tcagcaagag aagaatgaac aggatttgct tgcattggat   1980

aagtgggctt ctctatggaa ctggttcgat attagtaatt ggctctggta tattaagaac   2040

tcaagagaga ctgtgattac gatcatagta gttatggtcg taatattggt ggtcattata   2100

gtgatcatca tcgtgcttta tagactcaga aggtcaatgc taatgggtaa tccagatgac   2160

cgtataccga gggacacata cacattagag ccgaagatca gacatatgta cacaaacggt   2220

gggtttgatg caatggctga gaaaagatga                                    2250
```

<210> SEQ ID NO 17
<211> LENGTH: 2379
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
atggaggaga aagcattctc acctgaagtg atccctatgt tcacagcatt atctgaggga     60

gctactcctc aagatcttaa cacaatgctt aacacagtcg gaggacatca agcagcaatg    120

caaatgttga aagatacaat taacgaggaa gcagcagaat gggatagaat ctataagaga    180

tggataatat taggattgaa caagattgtt agaatgtatt ctcctgtgtc aatccttgat    240

ataagacaag gacctaaaga gcctttcaga gattacgtcg atagatttgc aagaaattgt    300

agagcaccta gaaagaaggg atgttggaaa tgtgggaaag aaggacatca aatgaaagat    360

tgtactgaga gacaagctaa cttcttggga aagatatggc cttcaagatg gaaacctaag    420

atgataggag gaataggagg atttattaaa gtcagacaat atgatcaaat attgattgaa    480

atatgtggac ataaagctat tggaacagtc ctagtgggtc caacacctgt caacatcatt    540

ggtagaaatc ttctcactca aatcggatgt acactcaatt tcccaatatc acctattgag    600

accgtgcctg tcaaattgaa acctggaatg gatggaccta aagtcaaaca atggccatta    660

actgaggaga agattaaagc actggtagaa atttgtacag agatggagaa agaaggaaag    720

atttccaaga ttggtcctga gaatccttat aatactcctg tctttgctat taagaagaag    780

gatagtacca aatggaggaa attagtcgat ttcagagaac ttaacaagag gactcaagac    840

ttctgggaag tgcaattggg aatcccacac cctgcaggat tgaagaagaa gaagtctgtc    900

actgtcctag atgtgggaga tgcatatttc agtgtcccac tggatgaagg tttcagaaag    960

tatacagcat tcacaatccc ttccattaat aatgaaacac ctggaataag atatcaatat   1020

aatgtcttac ctcaagggtg gaaaggatct ccagcaatat tccaatcatc aatgacaaag   1080

atcttggagc ctttcagagc tcagaatcca gagatagtta tttaccaata catggatgat   1140
```

```
ttgtatgttg ggtcagatct cgagatcgga cagcacagga tggagaatag atggcaagta   1200

atgattgtct ggcaagtcga tagaatgaga ataagaacat ggaaatcctt ggtgaaacat   1260

caccttacag aggaggcaga actggaactg gcagagaata gggaaatatt gaaagatcca   1320

gtgcatggtg tctattacga tccttctaaa gatctgatag cagagatcca gtactggcaa   1380

gcaacatgga ttcctgagtg ggaattcgtc aacacacctc cattagtgaa actatggtac   1440

caattagaga agaatgtcac cgagaacttc aacatgtgga agaacgatat ggtagatcaa   1500

atgcacgaag atatcatctc cttgtgggat caatcactta aaccttgtgt taaattgaca   1560

ccttgggtac ctgctcataa agggatagga ggaaacgaac aagtggataa attggtgtcc   1620

caagggatca ggaaagtctt gttcctagat ggaattgata aagctcaagc aaaggaaatt   1680

gtcgcaagct gtgataagtg tcaattaaag ggagaggcaa tgcacggaca agtcgattgt   1740

tcacctggta tttggcaact tgattgtaca catttggagg gtaaagttat tctagtagca   1800

gtacatgtcg cttctggtta tattgaggca gaagtgatac ctgctgagac aggacaggag   1860

accgcatact ttctacttaa gttagctatg aataaggagc tcaagaagat aataggacaa   1920

gttagagatc aagcagagca ccttaagaca gctgtccaaa tggcagtgtt tatacacaac   1980

tttaagagaa agggtggaat cggaggatat tccgcaggag agagaatctg gaaaggtcct   2040

gctaaattgt tatggaaagg agaaggagca gttgtaatac aagataattc tgatataaaa   2100

gtagtcccta gaaggaaagc taagattatt agagattatg ggaaacaaat ggcaggagct   2160

gattgtgtgt ttctaggagc agcaggatcc actatgggag ctgcatcaat gacacttacc   2220

gtgcaggcta gacagcttct ttcaggaatt gtacagcaac agaataattt gctaagagca   2280

attgaagctc aacaacactt acttcaactt acagtctggg gaatcaagca agcacctaca   2340

aaagcaaaga gaagagtcgt ccaaagagag aaaagataa                          2379


<210> SEQ ID NO 18
<211> LENGTH: 2247
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(2247)

<400> SEQUENCE: 18

atg aca gca tat atc cag aga tca cag tgc atc tca aca tca cta ctg       48
Met Thr Ala Tyr Ile Gln Arg Ser Gln Cys Ile Ser Thr Ser Leu Leu
1               5                   10                  15

gtt gtt ctc acc aca ttg gtc tcg tgt cag gct agc gca gag aat ttg       96
Val Val Leu Thr Thr Leu Val Ser Cys Gln Ala Ser Ala Glu Asn Leu
            20                  25                  30

tgg gta aca gtc tac tat gga gtc cct gta tgg aag gat gca gag aca      144
Trp Val Thr Val Tyr Tyr Gly Val Pro Val Trp Lys Asp Ala Glu Thr
        35                  40                  45

aca ttg ttc tgt gct agt gac gca aag gct tac gag acg gag aag cac      192
Thr Leu Phe Cys Ala Ser Asp Ala Lys Ala Tyr Glu Thr Glu Lys His
    50                  55                  60

aat gtg tgg gca act cac gca tgt gtc cca acc gat cca aat cct caa      240
Asn Val Trp Ala Thr His Ala Cys Val Pro Thr Asp Pro Asn Pro Gln
65                  70                  75                  80

gag att cat cta gag aat gtg act gaa gaa ttc aat atg tgg aag aat      288
Glu Ile His Leu Glu Asn Val Thr Glu Glu Phe Asn Met Trp Lys Asn
```

-continued

```
                85                  90                  95

aat atg gta gag caa atg cat aca gat atc att agt tta tgg gac cag      336
Asn Met Val Glu Gln Met His Thr Asp Ile Ile Ser Leu Trp Asp Gln
            100                 105                 110

tca ctt aaa ccc tgc gtt aaa ttg acg cct cta tgt gtg aca ctt caa      384
Ser Leu Lys Pro Cys Val Lys Leu Thr Pro Leu Cys Val Thr Leu Gln
        115                 120                 125

tgt act aat gtt aca aac aac ata aca gat gat atg aga gga gaa ctg      432
Cys Thr Asn Val Thr Asn Asn Ile Thr Asp Asp Met Arg Gly Glu Leu
    130                 135                 140

aag aac tgt agt ttc aac atg acg aca gag ttg cgt gac aag aaa cag      480
Lys Asn Cys Ser Phe Asn Met Thr Thr Glu Leu Arg Asp Lys Lys Gln
145                 150                 155                 160

aaa gtg tat tca cta ttc tat cgg ttg gat gta gta cag ata aat gag      528
Lys Val Tyr Ser Leu Phe Tyr Arg Leu Asp Val Val Gln Ile Asn Glu
            165                 170                 175

aat caa gga aac agg tcc aac aac tct aac aaa gag tac aga ctt att      576
Asn Gln Gly Asn Arg Ser Asn Asn Ser Asn Lys Glu Tyr Arg Leu Ile
            180                 185                 190

aat tgc aat acc agt gct atc acg caa gcc tgc cca aag gtt tca ttt      624
Asn Cys Asn Thr Ser Ala Ile Thr Gln Ala Cys Pro Lys Val Ser Phe
        195                 200                 205

gaa cca ata cct att cat tat tgt gca cct gct gga ttc gcc atc ctc      672
Glu Pro Ile Pro Ile His Tyr Cys Ala Pro Ala Gly Phe Ala Ile Leu
    210                 215                 220

aaa tgt aaa gac aag aag ttc aat gga aca gga ccc tgc cca tca gtt      720
Lys Cys Lys Asp Lys Lys Phe Asn Gly Thr Gly Pro Cys Pro Ser Val
225                 230                 235                 240

tca acc gtt cag tgc acc cac gga atc aag cct gta gtt agt act caa      768
Ser Thr Val Gln Cys Thr His Gly Ile Lys Pro Val Val Ser Thr Gln
            245                 250                 255

tta ttg tta aat ggg agc tta gct gaa gaa gaa gtt atg att aga tca      816
Leu Leu Leu Asn Gly Ser Leu Ala Glu Glu Glu Val Met Ile Arg Ser
            260                 265                 270

gag aat att acc aat aat gcg aag aac atc ttg gtt caa ttc aat act      864
Glu Asn Ile Thr Asn Asn Ala Lys Asn Ile Leu Val Gln Phe Asn Thr
        275                 280                 285

cca gtc cag atc aat tgc aca agg cct aat aat aat acc aga aag agt      912
Pro Val Gln Ile Asn Cys Thr Arg Pro Asn Asn Asn Thr Arg Lys Ser
    290                 295                 300

ata aga att ggg cca gga cag gca ttc tat gca aca gga gat ata atc      960
Ile Arg Ile Gly Pro Gly Gln Ala Phe Tyr Ala Thr Gly Asp Ile Ile
305                 310                 315                 320

gga gac att cga caa gcg cac tgc act gtt tct aag gcc act tgg aat     1008
Gly Asp Ile Arg Gln Ala His Cys Thr Val Ser Lys Ala Thr Trp Asn
            325                 330                 335

gaa aca ttg ggt aaa gtt gta aag caa ctt cgg aag cat ttc gga aat     1056
Glu Thr Leu Gly Lys Val Val Lys Gln Leu Arg Lys His Phe Gly Asn
            340                 345                 350

aac aca att att aga ttt gcg aac tca tct gga ggg gat ctg gaa gtg     1104
Asn Thr Ile Ile Arg Phe Ala Asn Ser Ser Gly Gly Asp Leu Glu Val
        355                 360                 365

aca aca cac tct ttc aat tgc ggt ggc gag ttc ttc tat tgt aat aca     1152
Thr Thr His Ser Phe Asn Cys Gly Gly Glu Phe Phe Tyr Cys Asn Thr
    370                 375                 380

agt gga tta ttt aac tct act tgg att tca aat acc tca gtc caa gga     1200
Ser Gly Leu Phe Asn Ser Thr Trp Ile Ser Asn Thr Ser Val Gln Gly
385                 390                 395                 400

tct aat tca aca ggg tct aac gat tct ata aca tta cct tgc cgt ata     1248
```

```
Ser Asn Ser Thr Gly Ser Asn Asp Ser Ile Thr Leu Pro Cys Arg Ile
            405                 410                 415

aag caa att att aat atg tgg caa aga atc ggg caa gcg atg tat gct     1296
Lys Gln Ile Ile Asn Met Trp Gln Arg Ile Gly Gln Ala Met Tyr Ala
            420                 425                 430

cca cct att caa ggc gtg att cgt tgc gtt tca aac ata aca ggg ttg     1344
Pro Pro Ile Gln Gly Val Ile Arg Cys Val Ser Asn Ile Thr Gly Leu
        435                 440                 445

atc ctg acc agg gat gga ggc tct acc aat tcc acc acc gag acc ttc     1392
Ile Leu Thr Arg Asp Gly Gly Ser Thr Asn Ser Thr Thr Glu Thr Phe
    450                 455                 460

cgt ccc ggt ggc gga gat atg cgg gat aac tgg aga tca gag ctc tat     1440
Arg Pro Gly Gly Gly Asp Met Arg Asp Asn Trp Arg Ser Glu Leu Tyr
465                 470                 475                 480

aag tat aag gtt gtg aag att gaa cct ctt gga gtt gcc cct aca aga     1488
Lys Tyr Lys Val Val Lys Ile Glu Pro Leu Gly Val Ala Pro Thr Arg
            485                 490                 495

gca aag aga agg gtg gtt ggc cga gag aag aga gca gtt ggc atc ggt     1536
Ala Lys Arg Arg Val Val Gly Arg Glu Lys Arg Ala Val Gly Ile Gly
            500                 505                 510

gct gtc ttt ctc gga ttt ctt gga gca gct gga tcc act atg gga gca     1584
Ala Val Phe Leu Gly Phe Leu Gly Ala Ala Gly Ser Thr Met Gly Ala
        515                 520                 525

gca tca atg aca cta aca gtg cag gct aga aat ttg ctt agc gga atc     1632
Ala Ser Met Thr Leu Thr Val Gln Ala Arg Asn Leu Leu Ser Gly Ile
    530                 535                 540

gtt cag cag cag agc aat tta cta aga gca att gaa gca cag caa cat     1680
Val Gln Gln Gln Ser Asn Leu Leu Arg Ala Ile Glu Ala Gln Gln His
545                 550                 555                 560

ctc tta aag ttg acg gtg tgg ggc att aaa caa cta caa gcg aga gtg     1728
Leu Leu Lys Leu Thr Val Trp Gly Ile Lys Gln Leu Gln Ala Arg Val
                565                 570                 575

ctt gcc gtc gaa aga tat ttg cga gac caa cag cta ttg ggt att tgg     1776
Leu Ala Val Glu Arg Tyr Leu Arg Asp Gln Gln Leu Leu Gly Ile Trp
            580                 585                 590

ggt tgt tct ggg aaa tta att tgc aca aca aat gtt cca tgg aac tcc     1824
Gly Cys Ser Gly Lys Leu Ile Cys Thr Thr Asn Val Pro Trp Asn Ser
        595                 600                 605

tcc tgg agt aat agg aat tta agt gag ata tgg gac aac atg aca tgg     1872
Ser Trp Ser Asn Arg Asn Leu Ser Glu Ile Trp Asp Asn Met Thr Trp
    610                 615                 620

ttg cag tgg gac aag gaa atc tca aat tat aca cag ata atc tat gga     1920
Leu Gln Trp Asp Lys Glu Ile Ser Asn Tyr Thr Gln Ile Ile Tyr Gly
625                 630                 635                 640

tta tta gaa gag tct cag aat cag caa gag aag aat gaa cag gat ttg     1968
Leu Leu Glu Glu Ser Gln Asn Gln Gln Glu Lys Asn Glu Gln Asp Leu
            645                 650                 655

ctt gca ttg gat aag tgg gct tct cta tgg aac tgg ttc gat att agt     2016
Leu Ala Leu Asp Lys Trp Ala Ser Leu Trp Asn Trp Phe Asp Ile Ser
            660                 665                 670

aat tgg ctc tgg tat att aag aac tca aga gag act gtg att acg atc     2064
Asn Trp Leu Trp Tyr Ile Lys Asn Ser Arg Glu Thr Val Ile Thr Ile
        675                 680                 685

ata gta gtt atg gtc gta ata ttg gtg gtc att ata gtg atc atc atc     2112
Ile Val Val Met Val Val Ile Leu Val Val Ile Ile Val Ile Ile Ile
    690                 695                 700

gtg ctt tat aga ctc aga agg tca atg cta atg ggt aat cca gat gac     2160
Val Leu Tyr Arg Leu Arg Arg Ser Met Leu Met Gly Asn Pro Asp Asp
705                 710                 715                 720
```

```
cgt ata ccg agg gac aca tac aca tta gag ccg aag atc aga cat atg     2208
Arg Ile Pro Arg Asp Thr Tyr Thr Leu Glu Pro Lys Ile Arg His Met
                725                 730                 735

tac aca aac ggt ggg ttt gat gca atg gct gag aaa aga                 2247
Tyr Thr Asn Gly Gly Phe Asp Ala Met Ala Glu Lys Arg
            740                 745


<210> SEQ ID NO 19
<211> LENGTH: 749
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Thr Ala Tyr Ile Gln Arg Ser Gln Cys Ile Ser Thr Ser Leu Leu
1               5                   10                  15

Val Val Leu Thr Thr Leu Val Ser Cys Gln Ala Ser Ala Glu Asn Leu
            20                  25                  30

Trp Val Thr Val Tyr Tyr Gly Val Pro Val Trp Lys Asp Ala Glu Thr
        35                  40                  45

Thr Leu Phe Cys Ala Ser Asp Ala Lys Ala Tyr Glu Thr Glu Lys His
    50                  55                  60

Asn Val Trp Ala Thr His Ala Cys Val Pro Thr Asp Pro Asn Pro Gln
65                  70                  75                  80

Glu Ile His Leu Glu Asn Val Thr Glu Glu Phe Asn Met Trp Lys Asn
                85                  90                  95

Asn Met Val Glu Gln Met His Thr Asp Ile Ile Ser Leu Trp Asp Gln
            100                 105                 110

Ser Leu Lys Pro Cys Val Lys Leu Thr Pro Leu Cys Val Thr Leu Gln
        115                 120                 125

Cys Thr Asn Val Thr Asn Asn Ile Thr Asp Asp Met Arg Gly Glu Leu
    130                 135                 140

Lys Asn Cys Ser Phe Asn Met Thr Thr Glu Leu Arg Asp Lys Lys Gln
145                 150                 155                 160

Lys Val Tyr Ser Leu Phe Tyr Arg Leu Asp Val Val Gln Ile Asn Glu
                165                 170                 175

Asn Gln Gly Asn Arg Ser Asn Asn Ser Asn Lys Glu Tyr Arg Leu Ile
            180                 185                 190

Asn Cys Asn Thr Ser Ala Ile Thr Gln Ala Cys Pro Lys Val Ser Phe
        195                 200                 205

Glu Pro Ile Pro Ile His Tyr Cys Ala Pro Ala Gly Phe Ala Ile Leu
    210                 215                 220

Lys Cys Lys Asp Lys Lys Phe Asn Gly Thr Gly Pro Cys Pro Ser Val
225                 230                 235                 240

Ser Thr Val Gln Cys Thr His Gly Ile Lys Pro Val Val Ser Thr Gln
                245                 250                 255

Leu Leu Leu Asn Gly Ser Leu Ala Glu Glu Glu Val Met Ile Arg Ser
            260                 265                 270

Glu Asn Ile Thr Asn Asn Ala Lys Asn Ile Leu Val Gln Phe Asn Thr
        275                 280                 285

Pro Val Gln Ile Asn Cys Thr Arg Pro Asn Asn Asn Thr Arg Lys Ser
    290                 295                 300

Ile Arg Ile Gly Pro Gly Gln Ala Phe Tyr Ala Thr Gly Asp Ile Ile
305                 310                 315                 320
```

```
Gly Asp Ile Arg Gln Ala His Cys Thr Val Ser Lys Ala Thr Trp Asn
                325                 330                 335

Glu Thr Leu Gly Lys Val Val Lys Gln Leu Arg Lys His Phe Gly Asn
            340                 345                 350

Asn Thr Ile Ile Arg Phe Ala Asn Ser Ser Gly Gly Asp Leu Glu Val
        355                 360                 365

Thr Thr His Ser Phe Asn Cys Gly Gly Glu Phe Phe Tyr Cys Asn Thr
    370                 375                 380

Ser Gly Leu Phe Asn Ser Thr Trp Ile Ser Asn Thr Ser Val Gln Gly
385                 390                 395                 400

Ser Asn Ser Thr Gly Ser Asn Asp Ser Ile Thr Leu Pro Cys Arg Ile
                405                 410                 415

Lys Gln Ile Ile Asn Met Trp Gln Arg Ile Gly Gln Ala Met Tyr Ala
            420                 425                 430

Pro Pro Ile Gln Gly Val Ile Arg Cys Val Ser Asn Ile Thr Gly Leu
        435                 440                 445

Ile Leu Thr Arg Asp Gly Gly Ser Thr Asn Ser Thr Thr Glu Thr Phe
    450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Pro Leu Gly Val Ala Pro Thr Arg
                485                 490                 495

Ala Lys Arg Arg Val Val Gly Arg Glu Lys Arg Ala Val Gly Ile Gly
            500                 505                 510

Ala Val Phe Leu Gly Phe Leu Gly Ala Ala Gly Ser Thr Met Gly Ala
        515                 520                 525

Ala Ser Met Thr Leu Thr Val Gln Ala Arg Asn Leu Leu Ser Gly Ile
    530                 535                 540

Val Gln Gln Gln Ser Asn Leu Leu Arg Ala Ile Glu Ala Gln Gln His
545                 550                 555                 560

Leu Leu Lys Leu Thr Val Trp Gly Ile Lys Gln Leu Gln Ala Arg Val
                565                 570                 575

Leu Ala Val Glu Arg Tyr Leu Arg Asp Gln Gln Leu Leu Gly Ile Trp
            580                 585                 590

Gly Cys Ser Gly Lys Leu Ile Cys Thr Thr Asn Val Pro Trp Asn Ser
        595                 600                 605

Ser Trp Ser Asn Arg Asn Leu Ser Glu Ile Trp Asp Asn Met Thr Trp
    610                 615                 620

Leu Gln Trp Asp Lys Glu Ile Ser Asn Tyr Thr Gln Ile Ile Tyr Gly
625                 630                 635                 640

Leu Leu Glu Glu Ser Gln Asn Gln Gln Glu Lys Asn Glu Gln Asp Leu
                645                 650                 655

Leu Ala Leu Asp Lys Trp Ala Ser Leu Trp Asn Trp Phe Asp Ile Ser
            660                 665                 670

Asn Trp Leu Trp Tyr Ile Lys Asn Ser Arg Glu Thr Val Ile Thr Ile
        675                 680                 685

Ile Val Val Met Val Val Ile Leu Val Val Ile Ile Val Ile Ile Ile
    690                 695                 700

Val Leu Tyr Arg Leu Arg Arg Ser Met Leu Met Gly Asn Pro Asp Asp
705                 710                 715                 720
```

-continued

```
Arg Ile Pro Arg Asp Thr Tyr Thr Leu Glu Pro Lys Ile Arg His Met
                725                 730                 735

Tyr Thr Asn Gly Gly Phe Asp Ala Met Ala Glu Lys Arg
            740                 745
```

What is claimed is:

1. A viral vector containing and expressing a nucleic acid encoding a Clade A Env-F hybrid based on BG505, wherein the Env signal sequence (SS), transmembrane region (TMR), and the cytoplasmic tail (CT) of HIV-Env-F are replaced with an analogous sequence from the Sendai virus F gene.

2. The vector of claim 1, wherein the nucleic acid comprises the nucleic acid sequence of SEQ ID NO: 18.

3. The vector of claim 1, wherein the nucleic acid encodes an amino acid sequence of the HIV immunogen comprises the amino acid sequence of SEQ ID NO: 19.

4. The vector of claim 1, wherein the vector is a canine distemper virus (CDV) or a vesicular stomatitis virus (VSV) vector.

5. A cell transfected with the vector of claim 1.

6. The cell of claim 5 wherein the cell is a Vero cell.

7. A method for eliciting an immune response against HIV comprising administering an effective amount of the vector of claim 1 to a mammal in need thereof.

8. The method of claim 7 further comprising administering an adjuvant.

9. The method of claim 8, wherein the adjuvant is comprised of an acrylic polymer.

* * * * *